(12) United States Patent  
Brain et al.

(10) Patent No.: US 8,957,074 B2  
(45) Date of Patent: Feb. 17, 2015

(54) PYRROLOPYRIMIDINE COMPOUNDS AS INHIBITORS OF CDK4/6

(75) Inventors: Christopher Thomas Brain, North Reading, MA (US); Young Shin Cho, Cambridge, MA (US); John William Giraldes, Quincy, MA (US); Bharat Lagu, Acton, MA (US); Julian Roy Levell, Arlington, MA (US); Michael J. Luzzio, Noank, CT (US); Lawrence Blas Perez, Hopkinton, MA (US); Yaping Wang, Boxborough, MA (US); Fan Yang, West Roxbury, MA (US)

(73) Assignee: Novartis AG, Basel (CH)

( * ) Notice: Subject to any disclaimer, the term of this patent is extended or adjusted under 35 U.S.C. 154(b) by 106 days.

(21) Appl. No.: 13/579,359

(22) PCT Filed: Feb. 17, 2011

(86) PCT No.: PCT/EP2011/052353  
§ 371 (c)(1),  
(2), (4) Date: Nov. 5, 2012

(87) PCT Pub. No.: WO2011/101409  
PCT Pub. Date: Aug. 25, 2011

(65) Prior Publication Data  
US 2013/0150342 A1    Jun. 13, 2013

Related U.S. Application Data

(60) Provisional application No. 61/429,997, filed on Jan. 5, 2011, provisional application No. 61/429,372, filed on Jan. 3, 2011, provisional application No. 61/306,248, filed on Feb. 19, 2010.

(51) Int. Cl.
| | |
|---|---|
| *A61K 31/50* | (2006.01) |
| *A61K 31/501* | (2006.01) |
| *C07D 401/00* | (2006.01) |
| *C07D 403/00* | (2006.01) |
| *C07D 405/00* | (2006.01) |
| *C07D 409/00* | (2006.01) |
| *A01N 43/90* | (2006.01) |
| *A61K 31/519* | (2006.01) |
| *C07D 487/00* | (2006.01) |
| *C07D 498/20* | (2006.01) |
| *C07D 487/04* | (2006.01) |
| *C07D 519/00* | (2006.01) |

(Continued)

(52) U.S. Cl.  
CPC ........... *C07D 498/20* (2013.01); *C07D 487/04* (2013.01); *C07D 519/00* (2013.01); *C07D 471/08* (2013.01); *C07D 471/10* (2013.01); *C07D 487/08* (2013.01); *C07D 498/08* (2013.01)  
USPC ................... 514/252.02; 514/265.1; 544/238; 544/280

(58) Field of Classification Search  
None  
See application file for complete search history.

(56) References Cited

U.S. PATENT DOCUMENTS

| 7,713,994 B2 | 5/2010 | Tsou et al. |
| 7,906,528 B2 | 3/2011 | Yuan et al. |

(Continued)

FOREIGN PATENT DOCUMENTS

| JP | 2006/241089 A1 | 9/2006 |
| WO | 03/074530 A1 | 9/2003 |

(Continued)

OTHER PUBLICATIONS

Foster, A. B. "Deuterium isotope effects in the metabolism of drugs and xenobiotics: implications for drug design", Advances in Drug Research, Jan. 1, 1985, pp. 1-40, vol. 14, Academic Press, London, GB.

(Continued)

*Primary Examiner* — Jeffrey H Murray  
(74) *Attorney, Agent, or Firm* — Laura Madden

(57) ABSTRACT

The invention is directed to novel pyrrolopyrimidine compounds of formula (I) wherein $R^1$, $R^{2Y}$, $R^4$, $R^8$-$R^{11}$, A and L are defined herein and to salts, including pharmaceutically acceptable salts thereof. The compounds of the present invention are CDK4/6 inhibitors and could be useful in the treatment of diseases and disorders mediated by CDK4/6, such as cancer, including mantle cell lymphoma, liposarcoma, non small cell lung cancer, melanoma, squamous cell esophageal cancer and breast cancer. The invention is further directed to pharmaceutical compositions comprising a compound of the invention. The invention is still further directed to methods of inhibiting CDK4/6 activity and to the treatment of disorders associated therewith using a compound of the invention or a pharmaceutical composition comprising a compound of the invention.

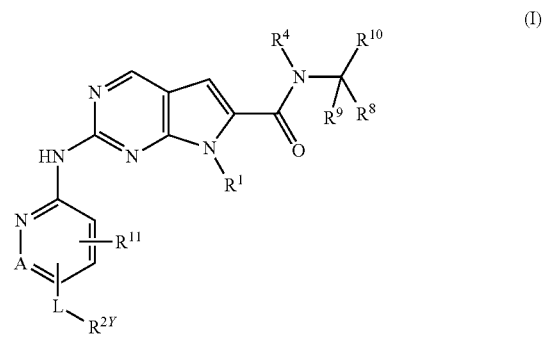

(I)

40 Claims, No Drawings

(51) Int. Cl.
C07D 471/08 (2006.01)
C07D 471/10 (2006.01)
C07D 487/08 (2006.01)
C07D 498/08 (2006.01)

(56) References Cited

U.S. PATENT DOCUMENTS

| | | | |
|---|---|---|---|
| 7,947,695 | B2 | 5/2011 | Freyne et al. |
| 7,968,557 | B2 | 6/2011 | Ha-Soon et al. |
| 7,998,978 | B2 | 8/2011 | Huang et al. |
| 8,153,640 | B2 | 4/2012 | Guillemont et al. |
| 8,324,225 | B2 | 12/2012 | Brain et al. |
| 8,415,355 | B2 | 4/2013 | Brain et al. |
| 8,685,980 | B2 | 4/2014 | Besong et al. |
| 2008/0139588 | A1 | 6/2008 | Clark et al. |
| 2008/0167309 | A1 | 7/2008 | Berdini et al. |
| 2008/0261973 | A1 | 10/2008 | Capraro et al. |
| 2009/0169558 | A1 | 7/2009 | Heng et al. |
| 2009/0203688 | A1 | 8/2009 | Gaul et al. |
| 2009/0318441 | A1 | 12/2009 | Brain et al. |
| 2010/0105653 | A1 | 4/2010 | Besong et al. |
| 2011/0142796 | A1 | 6/2011 | Connors et al. |
| 2011/0152244 | A1 | 6/2011 | Besong et al. |
| 2012/0115878 | A1 | 5/2012 | Calienni et al. |
| 2012/0207763 | A1 | 8/2012 | Brain et al. |
| 2013/0035336 | A1 | 2/2013 | Borland et al. |
| 2013/0184285 | A1 | 7/2013 | Brain et al. |

FOREIGN PATENT DOCUMENTS

| | | |
|---|---|---|
| WO | 2004072038 A1 | 2/2004 |
| WO | 2004065378 A1 | 8/2004 |
| WO | 2005/023761 A1 | 3/2005 |
| WO | 2005/023806 A2 | 3/2005 |
| WO | 2005/047289 A1 | 5/2005 |
| WO | 2005/085253 A1 | 9/2005 |
| WO | 2005/107760 A1 | 11/2005 |
| WO | 2006/076595 A1 | 7/2006 |
| WO | 2006/091737 A1 | 8/2006 |
| WO | 2007/030438 A2 | 3/2007 |
| WO | 2007/058990 A2 | 5/2007 |
| WO | 2007/104053 A2 | 9/2007 |
| WO | 2007/127382 A1 | 11/2007 |
| WO | 2008/135232 A1 | 11/2008 |
| WO | 2009/049028 A1 | 4/2009 |
| WO | 2009/098236 A1 | 8/2009 |
| WO | 2009/115084 A2 | 9/2009 |
| WO | 2011/101417 A1 | 8/2011 |
| WO | 2011/130232 A1 | 10/2011 |

OTHER PUBLICATIONS

Moriarty, K. J. et al. "The synthesis and SAR of 2-amino-pyrrolo[2,3-d]pyrimidines: A new class of Aurora-A kinase inhibitors", Bioorganic & Medicinal Chemistry Letters, Nov. 15, 2006, pp. 5778-5783, vol. 16, No. 22, Elsevier Science, GB.
Choi et al., "Design and synthesis of 7H-pyrrolo[2,3-d]pyrimidines as focal adhesion kinase inhibitors. Part 1", Bioorganic & Medicinal Chemistry Letters, 2006, vol. 16, No. 8, pp. 2173-2176.
Choi et al., "Design and synthesis of 7H-pyrrolo[2,3-d]pyrimidines as focal adhesion kinase inhibitors. Part 2", Bioorganic & Medicinal Chemistry Letters, 2006, vol. 16, No. 8, pp. 2689-2692.
Gaulon et al., "A General and Facile Rout to New Trisubstituted Purin-8-ones", Synthesis, 2005, vol. 13, pp. 2227-2233.
Hong et al., "Identification and Characterization of Small-Molecule Inducers of Epidermal Keratinocyte Differentiation", ACS Chemical Biology, 2007, 2(3) pp. 171-175.
Koretskaya et al., "5-Substituted Pyrimidine Derivatives.: III. Synthesis of Pyrrolo(2,3-D) Pyrimidines (5,7-Diazaindoles)", Khimiko-Farmatsevticheskii Zhurnal, 1968, 6 pp. 5-12.
Siddiqi et al., "Search for New Purine- and Ribose-Modified Adenosine Analogues as Selective Agonists and Antagonists at Adenosine Receptors", J. Med. Chem., 1995, 38, pp. 1174-1188.
Toogood, Peter L. et al., "Discovery of a Potent and Selective Inhibitor of Cyclin-Dependent Kinase 4/6" J. Med. Chem. 2005, 48, pp. 2388-2406.
Chemical Abstracts Service. 1-Piperazinecarboxylic acid, 4-[6-[[7-cyclopentyl-6 -[(dimethylamino)carbonyl]-5-methyl-7H-pyrrolo[2,3-d]pyrimidin-2-yl]amino]-3-pyridinyl]-,1-dimethylethyl ester; CAS Registry RN 959798-97-1.
Chemical Abstracts Service. 7H-Pyrrolo[2,3-d]pyrimidine-6-carboxamide, 7-cyclopentyl-N,N,5-trimethyl-2-[[5-(1-piperazinyl)-2-pyridinyl]amino]-; CAS Registry RN 959798-50-6.
Ortega et al., "Cyclin D-dependent kinases, INK4 inhibitors and cancer," Biochimica et Biophysica Acta 1602:73-87 (2002).
Shapiro, Geoffrey I., "Cyclin-Dependent Kinase Pathways As Targets for Cancer Treatment," Journal of Clinical Oncology 24(11):1770-1783 (Apr. 10, 2006).
Lundberg and Weinberg, "Functional Inactivation of the Retinoblastoma Protein Requires Sequential Modification by at Least Two Distinct Cyclin-cdk Complexes," Mol. Cell. Bio. 18(2):753-761 (Feb. 1998).
Kamb et al., "A Cell Cycle Regulator Potentially Involved in Genesis of Many Tumor Types," Science 264:436-440 (Apr. 15, 1994).
Sherr and Roberts, "CDK inhibitors: positive and negative regulators of G1-phase progression," Genes Dev. 13 (12):1501-1512 (1999).
Amin et al., "Characterization of 4 Mantle Cell Lymphoma Cell Lines," Arch Pathol Lab Med. 127:424-431 (2003).
Sharma et al., "Epidermal growth factor receptor mutations in lung cancer," Nature Reviews Cancer 7(3):169-181 (2007).
Bergsagel and Kuehl, "Critical roles for immunoglobulin translocations and cyclin D dysregulation in multiple myeloma," Immunological Reviews 194:96-104 (2003).
Jiang et al., "Amplification and Expression of the Human Cyclin D Gene in Esophageal Cancer," Cancer Res 52:2980-2983 (1992).
Arnold and Papanikolaou, "Cyclin D1 in Breast Cancer Pathogenesis," American Society of Clinical Oncology 23 (18):4215-4224 (Jun. 20, 2005).
Sirvent et al., "Detection of MDM2-CDK4 Amplification by Fluorescence in Situ Hybridization in 200 Paraffin-embedded Tumor Samples," Am J Surg Pathol 31:1476-1489 (2007).
Brambilla et al., "Alterations of Expression of Rb, p16INK4A and Cyclin D1 in non-small cell lung carcinoma and their clinical significance," Journal of Pathology 188:351-360 (1999).
Cowgill and Muscarella, "The genetics of pancreatic cancer," the American Journal of Surgery 186:279-286 (2003).
Gazzeri et al., "Mechanisms of p16INK4A inactivation in non small-cell lung cancers," Oncogene 16:497-504 (1998).
Dailey et al., "Mechanisms underlying differential responses to FGF signaling," Cytokine & Growth Factor Reviews 16:233-247 (2005).
Engelman, Jeffrey, "Targeting P13K signalling in cancer: opportunities, challenges and limitations," Nature Reviews Cancer 9:550-562 (Aug. 2009).
Garcia-Echeverria, Carlos, "Protein and lipid kinase inhibitors as targeted anticancer agents of the Ras/Raf/MEK and PI3K/PKB pathways," Purinergic Signalling 5:117-125 (2009).
Gray-Schopfer et al., "The role of B-RAF in melanoma," Cancer and Metastasis Reviews 24:165-183 (2005).
John et al., "Overview of molecular testing in non-small-cell cancer: mutational analysis, gene copy number, protein expression and other biomarkers of EGFR for the prediction of response to tyrosine kinase inhibitors," Oncogene 28: S14-S23 (2009).
Chemical Abstracts Service. 1-Piperazinecarboxylic acid, 4-[6-[[7-cyclopentyl-6 -[(dimethylamino)carbonyl]-5- methyl-7H-pyrrolo[2,3-d]pyrimidin-2-yl]amino]-3-pyridinyl]-1,1-dimethylethyl ester; CAS Registry RN 95979897-1. entered in STN Dec. 31, 2007.
Chemical Abstracts Service. 7H-Pyrrolo[2,3-d]pyrimidine-6-carboxamide, 7-cyclopentyl-N,N,5-trimethyl-24[[5-(1-piperaziny1)-2-pyridinyl]amino]-; CAS Registry RN 959798-50-6, entered in STN Dec. 31, 2007.

PYRROLOPYRIMIDINE COMPOUNDS AS INHIBITORS OF CDK4/6

FIELD OF THE INVENTION

The invention relates to new pyrrolopyrimidine compounds and pharmaceutical compositions thereof, specifically pyrrolopyrimidine compounds and pharmaceutical compositions thereof which are inhibitors of CDK4/6. The invention is also directed to the use of these compounds and compositions in the treatment of hyperproliferative disorders such as cancer.

BACKGROUND OF THE INVENTION

Mammalian cell cycle progression is a tightly controlled process in which transitions through different phases are conducted in a highly ordered manner and guarded by multiple checkpoints. The retinoblastoma protein (pRb) is the checkpoint protein for the G1 to S phase transition. pRb associates with a family of E2F transcription factors to prevent their activity in the absence of appropriate growth stimuli (See Ortega et al., *Biochimica et Biophysica Acta-Reviews on Cancer* 2002; 1602 (1):73-87; Shapiro, *Journal of Clinical Oncology* 2006; 24 (11):1770-1783). Upon mitogen stimulation, quiescent cells begin their entry into S phase by newly synthesizing D-cyclins, which are the activators of cyclin-dependent kinases 4 and 6 (CDK4/6). Once bound by the cyclins, CDK4/6 deactivate the pRb protein via phosphorylation. The phosphorylation of pRb releases E2F to direct the transcription of genes required for S phase. A full deactivation of pRb requires phosphorylations by both cyclin D-CDK4/6 and cyclin E-CDK2. Phosphorylations by CDK4/6 at specific sites of pRb (Ser780, Ser795) have been shown to be a prerequisite for cyclin E-CDK2 phosphorylation. (See Lundberg et al., *Molecular and Cellular Biology* 1998; 18 (2):753-761) In addition to D-cyclins, the activity of CDK4/6 is regulated by p16, encoded by INK4a gene, which inhibits the kinase activity. (See Kamb et al., *Science* 1994; 264 (5157):436-440) The CIP/KIP proteins, which are the inhibitors of cyclin E-CDK2, also bind to cyclin D-CDK4/6 complex, and this results in further activation of CDK2 by sequestering the CIP/KIP proteins away from their target. (See Sherr et al., *Genes & Development* 1999; 13 (12):1501-1512) Therefore, the cyclin D-CDK4/6 is a key enzyme complex that regulates the G1 to S phase.

The D-cyclin-CDK4/6-INK4a-pRb pathway is universally disrupted to favor cell proliferation in cancer. In a majority of cases (~80%), cancers maintain a functional pRb and utilize different mechanisms to increase the activity of CDK4/6 kinase. (See Ortega et al., *Biochimica et Biophysica Acta-Reviews on Cancer* 2002; 1602 (1):73-87; Shapiro, *Journal of Clinical Oncology* 2006; 24 (11):1770-1783)) In Mantle cell lymphoma (MCL), cyclin D1 is translocated to IgH promoter (t11:14) which results in constitutive expression of the protein, leading to activation of CDK4/6 (See Amin, et al., *Archives of Pathology & Laboratory Medicine* 2003; 127 (4):424-431; Oudat, et al., *Modern Pathology* 2001; 14 (1): 175A) This translocation is observed in >90% of the MCL cases and considered pathognomic for the disease. The D-cyclin is also translocated in 20% of multiple myelomas. (See Bergsagel et al., *Immunological Reviews* 2003; 194 (1):96-104)

In addition to translocation, D-cyclin abundance can also be increased by amplification or overexpression, and the examples of these can be found in squamous cell esophageal cancer, where a significant portion exhibits cyclin D1 amplification (See Jiang, et al., *Cancer Research* 1992; 52 (10): 2980-2983) and in breast cancer, where the overexpression of cyclin D1 is frequent (See Arnold et al., *Journal of Clinical Oncology* 2005). The CDK4/6 kinase activity can also be increased by amplification of the CDK4 gene itself and the co-amplifications of CDK4 and MDM2 genes are observed in almost all cases of dedifferentiated liposarcomas. (See Sirvent, et al., *American Journal of Surgical Pathology* 2007; 31 (10):1476-1489) The genetic inhibitor of CDK4/6 is also frequently inactivated in cancer to achieve CDK4/6 activation and the examples of this include non small cell lung cancer, melanoma and pancreatic cancer (Brambilla, et al., *Journal of Pathology* 1999; 188 (4):351-360; Cowgill et al., *American Journal of Surgery* 2003; 186 (3):279-286; Gazzeri, et al., *Oncogene* 1998; 16 (4):497-504; Kamb et al., *Science* 1994; 264 (5157):436-440; Ortega et al., *Biochimica et Biophysica Acta-Reviews on Cancer* 2002; 1602 (1):73-87).

In addition to these genetic defects directly related to the D-cyclin-CDK4/6-INK4a-pRb pathway, the activity of the CDK4/6 kinases can also be enhanced by oncogenic aberrations of the mitogen pathways that increase D-cyclin expression. The examples here include EGFR amplifications in non small cell lung cancer (NSCLC), activating K-Ras mutations in pancreatic cancer, V600E B-Raf mutation in melanoma and PTEN inactivation in colon cancer (See Dailey, et al., *Cytokine & Growth Factor Reviews* 2005; 16 (2):233-247; Engelman, *Nature Reviews Cancer* 2009; 9 (8):550-562; Garcia-Echeverria, *Purinergic Signalling* 2009; 5 (1):117-125, Gray-Schopfer et al., *Cancer and Metastasis Reviews* 2005; 24 (1):165-183, John, et al., *Oncogene* 2009; 28:S14-S23, Sharma, et al., *Nature Reviews Cancer* 2007; 7 (3):169-181).

Taken together, a large number of human neoplasms achieve enhanced cell proliferation by increasing CDK4/6 activity and a small molecule inhibitor of these kinases might provide an effective means to treat these diseases.

Inhibitors of CDKs are known and patent applications have been filed on such inhibitors. (See, for example, WO2007/140222)

Thus attempts have been made to prepare compounds that inhibit CDK4/6 activity and a number of such compounds have been disclosed in the art. However, in view of the number of pathological responses that are mediated by CDK4/6, there remains a continuing need for inhibitors of CDK4/6 which can be used in the treatment of a variety of conditions, including cancer.

SUMMARY OF THE INVENTION

The invention is directed to novel pyrrolopyrimidine compounds of formula (I)

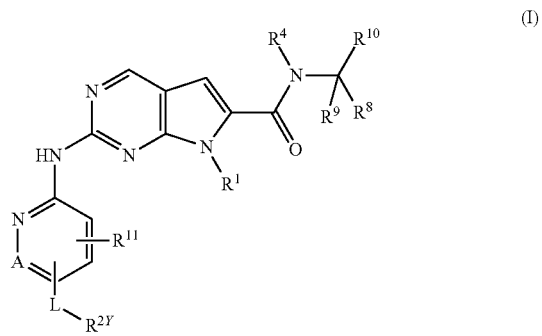

wherein $R^1$, $R^{2Y}$, $R^4$, $R^8$-$R^{11}$, A and L are defined herein and to salts, including pharmaceutically acceptable salts thereof.

The compounds of the present invention are CDK4/6 inhibitors and could be useful in the treatment of diseases and disorders mediated by CDK4/6, such as cancer, including mantle cell lymphoma, liposarcoma, non small cell lung cancer, melanoma, squamous cell esophageal cancer and breast cancer. The invention is further directed to pharmaceutical compositions comprising a compound of the invention. The invention is still further directed to methods of inhibiting CDK4/6 activity and to the treatment of disorders associated therewith using a compound of the invention or a pharmaceutical composition comprising a compound of the invention.

DETAILED DESCRIPTION OF THE INVENTION

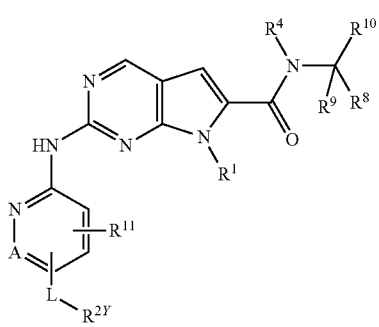

(I)

wherein:

$R^1$ is $C_{3-7}$ alkyl; $C_{4-7}$ cycloalkyl optionally substituted with one substituent selected from the group consisting of $C_{1-6}$ alkyl and OH; phenyl optionally substituted with one substitutent selected from the group consisting of $C_{1-6}$ alkyl, $C(CH_3)_2CN$, and OH; piperidinyl optionally substituted with one substituent selected from the group consisting of cyclopropyl and $C_{1-6}$ alkyl; tetrahydropyranyl optionally substituted with one substituent selected from the group consisting of cyclopropyl and $C_{1-6}$ alkyl; or bicyclo[2.2.1]heptanyl;

A is CH or N;

$R^{11}$ is hydrogen or $C_{1-4}$ alkyl;

L is a bond, C(O), or $S(O)_2$;

$R^{2Y}$ is

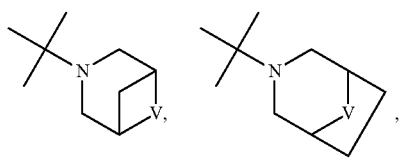

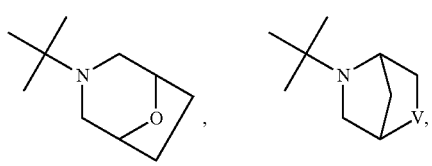

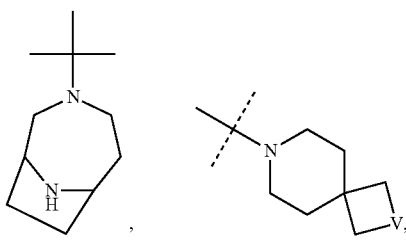

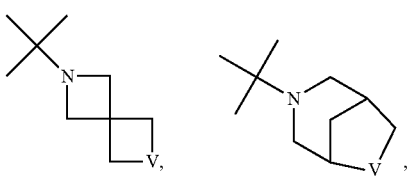

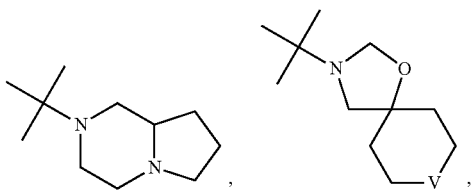

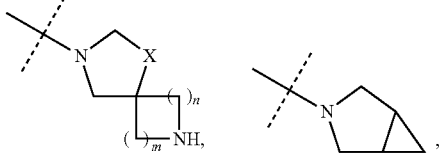

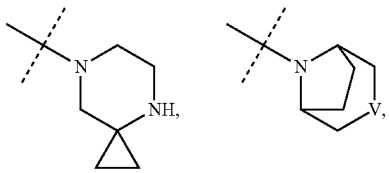

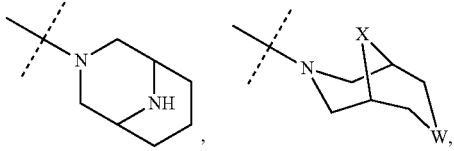

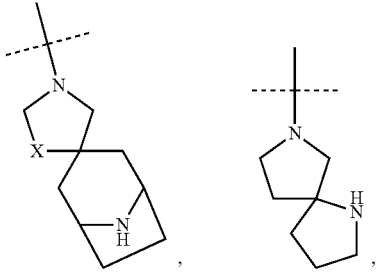

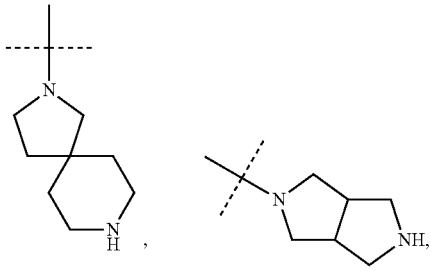

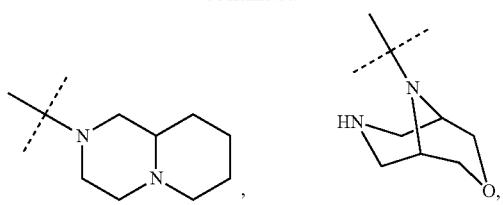

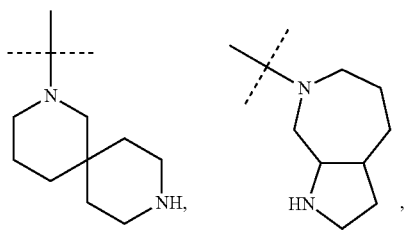

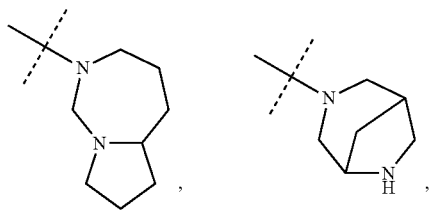

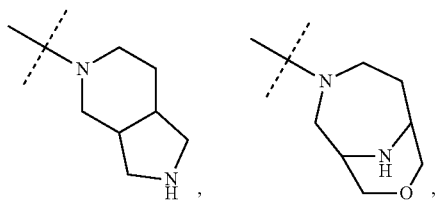

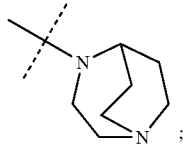

or

V is NH or CH$_2$;
X is O or CH$_2$;
W is O or NH;
m and n are each independently 1, 2, or 3 provided that m and n are not both 3;
each R$^{2Y}$ is optionally substituted with one to four substituents each independently selected from the group consisting of: C$_{1-3}$ alkyl optionally substituted with one or two substituents each independently selected from the group consisting of hydroxy, NH$_2$, and —S—C$_{1-3}$ alkyl; CD$_3$; halo; oxo; C$_{1-3}$ haloalkyl; hydroxy; NH$_2$; dimethylamino; benzyl; —C(O)—C$_{1-3}$alkyl optionally substituted with one or two substituents each independently selected from the group consisting of NH$_2$, —SCH$_3$ and NHC(O)CH$_3$; —S(O)$_2$—C$_{1-4}$alkyl; pyrrolidinyl-C(O)—; and —C(O)$_2$—C$_{1-3}$alkyl;

R$^4$ is hydrogen, deuterium, or C(R$^5$)(R$^6$)(R$^7$); and
R$^5$, R$^6$, R$^7$, R$^8$, R$^9$ and R$^{10}$ are each independently H or deuterium.

One embodiment of the present invention is a compound according to formula (I-B)

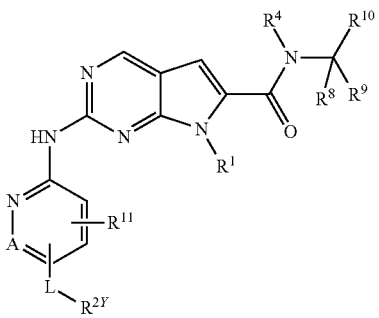

(I-B)

wherein
L is a bond or C(O);
R$^{2Y}$ is

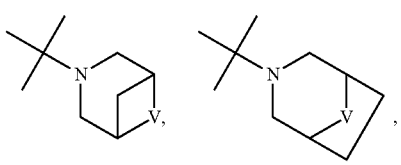

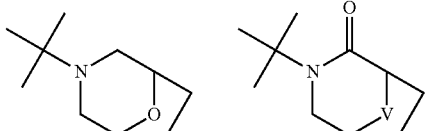

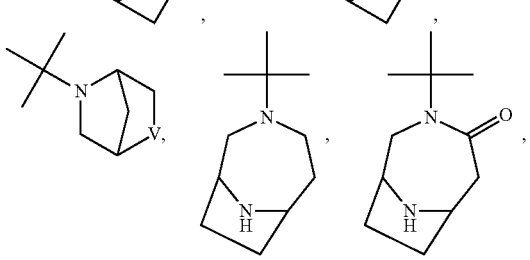

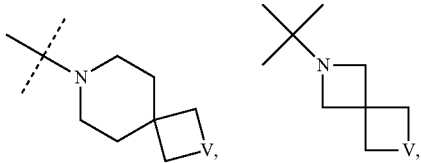

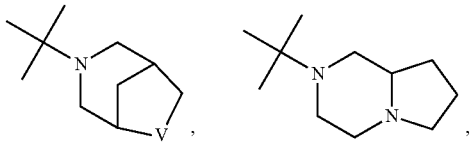

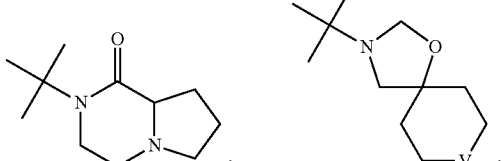

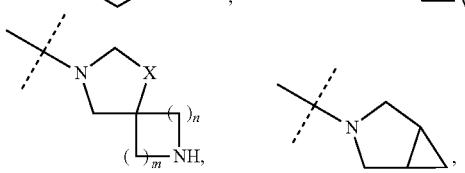

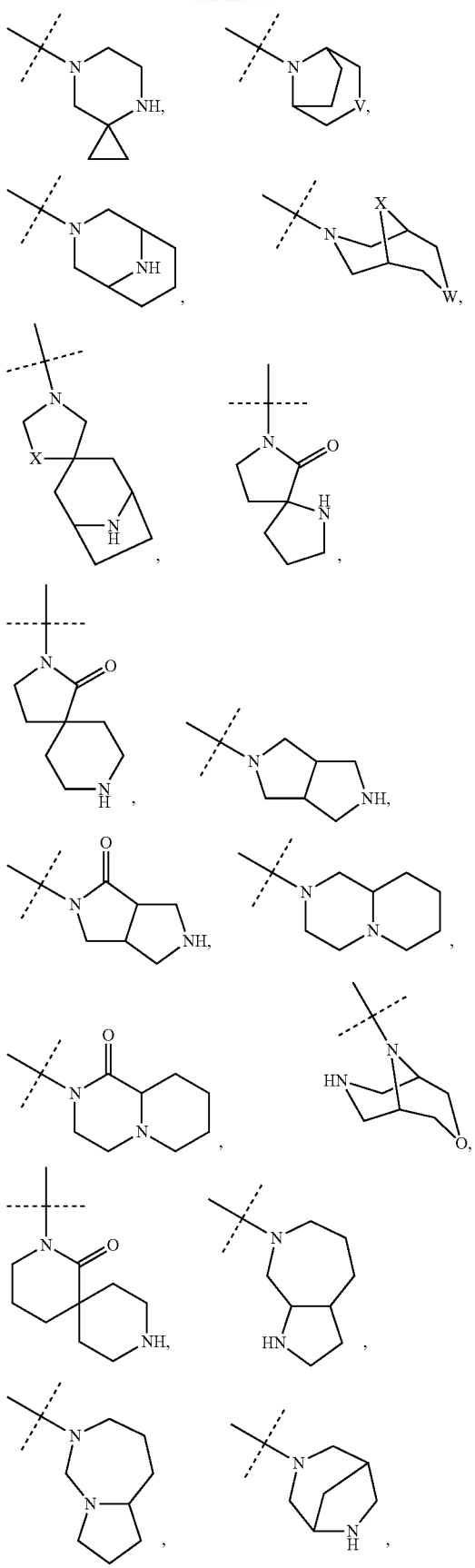
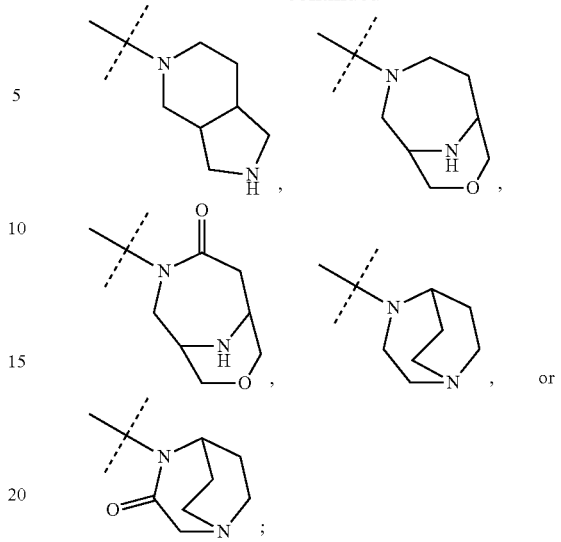

V is NH or CH$_2$;
X is O or CH$_2$;
W is O or NH;
m and n are each independently 1, 2, or 3 provided that m and n are not both 3;
each R$^{2Y}$ is optionally substituted with one to four substituents each independently selected from the group consisting of: C$_{1-3}$ alkyl optionally substituted with one or two substituents each independently selected from the group consisting of hydroxy, NH$_2$, and —S—C$_{1-3}$ alkyl; CD$_3$; C$_{1-3}$ haloalkyl; hydroxy; NH$_2$; dimethylamino; benzyl; —C(O)—C$_{1-3}$alkyl optionally substituted with one or two substituents each independently selected from the group consisting of NH$_{2'}$, —SCH$_3$ and NHC(O)CH$_3$; —S(O)$_2$—C$_{1-4}$alkyl; pyrrolidinyl-C(O)—; and —C(O)$_2$—C$_{1-3}$alkyl; and R$^1$, R$^4$-R$^{11}$, and A are as defined in formula (I) above.

Another embodiment of the present invention is a compound according to formula (I-C)

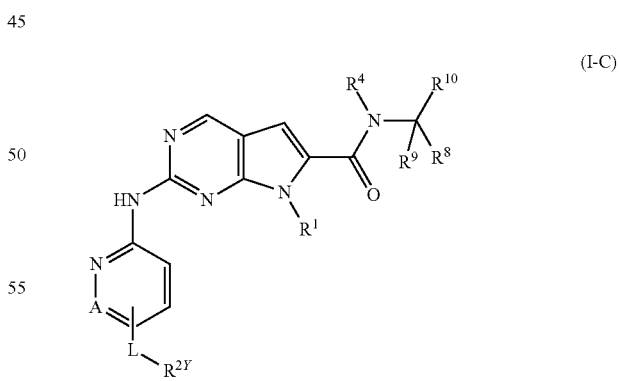

wherein:
R$^1$ is cyclobutyl, cyclopentyl, cyclohexyl, cycloheptyl, each of which is optionally substituted with one of methyl, ethyl, or OH;
A is CH or N;
L is a bond, —C(O)—, or S(O)$_2$—;

$R^{2Y}$ is

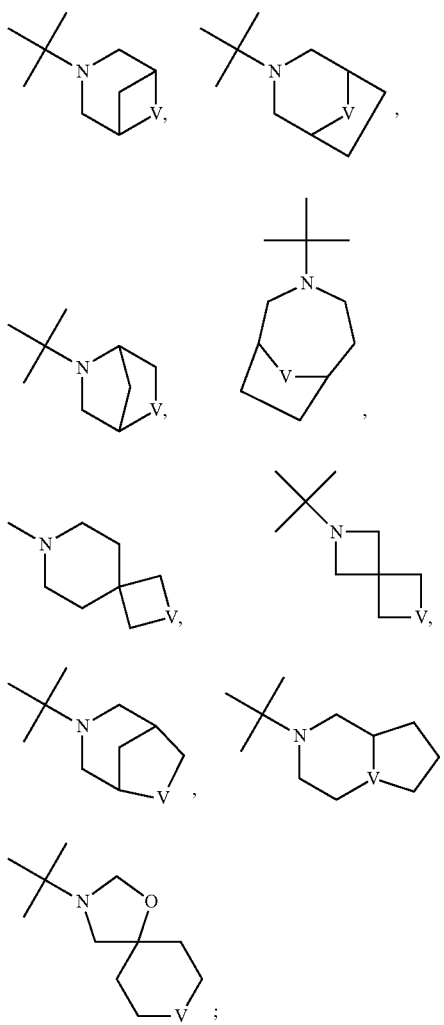

wherein each $R^{2Y}$ is optionally substituted with one or two substituents independently selected from halogen, methyl, ethyl, or oxo;

V is NH or $CH_2$; $R^4$ is hydrogen, deuterium, or $C(R^5)(R^6)(R^7)$; and $R^5, R^6, R^7, R^8, R^9$ and $R^{10}$ are each independently H or deuterium.

In one embodiment of the present invention L is a bond. In another embodiment L is C(O).

In one embodiment A is CH. In another embodiment A is N. Preferably A is CH.

Preferably $R^{11}$ is hydrogen or methyl. Hydrogen is most preferred.

Preferably $R^4$ is $C(R^5)(R^6)(R^7)$ and $R^5, R^6, R^7, R^8, R^9$ and $R^{10}$ are hydrogen.

Preferably $R^1$ is $C_{4-7}$ cycloalkyl optionally substituted with one $C_{1-6}$ alkyl. In a more preferred embodiment $R^1$ is optionally substituted cyclobutyl, cyclopentyl, cyclohexyl, and cycloheptyl. Cyclopentyl is most preferred. Unsubstituted cyclobutyl, cyclopentyl, cyclohexyl, and cycloheptyl are also preferred.

In another embodiment of the invention $R^{2Y}$ is:

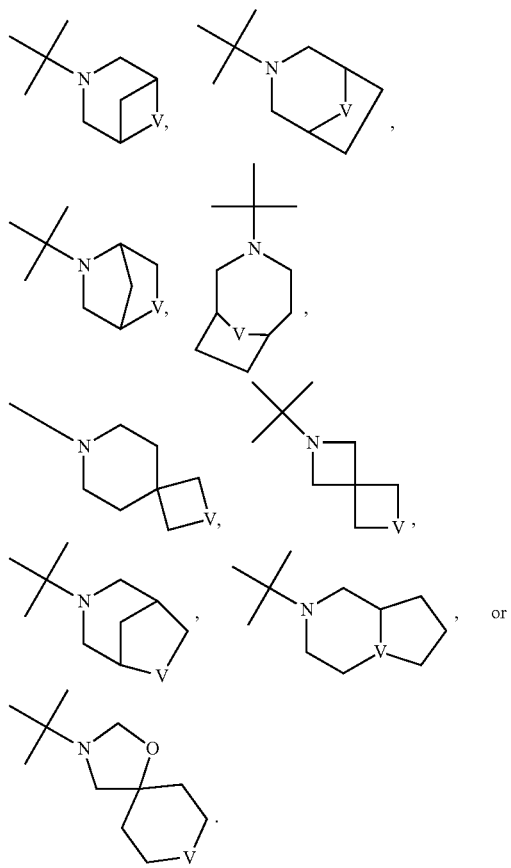

In another embodiment $R^{2Y}$ is:

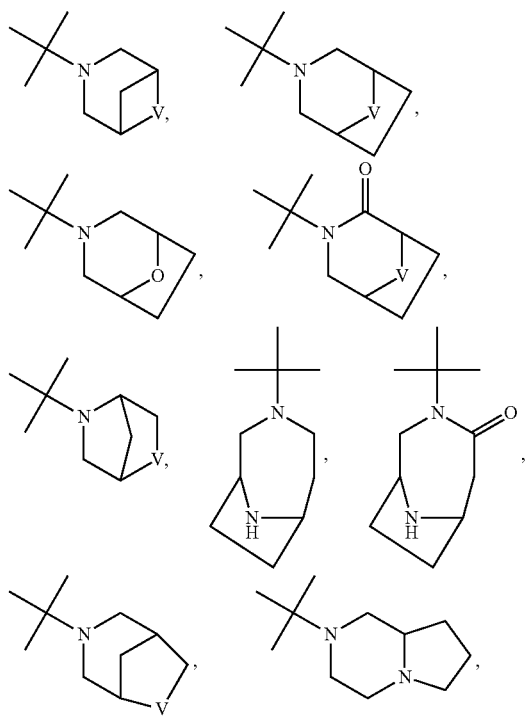

-continued
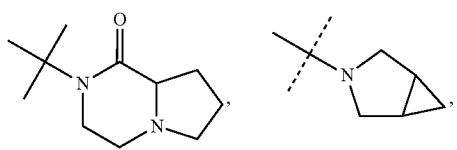
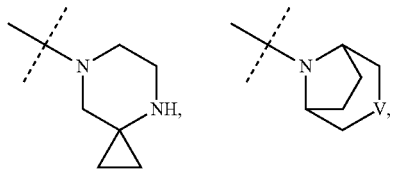
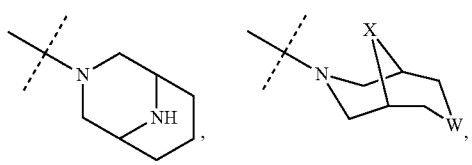
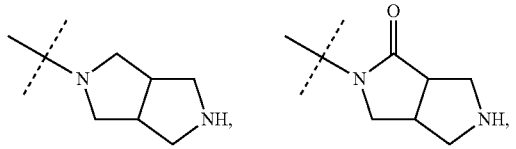
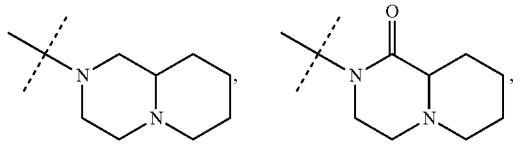
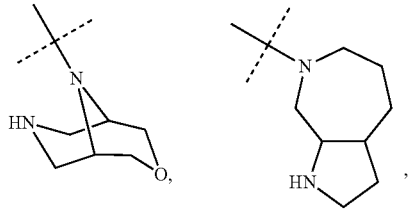
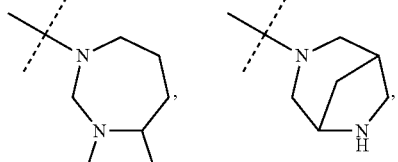
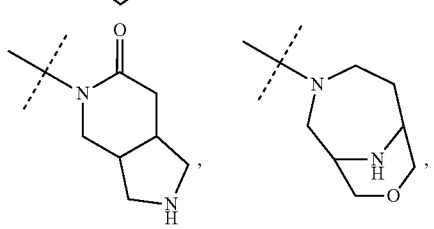
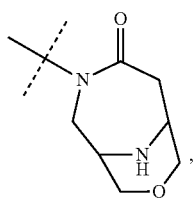
-continued
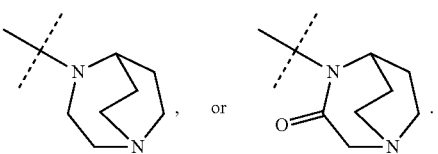
In another embodiment $R^{2Y}$ is:
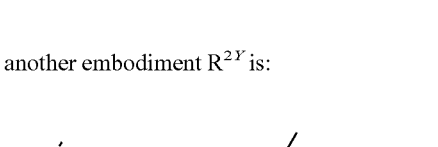
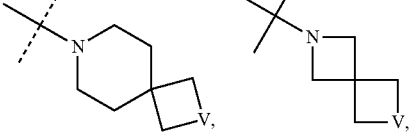
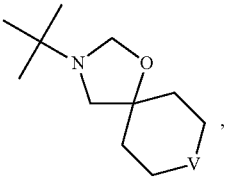
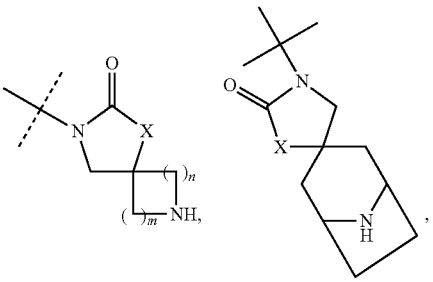
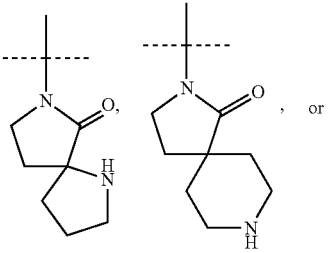
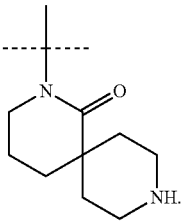
In another embodiment $R^{2Y}$ is
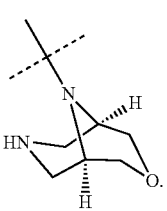

In another embodiment $R^{2Y}$ is

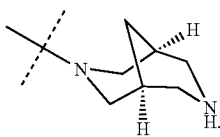

In another embodiment $R^{2Y}$ is

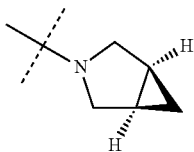 or 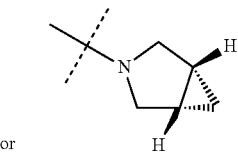.

In another embodiment $R^{2Y}$ is

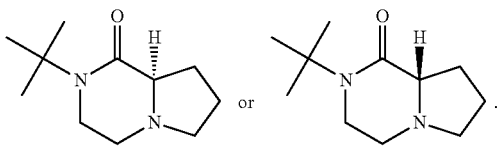 or 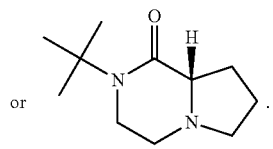.

In another embodiment $R^{2Y}$ is

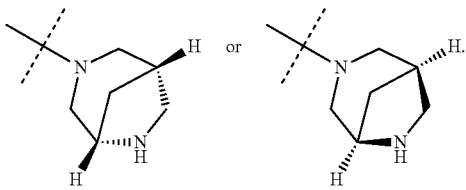 or 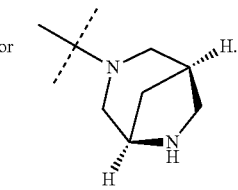.

In a preferred embodiment $R^{2Y}$ is

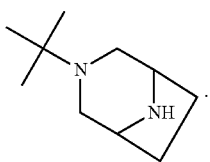.

In a preferred embodiment $R^{2Y}$ is

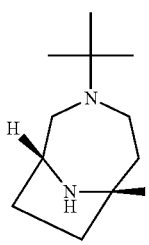 or 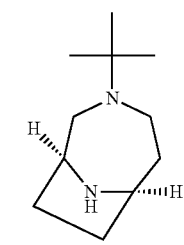

optionally substituted with one $C_{1-3}$alkyl.

In a preferred embodiment $R^{2Y}$ is

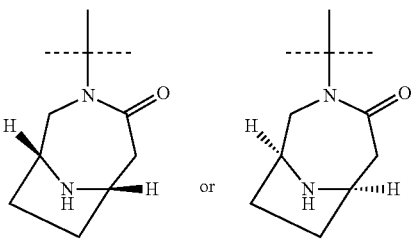

optionally substituted with one $C_{1-3}$alkyl.

In a preferred embodiment $R^{2Y}$ is

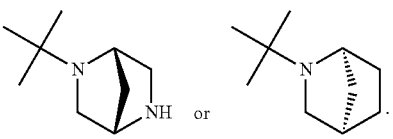.

In a preferred embodiment $R^{2Y}$ is

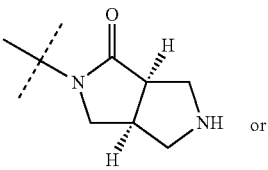

optionally substituted with one $C_{1-3}$alkyl.

In a preferred embodiment $R^{2Y}$ is

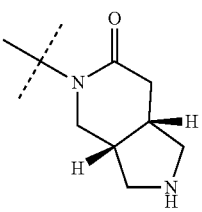

optionally substituted with one $C_{1-3}$alkyl.

In a preferred embodiment $R^{2Y}$ is

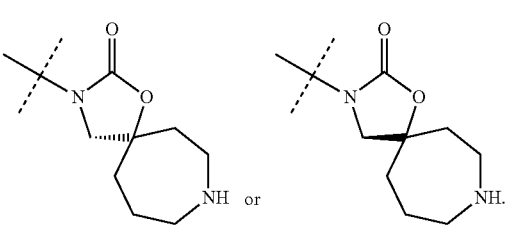

In a preferred embodiment $R^{2Y}$ is

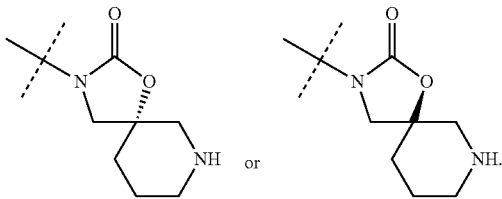

or

Preferably $R^{2Y}$ is unsubstituted.

Specific compounds of the present invention include:

Cyclopentyl-2-(5-(9-hydroxy-1,5,7-trimethyl-3,7-diazabicyclo[3.3.1]nonane-3-carbonyl)pyridin-2-ylamino)-N,N-dimethyl-7H-pyrrolo[2,3-d]pyrimidine-6-carboxamide;

2-(6-(2,6-Diazaspiro[3.3]heptane-2-carbonyl)pyridin-2-ylamino)-7-cyclopentyl-N,N-dimethyl-7H-pyrrolo[2,3-d]pyrimidine-6-carboxamide;

7-(4-tert-Butyl-phenyl)-2-[5-(3,8-diaza-bicyclo[3.2.1]octane-3-carbonyl)-pyridin-2-ylamino]-7H-pyrrolo[2,3-d]pyrimidine-6-carboxylic acid dimethylamide;

7-Cyclopentyl-2-[5-(4-oxo-3,9-diaza-bicyclo[4.2.1]non-3-yl)-pyridin-2-ylamino]-7H-pyrrolo[2,3-d]pyrimidine-6-carboxylic acid dimethylamide;

7-Cyclopentyl-2-[5-((1R,6S)-4-oxo-3,9-diaza-bicyclo[4.2.1]non-3-yl)-pyridin-2-ylamino]-7H-pyrrolo[2,3-d]pyrimidine-6-carboxylic acid dimethylamide;

7-Cyclopentyl-2-[5-(3,8-diaza-bicyclo[3.2.1]octane-3-carbonyl)-pyridin-2-ylamino]-7H-pyrrolo[2,3-d]pyrimidine-6-carboxylic acid dimethylamide;

7-Cycloheptyl-2-[5-(2,5-diaza-bicyclo[2.2.1]heptane-2-carbonyl)-pyridin-2-ylamino]-7H-pyrrolo[2,3-d]pyrimidine-6-carboxylic acid dimethylamide;

7-Cyclopentyl-2-[5-(3,8-diaza-bicyclo[3.2.1]octane-8-carbonyl)-pyridin-2-ylamino]-7H-pyrrolo[2,3-d]pyrimidine-6-carboxylic acid dimethylamide;

2-(5-(2,7-diazaspiro[3.5]nonane-7-carbonyl)pyridin-2-ylamino)-7-cycloheptyl-N,N-dimethyl-7H-pyrrolo[2,3-d]pyrimidine-6-carboxamide;

7-cyclopentyl-2-[5-(8-methyl-3,8-diaza-bicyclo[3.2.1]octane-3-carbonyl)-pyridin-2-ylamino]-7H-pyrrolo[2,3-d]pyrimidine-6-carboxylic acid dimethylamide;

7-Cyclopentyl-2-[5-((S,S)-2,5-diaza-bicyclo[2.2.1]heptane-2-carbonyl)-pyridin-2-ylamino]-7H-pyrrolo[2,3-d]pyrimidine-6-carboxylic acid methylamide;

7-(3-tert-Butyl-phenyl)-2-[5-(3,8-diaza-bicyclo[3.2.1]octane-3-carbonyl)-pyridin-2-ylamino]-7H-pyrrolo[2,3-d]pyrimidine-6-carboxylic acid dimethylamide;

2-(5-((1R,5S)-3-oxa-7,9-diazabicyclo[3.3.1]nonane-9-carbonyl)pyridin-2-ylamino)-7-cyclopentyl-N,N-dimethyl-7H-pyrrolo[2,3-d]pyrimidine-6-carboxamide;

7-[4-(Cyano-dimethyl-methyl)-phenyl]-2-[5-(3,8-diaza-bicyclo[3.2.1]octane-8-carbonyl)-pyridin-2-ylamino]-7H-pyrrolo[2,3-d]pyrimidine-6-carboxylic acid dimethylamide;

7-Cyclopentyl-2-[5-((1S,6R)-3,9-diaza-bicyclo[4.2.1]nonane-3-carbonyl)-pyridin-2-ylamino]-7H-pyrrolo[2,3-d]pyrimidine-6-carboxylic acid dimethylamide;

7-Cyclopentyl-2-[5-((1R,6S)-3,9-diaza-bicyclo[4.2.1]nonane-3-carbonyl)-pyridin-2-ylamino]-7H-pyrrolo[2,3-d]pyrimidine-6-carboxylic acid dimethylamide;

7-Cyclopentyl-2-[5-(3,6-diaza-bicyclo[3.2.1]octane-3-carbonyl)-pyridin-2-ylamino]-7H-pyrrolo[2,3-d]pyrimidine-6-carboxylic acid dimethylamide;

7-Cyclopentyl-2-[5-(hexahydro-pyrrolo[1,2-a]pyrazine-2-carbonyl)-pyridin-2-ylamino]-7H-pyrrolo[2,3-d]pyrimidine-6-carboxylic acid dimethylamide;

7-cyclopentyl-N,N-dimethyl-2-(5-(5'-oxo-8-azaspiro[bicyclo[3.2.1]octane-3,3'-pyrrolidine]-1'-yl)pyridin-2-ylamino)-7H-pyrrolo[2,3-d]pyrimidine-6-carboxamide;

7-Cyclopentyl-2[5-(1-oxo-hexahydro-pyrrolo[1,2-a]pyrazin-2-yl)-pyridin-2-ylamino]-7H-pyrrolo[2,3-d]pyrimidine-6-carboxylic acid dimethylamide;

7-cyclopentyl-N,N-dimethyl-2-(5-(2-oxo-1-oxa-3,8-diazaspiro[4.5]decan-3-yl)pyridin-2-ylamino)-7H-pyrrolo[2,3-d]pyrimidine-6-carboxamide;

7-Cyclopentyl-2-[5-((1S,6R)-4-oxo-3,9-diaza-bicyclo[4.2.1]non-3-yl)-pyridin-2-ylamino]-7H-pyrrolo[2,3-d]pyrimidine-6-carboxylic acid dimethylamide;

2-[5-(4-Oxo-3,9-diaza-bicyclo[4.2.1]non-3-yl)-pyridin-2-ylamino]-7-phenyl-7H-pyrrolo[2,3-d]pyrimidine-6-carboxylic acid dimethylamide; and 7-cyclohexyl-N,N-dimethyl-2-(5-(4-oxo-3,9-diazabicyclo[4.2.1]nonan-3-yl)pyridin-2-ylamino)-7H-pyrrolo[2,3-d]pyrimidine-6-carboxamide.

Preferred compounds of the present invention include compounds selected from the group consisting of:

7-Cyclopentyl-2-[5-(3,8-diaza-bicyclo[3.2.1]octane-3-carbonyl)-pyridin-2-ylamino]-7H-pyrrolo[2,3-d]pyrimidine-6-carboxylic acid dimethylamide 7-Cyclopentyl-2-[5-((S,S)-2,5-diaza-bicyclo[2.2.1]heptane-2-carbonyl)-pyridin-2-ylamino]-7H-pyrrolo[2,3-d]pyrimidine-6-carboxylic acid dimethylamide 7-Cyclopentyl-2-[5-((1R,6S)-4-oxo-3,9-diaza-bicyclo[4.2.1]non-3-yl)-pyridin-2-ylamino]-7H-pyrrolo[2,3-d]pyrimidine-6-carboxylic acid dimethylamide 7-Cyclopentyl-2-[5-((1S,5S)-3,6-diaza-bicyclo[3.2.1]octane-3-carbonyl)-pyridin-2-ylamino]-7H-pyrrolo[2,3-d]pyrimidine-6-carboxylic acid dimethylamide;

7-Cyclobutyl-2-[5-((1S,6R)-4-oxo-3,9-diaza-bicyclo[4.2.1]non-3-yl)-pyridin-2-ylamino]-7H-pyrrolo[2,3-d]pyrimidine-6-carboxylic acid dimethylamide 7-Cyclohexyl-2-[5-((1R,6S)-4-oxo-3,9-diaza-bicyclo[4.2.1]non-3-yl)-pyridin-2-ylamino]-7H-pyrrolo[2,3-d]pyrimidine-6-carboxylic acid dimethylamide 7-Cyclopentyl-2-[5-(3,8-diaza-bicyclo[3.2.1]octane-3-carbonyl)-6-methyl-pyridin-2-ylamino]-7H-pyrrolo[2,3-d]pyrimidine-6-carboxylic acid dimethylamide;

7-Cyclopentyl-2-[5-(3,8-diaza-bicyclo[3.2.1]octane-3-carbonyl)-4-methyl-pyridin-2-ylamino]-7H-pyrrolo[2,3-d]pyrimidine-6-carboxylic acid dimethylamide;

7-Cyclopentyl-2-[5-(3,9-diaza-bicyclo[3.3.1]nonane-3-carbonyl)-pyridin-2-ylamino]-7H-pyrrolo[2,3-d]pyrimidine-6-carboxylic acid dimethylamide;

7-cyclopentyl-N,N-dimethyl-2-(5-(3-oxo-1,4-diazabicyclo[3.2.2]nonan-4-yl)pyridin-2-ylamino)-7H-pyrrolo[2,3-d]pyrimidine-6-carboxamide; and 7-cyclopentyl-N,N-dimethyl-2-(5-((1R,6S)-9-methyl-4-oxo-3,9-diazabicyclo[4.2.1]nonan-3-yl)pyridin-2-ylamino)-7H-pyrrolo[2,3-d]pyrimidine-6-carboxamide.

Preferred compounds of the present invention include compounds selected from the group consisting of:

7-cyclopentyl-N,N-dimethyl-2-(5-((3aS,6aR)-1-oxohexahydropyrrolo[3,4-c]pyrrol-2(1H)-yl)pyridin-2-ylamino)-7H-pyrrolo[2,3-d]pyrimidine-6-carboxamide;

7-cyclopentyl-N,N-dimethyl-2-(5-((3aR,6aS)-1-oxohexahydropyrrolo[3,4-c]pyrrol-2(1H)-yl)pyridin-2-ylamino)-7H-pyrrolo[2,3-d]pyrimidine-6-carboxamide;

7-cycloheptyl-N,N-dimethyl-2-(5-(cis-6-oxotetrahydro-1H-pyrrolo[3,4-c]pyridin-5(6H,7H,7aH)-yl)pyridin-2-ylamino)-7H-pyrrolo[2,3-d]pyrimidine-6-carboxamide;

7-cyclopentyl-N,N-dimethyl-2-(5-(cis-6-oxotetrahydro-1H-pyrrolo[3,4-c]pyridin-5(6H,7H,7aH)-yl)pyridin-2-ylamino)-7H-pyrrolo[2,3-d]pyrimidine-6-carboxamide;

7-cyclopentyl-N,N-dimethyl-2-(5-(cis-6-oxotetrahydro-1H-pyrrolo[3,4-c]pyridin-5(6H,7H,7aH)-yl)pyridin-2-ylamino)-7H-pyrrolo[2,3-d]pyrimidine-6-carboxamide; and 7-cyclopentyl-N,N-dimethyl-2-(5-((3aR,6aS)-5-methyl-1-oxohexahydropyrrolo[3,4-c]pyrrol-2(1H)-yl)pyridin-2-ylamino)-7H-pyrrolo[2,3-d]pyrimidine-6-carboxamide.

Preferred compounds of the present invention include compounds selected from the group consisting of:

7-cyclopentyl-N,N-dimethyl-2-(5-((1R,3r,5S)-2'-oxo-8-azaspiro[bicyclo[3.2.1]octane-3,5'-oxazolidine]-3'-yl)pyridin-2-ylamino)-7H-pyrrolo[2,3-d]pyrimidine-6-carboxamide;

7-cyclopentyl-N,N-dimethyl-2-(5-(2-oxo-1-oxa-3,8-diazaspiro[4.6]undecan-3-yl)pyridin-2-ylamino)-7H-pyrrolo[2,3-d]pyrimidine-6-carboxamide;

7-cyclopentyl-N,N-dimethyl-2-(5-(2-oxo-1-oxa-3,7-diazaspiro[4.5]decan-3-yl)pyridin-2-ylamino)-7H-pyrrolo[2,3-d]pyrimidine-6-carboxamide;

7-Cyclopentyl-2-[5-((S)-2-oxo-1-oxa-3,7-diaza-spiro[4.5]dec-3-yl)-pyridin-2-ylamino]-7H-pyrrolo[2,3-d]pyrimidine-6-carboxylic acid dimethylamide; and 7-Cyclopentyl-2-[5-((R)-2-oxo-1-oxa-3,7-diaza-spiro[4.5]dec-3-yl)-pyridin-2-ylamino]-7H-pyrrolo[2,3-d]pyrimidine-6-carboxylic acid dimethylamide.

TERMS AND DEFINITIONS

As used herein, the term "alkyl" refers to a fully saturated branched or unbranched hydrocarbon moiety having 1 to 6 carbon atoms ($C_{1-6}$ alkyl), 3 to 7 carbon atoms ($C_{3-7}$ alkyl), 1 to 4 carbon atoms ($C_{1-4}$ alkyl), or 1 to 3 carbon atoms ($C_{1-3}$ alkyl). Representative examples of alkyl include, but are not limited to, methyl, ethyl, n-propyl, i-propyl, n-butyl, i-butyl, s-butyl, t-butyl, n-pentyl, 1-methylbutyl, 2-methylbutyl, 3-methylbutyl, 3,3-dimethylpropyl, hexyl, 2-methylpentyl, and the like.

As used herein, the term "cycloalkyl" refers to nonaromatic carbocyclic rings that are either partially or fully hydrogenated and may exist as a single ring, bicyclic ring, tricyclic ring, or a spiral ring. Unless specified otherwise, cycloalkyl refers to cyclic hydrocarbon groups of 3-14 carbon atoms. Cycloalkyl groups also refer to cyclic hydrocarbon groups having between 3 to 9 ring carbon atoms, or between 4 and 7 ring carbon atoms Exemplary monocyclic hydrocarbon groups include, but are not limited to, cyclopropyl, cyclobutyl, cyclopentyl, cyclopentenyl, cyclohexyl, cyclohexenyl, cycloheptyl and the like. Exemplary bicyclic hydrocarbon groups include bornyl, indyl, hexahydroindyl, tetrahydronaphthyl, decahydronaphthyl, bicyclo[2.1.1]hexyl, bicyclo[2.2.1]heptyl, bicyclo[2.2.1]heptenyl, 6,6-dimethylbicyclo[3.1.1]heptyl, 2,6,6-trimethylbicyclo[3.1.1]heptyl, bicyclo[2.2.2]octyl and the like. Exemplary tricyclic hydrocarbon groups include adamantyl and the like.

"Deuterium", or "D", or "d" refers to an isotope of hydrogen whose nucleus contains one proton and one neutron. When a particular position is designated as having deuterium, it is understood that the abundance of deuterium at that position is greater than the natural abundance of deuterium (typically 0.015%). Unless otherwise stated, when a position is designated specifically as "D" or "deuterium", the position is understood to have deuterium at an abundance that is greater than the natural abundance of deuterium.

As used herein, the term "halogen" or "halo" refers to fluoro, chloro, bromo, and Iodo.

As used herein, the term "haloalkyl" refers to an alkyl group wherein at least one hydrogen atom attached to a carbon atom of the alkyl group is replaced with halo, preferably fluoro. Examples of haloalkyl groups include mono-, di-, and tri-fluoromethyl, mono-, di-, and tri-chloromethyl, mono-, di-, tri-, tetra, and penta-fluoroethyl, and mono-, di-, tri-, tetra-, and penta-chloroethyl.

As used herein, the term "optionally substituted" indicates that a group such as alkyl, cyclalkyl, or a specific R group may be unsubstituted or substituted with one or more substituents as defined herein. The term "substituted" in reference to a group indicates that a hydrogen atom attached to an atom within the group is replaced. It would be understood that the term "substituted" includes the implicit provision that such substitution be in accordance with the permitted valance of the substituted atom and the substituent; and that the substitution results in a stable compound (i.e. one that does not spontaneously undergo transformations such as by rearrangement, cyclization, or elimination. In certain embodiments, a single atom may be substituted with more than one substituent so long as such substitution is in accordance with the permitted valance of the atom. Suitable substituents are defined herein for each substituted or optionally substituted group.

The term "compounds of the present invention" (unless specifically identified otherwise) refer to compounds of Formula (I) and salts thereof, including pharmaceutically acceptable salts of the compounds, as well as, all stereoisomers (including diastereoisomers and enantiomers), tautomers and isotopically labeled compounds. Solvates and hydrates are generally considered pharmaceutical compositions of the compounds of the present invention.

As used herein the symbols and conventions used in these processes, schemes, and examples are consistent with those used in the contemporary scientific literature, for example the *Journal of the American Chemical Society* or the *Journal of Biological Chemistry*. Unless otherwise noted, all starting materials were obtained from commercial suppliers and used without further purification. Specifically the following abbreviations may be used in the examples and throughout the specification.

ACN acetonitrile
AcOH acetic acid
aq. aqueous
BnBr benzylbromide
boc tert-butoxycarbonyl
C Celsius
cat. catalytic
CDI cabonyldiimidazole
CSA camphorsulfonic acid
conc. concentrated
$Cs_2CO_3$ cesium carbonate
Da Daltons
deg degrees
DIBAL, DIBAL-H diisobutylaluminum hydride
DIPEA diisopropylethylamine
DIPC N,N'-diisopropylcarbodiimide
DMF N, N-dimethylformamide
DMI 1,3 dimethyl-2-imidazolidinone
DMP Dess-Martin periodinane
DCC N,N-dicyclohexylcarbodiimide
DCE dichloroethane
DCM dichloromethane
DMAP 4-dimethylaminopyridine
DMSO dimethylsulfoxide EtOAc ethyl acetate
EtOH ethanol
eq equivalents
g gas
h hours
HATU O-(7-azabenzotriazol-1-yl)-N,N,N',N'-tetramethyluronium hexafluorophosphate
HMPA hexamethylphosphoramide
hep heptane
HCl hydrochloric acid
inh. inhibition
imid. Imidazole
K Kelvin
KHMDS potassium hexamethyldisilylazide
$K_2CO_3$ potassium carbonate
LDA lithiumdiisopropylamine
$LiBH_4$ lithium borohydride
LHMDS lithiumhexamethyldisilylazide
LC liquid chromatography
LC/MS liquid chromatography mass spectrum
M molar
MeCN acetonitrile
MeOH methanol
$MgSO_4$ magnesium sulfate
MHz megahertz
min minutes
mol. sieves molecular sieves
$NaBH_4$ sodium borohydride
N normal
NMR nuclear magnetic resonance
Pd/C palladium on carbon
PEG(750) O-(2-aminoethyl)-O'-methyl polyethylene glycol 750; $NH_2(CH_2CH_2O)_nCH_3$;
CAS# [80506-64-5]; Fluka 07964; AVERAGE MW=750
PS polystyrene
Py pyridine
PPM parts per million
RP reverse phase
RT room temperature
$R_t$ retention time
s solid
satd. saturated
TBS tert-butyldimethylsilyl
TMS trimethylsilyl
TBAF tetrabutylammonium fluoride
TBTU O-benzotriazol-1-yl-N,N, N,N'-tetramethyluronium tetrafluoroborate
TLC thin-layer chromatography
TEA triethylamine
TFA trifluoroacetic acid
THF tetrahydrofuran
h hours
min minutes
m/z mass to charge
MS mass spectrum
NMR nuclear magnetic resonance The skilled artisan will appreciate that salts, including pharmaceutically acceptable salts of the compounds of formula (I) may be prepared. As used herein, the terms "salt" or "salts" refers to an acid addition or base addition salt of a compound of the invention. The term "pharmaceutically acceptable salts" refers to salts that retain the biological effectiveness and properties of the compounds of this invention and, which typically are not biologically or otherwise undesirable. Accordingly the invention is further directed to salts, preferably pharmaceutically acceptable salts, of the compounds of formula (I).

Pharmaceutically acceptable acid addition salts can be formed with inorganic acids and organic acids, e.g., acetate, aspartate, benzoate, besylate, bromide/hydrobromide, bicarbonate/carbonate, bisulfate/sulfate, camphorsulfornate, chloride/hydrochloride, chlortheophyllonate, citrate, ethandisulfonate, fumarate, gluceptate, gluconate, glucuronate, hippurate, hydroiodide/iodide, isethionate, lactate, lactobionate, laurylsulfate, malate, maleate, malonate, mandelate, mesylate, methylsulphate, naphthoate, napsylate, nicotinate, nitrate, octadecanoate, oleate, oxalate, palmitate, pamoate, phosphate/hydrogen phosphate/dihydrogen phosphate, polygalacturonate, propionate, stearate, succinate, sulfosalicylate, tartrate, tosylate and trifluoroacetate salts.

Inorganic acids from which salts can be derived include, for example, hydrochloric acid, hydrobromic acid, sulfuric acid, nitric acid, phosphoric acid, and the like.

Organic acids from which salts can be derived include, for example, acetic acid, propionic acid, glycolic acid, oxalic acid, maleic acid, malonic acid, succinic acid, fumaric acid, tartaric acid, citric acid, benzoic acid, mandelic acid, methanesulfonic acid, ethanesulfonic acid, toluenesulfonic acid, sulfosalicylic acid, and the like.

Pharmaceutically acceptable base addition salts can be formed with inorganic and organic bases.

Inorganic bases from which salts can be derived include, for example, ammonium salts and metals from columns I to XII of the periodic table. In certain embodiments, the salts are derived from sodium, potassium, ammonium, calcium, magnesium, iron, silver, zinc, and copper; particularly suitable salts include ammonium, potassium, sodium, calcium and magnesium salts.

Organic bases from which salts can be derived include, for example, primary, secondary, and tertiary amines, substituted amines including naturally occurring substituted amines, cyclic amines, basic ion exchange resins, and the like. Certain organic amines include isopropylamine, benzathine, cholinate, diethanolamine, diethylamine, lysine, meglumine, piperazine and tromethamine.

The pharmaceutically acceptable salts of the present invention can be synthesized from a parent compound, a basic or acidic moiety, by conventional chemical methods. Generally, such salts can be prepared by reacting free acid forms of these compounds with a stoichiometric amount of the appropriate base (such as Na, Ca, Mg, or K hydroxide, carbonate, bicarbonate or the like), or by reacting free base forms of these compounds with a stoichiometric amount of the appropriate acid. Such reactions are typically carried out in water or in an organic solvent, or in a mixture of the two. Generally, use of non-aqueous media like ether, ethyl acetate, ethanol, isopropanol, or acetonitrile is desirable, where practicable. Lists of additional suitable salts can be found, e.g., in "Remington's Pharmaceutical Sciences", 20th ed., Mack Publishing Company, Easton, Pa., (1985); and in "Handbook of Pharmaceutical Salts: Properties, Selection, and Use" by Stahl and Wermuth (Wiley-VCH, Weinheim, Germany, 2002).

The compounds according to formula (I) may contain one or more asymmetric centers (also referred to as a chiral center) and may, therefore, exist as individual enantiomers, diastereomers, or other stereoisomeric forms, or as mixtures thereof. Chiral centers, such as chiral carbon atoms, may also be present in a substituent, such as an alkyl group. Where the stereochemistry of a chiral center present in formula (I), or in any chemical structure illustrated herein, is not specified, the structure is intended to encompass any stereoisomer or mixtures thereof. Thus, the compounds according to formula (I) containing one or more chiral centers may be used as racemic mixtures, enantiomerically enriched mixtures, or as enantiomerically pure individual stereoisomers.

As used herein, the term "isomers" refers to different compounds that have the same molecular formula but differ in arrangement and configuration of the atoms. Also as used herein, the term "an optical isomer" or "a stereoisomer" refers to any of the various stereo isomeric configurations which may exist for a given compound of the present invention and includes geometric isomers. It is understood that a substituent may be attached at a chiral center of a carbon atom. Therefore, the invention includes enantiomers, diastereomers or racemates of the compound. "Enantiomers" are a pair of stereoisomers that are non-superimposable mirror images of each other. A 1:1 mixture of a pair of enantiomers is a "racemic" mixture. The term is used to designate a racemic mixture where appropriate. "Diastereoisomers" are stereoisomers that have at least two asymmetric atoms, but which are not mirror-images of each other. The absolute stereochemistry is specified according to the Cahn-Ingold-Prelog R-S system. When a compound is a pure enantiomer the stereochemistry at each chiral carbon may be specified by either R or S. Stereochemistry can also be specified by using a heavy wedge-shaped bond or a hatched line, when the chemical structure of a compound or substituent is drawn. Resolved compounds whose absolute configuration is unknown can be designated (+) or (−) depending on the direction (dextro- or levorotatory) which they rotate plane polarized light at the wavelength of the sodium D line. Certain compounds described herein contain one or more asymmetric centers or axes and may thus give rise to enantiomers, diastereomers, and other stereoisomeric forms that may be defined, in terms of absolute stereochemistry, as (R)— or (S)—. The present invention is meant to include all such possible isomers, including racemic mixtures, optically pure forms and intermediate mixtures.

Optically active (R)- and (S)-isomers may be prepared using chiral synthons or chiral reagents, or resolved using conventional techniques. Any resulting racemates of final products or intermediates can be resolved into the optical antipodes by known methods, e.g., by separation of the diastereomeric salts thereof, obtained with an optically active acid or base, and liberating the optically active acidic or basic compound. In particular, a basic moiety may thus be employed to resolve the compounds of the present invention into their optical antipodes, e.g., by fractional crystallization of a salt formed with an optically active acid, e.g., tartaric acid, dibenzoyl tartaric acid, diacetyl tartaric acid, di-O,O'-p-toluoyl tartaric acid, mandelic acid, malic acid or camphor-10-sulfonic acid. Racemic products can also be resolved by chiral chromatography, e.g., high pressure liquid chromatography (HPLC) using a chiral adsorbent.

If a compound of the invention contains a double bond, the substituent may be E or Z configuration. If the compound contains a disubstituted cycloalkyl, the cycloalkyl substituent may have a cis- or trans-configuration. All tautomeric forms are also intended to be included.

Any asymmetric atom (e.g., carbon or the like) of the compound(s) of the present invention can be present in racemic or enantiomerically enriched, for example the (R)-, (S)- or (R,S)-configuration. In certain embodiments, each asymmetric atom has at least 50% enantiomeric excess, at least 60% enantiomeric excess, at least 70% enantiomeric excess, at least 80% enantiomeric excess, at least 90% enantiomeric excess, at least 95% enantiomeric excess, or at least 99% enantiomeric excess in the (R)- or (S)-configuration. Substituents at atoms with unsaturated bonds may, if possible, be present in cis-(Z)- or trans-(E)-form.

Any resulting mixtures of isomers can be separated on the basis of the physicochemical differences of the constituents, into the pure or substantially pure geometric or optical isomers, diastereomers, racemates, for example, by chromatography and/or fractional crystallization.

Substitution with heavier isotopes, particularly deuterium (i.e., $^2H$ or D) may afford certain therapeutic advantages resulting from greater metabolic stability, for example increased in vivo half-life or reduced dosage requirements or an improvement in therapeutic index. It is understood that deuterium in this context is regarded as a substituent of the compounds of the present invention. The concentration of such a heavier isotope, specifically deuterium, may be defined by the isotopic enrichment factor. The term "isotopic enrichment factor" as used herein means the ratio between the isotopic abundance and the natural abundance of a specified isotope. If a substituent in a compound of this invention is denoted deuterium, such compound has an isotopic enrichment factor for each designated deuterium atom of at least 3500 (52.5% deuterium incorporation at each designated deuterium atom), at least 4000 (60% deuterium incorporation), at least 4500 (67.5% deuterium incorporation), at least 5000 (75% deuterium incorporation), at least 5500 (82.5% deuterium incorporation), at least 6000 (90% deuterium incorporation), at least 6333.3 (95% deuterium incorporation), at least 6466.7 (97% deuterium incorporation), at least 6600 (99% deuterium incorporation), or at least 6633.3 (99.5% deuterium incorporation).

In addition to the deuterium-containing compounds presently exemplified, any formula given herein is also intended to represent unlabeled forms as well as isotopically labeled forms of the compounds. Isotopically labeled compounds have structures depicted by the formulas given herein except that one or more atoms are replaced by an atom having a selected atomic mass or mass number. Examples of isotopes that can be incorporated into compounds of the invention include isotopes of hydrogen, carbon, nitrogen, oxygen, phosphorous, fluorine, and chlorine, such as $^2H$, $^3H$, $^{11}C$, $^{13}C$, $^{14}C$, $^{15}N$, $^{18}F$, $^{31}P$, $^{32}P$, $^{35}S$, $^{38}Cl$, $^{125}I$ respectively. The invention includes various isotopically labeled compounds as defined herein, for example those into which radioactive isotopes, such as $^3H$, $^{13}C$, and $^{14}C$, are present. Such isotopically labeled compounds are useful in metabolic studies (with $^{14}C$), reaction kinetic studies (with, for example $^2H$ or $^3H$), detection or imaging techniques, such as positron emission tomography (PET) or single-photon emission computed tomography (SPECT) including drug or substrate tissue distribution assays, or in radioactive treatment of patients. In particular, an $^{18}F$ or labeled compound may be particularly desirable for PET or SPECT studies. Isotopically labeled compounds of this invention and prodrugs thereof can generally be prepared by carrying out the procedures disclosed in the schemes or in the examples and preparations described below by substituting a readily available isotopically labeled reagent for a non-isotopically labeled reagent.

Isotopically-labeled compounds of the present invention can generally be prepared by conventional techniques known to those skilled in the art or by processes analogous to those described in the accompanying Examples and Compound Preparations using an appropriate isotopically-labeled reagents in place of the non-labeled reagent previously employed.

Furthermore, the compounds of the present invention, including their salts, can also be obtained in the form of their hydrates, or include other solvents used for their crystallization. The compounds of the present invention may inherently or by design form solvates with pharmaceutically acceptable solvents (including water); therefore, it is intended that the invention embrace both solvated and unsolvated forms. The term "solvate" refers to a molecular complex of a compound of the present invention (including pharmaceutically acceptable salts thereof) with one or more solvent molecules. Such solvent molecules are those commonly used in the pharmaceutical art, which are known to be innocuous to the recipient, e.g., water, ethanol, and the like. The term "hydrate" refers to the complex where the solvent molecule is water. Moreover, pharmaceutically acceptable solvates in accordance with the invention include those wherein the solvent of crystallization may be isotopically substituted, e.g. $D_2O$, $d_6$-acetone, $d_6$-DMSO.

The present invention also provides pro-drugs of the compounds of the present invention that converts in vivo to the compounds of the present invention. A pro-drug is an active or inactive compound that is modified chemically through in vivo physiological action, such as hydrolysis, metabolism and the like, into a compound of this invention following administration of the prodrug to a subject. The suitability and techniques involved in making and using pro-drugs are well known by those skilled in the art. Prodrugs can be conceptually divided into two non-exclusive categories, bioprecursor prodrugs and carrier prodrugs. See *The Practice of Medicinal Chemistry*, Ch. 31-32 (Ed. Wermuth, Academic Press, San Diego, Calif., 2001). Generally, bioprecursor prodrugs are compounds, which are inactive or have low activity compared to the corresponding active drug compound, that contain one or more protective groups and are converted to an active form by metabolism or solvolysis. Both the active drug form and any released metabolic products should have acceptably low toxicity.

Carrier prodrugs are drug compounds that contain a transport moiety, e.g., that improve uptake and/or localized delivery to a site(s) of action. Desirably for such a carrier prodrug, the linkage between the drug moiety and the transport moiety is a covalent bond, the prodrug is inactive or less active than the drug compound, and any released transport moiety is acceptably non-toxic. For prodrugs where the transport moiety is intended to enhance uptake, typically the release of the transport moiety should be rapid. In other cases, it is desirable to utilize a moiety that provides slow release, e.g., certain polymers or other moieties, such as cyclodextrins. Carrier prodrugs can, for example, be used to improve one or more of the following properties: increased lipophilicity, increased duration of pharmacological effects, increased site-specificity, decreased toxicity and adverse reactions, and/or improvement in drug formulation (e.g., stability, water solubility, suppression of an undesirable organoleptic or physiochemical property). For example, lipophilicity can be increased by esterification of (a) hydroxyl groups with lipophilic carboxylic acids (e.g., a carboxylic acid having at least one lipophilic moiety), or (b) carboxylic acid groups with lipophilic alcohols (e.g., an alcohol having at least one lipophilic moiety, for example aliphatic alcohols).

Exemplary prodrugs are, e.g., esters of free carboxylic acids and S-acyl derivatives of thiols and O-acyl derivatives of alcohols or phenols, wherein acyl has a meaning as defined herein. Suitable prodrugs are often pharmaceutically acceptable ester derivatives convertible by solvolysis under physiological conditions to the parent carboxylic acid, e.g., lower alkyl esters, cycloalkyl esters, lower alkenyl esters, benzyl esters, mono- or di-substituted lower alkyl esters, such as the □-(amino, mono- or di-lower alkylamino, carboxy, lower alkoxycarbonyl)-lower alkyl esters, the □-(lower alkanoyloxy, lower alkoxycarbonyl or di-lower alkylaminocarbonyl)-lower alkyl esters, such as the pivaloyloxymethyl ester and the like conventionally used in the art. In addition, amines have been masked as arylcarbonyloxymethyl substituted derivatives which are cleaved by esterases in vivo releasing the free drug and formaldehyde (Bundgaard, *J. Med. Chem.* 2503 (1989)). Moreover, drugs containing an acidic NH group, such as imidazole, imide, indole and the like, have been masked with N-acyloxymethyl groups (Bundgaard, *Design of Prodrugs, Elsevier* (1985)). Hydroxy groups have been masked as esters and ethers. EP 039,051 (Sloan and Little) discloses Mannich-base hydroxamic acid prodrugs, their preparation and use.

Compositions

In another aspect, the present invention provides a pharmaceutical composition comprising a compound of formula (I) or a pharmaceutically acceptable salt thereof and a pharmaceutically acceptable carrier. The pharmaceutical composition can be formulated for particular routes of administration such as oral administration, parenteral administration, and rectal administration, etc. In addition, the pharmaceutical compositions of the present invention can be made up in a solid form (including without limitation capsules, tablets, pills, granules, powders or suppositories), or in a liquid form (including without limitation solutions, suspensions or emulsions). The pharmaceutical compositions can be subjected to conventional pharmaceutical operations such as sterilization and/or can contain conventional inert diluents, lubricating agents, or buffering agents, as well as adjuvants, such as preservatives, stabilizers, wetting agents, emulsifiers and buffers, etc.

Typically, the pharmaceutical compositions are tablets or gelatin capsules comprising the active ingredient together with a) diluents, e.g., lactose, dextrose, sucrose, mannitol, sorbitol, cellulose and/or glycine; b) lubricants, e.g., silica, talcum, stearic acid, its magnesium or calcium salt and/or polyethyleneglycol; for tablets also c) binders, e.g., magnesium aluminum silicate, starch paste, gelatin, tragacanth, methylcellulose, sodium carboxymethylcellulose and/or polyvinylpyrrolidone; if desired; d) disintegrants, e.g., starches, agar, alginic acid or its sodium salt, or effervescent mixtures; and/or e) absorbents, colorants, flavors and sweeteners.

Tablets may be either film coated or enteric coated according to methods known in the art. Suitable compositions for oral administration include an effective amount of a compound of the invention in the form of tablets, lozenges, aqueous or oily suspensions, dispersible powders or granules, emulsion, hard or soft capsules, or syrups or elixirs. Compositions intended for oral use are prepared according to any method known in the art for the manufacture of pharmaceutical compositions and such compositions can contain one or more agents selected from the group consisting of sweetening agents, flavoring agents, coloring agents and preserving agents in order to provide pharmaceutically elegant and palatable preparations. Tablets may contain the active ingredient in admixture with nontoxic pharmaceutically acceptable excipients which are suitable for the manufacture of tablets. These excipients are, for example, inert diluents, such as calcium carbonate, sodium carbonate, lactose, calcium phosphate or sodium phosphate; granulating and disintegrating agents, for example, corn starch, or alginic acid; binding agents, for example, starch, gelatin or acacia; and lubricating agents, for example magnesium stearate, stearic acid or talc. The tablets are uncoated or coated by known techniques to delay disintegration and absorption in the gastrointestinal tract and thereby provide a sustained action over a longer period. For example, a time delay material such as glyceryl monostearate or glyceryl distearate can be employed. Formulations for oral use can be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example, peanut oil, liquid paraffin or olive oil.

Certain injectable compositions are aqueous isotonic solutions or suspensions, and suppositories are advantageously prepared from fatty emulsions or suspensions. Said compositions may be sterilized and/or contain adjuvants, such as preserving, stabilizing, wetting or emulsifying agents, solution promoters, salts for regulating the osmotic pressure and/or buffers. In addition, they may also contain other therapeutically valuable substances. Said compositions are prepared according to conventional mixing, granulating or coating methods, respectively, and contain about 0.1-75%, or contain about 1-50%, of the active ingredient.

Suitable compositions for transdermal application include an effective amount of a compound of the invention with a suitable carrier. Carriers suitable for transdermal delivery include absorbable pharmacologically acceptable solvents to assist passage through the skin of the host. For example, transdermal devices are in the form of a bandage comprising a backing member, a reservoir containing the compound optionally with carriers, optionally a rate controlling barrier to deliver the compound of the skin of the host at a controlled and predetermined rate over a prolonged period of time, and means to secure the device to the skin.

Suitable compositions for topical application, e.g., to the skin and eyes, include aqueous solutions, suspensions, ointments, creams, gels or sprayable formulations, e.g., for delivery by aerosol or the like. Such topical delivery systems will in particular be appropriate for dermal application, e.g., for the treatment of skin cancer, e.g., for prophylactic use in sun creams, lotions, sprays and the like. They are thus particularly suited for use in topical, including cosmetic, formulations well-known in the art. Such may contain solubilizers, stabilizers, tonicity enhancing agents, buffers and preservatives.

As used herein a topical application may also pertain to an inhalation or to an intranasal application. They may be conveniently delivered in the form of a dry powder (either alone, as a mixture, for example a dry blend with lactose, or a mixed component particle, for example with phospholipids) from a dry powder inhaler or an aerosol spray presentation from a pressurised container, pump, spray, atomizer or nebuliser, with or without the use of a suitable propellant.

The present invention further provides anhydrous pharmaceutical compositions and dosage forms comprising the compounds of the present invention as active ingredients, since water may facilitate the degradation of certain compounds. Anhydrous pharmaceutical compositions and dosage forms of the invention can be prepared using anhydrous or low moisture containing ingredients and low moisture or low humidity conditions. An anhydrous pharmaceutical composition may be prepared and stored such that its anhydrous nature is maintained. Accordingly, anhydrous compositions are packaged using materials known to prevent exposure to water such that they can be included in suitable formulary kits. Examples of suitable packaging include, but are not limited to, hermetically sealed foils, plastics, unit dose containers (e.g., vials), blister packs, and strip packs.

The invention further provides pharmaceutical compositions and dosage forms that comprise one or more agents that reduce the rate by which the compound of the present invention as an active ingredient will decompose. Such agents, which are referred to herein as "stabilizers," include, but are not limited to, antioxidants such as ascorbic acid, pH buffers, or salt buffers, etc.

Methods of Use

The compounds of the present invention inhibitors of CDK4/6 and therefore may be capable of treating diseases wherein the underlying pathology is (at least in part) mediated by CDK4/6. Such diseases include cancer and other diseases in which there is a disorder of cell proliferation, apoptosis, or differentiation.

Thus the compounds of the present invention may be useful in the treatment of RB+ve (retinoblastoma protein positive) tumours, including tumours harbouring mutations in Ras, Raf, Growth Factor Receptors or over-expression of Growth Factor Receptors. The compounds of the present invention may also be useful in the treatment of tumours with amplifications of CDK4 and CDK6 genes as well as, tumours over-expressing cyclin partners of the cyclin dependent kinases. The compounds of the present invention may also be useful in the treatment of RB-ve tumours.

The compounds of the present invention may also be useful in the treatment tumours with genetic aberrations that activate the CDK4/6 kinase activity. These include, but are not limited to, cancers with D-cyclin translocations such as mantle cell lymphoma and multiple myeloma, D-cyclin amplifications such as breast cancer and squamous cell esophageal cancer, CDK4 amplifications such as liposarcoma, CDK6 amplifications or overexpressions such as T-cell lymphoma and p16 inactivation such as melanoma, non-small cell lung cancer and pancreatic cancer.

The compounds of the present invention may be useful in the treatment of cancers that have genetic aberrations in the upstream regulators of D-cyclins, where the defect results in an increase of D-cyclins abundance, can also be considered for treatment. These include, but are not limited to, acute myeloid leukemia with FLT3 activation, breast cancers with Her2/neu overexpression, ER dependency or triple negative phenotype, colon cancers with activating mutations of the MAPK, PI3K or WNT pathway, melanomas with activating mutations of MAPK pathway, non small cell lung cancers with activating aberrations of EGFR pathway and pancreatic cancers with activating aberrations of MAPK pathway including K-ras mutations.

Examples of cancers which may be treated with a compound of the present invention include but are not limited to, carcinoma, for example a carcinoma of the bladder, breast, colon (e.g. colorectal carcinomas such as colon adenocarcinoma and colon adenoma), kidney, epidermis, liver, lung (e.g. adenocarcinoma, small cell lung cancer and non-small cell lung carcinomas), oesophagus, gall bladder, ovary, pancreas (e.g. exocrine pancreatic carcinoma), stomach, cervix, thyroid, nose, head and neck, prostate, and skin (e.g. squamous cell carcinoma). Other examples of cancers that may be treated with a compound of the present invention include hematopoletic tumours of lymphoid lineage (e.g. leukemia, acute lymphocytic leukemia, mantle cell lymphoma, chronic lymphocytic leukaemia, B-cell lymphoma, (such as diffuse large B cell lymphoma), T-cell lymphoma, multiple myeloma, Hodgkin's lymphoma, non-Hodgkin's lymphoma, hairy cell lymphoma, and Burkett's lymphoma; hematopoietic tumours of myeloid lineage, for example acute and chronic myelogenous leukemias, myelodysplastic syndrome, and promyelocytic leukemia. Other cancers include thyroid follicular cancer; a tumour of mesenchymal origin, for example fibrosarcoma or habdomyosarcoma; a tumour of the central or peripheral nervous system, for example astrocytoma, neuroblastoma, glioma or schwannoma; melanoma;

seminoma; teratocarcinoma; osteosarcoma; xeroderma pigmentosum; retinoblastoma; keratoctanthoma; thyroid follicular cancer; and Kaposi's sarcoma.

One group of cancers includes human breast cancers (e.g. primary breast tumours, node-negative breast cancer, invasive duct adenocarcinomas of the breast, non-endometrioid breast cancers); and endometrial cancers. Another sub-set of cancers wherein compounds having CDK4/6 inhibitory activity may be of particular therapeutic benefit comprises glioblastoma multiforme, T cell ALL, sarcomas, familial melanoma and melanoma.

CDK4/6 inhibitors could also be useful in the treatment of viral infections, for example herpes virus, pox virus, Epstein-Barr virus, Sindbis virus, adenovirus, HIV, HPV, HCV and HCMV; prevention of AIDS development in HIV-infected individuals; chronic inflammatory diseases, for example systemic lupus erythematosus, autoimmune mediated glomerulonephritis, rheumatoid arthritis, psoriasis, inflammatory bowel disease, and autoimmune diabetes mellitus; cardiovascular diseases for example cardiac hypertrophy, restenosis, atherosclerosis; neurodegenerative disorders, for example Alzheimer's disease, AIDS-related dementia, Parkinson's disease, amyotropic lateral sclerosis, retinitis pigmentosa, spinal muscular atropy and cerebellar degeneration; glomerulonephritis; myelodysplastic syndromes, ischemic injury associated myocardial infarctions, stroke and reperfusion injury, arrhythmia, atherosclerosis, toxin-induced or alcohol related liver diseases, haematological diseases, for example, chronic anemia and aplastic anemia; degenerative diseases of the musculoskeletal system, for example, osteoporosis and arthritis, aspirin-sensitive rhinosinusitis, cystic fibrosis, multiple sclerosis, kidney diseases, ophthalmic diseases including age related macular degeneration, uveitis, and cancer pain.

The methods of treatment of the invention comprise administering a therapeutically effective amount of a compound according to formula (I), or a pharmaceutically acceptable salt thereof, to a subject in need thereof. Individual embodiments of the invention include methods of treating any one of the above mentioned disorders or diseases by administering an effective amount of a compound according to formula (I), or a pharmaceutically acceptable salt thereof, to a subject in need thereof.

The term "a therapeutically effective amount" of a compound of the present invention refers to an amount of the compound of the present invention that will elicit the biological or medical response of a subject, for example, reduction or inhibition of an enzyme or a protein activity, or ameliorate symptoms, alleviate conditions, slow or delay disease progression, or prevent a disease, etc. In one non-limiting embodiment, the term "a therapeutically effective amount" refers to the amount of the compound of the present invention that, when administered to a subject, is effective to (1) at least partially alleviating, inhibiting, preventing and/or ameliorating a condition, or a disorder or a disease (i) mediated by CDK4/6, or (ii) associated with CDK4/6 activity, or (iii) characterized by activity (normal or abnormal) of CDK4/6; or (2) reducing or inhibiting the activity of CDK4/6; or (3) reducing or inhibiting the expression of CDK4/6. In another non-limiting embodiment, the term "a therapeutically effective amount" refers to the amount of the compound of the present invention that, when administered to a cell, or a tissue, or a non-cellular biological material, or a medium, is effective to at least partially reducing or inhibiting the activity of CDK4/6; or at least partially reducing or inhibiting the expression of CDK4/6. The meaning of the term "a therapeutically effective amount" as illustrated in the above embodiment for CDK4/6 also applies by the same means to any other relevant proteins/peptides/enzymes.

As used herein, the term "subject" refers to an animal. Typically the animal is a mammal. A subject also refers to for example, primates (e.g., humans, male or female), cows, sheep, goats, horses, dogs, cats, rabbits, rats, mice, fish, birds and the like. In certain embodiments, the subject is a primate. In yet other embodiments, the subject is a human.

As used herein, the term "treat", "treating" or "treatment" of any disease or disorder refers in one embodiment, to ameliorating the disease or disorder (i.e., slowing or arresting or reducing the development of the disease or at least one of the clinical symptoms thereof). In another embodiment "treat", "treating" or "treatment" refers to alleviating or ameliorating at least one physical parameter including those which may not be discernible by the patient. In yet another embodiment, "treat", "treating" or "treatment" refers to modulating the disease or disorder, either physically, (e.g., stabilization of a discernible symptom), physiologically, (e.g., stabilization of a physical parameter), or both. In yet another embodiment, "treat", "treating" or "treatment" refers to preventing or delaying the onset or development or progression of the disease or disorder.

As used herein, a subject is "in need of" a treatment if such subject would benefit biologically, medically or in quality of life from such treatment.

The pharmaceutical composition or combination of the present invention can be in unit dosage of about 1-1000 mg of active ingredient(s) for a subject of about 50-70 kg, or about 1-500 mg or about 1-250 mg or about 1-150 mg or about 0.5-100 mg, or about 1-50 mg of active ingredients. The therapeutically effective dosage of a compound, the pharmaceutical composition, or the combinations thereof, is dependent on the species of the subject, the body weight, age and individual condition, the disorder or disease or the severity thereof being treated. A physician, clinician or veterinarian of ordinary skill can readily determine the effective amount of each of the active ingredients necessary to prevent, treat or inhibit the progress of the disorder or disease.

The above-cited dosage properties are demonstrable in vitro and in vivo tests using advantageously mammals, e.g., mice, rats, dogs, monkeys or isolated organs, tissues and preparations thereof. The compounds of the present invention can be applied in vitro in the form of solutions, e.g., aqueous solutions, and in vivo either enterally, parenterally, advantageously intravenously, e.g., as a suspension or in aqueous solution. The dosage in vitro may range between about $10^{-3}$ molar and $10^{-9}$ molar concentrations. A therapeutically effective amount in vivo may range depending on the route of administration, between about 0.1-500 mg/kg, or between about 1-100 mg/kg.

One embodiment of the present invention includes a method of modulating CDK4/6 activity in a subject comprising administering to the subject a therapeutically effective amount of a compound according to formula (I) or a pharmaceutically acceptable salt thereof.

Another embodiment of the present invention is a method for the treatment of a disorder or a disease mediated by CDK4/6 in a subject in need thereof, comprising administering to the subject a therapeutically effective amount of the compound of formula (I), or a pharmaceutically acceptable salt thereof.

Another embodiment of the present invention is a method of treating a disorder or a disease in mediated by CDK4/6, in a subject in need of treatment thereof comprising administration of a therapeutically effective amount of a compound according to formula (I), or a pharmaceutically acceptable salt thereof, wherein the disorder or the disease is selected from the group consisting of carcinomas with genetic aberrations that activate the CDK4/6 kinase activity. These include, but are not limited to, cancers with D-cyclin translocations such as mantle cell lymphoma and multiple myeloma, D-cyclin amplifications such as breast cancer and squamous cell esophageal cancer, CDK4 amplifications such as liposarcoma, CDK6 amplifications or overexpressions such as T-cell lymphoma and p16 inactivation such as melanoma, non small cell lung cancer and pancreatic cancer.

Another embodiment of the present invention is the use of a compound of formula (I), or a pharmaceutically acceptable salt thereof, for the treatment of a disorder or disease mediated by CDK4.

Another embodiment of the present invention is use of a compound of formula (I), or a pharmaceutically acceptable salt thereof, for the treatment of a disorder or a disease in mediated by CDK4, in a subject wherein the disorder or the disease is selected from the group consisting of carcinomas with genetic aberrations that activate the CDK4/6 kinase activity. These include, but are not limited to, cancers with D-cyclin translocations such as mantle cell lymphoma and multiple myeloma, D-cyclin amplifications such as breast cancer and squamous cell esophageal cancer, CDK4 amplifications such as liposarcoma, CDK6 amplifications or overexpressions such as T-cell lymphoma and p16 inactivation such as melanoma, non-small cell lung cancer and pancreatic cancer.

Another embodiment of the present invention is a compound according to formula (I), or a pharmaceutically acceptable salt thereof, for use as a medicament.

Another embodiment of the present invention is the use of a compound of formula (I), or a pharmaceutically acceptable salt thereof, in the manufacture of a medicament for the treatment of a disorder or disease mediated by CDK4/6 wherein the disorder or the disease is selected from the group consisting of carcinomas with genetic aberrations that activate the CDK4/6 kinase activity. These include, but are not limited to, cancers with D-cyclin translocations such as mantle cell lymphoma and multiple myeloma, D-cyclin amplifications such as breast cancer and squamous cell esophageal cancer, CDK4 amplifications such as liposarcoma, CDK6 amplifications or overexpressions such as T-cell lymphoma and p16 inactivation such as melanoma, non-small cell lung cancer and pancreatic cancer.

Combinations

The compounds of the present invention may be administered either simultaneously with, or before or after, one or more other therapeutic agents. The compounds of the present invention may be administered separately, by the same or different route of administration, or together in the same pharmaceutical composition as the other agents.

In one embodiment, the invention provides a product comprising a compound of formula (I), or a pharmaceutically acceptable salt thereof, and at least one other therapeutic agent as a combined preparation for simultaneous, separate or sequential use in therapy. In one embodiment, the therapy is the treatment of a disease or condition mediated by CDK4/6 inhibition. Products provided as a combined preparation include a composition comprising the compound of the present invention and the other therapeutic agent(s) together in the same pharmaceutical composition, or the compound of the present invention and the other therapeutic agent(s) in separate form, e.g. in the form of a kit.

In one embodiment, the invention provides a pharmaceutical composition comprising a compound of formula (I) or a pharmaceutically acceptable salt thereof, and another therapeutic agent(s). Optionally, the pharmaceutical composition may comprise a pharmaceutically acceptable excipient, as described above.

In one embodiment, the invention provides a kit comprising two or more separate pharmaceutical compositions, at least one of which contains a compound of formula (I) or a pharmaceutically acceptable salt thereof. In one embodiment, the kit comprises means for separately retaining said compositions, such as a container, divided bottle, or divided foil packet. An example of such a kit is a blister pack, as typically used for the packaging of tablets, capsules and the like.

The kit of the invention may be used for administering different dosage forms, for example, oral and parenteral, for administering the separate compositions at different dosage intervals, or for titrating the separate compositions against one another. To assist compliance, the kit of the invention typically comprises directions for administration.

In the combination therapies of the invention, the compound of the invention and the other therapeutic agent may be manufactured and/or formulated by the same or different manufacturers. Moreover, the compound of the invention and the other therapeutic may be brought together into a combination therapy: (i) prior to release of the combination product to physicians (e.g. in the case of a kit comprising the compound of the invention and the other therapeutic agent); (ii) by the physician themselves (or under the guidance of the physician) shortly before administration; (iii) in the patient themselves, e.g. during sequential administration of the compound of the invention and the other therapeutic agent.

Accordingly, the invention provides the use of a compound of formula (I), or a pharmaceutically acceptable salt thereof, for treating a disease or condition mediated by inhibition of CDK4/6, wherein the medicament is prepared for administration with another therapeutic agent. The invention also provides the use of another therapeutic agent for treating a disease or condition mediated by inhibition of CDK4/6, wherein the medicament is administered with a compound of the present invention.

The invention also provides a compound of formula (I), or a pharmaceutically acceptable salt thereof, for use in a method of treating a disease or condition mediated by CDK4/6 inhibition, wherein the compound of formula (I) is prepared for administration with another therapeutic agent. The invention also provides another therapeutic agent for use in a method of treating a disease or condition mediated by CDK4/6 inhibition, wherein the other therapeutic agent is prepared for administration with a compound of formula (I) or a pharmaceutically acceptable salt thereof. The invention also provides a compound of formula (I), or a pharmaceutically acceptable salt thereof, for use in a method of treating a disease or condition mediated by CDK4/6 inhibition, wherein the compound of formula (I), or a pharmaceutically acceptable salt thereof, is administered with another therapeutic agent. The invention also provides another therapeutic agent for use in a method of treating a disease or condition mediated by CDK4/6 inhibition, wherein the other therapeutic agent is administered with a compound of formula (I).

The invention also provides the use of a compound of formula (I), or a pharmaceutically acceptable salt thereof, for treating a disease or condition mediated by CDK4/6, wherein the patient has previously (e.g. within 24 hours) been treated with another therapeutic agent. The invention also provides the use of another therapeutic agent for treating a disease or condition mediated by CDK4/6, wherein the patient has previously (e.g. within 24 hours) been treated with a compound of formula (I) or a pharmaceutically acceptable salt thereof.

In one embodiment, the other therapeutic agent is selected from an anti-inflammatory, antiproliferative, chemotherapeutic agent, immunosuppressant, anti-cancer, cytotoxic agent or kinase inhibitor other than a compound of the present invention, or salt thereof. Further examples of agents that may be administered in combination with the compounds of the invention include, but are not limited to, a PTK inhibitor, cyclosporin A, CTLA4-Ig, antibodies selected from anti-ICAM-3, anti-IL-2 receptor, anti-CD45RB, anti-CD2, anti-CD3, anti-CD4, anti-CD80, anti-CD86, and monoclonal antibody OKT3, agents blocking the interaction between CD40 and gp39, fusion proteins constructed from CD40 and gp39, inhibitors of NF-kappa B function, non-steroidal antiinflammatory drugs, steroids, gold compounds, antiproliferative agents, FK506, mycophenolate mofetil, cytotoxic drugs, TNF-α inhibitors, anti-TNF antibodies or soluble TNF receptor, rapamycin, mTor inhibitors, leflunimide, cyclooxygenase-2 inhibitors, paclitaxel, cisplatin, carboplatin, doxorubicin, caminomycin, daunorubicin, aminopterin, methotrexate, methopterin, mitomycin C, ecteinascidin 743, porfiromycin, 5-fluorouracil, 6-mercaptopurine, gemcitabine, cytosine arabinoside, podophyllotoxin, etoposide, etoposide phosphate, teniposide, melphalan, vinblastine, vincristine, leurosidine, epothilone, vindesine, leurosine, B-Raf inhibitor, MEK inhibitor, PI3K inhibitor, HSP90 inhibitor, CDK1 inhibitor, CDK2 inhibitor, CDK5 inhibitor, CDK7 inhibitor, CDK8 inhibitor, CDK9 inhibitor, EGFR inhibitor, FGFR inhibitor, PDGFR inhibitor, Her2/neu inhibitor, FLT3 inhibitor, Antagonists of androgen, glucocorticoid and prosterone receptors, SMO inhibitor, WNT inhibitor, Bcl inhibitor, IAP inhibitor, Mcl inhibitor, MDM2 inhibitor, p52 inhibitor, proteosome inhibitors (Velcade), or derivatives thereof.

Specific individual combinations which may provide particular treatment benefits include co-treatment of mantle cell lymphoma or pancreatic cancer patients with mTOR inhibitors, such as Everolimus.

A compound of the present invention may also be used in combination with other agents, e.g., an additional protein kinase inhibitor that is or is not a compound of the invention, for treatment of a protein kinase-associated disorder in a subject. By the term "combination" is meant either a fixed combination in one dosage unit form, or a kit of parts for the combined administration where a compound of the present invention and a combination partner may be administered independently at the same time or separately within time intervals that especially allow that the combination partners show a cooperative, e.g., synergistic, effect, or any combination thereof.

The compounds of the invention may be administered, simultaneously or sequentially, with an antiinflammatory, antiproliferative, chemotherapeutic agent, immunosuppressant, anti-cancer, cytotoxic agent or kinase inhibitor other than a compound of the Formula I or pharmaceutically acceptable salt thereof. Further examples of agents that may be administered in combination with the compounds of the invention include, but are not limited to, a PTK inhibitor, cyclosporin A, CTLA4-Ig, antibodies selected from anti-ICAM-3, anti-IL-2 receptor, anti-CD45RB, anti-CD2, anti-CD3, anti-CD4, anti-CD80, anti-CD86, and monoclonal antibody OKT3, agents blocking the interaction between CD40 and gp39, fusion proteins constructed from CD40 and gp39, inhibitors of NF-kappa B function, non-steroidal antiinflammatory drugs, steroids, gold compounds, antiproliferative agents, FK506, mycophenolate mofetil, cytotoxic drugs, TNF-α inhibitors, anti-TNF antibodies or soluble TNF receptor, rapamycin, leflunimide, cyclooxygenase-2 inhibitors, paclitaxel, cisplatin, carboplatin, doxorubicin, caminomycin, daunorubicin, aminopterin, methotrexate, methopterin, mitomycin C, ecteinascidin 743, porfiromycin, 5-fluorouracil, 6-mercaptopurine, gemcitabine, cytosine arabinoside, podophyllotoxin, etoposide, etoposide phosphate, teniposide, melphalan, vinblastine, vincristine, leurosidine, epothilone, vindesine, leurosine, or derivatives thereof.

A compound of the invention and any additional agent may be formulated in separate dosage forms. Alternatively, to decrease the number of dosage forms administered to a patient, the compound of the invention and any additional agent may be formulated together in any combination. For example, the compound of the invention inhibitor may be formulated in one dosage form and the additional agent may be formulated together in another dosage form. Any separate dosage forms may be administered at the same time or different times.

Alternatively, a composition of this invention comprises an additional agent as described herein. Each component may be present in individual compositions, combination compositions, or in a single composition.

General Synthetic Procedures and Intermediates
General N—C Coupling Procedure 1

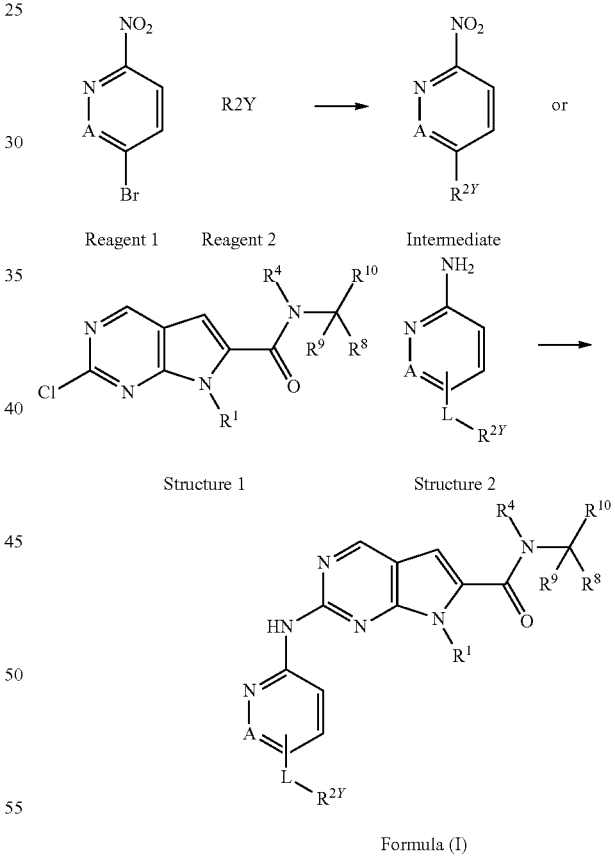

To an appropriate reaction vessel was combined compounds of structure 1 (1 equivalent) and compounds of general structure 2 (1 equivalent) in an appropriate solvent (such as but not limited to dioxane). To this resultant solution was added palladium (II) acetate (0.1 equivalent), ligand such as BINAP, XPhos or XantPhos (0.15 equivalent), and cesium carbonate (1.5 equivalents). Nitrogen was then gently bubbled through the reaction mixture (approximately 5 to 10 minutes). The resultant reaction mixture was then heated using either an oil bath or a microwave to approximately 100 to 130° C. for an appropriate amount of time whereby either TLC or HPLC MS analysis indicated that the reaction was complete. The reaction was removed from the heat source and allowed to cool. The mixture was then worked up by the addition of an appropriate solvent such as dichloromethane or ethyl acetate. The insolubles were removed by filtration and the organic filtrate extracted with water. The aqueous phase was back extracted. The organic phases were combined, dried over sodium or magnesium sulfate, filtered and concentrated to a residue. The crude residue was purified by silica gel chromatography using an appropriate mobile phase which yielded the desired intermediate or a compound of Formula (I).

Nitro Group Reduction Procedure 1

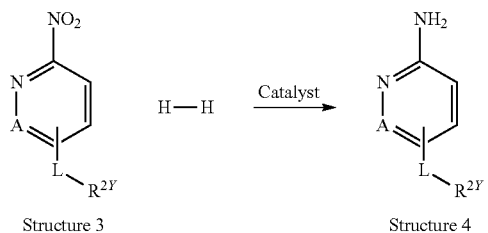

Structure 3        Structure 4

An appropriate reaction vessel was charged with a compound of structure 3. An appropriate solvent such as methanol, ethyl acetate, tetrahydrofuran or mixtures of these solvents were used to dissolve a compound of structure 3. To this resultant mixture and under a stream of nitrogen was added a catalyst such as palladium on carbon or palladium hydroxide (5 to 20% metal content on carbon or a suitable support) in 5 to 10 mole percent to structure 3. The resultant mixture was then purged and stirred under an atmosphere of hydrogen gas. After all the starting material was converted to product as determined by TLC or LCMS, the reaction vessel was removed from the hydrogen source and purged with nitrogen to remove residual hydrogen gas. The reaction mixture was filtered through a pad of celite under a stream of nitrogen and washed with an additional amount of solvent such as dichloromethane or methanol. The filtrates were combined and concentrated to a residue. The residue was dried under vacuum to a constant weight. The resultant material was either used directly in the next reaction or purified by either re-crystallization or silica gel chromatography and then used in the next reaction.

Procedures for Preparation of Amides of Formula 1

The following general procedures were used to couple carboxylic acids of Structure 5 with amines to form the corresponding amides of Structure 6.

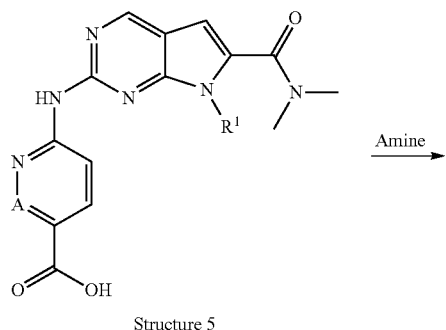

Structure 5

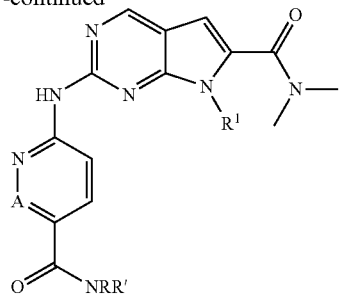

Structure 6

General Amide Formation Method 1

To a solution of carboxylic acid (1.01 mmol) in DMF (5 mL) was added O-(benzotriazol-1-yl)-N,N,N',N'-tetramethyluronium hexafluorophosphate (HBTU, 580 mg, 1.53 mmol, 1.5 equiv) and N,N-diisopropylethylamine (0.55 mL, 3.0 equiv) and the resulting mixture was stirred at room temperature for about 5 minutes. To the resultant mixture was added the Amine (1.18 mmol. 1.1 eq). The resulting mixture was stirred at room temperature for an appropriate time as determined by TLC or LCMS for completion and was then diluted with ethyl acetate and washed successively with 0.5M HCl, water, dried over $Na_2SO_4$, filtered and concentrated. The desired material was either used immediately in next step without further purification or purified by silica gel chromatography using an appropriate mobile phase and then used directly in the next reaction.

General Amide Formation Method 2

To a solution of carboxylic acid (in a salt form with 5 eq. of LiCl) (1 mmole, 1 equivalent) in DMF (5 mL) was added O-(benzotriazol-1-yl)-N,N,N',N'-tetramethyluronium hexafluorophosphate (HBTU, 580 mg, 1.53 mmol, 1.5 equiv) and N,N-diisopropylethylamine (0.55 mL, 3.0 equiv) and the resulting mixture was stirred at room temperature for about 5 minutes. To the resultant mixture was added the Amine (1.18 mmol. 1.1 eq). The mixture was stirred at room temperature for an appropriate time for reaction completion as determined by TLC or LCMS and was then diluted with ethyl acetate and washed successively with 0.5M HCl, water, dried over $Na_2SO_4$, filtered and concentrated. The desired material was either used immediately in next step without further purification or purified by silica gel chromatography using an appropriate mobile phase and then used directly in the next reaction.

General Amide Formation Method 3

To a solution of carboxylic acid (1 eq, which contained 5 eq of LiCl) in 1 ml of DMA or DMF, O-(benzotriazol-1-yl)-N,N,N',N'-tetramethyluronium tetrafluoroborate (TBTU, 1 eq.) was added and the resulting solution was stirred for about 10 min. An additional 3 ml of dichloromethane was then added (~0.03M final concentration), Amine (1 eq.) and DIPEA (4 eq.) were then added and stirred at RT until TLC and/or LCMS showed reaction was completed. The reaction mixture was diluted with dichloromethane, washed with water and then brine. The combined aqueous layers were back extracted with dichloromethane. The combined organic layers were dried over sodium sulfate or magnesium sulfate, then filtered, then concentrated and finally purified by silica gel column chromatography using an appropriate mobile phase and then used directly in the next reaction.

General Amide Formation Method 4

To a suspension/solution of a mixture of carboxylic acid (with the 5 equiv LiCl) (1 eq) in DMA/DCM (1:4, 0.07M) was added O-(benzotriazol-1-yl)-N,N,N',N'-tetramethyluronium tetrafluoroborate (TBTU, 1.5 eq, general procedure B1) or O-(benzotriazol-1-yl)-N,N,N',N'-tetramethyluronium hexafluorophosphate (HBTU, 1.5 equiv, general procedure B2) and the resulting mixture was stirred at room temperature for 5 min. The reaction mixture was treated with a solution of the Amine (1 equiv) in DMA/DCM (1:4, 0.07M) or a suspension of HCl salt of Amine (1.0 equiv) and sodium bicarbonate (1.5 quiv) in DMA/DCM (1:4, 0.07M). The resulting mixture was treated with N,N-diisopropylethylamine (4.0 eq) and stirred at room temperature for 1 h. The reaction mixture was diluted in ethyl acetate, washed with water, dried over $Na_2SO_4$, filtered and concentrated. The resultant residue was purified by silica gel column chromatography using an appropriate mobile phase and then used in the next reaction.

General Procedures for the Removal of Protecting Groups of Intermediates

Intermediates which contained protecting groups necessary for the synthesis of final compounds of Formula (I), these protecting groups were removed by standard procedures as described in "Protective Groups in Organic Synthesis, $3^{rd}$ Edition, by Green and Wutts.

Deprotection Method 1: BOC Removal Using HCl

To a stirring solution of the BOC protected amine of a compound of formula I, (1.0 mmol) in dichloromethane (4 mL) or other appropriate solvent was added a solution of 4M HCl in dioxane (2.54 mL, 10.2 mmol, 10 eq) at room temperature. The reaction was stirred at room temperature until all starting material was consumed as determined by LCMS or TLC. The reaction mixture was then filtered and washed with a solvent such as dichloromethane, ethyl acetate or diethyl ether. The residue was collected and taken up in water, basified with 1M NaOH and extracted with dichloromethane or a 20% isopropyl alcohol-dichloromethane mixture. The combined organic layers were dried over Na2SO4, filtered, and concentrated under reduced pressure to a residue. The crude residue was purified by silica gel chromatography using an appropriate mobile phase and then used directly in the next reaction.

Deprotection Method 2: BOC Removal Using Trifluoroacetic Acid

To a cold 0° C. stirring solution of the BOC protected amine of a compound of Formula 1, (1.0 mmol) in dichloromethane (4 mL) or other appropriate solvent was added 4 ml of anhydrous trifluoroacetic acid. The reaction was stirred at 0° C. and allowed to warm to room temperature and stir until all starting material was consumed as determined by LCMS or TLC. The reaction mixture was then concentrated under vacuum to a thick residue. The residue was extracted with a mixture of dichloromethane and saturated sodium bicarbonate. The aqueous was back extracted with dichloromethane. For very polar amines, a 20% isopropyl alcohol-dichloromethane mixture was used for the organic extracting solvent. The organic fractions were combined and dried over $Na_2SO_4$, filtered, and concentrated under reduced pressure to a residue. The combined organic layers were dried over sodium or magnesium sulfate, filtered, and concentrated under reduced pressure to a residue. The crude residue was purified by silica gel chromatography using an appropriate mobile phase and then used directly in the next reaction.

Deprotection Method 3: BOC Removal Using Trifluoroacetic Acid

A solution of the BOC protected amine of a compound of formula 1 in $CH_2Cl_2$ (0.1 M) was treated with an equal volume of trifluoroacetic acid at room temperature and stirred at room temperature for 1.0 h. The reaction mixture was concentrated in vacuo and treated with 7 N $NH_3$ in MeOH portionwise until the mixture was neutral. The resultant mixture was concentrated to a thick residue. The resultant residue was then purified by preparative HPLC or silica gel chromatography using 7 N $NH_3$ in MeOH/CH2Cl2 and then used directly in the next reaction.

General Reductive Amination Procedure

A compound of Formula (I) (1 equivalent) containing either a primary or secondary amine and with an excess (3 to 8 equivalents) of either an aldehyde (for example, formaldehyde, 37% solution in water) or ketone (for example, acetone) were combined into a suitable solvent such as tetrahydrofuran and allowed to stir at RT for 1 hr with magnesium sulfate (1 equivalent). Sodium triacetoxyborohydride (2 equivalents) was then added in a single portion and the reaction was allowed to stir until all starting material was consumed as determined by TLC or LCMS. The reaction was then stopped and taken up into ethyl acetate, neutralized with saturated $Na_2CO_3$ solution, and washed with brine. The aqueous layers were back extracted with ethyl acetate. The organic layers were combined and dried over $Na_2SO_4$. For very polar amines, a 20% isopropanol-chloroform solution was used as the extracting solvent. The volatiles were removed and the resulting residue was purified by silica gel chromatography using an appropriate mobile phase which gave the desired final product.

Procedures for the preparation of 2-chloro-7 $R^1$—N,N-dimethyl-7H-pyrrolo[2,3-d]pyrimidine-6-carboxamides intermediates

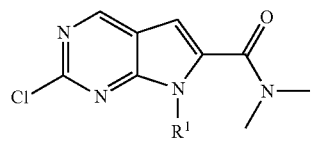

2 chloro-7 $R^2$—N,N-dimethyl-7H-pyrrolo[2,3-d]pyrimidine-6-carboxamide

Intermediate 1

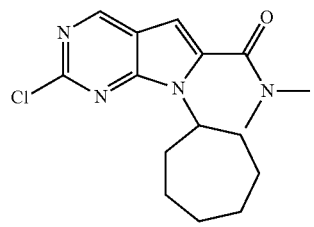 [SMILES: CN(C)C(=O)c1cc2cnc(Cl)nc2n1C1CCCCCC1]

Preparation of 2-chloro-7-cycloheptyl-N,N-dimethyl-7H-pyrrolo[2,3-d]pyrimidine-6-carboxamide

Step 1

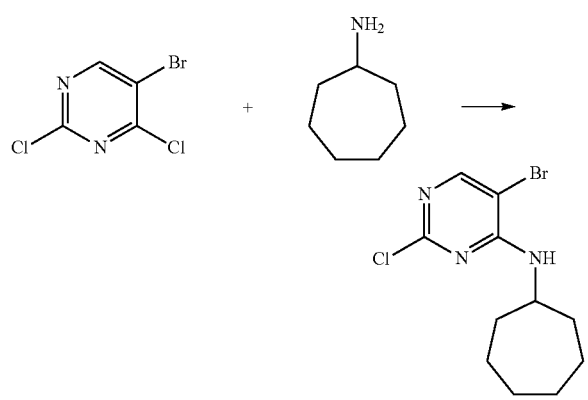

To a solution of 5-bromo-2,4-dichloropyrimidine (13.41 g, 58.8 mmol) in EtOAc (100 mL) was added DIPEA (13 mL, 1.3 equiv) followed by cycloheptanamine (8.6 mL, 1.1 equiv) and the resulting mixture was stirred at room temperature for 5 days. The reaction mixture was diluted with EtOAc (350 mL), washed with water (100 mL), brine (2×100 mL), dried over Na2SO4, filtered and concentrated. The crude product (18.1 g) was used for the next reaction without purification. 1H NMR (400 MHz, CD3OD) δ 8.10 (s, 1H), 4.17 (septet, J=4.6 Hz, 1H), 1.94 (m, 2H), 1.77-1.51 (m, 10Hz); MS m/z 305.3 (M+H)$^+$

Step 2

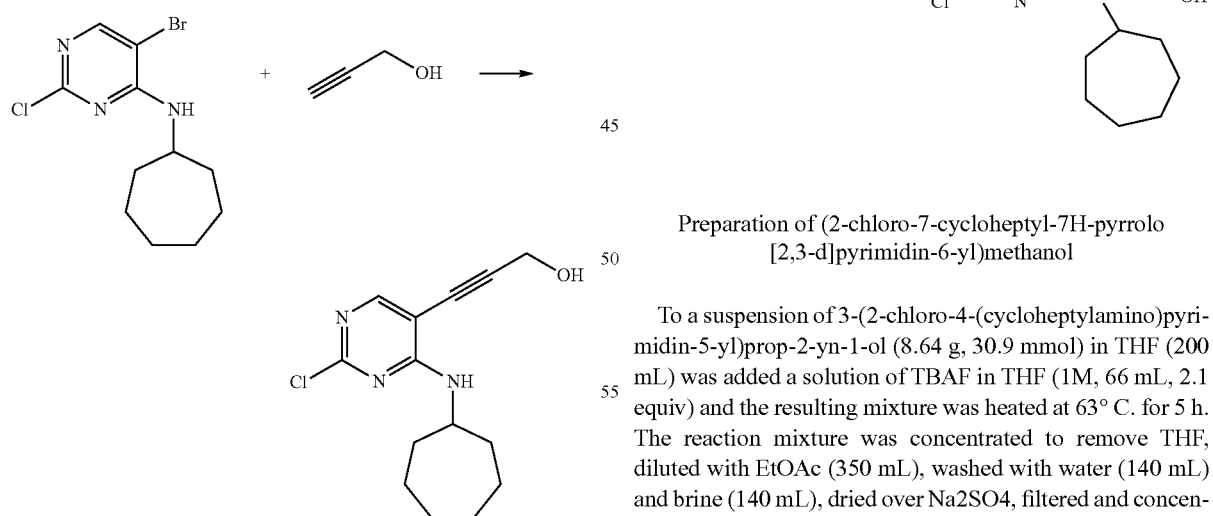

Preparation of 3-(2-chloro-4-(cycloheptylamino)pyrimidin-5-yl)prop-2-yn-1-ol

To a yellow solution of 5-bromo-2-chloro-N-cycloheptylpyrimidin-4-amine (18.1 g, 55.5 mmol) in THF (200 mL) were added propargyl alcohol (4.5 mL, 1.4 equiv) and a solution of tetrabutylammonium fluoride in THF (1M, 130 mL, 2.3 equiv) and the resulting brown mixture was treated with a stream of nitrogen for 15 min (bubble in the solution). The mixture was then treated with bis(triphenylphosphine)palladium(II) chloride (2.09 g, 0.054 equiv) and heated to reflux for 5 h. After cooling, the reaction mixture was filtered through a pad of celite (rinsed with EtOAc ~350 mL). The filtrate was concentrated to remove THF, further diluted with EtOAc (total volume 250 mL), washed with sat. NaHCO3 (2×150 mL) and water (150 mL), dried over Na2SO4, filtered and concentrated. Titration of the residue in acetone and CH2Cl2 provided 3-(2-chloro-4-(cycloheptylamino)pyrimidin-5-yl)prop-2-yn-1-ol (8.65 g) in 56% yield. 1H NMR (400 MHz, CD3OD) δ 7.98 (s, 1H), 4.45 (s, 2H), 4.19 (septet, J=4.5 Hz, 1H), 1.95 (m, 2H), 1.77-1.52 (m, 10Hz); MS m/z 280.4 (M+H)$^+$

Step 3

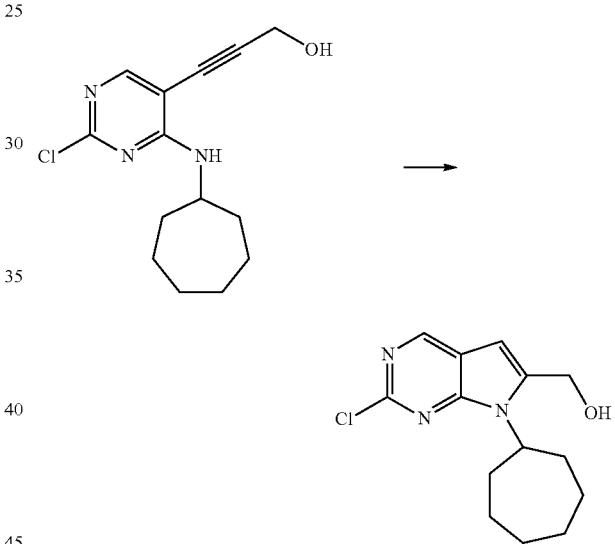

Preparation of (2-chloro-7-cycloheptyl-7H-pyrrolo[2,3-d]pyrimidin-6-yl)methanol

To a suspension of 3-(2-chloro-4-(cycloheptylamino)pyrimidin-5-yl)prop-2-yn-1-ol (8.64 g, 30.9 mmol) in THF (200 mL) was added a solution of TBAF in THF (1M, 66 mL, 2.1 equiv) and the resulting mixture was heated at 63° C. for 5 h. The reaction mixture was concentrated to remove THF, diluted with EtOAc (350 mL), washed with water (140 mL) and brine (140 mL), dried over Na2SO4, filtered and concentrated. Trituration of the residue using iPrOH, CH2Cl2, and MeCN followed by column chromatography of the mother liquor (EtOAc/heptane 20 to 100%) provided (2-chloro-7-cycloheptyl-7H-pyrrolo[2,3-d]pyrimidin-6-yl)methanol (6.24 g) in 72% yield. 1H NMR (400 MHz, CDCl3) δ 8.69 (s, 1H), 6.45 (s, 1H), 4.83 (s, 2H), 4.61 (m, 1H), 2.54 (m, 2H), 1.98-1.86 (m, 4H), 1.73-1.55 (m, 6H); MS m/z 280.4 (M+H)$^+$

Step 4

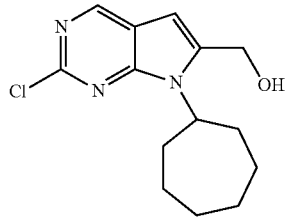

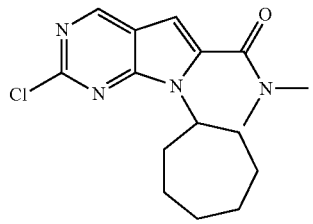

Preparation of 2-chloro-7-cycloheptyl-N,N-dimethyl-7H-pyrrolo[2,3-d]pyrimidine-6-carboxamide To a solution of (2-chloro-7-cycloheptyl-7H-pyrrolo[2,3-d]pyrimidin-6-yl)methanol (6.24 g, 22.3 mmol) in DMF (100 mL) were added a solution of dimethylamine in THF (2 M, 46 mL, 4.1 equiv) and sodium cyanide (1.04 g, 0.95 equiv) and the resulting mixture was stirred at room temperature for 4 min. The reaction mixture was treated with manganese dioxide (100.4 g, 45 equiv) in four portions over 1 h and stirred for additional 1 h. The reaction mixture was filtered through a pad of Celite (rinsed with EtOAc 600 mL). The filtrate was washed with water (200 mL). The aqueous phase was extracted with EtOAc (2×150 mL). Combined organics were washed with 4% aqueous solution of NaCl (2×250 mL), dried over Na2SO4, filtered and concentrated in vacuo. Trituration of the residue in MeCN followed by column chromatography of the mother liquor (EtOAc/Heptane 30 to 100%) provided 2-chloro-7-cycloheptyl-N,N-dimethyl-7H-pyrrolo[2,3-d]pyrimidine-6-carboxamide (6.07 g) in 85% yield. 1H NMR (400 MHz, CDCl3) δ 8.81 (s, 1H), 6.52 (s, 1H), 4.63 (tt, J=11, 4.0 Hz, 1H), 3.20 (s, 3H), 3.11 (s, 3H), 2.52 (m, 2H), 1.99 (m, 2H), 1.88 (m, 2H), 1.70 (m, 4H), 1.58 (m, 2H) MS m/z 321.5 (M+H)$^+$ Intermediate 2

2-chloro-7-cyclohexyl-N,N-dimethyl-7H-pyrrolo[2,3-d]pyrimidine-6-carboxamide was prepared in a similar manner to intermediate 1.

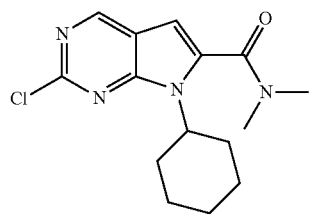 [SMILES: CN(C)C(=O)c1cc2cnc(Cl)nc2n1C1CCCCC1]

Step 1

(5-Bromo-2-chloro-pyrimidin-4-yl)-cyclohexyl-amine (23.2 g, 78% yield): 1H NMR (400 MHz, DMSO-d$_6$) δ ppm 1.01-1.17 (m, 1H) 1.20-1.31 (m, 3H) 1.35-1.50 (m, 2H) 1.60 (d, J=12.5 Hz, 1H) 1.65-1.83 (m, 4H) 3.89 (ddd, J=7.8, 3.8, 3.5 Hz, 1H) 7.26 (d, J=8.0 Hz, 1H) 8.22 (s, 1H); MS m/z 290.4 (M)$^+$.

Step 2

3-(2-Chloro-4-cyclohexylaminopyrimidin-5-yl)-prop-2-yn-1-ol (9.1 g, 43% yield): 1H NMR (400 MHz, DMSO-d$_6$) δ ppm 1.14 (t, J=12.9 Hz, 1H) 1.23-1.49 (m, 4H) 1.62 (d, J=13.1 Hz, 1H) 1.67-1.88 (m, 4H) 3.83-3.99 (m, 1H) 4.35 (d, J=6.1 Hz, 2H) 5.37 (t, J=5.8 Hz, 1H) 7.00 (d, J=8.1 Hz, 1H); MS m/z 266.3 (M+H)$^+$.

Step 3

(2-Chloro-7-cyclohexyl-7H-pyrrolo[2,3-d]pyrimidin-6-yl)-methanol (7.3 g, 81% yield): 1H NMR (400 MHz, DMSO-d$_6$) δ ppm 1.28 (t, J=12.6 Hz, 1H) 1.33-1.48 (m, 2H) 1.70 (d, J=12.1 Hz, 1H) 1.78-1.93 (m, 4H) 2.34-2.48 (m, 2H) 4.24-4.42 (m, 1H) 4.67 (d, J=5.1 Hz, 2H) 5.50 (t, J=5.6 Hz, 1H) 6.55 (s, 1H) 8.82 (s, 1H); MS m/z 266.5 (M+H)$^+$.

Step 4

2-Chloro-7-cyclohexyl-7H-pyrrolo[2,3-d]pyrimidine-6-carboxylic acid dimethylamide (0.85 g, 64% yield): 1H NMR (400 MHz, DMSO-d$_6$) δ ppm 1.22 (br. s., 1H) 1.36 (d, J=13.6 Hz, 2H) 1.66 (br. s., 1H) 1.85 (d, J=10.6 Hz, 4H) 2.30 (dd, J=12.4, 3.3 Hz, 2H) 3.04 (d, J=17.2 Hz, 6H) 4.34 (br. s., 1H) 6.80 (s, 1H) 8.97 (s, 1H); MS m/z 307.3 (M+H)$^+$.

Intermediate 3

Following the procedure for the preparation of intermediate one, 2-chloro-7-cyclopentyl-N,N-dimethyl-7H-pyrrolo[2,3-d]pyrimidine-6-carboxamide was prepared in a similar manner and is a known literature compound (see WO 2010/020675)

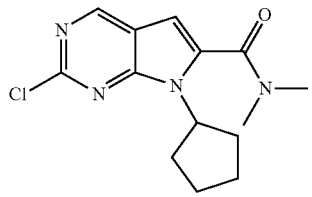 [SMILES: CN(C)C(=O)c1cc2cnc(Cl)nc2n1C1CCCC1]

Intermediate 4

Following the procedure for the preparation of intermediate one, 2-chloro-N,N-dimethyl-7-(tetrahydro-2H-pyran-3-yl)-7H-pyrrolo[2,3-d]pyrimidine-6-carboxamide was prepared in a similar manner.

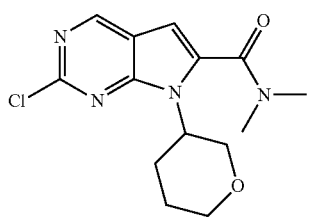 [SMILES: CN(C)C(=O)c1cc2cnc(Cl)nc2n1C1CCCOC1]

Step 1

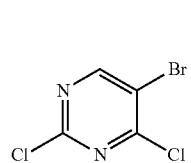 + 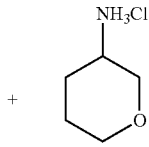 →

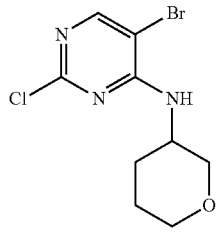

5-bromo-2-chloro-N-(tetrahydro-2H-pyran-3-yl)pyrimidin-4-amine (6.47 g) was prepared in 83% yield. 1H NMR (400 MHz, CD3OD) δ 8.16 (s, 1H), 4.20 (septet, J=4.0 Hz, 1H), 3.89 (ddd, J=11, 4.0, 1.5 Hz, 1H), 3.79 (dt, J=11, 4.0 Hz, 1H), 3.53 (m, 1H), 3.40 (dd, J=11, 8.1 Hz, 1H), 2.0 (m, 1H), 1.82-1.66 (m, 3H); MS m/z 293.3 (M+H)+

Step 2

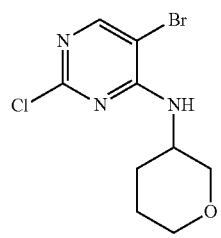 + 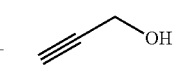 →

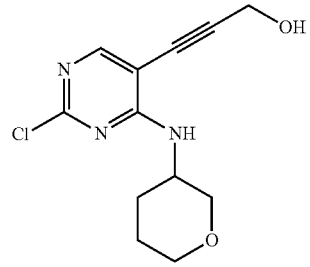

3-(2-chloro-4-(tetrahydro-2H-pyran-3-ylamino)pyrimidin-5-yl)prop-2-yn-1-ol (3.21 g) was prepared in 54% yield. 1H NMR (400 MHz, CD3OD) δ 8.05 (s, 1H), 4.45 (s, 1H), 4.21 (septet, J=4.0 Hz, 1H), 3.90 (ddd, J=11, 4.0, 1.0 Hz, 1H), 3.80 (dt, J=11, 4.0 Hz, 1H), 3.52 (m, 1H), 3.39 (dd, J=11, 8.3 Hz, 1H), 2.01 (m, 1H), 1.81-1.67 (m, 3H); MS m/z 268.4 (M+H)+

Step 3

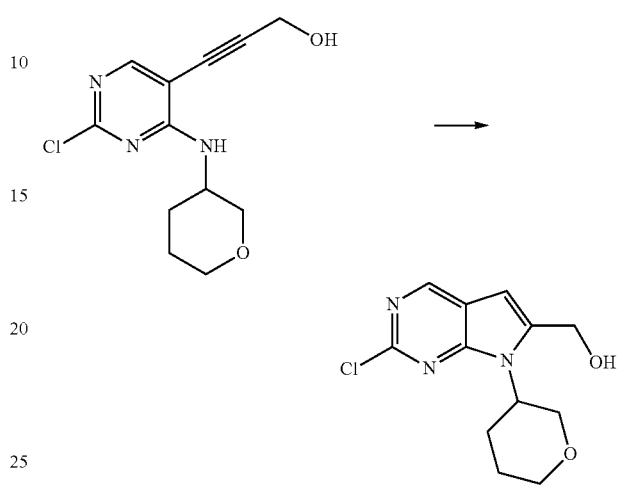

(2-chloro-7-(tetrahydro-2H-pyran-3-yl)-7H-pyrrolo[2,3-d]pyrimidin-6-yl)methanol (2.39 g) was prepared in 75% yield. 1H NMR (400 MHz, CD3OD) δ 8.72 (s, 1H), 6.59 (s, 1H), 4.77 (s, 2H), 4.62 (m, 1H), 4.42 (t, J=11 Hz, 1H), 4.00-3.91 (m, 2H), 3.57 (m, 1H), 2.92 (m, 1H), 2.07 (m, 1H), 1.87 (m, 2H); MS m/z 268.4 (M+H)+

Step 4

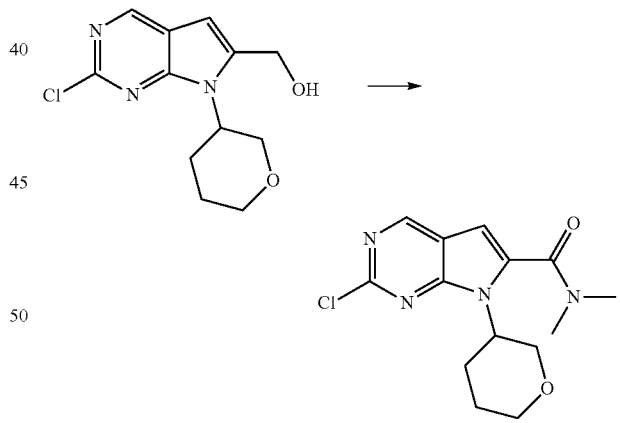

2-chloro-N,N-dimethyl-7-(tetrahydro-2H-pyran-3-yl)-7H-pyrrolo[2,3-d]pyrimidine-6-carboxamide (1.74 g) was prepared in 58% yield. 1H NMR (400 MHz, CD3OD) δ 8.87 (s, 1H), 6.81 (s, 1H), 4.53 (tt, J=11, 4.4 Hz, 1H), 4.32 (t, J=11 Hz, 1H), 3.95 (m, 2H), 3.52 (m, 1H), 3.17 (s, 3H), 3.15 (s, 3H), 2.77 (qt, J=12, 5.3 Hz, 1H), 2.09 (m, 1H), 1.87-1.78 (m, 2H); MS m/z 309.5 (M+H)+

Intermediate 5

Following the procedure for the preparation of intermediate one, 2-chloro-7-(4-(2-cyanopropan-2-yl)phenyl)-N,N- dimethyl-7H-pyrrolo[2,3-d]pyrimidine-6-carboxamide was prepared in a similar manner to intermediate 1.

Step 1

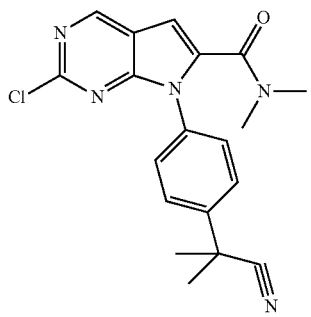 [SMILES: CN(C)C(=O)c1cc2cnc(Cl)nc2n1-c1ccc(C(C)(C)C#N)cc1]

2-(4-(5-bromo-2-chloropyrimidin-4-ylamino)phenyl)-2-methylpropanenitrile

5-Bromo-2,4-dichloropyrimidine (1.37 gm, 6 mmol), 2-(4-aminophenyl)-2-methylpropanenitrile (0.96 gm, 6 mmol) and diisopropyl ethylamine (1.6 mL, 9 mmol) were combined in 30 ml acetonitrile and stirred for 16 hr at RT. LC/MS at 16 hr indicated reaction was complete. Organics were washed sequentially with 1M citric acid solution, water, then brine. Organics were dried over sodium sulfate then decanted and evaporated to yield a crude material which was carried on as-is in the next step. (1.45 gm, 69%). MS m/z 353.3 (M+H)

Step 2

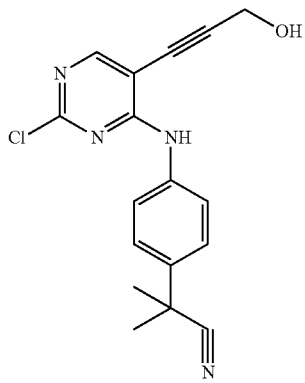 [SMILES: CC(C)(C#N)c1ccc(Nc2nc(Cl)ncc2C#CCO)cc1]

2-(4-(2-chloro-5-(3-hydroxyprop-1-ynyl)pyrimidin-4-ylamino)phenyl)-2-methylpropanenitrile 2-(4-(5-bromo-2-chloropyrimidin-4-ylamino)phenyl)-2-methylpropanenitrile (1.4 gm, 3.98 mmol), bis(triphenylphosphine) palladium(II) chloride (0.14 gm, 0.2 mmol), tetrabutyl ammonium fluoride (2.6 gm, 9.95 mmol) and propargyl alcohol (0.357 mL, 5.97 mmol) were combined into 12 mL THF in a screw cap high pressure vessel and heated in a 70° C. oil bath. After 2 hr the reaction appeared complete by LC/MS. Volatiles were removed and the residue taken up into EtOAc. Organic layer was filtered to remove insoluble soot. Organic layer was washed with water, brine and then dried over sodium sulfate. Volatiles were removed and the residue purified by NPLC (10-75% EtOAc in Heptane, Analogix). (869 mg, 67%). MS m/z 327.4 (M+H)

Step 3

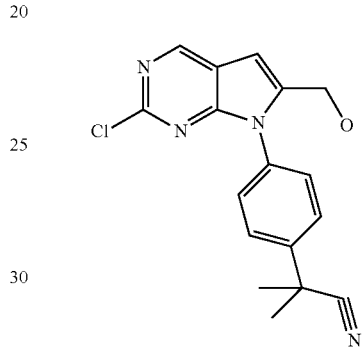

2-(4-(2-chloro-6-(hydroxymethyl)-7H-pyrrolo[2,3-d]pyrimidin-7-yl)phenyl)-2-methyl propanenitrile 2-(4-(2-chloro-5-(3-hydroxyprop-1-ynyl)pyrimidin-4-ylamino)phenyl)-2-methylpropanenitrile was reacted with a solution of 1M tetrabutylammonium fluoride in THF (5.85 mL, 5.85 mmol) diluted to 10 mL with additional dry THF for 1.5 hr at 60° C. Analytical LC indicates the reaction is complete (minimal shift in retention time). Volatiles were removed and the residue taken up into ethyl acetate. Organics were washed with water, brine then dried over sodium sulfate. Volatiles were removed and the residue purified by NPLC (10-75% ethyl acetate in Heptane, Analogix) to yield the desired product (589 mg, 68%). MS 327.3 m/z (M+H)

Step 4

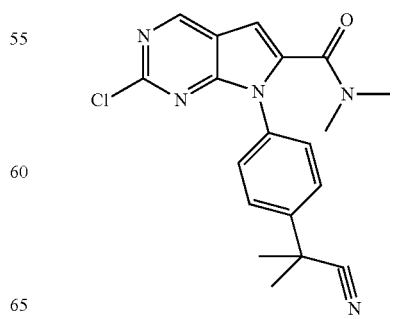

2-chloro-7-(4-(2-cyanopropan-2-yl)phenyl)-N,N-dimethyl-7H-pyrrolo[2,3-d]pyrimidine-6-carboxamide 2-(4-(2-chloro-6-(hydroxymethyl)-7H-pyrrolo[2,3-d]pyrimidin-7-yl)phenyl)-2-methylpropanenitrile (589 mg, 1.8 mmol), manganese dioxide (7.8 gm, 90 mmol) and 2 M dimethylamine solution in THF (4.51 ml, 9 mmol) were combined in 6 mL dry DMF. Reaction was stirred for 3 hrs whereupon the reaction appeared complete by LC/MS. Reaction was poured into brine and extracted into EtOAc. Combined organics were washed with water followed by brine and then dried over sodium sulfate. Volatiles were removed and the residue purified by NPLC (10-100% ethyl acetate in heptane, Analogix) to yield the pure desired compound. (345 mg, 52%). MS 367.7 m/z

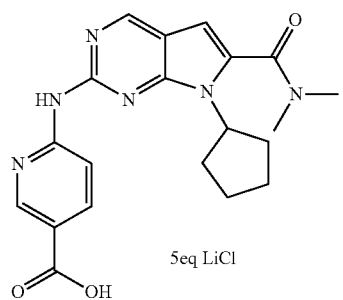 [SMILES: CN(C)C(=O)c1cc2cnc(Nc3ccc(C(=O)O)cn3)nc2n1C1CCCC1]

5eq LiCl

Intermediate 6

6-(7-cyclopentyl-6-(dimethylcarbamoyl)-7H-pyrrolo[2,3-d]pyrimidin-2-ylamino)nicotinic acid LiCl salt Step 1

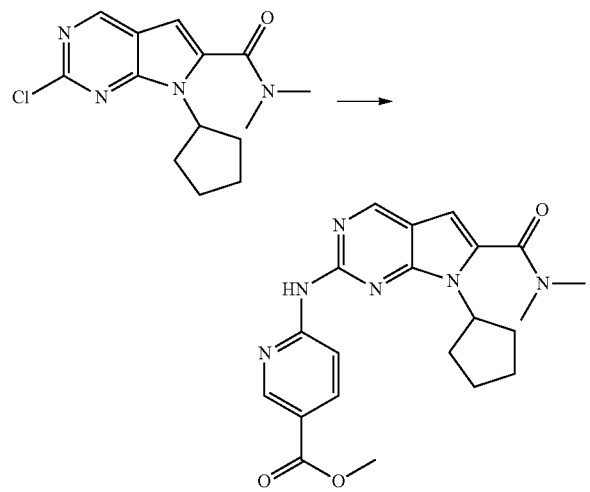

Preparation of Methyl 6-(7-cyclopentyl-6-(dimethylcarbamoyl)-7H-pyrrolo[2,3-d]pyrimidin-2-ylamino)nicotinate To a suspension of 2-chloro-7-cyclopentyl-N,N-dimethyl-7H-pyrrolo[2,3-d]pyrimidine-6-carboxamide (5.0 g, 17 mmol) in 1,4-dioxane (80 mL) in a sealed tube were added methyl 6-aminonicotinate (2.86 g, 1.10 eq), Pd(OAc)$_2$ (0.096 g, 0.025 eq) and BINAP (0.532 g, 0.050 eq). N2 was bubbled through the resulting mixture for 20 min to degas and treated with Cs$_2$CO$_3$ (8.35 g, 1.5 eq). The reaction mixture was heated at 100° C. for 2.2 h. The reaction mixture was cooled to room temperature, treated with 100 mL of heptane and sonicated. Red precipitate was collected by filtration and suspended in 200 mL of water. After sonication, the solid was collected by filtration, rinsed with water (3×50 mL) and dried. The solid was triturated in THF to obtain tan solid methyl 6-(7-cyclopentyl-6-(dimethylcarbamoyl)-7H-pyrrolo[2,3-d]pyrimidin-2-ylamino)nicotinate (6.6 g, 94% yield). The filtrated was concentrated in vacuo and purified by column chromatography (Ethyl acetate/Heptane) to give additional product (0.4 g, 6% yield). $^1$H NMR (400 MHz, DMSO-d6) δ ppm 10.33 (s, 1H), 8.89 (s, 1H), 8.83 (d, J=2.1 Hz, 1H), 8.44 (d, J=8.9 Hz, 1H), 8.22 (dd, J=8.9, 2.2 Hz, 1H), 6.67 (s, 1H), 4.77 (m, 1H), 3.86 (s, 3H), 3.06 (s, 6H), 2.42 (m, 2H), 2.00 (m, 4H), 1.68 (m, 2H); MS m/z 409.4 (M+H)$^+$.

Step 2

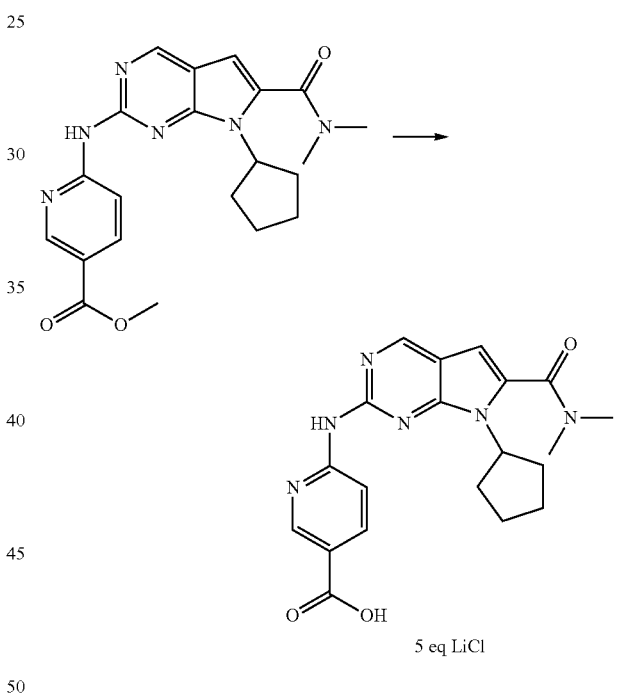

5 eq LiCl

Preparation of 6-(7-cyclopentyl-6-(dimethylcarbamoyl)-7H-pyrrolo[2,3-d]pyrimidin-2-ylamino)nicotinic acid LiCl salt To a suspension of methyl 6-(7-cyclopentyl-6-(dimethylcarbamoyl)-7H-pyrrolo[2,3-d]pyrimidin-2-ylamino)nicotinate (1.0 g, 2.4 mmol) in 2-propanol (60 mL) were added LIOH (0.29 g, 5.0 eq) and water (12 mL) and the resulting mixture was stirred at 60° C. for 1 h. the suspension became clear gradually. After cooling to room temperature, the reaction mixture was treated with 1N HCl (12.24 mL, 5 eq) and concentrated in vacuo. Light yellow solid (1.40 g, 95% yield) of a mixture of 6-(7-cyclopentyl-6-(dimethylcarbamoyl)-7H-pyrrolo[2,3-d]pyrimidin-2-ylamino)nicotinic acid and LiCl (5 equiv) was used for the next reaction without further purification. $^1$H NMR (400 MHz, DMSO-d6) δ ppm 13.30 (br s, 1H), 11.24 (br s, 1H), 9.03 (s, 1H), 8.88 (d, J=2.2 Hz, 1H), 8.31 (dd, J=8.7, 2.2 Hz, 1H), 8.11 (d, J=8.7 Hz, 1H), 6.81 (s, 1H), 4.79 (m, 1H), 3.06 (s, 6H), 2.41 (m, 2H), 2.02 (m, 4H), 1.67 (m, 2H); MS ink 395.4 (M+H)$^+$.

Intermediate 7

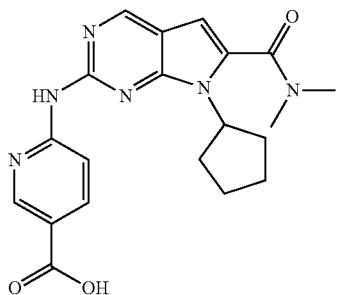 [SMILES: CN(C)C(=O)c1cc2cnc(Nc3ccc(C(=O)O)cn3)nc2n1C1CCCC1]

Preparation of 6-(7-cyclopentyl-6-(dimethylcarbamoyl)-7H-pyrrolo[2,3-d]pyrimidin-2-ylamino) nicotinic acid To a suspension of methyl 6-(7-cyclopentyl-6-(dimethylcarbamoyl)-7H-pyrrolo[2,3-d]pyrimidin-2-ylamino)nicotinate (2.0 g, 4.9 mmol) in THF (6 mL) was added 1M LiOH (aq) (6 mL, 1.2 equiv) and the slurry stirred at 45° C. for 12 hours (the slurry became clear). After cooling to room temperature, the THF was evaporated and the reaction mixture was treated with 1N HCl until pH=1-2. The resulting precipitate was filtered and the filtrate extracted with 20% Isopropanol/CH$_2$Cl$_2$ (3×100 mL), the combined organic layers dried, filtered, and concentrated to a tan solid. The tan solid was triturated in acetone giving 6-(7-cyclopentyl-6-(dimethylcarbamoyl)-7H-pyrrolo[2,3-d]pyrimidin-2-ylamino) nicotinic acid as the desired product as a tan solid (1.56 g, 73% yield) which was used without further purification.

$^1$H NMR (400 MHz, DMSO-d$_6$) δ 10.75 (br. s, 1H), 8.95 (s, 1H), 8.84 (d, J=2.5 Hz, 1H), 8.24-8.33 (m, 1H), 8.13-8.24 (m, 1H), 6.74 (s, 1H), 4.79 (quin, J=8.8 Hz, 1H), 3.06 (s, 1H), 2.30-2.46 (m, 3H), 1.90-2.09 (m, 5H), 1.48-1.76 (m, 3H), 1.04 (d, J=6.1 Hz, 1H); MS m/z 395.5 (M+H)$^+$ Intermediate 8

Following the procedure for the preparation of intermediate one, 2-chloro-7-(4-(2-cyanopropan-2-yl)phenyl)-N,N-dimethyl-7H-pyrrolo[2,3-d]pyrimidine-6-carboxamide was prepared in a similar manner to intermediate 1

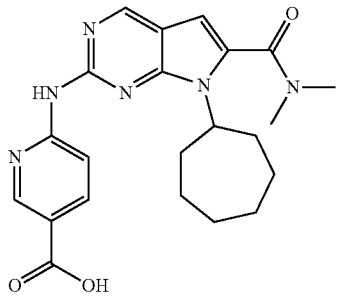 [SMILES: CN(C)C(=O)c1cc2cnc(Nc3ccc(C(=O)O)cn3)nc2n1C1CCCCCC1]

6-(7-Cycloheptyl-6-dimethylcarbamoyl-7H-pyrrolo[2,3-d]pyrimidin-2-ylamino)-nicotinic acid Step 1

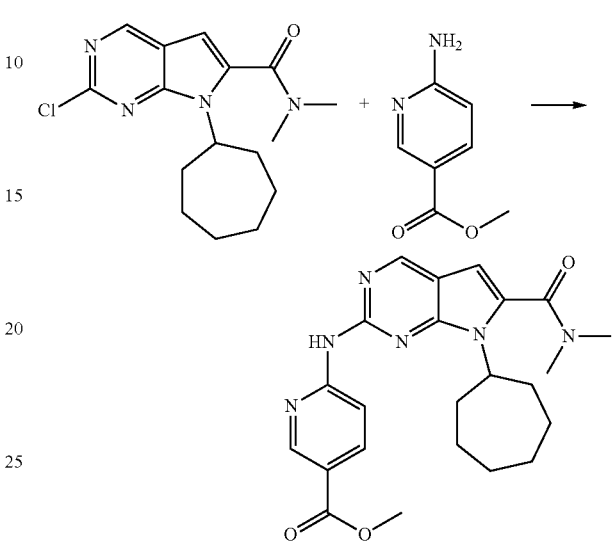

To a mixture of 2-Chloro-7-cycloheptyl-7H-pyrrolo[2,3-d]pyrimidine-6-carboxylic acid dimethylamide (517 mg, 1.2 mmol, 1.0 eq), 6-Amino-nicotinic acid methyl ester (221 mg, 1.5 mmol, 1.2 eq), Cs$_2$CO$_3$ (591 mg, 1.8 mmol, 1.5 eq) and BINAP (38 mg, 0.06 mmol, 0.05 eq) was bubbled in N$_2$ via a pipette for 3 min. Pd(OAc)$_2$ (14 mg, 0.06 mmol, 0.05 eq) was added and the flask was sealed and stirred in an oil bath heated to 130° C. for 3 hr. The mixture was filtered through a pad of celite and washed with etOAc. The organic layer was washed with water, then brine and the organic layers combined, dried over Na$_2$SO$_4$. The solvent was evaporated and the brown solid was triturated with acetonitrile, filtered, washed with ACN and dried under high vacuum to yield the title compound as a light pink solid (236 mg, 0.53 mmol, 44% yield). $^1$H NMR (400 MHz, chloroform-d) δ ppm 8.84-8.90 (m, 1H) 8.69 (s, 1H) 8.61 (d, J=9.09 Hz, 1H) 8.51 (br s, 1H) 8.20-8.26 (m, 1H) 6.40 (s, 1H) 4.40-4.53 (m, 1H) 3.87 (s, 3H) 3.10 (s, 6H) 2.48-2.64 (m, 2H) 1.90-2.00 (m, 2H) 1.76-1.86 (m, 2H) 1.63-1.72 (m, 4H) 1.45-1.56 (m, 2H). MS (m/z, MH+): 437.5

Step 2

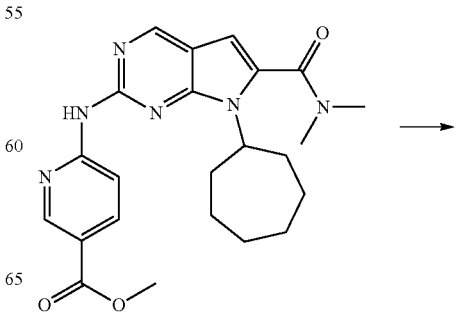

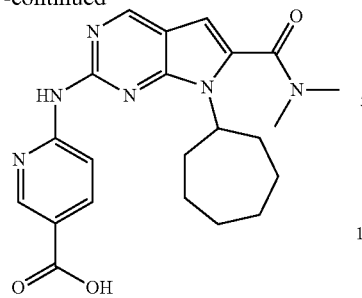

Preparation of 6-(7-Cycloheptyl-6-dimethylcarbamoyl-7H-pyrrolo[2,3-d]pyrimidin-2-ylamino)-nicotinic acid To a solution of 6-(7-Cycloheptyl-6-dimethylcarbamoyl-7H-pyrrolo[2,3-d]pyrimidin-2-ylamino)-nicotinic acid methyl ester (146 mg, 0.33 mmol, 1.0 eq) in THF (1.5 mL) was added LiOH (94.7 mg, 4.0 mmol, 12 eq) in 1.5 mL of water. The mixture was stirred at room temperature for 48 h. The reaction mixture was cooled to 0° C. in an ice bath and was acidified with 1N HCl until pH was about 1-2. The solid precipitate was filtered and washed to give the title compound as a light pink solid (52 mg, 0.124 mmol, 37%) and used as is; alternatively it can be extracted out with 20% Isopropanol in dichloromethane) $^1$H NMR (400 MHz, DMSO-$d_6$) δ ppm 12.99 (br s, 1H) 10.38 (br s, 1H) 8.87 (s, 1H) 8.81 (d, J=2.01 Hz, 1H) 8.53 (d, J=9.03 Hz, 1H) 8.19 (dd, J=9.03, 2.01 Hz, 1H) 6.67 (s, 1H) 4.44 (br s, 1H) 3.07 (d, J=13.05 Hz, 6H) 2.54-2.60 (m, 2H) 1.87-1.98 (m, 2H) 1.75-1.87 (m, 2H) 1.59-1.75 (m, 4H) 1.49 (m, 2H). MS (m/z, MH+): 423.5

Intermediate 9

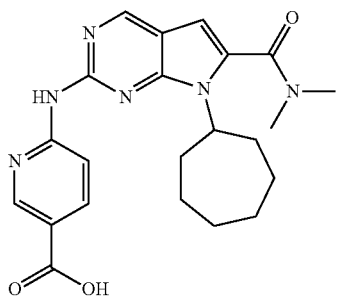

5 eq LiCl

Following the procedure for the preparation of intermediate 6,6-(7-cycloheptyl-6-(dimethylcarbamoyl)-7H-pyrrolo[2,3-d]pyrimidin-2-ylamino)nicotinic acid and 5 equiv LiCl was prepared in a similar manner to intermediate 6. $^1$H NMR (400 MHz, DMSO-d6) δ ppm 9.70 (br s, 1H), 8.81 (s, 1H), 8.71 (s, 1H), 8.42 (d, J=8.53 Hz, 1H), 8.10 (dd, J1=8.53, J2=2.01 Hz, 1H), 6.63 (s, 1H), 4.41 (m, 1H), 3.07 (d, 6H), 2.70-2.52 (m, 2H), 1.99-1.39 (m, 10H)

MS m/z 422.9 (M+H)$^+$.

EXAMPLES

Example 1

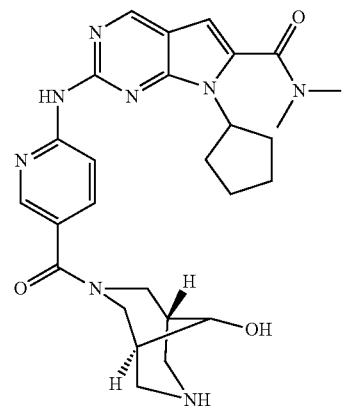 [SMILES: CN(C)C(=O)c1cc2cnc(Nc3ccc(C(=O)N4C[C@H]5CNC[C@@H](C4)C5O)cn3)nc2n1C1CCCC1]

7-Cyclopentyl-2-(5-((1R,5S)-9-hydroxy-3,7-diazabicyclo[3.3.1]nonane-3-carbonyl)pyridin-2-ylamino)-N,N-dimethyl-7H-pyrrolo[2,3-d]pyrimidine-6-carboxamide

Step 1

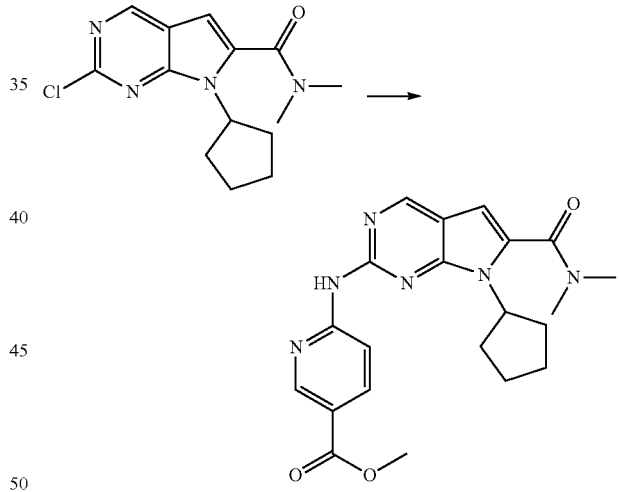

Preparation of Methyl 6-(7-cyclopentyl-6-(dimethylcarbamoyl)-7H-pyrrolo[2,3-d]pyrimidin-2-ylamino) nicotinate Following general N—C coupling procedure 1, 2-chloro-7-cyclopentyl-N,N-dimethyl-7H-pyrrolo[2,3-d]pyrimidine-6-carboxamide (5.0 g, 17 mmol) was combined with methyl 6-aminonicotinate (2.86 g, 1.10 eq) which gave methyl 6-(7-cyclopentyl-6-(dimethylcarbamoyl)-7H-pyrrolo[2,3-d]pyrimidin-2-ylamino)nicotinate (6.6 g) in 94% yield. $^1$H NMR (400 MHz, DMSO-d6) δ ppm 10.33 (s, 1H), 8.89 (s, 1H), 8.83 (d, J=2.1 Hz, 1H), 8.44 (d, J=8.9 Hz, 1H), 8.22 (dd, J=8.9, 2.2 Hz, 1H), 6.67 (s, 1H), 4.77 (m, 1H), 3.86 (s, 3H), 3.06 (s, 6H), 2.42 (m, 2H), 2.00 (m, 4H), 1.68 (m, 2H); MS m/z 409.4 (M+H)$^+$.

Step 2

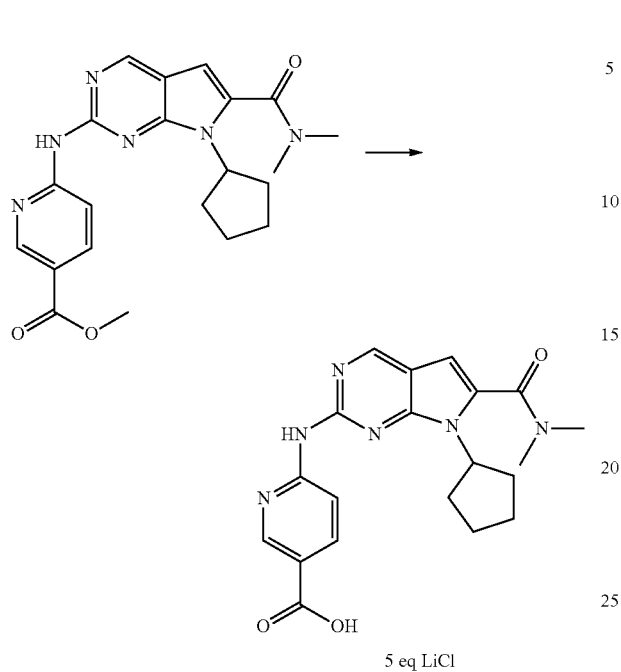

5 eq LiCl

Preparation of 6-(7-cyclopentyl-6-(dimethylcarbamoyl)-7H-pyrrolo[2,3-d]pyrimidin-2-ylamino)nicotinic acid and 5 equiv LiCl To a suspension of methyl 6-(7-cyclopentyl-6-(dimethylcarbamoyl)-7H-pyrrolo[2,3-d]pyrimidin-2-ylamino)nicotinate (1.0 g, 2.4 mmol) in 2-propanol (60 mL) were added LiOH (0.29 g, 5.0 eq) and water (12 mL) and the resulting mixture was stirred at 60° C. for 1 h. After cooling to room temperature, the reaction mixture was treated with 1N HCl (12.24 mL, 5 eq) and concentrated in vacuo which gave 6-(7-cyclopentyl-6-(dimethylcarbamoyl)-7H-pyrrolo[2,3-d]pyrimidin-2-ylamino)nicotinic acid as a light yellow solid (1.40 g) in 95% yield as the LiCl (5 equiv) co-salt and was used for the next reaction without further purification. $^1$H NMR (400 MHz, DMSO-d6) δ ppm 13.30 (br s, 1H), 11.24 (br s, 1H), 9.03 (s, 1H), 8.88 (d, J=2.2 Hz, 1H), 8.31 (dd, J=8.7, 2.2 Hz, 1H), 8.11 (d, J=8.7 Hz, 1H), 6.81 (s, 1H), 4.79 (m, 1H), 3.06 (s, 6H), 2.41 (m, 2H), 2.02 (m, 4H), 1.67 (m, 2H); MS m/z 395.4 (M+H)$^+$.

Step 3

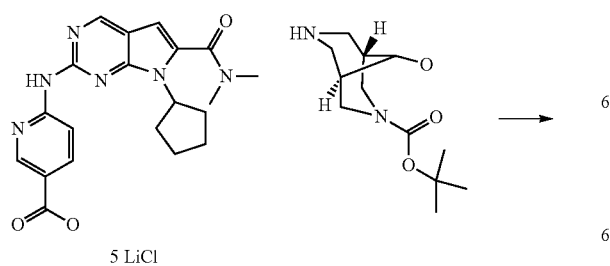

5 LiCl

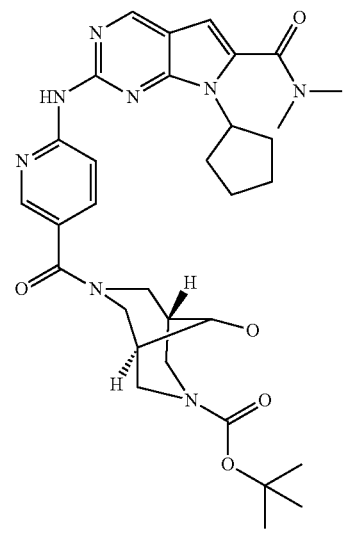

Following general amide formation method 1, 6-(7-cyclopentyl-6-(dimethylcarbamoyl)-7H-pyrrolo[2,3-d]pyrimidin-2-ylamino)nicotinic acid with 5 equiv LiCl was combined with (1R,5S)-tert-butyl 9-hydroxy-3,7-diazabicyclo[3.3.1]nonane-3-carboxylate which gave (1R,5S)-tert-butyl 7-(6-(7-cyclopentyl-6-(dimethylcarbamoyl)-7H-pyrrolo[2,3-d]pyrimidin-2-ylamino)nicotinoyl)-9-hydroxy-3,7-diazabicyclo[3.3.1]nonane-3-carboxylate (158 mg) in 77% yield. $^1$H NMR (400 MHz, CDCl$_3$) δ ppm 8.76 (s, 1H), 8.56 (d, J=8.59 Hz, 1H), 8.41 (s, 1H), 8.28 (br s, 1H), 7.92 (d, J=7.07 Hz, 1H), 6.47 (s, 1H), 4.80 (m, 1H), 4.67-4.29 (m, 2H), 4.14-3.68 (m, 3H), 3.48 (m, 1H), 3.24-2.99 (m, 7H), 2.60 (m, 2H), 2.26-1.54 (m, 10H), 1.49 (s, 9H); LCMS m/z 619.0 (M+H)$^+$.

Step 4

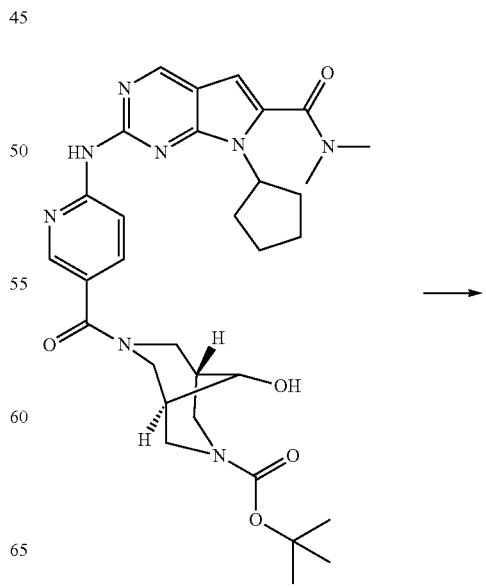

-continued

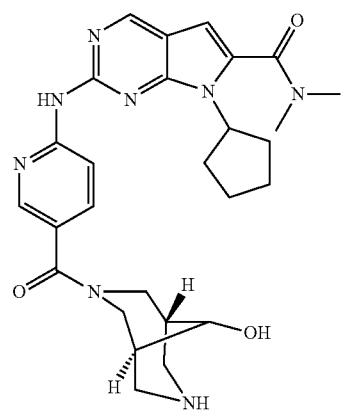

Preparation of 7-Cyclopentyl-2-(5-(((1R,5S)-9-hydroxy-3,7-diazabicyclo[3.3.1]nonane-3-carbonyl)pyridin-2-ylamino)-N,N-dimethyl-7H-pyrrolo[2,3-d]pyrimidine-6-carboxamide Following deprotection method 2, (1R,5S)-tert-butyl 7-(6-(7-cyclopentyl-6-(dimethylcarbamoyl)-7H-pyrrolo[2,3-d]pyrimidin-2-ylamino)nicotinoyl)-9-hydroxy-3,7-diazabicyclo[3.3.1]nonane-3-carboxylate was converted to 7-Cyclopentyl-2-(5-(((1R,5S)-9-hydroxy-3,7-diazabicyclo[3.3.1]nonane-3-carbonyl)pyridin-2-ylamino)-N,N-dimethyl-7H-pyrrolo[2,3-d]pyrimidine-6-carboxamide (47 mg) in 93% yield. $^1$H NMR (400 MHz, CDCl$_3$) δ ppm 9.04 (s, 1H), 8.85 (s, 1H), 8.60 (d, J=8.59 Hz, 1H), 8.50 (s, 1H), 7.83 (dd, J1=8.84 Hz, J2=2.27 Hz, 1H), 6.49 (s, 1H), 4.91-4.33 (m, 2H), 4.16-3.10 (m, 12H), 3.10-2.36 (m, 5H), 2.28-1.53 (m, 8H); HRMS m/z 519.2849 (M+H)$^+$.

Example 2

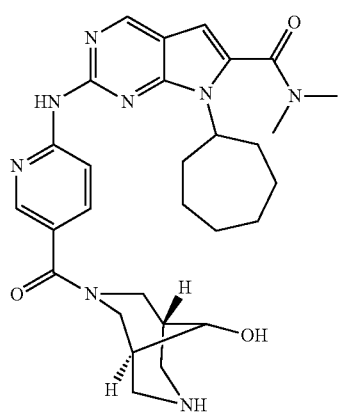 [SMILES: CN(C)C(=O)c1cc2cnc(Nc3ccc(C(=O)N4C[C@H]5CNC[C@@H](C4)C5O)cn3)nc2n1C1CCCCCC1]

7-cycloheptyl-2-(5-(((1R,5S)-9-hydroxy-3,7-diazabicyclo[3.3.1]nonane-3-carbonyl)pyridin-2-ylamino)-N,N-dimethyl-7H-pyrrolo[2,3-d]pyrimidine-6-carboxamide Step 1

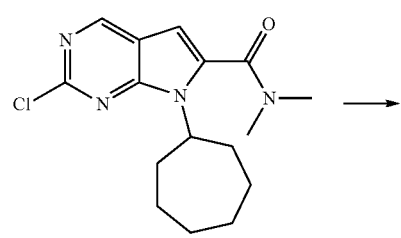

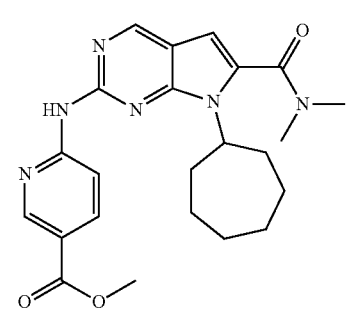

Preparation of 6-(7-cycloheptyl-6-(dimethylcarbamoyl)-7H-pyrrolo[2,3-d]pyrimidin-2-ylamino)nicotinic acid-5 LiCl Following step 1 in the preparation of EXAMPLE 1, in an analogous manner, 6-(7-cycloheptyl-6-dimethylcarbamoyl-7H-pyrrolo[2,3-d]pyrimidin-2-ylamino)-nicotinic acid methyl ester (1.34 g) was obtained in 52% yield. $^1$H NMR (400 MHz, CDCl3) δ ppm 8.95 (d, J=2.0 Hz, 1H), 8.77 (s, 1H), 8.71 (d, J=8.6 Hz, 1H), 8.33 (dd, J=8.8, 2.1 Hz, 1H), 6.50 (s, 1H), 4.55 (m, 1H), 3.97 (s, 3H), 3.29 (s, 6H), 2.65 (m, 2H), 2.04 (m, 2H), 1.91 (m, 2H), 1.83-1.70 (m, 4H), 1.60 (m, 2H); MS m/z 437.5 (M+H)$^+$.

Step 2

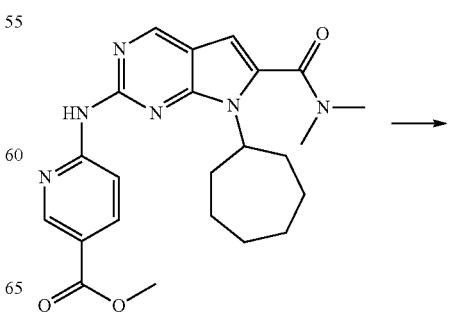

-continued

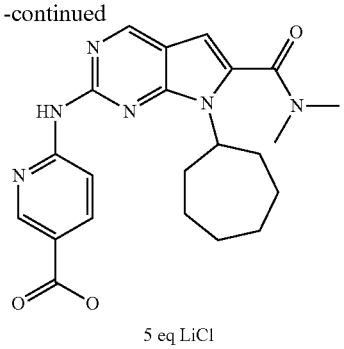

5 eq LiCl

Preparation of 6-(7-cycloheptyl-6-(dimethylcarbamoyl)-7H-pyrrolo[2,3-d]pyrimidin-2-ylamino)nicotinic acid and 5 equiv LiCl Following step 2 in the preparation of example 1, in an analogous manner, 6-(7-cycloheptyl-6-(dimethylcarbamoyl)-7H-pyrrolo[2,3-d]pyrimidin-2-ylamino)nicotinic acid-5 equiv LiCl (1.87 g) was obtained in quantitative yield. $^1$H NMR (400 MHz, DMSO-d6) δ ppm 9.70 (br s, 1H), 8.81 (s, 1H), 8.71 (s, 1H), 8.42 (d, J=8.53 Hz, 1H), 8.10 (dd, J1=8.53, J2=2.01 Hz, 1H), 6.63 (s, 1H), 4.41 (m, 1H), 3.07 (d, 6H), 2.70-2.52 (m, 2H), 1.99-1.39 (m, 10H); MS m/z 422.9 (M+H)$^+$.

Step 3

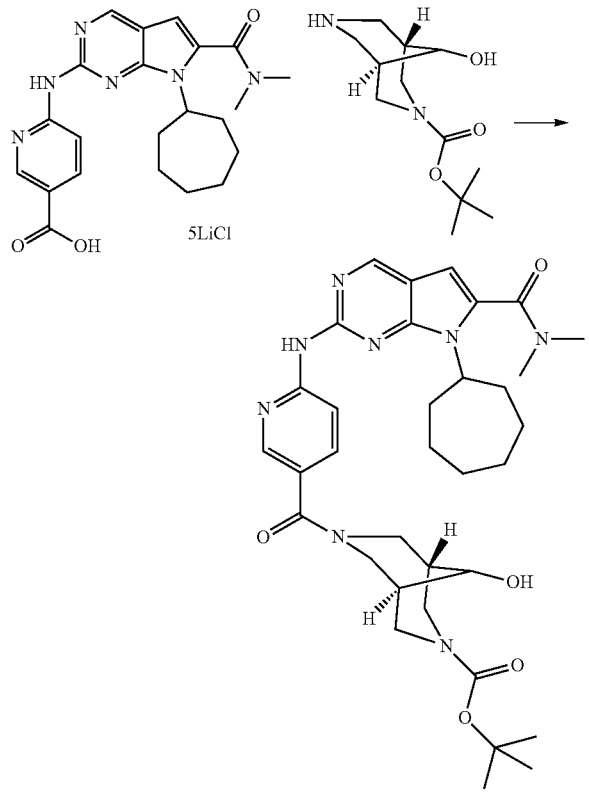

Preparation of 7-cycloheptyl-2-(5-((1R,5S)-9-hydroxy-3,7-diazabicyclo[3.3.1]nonane-3-carbonyl)pyridin-2-ylamino)-N,N-dimethyl-7H-pyrrolo[2,3-d]pyrimidine-6-carboxamide Following general amide formation method 1, 6-(7-cycloheptyl-6-(dimethylcarbamoyl)-7H-pyrrolo[2,3-d]pyrimidin-2-ylamino)nicotinic acid with 5 equiv LiCl was combined with (1R,5S)-tert-butyl 9-hydroxy-3,7-diazabicyclo[3.3.1]nonane-3-carboxylate which gave (1R,5S)-tert-butyl 7-(6-(7-cycloheptyl-6-(dimethylcarbamoyl)-7H-pyrrolo[2,3-d]pyrimidin-2-ylamino)nicotinoyl)-9-hydroxy-3,7-diazabicyclo[3.3.1]nonane-3-carboxylate (170 mg) in 83% yield. $^1$H NMR (400 MHz, CDCl$_3$) δ ppm 8.75 (s, 1H), 8.67 (d, J=8.59 Hz, 1H), 8.42 (s, 1H), 8.31 (br s, 1H), 7.92 (d, J=8.08 Hz, 1H), 6.46 (s, 1H), 4.74-3.40 (m, 7H), 3.22-2.94 (m, 7H), 2.65 (m, 2H), 2.16-1.54 (m, 13H), 1.49 (s, 9H); LCMS m/z 647.1 (M+H)$^+$.

Step 4

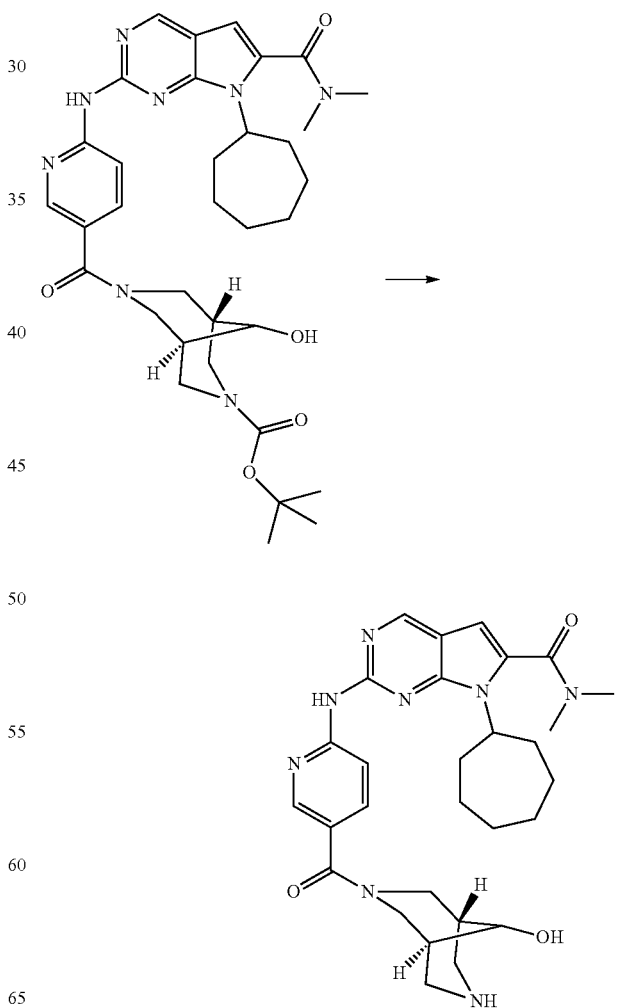

Preparation of 7-cycloheptyl-2-(5-((1R,5S)-9-hydroxy-3,7-diazabicyclo[3.3.1]nonane-3-carbonyl)pyridin-2-ylamino)-N,N-dimethyl-7H-pyrrolo[2,3-d]pyrimidine-6-carboxamide Following deprotection method 2, (1R,5S)-tert-butyl 7-(6-(7-cycloheptyl-6-(dimethylcarbamoyl)-7H-pyrrolo[2,3-d]pyrimidin-2-ylamino)nicotinoyl)-9-hydroxy-3,7-diazabicyclo[3.3.1]nonane-3-carboxylate was converted to 7-cycloheptyl-2-(5-((1R,5S)-9-hydroxy-3,7-diazabicyclo[3.3.1]nonane-3-carbonyl)pyridin-2-ylamino)-N,N-dimethyl-7H-pyrrolo[2,3-d]pyrimidine-6-carboxamide (43 mg) in 96% yield. $^1$H NMR (400 MHz, CDCl$_3$) δ ppm 9.34 (s, 1H), 8.88 (m, 1H), 8.74 (m, 1H), 8.54 (m, 1H), 7.85 (dd, J1=8.59 Hz, J2=2.02 Hz, 1H), 6.48 (s, 1H), 4.80-4.38 (m, 2H), 4.17-3.09 (m, 12H), 3.07-2.52 (m, 5H), 2.23-1.50 (m, 12H); HRMS m/z 547.3161 (M+H)$^+$.

Example 3

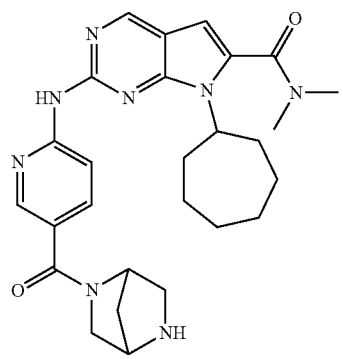 [SMILES: CN(C)C(=O)c1cc2cnc(Nc3ccc(C(=O)N4CC5CC4CN5)cn3)nc2n1C1CCCCCC1]

7-Cycloheptyl-2-[5-(2,5-diaza-bicyclo[2.2.1]heptane-2-carbonyl)-pyridin-2-ylamino]-7H-pyrrolo[2,3-d]pyrimidine-6-carboxylic acid dimethylamide Step 1

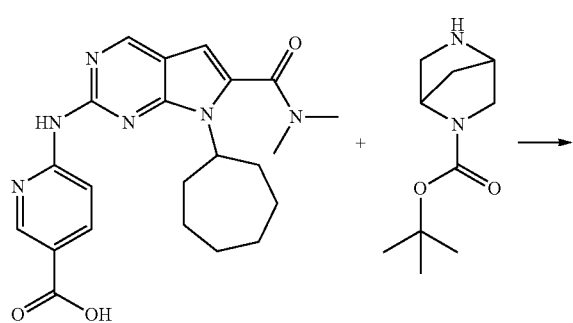

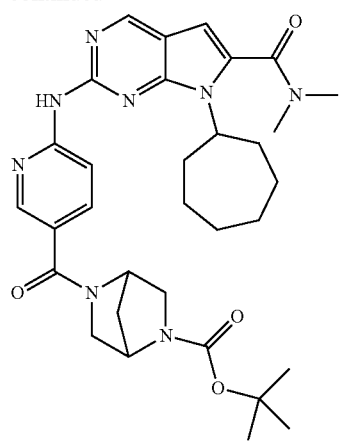

Preparation of 5-[6-(7-Cycloheptyl-6-dimethylcarbamoyl-7H-pyrrolo[2,3-d]pyrimidin-2-ylamino)-pyridine-3-carbonyl]-2,5-diaza-bicyclo[2.2.1]heptane-2-carboxylic acid tert-butyl ester Following general amide formation method 1, 6-(7-Cycloheptyl-6-dimethylcarbamoyl-7H-pyrrolo[2,3-d]pyrimidin-2-ylamino)-nicotinic acid (52.5 mg, 0.124 mmol, 1.0 eq) was combined with 2,5-Diaza-bicyclo[2.2.1]heptane-2-carboxylic acid tert-butyl ester (32.0 mg, 0.162 mmol, 1.5 eq) which gave 5-[6-(7-Cycloheptyl-6-dimethylcarbamoyl-7H-pyrrolo[2,3-d]pyrimidin-2-ylamino)-pyridine-3-carbonyl]-2,5-diaza-bicyclo[2.2.1]heptane-2-carboxylic acid tert-butyl ester (59 mg, 0.09 mmol, 76% yield). $^1$H NMR (400 MHz, chloroform-d) δ ppm 9.12 (br s, 1H) 8.85 (s, 1H) 8.73 (br s, 1H) 8.61 (br s, 1H) 7.98 (br s, 1H) 6.48 (s, 1H) 4.47-4.65 (m, 2H) 3.72 (br s, 1H) 3.52-3.69 (m, 2H) 3.46 (t, J=8.59 Hz, 1H) 3.18 (s, 6H) 2.58-2.74 (m, 2H) 1.99-2.09 (m, 2H) 1.83-1.99 (m, 5H) 1.65-1.83 (m, 4H) 1.55-1.65 (m, 2H) 1.37-1.55 (m, 9H)

MS (m/z, MH+): 603.6

Step 2

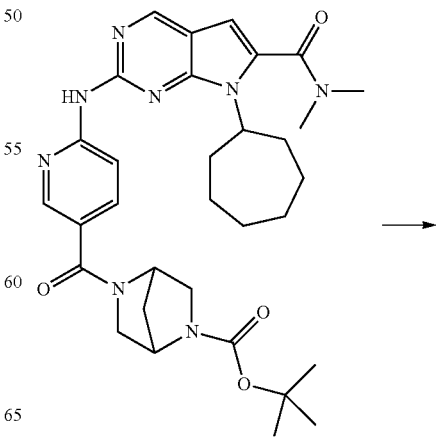

59

-continued

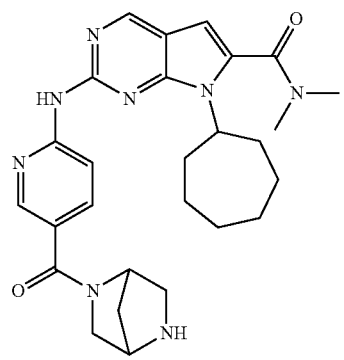

Preparation of 7-Cycloheptyl-2-[5-(2,5-diaza-bicyclo [2.2.1]heptane-2-carbonyl)-pyridin-2-ylamino]-7H-pyrrolo[2,3-d]pyrimidine-6-carboxylic acid dimethylamide Following deprotection method 1, 5-[6-(7-Cycloheptyl-6-dimethylcarbamoyl-7H-pyrrolo[2,3-d]pyrimidin-2-ylamino)-pyridine-3-carbonyl]-2,5-diaza-bicyclo[2.2.1]heptane-2-carboxylic acid tert-butyl ester (50 mg, 0.083 mmol, 1.0 eq) was converted to 7-Cycloheptyl-2-[5-(2,5-diaza-bicyclo[2.2.1]heptane-2-carbonyl)-pyridin-2-ylamino]-7H-pyrrolo[2,3-d]pyrimidine-6-carboxylic acid dimethylamide as a white solid (24 mg, 0.05 mmol) in 57% yield. $^1$H NMR (400 MHz, chloroform-d) δ ppm 8.89 (br s, 1H) 8.83 (br s, 1H) 8.65-8.78 (m, 1H) 8.51-8.65 (m, 1H) 7.89-8.05 (m, 1H) 6.48 (s, 1H) 4.52 (br s, 2H) 3.84-3.97 (m, 1H) 3.66-3.85 (m, 1H) 3.40-3.54 (m, 1H) 3.24-3.40 (m, 1H) 3.19 (s, 6H) 2.67 (d, J=11.54 Hz, 2H) 2.03 (s, 3H) 1.83-1.99 (m, 5H) 1.64-1.83 (m, 4H) 1.50-1.65 (m, 2H); HR-MS (m/z, MH+): 503.2071.

Example 4

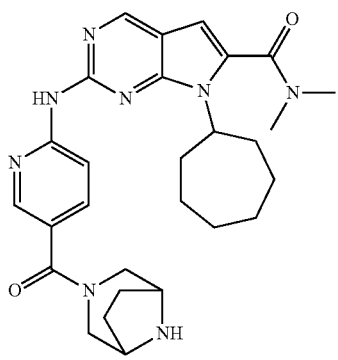 [SMILES: CN(C)C(=O)c1cc2cnc(Nc3ccc(C(=O)N4CC5CCC(C4)N5)cn3)nc2n1C1CCCCCC1]

60

2-(5-(3,8-diazabicyclo[3.2.1]octane-3-carbonyl)pyridin-2-ylamino)-7-cycloheptyl-N,N-dimethyl-7H-pyrrolo[2,3-d]pyrimidine-6-carboxamide Step 1

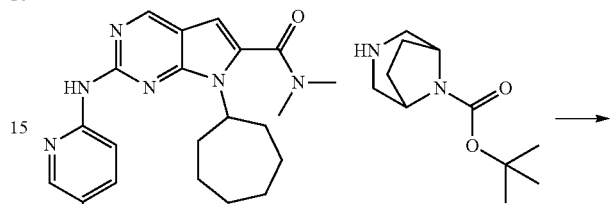

Preparation of tert-butyl 3-(6-(7-cycloheptyl-6-(dimethylcarbamoyl)-7H-pyrrolo[2,3-d]pyrimidin-2-ylamino)nicotinoyl)-3,8-diazabicyclo[3.2.1]octane-8-carboxylate Following amide formation method 1, 6-(7-Cycloheptyl-6-dimethylcarbamoyl-7H-pyrrolo[2,3-d]pyrimidin-2-ylamino)-nicotinic acid (75 mg, 0.178 mmol, 1.0 eq) was combined with tert-butyl 3,8-diazabicyclo[3.2.1]octane-8-carboxylate (37.7 mg, 0.18 mmol, 1.0 eq) to give tert-butyl 3-(6-(7-cycloheptyl-6-(dimethylcarbamoyl)-7H-pyrrolo[2,3-d]pyrimidin-2-ylamino)nicotinoyl)-3,8-diazabicyclo[3.2.1]octane-8-carboxylate as a white solid (80 mg, 0.130 mmol, 73% yield). $^1$H NMR (400 MHz, chloroform-d) δ ppm 8.76 (s, 1H) 8.68 (d, J=8.59 Hz, 1H) 8.42-8.57 (m, 1H) 8.40 (d, J=2.02 Hz, 1H) 7.83 (dd, J=8.59, 2.02 Hz, 1H) 6.49 (s, 1H) 4.46-4.62 (m, 2H) 4.29 (br s, 2H) 3.19 (s, 6H) 2.56-2.73 (m, 2H) 1.84-2.12 (m, 8H) 1.65-1.84 (m, 6H) 1.54-1.65 (m, 3H) 1.52 (s, 9H); MS (m/z, MH+): 617.7.

61

Step 2

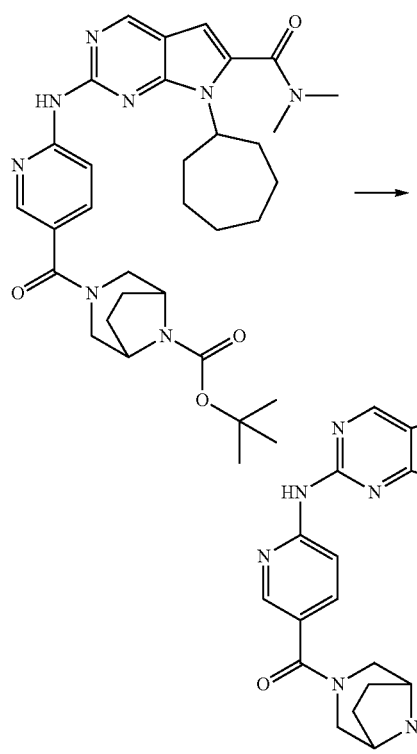

Preparation of 2-(5-(3,8-diazabicyclo[3.2.1]octane-3-carbonyl)pyridin-2-ylamino)-7-cycloheptyl-N,N-dimethyl-7H-pyrrolo[2,3-d]pyrimidine-6-carboxamide Following deprotection method 1, tert-butyl 3-(6-(7-cycloheptyl-6-(dimethylcarbamoyl)-7H-pyrrolo[2,3-d]pyrimidin-2-ylamino)nicotinoyl)-3,8-diazabicyclo[3.2.1]octane-8-carboxylate was converted to 2-(5-(3,8-diazabicyclo[3.2.1]octane-3-carbonyl)pyridin-2-ylamino)-7-cycloheptyl-N,N-dimethyl-7H-pyrrolo[2,3-d]pyrimidine-6-carboxamide as a white solid (60 mg, 0.116 mmol) in 96% yield. $^1$H NMR (400 MHz, chloroform-d) δ ppm 8.68 (s, 1H) 8.60 (d, J=9.09 Hz, 1H) 8.32 (d, J=2.02 Hz, 1H) 8.20 (s, 1H) 7.73 (dd, J=8.84, 2.27 Hz, 1H) 6.39 (s, 1H) 4.33-4.57 (m, 2H) 3.10 (s, 6H) 2.45-2.68 (m, 2H) 1.86-2.00 (m, 3H) 1.79 (br s, 7H) 1.56-1.73 (m, 7H) 1.40-1.56 (m, 3H); HR-MS (m/z, MH+): 517.3027.

Example 5

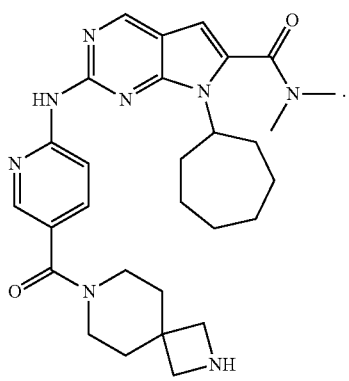 [SMILES: CN(C)C(=O)c1cc2cnc(Nc3ccc(C(=O)N4CCC5(CC4)CNC5)cn3)nc2n1C1CCCCCC1]

62

2-(5-(2,7-diazaspiro[3.5]nonane-7-carbonyl)pyridin-2-ylamino)-7-cycloheptyl-N,N-dimethyl-7H-pyrrolo[2,3-d]pyrimidine-6-carboxamide

Step 1

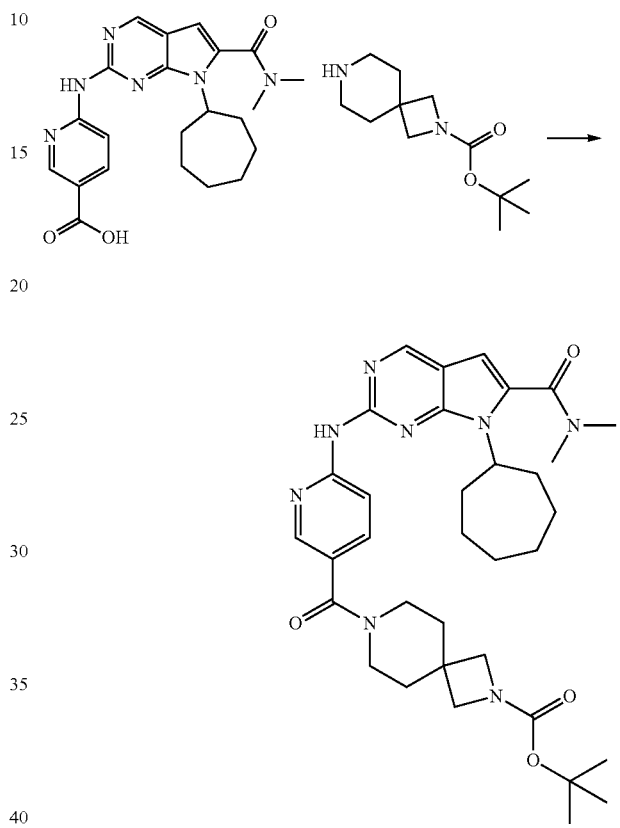

Preparation of tert-butyl 7-(6-(7-cycloheptyl-6-(dimethylcarbamoyl)-7H-pyrrolo[2,3-d]pyrimidin-2-ylamino)nicotinoyl)-2,7-diazaspiro[3.5]nonane-2-carboxylate Following general amide formation method 1, 6-(7-Cycloheptyl-6-dimethylcarbamoyl-7H-pyrrolo[2,3-d]pyrimidin-2-ylamino)-nicotinic acid (80 mg, 0.19 mmol, 1.0 eq) was combined with tert-butyl 2,7-diazaspiro[3.5]nonane-2-carboxylate (47.1 mg, 0.208 mmol, 1.1 eq) to afford tert-butyl 7-(6-(7-cycloheptyl-6-(dimethylcarbamoyl)-7H-pyrrolo[2,3-d]pyrimidin-2-ylamino)nicotinoyl)-2,7-diazaspiro[3.5]nonane-2-carboxylate as a white solid (22 mg, 0.035 mmol) in 18.4% yield. $^1$H NMR (400 MHz, chloroform-d) δ ppm 8.67 (s, 1H) 8.60 (d, J=8.59 Hz, 1H) 8.31 (d, J=2.02 Hz, 1H) 8.16-8.28 (m, 1H) 7.74 (dd, J=8.59, 2.53 Hz, 1H) 6.39 (s, 1H) 5.23 (s, 1H) 4.38-4.51 (m, 1H) 3.63 (s, 4H) 3.52 (br s, 2H) 3.10 (s, 6H) 2.48-2.66 (m, 2H) 1.86-2.03 (m, 2H) 1.56-1.85 (m, 9H) 1.42-1.56 (m, 4H) 1.38 (s, 9H). MS (m/z, MH+): 631.7

Step 2

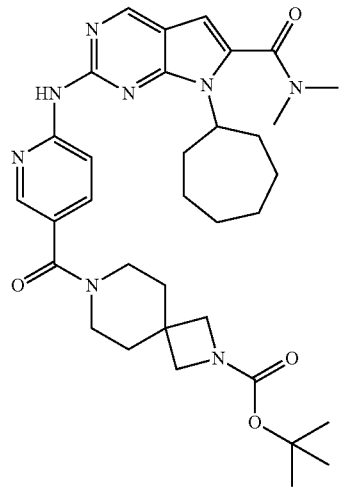

Preparation of 2-(5-(2,7-diazaspiro[3.5]nonane-7-carbonyl)pyridin-2-ylamino)-7-cycloheptyl-N,N-dimethyl-7H-pyrrolo[2,3-d]pyrimidine-6-carboxamide Following deprotection method 1, tert-butyl 7-(6-(7-cycloheptyl-6-(dimethylcarbamoyl)-7H-pyrrolo[2,3-d]pyrimidin-2-ylamino)nicotinoyl)-2,7-diazaspiro[3.5]nonane-2-carboxylate was converted to 2-(5-(2,7-diazaspiro[3.5]nonane-7-carbonyl)pyridin-2-ylamino)-7-cycloheptyl-N,N-dimethyl-7H-pyrrolo[2,3-d]pyrimidine-6-carboxamide as an off-white solid (25 mg, 0.05 mmol) in 69% yield. $^1$H NMR (400 MHz, chloroform-d) δ ppm 9.05 (s, 1H) 8.48-8.59 (m, 1H) 8.04-8.13 (m, 1H) 7.39-7.48 (m, 1H) 6.92 (s, 1H) 4.53-4.68 (m, 1H) 3.95 (s, 4H) 3.49-3.83 (m, 4H) 3.18 (d, J=3.54 Hz, 6H) 2.46-2.69 (m, 2H) 2.03 (s, 10H) 1.65-1.82 (m, 4H) 1.58 (none, 2H); HR-MS (m/z, MH+): 531.3199.

Example 6

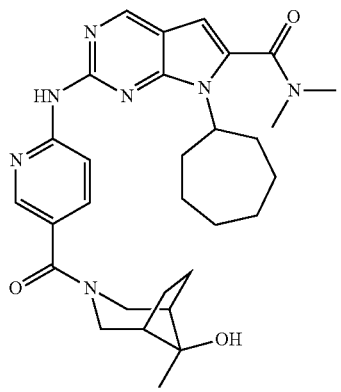 [SMILES: CN(C)C(=O)c1cc2cnc(Nc3ccc(C(=O)N4CC5CCC(C4)C5(C)O)cn3)nc2n1C1CCCCCC1]

7-cycloheptyl-2-(5-(8-hydroxy-8-methyl-3-azabicyclo[3.2.1]octane-3-carbonyl)pyridin-2-ylamino)-N,N-dimethyl-7H-pyrrolo[2,3-d]pyrimidine-6-carboxamide Step 1

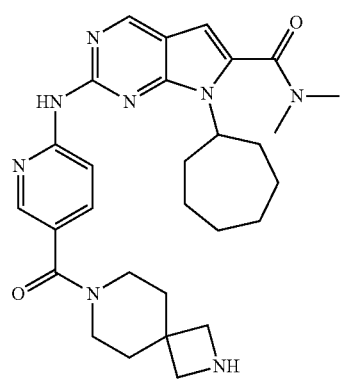

Preparation of 3-benzyl-8-methyl-3-azabicyclo[3.2.1]octan-8-ol 3-benzyl-3-azabicyclo[3.2.1]octan-8-one (200 mg, 0.93 mmol) was dissolved in Et2O (2 ml) and added to a solution of MeMgBr (3 ml 1M Et2O solution) in Et2O. The resulting reaction mixture was stirred at room temperature overnight. The mixture was diluted with Et2O and washed with sat. aq. NH4Cl solution and 1N NaOH. Aqueous layers were back-extracted with Et2O. The combined organic layers were dried over Na2SO4, filtered and concentrated which gave benzyl-8-methyl-3-azabicyclo[3.2.1]octan-8-ol (110 mg, 51% yield). 1H NMR (400 MHz, CDCl3) δ ppm 7.51-7.18 (m, 5H) 3.60 (br. s., 2H) 2.73 (d, J=10.11 Hz, 2H) 2.52 (d, J=9.60 Hz, 2H) 1.85 (br. s., 2H) 1.71 (br. s., 4H) 1.55 (br. s., 1H) 1.31 (s, 3H).

Step 2

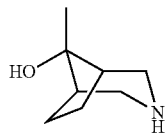

Preparation of 8-methyl-3-azabicyclo[3.2.1]octan-8-ol

A sample of 3-benzyl-8-methyl-3-azabicyclo[3.2.1]octan-8-ol (110 mg, 0.48 mmol) was dissolved in MeOH (20 ml) and the atmosphere was replaced with N2 (3×). 10% Pd/C (cat.) was added and the atmosphere was replaced with H2 (3×). The resulting reaction mixture was stirred at RT at balloon pressure overnight. When TLC showed no more UV active spot the Pd/C was filtered off (always keeping wet with MeOH) and the filtrate was concentrated which gave 8-methyl-3-azabicyclo[3.2.1]octan-8-ol (70 mg, 99% yield).

NMR shows no more benzyl. Used directly.

Step 3

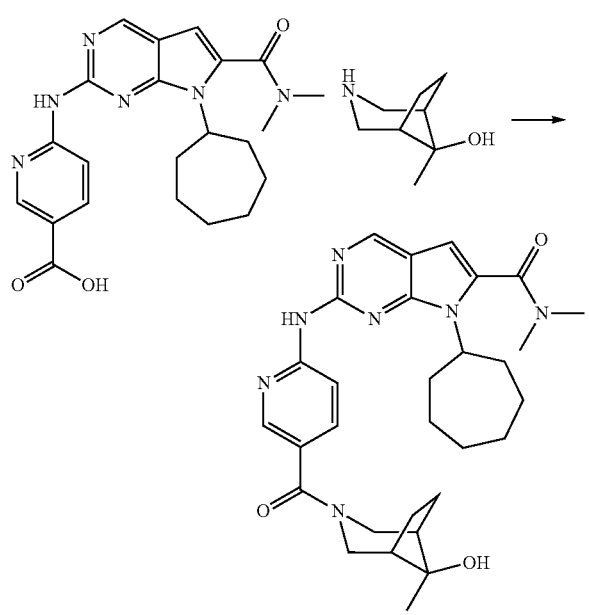

Preparation of 7-cycloheptyl-2-(5-(8-hydroxy-8-methyl-3-azabicyclo[3.2.1]octane-3-carbonyl)pyridin-2-ylamino)-N,N-dimethyl-7H-pyrrolo[2,3-d]pyrimidine-6-carboxamide Following general amide formation method 3, 6-(7-cycloheptyl-6-(dimethylcarbamoyl)-7H-pyrrolo[2,3-d]pyrimidin-2-ylamino)nicotinic acid was combined with 8-methyl-3-azabicyclo[3.2.1]octan-8-ol which gave 7-cycloheptyl-2-(5-(8-hydroxy-8-methyl-3-azabicyclo[3.2.1]octane-3-carbonyl)pyridin-2-ylamino)-N,N-dimethyl-7H-pyrrolo[2,3-d]pyrimidine-6-carboxamide (68 mg) in 26% yield. 1H NMR (400 MHz, CDCl3) δ ppm 9.65 (s, 1H) 8.93-8.86 (m, 1H) 8.68 (d, J=8.59 Hz, 1H) 8.55 (d, J=2.02 Hz, 1H) 7.82 (dd, J=8.84, 2.27 Hz, 1H) 6.52-6.39 (m, 1H) 4.45-4.60 (m, 1H) 4.39 (br. s., 1H) 3.96 (br. s., 1H) 3.63-3.39 (m, 2H) 3.15 (s, 6H) 2.76-2.51 (m, 3H) 2.14 (br. s., 1H) 2.07-1.93 (m, 2H) 1.85 (ddd, J=6.95, 3.41, 3.28 Hz, 3H) 1.80-1.61 (m, 7H) 1.61-1.48 (m, 2H) 1.48-1.36 (m, 1H) 1.30 (s, 3H); HR-MS (m/z MH+) 546.32 RT 3.99 min.

Example 7

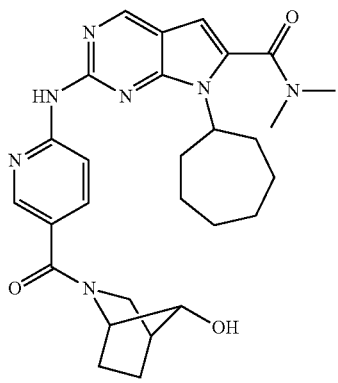 [SMILES: CN(C)C(=O)c1cc2cnc(Nc3ccc(C(=O)N4CC5CCC4C5O)cn3)nc2n1C1CCCCCC1]

7-cycloheptyl-2-(5-((1R,4R,7R)-7-hydroxy-2-azabicyclo[2.2.1]heptane-2-carbonyl)pyridin-2-ylamino)-N,N-dimethyl-7H-pyrrolo[2,3-d]pyrimidine-6-carboxamide Following general amide formation method 3, 6-(7-cycloheptyl-6-(dimethylcarbamoyl)-7H-pyrrolo[2,3-d]pyrimidin-2-ylamino)nicotinic acid was combined with (1R,4R,7R)-2-azabicyclo[2.2.1]heptan-7-ol which gave 7-cycloheptyl-2-(5-((1R,4R,7R)-7-hydroxy-2-azabicyclo[2.2.1]heptane-2-carbonyl)pyridin-2-ylamino)-N,N-dimethyl-7H-pyrrolo[2,3-d]pyrimidine-6-carboxamide (50 mg) in 77% yield.

1H NMR (400 MHz, CDCl3) δ ppm 9.79 (s, 0.8H, Rotamer) 9.58 (s, 0.2H, Rotamer) 8.93-8.82 (m, 1H) 8.76-8.55 (m, 2H) 7.90 (dd, J=8.84, 2.27 Hz, 1H) 6.45 (s, 1H) 4.59-4.439 (m, 1H) 4.41 (br. s., 0.2H, Rotamer) 4.27 (br. s., 0.2H, Rotamer) 4.20 (br. s., 0.8H, Rotamer) 4.06 (s, 0.8H, Rotamer) 3.73-3.57 (m, 2H) 3.07-3.39 (m, 7H) 2.75-2.54 (m, 2H) 2.42 (br. s., 0.8H, Rotamer) 2.35 (br. s., 0.2H, Rotamer) 2.20-1.93 (m, 4H) 1.93-1.63 (m, 7H) 1.62-1.42 (m, 3H); HR-MS (m/z MH+) 518.29 RT 3.66 min

Example 8

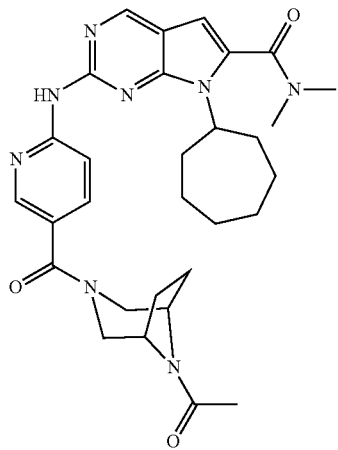 [SMILES: CC(=O)N1C2CCC1CN(C(=O)c1ccc(Nc3ncc4cc(C(=O)N(C)C)n(C5CCCCCC5)c4n3)nc1)C2]

2-(5-(8-acetyl-3,8-diazabicyclo[3.2.1]octane-3-carbonyl)pyridin-2-ylamino)-7-cycloheptyl-N,N-dimethyl-7H-pyrrolo[2,3-d]pyrimidine-6-carboxamide Following general amide formation method 3, 6-(7-cycloheptyl-6-(dimethylcarbamoyl)-7H-pyrrolo[2,3-d]pyrimidin-2-ylamino)nicotinic acid was combined with 1-(3,8-diazabicyclo[3.2.1]octan-8-yl)ethanone which gave 2-(5-(8-acetyl-3,8-diazabicyclo[3.2.1]octane-3-carbonyl)pyridin-2-ylamino)-7-cycloheptyl-N,N-dimethyl-7H-pyrrolo[2,3-d]pyrimidine-6-carboxamide (63 mg) in 88% yield. 1H NMR (400 MHz, CDCl3) δ ppm 9.69 (s, 1H) 8.90 (s, 1H) 8.72 (d, J=8.59 Hz, 1H) 8.51 (d, J=2.02 Hz, 1H) 7.78 (dd, J=8.84, 2.27 Hz, 1H) 6.46 (s, 1H) 4.71 (br. s., 1H) 4.51 (tt, J=11.12, 4.04 Hz, 1H) 4.16 (br. s., 1H) 3.24-3.10 (m, 7H) 2.70-2.55 (m, 2H) 2.18-2.06 (m, 4H) 2.01 (ddd, J=13.64, 7.07, 4.04 Hz, 4H) 1.95-1.79 (m, 5H) 1.79-1.62 (m, 5H) 1.62-1.49 (m, 2H). HR-MS (m/z MH+) 559.31 RT 3.89 min.

Example 9

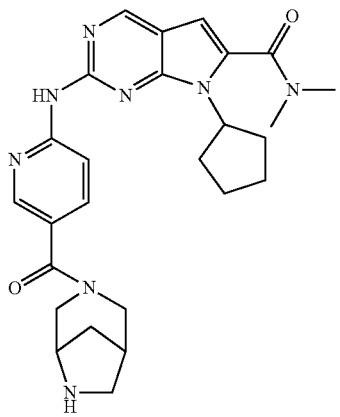 [SMILES: CN(C)C(=O)c1cc2cnc(Nc3ccc(C(=O)N4CC5CNC(C5)C4)cn3)nc2n1C1CCCC1]

7-Cyclopentyl-2-[5-(3,6-diaza-bicyclo[3.2.1]octane-3-carbonyl)-pyridin-2-ylamino]-7H-pyrrolo[2,3-d]pyrimidine-6-carboxylic acid dimethylamide Step 1

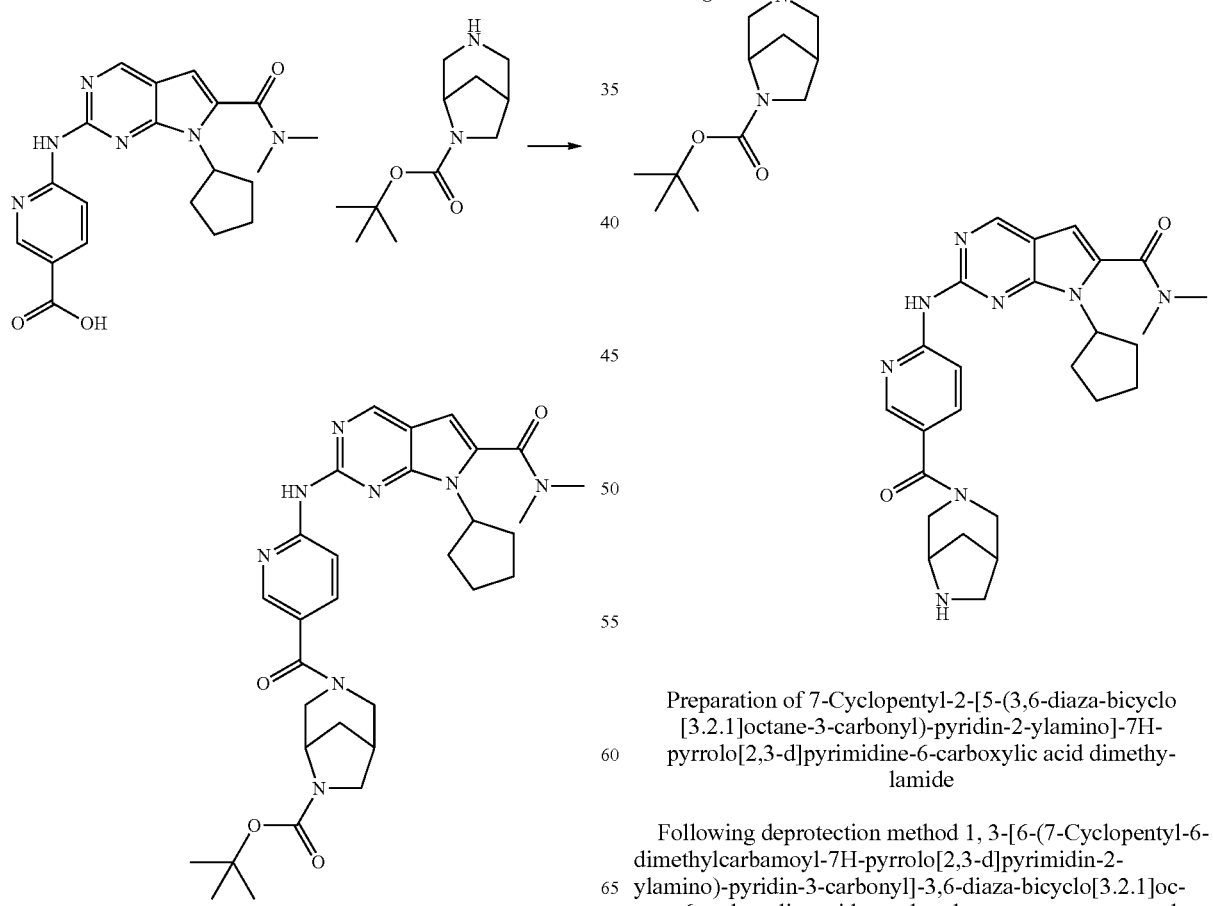

Preparation of 3-[6-(7-Cyclopentyl-6-dimethylcarbamoyl-7H-pyrrolo[2,3-d]pyrimidin-2-ylamino)-pyridine-3-carbonyl]-3,6-diaza-bicyclo[3.2.1]octane-6-carboxylic acid tert-butyl ester Following general amide formation method 1, 6-(7-Cyclopentyl-6-dimethylcarbamoyl-7H-pyrrolo[2,3-d]pyrimidin-2-ylamino)-nicotinic acid (in a salt form with 5 eq. of LiCl) (571 mg, 0.942 mmol) was combined with tert-butyl 3,6-diazabicyclo[3.2.1]octane-6-carboxylate (200 mg, 0.942 mmol) to give 446 mg of 3-[6-(7-Cyclopentyl-6-dimethylcarbamoyl-7H-pyrrolo[2,3-d]pyrimidin-2-ylamino)-pyridine-3-carbonyl]-3,6-diaza-bicyclo[3.2.1]octane-6-carboxylic acid tert-butyl ester in 80% yield. MS (ESI) m/e (M+H$^+$): 588.9.

Step 2

Preparation of 7-Cyclopentyl-2-[5-(3,6-diaza-bicyclo[3.2.1]octane-3-carbonyl)-pyridin-2-ylamino]-7H-pyrrolo[2,3-d]pyrimidine-6-carboxylic acid dimethylamide Following deprotection method 1, 3-[6-(7-Cyclopentyl-6-dimethylcarbamoyl-7H-pyrrolo[2,3-d]pyrimidin-2-ylamino)-pyridin-3-carbonyl]-3,6-diaza-bicyclo[3.2.1]octane-6-carboxylic acid tert-butyl ester was converted to 7-cyclopentyl-2-[5-(3,6-diaza-bicyclo[3.2.1]octane-3-carbonyl)-pyridin-2-ylamino]-7H-pyrrolo[2,3-d]pyrimidine-6-carboxylic acid dimethylamide as the di-hydrochloride salt (275 mg) in 72% yield. 1H NMR (400 MHz, DMSO-$d_6$) δ ppm 9.58 (1H, br. s.), 9.01 (1H, s), 8.46 (1H, br. s.), 8.05 (1H, br. s.), 7.92 (1H, br. s.), 6.88 (1H, s.), 4.80 (1H, quin.), 4.0 (1H, br. s), 3.57 (4H, br. s), 3.17 (3H, br. s.), 3.07 (6H, s), 2.59-2.75 (1H, m), 2.35-2.45 (2H, br. m), 1.84-2.09 (6H, m), 1.66-1.70 (2H, m). MS (ESI) m/e (M+H$^+$): 489.9.

Step 3

Separation of 215 mg of the approximate 1 to 1 mixture of enantiomers of the racemate 7-Cyclopentyl-2-[5-(3,6-diaza-bicyclo[3.2.1]octane-3-carbonyl)-pyridin-2-ylamino]-7H-pyrrolo[2,3-d]pyrimidine-6-carboxylic acid dimethylamide was done using the following conditions: As—H, 4.6×100 mm, SFC, 4 g/min, 40 C, 30% MeOH 0.2% diethyl amine gave approximately 68 mg of each enantiomer 7-cyclopentyl-2-[5-((1S,5S)-3,6-diaza-bicyclo[3.2.1]octane-3-carbonyl)-pyridin-2-ylamino]-7H-pyrrolo[2,3-d]pyrimidine-6-carboxylic acid dimethylamide (isomer 1) and 7-cyclopentyl-2-[5-((1R,5R)-3,6-diaza-bicyclo[3.2.1]octane-3-carbonyl)-pyridin-2-ylamino]-7H-pyrrolo[2,3-d]pyrimidine-6-carboxylic acid dimethylamide (isomer 2)

Example 10

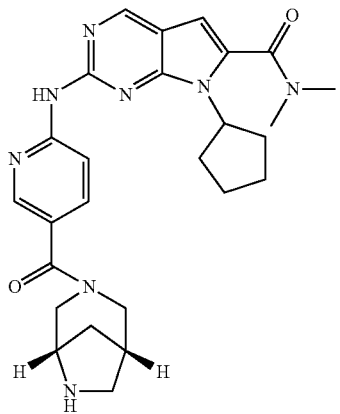 [SMILES: CN(C)C(=O)c1cc2cnc(Nc3ccc(C(=O)N4C[C@@H]5CN[C@@H](C5)C4)cn3)nc2n1C1CCCC1]

Enantiomer 1: 7-Cyclopentyl-2-[5-((1S,5S)-3,6-diaza-bicyclo[3.2.1]octane-3-carbonyl)-pyridin-2-ylamino]-7H-pyrrolo[2,3-d]pyrimidine-6-carboxylic acid dimethylamide 1H NMR (400 MHz, DMSO-$d_6$) δ ppm 10.02 (1H, s), 8.85 (1H, s), 8.32-8.38 (2H, m), 7.86 (1H, br. s.), 6.66 (1H, s), 4.71-4.79 (1H, quin.), 3.32-3.38 (4H, br. s.), 3.05-3.07 (6H, d), 2.86 (2H, br. s.), 2.72-2.74 (1H, d), 2.33-2.55 (2H, m), 1.95-2.05 (4H, br. s.), 1.53-1.79 (4H, m), 1.22-1.35 (2H, m)

MS (ESI) m/e (M+H$^+$): 489.1

Example 11

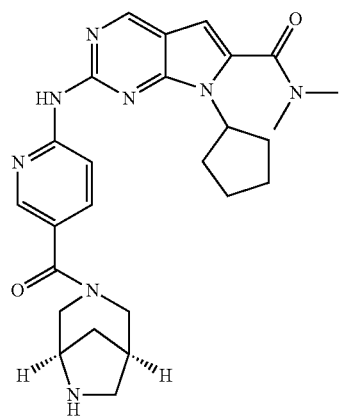 [SMILES: CN(C)C(=O)c1cc2cnc(Nc3ccc(C(=O)N4C[C@H]5CN[C@H](C5)C4)cn3)nc2n1C1CCCC1]

Enantiomer 2: 7-Cyclopentyl-2-[5-((1R,5R)-3,6-diaza-bicyclo[3.2.1]octane-3-carbonyl)-pyridin-2-ylamino]-7H-pyrrolo[2,3-d]pyrimidine-6-carboxylic acid dimethylamide 1H NMR (400 MHz, DMSO-$d_6$) δ ppm 10.03 (1H, br. s), 8.85 (1H, s), 8.33-8.36 (2H, d), 7.85 (1H, br. s.), 6.66 (1H, s), 4.72-4.80 (1H, quin.), 3.25-3.55 (5H, br. m), 3.06 (6H, d), 2.77-2.90 (2H, br. s.), 2.37-2.60 (2H, m), 1.99 (4H, br. s), 1.66-1.79 (4H, m), 1.24-1.37 (2H, br. s)

MS (ESI) m/e (M+H$^+$): 489.0

Example 12

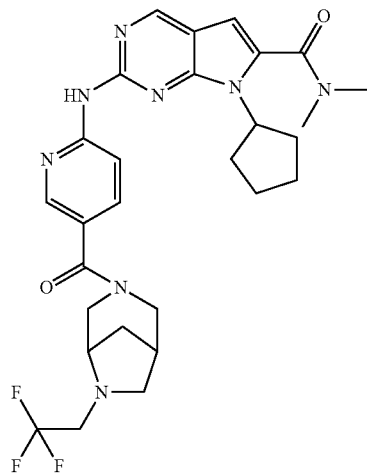 [SMILES: CN(C)C(=O)c1cc2cnc(Nc3ccc(C(=O)N4CC5CC(C4)N(CC(F)(F)F)C5)cn3)nc2n1C1CCCC1]

7-Cyclopentyl-2-{5-[6-(2,2,2-trifluoro-ethyl)-3,6-diaza-bicyclo[3.2.1]octane-3-carbonyl]-pyridin-2-ylamino}-7H-pyrrolo[2,3-d]pyrimidine-6-carboxylic acid dimethylamide

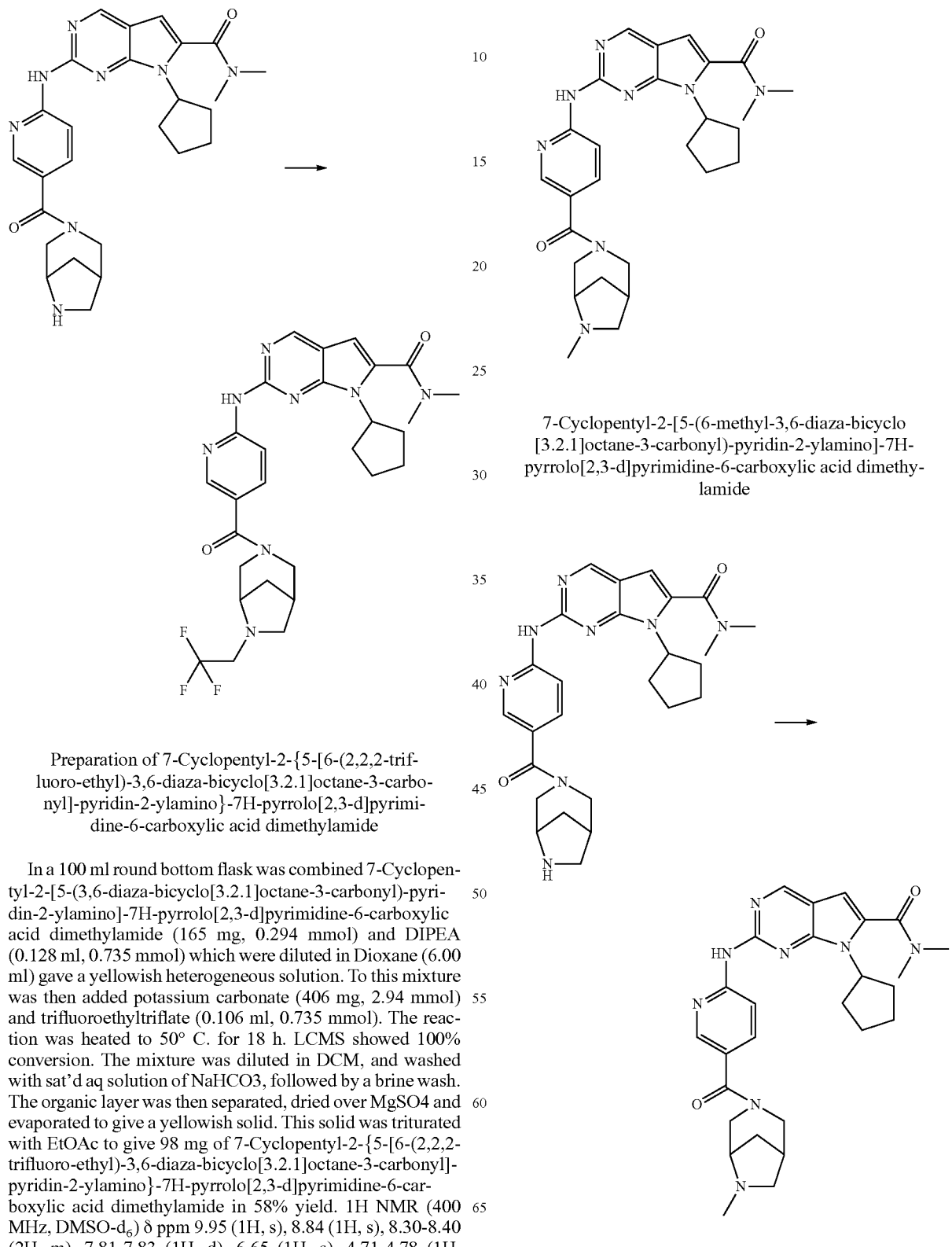

Preparation of 7-Cyclopentyl-2-{5-[6-(2,2,2-trifluoro-ethyl)-3,6-diaza-bicyclo[3.2.1]octane-3-carbonyl]-pyridin-2-ylamino}-7H-pyrrolo[2,3-d]pyrimidine-6-carboxylic acid dimethylamide In a 100 ml round bottom flask was combined 7-Cyclopentyl-2-[5-(3,6-diaza-bicyclo[3.2.1]octane-3-carbonyl)-pyridin-2-ylamino]-7H-pyrrolo[2,3-d]pyrimidine-6-carboxylic acid dimethylamide (165 mg, 0.294 mmol) and DIPEA (0.128 ml, 0.735 mmol) which were diluted in Dioxane (6.00 ml) gave a yellowish heterogeneous solution. To this mixture was then added potassium carbonate (406 mg, 2.94 mmol) and trifluoroethyltriflate (0.106 ml, 0.735 mmol). The reaction was heated to 50° C. for 18 h. LCMS showed 100% conversion. The mixture was diluted in DCM, and washed with sat'd aq solution of NaHCO3, followed by a brine wash. The organic layer was then separated, dried over MgSO4 and evaporated to give a yellowish solid. This solid was triturated with EtOAc to give 98 mg of 7-Cyclopentyl-2-{5-[6-(2,2,2-trifluoro-ethyl)-3,6-diaza-bicyclo[3.2.1]octane-3-carbonyl]-pyridin-2-ylamino}-7H-pyrrolo[2,3-d]pyrimidine-6-carboxylic acid dimethylamide in 58% yield. 1H NMR (400 MHz, DMSO-$d_6$) δ ppm 9.95 (1H, s), 8.84 (1H, s), 8.30-8.40 (2H, m), 7.81-7.83 (1H, d), 6.65 (1H, s), 4.71-4.78 (1H, quin.), 3.23-3.42 (7H, m), 3.06 (7H, br. s.), 2.30-2.45 (2H, br. s.), 1.99 (4H, br. s.), 1.55-1.75 (4H, d), 1.24-1.35 (2H, br. s). MS (ESI) m/e (M+H$^+$): 570.9

Example 13

7-Cyclopentyl-2-[5-(6-methyl-3,6-diaza-bicyclo[3.2.1]octane-3-carbonyl)-pyridin-2-ylamino]-7H-pyrrolo[2,3-d]pyrimidine-6-carboxylic acid dimethylamide

Preparation of 7-Cyclopentyl-2-[5-(6-methyl-3,6-diaza-bicyclo[3.2.1]octane-3-carbonyl)-pyridin-2-ylamino]-7H-pyrrolo[2,3-d]pyrimidine-6-carboxylic acid dimethylamide In a 50 mL round-bottomed flask was combined 7-Cyclopentyl-2-[5-(3,6-diaza-bicyclo[3.2.1]octane-3-carbonyl)-pyridin-2-ylamino]-7H-pyrrolo[2,3-d]pyrimidine-6-carboxylic acid dimethylamide (183 mg, 0.326 mmol) and formaldehyde (37% solution in water) (0.135 ml, 4.89 mmol) and in MeOH (4.00 ml)/DCM (4.00 ml) to give a yellowish solution. After 1.5 h stirring at room temperature, sodium triacetoxyborohydride (90 mg, 0.424 mmol) was added and the reaction was then stirred for another 12 h. LCMS showed complete conversion. The mixture was then diluted with dichloromethane, washed with saturated aqueous solution of NaHCO3 followed by brine. Combined organic phases were then dried over MgSO4 and evaporated to give a light yellow solid. Trituration with ethyl acetate then with dichloromethane followed by filtration gave 30 mg of 7-Cyclopentyl-2-[5-(6-methyl-3,6-diaza-bicyclo[3.2.1]octane-3-carbonyl)-pyridin-2-ylamino]-7H-pyrrolo[2,3-d]pyrimidine-6-carboxylic acid dimethylamide in 18% yield. 1H NMR (400 MHz, MeOD) δ ppm 8.81 (1H, s), 8.54 (2H, d), 8.42 (1H, s), 7.90 (1H, d, J=8.53 Hz), 6.66 (1H, s), 4.91 (3H, s), 4.77-4.87 (1H, quin.), 3.30 (4H, br. s), 3.16-3.20 (7H, m), 2.65-2.90 (3H, br. s.), 2.50-2.60 (2H, m), 1.93-2.25 (5H, m), 1.76 (2H, br. s). MS (ESI) m/e (M+H+): 502.9

Example 14

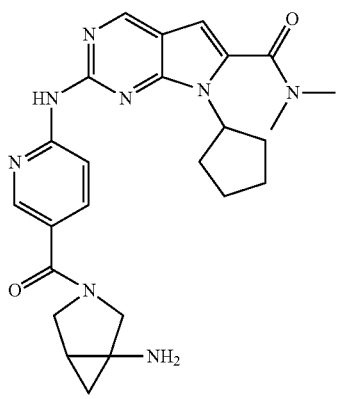 [SMILES: CN(C)C(=O)c1cc2cnc(Nc3ccc(C(=O)N4CC5CC5(N)C4)cn3)nc2n1C1CCCC1]

2-[5-(1-Amino-3-aza-bicyclo[3.1.0]hexane-3-carbonyl)-pyridin-2-ylamino]-7-cyclopentyl-7H-pyrrolo[2,3-d]pyrimidine-6-carboxylic acid dimethylamide

Step 1

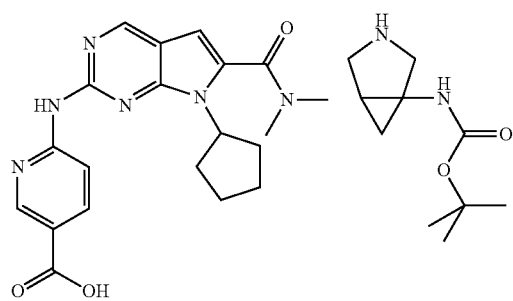

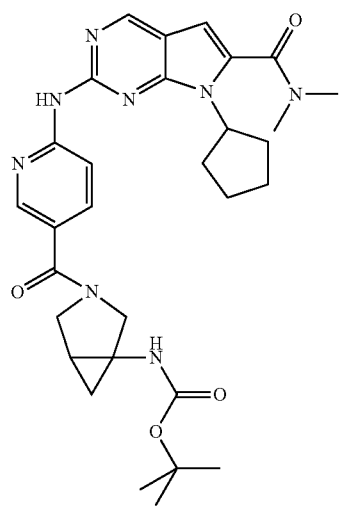

Preparation of {3-[6-(7-Cyclopentyl-6-dimethylcarbamoyl-7H-pyrrolo[2,3-d]pyrimidin-2-ylamino)-pyridine-3-carbonyl]-3-aza-bicyclo[3.1.0]hex-1-yl}-carbamic acid tert-butyl ester Following general amide formation method 1, 6-(7-Cyclopentyl-6-dimethylcarbamoyl-7H-pyrrolo[2,3-d]pyrimidin-2-ylamino)-nicotinic (550 mg, 0.907 mmol) was combined with (3-Aza-bicyclo[3.1.0]hex-1-yl)-carbamic acid tert-butyl ester (180 mg, 0.907 mmol) which gave 260 mg of {3-[6-(7-Cyclopentyl-6-dimethylcarbamoyl-7H-pyrrolo[2,3-d]pyrimidin-2-ylamino)-pyridine-3-carbonyl]-3-aza-bicyclo[3.1.0]hex-1-yl}-carbamic acid tert-butyl ester in 50% yield.

MS (ESI) m/e (M+H+): 575.4

Step 2

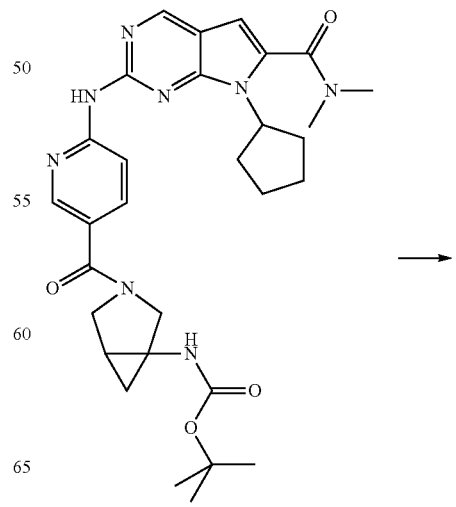

-continued

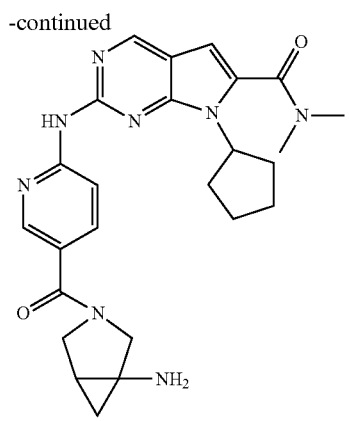

Preparation of 2-[5-(1-amino-3-aza-bicyclo[3.1.0] hexane-3-carbonyl)-pyridin-2-ylamino]-7-cyclopentyl-7H-pyrrolo[2,3-d]pyrimidine-6-carboxylic acid dimethylamide di-hydrochloride Following deprotection method 1, {3-[6-(7-Cyclopentyl-6-dimethylcarbamoyl-7H-pyrrolo[2,3-d]pyrimidin-2-ylamino)-pyridine-3-carbonyl]-3-aza-bicyclo[3.1.0]hex-1-yl}-carbamic acid tert-butyl ester (250 mg, 0.435 mmol) was converted to 2-[5-(1-amino-3-aza-bicyclo[3.1.0]hexane-3-carbonyl)-pyridin-2-ylamino]-7-cyclopentyl-7H-pyrrolo[2,3-d]pyrimidine-6-carboxylic acid dimethylamide di-hydrochloride (210 mg). 1H NMR (400 MHz, DMSO-$d_6$) δ ppm 9.04 (1H, s), 8.99 (1H, s), 8.53 (1H, s), 8.11 (1H, d), 7.83 (1H, br. 5.), 6.86 (1H, s), 4.75-4.84 (1H, quin.), 3.25-4.10 (6H, m), 3.07 (6H, s), 2.24-2.40 (2H, d), 2.00-2.08 (5H, m), 1.65-1.67 (2H, d), 1.31 (1H, br. s.), 0.82 (1H, br. s.); MS (ESI) m/e (M+H$^+$): 475.1.

Step 3

Separation of 200 mg of the approximate 1 to 1 mixture of enantiomers of the racemate 2-[5-(1-Amino-3-aza-bicyclo[3.1.0]hexane-3-carbonyl)-pyridin-2-ylamino]-7-cyclopentyl-7H-pyrrolo[2,3-d]pyrimidine-6-carboxylic acid dimethylamide was done using the following conditions, As—H, 4.6×100 mm, SFC, 4 g/min, 40 C, 45% MeOH 0.2% DEA in CO2 gave approximately 56 mg of each enantiomer 2-[5-((S)-1-Amino-3-aza-bicyclo[3.1.0]hexane-3-carbonyl)-pyridin-2-ylamino]-7-cyclopentyl-7H-pyrrolo[2,3-d]pyrimidine-6-carboxylic acid dimethylamide and 2-[5-((R)-1-Amino-3-aza-bicyclo[3.1.0]hexane-3-carbonyl)-pyridin-2-ylamino]-7-cyclopentyl-7H-pyrrolo[2,3-d]pyrimidine-6-carboxylic acid dimethylamide.

Example 15

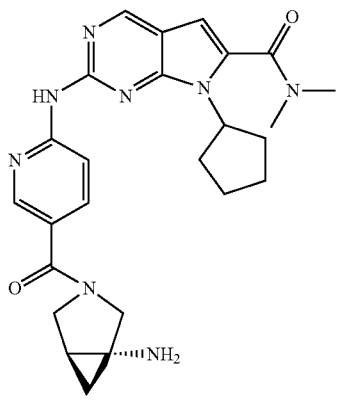

Enantiomer 1: Preparation of 2-[5-((S)-1-Amino-3-aza-bicyclo[3.1.0]hexane-3-carbonyl)-pyridin-2-ylamino]-7-cyclopentyl-7H-pyrrolo[2,3-d]pyrimidine-6-carboxylic acid dimethylamide 1H NMR (400 MHz, DMSO-$d_6$) δ ppm 10.07 (1H, d), 8.86 (1H, s), 8.41 (1H, br. s.), 8.34-8.37 (1H, t), 7.88 (1H, d), 6.66 (1H, s), 4.73-4.80 (1H, quin.), 3.50-4.09 (2H, m), 3.20-3.45 (4H, br. s), 3.05-3.07 (6H, d), 2.44 (2H, br. s.), 2.00 (4H, br. s.), 1.66 (2H, br. s.), 1.32 (1H, br. s.), 1.24 (1H, m), 0.38 (1H, br. s.); MS (ESI) m/e (M+H$^+$): 475.4

Example 16

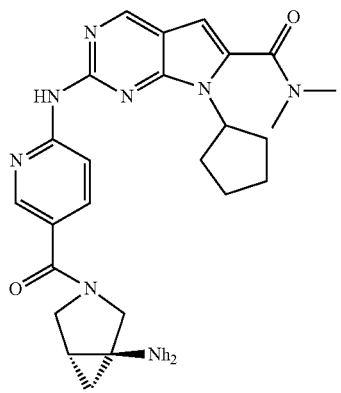

Enantiomer 2: 2-[5-((R)-1-Amino-3-aza-bicyclo[3.1.0]hexane-3-carbonyl)-pyridin-2-ylamino]-7-cyclopentyl-7H-pyrrolo[2,3-d]pyrimidine-6-carboxylic acid dimethylamide
1H NMR (400 MHz, DMSO-$d_6$) δ ppm 10.07 (1H, d), 8.86 (1H, s), 8.33-8.39 (1H, t), 7.86-7.88 (1H, d), 6.66 (1H, s), 4.73-4.80 (1H, quin.), 3.40-4.20 (2H, m), 3.25-3.37 (4H, m), 3.05-3.07 (6H, d), 2.44 (2H, br. s.), 2.00 (4H, br. s.), 1.66 (2H, br. s.), 1.24-1.37 (2H, m), 0.38 (1H, d). MS (ESI) m/e (M+H$^+$): 475.3

Example 17

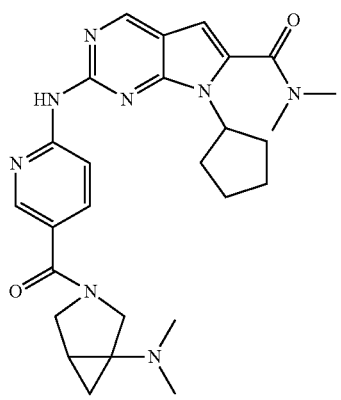 [SMILES: CN(C)C(=O)c1cc2cnc(Nc3ccc(C(=O)N4CC5CC5(N(C)C)C4)cn3)nc2n1C1CCCC1]

7-Cyclopentyl-2-[5-(1-dimethylamino-3-aza-bicyclo [3.1.0]hexane-3-carbonyl)-pyridin-2-ylamino]-7H-pyrrolo[2,3-d]pyrimidine-6-carboxylic acid dimethylamide

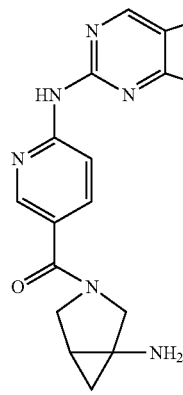

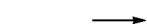

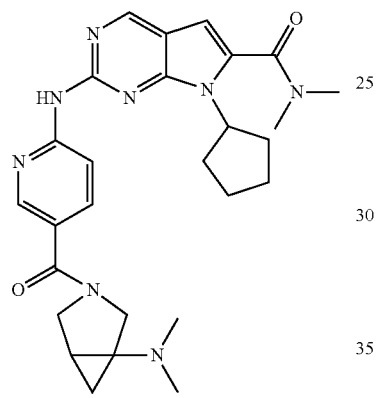

Preparation of 7-Cyclopentyl-2-[5-(1-dimethylamino-3-aza-bicyclo[3.1.0]hexane-3-carbonyl)-pyridin-2-ylamino]-7H-pyrrolo[2,3-d]pyrimidine-6-carboxylic acid dimethylamide In a 50 mL round-bottomed flask was combined 2-[5-(1-Amino-3-aza-bicyclo[3.1.0]hexane-3-carbonyl)-pyridin-2-ylamino]-7-cyclopentyl-7H-pyrrolo[2,3-d]pyrimidine-6-carboxylic acid dimethylamide (k) (200 mg, 0.421 mmol) and formaldehyde (37% in water (0.967 ml, 10.54 mmol) in THF (3.000 ml)/methanol (3.000 ml)/DCM (3.000 ml) to give a yellowish suspension. After 2 h stirring at r.t., sodium triacetoxyborohydride (223 mg, 1.054 mmol) was added and the reaction was stirred for another 16 h. Finally the reaction mixture was washed with NaHCO3 and brine, dried over MgSO4 and evaporated to give a light brown solid. This solid was triturated with EtOAc to give 50 mg of 7-Cyclopentyl-2-[5-(1-dimethylamino-3-aza-bicyclo[3.1.0]hexane-3-carbonyl)-pyridin-2-ylamino]-7H-pyrrolo[2,3-d]pyrimidine-6-carboxylic acid dimethylamide (n) in 24% yield and >90% purity. 1H NMR (400 MHz, DMSO-$d_6$) δ ppm 10.01 (1H, br. s.), 8.86 (1H, br. s.), 8.45 (1H, d), 8.33 (1H, t), 7.91 (1H, br. s.), 6.65 (1H, s), 4.69-4.90 (1H, quin.), 3.75-3.92 (2H, m), 3.21-3.36 (3H, m), 3.06 (6H, br. s.), 2.40 (2H, br. s.), 2.29-2.35 (6H, d), 2.00 (4H, br. s.), 1.40-1.76 (2H, m), 1.36-1.43 (1H, d), 0.46 (1H, br. s.); MS (ESI) m/e (M+H+): 503.4

Example 18

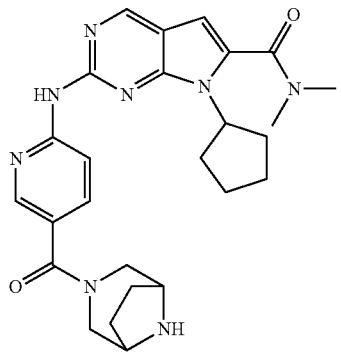 [SMILES: CN(C)C(=O)c1cc2cnc(Nc3ccc(C(=O)N4CC5CCC(C4)N5)cn3)nc2n1C1CCCC1]

7-Cyclopentyl-2-[5-(3,8-diaza-bicyclo[3.2.1]octane-3-carbonyl)-pyridin-2-ylamino]-7H-pyrrolo[2,3-d] pyrimidine-6-carboxylic acid dimethylamide Step 1

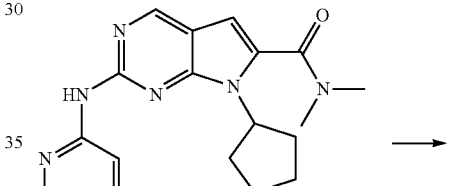

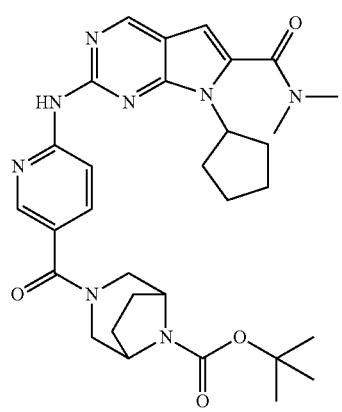 [SMILES: CN(C)C(=O)c1cc2cnc(Nc3ccc(C(=O)N4CC5CCC(C4)N5C(=O)OC(C)(C)C)cn3)nc2n1C1CCCC1]

Preparation of 3-[6-(7-Cyclopentyl-6-dimethylcarbamoyl-7H-pyrrolo[2,3-d]pyrimidin-2-ylamino)-pyridine-3-carbonyl]-3,8-diaza-bicyclo[3.2.1]octane-8-carboxylic acid tert-butyl ester Following general amide formation method 1, 6-(7-cyclopentyl-6-(dimethylcarbamoyl)-7H-pyrrolo[2,3-d]pyrimidin-2-ylamino)nicotinic acid (400 mg, 1.01 mmol) was combined with 3,8-Diaza-bicyclo[3.2.1]octane-8-carboxylic acid tert-butyl ester (250 mg, 1.18 mmol. 1.1 eq) which yielded 3-[6-(7-Cyclopentyl-6-dimethylcarbamoyl-7H-pyrrolo[2,3-d]pyrimidin-2-ylamino)-pyridine-3-carbonyl]-3,8-diaza-bicyclo[3.2.1]octane-8-carboxylic acid tert-butyl ester after work up and was immediately used in next step without further purification.

MS m/z 589.7 (M+H)+.

Step 2

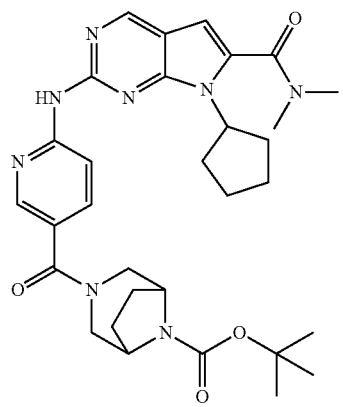

→

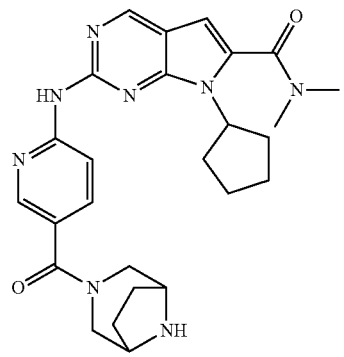

Preparation of 7-cyclopentyl-2-[5-(3,8-diaza-bicyclo[3.2.1]octane-3-carbonyl)-pyridin-2-ylamino]-7H-pyrrolo[2,3-d]pyrimidine-6-carboxylic acid dimethylamide Following deprotection method 1, 3-[6-(7-Cyclopentyl-6-dimethylcarbamoyl-7H-pyrrolo[2,3-d]pyrimidin-2-ylamino)-pyridine-3-carbonyl]-3,8-diaza-bicyclo[3.2.1]octane-8-carboxylic acid tert-butyl ester was converted to 7-cyclopentyl-2-[5-(3,8-diaza-bicyclo[3.2.1]octane-3-carbonyl)-pyridin-2-ylamino]-7H-pyrrolo[2,3-d]pyrimidine-6-carboxylic acid dimethylamide as a white solid (0.290 g, 0.594 mmol) in 59% yield. $^1$H NMR (400 MHz, CDCl$_3$) δ ppm 1.74 (m, 8H), 2.07 (m, 5H), 2.58 (m, 2H), 3.50 (br 5, 2H), 3.17 (s, 7H), 4.81 (quin, J=8.8 Hz, 1H), 6.48 (s, 1H), 7.79 (dd, J=8.8, 2.3 Hz), 8.30 (s, 1H), 8.39 (d, J=2.5 Hz, 1H), 8.56 (d, J=8.6 Hz, 1H), 8.77 (s, 1H);

MS m/z 489.6 (M+H)+.

Alternative Procedure for Example 18

Synthesis of 7-Cyclopentyl-2-[5-(3,8-diaza-bicyclo[3.2.1]octane-3-carbonyl)-pyridin-2-ylamino]-7H-pyrrolo[2,3-d]pyrimidine-6-carboxylic acid dimethylamide

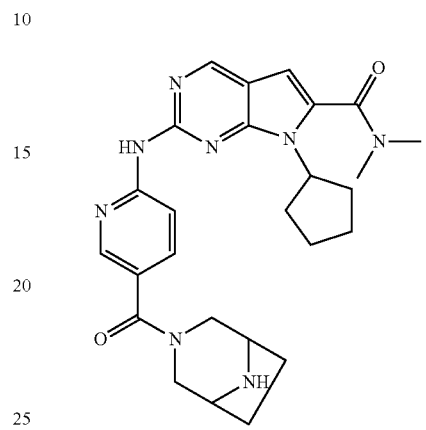

Step 1: Synthesis of 6-(7-cyclopentyl-6-(dimethylcarbamoyl)-7H-pyrrolo[2,3-d]pyrimidin-2-ylamino) nicotinic acid To a suspension of methyl 6-(7-cyclopentyl-6-(dimethylcarbamoyl)-7H-pyrrolo[2,3-d]pyrimidin-2-ylamino)nicotinate (2.0 g, 4.9 mmol) in THF (6 mL) was added 1M LiOH (aq) (6 mL, 1.2 equiv) and the slurry stirred at 45° C. for 12 hours (the slurry became clear). After cooling to room temperature, the THF was evaporated and the reaction mixture was treated with 1N HCl until pH=1-2. The resulting precipitate was filtered and the filtrate extracted with 20% Isopropanol/CH$_2$Cl$_2$ (3×100 mL), the combined organic layers dried, filtered, and concentrated to a tan solid. The tan solid was triturated in acetone giving the desired product as a tan solid (1.56 g, 73% yield) which was used without further purification. MS: (M+H)=395.5

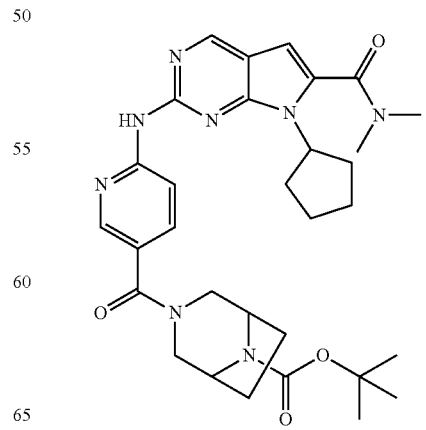

Step 2: Synthesis of 3-[6-(7-Cyclopentyl-6-dimethyl-carbamoyl-7H-pyrrolo[2,3-d]pyrimidin-2-ylamino)-pyridine-3-carbonyl]-3,8-diaza-bicyclo[3.2.1]octane-8-carboxylic acid tert-butyl ester To a solution of 6-(7-cyclopentyl-6-(dimethylcarbamoyl)-7H-pyrrolo[2,3-d]pyrimidin-2-ylamino)nicotinic acid (400 mg, 1.01 mmol) in DMF (5 mL) was added O-(benzotriazol-1-yl)-N,N,N',N'-tetramethyluronium hexafluorophosphate (HBTU, 580 mg, 1.53 mmol, 1.5 equiv) and N,N-diisopropylethylamine (0.55 mL, 3.0 equiv) and the resulting mixture stirred at room temperature for 5 minutes. To the reaction mixture was added 3,8-Diaza-bicyclo[3.2.1]octane-8-carboxylic acid Pert-butyl ester (250 mg, 1.18 mmol. 1.1 eq). The resulting mixture was stirred at room temperature for 30 minutes. The reaction mixture was diluted in EtOAc, washed with 0.5M HCl, water, dried over Na$_2$SO$_4$, filtered and concentrated. Material was immediately used in next step without further purification. MS: (M+H)=589.7

Step 3: Synthesis of the Title Compound

To a stirring solution of 3-[6-(7-Cyclopentyl-6-dimethyl-carbamoyl-7H-pyrrolo[2,3-d]pyrimidin-2-ylamino)-pyridine-3-carbonyl]-3,8-diaza-bicyclo[3.2.1]octane-8-carboxylic acid tert-butyl ester (0.232 g, 1.0 mmol) in CH$_2$Cl$_2$ (4 mL) was added a solution of 4M HCl in dioxane (2.54 mL, 10.14 mmol, 10 eq) at 25° C. After 4 hours stirring at 25° C. the reaction mixture was filtered and washed with CH$_2$Cl$_2$ (5 mL). The residue was collected and taken up in water then basified with 1M NaOH and extracted with CH$_2$Cl$_2$ (2×15 mL).

The combined organic layers were dried over Na$_2$SO$_4$, filtered, and concentrated under reduced pressure to a tan solid. The crude was purified using Column Chromatography (MeOH/CH$_2$Cl$_2$) giving the desired product as a white solid (0.290 g, 0.594 mmol, 59%). $^1$H NMR (400 MHz, CDCl$_3$) δ 8.77 (s, 1H), 8.56 (d, J=8.6 Hz, 1H), 8.39 (d, J=2.5 Hz, 1H), 8.30 (s, 1H), 7.79 (dd, J=8.8, 2.3 Hz), 6.48 (s, 1H), 4.81 (quin, J=8.8 Hz, 1H), 3.50 (br s, 2H), 3.17 (s, 7H), 2.58 (m, 2H), 2.07 (m, 5H), 1.74 (m, 8H); MS m/z 489.6 (M+H)$^+$.

Example 19

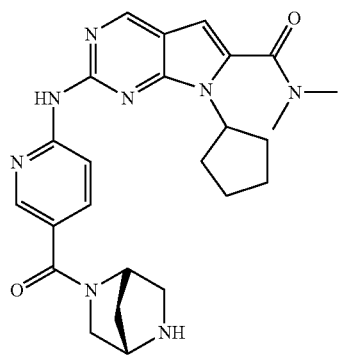

7-Cyclopentyl-2-[5-((S,S)-2,5-diaza-bicyclo[2.2.1]heptane-2-carbonyl)-pyridin-2-ylamino]-7H-pyrrolo[2,3-d]pyrimidine-6-carboxylic acid dimethylamide

Step 1

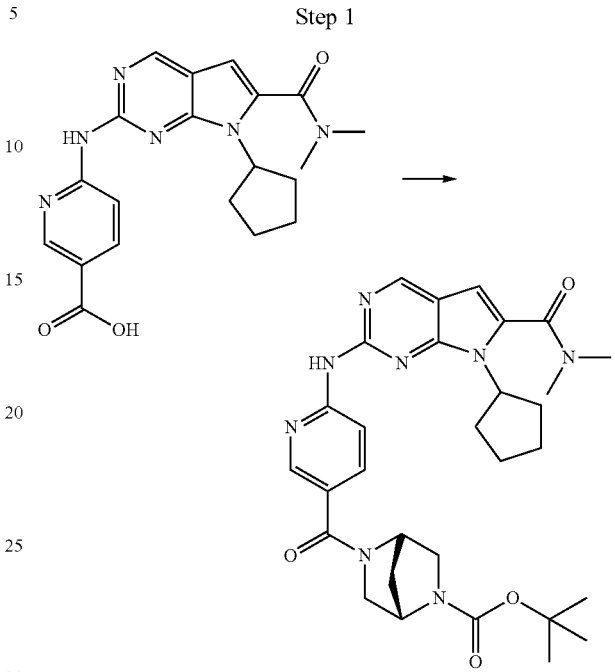

Preparation of 5-[6-(7-Cyclopentyl-6-dimethylcarbamoyl-7H-pyrrolo[2,3-d]pyrimidin-2-ylamino)-pyridine-3-carbonyl]-(S,S)-2,5-diaza-bicyclo[2.2.1]heptane-2-carboxylic acid tert-butyl ester Following general amide formation method 1, 6-(7-cyclopentyl-6-(dimethylcarbamoyl)-7H-pyrrolo[2,3-d]pyrimidin-2-ylamino)nicotinic acid (0.150 g, 0.380 mmol) was combined with (S,S)-2,5-diaza-bicyclo[2.2.1]heptane-2-carboxylic acid tert-butyl ester (100 mg, 0.504 mmol, 1.3 eq), which gave 5-[6-(7-Cyclopentyl-6-dimethylcarbamoyl-7H-pyrrolo[2,3-d]pyrimidin-2-ylamino)-pyridine-3-carbonyl]-(S,S)-2,5-diaza-bicyclo[2.2.1]heptane-2-carboxylic acid tert-butyl ester and used directly in the next step. MS m/z 575.7 (M+H)$^+$.

Step 2

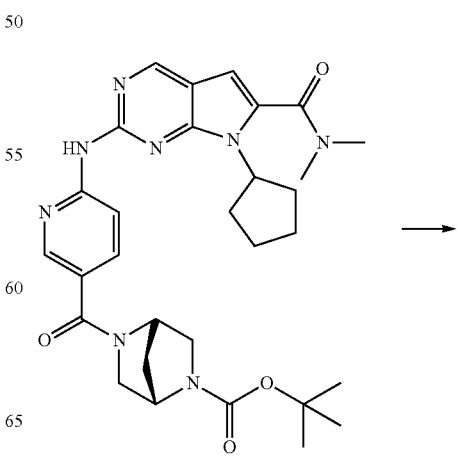

83
-continued

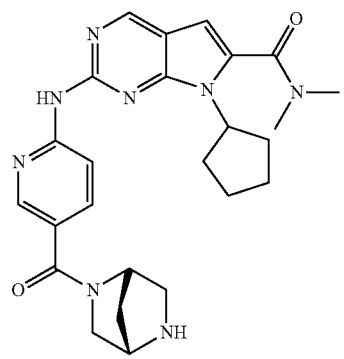

Preparation of 7-Cyclopentyl-2-[5-((S,S)-2,5-diaza-bicyclo[2.2.1]heptane-2-carbonyl)-pyridin-2-ylamino]-7H-pyrrolo[2,3-d]pyrimidine-6-carboxylic acid dimethylamide Following deprotection method 1, 5-[6-(7-Cyclopentyl-6-dimethylcarbamoyl-7H-pyrrolo[2,3-d]pyrimidin-2-ylamino)-pyridine-3-carbonyl]-(S,S)-2,5-diaza-bicyclo[2.2.1]heptane-2-carboxylic acid tert-butyl ester was converted to 7-cyclopentyl-2-[5-((S,S)-2,5-diaza-bicyclo[2.2.1]heptane-2-carbonyl)-pyridin-2-ylamino]-7H-pyrrolo[2,3-d]pyrimidine-6-carboxylic acid dimethylamide as a white solid (55 mg, 0.110 mmol) in 29% yield. $^1$H NMR (400 MHz, CDCl$_3$) δ ppm 1.91-2.14 (m, 5H), 2.43-2.62 (m, 2H), 2.99-3.07 (m, 1H), 3.09 (s, 6H), 3.16 (d, J=10.11 Hz, 1H), 3.35 (d, J=11.12 Hz, 1H), 3.51-3.76 (m, 2H), 3.80 (br. s., 1H), 4.74 (quin, J=8.84 Hz, 1H), 6.41 (s, 1H), 7.77-7.96 (m, 1H), 8.41-8.56 (m, 2H), 8.68-8.84 (m, 2H). MS m/z 475.5 (M+H)$^+$.

Example 20

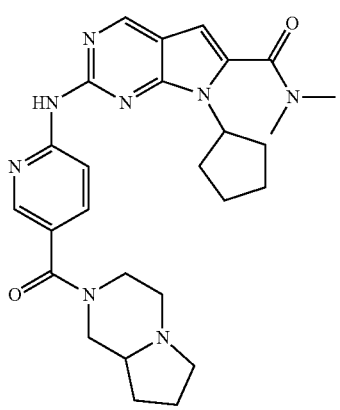

84
7-Cyclopentyl-2-[5-(hexahydro-pyrrolo[1,2-a]pyrazine-2-carbonyl)-pyridin-2-ylamino]-7H-pyrrolo[2,3-d]pyrimidine-6-carboxylic acid dimethylamide

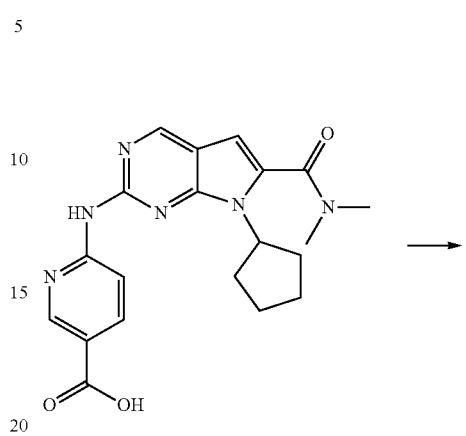

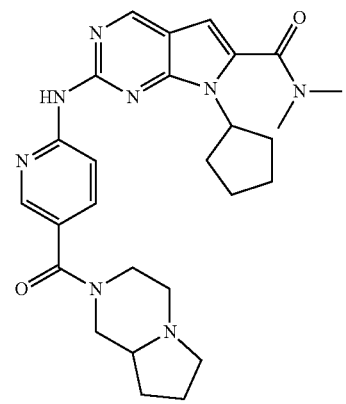 [SMILES: CN(C)C(=O)c1cc2cnc(Nc3ccc(C(=O)N4CCN5CCCC5C4)cn3)nc2n1C1CCCC1]

Preparation of 7-Cyclopentyl-2-[5-(hexahydro-pyrrolo[1,2-a]pyrazine-2-carbonyl)-pyridin-2-ylamino]-7H-pyrrolo[2,3-d]pyrimidine-6-carboxylic acid dimethylamide Following general amide formation method 2, 6-(7-cyclopentyl-6-(dimethylcarbamoyl)-7H-pyrrolo[2,3-d]pyrimidin-2-ylamino)nicotinic acid containing 5 eq of lithium Chloride (88 mg, 0.146 mmol) was combined with octahydro-pyrrolo[1,2-a]pyrazine (0.050 mL, 0.264 mmol, 1.6 eq) which gave after purification 7-cyclopentyl-2-[5-(hexahydro-pyrrolo[1,2-a]pyrazine-2-carbonyl)-pyridin-2-ylamino]-7H-pyrrolo[2,3-d]pyrimidine-6-carboxylic acid dimethylamide as a white solid (40 mg, 0.077 mmol) in 29% yield. $^1$H NMR (400 MHz, CD$_2$Cl$_2$) δ ppm 1.30 (br. s., 2H), 1.49 (s, 1H), 1.57-1.84 (m, 6H), 1.88 (d, J=10.04 Hz, 2H), 2.00-2.20 (m, 5H), 2.35 (br. s., 2H), 2.59 (dd, J=12.05, 9.03 Hz, 2H), 3.07-3.37 (m, 10H), 4.83 (quin, J=8.84 Hz, 1H), 6.51 (s, 1H), 7.83 (dd, J=8.78, 2.26 Hz, 1H), 8.43 (d, J=2.01 Hz, 2H), 8.59 (d, J=8.53 Hz, 1H), 8.82 (s, 1H)

Example 21

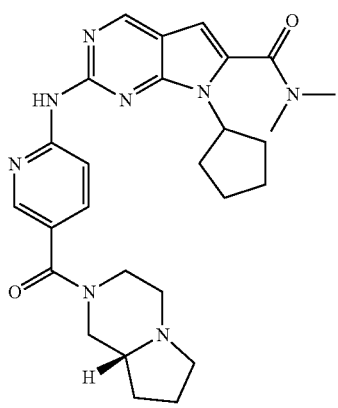 [SMILES: CN(C)C(=O)c1cc2cnc(Nc3ccc(C(=O)N4CCN5CCC[C@@H]5C4)cn3)nc2n1C1CCCC1]

7-Cyclopentyl-2-[5-((R)-hexahydro-pyrrolo[1,2-a]
pyrazine-2-carbonyl)-pyridin-2-ylamino]-7H-pyrrolo
[2,3-d]pyrimidine-6-carboxylic acid dimethylamide

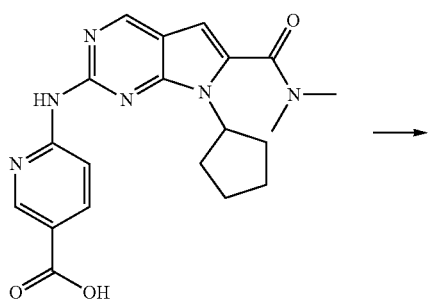

→

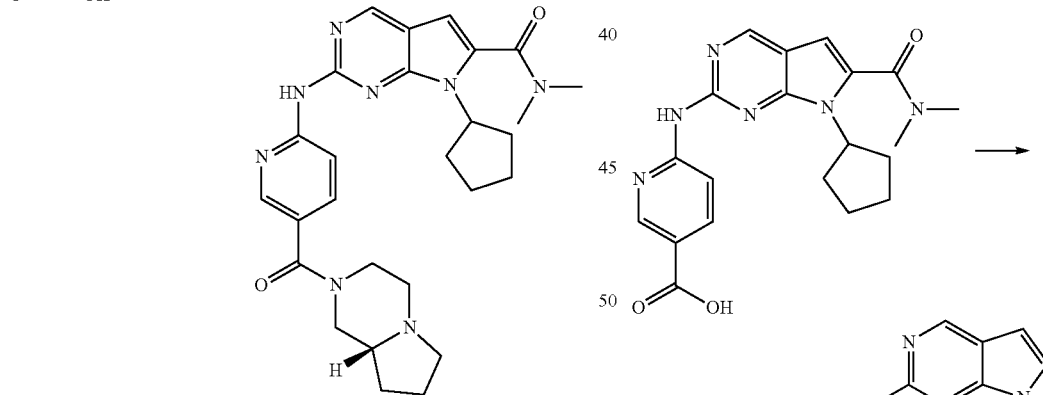

Preparation of 7-Cyclopentyl-2-[5-((R)-hexahydro-
pyrrolo[1,2-a]pyrazine-2-carbonyl)-pyridin-2-
ylamino]-7H-pyrrolo[2,3-d]pyrimidine-6-carboxylic
acid dimethylamide Following general amide formation method 2, 6-(7-cyclopentyl-6-(dimethylcarbamoyl)-7H-pyrrolo[2,3-d]pyrimidin-2-ylamino)nicotinic acid containing 5 eq of lithium chloride (100 mg, 0.165 mmol) was combined with (R)-octahydro-pyrrolo[1,2-a]pyrazine (40 mg, 0.317 mmol, 1.9 eq) which gave after purification 7-Cyclopentyl-2-[5-((R)-hexahydro-pyrrolo[1,2-a]pyrazine-2-carbonyl)-pyridin-2-ylamino]-7H-pyrrolo[2,3-d]pyrimidine-6-carboxylic acid dimethylamide as a white solid (60 mg, 0.113 mmol) in 69% yield. $^1$H NMR (400 MHz, CDCl$_3$) δ ppm 1.20-1.33 (m, 2H), 1.69 (br. s., 3H), 1.69-1.81 (m, 4H), 1.81-1.95 (m, 2H), 1.95-2.16 (m, 6H), 2.16-2.35 (m, 2H), 2.48-2.68 (m, 2H), 3.08-3.15 (m, 2H), 3.15-3.23 (m, 7H), 4.80 (quin, J=8.78 Hz, 2H), 6.48 (s, 1H), 7.82 (dd, J=8.78, 2.26 Hz, 1H), 8.24 (s, 1H), 8.41 (d, J=2.01 Hz, 1H), 8.56 (d, J=8.53 Hz, 1H), 8.77 (s, 1H); HRMS calc for m/z=503.2883. Found m/z=503.2898 (M+H).

Example 22

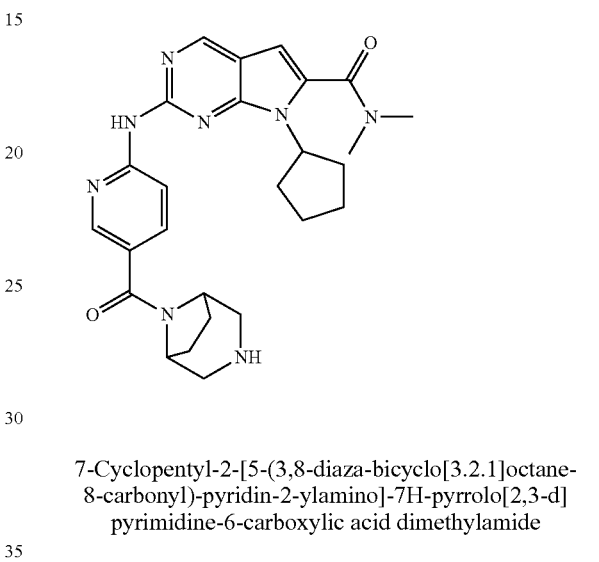

7-Cyclopentyl-2-[5-(3,8-diaza-bicyclo[3.2.1]octane-
8-carbonyl)-pyridin-2-ylamino]-7H-pyrrolo[2,3-d]
pyrimidine-6-carboxylic acid dimethylamide Step 1

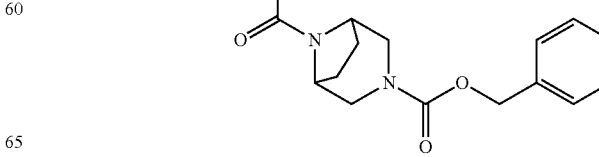

Preparation of 8-[6-(7-Cyclopentyl-6-dimethylcar-bamoyl-7H-pyrrolo[2,3-d]pyrimidin-2-ylamino)-pyridine-3-carbonyl]-3,8-diaza-bicyclo[3.2.1]octane-3-carboxylic acid benzyl ester Following general amide formation method 1, 6-(7-cyclopentyl-6-(dimethylcarbamoyl)-7H-pyrrolo[2,3-d]pyrimidin-2-ylamino) nicotinic acid (700 mg, 1.78 mmol) was combined with 3,8-diaza-bicyclo[3.2.1]octane-3-carboxylic acid benzyl ester (520 mg, 2.11 mmol, 1.2 eq) (Reference: PCT Int. Appl., 2009067108, 28 May 2009) which gave after purification 8-[6-(7-cyclopentyl-6-dimethylcarbamoyl-7H-pyrrolo[2,3-d]pyrimidin-2-ylamino)-pyridine-3-carbonyl]-3,8-diaza-bicyclo[3.2.1]octane-3-carboxylic acid benzyl ester as an off-white solid (550 mg, 0.839 mmol) in 47% yield. $^1$H NMR (400 MHz, MeOD) δ ppm 1.66-1.86 (m, 2H) 1.91-2.18 (m, 8H) 2.41-2.65 (m, 2H) 2.82 (br. s., 2H) 2.98 (br. s., 2H) 3.11-3.22 (m, 6H) 4.17 (br. s., 1H) 4.64 (br. s., 1H) 4.74-4.84 (m, 1H) 6.65 (s, 1H) 7.92 (dd, J=8.84, 2.27 Hz, 1H) 8.48 (d, J=2.53 Hz, 1H) 8.53 (d, J=9.60 Hz, 1H) 8.82 (s, 1H); MS m/z 623.5 (M+H)$^+$.

Step 2

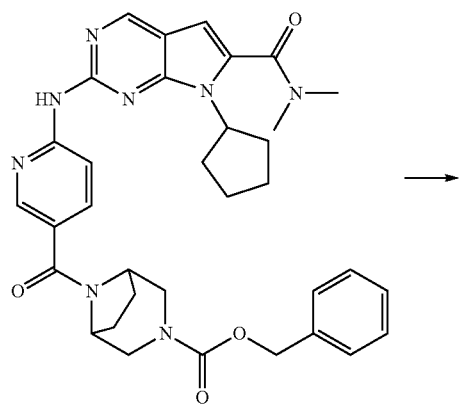

Preparation of 7-Cyclopentyl-2-[5-(3,8-diaza-bicyclo[3.2.1]octane-8-carbonyl)-pyridin-2-ylamino]-7H-pyrrolo[2,3-d]pyrimidine-6-carboxylic acid dimethylamide A suspension of the 8-[6-(7-Cyclopentyl-6-dimethylcarbamoyl-7H-pyrrolo[2,3-d]pyrimidin-2-ylamino)-pyridine-3-carbonyl]-3,8-diaza-bicyclo[3.2.1]octane-3-carboxylic acid benzyl ester (550 mg, 0.883 mmol) and 10% Pd/C (100 mg, 0.1 eq), in methanol (10 mL) was evacuated and then purged with N$_2$ 3 times and then backfilled with hydrogen under balloon pressure and stirred for 16 hr. The reaction mixture was then filtered through a pad of Celite and the filtrate concentrated to a colorless oil. To the oil was added ethyl acetate/heptane and the resulting precipitate triturated which gave 7-cyclopentyl-2-[5-(3,8-diaza-bicyclo[3.2.1]octane-8-carbonyl)-pyridin-2-ylamino]-7H-pyrrolo[2,3-d]pyrimidine-6-carboxylic acid dimethylamide as a white solid (260 mg, 0.532 mmol) in 60% yield. $^1$H NMR (400 MHz, MeOD) δ ppm 1.68-1.84 (m, 2H) 1.94-2.12 (m, 8H) 2.12-2.18 (m, 1H) 2.45-2.61 (m, 2H) 2.77 (br. s., 2H) 2.93-3.11 (m, 2H) 3.16 (s, 6H) 4.16 (br. s., 1H) 4.64 (br. s., 1H) 4.80 (t, J=8.84 Hz, 1H) 6.64 (s, 1H) 7.92 (dd, J=8.59, 2.53 Hz, 1H) 8.47-8.57 (m, 2H) 8.85 (s, 1H); MS m/z 489.9 (M+H)$^+$.

Example 23

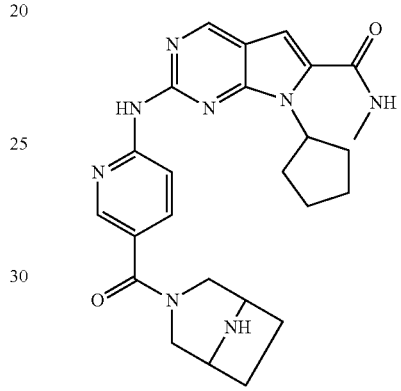

7-Cyclopentyl-2-[5-(3,8-diaza-bicyclo[3.2.1]octane-3-carbonyl)-pyridin-2-ylamino]-7H-pyrrolo[2,3-d]pyrimidine-6-carboxylic acid methylamide Step 1

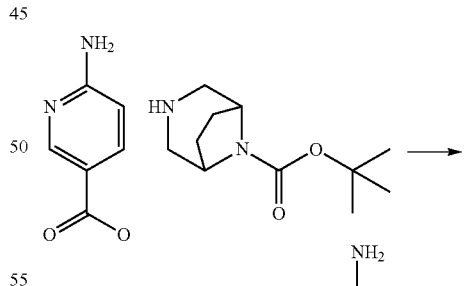

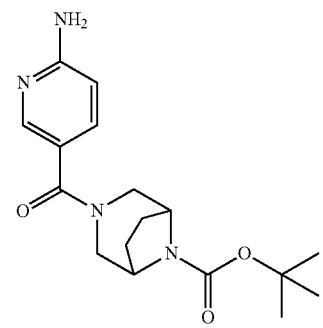

Preparation of 3-(6-Amino-pyridine-3-carbonyl)-3,8-diaza-bicyclo[3.2.1]octane-8-carboxylic acid tert-butyl ester Following general amide formation method 1, 2-aminopyridyl-5-carboxylic acid (0.651 g, 4.71 mmol), was combined with 3,8-diaza-bicyclo[3.2.1]octane-8-carboxylic acid tert-butyl ester (1.00 g, 4.71 mmol) which gave after purification 3-(6-Amino-pyridine-3-carbonyl)-3,8-diaza-bicyclo[3.2.1]octane-8-carboxylic acid tert-butyl ester as a white solid (0.780 g, 2.35 mmol) in 50% yield. $^1$H NMR (400 MHz, CDCl$_3$) δ ppm 1.42-1.54 (m, 17H) 1.67-1.87 (m, 4H) 1.94 (br. s., 4H) 3.10 (br. s., 2H) 3.18 (br. s., 2H) 3.82 (d, J=12.63 Hz, 2H) 3.94 (br. s., 2H) 4.81 (br. s., 4H) 6.53 (d, J=8.59 Hz, 2H) 7.67 (dd, J=8.59, 2.02 Hz, 2H) 8.28 (s, 2H); MS m/z 277.4 (M+H)$^+$.

Step 2

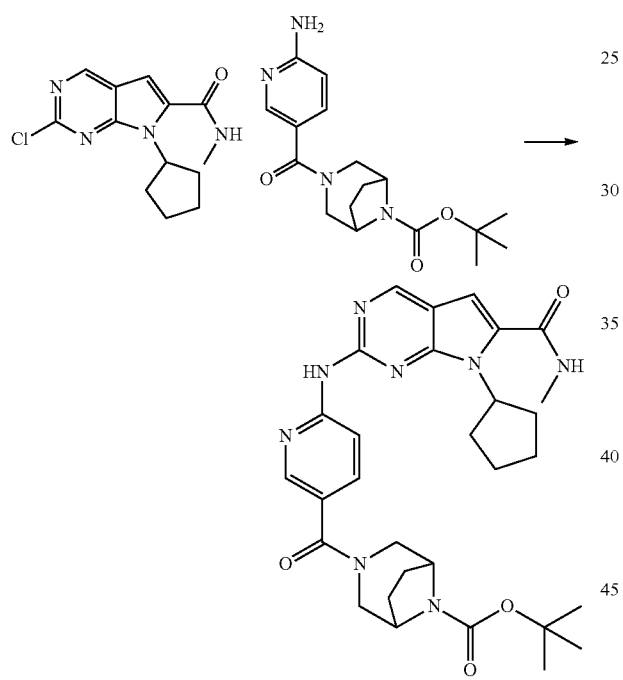

Preparation of 3-[6-(7-Cyclopentyl-6-methylcarbamoyl-7H-pyrrolo[2,3-d]pyrimidin-2-ylamino)-pyridine-3-carbonyl]-3,8-diaza-bicyclo[3.2.1]octane-8-carboxylic acid tert-butyl ester Following general N—C coupling procedure 1, 2-Chloro-7-cyclopentyl-7H-pyrrolo[2,3-d]pyrimidine-6-carboxylic acid methylamide, see WO 2010020675, (0.150 g, 0.538 mmol) was combined with 3-(6-amino-pyridine-3-carbonyl)-3,8-diaza-bicyclo[3.2.1]octane-8-carboxylic acid tert-butyl ester (0.188 g, 0.565 mmol, 1.05 eq), which gave 3-[6-(7-cyclopentyl-6-methylcarbamoyl-7H-pyrrolo[2,3-d]pyrimidin-2-ylamino)-pyridine-3-carbonyl]-3,8-diaza-bicyclo[3.2.1]octane-8-carboxylic acid tert-butyl ester as a yellow solid and was used directly in step 3. MS m/z 575.9 (M+H)$^+$.

Step 3

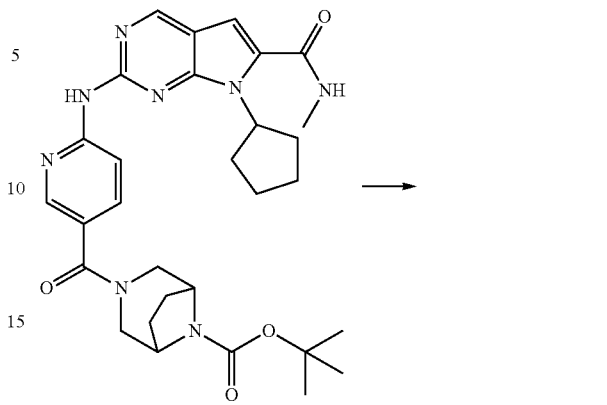

Preparation of 7-cyclopentyl-2-[5-(3,8-diaza-bicyclo[3.2.1]octane-3-carbonyl)-pyridin-2-ylamino]-7H-pyrrolo[2,3-d]pyrimidine-6-carboxylic acid methylamide Following deprotection method 1, 3-[6-(7-cyclopentyl-6-methylcarbamoyl-7H-pyrrolo[2,3-d]pyrimidin-2-ylamino)-pyridine-3-carbonyl]-3,8-diaza-bicyclo[3.2.1]octane-8-carboxylic acid tert-butyl ester was converted to 7-cyclopentyl-2-[5-(3,8-diaza-bicyclo[3.2.1]octane-3-carbonyl)-pyridin-2-ylamino]-7H-pyrrolo[2,3-d]pyrimidine-6-carboxylic acid methylamide (60 mg, 0.126 mmol) in 24% yield. $^1$H NMR (400 MHz, MeOD) δ ppm 1.68-1.87 (m, 3H) 1.92-2.04 (m, 3H) 2.04-2.19 (m, 7H) 2.53-2.71 (m, 2H) 2.84 (d, J=12.63 Hz, 2H) 2.94 (s, 3H) 3.11 (br. s., 3H) 4.22 (br. s., 1H) 4.68 (br. s., 1H) 5.49 (quin, J=9.01, 8.84 Hz, 1H) 6.87 (s, 1H) 7.91 (dd, J=8.59, 2.53 Hz, 1H) 8.46 (d, J=2.02 Hz, 1H) 8.58 (d, J=8.59 Hz, 1H) 8.80 (s, 1H); MS m/z 475.1 (M+H)$^+$.

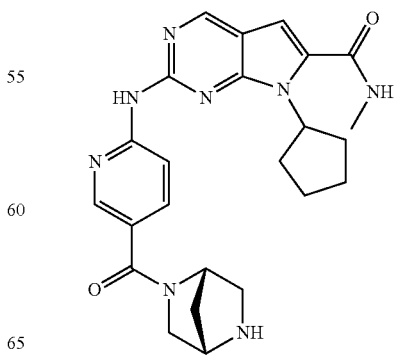

Example 24

7-Cyclopentyl-2-[5-((S,S)-2,5-diaza-bicyclo[2.2.1]heptane-2-carbonyl)-pyridin-2-ylamino]-7H-pyrrolo[2,3-d]pyrimidine-6-carboxylic acid methylamide

Step 1

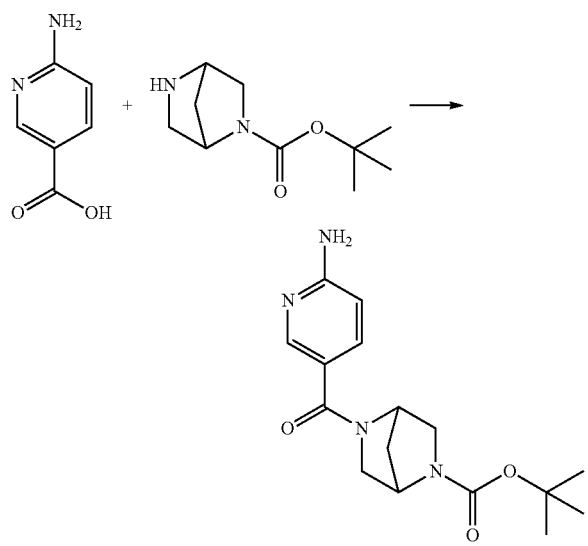

Preparation of 5-(6-Amino-pyridine-3-carbonyl)-(S,S)2,5-diaza-bicyclo[2.2.1]heptane-2-carboxylic acid tert-butyl ester Following general amide formation method 1, 2-aminopyridyl-5-carboxylic acid (0.697 g, 5.04 mmol), was combined with (S,S)-2,5-Diaza-bicyclo[2.2.1]heptane-2-carboxylic acid tert-butyl ester (1.00 g, 5.04 mmol, 1.0 eq) which after purification gave 5-(6-Amino-pyridine-3-carbonyl)-2,5-diaza-bicyclo[2.2.1]heptane-2-carboxylic acid tert-butyl ester as a white solid (350 mg, 1.01 mmol) in 20% yield. $^1$H NMR (400 MHz, CDCl$_3$) δ ppm 1.36-1.63 (m, 10H) 1.93 (br. s., 2H) 3.34-3.86 (m, 4H) 4.35-5.07 (m, 3H) 6.55 (d, J=8.59 Hz, 1H) 7.71 (br. s., 1H) 8.29 (br. s., 1H); MS m/z 319.4 (M+H)$^+$.

Step 2

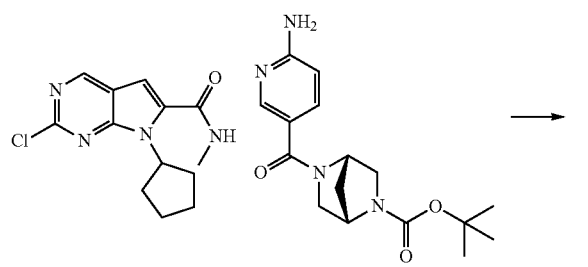

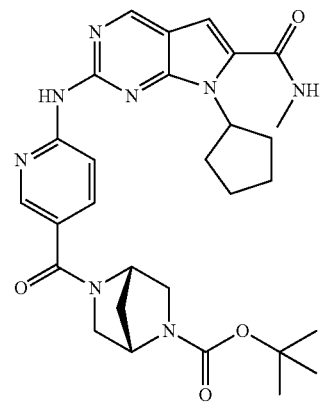

Preparation of (1S,4S)-5-[6-(7-Cyclopentyl-6-methylcarbamoyl-7H-pyrrolo[2,3-d]pyrimidin-2-ylamino)-pyridine-3-carbonyl]-2,5-diaza-bicyclo[2.2.1]heptane-2-carboxylic acid tert-butyl ester Following general N—C coupling procedure 1, 2-chloro-7-cyclopentyl-7H-pyrrolo[2,3-d]pyrimidine-6-carboxylic acid methylamide, see WO 2010020675, (0.120 g, 0.431 mmol) was combined with (1S,4S)-5-(6-amino-pyridine-3-carbonyl)-2,5-diaza-bicyclo[2.2.1]heptane-2-carboxylic acid tert-butyl ester (0.144 g, 0.452 g, 1.05 eq), which gave (1S,4S)-5-[6-(7-Cyclopentyl-6-methylcarbamoyl-7H-pyrrolo[2,3-d]pyrimidin-2-ylamino)-pyridine-3-carbonyl]-2,5-diaza-bicyclo[2.2.1]heptane-2-carboxylic acid tert-butyl ester as a yellow solid. This material was used directly in the following step 3. MS m/z 561.5 (M+H)$^+$.

Step 3

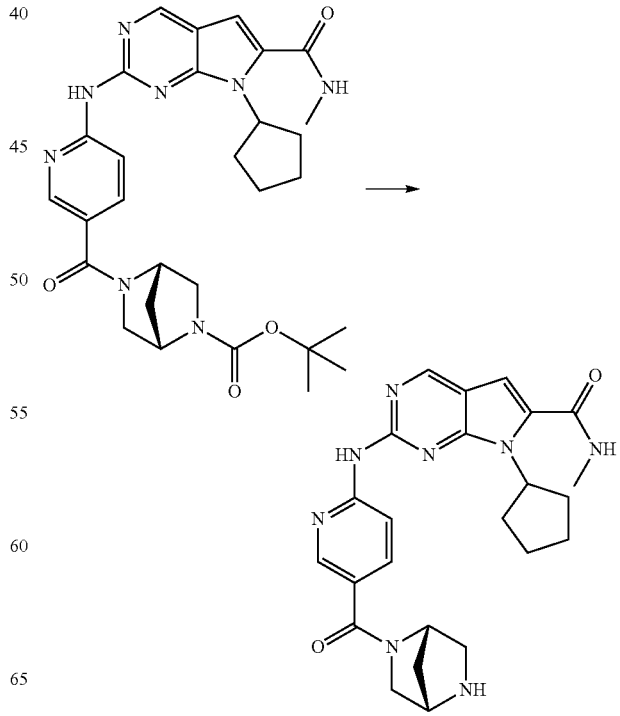

Preparation of 7-Cyclopentyl-2-[5-((1S,4S)-2,5-diaza-bicyclo[2.2.1]heptane-2-carbonyl)-pyridin-2-ylamino]-7H-pyrrolo[2,3-d]pyrimidine-6-carboxylic acid methylamide Following deprotection method 1, (1S,4S)-5-[6-(7-Cyclopentyl-6-methylcarbamoyl-7H-pyrrolo[2,3-d]pyrimidin-2-ylamino)-pyridine-3-carbonyl]-2,5-diaza-bicyclo[2.2.1]heptane-2-carboxylic acid tert-butyl ester was converted to 7-cyclopentyl-2-[5-((1S,4S)-2,5-diaza-bicyclo[2.2.1]heptane-2-carbonyl)-pyridin-2-ylamino]-7H-pyrrolo[2,3-d]pyrimidine-6-carboxylic acid methylamide (70 mg, 0.152 mmol) in 35% yield. $^1$H NMR (400 MHz, MeOD) δ ppm 1.70-1.85 (m, 3H) 1.90 (s, 3H) 2.02-2.15 (m, 4H) 2.58 (d, J=9.09 Hz, 2H) 2.92 (s, 3H) 3.01 (t, J=9.35 Hz, 1H) 3.15 (dd, J=13.89, 10.36 Hz, 1H) 3.39-3.50 (m, 1H) 3.66 (dd, J=11.37, 2.27 Hz, 1H) 3.71-3.80 (m, 1H) 5.47 (quin, J=8.84 Hz, 1H) 6.88 (s, 1H) 7.83-8.02 (m, 1H) 8.42-8.60 (m, 2H) 8.82 (s, 1H); MS m/z 461.5 (M+H)$^+$.

Example 25

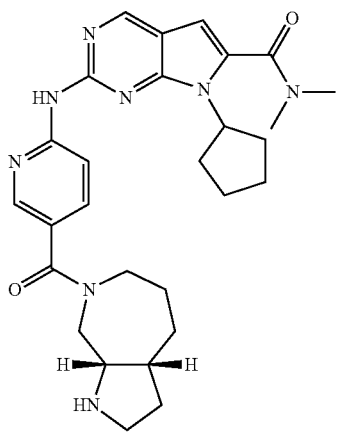 [SMILES: CN(C)C(=O)c1cc2cnc(Nc3ccc(C(=O)N4CCC[C@@H]5CCN[C@@H]5C4)cn3)nc2n1C1CCCC1]

7-Cyclopentyl-2-[5-((3aR,8aS)-octahydro-pyrrolo[2,3-c]azepine-7-carbonyl)-pyridin-2-ylamino]-7H-pyrrolo[2,3-d]pyrimidine-6-carboxylic acid dimethylamide Step 1

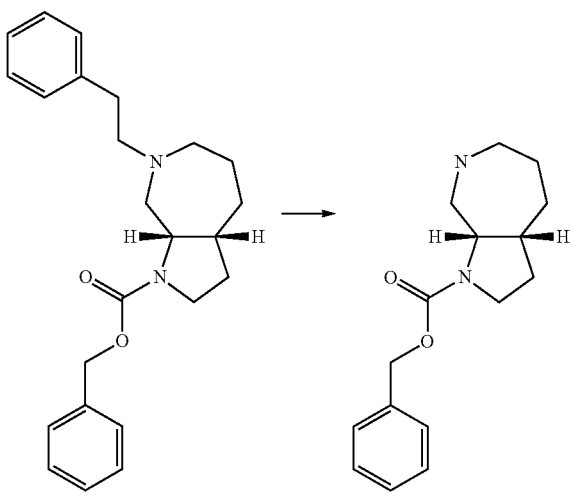 [SMILES: O=C(OCc1ccccc1)N1CC[C@H]2CCCN(CCc3ccccc3)C[C@H]21 ; O=C(OCc1ccccc1)N1CC[C@H]2CCCNC[C@H]21]

(3aR,8aS)-7-Phenethyl-octahydro-pyrrolo[2,3-c]azepine-1-carboxylic acid benzyl ester To a suspension of (3aR,8aS)-7-Phenethyl-decahydro-pyrrolo[2,3-c]azepine (4.0 g, 16.37 mmol) (Reference: PCT Int. Appl., 2005097791, 20 Oct. 2005) in ethyl acetate (100 mL) was added a solution of potassium carbonate (6.79 g, 49.1 mmol, 3.0 eq) in water (100 mL). The biphasic solution was cooled to 0° C. then benzylchloroformate (2.80 mL, 19.64 mmol, 1.2 eq) added dropwise. The resulting mixture was stirred for 3 hr at 23° C. The mixture was partitioned and the aqueous layer extracted with Ethyl Acetate. The combined organic layers were washed with water followed by brine and the organic layer dried (Na$_2$SO$_4$), filtered, and the filtrate concentrated to yield an orange oil. The crude was purified using silica gel chromatography (1:2 Ethyl Acetate/Heptane to 100% Ethyl Acetate followed by 12:1 CH$_2$Cl$_2$/Methanol) giving (3aR,8aS)-7-Phenethyl-octahydro-pyrrolo[2,3-c]azepine-1-carboxylic acid benzyl ester.

$^1$H NMR (400 MHz, CDCl$_3$) δ ppm 1.31-1.52 (m, 1H) 1.52-1.81 (m, 3H) 1.81-2.03 (m, 2H) 2.25-2.53 (m, 3H) 2.53-2.68 (m, 2H) 2.68-2.97 (m, 3H) 3.21-3.40 (m, 1H) 3.40-3.55 (m, 1H) 3.93-4.16 (m, 1H) 5.05 (d, J=12.05 Hz, 1H) 5.13 (d, J=4.52 Hz, 1H) 7.04 (d, J=7.03 Hz, 1H) 7.12-7.30 (m, 6H) 7.30-7.44 (m, 3H).

Step 2

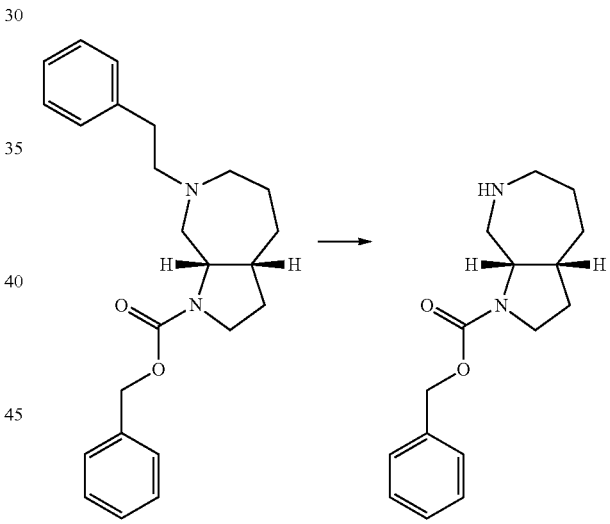

(3aR,8aS)-Octahydro-pyrrolo[2,3-c]azepine-1-carboxylic acid benzyl ester

To a solution of (3aR,8aS)-7-Phenethyl-octahydro-pyrrolo[2,3-c]azepine-1-carboxylic acid benzyl ester (1.0 g, 2.64 mmol) in 1,2-dichloroethane (20 mL) was added 1-chloroethyl carbonochloridate (0.286 mL, 2.64 mmol, 1.0 eq) at 0° C. The reaction was stirred with warming to 23° C. over 1 hr, then refluxed for 3 hr. The solvent was removed in vacuo then 20 mL methanol added and the reaction mixture heated to 50° C. for 1 hr. The reaction was concentrated and purified using chromatography (1:2 Ethyl Acetate/Heptane to 100% Ethyl Acetate followed by 12:1 CH$_2$Cl$_2$1-Methanol) giving (3aR,8aS)-Octahydro-pyrrolo[2,3-c]azepine-1-carboxylic acid benzyl ester.

MS m/z 379.3 (M+H)$^+$.

Step 3

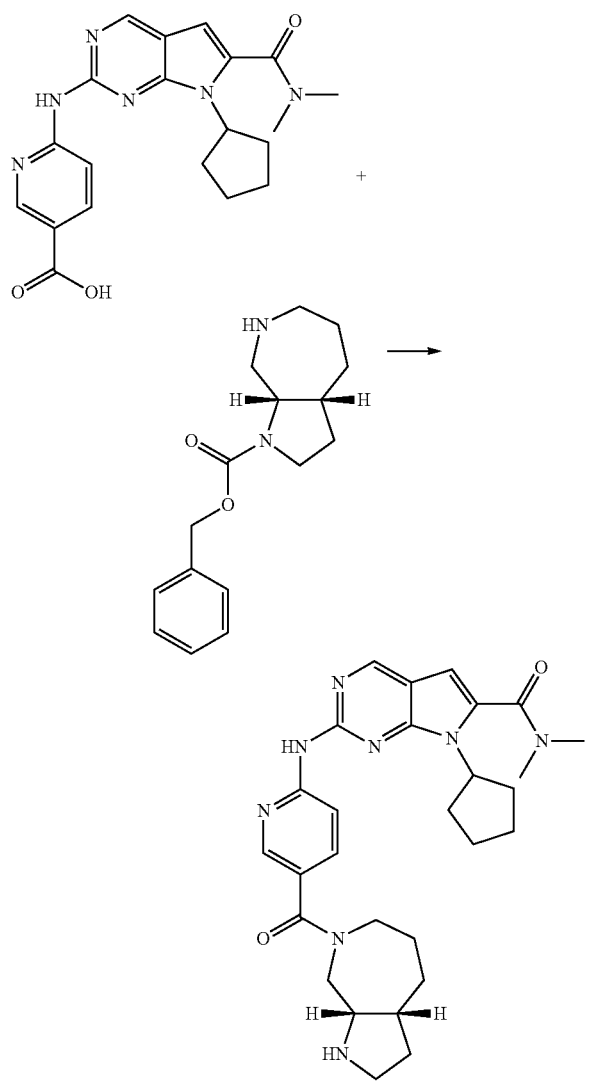

7-Cyclopentyl-2-[5-(3aR,8aS)-octahydro-pyrrolo[2,3-c]azepine-7-carbonyl)-pyridin-2-ylamino]-7H-pyrrolo[2,3-d]pyrimidine-6-carboxylic acid dimethylamide A solution of 6-(7-cyclopentyl-6-(dimethylcarbamoyl)-7H-pyrrolo[2,3-d]pyrimidin-2-ylamino) nicotinic acid (5 eq of Lithium Chloride) (0.088 g, 0.146 mmol), HBTU (0.086 mg, 0.226 mmol, 1.6 eq) and triethylamine (0.100 mL, 0.717 mmol, 4.9 eq) in DMF (3 mL) was stirred at 23° C. for 5 minutes, then (3aR,8aS)-Octahydro-pyrrolo[2,3-c]azepine-1-carboxylic acid benzyl ester (0.040 mg, 0.146 mmol, 1.0 eq) was added and the reaction stirred at 23° C. for 1.5 hr. The reaction mixture was diluted with Ethyl Acetate, the mixture washed with 0.5M HCl (aq), then water (3×), brine, the organic layer dried ($Na_2SO_4$), filtered, and the filtrate concentrated. The crude was purified using chromatography (Methanol/$CH_2Cl_2$) giving a white solid. To the resulting solid (42 mg) was added 10% Pd/C (15 mg) followed by methanol (5 mL). The suspension was blanketed with $H_2$ balloon with stirring for 6 hr. The contents of the reaction were filtered through Celite and the filtrate concentrated to a white solid that was burified by trituration from Ethyl Acetate/Heptane followed by chromatography (methanol/$CH_2Cl_2$) mixtures gave 7-cyclopentyl-2-[5-((3aR,8aS)-octahydro-pyrrolo[2,3-c]azepine-7-carbonyl)-pyridin-2-ylamino]-7H-pyrrolo[2,3-d]pyrimidine-6-carboxylic acid dimethylamide. (20 mg, 0.039 mmol, 27%). $^1$H NMR (400 MHz, MeOD) δ ppm 1.62-1.84 (m, 5H) 1.84-1.99 (m, 2H) 1.99-2.20 (m, 4H) 2.31 (dd, J=13.05, 5.02 Hz, 1H) 2.47-2.62 (m, 2H) 2.63-2.80 (m, 1H) 3.18-3.27 (m, 1H) 3.38-3.61 (m, 2H) 3.77 (d, J=13.05 Hz, 1H) 3.84-3.98 (m, 1H) 4.04 (t, J=7.53 Hz, 1H) 4.06-4.19 (m, 1H) 4.80 (quin, J=9.03, 8.87 Hz, 1H) 6.67 (s, 1H) 7.93 (dd, J=8.78, 2.26 Hz, 1H) 8.45 (d, J=2.01 Hz, 1H) 8.53 (d, J=8.53 Hz, 1H) 8.82 (s, 1H); HRMS calc for m/z=517.3039. Found m/z=517.3044 (M+H)$^+$.

Example 26

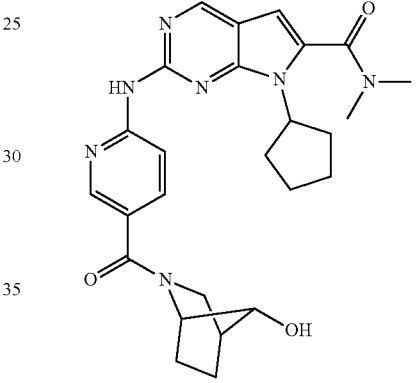

7-cycloheptyl-2-(5-((1R,4R,7R)-7-hydroxy-2-azabicyclo[2.2.1]heptane-2-carbonyl)pyridin-2-ylamino)-N,N-dimethyl-7H-pyrrolo[2,3-d]pyrimidine-6-carboxamide The 6-(7-cyclopentyl-6-(dimethylcarbamoyl)-7H-pyrrolo[2,3-d]pyrimidin-2-ylamino)nicotinic acid was combined with (1R,4R,7R)-2-azabicyclo[2.2.1]heptan-7-ol following amide formation method 3 which gave 7-cycloheptyl-2-(5-((1R,4R,7R)-7-hydroxy-2-azabicyclo[2.2.1]heptane-2-carbonyl)pyridin-2-ylamino)-N,N-dimethyl-7H-pyrrolo[2,3-d]pyrimidine-6-carboxamide (47 mg, 78% yield). 1H NMR (400 MHz, CDCl3) δ ppm 9.75 (br. s., 0.8H, Rotamer) 9.60 (br. s., 0.2H, Rotamer) 8.88 (s, 1H) 8.60-8.50 (m, 1H) 8.61-8.41 (m, 1H) 7.93-7.81 (m, 1H) 6.47 (s, 1H) 4.86-4.71 (m, J=8.97, 8.97, 8.84, 8.59 Hz, 1H) 4.39 (br. s., 0.2H, Rotamer) 4.24 (br. s., 0.2H, Rotamer) 4.19 (br. s., 0.8H, Rotamer) 4.05 (s, 0.8H, Rotamer) 3.73 (br. s., 0.8H, Rotamer) 3.67 (s, 0.2H, Rotamer) 3.65-3.62 (m, 0.8H, Rotamer) 3.46 (m, 0.2H, Rotamer) 3.24-3.21 (d, J=11.62 Hz, 0.8H, Rotamer) 3.16 (d, J=11.62 Hz, 0.2H, Rotamer) 3.15 (s, 6H) 2.66-2.6648 (m, 2H) 2.41 (br. s., 0.8H, Rotamer) 2.34 (br. s., 0.2H, Rotamer) 2.15-1.93 (m, 6H) 1.64-1.91 (m, 3H) 1.59-1.48 (m, 0.8H, Rotamer) 1.44 (br. s., 0.2H, Rotamer); HR-MS (m/z MH+) 490.26 RT 3.21 min

Example 27

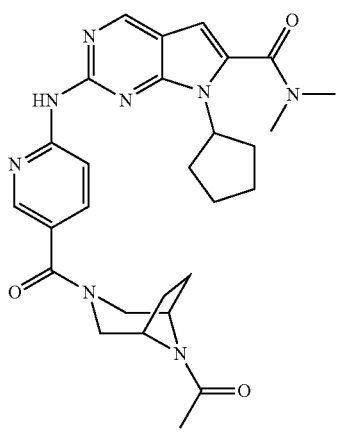 [SMILES: CC(=O)N1C2CCC1CN(C(=O)c1ccc(Nc3ncc4cc(C(=O)N(C)C)n(C5CCCC5)c4n3)nc1)C2]

2-(5-(8-acetyl-3,8-diazabicyclo[3.2.1]octane-3-carbonyl)pyridin-2-ylamino)-7-cyclopentyl-N,N-dimethyl-7H-pyrrolo[2,3-d]pyrimidine-6-carboxamide The 6-(7-cyclopentyl-6-(dimethylcarbamoyl)-7H-pyrrolo[2,3-d]pyrimidin-2-ylamino)nicotinic acid was combined with 1-(3,8-diazabicyclo[3.2.1]octan-8-yl)ethanone following amide formation method 3 which gave 2-(5-(8-acetyl-3,8-diazabicyclo[3.2.1]octane-3-carbonyl)pyridin-2-ylamino)-7-cyclopentyl-N,N-dimethyl-7H-pyrrolo[2,3-d]pyrimidine-6-carboxamide (43 mg, 62% yield). 1H NMR (400 MHz, MeOD) δ ppm 8.80 (s, 1H) 8.53 (d, J=8.59 Hz, 1H) 8.39 (d, J=2.02 Hz, 1H) 7.86 (dd, J=8.59, 2.02 Hz, 1H) 6.65 (s, 1H) 4.80-4.73 (m, 1H) 4.73-4.25 (m, 3H) 3.86-3.41 (m, 2H) 3.16 (s, 7H) 2.64-2.42 (m, 2H) 2.23-1.99 (m, 8H) 1.91 (br. s., 2H) 1.83-1.61 (m, 3H); HR-MS (m/z MH+) 531.28 RT 4.27 min

Example 28

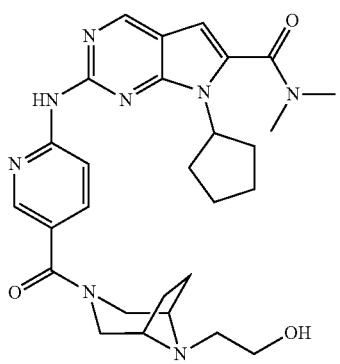 [SMILES: CN(C)C(=O)c1cc2cnc(Nc3ccc(C(=O)N4CC5CCC(C4)N5CCO)cn3)nc2n1C1CCCC1]

Preparation of 7-cyclopentyl-2-(5-(8-(2-hydroxyethyl)-3,8-diazabicyclo[3.2.1]octane-3-carbonyl)pyridin-2-ylamino)-N,N-dimethyl-7H-pyrrolo[2,3-d]pyrimidine-6-carboxamide The 6-(7-cyclopentyl-6-(dimethylcarbamoyl)-7H-pyrrolo[2,3-d]pyrimidin-2-ylamino)nicotinic acid was combined with 2-(3,8-diazabicyclo[3.2.1]octan-8-yl)ethanol following amide formation method 3 which gave 7-cyclopentyl-2-(5-(8-(2-hydroxyethyl)-3,8-diazabicyclo[3.2.1]octane-3-carbonyl)pyridin-2-ylamino)-N,N-dimethyl-7H-pyrrolo[2,3-d]pyrimidine-6-carboxamide (18 mg, 59% yield). $^1$H NMR (400 MHz, CDCl$_3$) δ ppm 9.00-8.87 (m, 1H) 8.87-8.78 (m, 1H) 8.57 (d, J=8.08 Hz, 1H) 8.44 (s, 1H) 7.79 (dd, J=8.59, 2.53 Hz, 1H) 6.54-6.43 (m, 1H) 4.81 (dq, J=9.09, 8.93 Hz, 1H) 4.51 (br. s., 1H) 3.82-3.49 (m, 4H) 3.40-2.99 (m, 10H) 2.69-2.44 (m, 4H) 2.16-1.99 (m, 4H) 1.91 (d, J=5.56 Hz, 2H) 1.83-1.45 (m, 4H); HR-MS (m/z MH+) 533.30 RT 2.56 min

Example 29

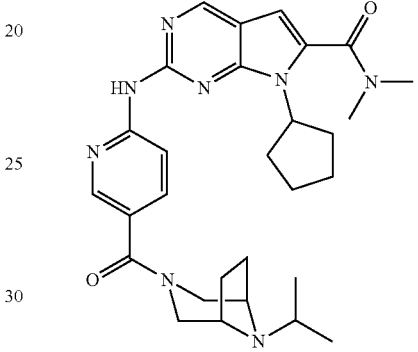

7-cyclopentyl-2-(5-(8-isopropyl-3,8-diazabicyclo[3.2.1]octane-3-carbonyl)pyridin-2-ylamino)-N,N-dimethyl-7H-pyrrolo[2,3-d]pyrimidine-6-carboxamide To a solution of 2-(5-(3,8-diazabicyclo[3.2.1]octane-3-carbonyl)pyridin-2-ylamino)-7-cyclopentyl-N,N-dimethyl-7H-pyrrolo[2,3-d]pyrimidine-6-carboxamide (42 mg, 0.086 mmol) in 6 ml of DCM, acetone (0.6 ml) was added and the resulting reaction mixture was stirred for 1H at room temperature. Na(AcO)3BH (55 mg, 0.26 mmol) was added and the resulting reaction mixture was stirred at room temperature overnight. When LCMS showed the reaction was complete the reaction mixture was diluted with DCM, washed with sat NaHCO3 (2×), brine. The combined aqueous layers were backextracted with DCM and the combined organic layers were dried over Na2SO4, filtered and purified by column chromatography (0-20% MeOH/CHCl2) which gave 7-cyclopentyl-2-(5-(8-isopropyl-3,8-diazabicyclo[3.2.1]octane-3-carbonyl)pyridin-2-ylamino)-N,N-dimethyl-7H-pyrrolo[2,3-d]pyrimidine-6-carboxamide (64 mg, 88% yield).

1H NMR (400 MHz, CDCl3) δ ppm 9.43 (br. s., 1H) 8.88 (s, 1H) 8.57 (d, J=8.59 Hz, 1H) 8.48 (d, J=2.53 Hz, 1H) 7.77 (dd, J=8.84, 2.27 Hz, 1H) 6.47 (s, 1H) 4.80 (quin, J=8.84 Hz, 1H) 4.39 (br. s., 1H) 3.74-3.30 (m, 4H) 3.26-3.04 (m, 7H) 2.68-2.49 (m, 3H) 2.18-1.95 (m, 4H) 1.86 (br. s., 2H) 1.79-1.62 (m, 3H) 1.53 (br. s., 1H) 1.07 (d, J=6.06 Hz, 6H)

HR-MS (m/z MH+) 531.32 RT 2.71 min

Example 30

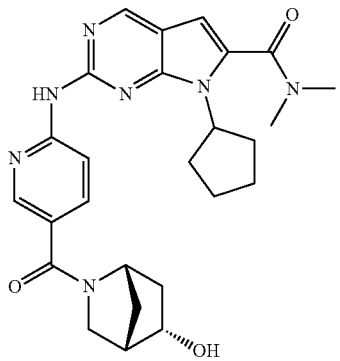 [SMILES: CN(C)C(=O)c1cc2cnc(Nc3ccc(C(=O)N4C[C@@H]5C[C@H]4C[C@@H]5O)cn3)nc2n1C1CCCC1]

7-cyclopentyl-2-(5-((1S,4S,5S)-5-hydroxy-2-azabi-
cyclo[2.2.1]heptane-2-carbonyl)pyridin-2-ylamino)-
N,N-dimethyl-7H-pyrrolo[2,3-d]pyrimidine-6-car-
boxamide The 6-(7-cyclopentyl-6-(dimethylcarbamoyl)-7H-pyrrolo
[2,3-d]pyrimidin-2-ylamino)nicotinic acid was combined
with (1S,4S,5S)-2-azabicyclo[2.2.1]heptan-5-ol following
amide formation method 3 which gave 7-cyclopentyl-2-(5-
((1S,4S,5S)-5-hydroxy-2-azabicyclo[2.2.1]heptane-2-car-
bonyl)pyridin-2-ylamino)-N,N-dimethyl-7H-pyrrolo[2,3-d]
pyrimidine-6-carboxamide (40 mg, 63% yield). 1H NMR
(400 MHz, CDCl3) δ ppm 9.84 (br. s., 0.4H, Rotamer) 9.54
(br. s., 0.6H, Rotamer) 8.98-8.82 (m, 1H) 8.80 (s, 0.4H, Rota-
mer) 8.59 (s, 0.6H, Rotamer) 8.57-8.48 (m, 1H) 7.97 (d,
J=7.07 Hz, 0.4H, Rotamer) 7.86 (d, J=6.57 Hz, 0.6H, Rota-
mer) 6.46 (s, 1H) 4.78 (m, 1H) 4.74 (br. s., 0.4H, Rotamer)
4.46 (br. s., 1H) 4.17 (br. s., 0.6H, Rotamer) 4.07 (d, J=9.09
Hz, 0.4H, Rotamer) 3.91 (d, 1=11.62 Hz, 0.6H, Rotamer)
3.64-3.49 (m, 0.6H, Rotamer) 3.49-3.269 (m, 1H+0.4H,
Rotamer) 3.15 (s, 6H) 2.73 (m, 0.6H, Rotamer) 2.67 (m, 0.4H,
Rotamer) 2.57 (m, 2H) 2.25-1.92 (m, 5H) 1.81-1.42 (m, 5H)
HR-MS (m/z MH+) 490.26 RT 4.25 min

Example 31

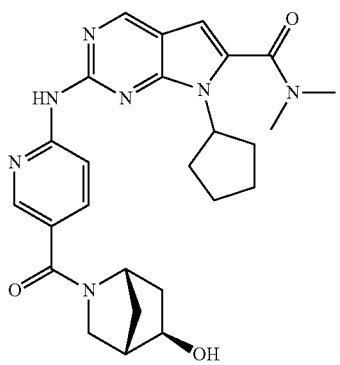 [SMILES: CN(C)C(=O)c1cc2cnc(Nc3ccc(C(=O)N4C[C@@H]5C[C@H]4C[C@H]5O)cn3)nc2n1C1CCCC1]

7-cyclopentyl-2-(5-((1S,4S,5R)-5-hydroxy-2-azabi-
cyclo[2.2.1]heptane-2-carbonyl)pyridin-2-ylamino)-
N,N-dimethyl-7H-pyrrolo[2,3-d]pyrimidine-6-car-
boxamide The 6-(7-cyclopentyl-6-(dimethylcarbamoyl)-7H-pyrrolo
[2,3-d]pyrimidin-2-ylamino)nicotinic acid was combined
with (1S,4S,5R)-2-azabicyclo[2.2.1]heptan-5-ol following
amide formation method 3 which gave 7-cyclopentyl-2-(5-
((1S,4S,5R)-5-hydroxy-2-azabicyclo[2.2.1]heptane-2-car-
bonyl)pyridin-2-ylamino)-N,N-dimethyl-7H-pyrrolo[2,3-d]
pyrimidine-6-carboxamide (40 mg) in 60% yield. 1H NMR
(400 MHz, CDCl3) δ ppm 9.51-9.43 (m, 0.3H, Rotamer)
9.43-9.35 (m, 0.7H, Rotamer) 8.87 (s, 1H) 8.66-8.60 (m,
0.3H, Rotamer) 8.60-8.52 (m, 0.7H, Rotamer+1H) 7.94-7.84
(m, 1H) 6.48 (s, 1H) 4.86-4.75 (m, 1H) 4.75-4.71 (m, 0.3H,
Rotamer) 4.32-4.25 (m, 0.7H, Rotamer) 4.21-4.13 (m, 0.7H,
Rotamer) 4.08-4.02 (m, 0.3H, Rotamer) 3.61-3.50 (m, 1H)
3.15 (s, 6H) 3.10-3.01 (m, 1H) 2.93-2.83 (m, 0.7H, Rotamer)
2.78-2.67 (m, 0.3H, Rotamer H) 2.65-2.50 (m, 3H) 2.36-2.20
(m, 1H) 2.15-1.99 (m, 4H) 1.99-1.88 (m, 1H) 1.80-1.65 (m,
2H) 1.59 (none, 2H). HR-MS (m/z MH+) 490.26 RT 4.34 min

Example 32

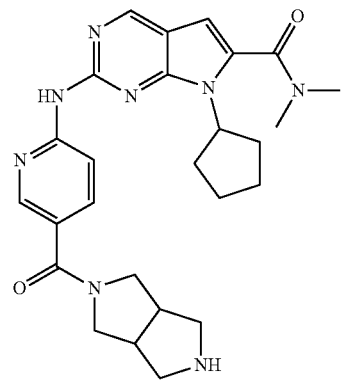 [SMILES: CN(C)C(=O)c1cc2cnc(Nc3ccc(C(=O)N4CC5CNCC5C4)cn3)nc2n1C1CCCC1]

7-cyclopentyl-N,N-dimethyl-2-(5-(octahydropyrrolo
[3,4-c]pyrrole-2-carbonyl)pyridin-2-ylamino)-7H-
pyrrolo[2,3-d]pyrimidine-6-carboxamide Step 1

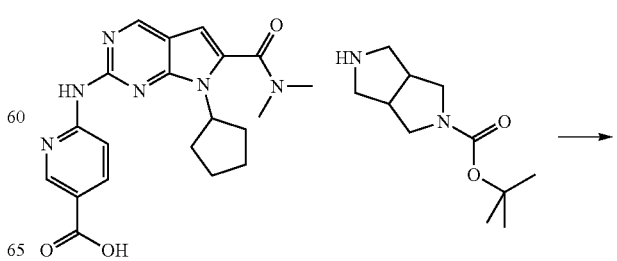

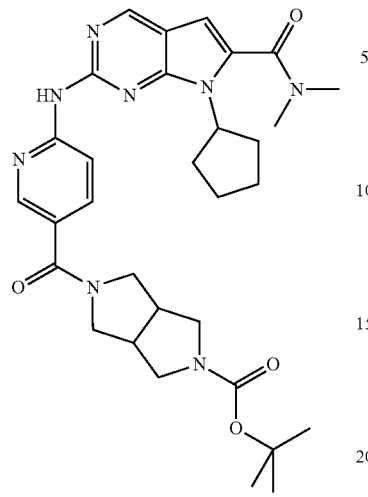

Preparation of tert-butyl 5-(6-(7-cyclopentyl-6-(dimethylcarbamoyl)-7H-pyrrolo[2,3-d]pyrimidin-2-ylamino)nicotinoyl)hexahydropyrrolo[3,4-c]pyrrole-2(1H)-carboxylate The 6-(7-cyclopentyl-6-(dimethylcarbamoyl)-7H-pyrrolo[2,3-d]pyrimidin-2-ylamino)nicotinic acid was combined with tert-butyl hexahydropyrrolo[3,4-c]pyrrole-2(1H)-carboxylate following amide formation method 3 which gave tert-butyl 5-(6-(7-cyclopentyl-6-(dimethylcarbamoyl)-7H-pyrrolo[2,3-d]pyrimidin-2-ylamino)nicotin oyl)hexahydropyrrolo[3,4-c]pyrrole-2(1H)-carboxylate (45 mg) in 63% yield. HR-MS (m/z MH+) 589.33 RT 4.31 min Step 2

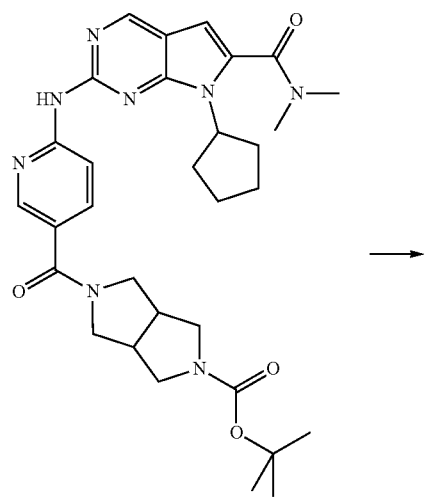

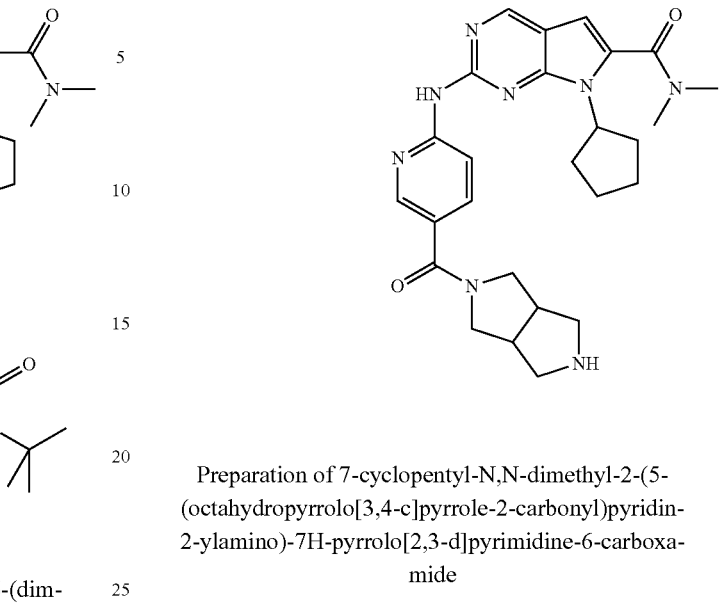

Preparation of 7-cyclopentyl-N,N-dimethyl-2-(5-(octahydropyrrolo[3,4-c]pyrrole-2-carbonyl)pyridin-2-ylamino)-7H-pyrrolo[2,3-d]pyrimidine-6-carboxamide Following deprotection method 1, tert-butyl 5-(6-(7-cyclopentyl-6-(dimethylcarbamoyl)-7H-pyrrolo[2,3-d]pyrimidin-2-ylamino)nicotinoyl) hexahydropyrrolo[3,4-c]pyrrole-2(1H)-carboxylate (45 mg, 0.076 mmol) was converted to 7-cyclopentyl-N,N-dimethyl-2-(5-(octahydropyrrolo[3,4-c]pyrrole-2-carbonyl)pyridin-2-ylamino)-7H-pyrrolo[2,3-d]pyrimidine-6-carboxamide (18 mg) in 48% yield. 1H NMR (400 MHz, CDCl3) δ ppm 9.18 (br. s., 1H) 8.86 (s, 1H) 8.51-8.66 (m, 2H) 7.90 (dd, J=8.84, 2.27 Hz, 1H) 6.55-6.43 (m, 1H) 4.81 (quin, J=8.84 Hz, 1H) 3.88 (br. s., 2H) 3.57 (br. s., 2H) 3.24-3.05 (m, 8H) 2.95-2.68 (m, 4H) 2.68-2.51 (m, 2H) 2.44 (br. s., 1H) 2.18-1.96 (m, 4H) 1.82-1.65 (m, 2H). HR-MS (m/z MH+) 489.27 RT 3.30 min Example 33

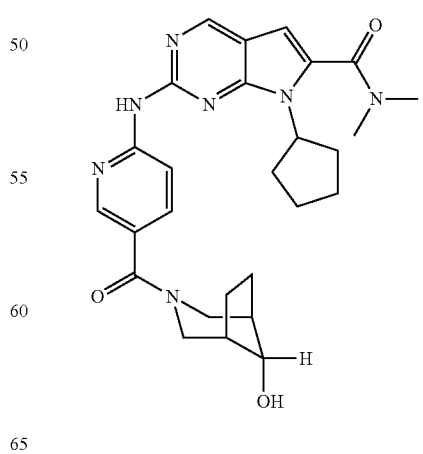

7-cyclopentyl-2-(5-((1R,5S,8r)-8-hydroxy-3-azabi-cyclo[3.2.1]octane-3-carbonyl)pyridin-2-ylamino)-N,N-dimethyl-7H-pyrrolo[2,3-d]pyrimidine-6-car-boxamide

Example 34

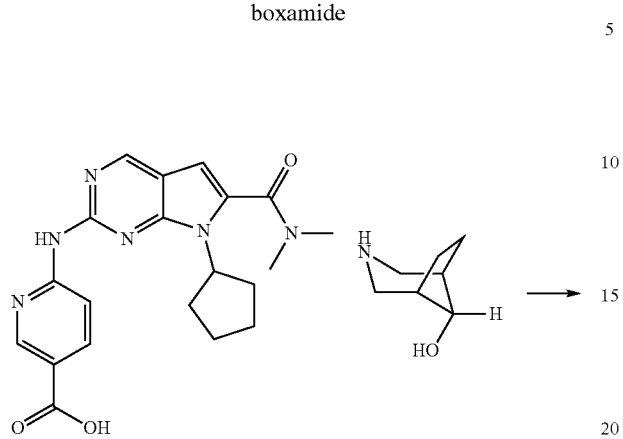

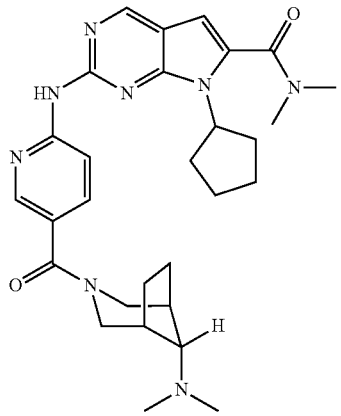 [SMILES: CN(C)C(=O)c1cc2cnc(Nc3ccc(C(=O)N4CC5CCC(C4)C5N(C)C)cn3)nc2n1C1CCCC1]

7-cyclopentyl-2-(5-(8-(dimethylamino)-3-azabicyclo[3.2.1]octane-3-carbonyl)pyridin-2-ylamino)-N,N-dimethyl-7H-pyrrolo[2,3-d]pyrimidine-6-carboxamide Step 1

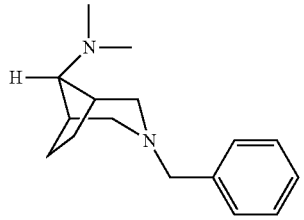 [SMILES: CN(C)C1C2CCC1CN(Cc1ccccc1)C2]

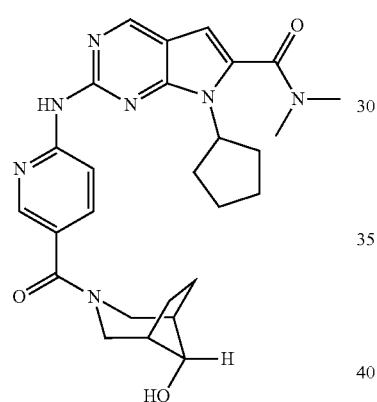

Preparation of 7-cyclopentyl-2-(5-((1R,5S,8r)-8-hydroxy-3-azabicyclo[3.2.1]octane-3-carbonyl)pyridin-2-ylamino)-N,N-dimethyl-7H-pyrrolo[2,3-d]pyrimidine-6-carboxamide Following general amide formation method 3, 6-(7-cyclopentyl-6-(dimethylcarbamoyl)-7H-pyrrolo[2,3-d]pyrimidin-2-ylamino)nicotinic acid was combined with 3-azabicyclo[3.2.1]octan-8-ol (for preparation see WO 2007 040282) which gave 7-cyclopentyl-2-(5-((1R,5S,8r)-8-hydroxy-3-azabicyclo[3.2.1]octane-3-carbonyl)pyridin-2-ylamino)-N,N-dimethyl-7H-pyrrolo[2,3-d]pyrimidine-6-carboxamide (50 mg) in 71% yield. 1H NMR (400 MHz, CDCl3) δ ppm 9.03 (s, 1H) 8.84 (s, 1H) 8.56 (d, J=9.60 Hz, 1H) 8.48 (s, 1H) 7.80 (dd, J=8.84, 2.27 Hz, 1H) 6.48 (s, 1H) 4.80 (quin, J=8.84 Hz, 1H) 4.38 (br. s., 1H) 4.08 (t, J=4.80 Hz, 1H) 3.87 (br. s., 1H) 3.55-3.38 (m, 2H) 3.16 (s, 6H) 2.68 (br. s., 1H) 2.65-2.52 (m, J=11.81, 8.75, 8.75, 8.59 Hz, 2H) 2.21-1.91 (m, 6H) 1.81-1.65 (m, 5H) 1.49 (br. s., 1H). HR-MS (m/z MH+) 504.27 RT 3.55 min Preparation of 3-benzyl-N,N-dimethyl-3-azabicyclo[3.2.1]octan-8-amine To a solution of 3-benzyl-3-azabicyclo[3.2.1]octan-8-one (107 mg, 0.50 mmol) in DCM (2 ml) was added dimethylamine (2 ml, 1M in THF) and the resulting reaction mixture was stirred at room temperature for 1H. Na(AcO)3BH (316 mg, 1.49 mmol) was added and the reaction mixture was stirred at room temperature overnight. When TLC shows completion reaction mixture was diluted with DCM and washed with water and brine. Combined aqueous layers were backextracted with DCM. Combined organic layers were dried over Na2SO4, filtered, concentrated and purified by column chromatography which gave 3-benzyl-N,N-dimethyl-3-azabicyclo[3.2.1]octan-8-amine (80 mg) in 67% yield. 1H NMR (400 MHz, MeOD) δ ppm 7.47-7.23 (m, 5H) 3.86 (s, 2H) 2.88 (d, J=11.62 Hz, 2H) 2.72 (dd, J=12.38, 3.28 Hz, 2H) 2.52 (s, 7H) 2.35 (br. s., 2H) 1.90-1.73 (m, 4H)

Step 2

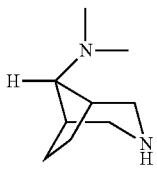

Preparation of
N,N-dimethyl-3-azabicyclo[3.2.1]octan-8-amine 3-benzyl-N,N-dimethyl-3-azabicyclo[3.2.1]octan-8-amine (80 mg, 0.45 mmol) was dissolved in MeOH (10 ml) and the atmosphere was replaced with N2 (3×). 10% Pd/C (cat.) was added and the atmosphere was replaced with H2 (3×). The resulting reaction mixture was stirred at RT at balloon pressure overnight. When TLC showed no more UV active spot the Pd/C was filtered off (always keeping wet with MeOH) and the filtrate was concentrated which gave N,N-dimethyl-3-azabicyclo[3.2.1]octan-8-amine (44 mg) in 87% yield. 1H NMR (400 MHz, MeOD) δ ppm 3.45 (d, J=12.13 Hz, 2H) 2.88 (dd, J=12.38, 2.78 Hz, 2H) 2.35 (d, J=2.02 Hz, 2H) 2.31-2.23 (m, 6H) 2.11 (t, J=4.80 Hz, 1H) 2.06-1.92 (m, 2H) 1.89-1.79 (m, 2H)

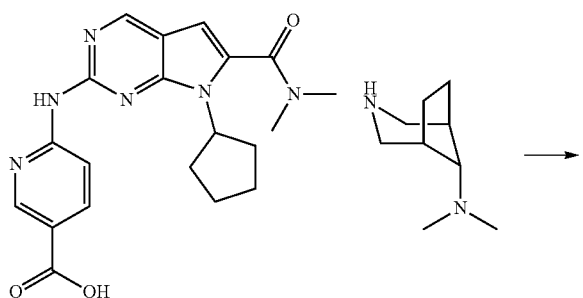

Preparation of 7-cyclopentyl-2-(5-(8-(dimethylamino)-3-azabicyclo[3.2.1]octane-3-carbonyl)pyridin-2-ylamino)-N,N-dimethyl-7H-pyrrolo[2,3-d]pyrimidine-6-carboxamide The 6-(7-cyclopentyl-6-(dimethylcarbamoyl)-7H-pyrrolo[2,3-d]pyrimidin-2-ylamino)nicotinic acid was combined with N,N-dimethyl-3-azabicyclo[3.2.1]octan-8-amine following amide formation method 3 which gave 7-cyclopentyl-2-(5-(8-(dimethylamino)-3-azabicyclo[3.2.1]octane-3-carbonyl)pyridin-2-ylamino)-N,N-dimethyl-7H-pyrrolo[2,3-d]pyrimidine-6-carboxamide (12 mg) 14% yield. 1H NMR (400 MHz, CDCl3) δ ppm 8.82 (s, 1H) 8.76 (s, 1H) 8.55 (d, J=9.60 Hz, 1H) 8.44 (d, J=2.02 Hz, 1H) 7.78 (dd, J=8.59, 2.02 Hz, 1H) 6.48 (s, 1H) 4.87-4.73 (m, 1H) 4.31 (br. s., 1H) 3.75 (br. s., 1H) 3.35 (m, 2H) 3.16 (s, 6H) 2.68-2.51 (m, 2H) 2.30 (s, 7H) 2.16-1.97 (m, 6H) 1.86-1.66 (m, 6H). HR-MS (m/z MH+) 531.32 RT 2.67 min Example 35

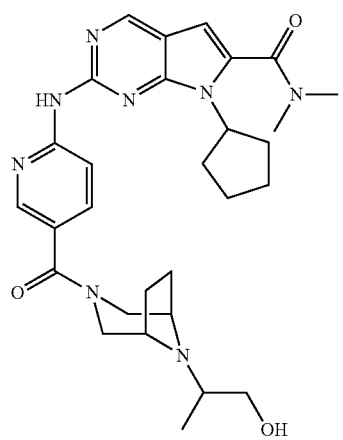 [SMILES: CC(CO)N1C2CCC1CN(C(=O)c1ccc(Nc3ncc4cc(C(=O)N(C)C)n(C5CCCC5)c4n3)nc1)C2]

7-cyclopentyl-2-(5-(8-(1-hydroxypropan-2-yl)-3,8-diazabicyclo[3.2.1]octane-3-carbonyl)pyridin-2-ylamino)-N,N-dimethyl-7H-pyrrolo[2,3-d]pyrimidine-6-carboxamide To a solution of 2-(5-(3,8-diazabicyclo[3.2.1]octane-3-carbonyl)pyridin-2-ylamino)-7-cyclopentyl-N,N-dimethyl-7H-pyrrolo[2,3-d]pyrimidine-6-carboxamide (105 mg, 0.22 mmol) in dichloromethane (2 ml) 1-hydroxypropan-2-one (2 ml) was added and the resulting reaction mixture was stirred for 1H at room temperature. Sodium triacetoxyborohydride was added and the reaction mixture was stirred at room temperature overnight. When TLC/LCMS show completion the reaction mixture is diluted with dichloromethane, washed with sat NaHCO3 (2×) and brine. The combined aqueous layers back extracted with dichloromethane and the combined organic layers are dried over sodium sulfate, filtered, concentrated and purified by column chromatography (0-20% methanol/dichloromethane) which gave 7-cyclopentyl-2-(5-(8-(1-hydroxypropan-2-yl)-3,8-diazabicyclo[3.2.1]octane-3-carbonyl)pyridin-2-ylamino)-N,N-dimethyl-7H-pyrrolo[2,3-d]pyrimidine-6-carboxamide (39 mg, 33% yield). 1H NMR (400 MHz, CDCl3) δ ppm 9.07 (s, 1H) 8.85 (s, 1H) 8.57 (d, J=9.09 Hz, 1H) 8.45 (s, 1H) 7.78 (dd, J=8.59, 2.53 Hz, 1H) 6.48 (s, 1H) 4.81 (dq, J=9.09, 8.93 Hz, 1H) 4.48 (br. s., 1H) 3.75-3.30 (m, 6H) 3.23-3.00 (m, 7H) 2.69-2.50 (m, 3H) 2.16-1.97 (m, 5H) 1.97-1.66 (m, 6H) 1.10 (d, J=6.06 Hz, 3H); HR-MS (m/z MH+) 547.32 RT 2.54 min.

Example 36

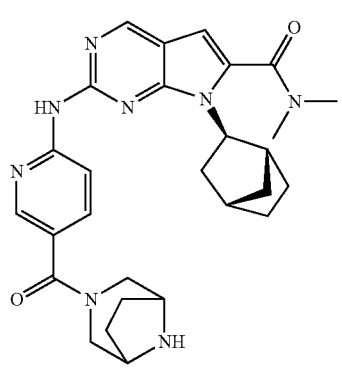

7-(1R,2R,4S)-Bicyclo[2.2.1]hept-2-yl-2-[5-(3,8-diaza-bicyclo[3.2.1]octane-3-carbonyl)-pyridin-2-ylamino]-7H-pyrrolo[2,3-d]pyrimidine-6-carboxylic acid dimethylamide

Step 1

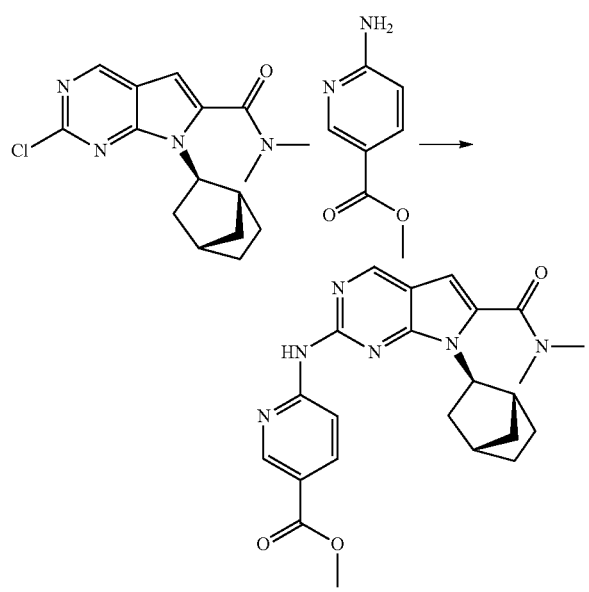

Preparation of 6-(7-exo-bicyclo[2.2.1]hept-2-yl-6-dimethylcarbamoyl-7H-pyrrolo[2,3-d]pyrimidin-2-ylamino)-nicotinic acid methyl ester Following general N—C coupling procedure 1, 7-exo-bicyclo[2.2.1]hept-2-yl-2-chloro-7H-pyrrolo[2,3-d]pyrimidine-6-carboxylic acid dimethylamide (267 mg, 0.84 mmol), was combined with methyl 6-aminonicotinate (140 mg, 0.92 mmol), which gave after purification 6-(7-exo-bicyclo[2.2.1]hept-2-yl-6-dimethylcarbamoyl-7H-pyrrolo[2,3-d]pyrimidin-2-ylamino)-nicotinic acid methyl ester (364 mg) and used as is without further characterization. MS m/z 435.5 (MH$^+$)

Step 2

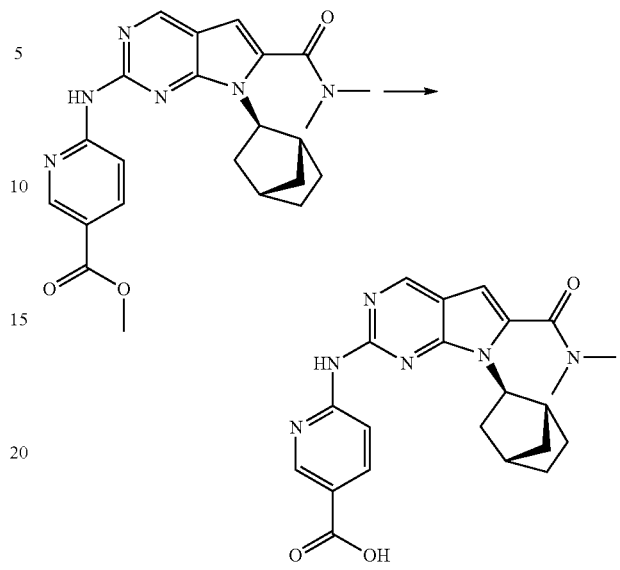

Preparations of 6-(7-exo-Bicyclo[2.2.1]hept-2-yl-6-dimethylcarbamoyl-7H-pyrrolo[2,3-d]pyrimidin-2-ylamino)-nicotinic acid To 6-(7-exo-bicyclo[2.2.1]hept-2-yl-6-dimethylcarbamoyl-7H-pyrrolo[2,3-d]pyrimidin-2-ylamino)-nicotinic acid methyl ester (364 mg, 0.84 mmol) in tetrahydrofuran (25 mL), was added 5 ml of an aqueous solution of lithium hydroxide (176 mg, 4.19 mmol). The mixture was heated to 60° C. for 18 hours, then cooled and then acidified with 6N hydrochloric acid to pH 4. The resultant mixture was then diluted with water and extracted with a 20% 2-propanol in chloroform solution (3×). The organic layer was washed with brine, then dried over anhydrous sodium sulfate, filtered and concentrated which gave 6-(7-exo-Bicyclo[2.2.1]hept-2-yl-6-dimethylcarbamoyl-7H-pyrrolo[2,3-d]pyrimidin-2-ylamino)-nicotinic acid as a brown powder and was used directly. $^1$H NMR (400 MHz, DMSO-d6) δ 12.94 (br. s, 1H), 10.26 (s, 1H), 8.86 (s, 1H), 8.82 (s, 1H), 8.37 (d, J=9.1 Hz, 1H), 8.22 (dd, J=9.1, 2.5 Hz, 1H), 6.68 (s, 1H), 4.37 (m, 1H), 3.05 (s, 6H), 2.85 (m, 1H), 2.67 (m, 1H), 2.36 (m, 1H) 1.80 (m, 1H), 1.57 (m, 2H), 1.23 (m, 4H). MS m/z 421.5 (MH$^+$),

Step 3

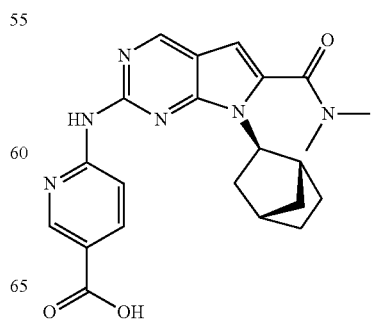

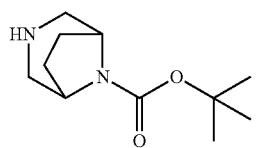

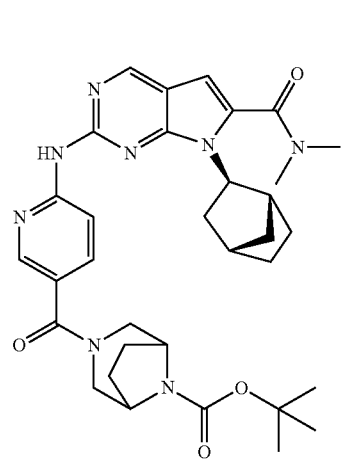

Preparation of 3-[6-((1R,2R,4S)-7-Bicyclo[2.2.1]
hept-2-yl-6-dimethylcarbamoyl-7H-pyrrolo[2,3-d]
pyrimidin-2-ylamino)-pyridine-3-carbonyl]-3,8-
diaza-bicyclo[3.2.1]octane-8-carboxylic acid tert-
butyl ester Following general amide formation method 1, 6-(7-exo-Bicyclo[2.2.1]hept-2-yl-6-dimethylcarbamoyl-7H-pyrrolo[2,3-d]pyrimidin-2-ylamino)-nicotinic acid (100 mg, 0.24 mmol), was combined with 3,8-diaza-bicyclo[3.2.1]octane-8-carboxylic acid tert-butyl ester (61 mg, 0.29 mmol) which gave 3-[6-((1R,2R,4S)-7-Bicyclo[2.2.1]hept-2-yl-6-dimethylcarbamoyl-7H-pyrrolo[2,3-d]pyrimidin-2-ylamino)-pyridine-3-carbonyl]-3,8-diaza-bicyclo[3.2.1]octane-8-carboxylic acid tert-butyl ester which was used directly without purification or further characterization.

Step 4

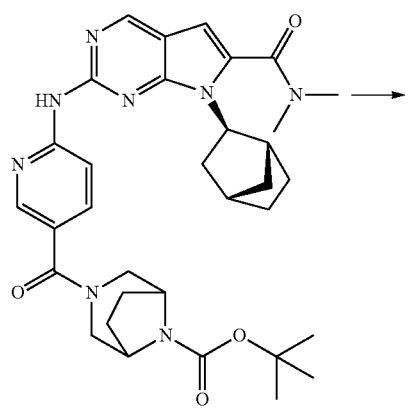

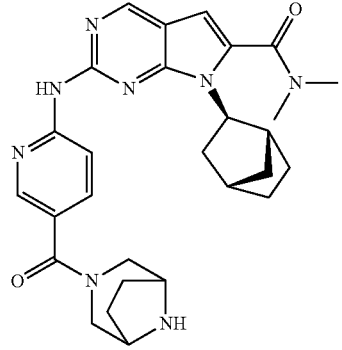 [SMILES: CN(C)C(=O)c1cc2cnc(Nc3ccc(C(=O)N4CC5CCC(C4)N5)cn3)nc2n1[C@@H]1C[C@H]2CC[C@@H]1C2]

Following deprotection method 2, 3-[6-((1R,2R,4S)-7-Bicyclo[2.2.1]hept-2-yl-6-dimethylcarbamoyl-7H-pyrrolo[2,3-d]pyrimidin-2-ylamino)-pyridine-3-carbonyl]-3,8-diaza-bicyclo[3.2.1]octane-8-carboxylic acid tert-butyl ester was converted to 7-(1R,2R,4S)-Bicyclo[2.2.1]hept-2-yl-2-[5-(3,8-diaza-bicyclo[3.2.1]octane-3-carbonyl)-pyridin-2-ylamino]-7H-pyrrolo[2,3-d]pyrimidine-6-carboxylic acid dimethylamide (40 mg) in 33% yield. $^1$H NMR (400 MHz, DMSO-d6) δ 9.87 (s, 1H), 8.81 (s, 1H), 8.28 (m, 2H), 7.81 (m, 1H), 6.65 (s, 1H), 4.35 (m, 1H), 4.21 (br. s, 1H), 3.35 (m, 4H), 3.04 (s, 6H), 2.88-2.85 (m, 2H), 2.65 (s, 1H), 2.35 (m, 1H) 1.81-1.75 (m, 1H), 1.61-1.54 (m, 6H), 1.23 (m, 3H).

MS m/z 515.7 (MH$^+$),

Example 37

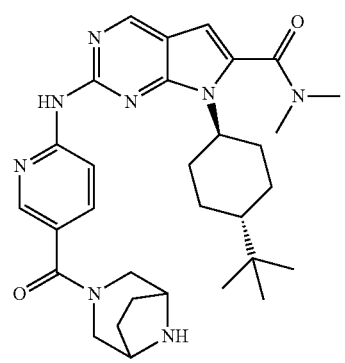 [SMILES: CN(C)C(=O)c1cc2cnc(Nc3ccc(C(=O)N4CC5CCC(C4)N5)cn3)nc2n1[C@H]1CC[C@H](C(C)(C)C)CC1]

7-(4-tert-Butyl-cyclohexyl)-2-[5-(3,8-diaza-bicyclo
[3.2.1]octane-3-carbonyl)-pyridin-2-ylamino]-7H-
pyrrolo[2,3-d]pyrimidine-6-carboxylic acid dimethy-
lamide Step 1

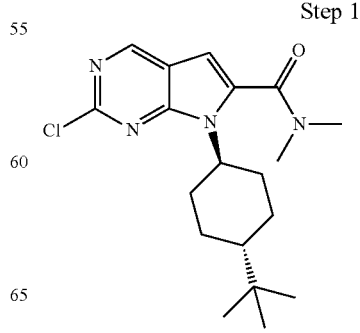

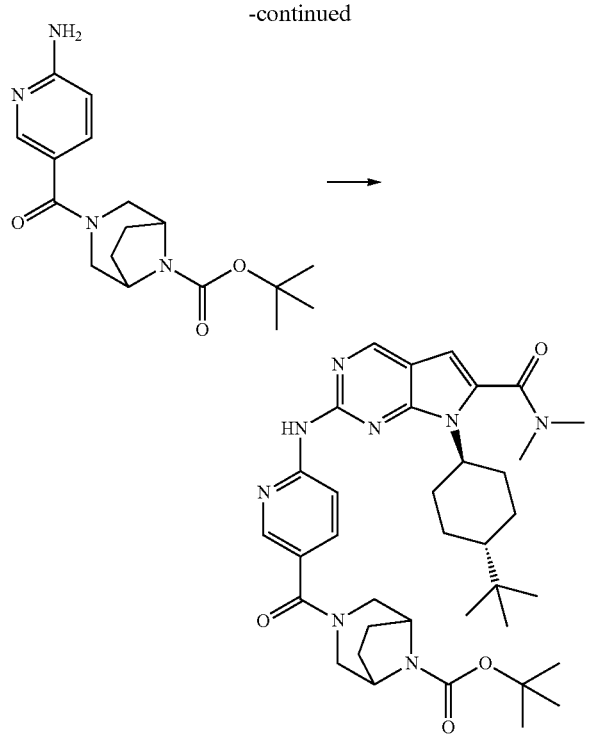

Preparation of 3-{6-[7-(4-tert-Butyl-cyclohexyl)-6-dimethylcarbamoyl-7H-pyrrolo[2,3-d]pyrimidin-2-ylamino]-pyridine-3-carbonyl}-3,8-diaza-bicyclo[3.2.1]octane-8-carboxylic acid tert-butylester Following General N—C coupling procedure 1 trans-7-(4-tert-butyl-cyclohexyl)-2-chloro-7H-pyrrolo[2,3-d]pyrimidine-6-carboxylic acid dimethylamide (157 mg, 0.43 mmol), was combined with 3-(6-Amino-pyridine-3-carbonyl)-3,8-diaza-bicyclo[3.2.1]octane-8-carboxylic acid tert-butyl ester, which gave upon work up gave 3-{6-[7-(4-tert-Butyl-cyclohexyl)-6-dimethylcarbamoyl-7H-pyrrolo[2,3-d]pyrimidin-2-ylamino]-pyridine-3-carbonyl}-3,8-diaza-bicyclo[3.2.1]octane-8-carboxylic acid tert-butylester and was used as is.

Step 2

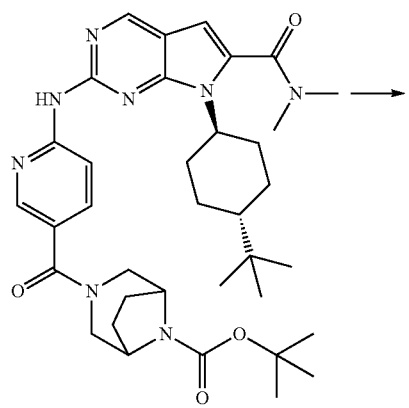

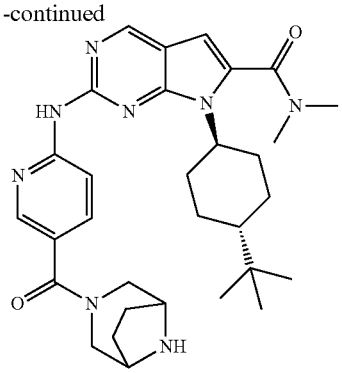

Preparation of trans-7-(4-tert-Butyl-cyclohexyl)-2-[5-(3,8-diaza-bicyclo[3.2.1]octane-3-carbonyl)-pyridin-2-ylamino]-7H-pyrrolo[2,3-d]pyrimidine-6-carboxylic acid dimethylamide Following deprotection method 2, 3-{6-[7-(4-tert-Butyl-cyclohexyl)-6-dimethylcarbamoyl-7H-pyrrolo[2,3-d]pyrimidin-2-ylamino]-pyridine-3-carbonyl}-3,8-diaza-bicyclo[3.2.1]octane-8-carboxylic acid tert-butyl ester was converted to trans-7-(4-tert-Butyl-cyclohexyl)-2-[5-(3,8-diaza-bicyclo[3.2.1]octane-3-carbonyl)-pyridin-2-ylamino]-7H-pyrrolo[2,3-d]pyrimidine-6-carboxylic acid dimethylamide (90 mg) in 37% yield. $^1$H NMR (400 MHz, DMSO-d6) δ 10.06 (s, 1H), 8.85 (s, 1H), 8.47-8.43 (m, 2H), 7.78 (dd, J=8.6, 2.5 Hz 1H), 6.65 (s, 1H), 4.45 (m, 1H), 4.25 (m, 1H), 4.03 (m, 1H), 3.08 (s, 3H), 3.05 (s, 3H), 2.83 (m, 2H), 2.61 (m, 4H), 1.94-1.81 (m, 8H), 1.15 (m, 3H), 0.91 (s, 9H). MS m/z 559.7 (MH$^+$)

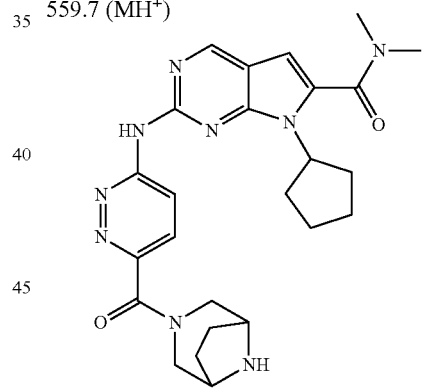

Example 38

7-Cyclopentyl-2-[6-(3,8-diaza-bicyclo[3.2.1]octane-3-carbonyl)-pyridazin-3-ylamino]-7H-pyrrolo[2,3-d]pyrimidine-6-carboxylic acid dimethylamide Step 1

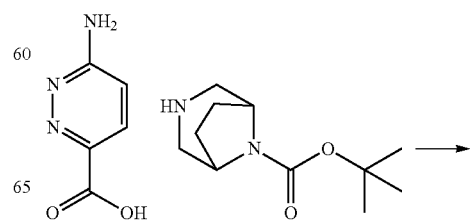

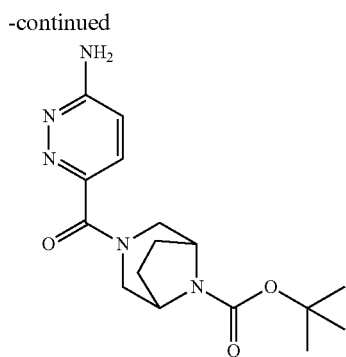

Preparation of 3-(6-Amino-pyridazine-3-carbonyl)-3,8-diaza-bicyclo[3.2.1]octane-8-carboxylic acid tert-butyl ester Following general amide formation method 1, 6-amino-pyridazine-3-carboxylic acid (212 mg, 1.0 mmol) was combined with 3,8-diaza-bicyclo[3.2.1]octane-8-carboxylic acid tert-butyl ester (139 mg, 1.0 mmol), which gave 3-(6-Amino-pyridazine-3-carbonyl)-3,8-diaza-bicyclo[3.2.1]octane-8-carboxylic acid tert-butyl ester as a white solid (169 mg, 0.51 mmol) in 51% yield. MS m/z 334.4 (M+H)$^+$.

Step 2

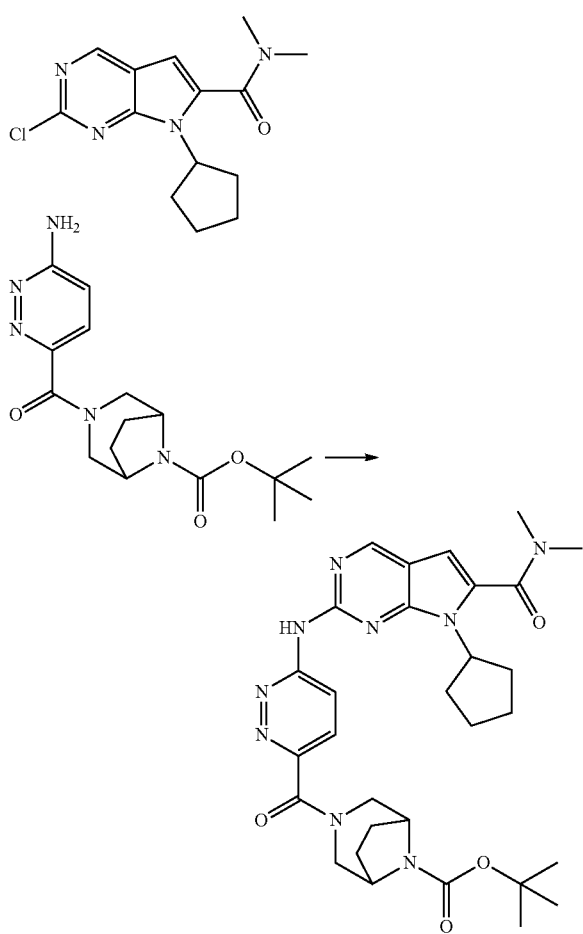

Preparation of 3-[6-(7-Cyclopentyl-6-dimethylcarbamoyl-7H-pyrrolo[2,3-d]pyrimidin-2-ylamino)-pyridazine-3-carbonyl]-3,8-diaza-bicyclo[3.2.1]octane-8-carboxylic acid tert-butyl ester Following general N—C coupling procedure 1, 2-chloro-7-cyclopentyl-7H-pyrrolo[2,3-d]pyrimidine-6-carboxylic acid dimethylamide (98 mg, 0.336 mmol), was combined with 3-(6-amino-pyridazine-3-carbonyl)-3,8-diaza-bicyclo[3.2.1]octane-8-carboxylic acid tert-butyl ester (112 mg, 0.336 mmol) which gave 3-[6-(7-Cyclopentyl-6-dimethylcarbamoyl-7H-pyrrolo[2,3-d]pyrimidin-2-ylamino)-pyridazine-3-carbonyl]-3,8-diaza-bicyclo[3.2.1]octane-8-carboxylic acid tert-butyl ester (115 mg, 0.195 mmol) in 58% yield. MS m/z 590.6 (M+H)$^+$.

Step 3

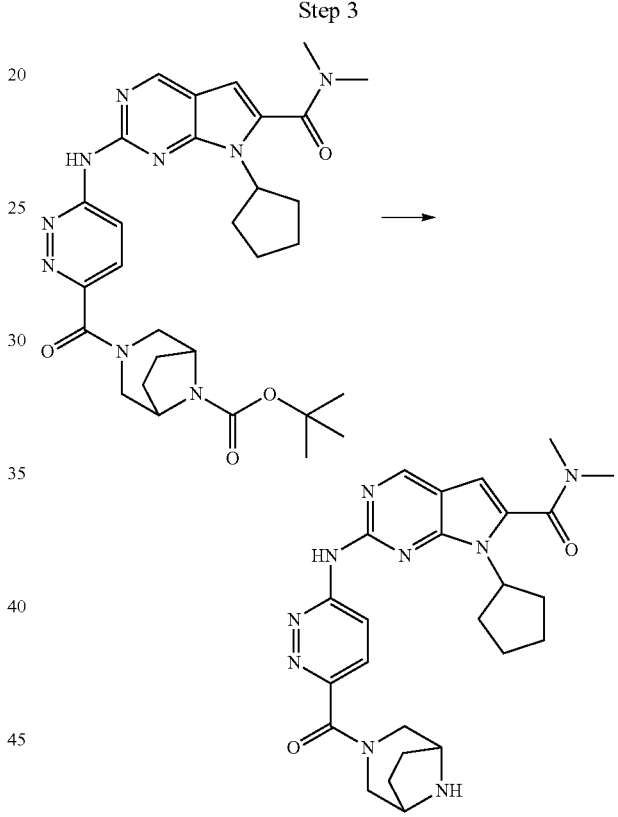

Preparation of 7-Cyclopentyl-2-[6-(3,8-diaza-bicyclo[3.2.1]octane-3-carbonyl)-pyridazin-3-ylamino]-7H-pyrrolo[2,3-d]pyrimidine-6-carboxylic acid dimethylamide Following deprotection method 2, 3-[6-(7-cyclopentyl-6-dimethylcarbamoyl-7H-pyrrolo[2,3-d]pyrimidin-2-ylamino)-pyridazine-3-carbonyl]-3,8-diaza-bicyclo[3.2.1]octane-8-carboxylic acid tert-butyl ester (110 mg, 0.187 mmol) was converted to 7-Cyclopentyl-2-[6-(3,8-diaza-bicyclo[3.2.1]octane-3-carbonyl)-pyridazin-3-ylamino]-7H-pyrrolo[2,3-d]pyrimidine-6-carboxylic acid dimethylamide as a white solid (55 mg, 0.112 mmol) in 60% yield. $^1$H NMR (400 MHz, DMSO): δ, 10.71 (s, 1H), 8.88 (s, 1H), 8.60 (d, J=8 Hz, 1H), 7.82 (d, J=8 Hz, 1H), 6.68 (s, 1H), 4.81-4.72 (m, 1H), 4.22 (d, J=12 Hz, 1H), 3.53 (d, J=12 Hz, 1H), 3.48 (br s, 1H), 3.29 (br s, 1H), 3.27 (d, J=12 Hz, 1H), 3.06 (s, 3H), 3.05 (s, 3H) 2.93 (d, J=12 Hz, 1H), 2.42-2.33 (m, 2H), 2.01-1.96 (m, 4H), 1.72-1.58 (m, 6H). HRMS calcd for C25H31N9O2. H+ (M+H)+ 1490.2679. Found 490.2676 (M+H)+.

Example 39

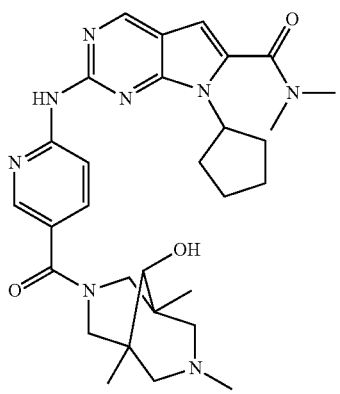 [SMILES: CN1CC2(C)CN(C(=O)c3ccc(Nc4ncc5cc(C(=O)N(C)C)n(C6CCCC6)c5n4)nc3)CC(C)(C1)C2O]

7-Cyclopentyl-2-(5-(9-hydroxy-1,5,7-trimethyl-3,7-diazabicyclo[3.3.1]nonane-3-carbonyl)pyridin-2-ylamino)-N,N-dimethyl-7H-pyrrolo[2,3-d]pyrimidine-6-carboxamide

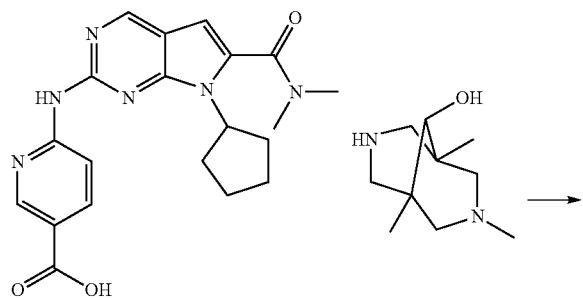

Preparation of 7-Cyclopentyl-2-(5-(9-hydroxy-1,5,7-trimethyl-3,7-diazabicyclo[3.3.1]nonane-3-carbonyl)pyridin-2-ylamino)-N,N-dimethyl-7H-pyrrolo[2,3-d]pyrimidine-6-carboxamide Following amide formation method 1, 6-(7-cyclopentyl-6-(dimethylcarbamoyl)-7H-pyrrolo[2,3-d]pyrimidin-2-ylamino)nicotinic acid with 5 equiv LiCl and 1,3,5-trimethyl-3,7-diazabicyclo[3.3.1]nonan-9-ol were combined and gave 7-cyclopentyl-2-(5-(9-hydroxy-1,5,7-trimethyl-3,7-diazabicyclo[3.3.1]nonane-3-carbonyl)pyridin-2-ylamino)-N,N-dimethyl-7H-pyrrolo[2,3-d]pyrimidine-6-carboxamide (266 mg) in 68% yield. $^1$H NMR (400 MHz, CDCl$_3$) δ ppm 8.77 (s, 1H), 8.56 (d, J=8.6 Hz, 1H), 8.33 (s, 1H), 8.17 (br s, 1H), 7.72 (d, J=8.6 Hz, 1H), 6.49 (s, 1H), 4.81 (m, 2H), 3.74 (br m, 1H), 3.26 (s, 1H), 3.18 (s, 6H), 3.07 (br m, 1H), 2.70-2.56 (m, 4H), 2.29 (br m, 3H), 2.19 (s, 3H), 2.15-2.03 (m, 4H), 1.89 (m, 1H), 1.75 (m, 2H), 1.00 (br s, 3H), 0.83 (br s 3H)

HRMS m/z 561.3301 (M+H)+.

Example 40

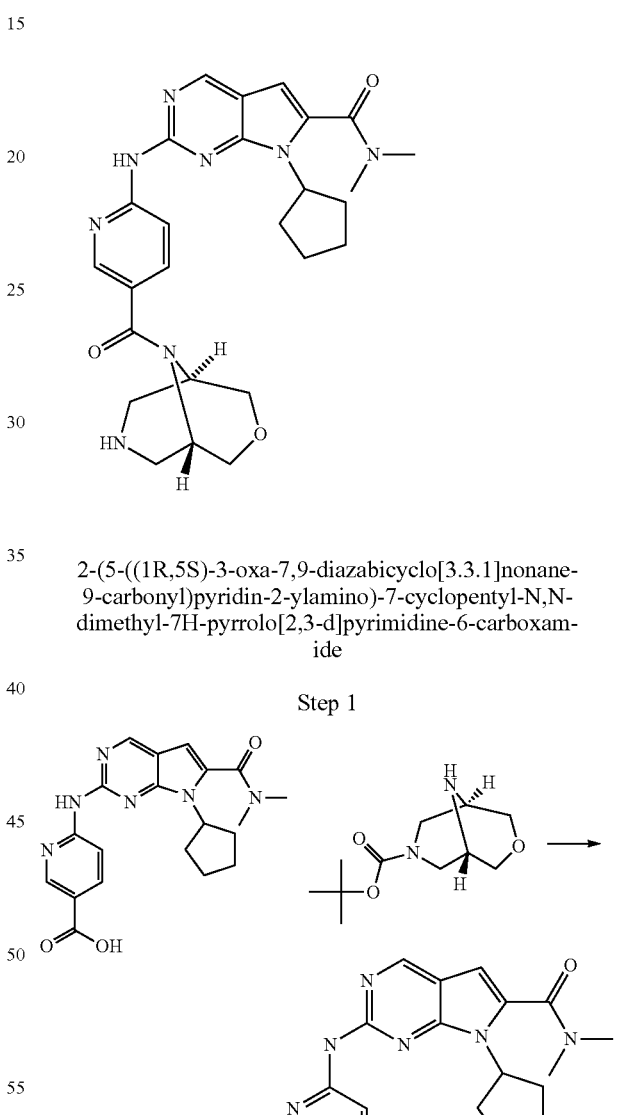

2-(5-((1R,5S)-3-oxa-7,9-diazabicyclo[3.3.1]nonane-9-carbonyl)pyridin-2-ylamino)-7-cyclopentyl-N,N-dimethyl-7H-pyrrolo[2,3-d]pyrimidine-6-carboxamide Step 1

Preparation of 2-(5-((1R,5S)-3-oxa-7,9-diazabicyclo[3.3.1]nonane-9-carbonyl)pyridin-2-ylamino)-7-cyclopentyl-N,N-dimethyl-7H-pyrrolo[2,3-d]pyrimidine-6-carboxamide Following general amide formation method 2, 6-(7-cyclopentyl-6-(dimethylcarbamoyl)-7H-pyrrolo[2,3-d]pyrimidin-2-ylamino)nicotinic acid with 5 equiv LiCl and (1R,5S)-tert-butyl 3-oxa-7,9-diazabicyclo[3.3.1]nonane-7-carboxylate were combined and gave (1R,5S)-tert-butyl 9-(6-(7-cyclopentyl-6-(dimethylcarbamoyl)-7H-pyrrolo[2,3-d]pyrimidin-2-ylamino)nicotinoyl)-3-oxa-7,9-diazabicyclo[3.3.1]nonane-7-carboxylate (115 mg) in 85% yield. ¹H NMR (400 MHz, CDCl₃) δ ppm 8.78 (s, 1H), 8.60 (d, J=9.09 Hz, 1H), 8.44 (d, J=2.02 Hz, 2H), 7.85 (dd, J1=8.59 Hz, J2=2.02 Hz, 1H), 6.49 (s, 1H), 4.82 (m, 1H), 4.59-3.75 (m, 6H), 3.17 (s, 4H), 3.02 (s, 2H), 2.95 (s, 2H), 2.81 (m, 4H), 2.57 (m, 1H), 2.09 (m, 4H), 1.75 (m, 1H), 1.49 (m, 9H) LCMS m/z 604.9 (M+H)⁺.

Step 2

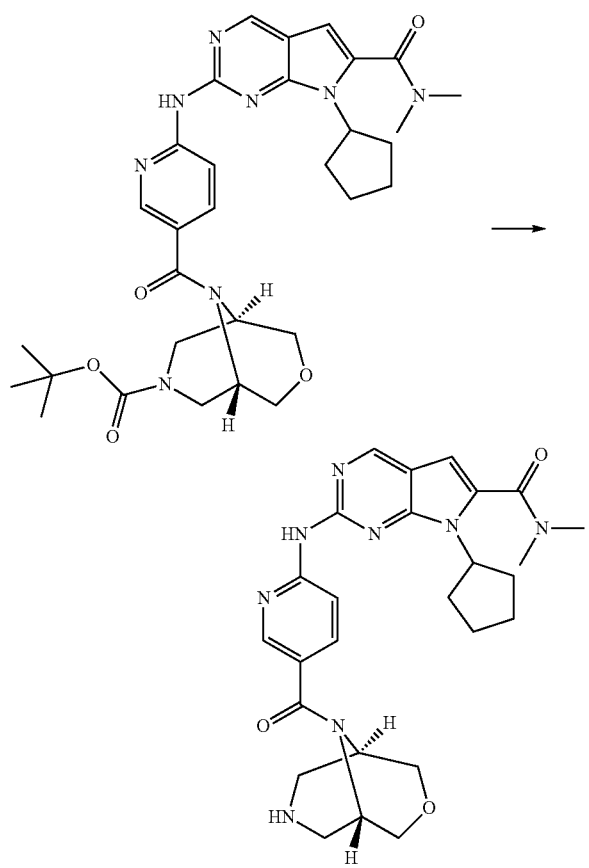

Preparation of 2-(5-((1R,5S)-3-oxa-7,9-diazabicyclo[3.3.1]nonane-9-carbonyl)pyridin-2-ylamino)-7-cyclopentyl-N,N-dimethyl-7H-pyrrolo[2,3-d]pyrimidine-6-carboxamide Following deprotection method 2, (1R,5S)-tert-butyl 9-(6-(7-cyclopentyl-6-(dimethylcarbamoyl)-7H-pyrrolo[2,3-d]pyrimidin-2-ylamino)nicotinoyl)-3-oxa-7,9-diazabicyclo[3.3.1]nonane-7-carboxylate was converted to 2-(5-((1R,5S)-3-oxa-7,9-diazabicyclo[3.3.1]nonane-9-carbonyl)pyridin-2-ylamino)-7-cyclopentyl-N,N-dimethyl-7H-pyrrolo[2,3-d]pyrimidine-6-carboxamide (80 mg) was obtained in 83% yield. ¹H NMR (400 MHz, CDCl₃) δ ppm 8.82 (s, 1H), 8.63 (d, J=8.6 Hz, 1H), 8.56 (s, 1H), 8.47 (d, J=2.0 Hz, 1H), 7.87 (dd, J1=8.78 Hz, J2=2.26 Hz, 1H), 6.51 (s, 1H), 4.83 (m, 1H), 4.47 (s, 1H), 4.09 (m, 4H), 3.77 (s, 1H), 3.45-3.21 (m, 4H), 3.19 (s, 6H), 2.59 (m, 2H), 2.11 (m, 5H), 1.77 (m, 2H). HRMS m/z 505.2665 (M+H)⁺.

Example 41

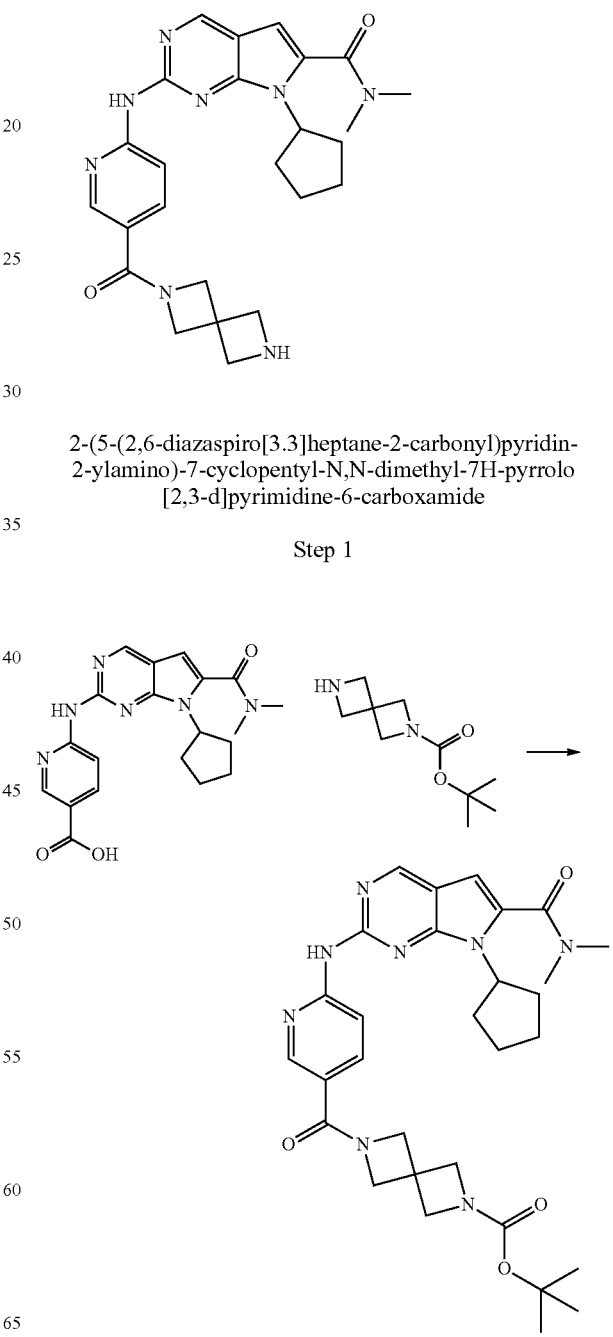

2-(5-(2,6-diazaspiro[3.3]heptane-2-carbonyl)pyridin-2-ylamino)-7-cyclopentyl-N,N-dimethyl-7H-pyrrolo[2,3-d]pyrimidine-6-carboxamide Step 1

Preparation of tert-butyl 6-(6-(7-cyclopentyl-6-(dimethylcarbamoyl)-7H-pyrrolo[2,3-d]pyrimidin-2-ylamino)nicotinoyl)-2,6-diazaspiro[3.3]heptane-2-carboxylate Following amide formation method 1, 6-(7-cyclopentyl-6-dimethylcarbamoyl-7H-pyrrolo[2,3-d]pyrimidin-2-ylamino)-nicotinic acid (199 mg, 0.5 mmol, 1.0 eq) and tert-butyl 2,6-diazaspiro[3.3]heptane-2-carboxylate (100 mg, 0.5 mmol, 1.0 eq) were combined and gave tert-butyl 6-(6-(7-cyclopentyl-6-(dimethylcarbamoyl)-7H-pyrrolo[2,3-d]pyrimidin-2-ylamino)nicotinoyl)-2,6-diazaspiro[3.3]heptane-2-carboxylate as a white solid (214 mg, 0.37 mmol) in 74% yield. ¹H NMR (400 MHz, chloroform-d) δ ppm 8.79 (s, 1H) 8.53-8.66 (m, 2H) 8.08 (dd, J=8.84, 2.27 Hz, 1H) 6.53 (s, 1H) 4.74-4.92 (m, 1H) 4.20-4.61 (m, 4H) 4.07-4.16 (m, 4H) 3.18 (br s, 6H) 2.47-2.65 (m, 2H) 2.03-2.20 (m, 4H) 1.68-1.85 (m, 3H) 1.46 (s, 9H). MS (m/z, MH+): 575.6

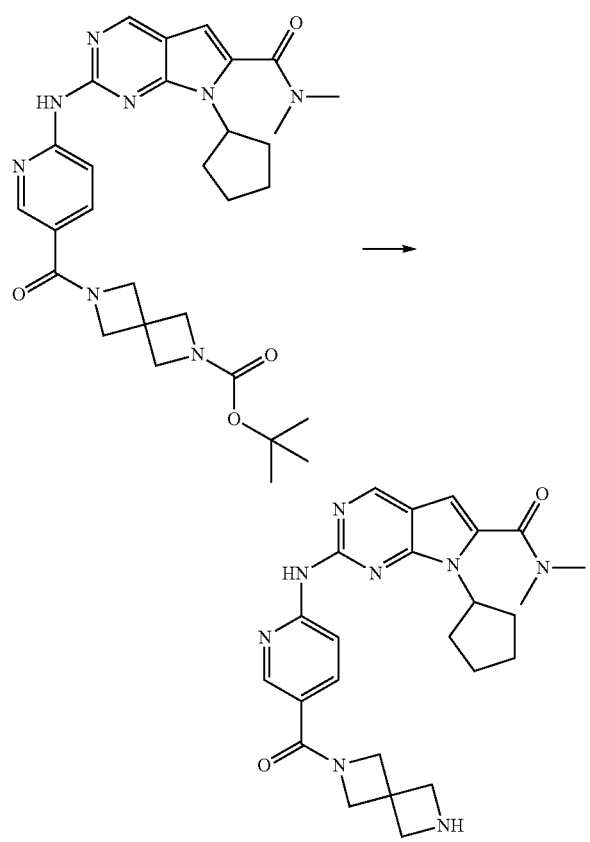

Step 2

Preparation of 2-(5-(2,6-diazaspiro[3.3]heptane-2-carbonyl)pyridin-2-ylamino)-7-cyclopentyl-N,N-dimethyl-7H-pyrrolo[2,3-d]pyrimidine-6-carboxamide Following deprotection method 2, tert-butyl 6-(6-(7-cyclopentyl-6-(dimethylcarbamoyl)-7H-pyrrolo[2,3-d]pyrimidin-2-ylamino)nicotinoyl)-2,6-diazaspiro[3.3]heptane-2-carboxylate (120 mg, 0.21 mmol, 1.0 eq) was converted to 2-(5-(2,6-diazaspiro[3.3]heptane-2-carbonyl)pyridin-2-ylamino)-7-cyclopentyl-N,N-dimethyl-7H-pyrrolo[2,3-d]pyrimidine-6-carboxamide (35 mg, 0.076 mmol) in 36% yield. ¹H NMR (400 MHz, chloroform-d) δ ppm 8.89 (br. s., 1H) 8.84 (s, 1H) 8.66 (s, 1H) 8.58 (d, J=8.59 Hz, 1H) 8.05 (dd, J=9.09, 2.53 Hz, 1H) 6.50 (s, 1H) 4.74-4.92 (m, J=9.09, 8.84, 8.72, 8.72 Hz, 1H) 4.51 (br. s., 2H) 4.33 (br s, 2H) 3.83 (d, J=8.08 Hz, 4H) 3.18 (s, 6H) 2.51-2.69 (m, 2H) 2.01-2.19 (m, 4H) 1.63-1.91 (m, 3H). HR-MS (m/z, MH+): 475.2584.

Example 42

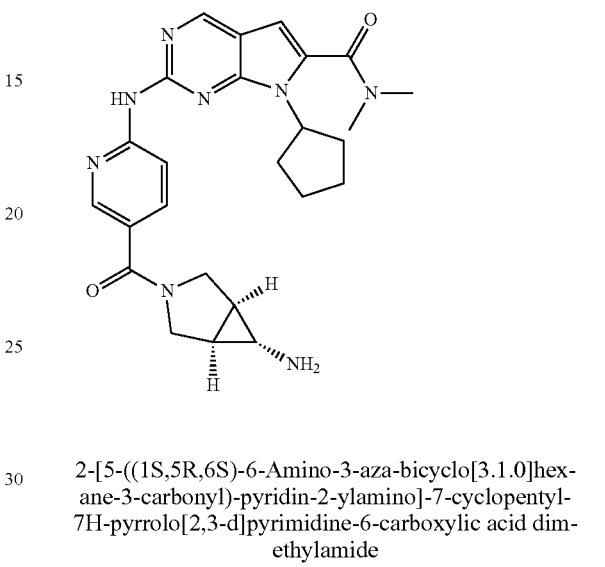

2-[5-((1S,5R,6S)-6-Amino-3-aza-bicyclo[3.1.0]hexane-3-carbonyl)-pyridin-2-ylamino]-7-cyclopentyl-7H-pyrrolo[2,3-d]pyrimidine-6-carboxylic acid dimethylamide Step 1

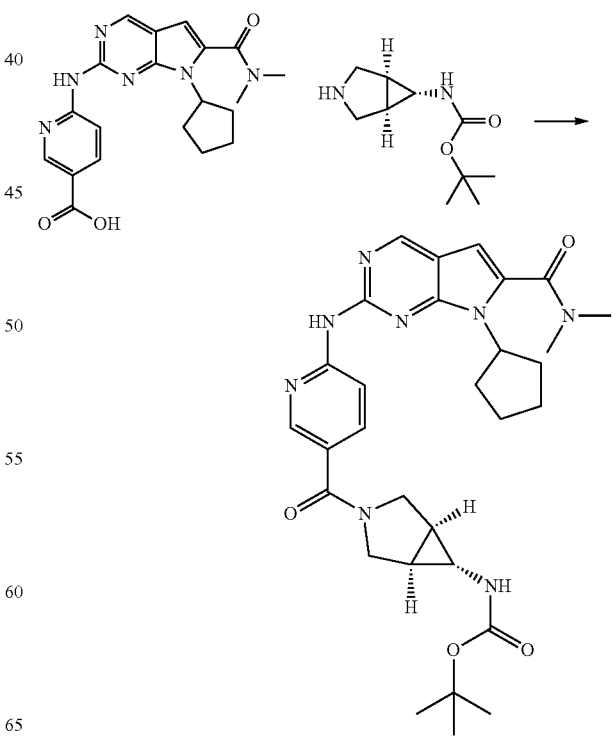

Preparation {(1S,5R,6S)-3-[6-(7-cyclopentyl-6-dimethylcarbamoyl-7H-pyrrolo[2,3-d]pyrimidin-2-ylamino)-pyridine-3-carbonyl]-3-aza-bicyclo[3.1.0]hex-6-yl}-carbamic acid tert-butyl ester Following general amide formation method 1, 6-(7-cyclopentyl-6-dimethylcarbamoyl-7H-pyrrolo[2,3-d]pyrimidin-2-ylamino)-nicotinic acid (100 mg, 0.254 mmol, 1.0 eq) was combined with (1S,5R,6S)-(3-Aza-bicyclo[3.1.0]hex-6-yl)-carbamic acid tert-butyl ester (55.3 mg, 0.279 mmol, 1.1 eq) which gave {(1S,5R,6S)-3-[6-(7-cyclopentyl-6-dimethylcarbamoyl-7H-pyrrolo[2,3-d]pyrimidin-2-ylamino)-pyridine-3-carbonyl]-3-aza-bicyclo[3.1.0]hex-6-yl}-carbamic acid tert-butyl ester as an oil (165 mg) and was used directly without purification. MS m/z 575.4 (M+H)$^+$ Step 2

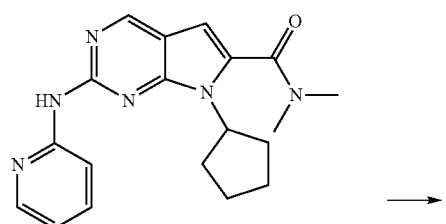

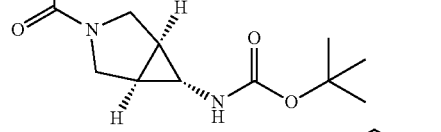

Preparation of 2-[5-((1S,5R,6S)-6-Amino-3-aza-bicyclo[3.1.0]hexane-3-carbonyl)-pyridin-2-ylamino]-7-cyclopentyl-7H-pyrrolo[2,3-d]pyrimidine-6-carboxylic acid dimethylamide Following deprotection method 2, {(1S,5R,6S)-3-[6-(7-cyclopentyl-6-dimethylcarbamoyl-7H-pyrrolo[2,3-d]pyrimidin-2-ylamino)-pyridine-3-carbonyl]-3-aza-bicyclo[3.1.0]hex-6-yl}-carbamic acid tert-butyl ester was converted to 2-[5-((1S,5R,6S)-6-Amino-3-aza-bicyclo[3.1.0]hexane-3-carbonyl)-pyridin-2-ylamino]-7-cyclopentyl-7H-pyrrolo[2,3-d]pyrimidine-6-carboxylic acid dimethylamide (76 mg) in 56% yield. 1H NMR (400 MHz, DMSO-d$_6$) δ ppm 1.47 (br. s., 2H) 1.66 (br. s., 3H) 2.00 (br. s., 6H) 2.34-2.48 (m, 2H) 2.69 (s, 1H) 3.06 (br. s., 7H) 3.36-3.53 (m, 2H) 3.75 (d, J=5.56 Hz, 1H) 3.88 (d, J=12.13 Hz, 1H) 4.76 (quin, J=8.84 Hz, 1H) 6.65 (s, 1H) 7.87 (dd, J=8.59, 2.53 Hz, 1H) 8.33 (d, J=8.59 Hz, 1H) 8.40 (d, J=2.02 Hz, 1H) 8.85 (s, 1H) 9.95 (s, 1H). MS m/z 475.5 (M+H)$^+$.

Example 43

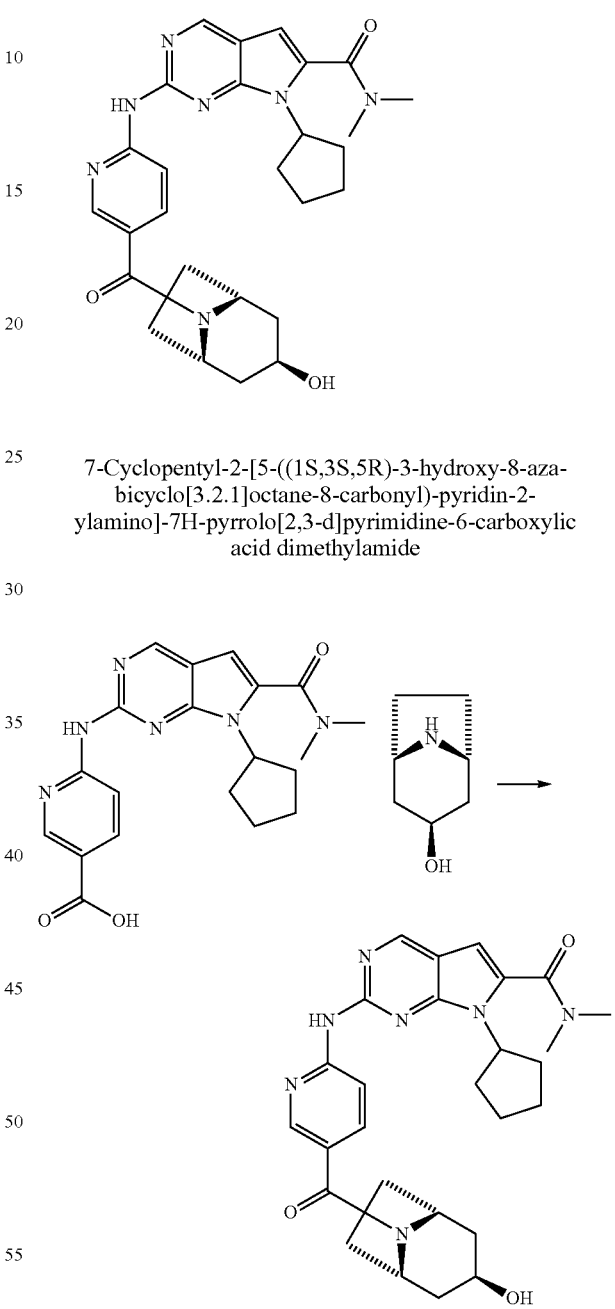

7-Cyclopentyl-2-[5-(((1S,3S,5R)-3-hydroxy-8-aza-bicyclo[3.2.1]octane-8-carbonyl)-pyridin-2-ylamino]-7H-pyrrolo[2,3-d]pyrimidine-6-carboxylic acid dimethylamide

Preparation of 7-Cyclopentyl-2-[5-((1S,3S,5R)-3-hydroxy-8-aza-bicyclo[3.2.1]octane-8-carbonyl)-pyridin-2-ylamino]-7H-pyrrolo[2,3-d]pyrimidine-6-carboxylic acid dimethylamide Following general amide formation method 1, 6-(7-Cyclopentyl-6-dimethylcarbamoyl-7H-pyrrolo[2,3-d]pyrimidin-2-ylamino)-nicotinic acid (120 mg, 0.304 mmol, 1.0 eq) was combined with (1S,3S,5R)-8-Aza-bicyclo[3.2.1]octan-3-ol (46.4 mg, 0.365 mmol, 1.2 eq) which gave 7-cyclopentyl-2-[5-((1S,3S,5R)-3-hydroxy-8-aza-bicyclo[3.2.1]octane-8-carbonyl)-pyridin-2-ylamino]-7H-pyrrolo[2,3-d]pyrimidine-6-carboxylic acid dimethylamide (110 mg) in 72% yield. 1H NMR (400 MHz, CDCl₃-d) δ ppm 1.58-1.71 (m, 2H) 1.79 (br. s., 2H) 1.88-2.11 (m, 8H) 2.22 (d, J=7.58 Hz, 3H) 2.42-2.58 (m, 2H) 3.08 (s, 6H) 4.16 (br. s., 2H) 4.72 (quin, J=8.84 Hz, 2H) 6.40 (s, 1H) 7.81 (dd, J=8.59, 2.02 Hz, 1H) 8.12 (br. s., 1H) 8.38 (d, J=2.02 Hz, 1H) 8.47 (br. s., 1H) 8.68 (s, 1H). MS m/z 504.6 (M+H)⁺.

Example 44

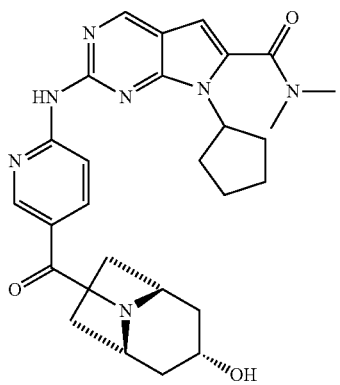

7-Cyclopentyl-2-[5-((1S,3R,5R)-3-hydroxy-8-aza-bicyclo[3.2.1]octane-8-carbonyl)-pyridin-2-ylamino]-7H-pyrrolo[2,3-d]pyrimidine-6-carboxylic acid dimethylamide Preparation of 7-Cyclopentyl-2-[5-((1S,3R,5R)-3-hydroxy-8-aza-bicyclo[3.2.1]octane-8-carbonyl)-pyridin-2-ylamino]-7H-pyrrolo[2,3-d]pyrimidine-6-carboxylic acid dimethylamide Following general amide formation method 1, 6-(7-Cyclopentyl-6-dimethylcarbamoyl-7H-pyrrolo[2,3-d]pyrimidin-2-ylamino)-nicotinic acid was combined with (1S,3R,5R)-8-Aza-bicyclo[3.2.1]octan-3-ol which gave 7-cyclopentyl-2-[5-((1S,3R,5R)-3-hydroxy-8-aza-bicyclo[3.2.1]octane-8-carbonyl)-pyridin-2-ylamino]-7H-pyrrolo[2,3-d]pyrimidine-6-carboxylic acid dimethylamide.

Example 45

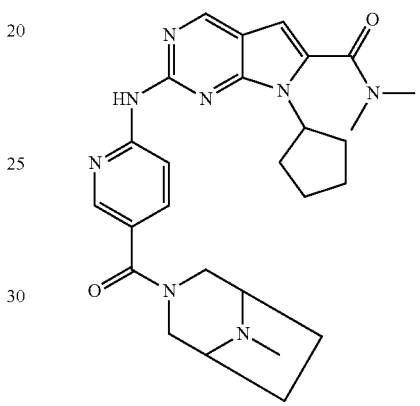

7-cyclopentyl-2-[5-(8-methyl-3,8-diaza-bicyclo[3.2.1]octane-3-carbonyl)-pyridin-2-ylamino]-7H-pyrrolo[2,3-d]pyrimidine-6-carboxylic acid dimethylamide

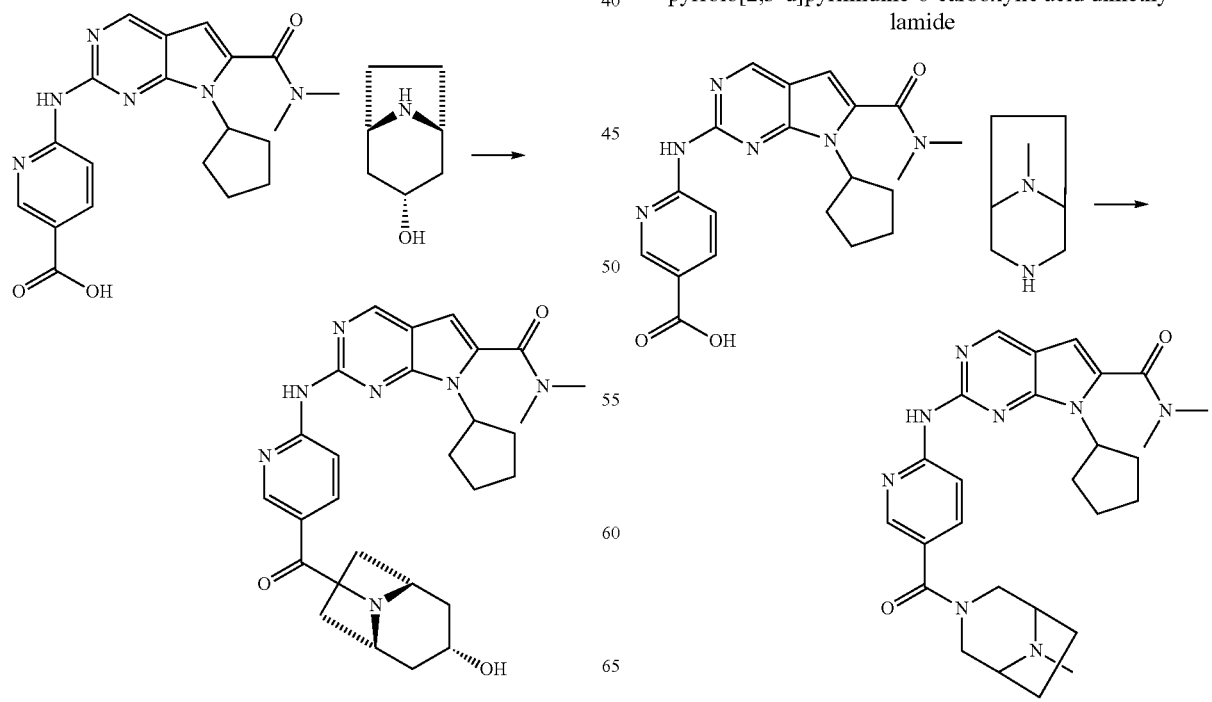

Preparation of 7-cyclopentyl-2-[5-(8-methyl-3,8-diaza-bicyclo[3.2.1]octane-3-carbonyl)-pyridin-2-ylamino]-7H-pyrrolo[2,3-d]pyrimidine-6-carboxylic acid dimethylamide Following general amide formation method 1, 6-(7-Cyclopentyl-6-dimethylcarbamoyl-7H-pyrrolo[2,3-d]pyrimidin-2-ylamino)-nicotinic acid (100 mg, 0.254 mmol, 1.0 eq) was combined with 8-Methyl-3,8-diaza-bicyclo[3.2.1]octane (55.5 mg, 0.279 mmol, 1.1 eq) which gave 7-cyclopentyl-2-[5-(8-methyl-3,8-diaza-bicyclo[3.2.1]octane-3-carbonyl)-pyridin-2-ylamino]-7H-pyrrolo[2,3-d]pyrimidine-6-carboxylic acid dimethylamide as solid (77 mg) in 60% yield. 1H NMR (400 MHz, DMSO-$d_6$) δ ppm 1.56-1.76 (m, 4H) 2.01 (br. s., 6H) 2.44 (br. s., 4H) 3.06 (br. s., 8H) 3.33 (br. s., 4H) 3.49 (br. s., 4H) 4.76 (quin, J=8.84 Hz, 1H) 6.66 (s, 1H) 7.82-7.88 (m, 1H) 8.33-8.41 (m, 2H) 8.85 (s, 1H) 10.05 (s, 1H)

MS m/z 503.6 (M+H)$^+$.

Example 46

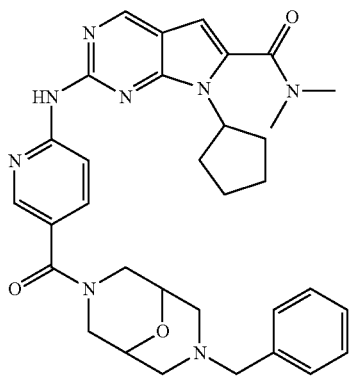 [SMILES: CN(C)C(=O)c1cc2cnc(Nc3ccc(C(=O)N4CC5CN(Cc6ccccc6)CC(C4)O5)cn3)nc2n1C1CCCC1]

2-[5-(7-Benzyl-9-oxa-3,7-diaza-bicyclo[3.3.1]nonane-3-carbonyl)-pyridin-2-ylamino]-7-cyclopentyl-7H-pyrrolo[2,3-d]pyrimidine-6-carboxylic acid dimethylamide

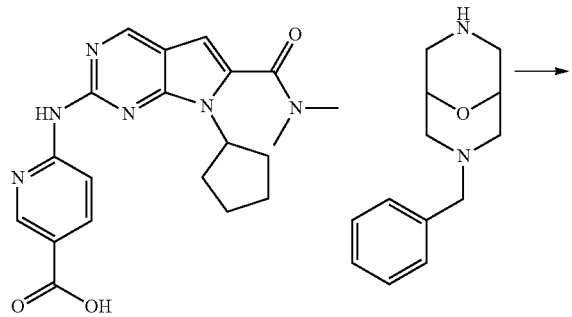

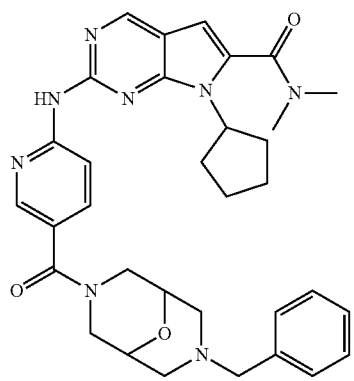

Preparation of 2-[5-(7-Benzyl-9-oxa-3,7-diaza-bicyclo[3.3.1]nonane-3-carbonyl)-pyridin-2-ylamino]-7-cyclopentyl-7H-pyrrolo[2,3-d]pyrimidine-6-carboxylic acid dimethylamide Following general amide formation method 1, 6-(7-cyclopentyl-6-dimethylcarbamoyl-7H-pyrrolo[2,3-d]pyrimidin-2-ylamino)-nicotinic acid (200 mg, 0.507 mmol, 1.0 eq) was combined with 3-benzyl-9-oxa-3,7-diaza-bicyclo[3.3.1]nonane (162 mg, 0.558 mmol, 1.1 eq) (Reference: PCT Int. Appl. 2006137769, 2 Dec. 2006) which gave 2-[5-(7-Benzyl-9-oxa-3,7-diaza-bicyclo[3.3.1]nonane-3-carbonyl)-pyridin-2-ylamino]-7-cyclopentyl-7H-pyrrolo[2,3-d]pyrimidine-6-carboxylic acid dimethylamide as solid (131 mg) in 39% yield.

1H NMR (400 MHz, CHLOROFORM-d) δ ppm 1.64-1.83 (m, 3H) 2.04 (d, J=7.07 Hz, 2H) 2.12 (d, J=6.57 Hz, 2H) 2.58 (br. s., 4H) 3.18 (s, 6H) 3.45 (br. s., 3H) 3.49-3.57 (m, 1H) 3.67-3.80 (m, 1H) 3.84 (br. s., 2H) 4.02 (br. s., 1H) 4.66-4.88 (m, 2H) 6.51 (s, 1H) 7.22-7.28 (m, 1H) 7.31-7.37 (m, 5H) 7.85 (dd, J=8.84, 2.27 Hz, 1H) 8.27 (br. s., 1H) 8.43 (s, 1H) 8.51 (br. s., 1H) 8.78 (s, 1H). MS m/z 595.6 (M+H)$^+$.

Example 47

127

7-Cyclopentyl-2-[5-(9-oxa-3,7-diaza-bicyclo[3.3.1]nonane-3-carbonyl)-pyridin-2-ylamino]-7H-pyrrolo[2,3-d]pyrimidine-6-carboxylic acid dimethylamide

Step 1

Preparation of 7-[6-(7-Cyclopentyl-6-dimethylcarbamoyl-7H-pyrrolo[2,3-d]pyrimidin-2-ylamino)-pyridine-3-carbonyl]-9-oxa-3,7-diaza-bicyclo[3.3.1]nonane-3-carboxylic acid tert-butyl ester Following general amide formation method 1, 6-(7-Cyclopentyl-6-dimethylcarbamoyl-7H-pyrrolo[2,3-d]pyrimidin-2-ylamino)-nicotinic acid (266 mg, 0.438 mmol, 1.0 eq) was combined with 9-Oxa-3,7-diaza-bicyclo[3.3.1]nonane-3-carboxylic acid tert-butyl ester (100 mg, 0.438 mmol, 1.0 eq) which gave 7-[6-(7-Cyclopentyl-6-dimethylcarbamoyl-7H-pyrrolo[2,3-d]pyrimidin-2-ylamino)-pyridine-3-carbonyl]-9-oxa-3,7-diaza-bicyclo[3.3.1]nonane-3-carboxylic acid tert-butyl ester as a light pink powder (90 mg) in 34% yield. MS m/z 605.2 (M+H)$^+$.

Step 2

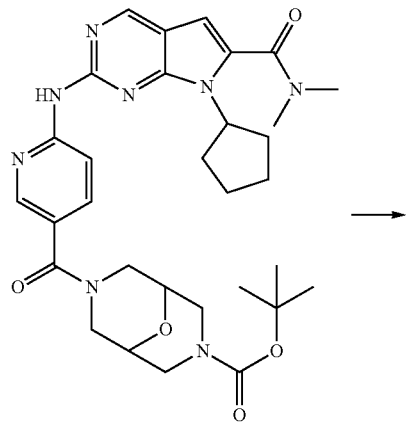

128

-continued

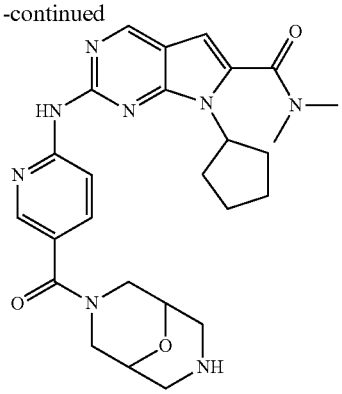

Preparation of 7-Cyclopentyl-2-[5-(9-oxa-3,7-diaza-bicyclo[3.3.1]nonane-3-carbonyl)-pyridin-2-ylamino]-7H-pyrrolo[2,3-d]pyrimidine-6-carboxylic acid dimethylamide Following deprotection method 2, 7-[6-(7-Cyclopentyl-6-dimethylcarbamoyl-7H-pyrrolo[2,3-d]pyrimidin-2-ylamino)-pyridine-3-carbonyl]-9-oxa-3,7-diaza-bicyclo[3.3.1]nonane-3-carboxylic acid tert-butyl ester was converted to 7-cyclopentyl-2-[5-(9-oxa-3,7-diaza-bicyclo[3.3.1]nonane-3-carbonyl)-pyridin-2-ylamino]-7H-pyrrolo[2,3-d]pyrimidine-6-carboxylic acid dimethylamide (15 mg) in 18% yield. 1H NMR (400 MHz, CHLOROFORM-d) δ ppm 1.75 (d, J=6.06 Hz, 3H) 2.06-2.18 (m, 5H) 2.49-2.66 (m, 2H) 3.03-3.14 (m, 2H) 3.18 (s, 6H) 3.42 (dd, J=12.63, 2.02 Hz, 2H) 3.63 (br. s., 1H) 3.81 (br. s., 2H) 4.83 (t, J=8.84 Hz, 1H) 6.50 (s, 1H) 7.85 (dd, J=8.59, 2.53 Hz, 1H) 8.42 (br. 5., 1H) 8.45-8.51 (m, 1H) 8.60 (d, J=9.09 Hz, 1H) 8.79 (s, 1H) MS m/z 505.1 (M+H)$^+$.

Example 48

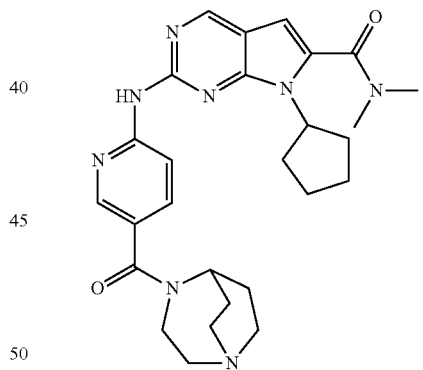

7-Cyclopentyl-2-[5-(1,4-diaza-bicyclo[3.2.2]nonane-4-carbonyl)-pyridin-2-ylamino]-7H-pyrrolo[2,3-d]pyrimidine-6-carboxylic acid dimethylamide

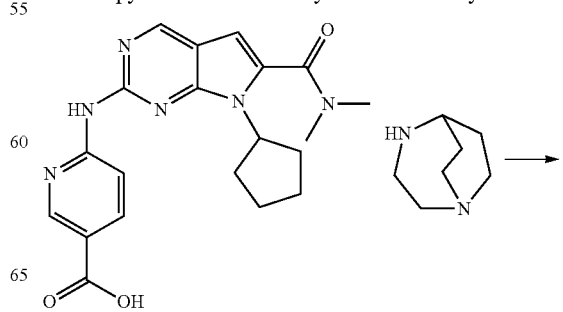

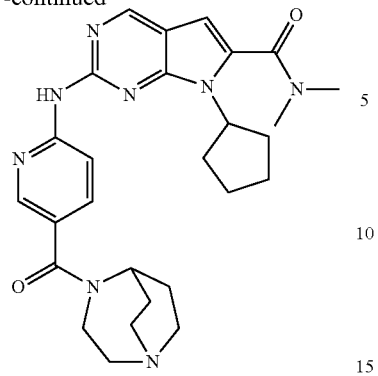

Preparation of 7-Cyclopentyl-2-[5-(1,4-diaza-bicyclo[3.2.2]nonane-4-carbonyl)-pyridin-2-ylamino]-7H-pyrrolo[2,3-d]pyrimidine-6-carboxylic acid dimethylamide Following general amide formation method 1, 6-(7-Cyclopentyl-6-dimethylcarbamoyl-7H-pyrrolo[2,3-d]pyrimidin-2-ylamino)-nicotinic acid (120 mg, 0.198 mmol, 1.0 eq) was combined with 1,4-Diaza-bicyclo[3.2.2]nonane (43.3 mg, 0.218 mmol, 1.1 eq) which gave 7-cyclopentyl-2-[5-(1,4-diaza-bicyclo[3.2.2]nonane-4-carbonyl)-pyridin-2-ylamino]-7H-pyrrolo[2,3-d]pyrimidine-6-carboxylic acid dimethylamide (25 mg) in 23% yield. $^1$H NMR (400 MHz, CDCl$_3$-d) δ ppm 1.64-1.81 (m, 2H) 1.86 (br. s., 2H) 2.00-2.22 (m, 6H) 2.51-2.70 (m, 2H) 3.03-3.16 (m, 5H) 3.18 (s, 7H) 3.79 (br. s., 2H) 4.83 (quin, J=8.84 Hz, 1H) 6.50 (s, 1H) 7.81 (dd, J=8.84, 2.27 Hz, 1H) 8.35-8.44 (m, 2H) 8.58 (d, J=8.59 Hz, 1H) 8.79 (s, 1H). HRMS m/z, (M+H)$^+$: 503.2891

Example 49

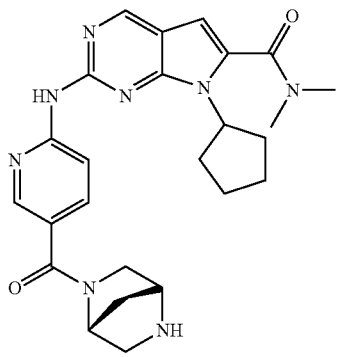

7-Cyclopentyl-2-[5-((R,R)-2,5-diaza-bicyclo[2.2.1]heptane-2-carbonyl)-pyridin-2-ylamino]-7H-pyrrolo[2,3-d]pyrimidine-6-carboxylic acid dimethylamide

Step 1

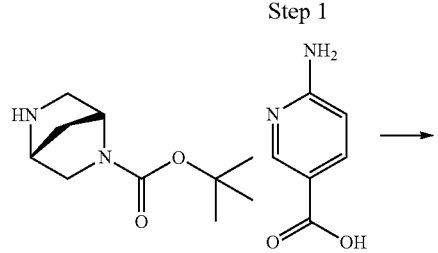

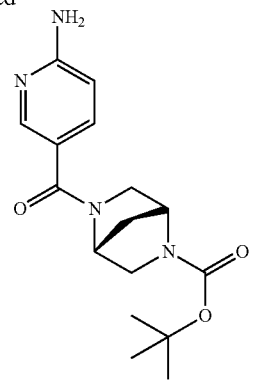

Preparation of 5-(6-Amino-pyridine-3-carbonyl)-(R,R)-2,5-diaza-bicyclo[2.2.1]heptane-2-carboxylic acid tert-butyl ester Using amide formation method 1, (R,R)-2,5-Diaza-bicyclo[2.2.1]heptane-2-carboxylic acid tert-butyl ester (1.0 g, 4.26 mmol, 1.0 eq) was combined with 6-Amino-nicotinic acid (588 mg, 4.26 mmol, 1.0 eq) to give 5-(6-Amino-pyridine-3-carbonyl)-(R,R)-2,5-diaza-bicyclo[2.2.1]heptane-2-carboxylic acid tert-butyl ester (420 mg, 31% yield). 1H NMR (400 MHz, CHLOROFORM-d) δ ppm 1.35-1.40 (m, 3H) 1.40-1.51 (m, 9H) 1.89 (br. s., 2H) 3.31-3.50 (m, 2H) 3.55 (d, J=9.09 Hz, 1H) 3.67 (dd, J=13.14, 6.57 Hz, 1H) 4.50 (br. s., 1H) 4.64 (br. s., 1H) 4.91 (br. s., 1H) 6.51 (d, J=6.57 Hz, 1H) 7.64 (br. s., 1H) 8.24 (br. s., 1H); MS m/z 637.0 (M+H)$^+$.

Step 2

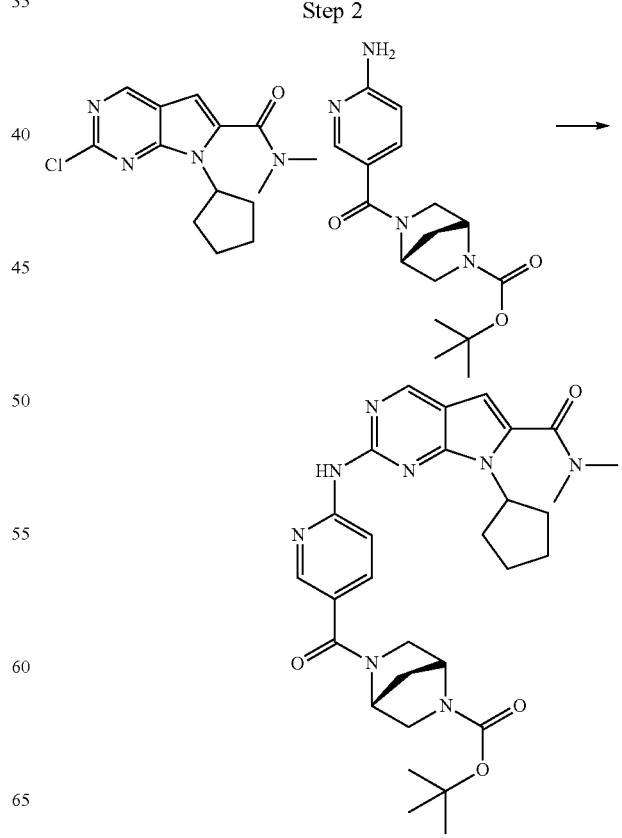

Preparation of 5-[6-(7-cyclopentyl-6-dimethylcarbamoyl-7H-pyrrolo[2,3-d]pyrimidin-2-ylamino)-pyridine-3-carbonyl]-(R,R)-2,5-diaza-bicyclo[2.2.1]heptane-2-carboxylic acid tert-butyl ester Following general N—C coupling procedure 1, 2-Chloro-7-cyclopentyl-7H-pyrrolo[2,3-d]pyrimidine-6-carboxylic acid dimethylamide (200 mg, 0.683 mmol, 1.0 eq) was combined with 5-(6-Amino-pyridine-3-carbonyl)-(R,R)-2,5-diaza-bicyclo[2.2.1]heptane-2-carboxylic acid tert-butyl ester (217 mg, 0.683 mmol, 1.0 eq) which gave 5-[6-(7-Cyclopentyl-6-dimethylcarbamoyl-7H-pyrrolo[2,3-d]pyrimidin-2-ylamino)-pyridine-3-carbonyl]-(R,R)-2,5-diaza-bicyclo[2.2.1]heptane-2-carboxylic acid tert-butyl ester (100 mg) in 25% yield. 1H NMR (400 MHz, CDCl3-d) δ ppm 1.47 (br. s., 5H) 1.52 (br. s., 5H) 1.69-1.83 (m, 2H) 1.83-2.00 (m, 2H) 2.06-2.20 (m, 4H) 2.59 (br. s., 2H) 3.18 (s, 6H) 3.38-3.58 (m, 2H) 3.58-3.82 (m, 3H) 4.56 (br. s., 1H) 4.75-4.91 (m, 1H) 6.50 (s, 1H) 7.96 (br. s., 1H) 8.35 (br. s., 1H) 8.52 (br. s., 1H) 8.59 (br. s., 1H) 8.78 (s, 1H)

HRMS m/z, (M+H)$^+$: 575.3109.

Step 3

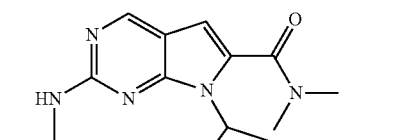

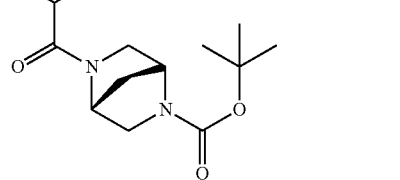

Preparation of 7-cyclopentyl-2-[5-((R,R)-2,5-diaza-bicyclo[2.2.1]heptane-2-carbonyl)-pyridin-2-ylamino]-7H-pyrrolo[2,3-d]pyrimidine-6-carboxylic acid dimethylamide Following deprotection method 2, 5-[6-(7-Cyclopentyl-6-dimethylcarbamoyl-7H-pyrrolo[2,3-d]pyrimidin-2-ylamino)-pyridine-3-carbonyl]-(R,R)-2,5-diaza-bicyclo[2.2.1]heptane-2-carboxylic acid tert-butyl ester was converted to 7-Cyclopentyl-2-[5-((R,R)-2,5-diaza-bicyclo[2.2.1]heptane-2-carbonyl)-pyridin-2-ylamino]-7H-pyrrolo[2,3-d]pyrimidine-6-carboxylic acid dimethylamide (20 mg) in 22% yield. 1H NMR (400 MHz, CHLOROFORM-d) δ ppm 1.65-1.85 (m, 4H) 2.03 (s, 2H) 2.06-2.19 (m, 6H) 2.59 (br. s., 2H) 3.18 (s, 7H) 3.33 (d, J=9.60 Hz, 1H) 3.52 (br. s., 1H) 3.78 (br. s., 2H) 4.72-4.94 (m, 1H) 6.38-6.54 (m, 1H) 7.96 (d, J=9.09 Hz, 1H) 8.56 (s, 1H) 8.61 (d, J=8.59 Hz, 1H) 8.84 (br. s., 1H); HRMS m/z, (M+H)$^+$: 475.2582.

Example 50

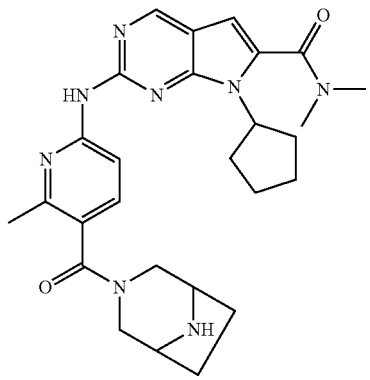

7-Cyclopentyl-2-[5-(3,8-diaza-bicyclo[3.2.1]octane-3-carbonyl)-6-methyl-pyridin-2-ylamino]-7H-pyrrolo[2,3-d]pyrimidine-6-carboxylic acid dimethylamide Step 1

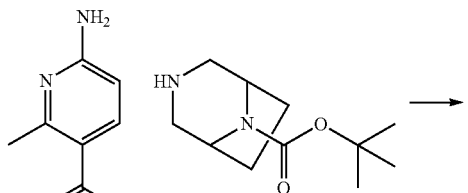

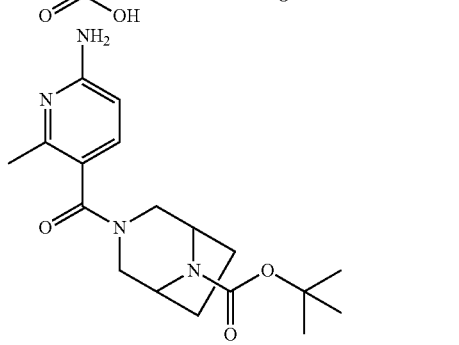

Preparation of (3-(6-Amino-2-methyl-pyridine-3-carbonyl)-3,8-diaza-bicyclo[3.2.1]octane-8-carboxylic acid tert-butyl ester Following general amide formation method 1, 3,8-diaza-bicyclo[3.2.1]octane-8-carboxylic acid tert-butyl ester (279 mg, 1.31 mmol, 1.0 eq) was combined with 6-amino-2-methylnicotinic acid (200 mg, 1.31 mmol, 1.0 eq) which gave 3-(6-Amino-2-methyl-pyridine-3-carbonyl)-3,8-diaza-bicyclo[3.2.1]octane-8-carboxylic acid tert-butyl ester (400 mg) in 88% yield. MS m/z 346.6 (M+H)+.

Step 2

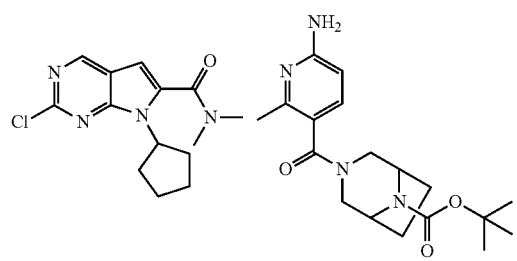

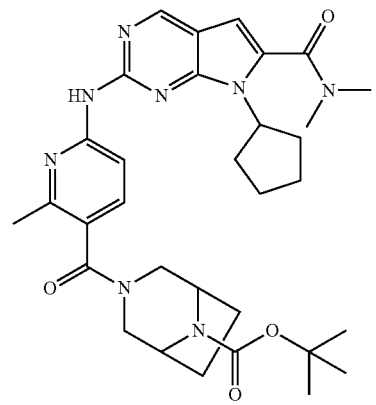

Preparation of 3-[6-(7-Cyclopentyl-6-dimethylcarbamoyl-7H-pyrrolo[2,3-d]pyrimidin-2-ylamino)-2-methyl-pyridine-3-carbonyl]-3,8-diaza-bicyclo[3.2.1]octane-8-carboxylic acid tert-butyl ester Following general N—C coupling procedure 1, 2-Chloro-7-cyclopentyl-7H-pyrrolo[2,3-d]pyrimidine-6-carboxylic acid dimethylamide (127 mg, 0.433 mmol, 1.0 eq) was combined with 3-(6-Amino-2-methyl-pyridine-3-carbonyl)-3,8-diaza-bicyclo[3.2.1]octane-8-carboxylic acid tert-butyl ester (180 mg, 0.520 mmol, 1.2 eq) which gave 3-[6-(7-Cyclopentyl-6-dimethylcarbamoyl-7H-pyrrolo[2,3-d]pyrimidin-2-ylamino)-2-methyl-pyridine-3-carbonyl]-3,8-diazabicyclo[3.2.1]octane-8-carboxylic acid tert-butyl ester (70 mg) in 27% yield. 1H NMR (400 MHz, CHLOROFORM-d) δ ppm 1.51 (s, 10H) 1.61 (t, J=8.34 Hz, 1H) 1.68-1.81 (m, 2H) 1.81-1.93 (m, 1H) 1.95-2.18 (m, 7H) 2.48 (br. s., 2H) 2.56 (d, J=8.59 Hz, 3H) 2.62 (br. s., 1H) 3.09 (d, J=7.58 Hz, 1H) 3.18 (s, 7H) 3.26-3.36 (m, 1H) 3.40 (br. s., 1H) 4.17 (br. s., 1H) 4.37 (br. s., 1H) 4.58 (d, J=13.14 Hz, 1H) 4.74-4.89 (m, J=9.09, 8.84, 8.72, 8.72 Hz, 1H) 6.48 (s, 1H) 7.50 (br. s., 1H) 8.11 (br. s., 1H) 8.38 (d, J=8.08 Hz, 1H) 8.76 (s, 1H). HRMS m/z, (M+H)+: 603.3417.

Step 3

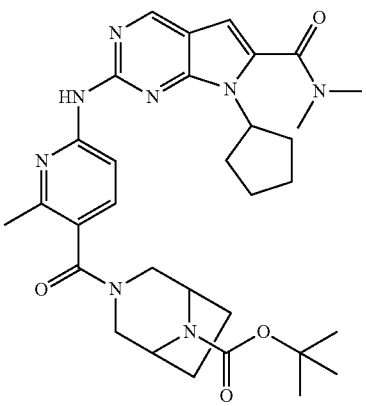

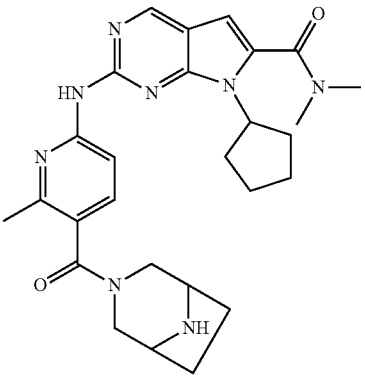

Preparation of 7-Cyclopentyl-2-[5-(3,8-diaza-bicyclo[3.2.1]octane-3-carbonyl)-6-methyl-pyridin-2-ylamino]-7H-pyrrolo[2,3-d]pyrimidine-6-carboxylic acid dimethylamide Following deprotection method 2, 3-[6-(7-Cyclopentyl-6-dimethylcarbamoyl-7H-pyrrolo[2,3-d]pyrimidin-2-ylamino)-2-methyl-pyridine-3-carbonyl]-3,8-diaza-bicyclo[3.2.1]octane-8-carboxylic acid tert-butyl ester was converted to 7-cyclopentyl-2-[5-(3,8-diaza-bicyclo[3.2.1]octane-3-carbonyl)-6-methyl-pyridin-2-ylamino]-7H-pyrrolo[2,3-d]pyrimidine-6-carboxylic acid dimethylamide (36 mg) in 71% yield. 1H NMR (400 MHz, CDCl3-d) δ ppm 1.61-1.79 (m, 3H) 1.79-1.97 (m, 3H) 1.97-2.18 (m, 5H) 2.50 (br. s., 3H) 2.52-2.70 (m, 3H) 3.09 (d, J=12.63 Hz, 1H) 3.18 (s, 7H) 3.34 (q, J=11.79 Hz, 2H) 3.46 (br. s., 1H) 3.69 (br. s., 1H) 4.55 (d, J=12.13 Hz, 1H) 4.81 (quin, J=8.84 Hz, 1H) 6.48 (s, 1H) 7.49 (br. s., 1H) 8.03 (s, 1H) 8.35 (d, J=8.59 Hz, 1H) 8.76 (s, 1H). HRMS m/z, (M+H)+: 503.2904.

135

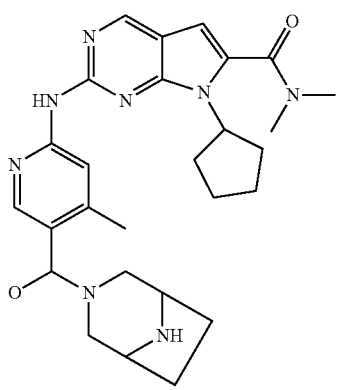 [SMILES: Cc1cc(Nc2ncc3cc(C(=O)N(C)C)n(C4CCCC4)c3n2)ncc1C(O)N1CC2CCC(C1)N2]

Example 51

7-Cyclopentyl-2-[5-(3,8-diaza-bicyclo[3.2.1]octane-3-carbonyl)-4-methyl-pyridin-2-ylamino]-7H-pyrrolo[2,3-d]pyrimidine-6-carboxylic acid dimethylamide

Step 1

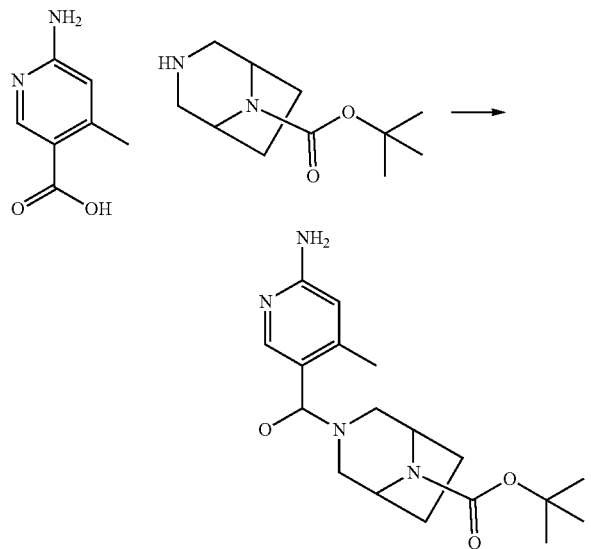

Preparation of 3-(6-Amino-4-methyl-pyridine-3-carbonyl)-3,8-diaza-bicyclo[3.2.1]octane-8-carboxylic acid tert-butyl ester Following general amide formation method 1, 3,8-Diaza-bicyclo[3.2.1]octane-8-carboxylic acid tert-butyl ester (279 mg, 1.31 mmol, 1.0 eq) was combined with 6-Amino-4-methylnicotinic acid (200 mg, 1.31 mmol, 1.0 eq) to give 3-(6-Amino-4-methyl-pyridine-3-carbonyl)-3,8-diaza-bicyclo[3.2.1]octane-8-carboxylic acid tert-butyl ester (251 mg) in 55% yield. MS m/z 347.0 (M+H)+.

136

Step 2

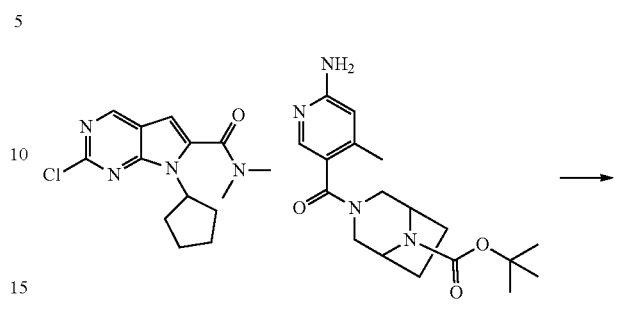

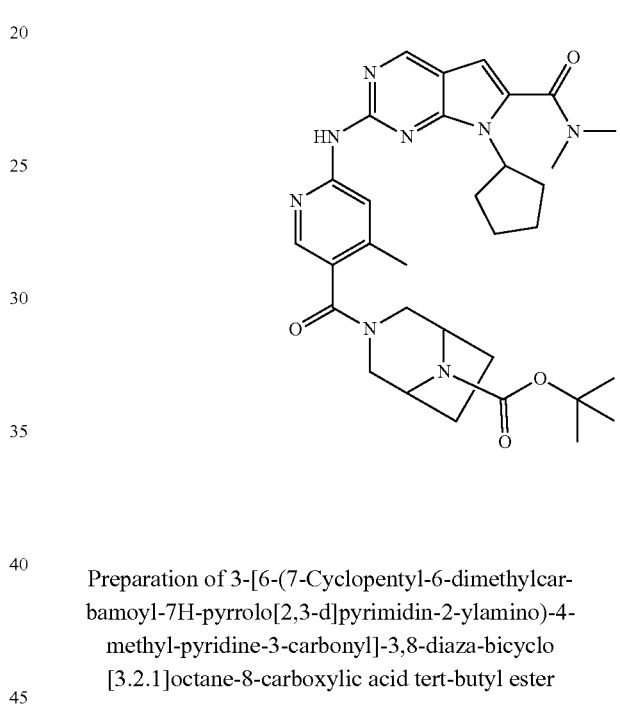

Preparation of 3-[6-(7-Cyclopentyl-6-dimethylcarbamoyl-7H-pyrrolo[2,3-d]pyrimidin-2-ylamino)-4-methyl-pyridine-3-carbonyl]-3,8-diaza-bicyclo[3.2.1]octane-8-carboxylic acid tert-butyl ester Following general N—C coupling procedure 1, 1,2-Chloro-7-cyclopentyl-7H-pyrrolo[2,3-d]pyrimidine-6-carboxylic acid dimethylamide (140 mg, 0.479 mmol, 1.0 eq) was combined with 3-(6-Amino-4-methyl-pyridine-3-carbonyl)-3,8-diaza-bicyclo[3.2.1]octane-8-carboxylic acid tert-butyl ester (199 mg, 0.574 mmol, 1.2 eq) which gave 3-[6-(7-Cyclopentyl-6-dimethylcarbamoyl-7H-pyrrolo[2,3-d]pyrimidin-2-ylamino)-4-methyl-pyridine-3-carbonyl]-3,8-diaza-bicyclo[3.2.1]octane-8-carboxylic acid tert-butyl ester (114 mg) in 38% yield. 1H NMR (400 MHz, CHLOROFORM-d) δ ppm 1.51 (s, 10H) 1.59 (d, J=9.60 Hz, 2H) 1.67-1.80 (m, 2H) 1.80-1.90 (m, 1H) 1.99 (br. s., 2H) 2.07 (s, 4H) 2.42-2.66 (m, 5H) 3.01-3.14 (m, 1H) 3.18 (s, 6H) 3.26-3.36 (m, 1H) 3.36-3.48 (m, 1H) 4.17 (br. s., 1H) 4.36 (br. s., 1H) 4.58 (d, J=12.63 Hz, 1H) 4.75-4.88 (m, J=9.09, 8.84, 8.72, 8.72 Hz, 1H) 6.49 (s, 1H) 7.50 (br. s., 1H) 8.39 (br. s., 1H) 8.75 (s, 1H)

HRMS m/z, (M+H)+: 603.3405.

Step 3

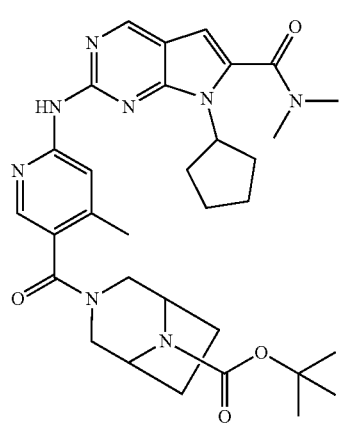

Example 52

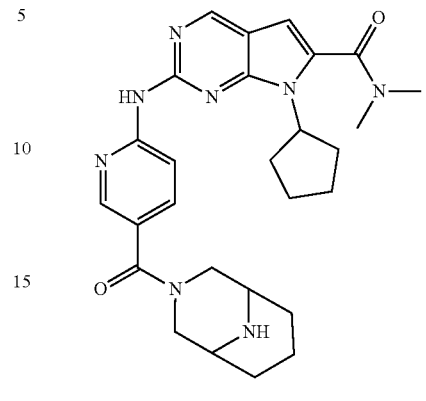

7-Cyclopentyl-2-[5-(3,9-diaza-bicyclo[3.3.1]nonane-3-carbonyl)-pyridin-2-ylamino]-7H-pyrrolo[2,3-d]pyrimidine-6-carboxylic acid dimethylamide Step 1

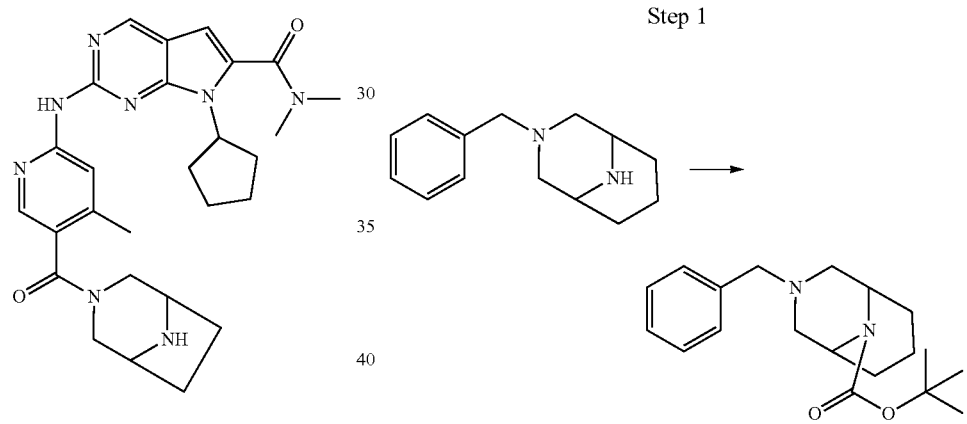

Preparation of 3-Benzyl-3,9-diaza-bicyclo[3.3.1]nonane-9-carboxylic acid tert-butyl ester To a solution of 3-benzyl-3,9-diaza-bicyclo[3.3.1]nonane (755 mg, 3.49 mmol, 1.0 eq) in $CH_2Cl_2$ (10 mL) was added di-tert-butylcarbonate (990 mg, 4.54 mmol, 1.3 eq) and triethylamine (0.730 mL, 5.24 mmol, 1.5 eq) and the mixture stirred for 16 hours at 23° C.

The reaction mixture was diluted with $CH_2Cl_2$ and washed with water. The organic was collected and dried ($Na_2SO_4$), filtered, and concentrated to an oil. The crude was purified using silica gel chromatography eluting with ethyl acetate/heptane mixtures which gave the desired product as a colorless oil (477 mg) in 41% yield. 1H NMR (400 MHz, CHLOROFORM-d) δ ppm 1.48 (s, 9H) 1.51-1.64 (m, 1H) 1.64-1.75 (m, 2H) 1.75-1.93 (m, 2H) 2.21-2.39 (m, 2H) 2.79-2.92 (m, 3H) 3.40 (s, 2H) 4.06 (br. s., 1H) 4.18 (br. s., 1H) 7.21-7.30 (m, 1H) 7.34 (d, J=4.55 Hz, 4H).

Preparation of 7-Cyclopentyl-2-[5-(3,8-diaza-bicyclo[3.2.1]octane-3-carbonyl)-4-methyl-pyridin-2-ylamino]-7H-pyrrolo[2,3-d]pyrimidine-6-carboxylic acid dimethylamide Following deprotection method 2, 3-[6-(7-Cyclopentyl-6-dimethylcarbamoyl-7H-pyrrolo[2,3-d]pyrimidin-2-ylamino)-4-methyl-pyridine-3-carbonyl]-3,8-diaza-bicyclo[3.2.1]octane-8-carboxylic acid tert-butyl ester was converted to 7-cyclopentyl-2-[5-(3,8-diaza-bicyclo[3.2.1]octane-3-carbonyl)-4-methyl-pyridin-2-ylamino]-7H-pyrrolo[2,3-d]pyrimidine-6-carboxylic acid dimethylamide (50 mg) in 57% yield. 1H NMR (400 MHz, CHLOROFORM-d) δ ppm 1.61-1.80 (m, 5H) 1.80-1.98 (m, 4H) 1.99-2.18 (m, 6H) 2.34-2.64 (m, 7H) 3.08-3.23 (m, 10H) 3.27-3.38 (m, 2H) 3.38-3.47 (m, 1H) 3.50 (br. s., 1H) 4.57 (d, J=13.64 Hz, 1H) 4.81 (quin, J=8.84 Hz, 1H) 6.48 (s, 1H) 7.48 (br. s., 1H) 7.99 (s, 1H) 8.36 (d, J=8.59 Hz, 1H) 8.75 (s, 1H)

HRMS m/z, (M+H)+: 503.2894.

Step 2

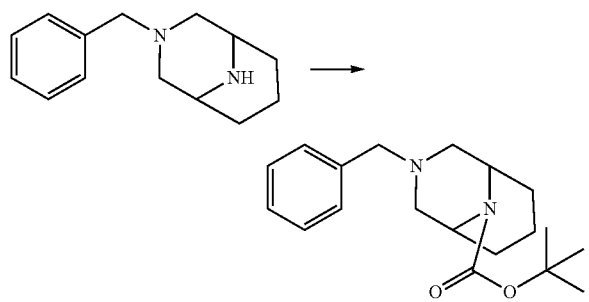

Preparation of 3,9-Diaza-bicyclo[3.3.1]nonane-9-carboxylic acid tert-butyl ester A mixture of benzyl-3,9-diaza-bicyclo[3.3.1]nonane-9-carboxylic acid tert-butyl ester (477 mg, 1.51 mmol, 1.0 eq) and palladium hydroxide on carbon (466 mg) in ethanol (10 mL) was stirred with hydrogenation under ballon pressure until no more hydrogen uptake. The reaction was then filtered through celite and concentrated under reduced pressure. The crude was purified using chromatography (MeOH/Ethyl Acetate) which gave 3,9-Diaza-bicyclo[3.3.1]nonane-9-carboxylic acid tert-butyl ester (170 mg) in 47% yield. 1H NMR (400 MHz, CHLOROFORM-d) δ ppm 1.49 (s, 11H) 1.57-1.70 (m, 1H) 1.70-1.79 (m, 2H) 1.79-2.01 (m, 2H) 2.43-2.58 (m, J=19.14, 12.69, 6.32, 6.32 Hz, 1H) 2.93-3.05 (m, 2H) 3.05-3.18 (m, 2H) 3.99 (br. s., 1H) 4.11 (br. s., 1H)

Step 3

Preparation of 3-(6-Amino-pyridine-3-carbonyl)-3,9-diaza-bicyclo[3.3.1]nonane-9-carboxylic acid tert-butyl ester Following general amide formation method 1, 3,9-diaza-bicyclo[3.3.1]nonane-9-carboxylic acid tert-butyl ester (170 mg, 0.751 mmol, 1.1 eq) was combined with 6-amino-nicotinic acid (94 mg, 0.683 mmol, 1.0 eq) which gave 3-(6-amino-pyridine-3-carbonyl)-3,9-diaza-bicyclo[3.3.1]nonane-9-carboxylic acid tert-butyl ester (170 mg) in 72% yield. 1H NMR (400 MHz, CDCl$_3$-d) δ ppm 1.50 (s, 9H) 1.55-1.72 (m, 2H) 1.74-1.98 (m, 4H) 3.20 (qd, J=7.41, 4.55 Hz, 3H) 3.65-3.82 (m, J=13.20, 6.66, 6.66, 4.29 Hz, 2H) 4.18 (br. s., 1H) 4.28 (br. s., 1H) 4.66 (br. s., 1H) 4.85 (br. s., 1H) 6.58 (d, J=8.59 Hz, 1H) 7.57 (dd, J=8.59, 2.02 Hz, 1H) 8.04 (s, 1H) 8.16 (d, J=2.02 Hz, 1H) MS m/z 291.4 (M+H)$^+$.

Step 4

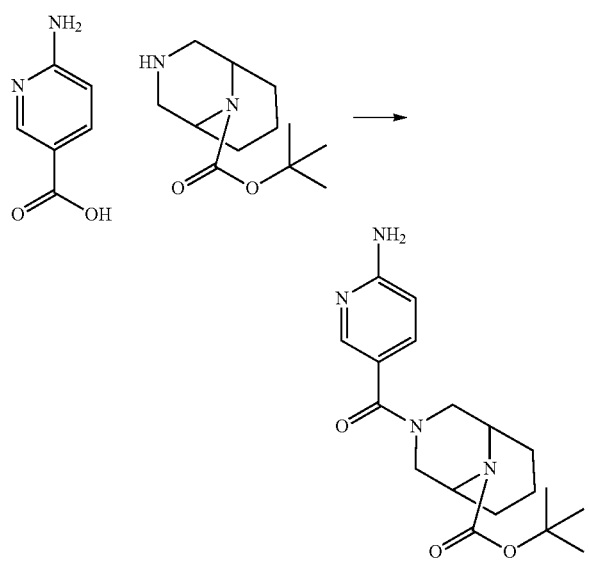

Preparation of 3-[6-(7-Cyclopentyl-6-dimethylcarbamoyl-7H-pyrrolo[2,3-d]pyrimidin-2-ylamino)-pyridine-3-carbonyl]-3,9-diaza-bicyclo[3.3.1]nonane-9-carboxylic acid tert-butyl ester Following general N—C coupling procedure 1, 2-Chloro-7-cyclopentyl-7H-pyrrolo[2,3-d]pyrimidine-6-carboxylic acid dimethylamide (100 mg, 0.342 mmol, 1.0 eq) was combined with 3-(6-Amino-pyridine-3-carbonyl)-3,9-diaza-bicyclo[3.3.1]nonane-9-carboxylic acid tert-butyl ester (130 mg, 0.376 mmol, 1.1 eq) which gave 3-[6-(7-Cyclopentyl-6-dimethylcarbamoyl-7H-pyrrolo[2,3-d]pyrimidin-2-ylamino)-pyridine-3-carbonyl]-3,9-diaza-bicyclo[3.3.1]nonane-9-carboxylic acid tert-butyl ester (121 mg) in 59% yield. 1H NMR (400 MHz, CHLOROFORM-d) δ ppm 1.51 (s, 10H) 1.56-1.70 (m, 3H) 1.70-1.81 (m, 3H) 1.88 (br. s., 3H) 2.05-2.24 (m, 6H) 2.50-2.67 (m, 2H) 3.18 (s, 7H) 3.55 (br. s.,

141

1H) 3.91 (br. s., 1H) 4.25 (br. s., 1H) 4.78-4.90 (m, 1H) 6.50 (s, 1H) 7.80 (dd, J=8.84, 2.27 Hz, 1H) 8.28 (br. s., 1H) 8.41 (s, 1H) 8.59 (d, J=8.59 Hz, 1H) 8.78 (s, 1H); MS/m/z 603.6 (M+H)$^+$.

Step 5

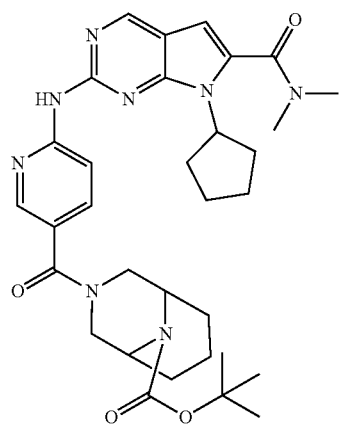

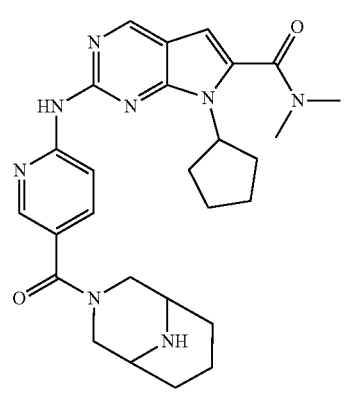

Following deprotection method 2, 3-[6-(7-Cyclopentyl-6-dimethylcarbamoyl-7H-pyrrolo[2,3-d]pyrimidin-2-ylamino)-pyridine-3-carbonyl]-3,9-diaza-bicyclo[3.3.1]nonane-9-carboxylic acid tert-butyl ester was converted to 7-cyclopentyl-2-[5-(3,9-diaza-bicyclo[3.3.1]nonane-3-carbonyl)-pyridin-2-ylamino]-7H-pyrrolo[2,3-d]pyrimidine-6-carboxylic acid dimethylamide (86 mg) in 96% yield. 1H NMR (400 MHz, CDCl$_3$-d) δ ppm 1.71-1.82 (m, 3H) 2.02-2.21 (m, 8H) 2.60 (dd, J=12.13, 8.59 Hz, 2H) 3.18 (s, 6H) 3.36 (br. s., 2H) 4.83 (quin, J=8.84 Hz, 1H) 6.50 (s, 1H) 7.82 (dd, J=8.84, 2.27 Hz, 1H) 8.44 (s, 1H) 8.47 (s, 1H) 8.61 (d, J=8.59 Hz, 1H) 8.81 (s, 1H)

HRMS m/z, (M+H)$^+$: 503.2893.

142

Example 53

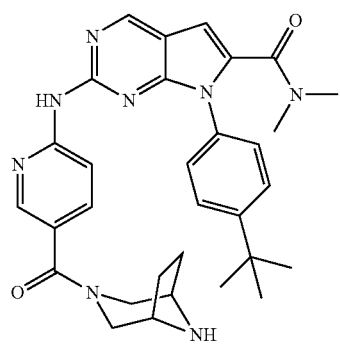

7-(4-tert-Butyl-phenyl)-2-[5-(3,8-diaza-bicyclo[3.2.1]octane-3-carbonyl)-pyridin-2-ylamino]-7H-pyrrolo[2,3-d]pyrimidine-6-carboxylic acid dimethylamide Step 1

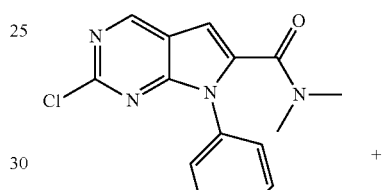

+

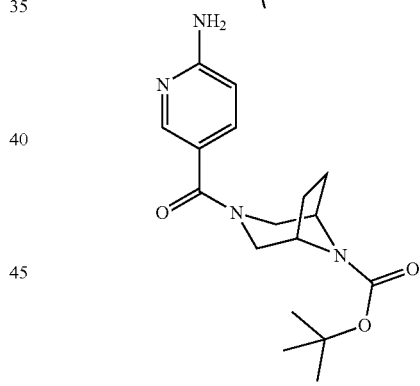

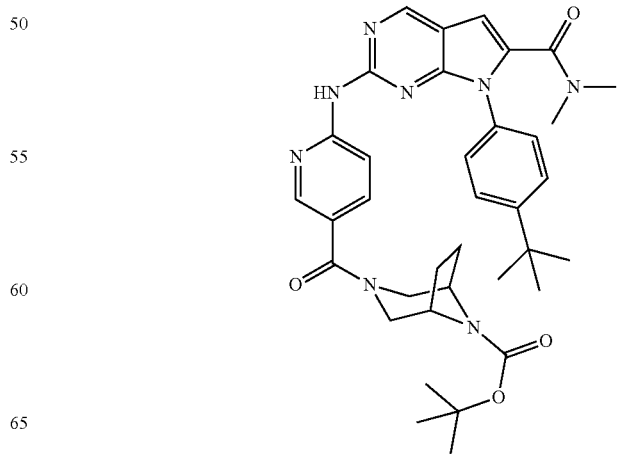

Preparation of 3-{6-[7-(4-tert-Butyl-phenyl)-6-dimethylcarbamoyl-7H-pyrrolo[2,3-d]pyrimidin-2-ylamino]-pyridine-3-carbonyl}-3,8-diaza-bicyclo[3.2.1]octane-8-carboxylic acid tert-butyl ester Following general N—C coupling procedure 1, 7-(4-tert-Butyl-phenyl)-2-chloro-7H-pyrrolo[2,3-d]pyrimidine-6-carboxylic acid dimethylamide (100 mg, 0.280 mmol, 1.0 eq) was combined with 3-(6-Amino-pyridine-3-carbonyl)-3,8-diaza-bicyclo[3.2.1]octane-8-carboxylic acid tert-butyl ester (93 mg, 0.280 mmol, 1.0 eq) which gave 3-{6-[7-(4-tert-Butyl-phenyl)-6-dimethylcarbamoyl-7H-pyrrolo[2,3-d]pyrimidin-2-ylamino]-pyridine-3-carbonyl}-3,8-diaza-bicyclo[3.2.1]octane-8-carboxylic acid tert-butyl ester (112 mg) in 58% yield. 1H NMR (400 MHz, DMSO-d$_6$) δ ppm 1.36 (s, 9H) 1.43 (s, 9H) 1.47-1.69 (m, 2H) 1.80 (br. s., 2H) 2.90 (br. s., 3H) 3.05 (br. s., 3H) 4.12 (br. s., 2H) 6.92 (s, 1H) 7.41 (m, J=8.59 Hz, 2H) 7.59 (m, J=8.59 Hz, 2H) 7.68 (dd, J=8.84, 2.27 Hz, 1H) 8.28-8.34 (m, 2H) 8.95 (s, 1H) 10.05 (s, 1H). MS m/z 653.7 (M+H)$^+$.

Step 2

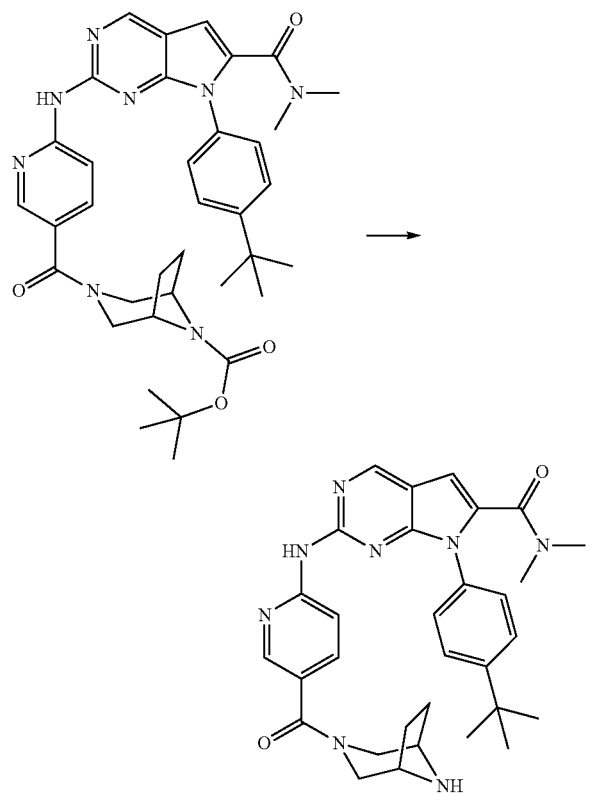

Preparation of 7-(4-tert-Butyl-phenyl)-2-[5-(3,8-diaza-bicyclo[3.2.1]octane-3-carbonyl)-pyridin-2-ylamino]-7H-pyrrolo[2,3-d]pyrimidine-6-carboxylic acid dimethylamide Following deprotection method 2, 3-{6-[7-(4-tert-Butyl-phenyl)-6-dimethylcarbamoyl-7H-pyrrolo[2,3-d]pyrimidin-2-ylamino]-pyridine-3-carbonyl}-3,8-diaza-bicyclo[3.2.1]octane-8-carboxylic acid tert-butyl ester was converted to 7-(4-tert-Butyl-phenyl)-2-[5-(3,8-diaza-bicyclo[3.2.1]octane-3-carbonyl)-pyridin-2-ylamino]-7H-pyrrolo[2,3-d]pyrimidine-6-carboxylic acid dimethylamide (67 mg) in 79%. 1H NMR (400 MHz, DMSO-d$_6$) δ ppm 1.32 (s, 9H) 1.61 (br. s., 3H) 2.86 (br. s., 3H) 2.94 (br. s., 3H) 3.39 (br. s., 2H) 6.91 (s, 1H) 7.33-7.45 (m, 2H) 7.45-7.57 (m, 2H) 7.61 (dd, J=8.59, 2.53 Hz, 1H) 8.27 (d, J=2.02 Hz, 1H) 8.31 (d, J=9.09 Hz, 1H) 8.96 (s, 1H) 10.04 (s, 1H). MS m/z 552.9 (M+H)$^+$.

Example 54

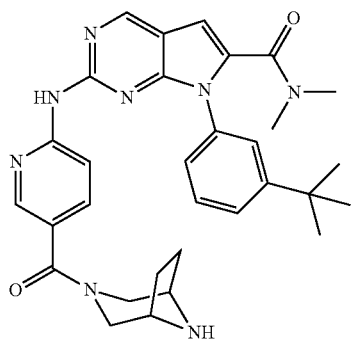

7-(3-tert-Butyl-phenyl)-2-[5-(3,8-diaza-bicyclo[3.2.1]octane-3-carbonyl)-pyridin-2-ylamino]-7H-pyrrolo[2,3-d]pyrimidine-6-carboxylic acid dimethylamide Step 1

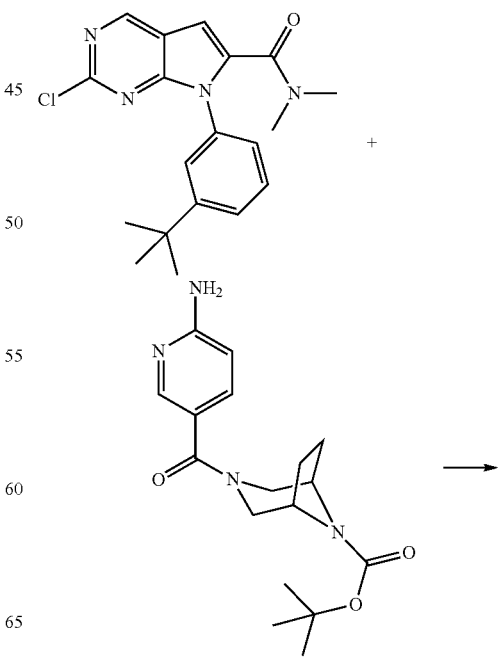

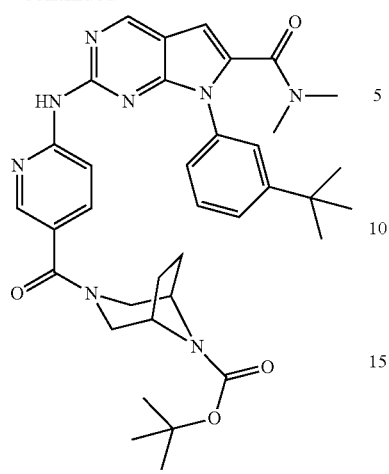

Preparation of 3-{6-[7-(3-tert-Butyl-phenyl)-6-dimethylcarbamoyl-7H-pyrrolo[2,3-d]pyrimidin-2-ylamino]-pyridine-3-carbonyl}-3,8-diaza-bicyclo[3.2.1]octane-8-carboxylic acid tert-butyl ester Following general N—C coupling procedure 1, 7-(3-tert-Butyl-phenyl)-2-chloro-7H-pyrrolo[2,3-d]pyrimidine-6-carboxylic acid dimethylamide (100 mg, 0.280 mmol, 1.0 eq) was combined with 3-(6-Amino-pyridine-3-carbonyl)-3,8-diaza-bicyclo[3.2.1]octane-8-carboxylic acid tert-butyl ester (93 mg, 0.280 mmol, 1.0 eq) to give 3-{6-[7-(3-tert-Butyl-phenyl)-6-dimethylcarbamoyl-7H-pyrrolo[2,3-d]pyrimidin-2-ylamino]-pyridine-3-carbonyl}-3,8-diaza-bicyclo[3.2.1]octane-8-carboxylic acid tert-butyl ester (116 mg) in 60% yield. 1H NMR (400 MHz, DMSO-$d_6$) δ ppm 1.32 (s, 9H) 1.43 (s, 9H) 1.59 (br. s., 2H) 1.81 (br. s., 2H) 2.86 (br. s., 3H) 2.94 (br. s., 3H) 4.12 (br. s., 2H) 6.91 (s, 1H) 7.37-7.43 (m, 2H) 7.45-7.58 (m, 2H) 7.67 (dd, J=8.84, 2.27 Hz, 1H) 8.32 (dd, J=5.81, 2.78 Hz, 2H) 8.96 (s, 1H) 10.05 (s, 1H). MS m/z 653.7 $(M+H)^+$.

Step 2

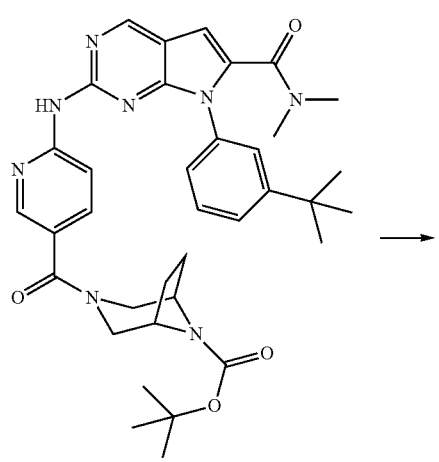

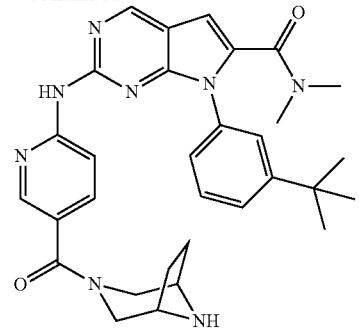

Preparation of 7-(3-tert-Butyl-phenyl)-2-[5-(3,8-diaza-bicyclo[3.2.1]octane-3-carbonyl)-pyridin-2-ylamino]-7H-pyrrolo[2,3-d]pyrimidine-6-carboxylic acid dimethylamide Following deprotection method 2, 3-{6-[7-(3-tert-Butyl-phenyl)-6-dimethylcarbamoyl-7H-pyrrolo[2,3-d]pyrimidin-2-ylamino]-pyridine-3-carbonyl}-3,8-diaza-bicyclo[3.2.1]octane-8-carboxylic acid tert-butyl ester was converted to 7-(3-tert-Butyl-phenyl)-2-[5-(3,8-diaza-bicyclo[3.2.1]octane-3-carbonyl)-pyridin-2-ylamino]-7H-pyrrolo[2,3-d]pyrimidine-6-carboxylic acid dimethylamide (75 mg) in 89%. 1H NMR (400 MHz, DMSO-$d_6$) δ ppm 1.36 (s, 10H) 1.60 (br. s., 2H) 1.70 (br. s., 2H) 2.90 (br. s., 3H) 3.05 (br. s., 3H) 3.57 (br. s., 2H) 6.92 (5, 1H) 7.41 (m, J=8.59 Hz, 2H) 7.59 (m, J=8.59 Hz, 2H) 7.66 (dd, J=8.84, 2.27 Hz, 1H) 8.29 (d, J=2.02 Hz, 1H) 8.31 (d, J=8.59 Hz, 1H) 8.95 (s, 1H) 10.05 (s, 1H). MS m/z 552.9 $(M+H)^+$.

Example 55

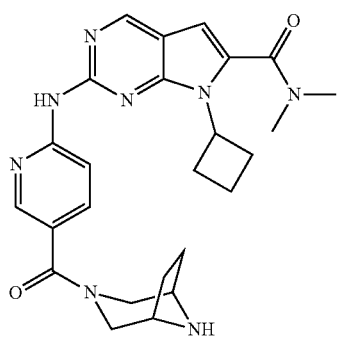 [SMILES: CN(C)C(=O)c1cc2cnc(Nc3ccc(C(=O)N4CC5CCC(C4)N5)cn3)nc2n1C1CCC1]

7-(3-tert-Butyl-phenyl)-2-[5-(3,8-diaza-bicyclo[3.2.1]octane-3-carbonyl)-pyridin-2-ylamino]-7H-pyrrolo[2,3-d]pyrimidine-6-carboxylic acid dimethylamide

Step 1

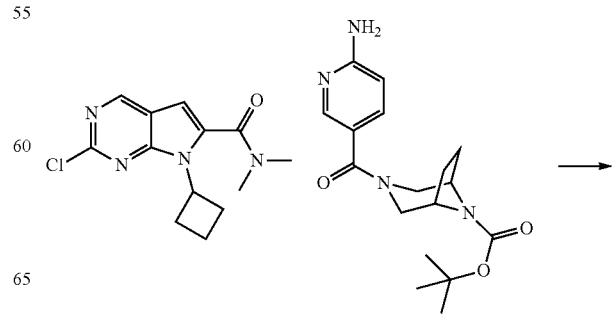

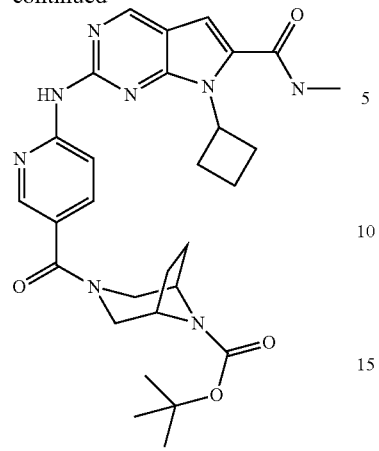

Preparation of 3-[6-(7-Cyclobutyl-6-methylcarbamoyl-7H-pyrrolo[2,3-d]pyrimidin-2-ylamino)-pyridine-3-carbonyl]-3,8-diaza-bicyclo[3.2.1]octane-8-carboxylic acid tert-butyl ester Following general N—C coupling procedure 1, 2-Chloro-7-cyclobutyl-7H-pyrrolo[2,3-d]pyrimidine-6-carboxylic acid dimethylamide (200 mg, 0.718 mmol, 1.0 eq) was combined with 3-(6-Amino-pyridine-3-carbonyl)-3,8-diaza-bicyclo[3.2.1]octane-8-carboxylic acid tert-butyl ester (262 mg, 0.789 mmol, 1.1 eq) to give 3-[6-(7-Cyclobutyl-6-methylcarbamoyl-7H-pyrrolo[2,3-d]pyrimidin-2-ylamino)-pyridine-3-carbonyl]-3,8-diaza-bicyclo[3.2.1]octane-8-carboxylic acid tert-butyl ester (218 mg, 50% yield). 1H NMR (400 MHz, CHLOROFORM-d) δ ppm 1.51 (s, 9H) 1.62 (br. s., 1H) 1.67 (br. s., 1H) 1.77-2.07 (m, 6H) 2.41-2.58 (m, 2H) 3.17 (s, 6H) 3.19-3.29 (m, 2H) 3.64 (br. s., 1H) 4.28 (br. s., 2H) 4.54 (br. s., 1H) 5.01 (dq, J=8.84, 8.67 Hz, 1H) 6.50 (s, 1H) 7.83 (dd, J=8.84, 2.27 Hz, 1H) 8.42 (d, J=2.02 Hz, 2H) 8.67 (d, J=9.09 Hz, 1H) 8.78 (s, 1H); MS m/z 574.9 (M+H)+.

Step: 2

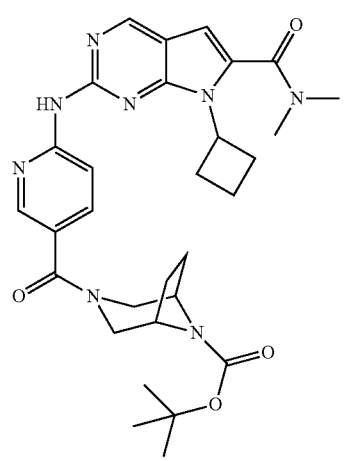

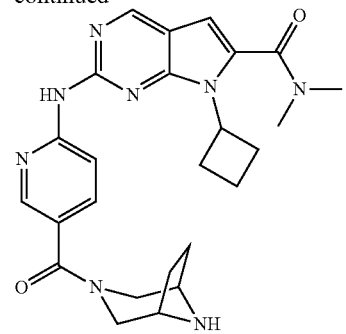

Preparation of 7-Cyclobutyl-2-[5-(3,8-diaza-bicyclo[3.2.1]octane-3-carbonyl)-pyridin-2-ylamino]-7H-pyrrolo[2,3-d]pyrimidine-6-carboxylic acid dimethylamide Following deprotection method 2, 3-[6-(7-Cyclobutyl-6-methylcarbamoyl-7H-pyrrolo[2,3-d]pyrimidin-2-ylamino)-pyridine-3-carbonyl]-3,8-diaza-bicyclo[3.2.1]octane-8-carboxylic acid tert-butyl ester was converted to 7-Cyclobutyl-2-[5-(3,8-diaza-bicyclo[3.2.1]octane-3-carbonyl)-pyridin-2-ylamino]-7H-pyrrolo[2,3-d]pyrimidine-6-carboxylic acid dimethylamide (128 mg) in 74%. 1H NMR (400 MHz, CHLOROFORM-d) δ ppm 1.78-2.08 (m, 10H) 2.45-2.57 (m, 2H) 3.17 (s, 6H) 3.20-3.31 (m, 3H) 3.56 s., 3H) 4.53 (br. s., 1H) 5.01 (quin, J=8.84 Hz, 1H) 6.49 (s, 1H) 7.82 (dd, J=8.59, 2.02 Hz, 1H) 8.43 (s, 1H) 8.60 (s, 1H) 8.67 (d, J=9.60 Hz, 1H) 8.81 (s, 1H); MS m/z 474.9 (M+H)+.

Example 56

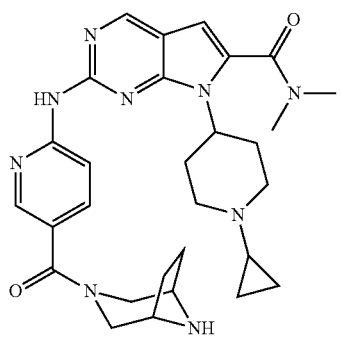 [SMILES: CN(C)C(=O)c1cc2cnc(Nc3ccc(C(=O)N4CC5CCC(C4)N5)cn3)nc2n1C1CCN(C2CC2)CC1]

7-(3-tert-Butyl-phenyl)-2-[5-(3,8-diaza-bicyclo[3.2.1]octane-3-carbonyl)-pyridin-2-ylamino]-7H-pyrrolo[2,3-d]pyrimidine-6-carboxylic acid dimethylamide Step 1

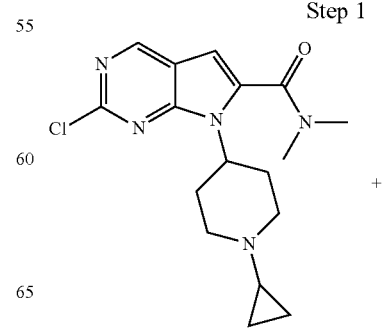

+

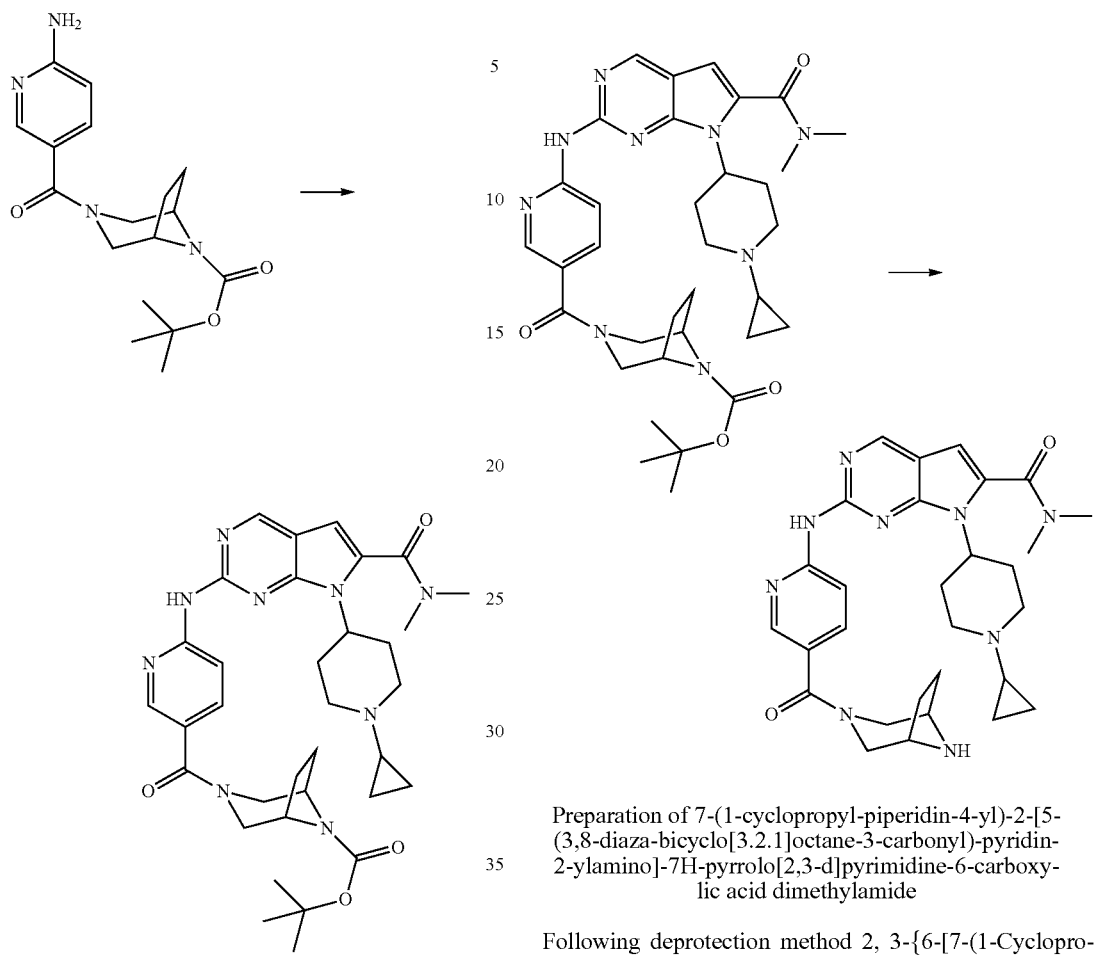

Preparation of 3-{6-[7-(1-Cyclopropyl-piperidin-4-yl)-6-dimethylcarbamoyl-7H-pyrrolo[2,3-d]pyrimidin-2-ylamino]-pyridine-3-carbonyl}-3,8-diaza-bicyclo[3.2.1]octane-8-carboxylic acid tert-butyl ester Using General Buchwald method 1, 2-Chloro-7-(1-cyclopropyl-piperidin-4-yl)-7H-pyrrolo[2,3-d]pyrimidine-6-carboxylic acid dimethylamide (95 mg, 0.273 mmol, 1.0 eq) was combined with 3-(6-Amino-pyridine-3-carbonyl)-3,8-diaza-bicyclo[3.2.1]octane-8-carboxylic acid tert-butyl ester (100 mg, 0.300 mmol, 1.1 eq) to give 3-{6-[7-(1-Cyclopropyl-piperidin-4-yl)-6-dimethylcarbamoyl-7H-pyrrolo[2,3-d]pyrimidin-2-ylamino]-pyridine-3-carbonyl}-3,8-diaza-bicyclo[3.2.1]octane-8-carboxylic acid tert-butyl ester (131 mg, 71% yield). 1H NMR (400 MHz, CHLOROFORM-d) δ ppm 0.46 (br. s., 2H) 0.54 (br. s., 2H) 1.52 (s, 10H) 1.61 (br. s., 2H) 1.71 (br. s., 2H) 1.88 (d, J=10.11 Hz, 3H) 1.96 (d, J=6.06 Hz, 2H) 2.37 (t, J=11.62 Hz, 2H) 2.79-3.01 (m, 2H) 3.20 (s, 10H) 3.63 (br. s., 2H) 4.27 (br. s., 2H) 4.41 (br. s., 2H) 6.50 (s, 1H) 7.69 (br. s., 1H) 8.22 (s, 1H) 8.41 (s, 1H) 8.63 (d, J=8.59 Hz, 1H) 8.77 (s, 1H); MS m/z 644.6 (M+H)$^+$.

Preparation of 7-(1-cyclopropyl-piperidin-4-yl)-2-[5-(3,8-diaza-bicyclo[3.2.1]octane-3-carbonyl)-pyridin-2-ylamino]-7H-pyrrolo[2,3-d]pyrimidine-6-carboxylic acid dimethylamide Following deprotection method 2, 3-{6-[7-(1-Cyclopropyl-piperidin-4-yl)-6-dimethylcarbamoyl-7H-pyrrolo[2,3-d]pyrimidin-2-ylamino]-pyridine-3-carbonyl}-3,8-diaza-bicyclo[3.2.1]octane-8-carboxylic acid tert-butyl ester was converted to 7-(1-Cyclopropyl-piperidin-4-yl)-2-[5-(3,8-diaza-bicyclo[3.2.1]octane-3-carbonyl)-pyridin-2-ylamino]-7H-pyrrolo[2,3-d]pyrimidine-6-carboxylic acid dimethylamide (25 mg) in 27%. 1H NMR (400 MHz, CHLOROFORM-d) δ ppm 0.44-0.62 (m, 4H) 1.28 (d, J=4.55 Hz, 2H) 1.75 (br. s., 1H) 1.91 (br. s., 3H) 2.02 (br. s., 2H) 2.41 (br. s., 2H) 2.93 (dd, J=12.38, 3.79 Hz, 2H) 3.20 (s, 6H) 3.78 (br. s., 2H) 4.43 (t, J=12.38 Hz, 1H) 6.51 (s, 1H) 7.71 (dd, J=8.59, 2.02 Hz, 1H) 8.44 (s, 1H) 8.46 (br. s., 1H) 8.64 (d, J=8.59 Hz, 1H) 8.79 (s, 1H); MS m/z 544.6 (M+H)$^+$.

Example 57

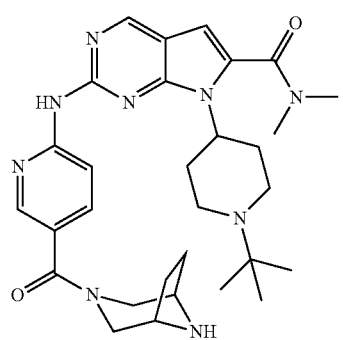 [SMILES: CN(C)C(=O)c1cc2cnc(Nc3ccc(C(=O)N4CC5CCC(C4)N5)cn3)nc2n1C1CCN(C(C)(C)C)CC1]

151

7-(1-tert-Butyl-piperidin-4-yl)-2-[5-(3,8-diaza-bicyclo[3.2.1]octane-3-carbonyl)-pyridin-2-ylamino]-7H-pyrrolo[2,3-d]pyrimidine-6-carboxylic acid dimethylamide Step 1

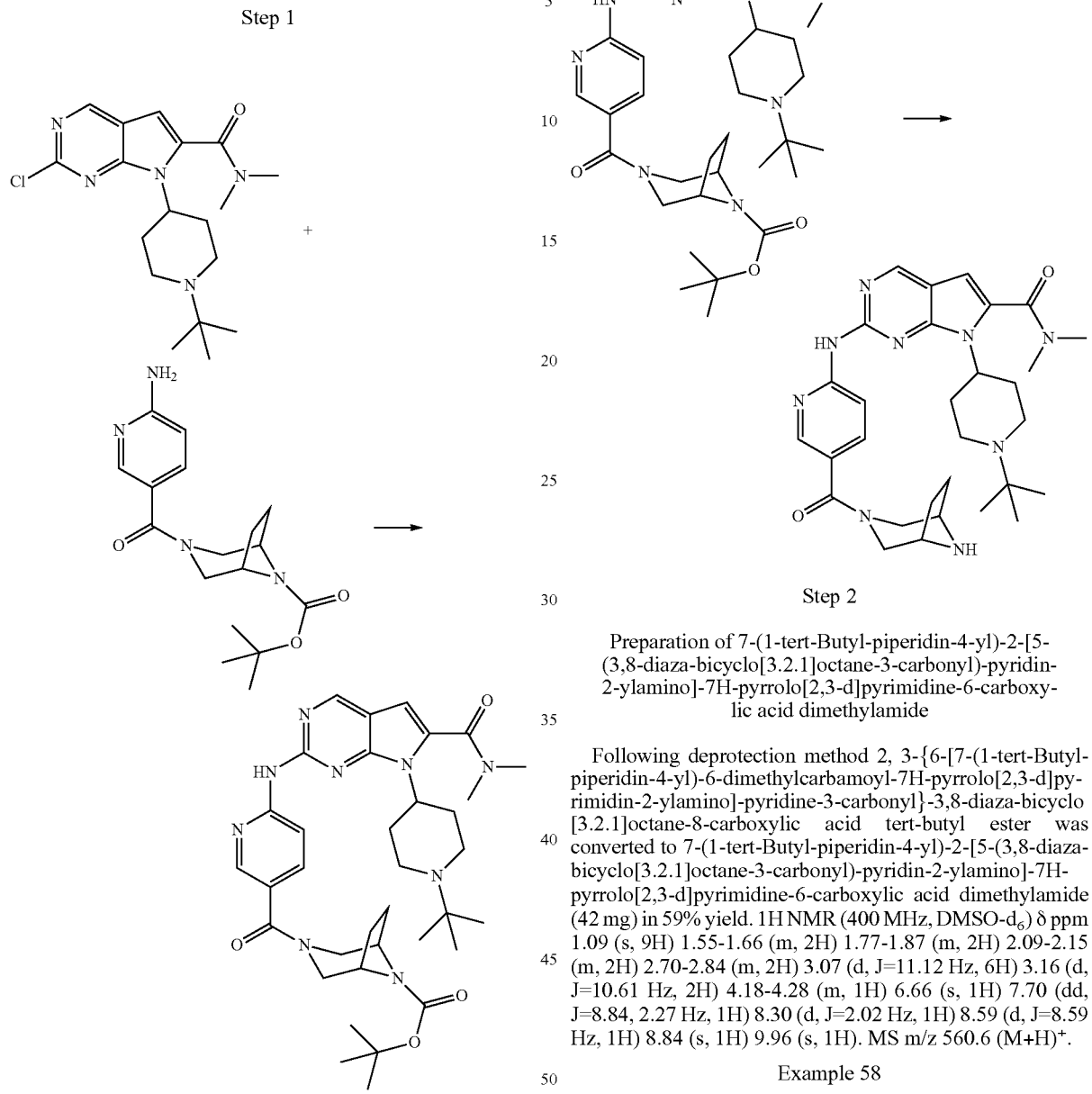

Preparation of 3-{6-[7-(1-tert-Butyl-piperidin-4-yl)-6-dimethylcarbamoyl-7H-pyrrolo[2,3-d]pyrimidin-2-ylamino]-pyridine-3-carbonyl}-3,8-diaza-bicyclo[3.2.1]octane-8-carboxylic acid tert-butyl ester Following general N—C coupling procedure 1, 1,7-(1-tert-Butyl-piperidin-4-yl)-2-chloro-7H-pyrrolo[2,3-d]pyrimidine-6-carboxylic acid dimethylamide (90 mg, 0.247 mmol, 1.0 eq) was combined with 3-(6-Amino-pyridine-3-carbonyl)-3,8-diaza-bicyclo[3.2.1]octane-8-carboxylic acid tert-butyl ester (90 mg, 0.272 mmol, 1.1 eq) which gave 3-{6-[7-(1-tert-Butyl-piperidin-4-yl)-6-dimethylcarbamoyl-7H-pyrrolo[2,3-d]pyrimidin-2-ylamino]-pyridine-3-carbonyl}-3,8-diaza-bicyclo[3.2.1]octane-8-carboxylic acid tert-butyl ester (80 mg) in 47% yield. MS m/z 660.3 (M+H)$^+$.

152

Step 2

Preparation of 7-(1-tert-Butyl-piperidin-4-yl)-2-[5-(3,8-diaza-bicyclo[3.2.1]octane-3-carbonyl)-pyridin-2-ylamino]-7H-pyrrolo[2,3-d]pyrimidine-6-carboxylic acid dimethylamide Following deprotection method 2, 3-{6-[7-(1-tert-Butyl-piperidin-4-yl)-6-dimethylcarbamoyl-7H-pyrrolo[2,3-d]pyrimidin-2-ylamino]-pyridine-3-carbonyl}-3,8-diaza-bicyclo[3.2.1]octane-8-carboxylic acid tert-butyl ester was converted to 7-(1-tert-Butyl-piperidin-4-yl)-2-[5-(3,8-diaza-bicyclo[3.2.1]octane-3-carbonyl)-pyridin-2-ylamino]-7H-pyrrolo[2,3-d]pyrimidine-6-carboxylic acid dimethylamide (42 mg) in 59% yield. 1H NMR (400 MHz, DMSO-d$_6$) δ ppm 1.09 (s, 9H) 1.55-1.66 (m, 2H) 1.77-1.87 (m, 2H) 2.09-2.15 (m, 2H) 2.70-2.84 (m, 2H) 3.07 (d, J=11.12 Hz, 6H) 3.16 (d, J=10.61 Hz, 2H) 4.18-4.28 (m, 1H) 6.66 (s, 1H) 7.70 (dd, J=8.84, 2.27 Hz, 1H) 8.30 (d, J=2.02 Hz, 1H) 8.59 (d, J=8.59 Hz, 1H) 8.84 (s, 1H) 9.96 (s, 1H). MS m/z 560.6 (M+H)$^+$.

Example 58

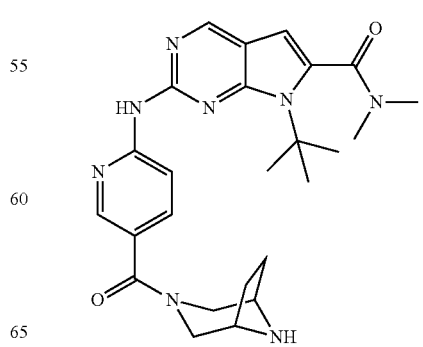

7-tert-Butyl-2-[5-(3,8-diaza-bicyclo[3.2.1]octane-3-carbonyl)-pyridin-2-ylamino]-7H-pyrrolo[2,3-d]pyrimidine-6-carboxylic acid dimethylamide Step 1

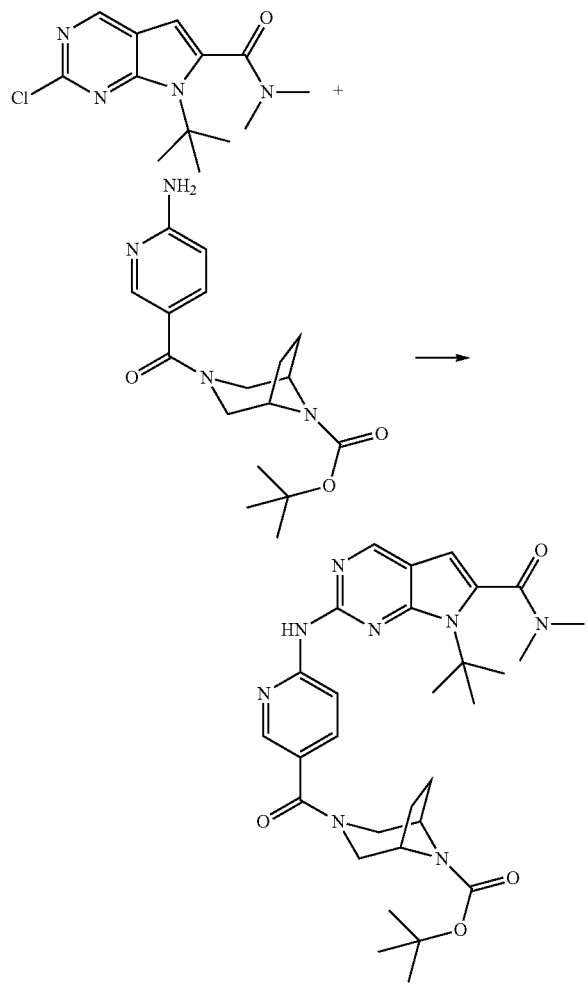

Preparation of 3-[6-(7-tert-Butyl-6-dimethylcarbamoyl-7H-pyrrolo[2,3-d]pyrimidin-2-ylamino)-pyridine-3-carbonyl]-3,8-diaza-bicyclo[3.2.1]octane-8-carboxylic acid tert-butyl ester Following general N—C coupling procedure 1, 7-tert-Butyl-2-chloro-7H-pyrrolo[2,3-d]pyrimidine-6-carboxylic acid dimethylamide (150 mg, 0.534 mmol, 1.0 eq) was combined with 3-(6-Amino-pyridine-3-carbonyl)-3,8-diaza-bicyclo[3.2.1]octane-8-carboxylic acid tert-butyl ester (178 mg, 0.534 mmol, 1.0 eq) which gave 3-[6-(7-tert-Butyl-6-dimethylcarbamoyl-7H-pyrrolo[2,3-d]pyrimidin-2-ylamino)-pyridine-3-carbonyl]-3,8-diaza-bicyclo[3.2.1]octane-8-carboxylic acid tert-butyl ester (189 mg) in 61% yield. 1H NMR (400 MHz, DMSO-$d_6$) δ ppm 1.43 (s, 10H) 1.59 (br. s., 2H) 1.74-1.84 (m, 12H) 3.00 (d, J=2.53 Hz, 7H) 4.14 (br. s., 2H) 6.48 (s, 1H) 7.85 (dd, J=8.84, 2.27 Hz, 1H) 8.28-8.39 (m, 2H) 8.80 (s, 1H) 9.89 (s, 1H). MS m/z 577.6 (M+H)$^+$.

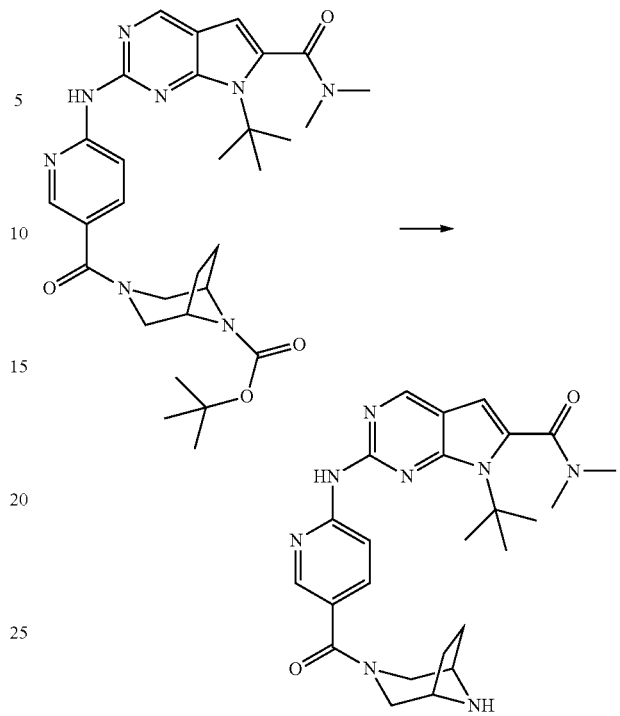

Step 2

7-tert-Butyl-2-[5-(3,8-diaza-bicyclo[3.2.1]octane-3-carbonyl)-pyridin-2-ylamino]-7H-pyrrolo[2,3-d]pyrimidine-6-carboxylic acid dimethylamide Following deprotection method 1, 3-[6-(7-tert-Butyl-6-dimethylcarbamoyl-7H-pyrrolo[2,3-d]pyrimidin-2-ylamino)-pyridine-3-carbonyl]-3,8-diaza-bicyclo[3.2.1]octane-8-carboxylic acid tert-butyl ester was converted to 7-tert-Butyl-2-[5-(3,8-diaza-bicyclo[3.2.1]octane-3-carbonyl)-pyridin-2-ylamino]-7H-pyrrolo[2,3-d]pyrimidine-6-carboxylic acid dimethylamide (80 mg) in 48% yield. 1H NMR (400 MHz, DMSO-$d_6$) δ ppm 1.46-1.69 (m, 4H) 1.78 (s, 9H) 3.00 (d, J=2.53 Hz, 6H) 3.42 (br. s., 4H) 4.20 (br. s., 1H) 6.48 (s, 1H) 7.79 (dd, J=8.59, 2.53 Hz, 1H) 8.29-8.35 (m, 2H) 8.80 (s, 1H) 9.86 (s, 1H). MS m/z 476.8 (M+H)$^+$.

Example 59

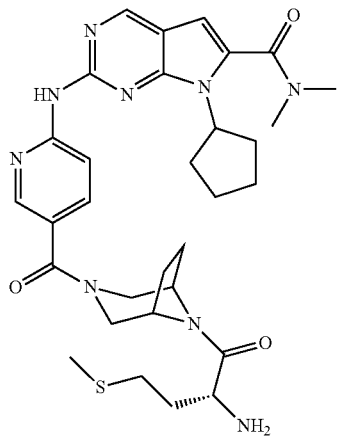 [SMILES: CSCC[C@@H](N)C(=O)N1C2CCC1CN(C(=O)c1ccc(Nc3ncc4cc(C(=O)N(C)C)n(C5CCCC5)c4n3)nc1)C2]

155

2-{5-[8-((R)-2-Amino-4-methylsulfanyl-butyryl)-3,8-diaza-bicyclo[3.2.1]octane-3-carbonyl]-pyridin-2-ylamino}-7-cyclopentyl-7H-pyrrolo[2,3-d]pyrimidine-6-carboxylic acid dimethylamide Step 1

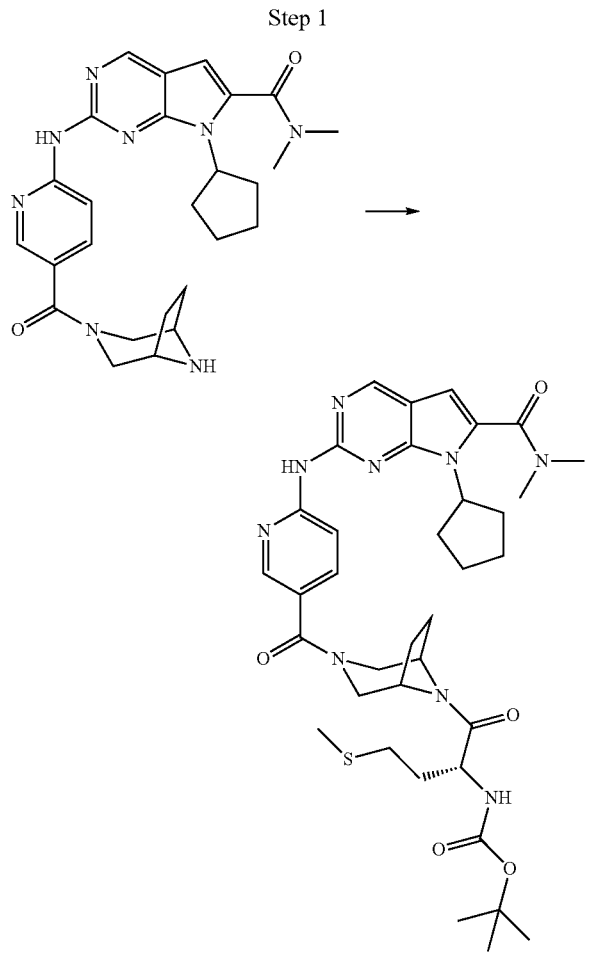

Preparation of ((R)-1-{3-[6-(7-Cyclopentyl-6-dimethylcarbamoyl-7H-pyrrolo[2,3-d]pyrimidin-2-ylamino)-pyridine-3-carbonyl]-3,8-diaza-bicyclo[3.2.1]octane-8-carbonyl}-3-methylsulfanyl-propyl)-carbamic acid tert-butyl ester Following general amide formation method 1, 7-Cyclopentyl-2-[5-(3,8-diaza-bicyclo[3.2.1]octane-3-carbonyl)-pyridin-2-ylamino]-7H-pyrrolo[2,3-d]pyrimidine-6-carboxylic acid dimethylamide (100 mg, 0.205 mmol, 1.0 eq) was combined with BOC-D-Methionine (51 mg, 0.205 mmol, 1.0 eq) which gave ((R)-1-{3-[6-(7-Cyclopentyl-6-dimethylcarbamoyl-7H-pyrrolo[2,3-d]pyrimidin-2-ylamino)-pyridine-3-carbonyl]-3,8-diaza-bicyclo[3.2.1]octane-8-carbonyl}-3-methylsulfanyl-propylcarbamic acid tert-butyl ester (105 mg) in 68% yield. 1H NMR (400 MHz, CHLOROFORM-d) δ ppm 1.39-1.56 (m, 14H) 1.63 (br. s., 2H) 1.68-1.82 (m, 3H) 1.82-1.99 (m, 4H) 1.99-2.18 (m, 10H) 2.48-2.68 (m, 5H) 3.18 (s, 7H) 3.73 (dd, J=10.36, 6.82 Hz, 1H) 4.51 (br. s., 1H) 4.69 (br. s., 3H) 4.77-4.89 (m, 2H) 5.28 (t, J=10.11 Hz, 1H) 6.51 (s, 1H) 7.80 (d, J=6.57 Hz, 1H) 8.36 (br. s., 1H) 8.42 (d, J=2.02 Hz, 1H) 8.59 (br. s., 1H) 8.80 (s, 1H). HRMS m/z, (M+H)$^+$: 720.3682.

156

Step 2

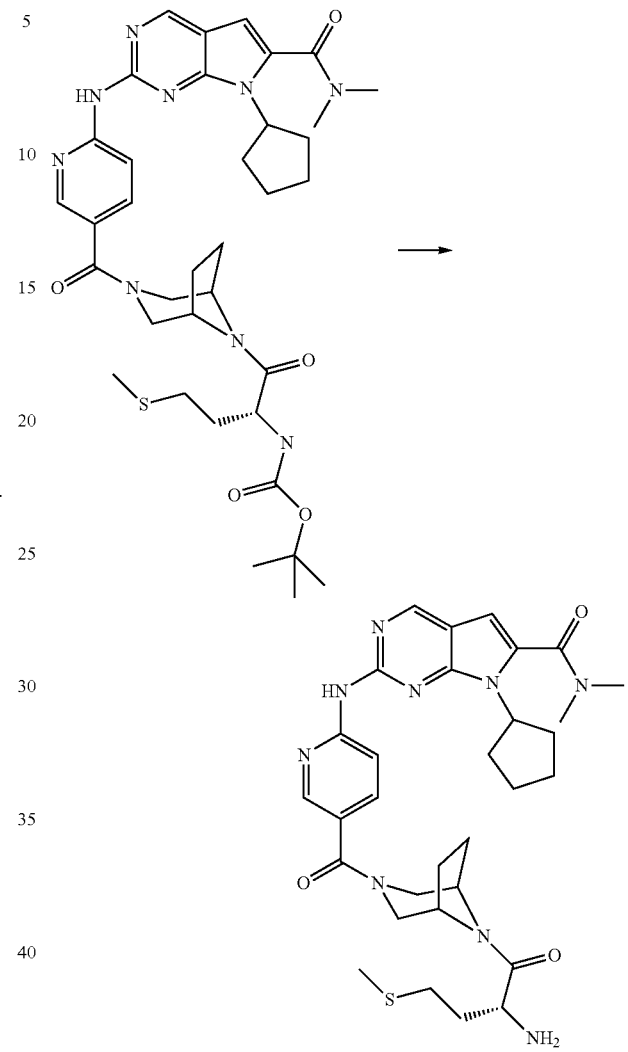

Preparation of 2-{5-[8-((R)-2-Amino-4-methylsulfanyl-butyryl)-3,8-diaza-bicyclo[3.2.1]octane-3-carbonyl]-pyridin-2-ylamino}-7-cyclopentyl-7H-pyrrolo[2,3-d]pyrimidine-6-carboxylic acid dimethylamide Following deprotection method 2, ((R)-1-{3-[6-(7-Cyclopentyl-6-dimethylcarbamoyl-7H-pyrrolo[2,3-d]pyrimidin-2-ylamino)-pyridine-3-carbonyl]-3,8-diaza-bicyclo[3.2.1]octane-8-carbonyl}-3-methylsulfanyl-propyl)-carbamic acid tert-butyl ester was converted to 2-{5-[8-((R)-2-Amino-4-methylsulfanyl-butyryl)-3,8-diaza-bicyclo[3.2.1]octane-3-carbonyl]-pyridin-2-ylamino}-7-cyclopentyl-7H-pyrrolo[2,3-d]pyrimidine-6-carboxylic acid dimethylamide (60 mg, 91%). 1H NMR (400 MHz, CHLOROFORM-d) δ ppm 1.67-1.83 (m, 3H) 1.88 (br. s., 3H) 1.98-2.21 (m, 10H) 2.53-2.67 (m, 3H) 2.67-2.84 (m, 2H) 3.18 (s, 7H) 3.84 (br. s., 1H) 3.95 (br. s., 1H) 4.45 (br. s., 1H) 4.83 (dq, J=9.09, 8.93 Hz, 2H) 6.50 (s, 1H) 7.83 (d, J=6.57 Hz, 1H) 8.44 (d, J=11.62 Hz, 1H) 8.53-8.66 (m, 1H) 8.85 (s, 1H). HRMS m/z, (M+H)$^+$: 620.3113.

Example 60

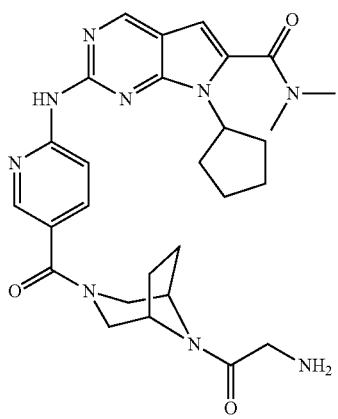 [SMILES: CN(C)C(=O)c1cc2cnc(Nc3ccc(C(=O)N4CC5CCC(C4)N5C(=O)CN)cn3)nc2n1C1CCCC1]

2-{5-[8-(2-Amino-acetyl)-3,8-diaza-bicyclo[3.2.1]
octane-3-carbonyl]-pyridin-2-ylamino}-7-cyclopentyl-7H-pyrrolo[2,3-d]pyrimidine-6-carboxylic acid dimethylamide Preparation of (2-{3-[6-(7-Cyclopentyl-6-dimethylcarbamoyl-7H-pyrrolo[2,3-d]pyrimidin-2-ylamino)-pyridine-3-carbonyl]-3,8-diaza-bicyclo[3.2.1]oct-8-yl}-2-oxo-ethyl)-carbamic acid tert-butyl ester Following general amide formation method 1, 1,7-Cyclopentyl-2-[5-(3,8-diaza-bicyclo[3.2.1]octane-3-carbonyl)-pyridin-2-ylamino]-7H-pyrrolo[2,3-d]pyrimidine-6-carboxylic acid dimethylamide (100 mg, 0.205 mmol, 1.0 eq) was combined with BOC-Glycine (39.4 mg, 0.225 mmol, 1.1 eq) which gave (2-{3-[6-(7-Cyclopentyl-6-dimethylcarbamoyl-7H-pyrrolo[2,3-d]pyrimidin-2-ylamino)-pyridine-3-carbonyl]-3,8-diaza-bicyclo[3.2.1]oct-8-yl}-2-oxo-ethyl)-carbamic acid tert-butyl ester (71 mg) in 53% yield. 1H NMR (400 MHz, CHLOROFORM-d) δ ppm 1.39 (s, 9H) 1.42-1.59 (m, 1H) 1.59-1.75 (m, 3H) 1.85 (d, J=7.58 Hz, 2H) 2.00 (dd, J=14.65, 7.58 Hz, 5H) 2.41-2.60 (m, 2H) 3.09 (s, 6H) 3.89 (br. s., 2H) 4.12 (br. s., 1H) 4.53-4.81 (m, 2H) 5.35 (br. s., 1H) 6.42 (s, 1H) 7.71 (dd, J=8.84, 2.3 Hz, 1H) 8.31 (d, J=2.0 Hz, 1H) 8.48 (d, J=8.59 Hz, 1H) 8.69 (s, 1H); HRMS m/z, (M+H)$^+$: 646.3467.

Step 1

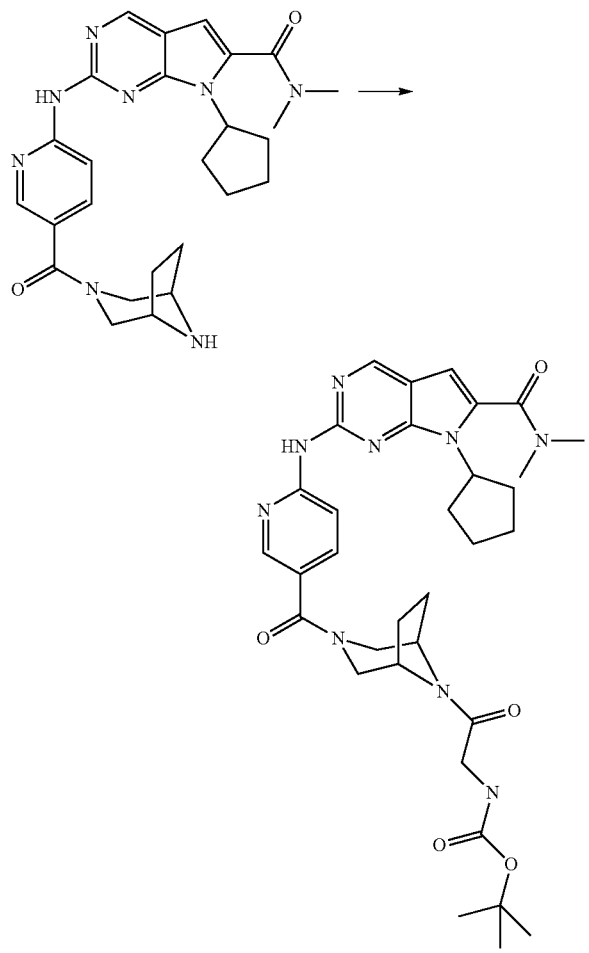

Step 2

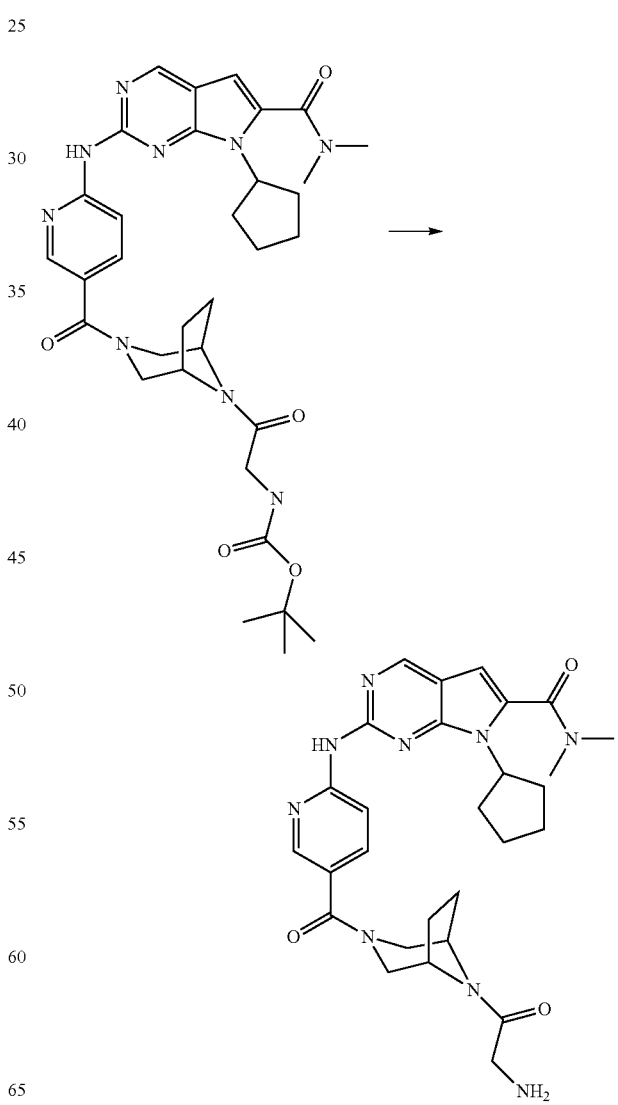

Preparation of 2-{5-[8-(2-Amino-acetyl)-3,8-diaza-bicyclo[3.2.1]octane-3-carbonyl]-pyridin-2-ylamino}-7-cyclopentyl-7H-pyrrolo[2,3-d]pyrimidine-6-carboxylic acid dimethylamide Following deprotection method 2, (2-{3-[6-(7-Cyclopentyl-6-dimethylcarbamoyl-7H-pyrrolo[2,3-d]pyrimidin-2-ylamino)-pyridine-3-carbonyl]-3,8-diaza-bicyclo[3.2.1]oct-8-yl}-2-oxo-ethyl)-carbamic acid tert-butyl ester was converted to 2-{5-[8-(2-amino-acetyl)-3,8-diaza-bicyclo[3.2.1]octane-3-carbonyl]-pyridin-2-ylamino}-7-cyclopentyl-7H-pyrrolo[2,3-d]pyrimidine-6-carboxylic acid dimethylamide (48 mg) in 89% yield. 1H NMR (400 MHz, CHLOROFORM-d) δ ppm 1.06 (s, 3H) 1.37 (s, 2H) 1.46 (br. s., 3H) 1.62 (br. s., 2H) 1.82 (d, J=17.68 Hz, 5H) 2.30 (br. s., 3H) 2.86-2.97 (m, 6H) 3.79 (br. s., 2H) 3.98 (br. s., 1H) 4.43 (br. s., 2H) 4.49-4.69 (m, 1H) 6.27 (s, 1H) 7.64 (br. s., 1H) 8.28 (br. s., 4H) 8.72 (br. s., 1H). HRMS m/z, (M+H)$^+$: 546.2932.

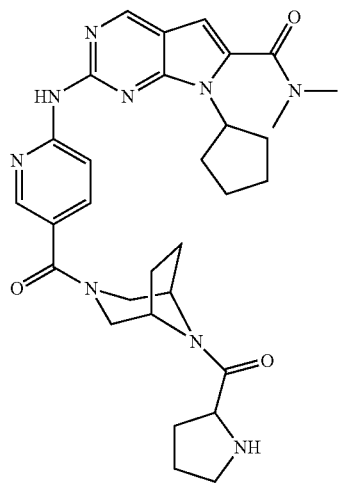 [SMILES: CN(C)C(=O)c1cc2cnc(Nc3ccc(C(=O)N4CC5CCC(C4)N5C(=O)C4CCCN4)cn3)nc2n1C1CCCC1]

Example 61

7-Cyclopentyl-2-{5-[8-(pyrrolidine-2-carbonyl)-3,8-diaza-bicyclo[3.2.1]octane-3-carbonyl]-pyridin-2-ylamino}-7H-pyrrolo[2,3-d]pyrimidine-6-carboxylic acid dimethylamide

Step 1

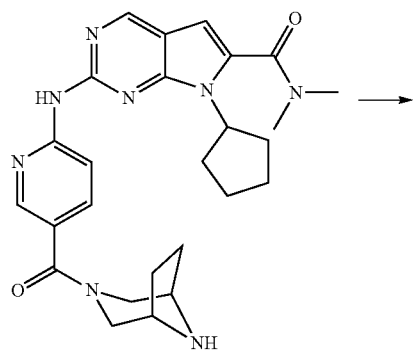

-continued

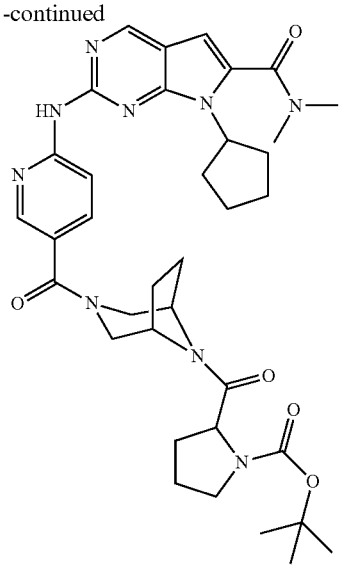

Preparation of 2-{3-[6-(7-Cyclopentyl-6-dimethylcarbamoyl-7H-pyrrolo[2,3-d]pyrimidin-2-ylamino)-pyridine-3-carbonyl]-3,8-diaza-bicyclo[3.2.1]octane-8-carbonyl}-pyrrolidine-1-carboxylic acid tert-butyl ester Following general amide formation method 1, 7-cyclopentyl-2-[5-(3,8-diaza-bicyclo[3.2.1]octane-3-carbonyl)-pyridin-2-ylamino]-7H-pyrrolo[2,3-d]pyrimidine-6-carboxylic acid dimethylamide (100 mg, 0.205 mmol, 1.0 eq) was combined with BOC-Proline (48.5 mg, 0.225 mmol, 1.1 eq) which gave 2-{3-[6-(7-Cyclopentyl-6-dimethylcarbamoyl-7H-pyrrolo[2,3-d]pyrimidin-2-ylamino)-pyridine-3-carbonyl]-3,8-diaza-bicyclo[3.2.1]octane-8-carbonyl}-pyrrolidine-1-carboxylic acid tert-butyl ester (95 mg) in 64% yield. 1H NMR (400 MHz, CHLOROFORM-d) δ ppm 1.36-1.57 (m, 12H) 1.63-1.86 (m, 5H) 1.91 (br. s., 4H) 1.99-2.29 (m, 10H) 2.45-2.67 (m, 2H) 3.18 (s, 7H) 3.43 (d, J=6.57 Hz, 2H) 3.60 (br. s., 3H) 4.42 (br. s., 2H) 4.56 (br. s., 2H) 4.68-4.94 (m, 2H) 6.53 (s, 1H) 7.83 (d, J=8.08 Hz, 1H) 8.41 (br. s., 1H) 8.58 (d, J=8.59 Hz, 1H) 8.76-8.80 (m, 1H). HRMS m/z, (M+H)$^+$: 686.3769.

Step 2

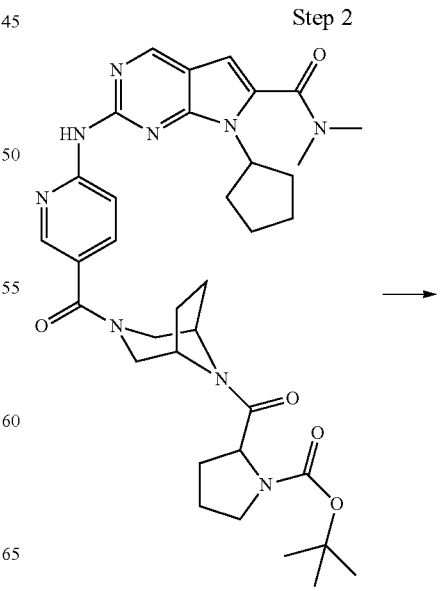

161

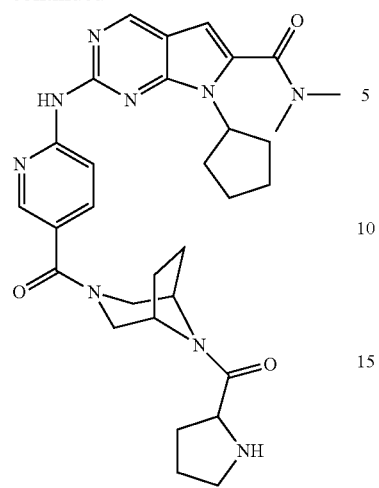

7-Cyclopentyl-2-{5-[8-(pyrrolidine-2-carbonyl)-3,8-diaza-bicyclo[3.2.1]octane-3-carbonyl]-pyridin-2-ylamino}-7H-pyrrolo[2,3-d]pyrimidine-6-carboxylic acid dimethylamide Following deprotection method 2, 2-{3-[6-(7-Cyclopentyl-6-dimethylcarbamoyl-7H-pyrrolo[2,3-d]pyrimidin-2-ylamino)-pyridine-3-carbonyl]-3,8-diaza-bicyclo[3.2.1]octane-8-carbonyl}-pyrrolidine-1-carboxylic acid tert-butyl ester was converted to 7-cyclopentyl-2-{5-[8-(pyrrolidine-2-carbonyl)-3,8-diaza-bicyclo[3.2.1]octane-3-carbonyl]-pyridin-2-ylamino}-7H-pyrrolo[2,3-d]pyrimidine-6-carboxylic acid dimethylamide (36 mg) in 65% yield. 1H NMR (400 MHz, CHLOROFORM-d) δ ppm 1.67-1.84 (m, 3H) 1.90 (dd, J=13.14, 6.57 Hz, 3H) 1.99-2.28 (m, 10H) 2.45-2.69 (m, 3H) 3.19 (s, 6H) 3.38-3.67 (m, 3H) 4.31 (br. s., 1H) 4.71 (br. s., 1H) 4.76-4.89 (m, 2H) 4.92 (dd, J=8.84, 6.82 Hz, 1H) 6.51 (s, 1H) 7.87 (dd, J=8.84, 2.27 Hz, 1H) 8.63 (t, J=8.59 Hz, 1H) 8.86 (s, 1H)

HRMS m/z. (M+H)+: 586.3278.

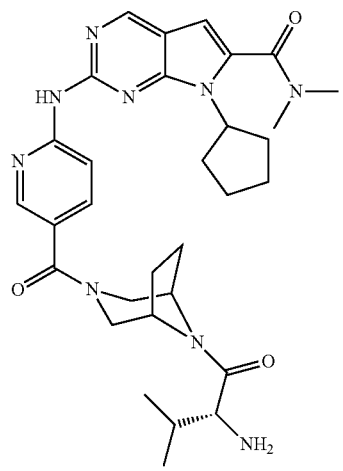 [SMILES: CC(C)[C@@H](N)C(=O)N1C2CCC1CN(C(=O)c1ccc(Nc3ncc4cc(C(=O)N(C)C)n(C5CCCC5)c4n3)nc1)C2]

162

Example 62

2-{5-[8-((R)-2-Amino-3-methyl-butyryl)-3,8-diaza-bicyclo[3.2.1]octane-3-carbonyl]-pyridin-2-ylamino}-7-cyclopentyl-7H-pyrrolo[2,3-d]pyrimidine-6-carboxylic acid dimethylamide Step 1

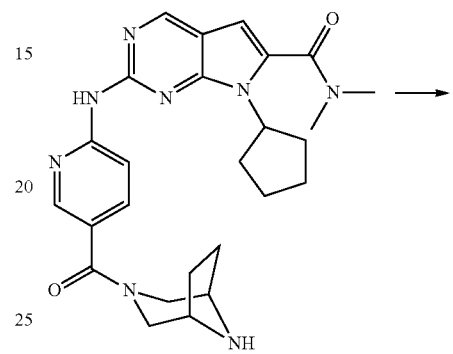

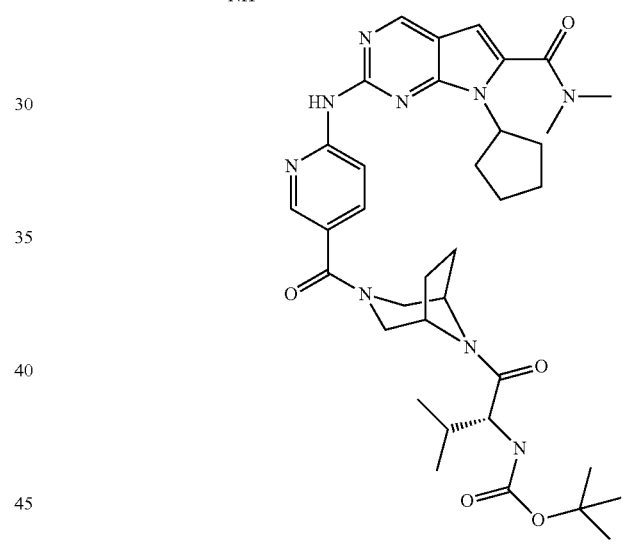

Preparation of ((R)-1-{3-[6-(7-Cyclopentyl-6-dimethylcarbamoyl-7H-pyrrolo[2,3-d]pyrimidin-2-ylamino)-pyridine-3-carbonyl]-3,8-diaza-bicyclo[3.2.1]octane-8-carbonyl}-2-methyl-propyl)-carbamic acid tert-butyl ester Following general amide formation method 1, 7-cyclopentyl-2-[5-(3,8-diaza-bicyclo[3.2.1]octane-3-carbonyl)-pyridin-2-ylamino]-7H-pyrrolo[2,3-d]pyrimidine-6-carboxylic acid dimethylamide (60 mg, 0.123 mmol, 1.0 eq) was combined with BOC-D-Valine (26.7 mg, 0.123 mmol, 1.0 eq) which gave ((R)-1-{3-[6-(7-Cyclopentyl-6-dimethylcarbamoyl-7H-pyrrolo[2,3-d]pyrimidin-2-ylamino)-pyridine-3-carbonyl]-3,8-diaza-bicyclo[3.2.1]octane-8-carbonyl}-2-methyl-propyl)-carbamic acid tert-butyl ester (82 mg) in 92% yield. HRMS m/z, (M+H)+: 688.3961.

163

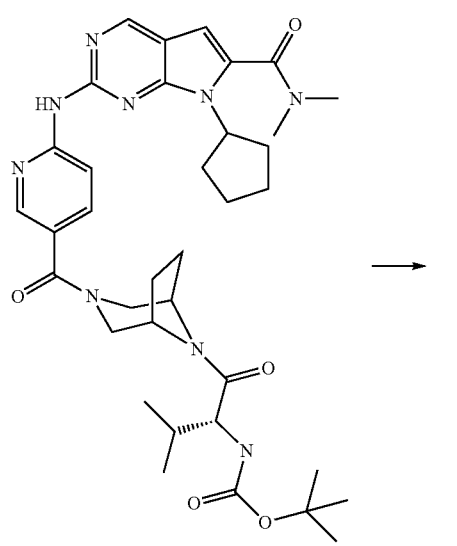

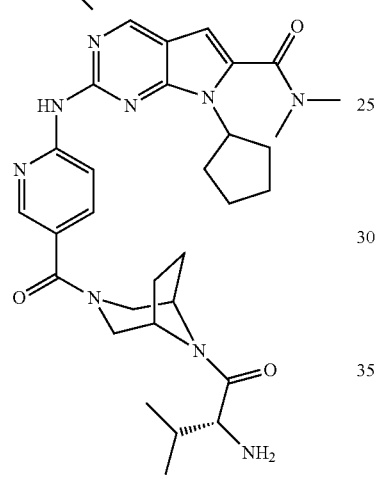

Step 2

Preparation of 2-{5-[8-((R)-2-Amino-3-methyl-butyryl)-3,8-diaza-bicyclo[3.2.1]octane-3-carbonyl]-pyridin-2-ylamino}-7-cyclo pentyl-7H-pyrrolo[2,3-d]pyrimidine-6-carboxylic acid dimethylamide Following deprotection method 2, ((R)-1-{3-[6-(7-Cyclopentyl-6-dimethylcarbamoyl-7H-pyrrolo[2,3-d]pyrimidin-2-ylamino)-pyridine-3-carbonyl]-3,8-diaza-bicyclo[3.2.1]octane-8-carbonyl}-2-methyl-propyl)-carbamic acid tert-butyl ester was converted to 2-{5-[8-((R)-2-amino-3-methyl-butyryl)-3,8-diaza-bicyclo[3.2.1]octane-3-carbonyl]-pyridin-2-ylamino}-7-cyclopentyl-7H-pyrrolo[2,3-d]pyrimidine-6-carboxylic acid dimethylamide (20 mg) in 28% yield. 1H NMR (400 MHz, CHLOROFORM-d) δ ppm 1.05 (d, J=6.06 Hz, 6H) 1.13 (br. s., 1H) 1.81 (d, J=6.06 Hz, 4H) 1.99 (br. s., 4H) 2.13 (br. s., 6H) 2.65 (br. s., 3H) 2.87 (s, 8H) 3.23 (s, 7H) 3.68 (br. s., 1H) 4.39 (br. s., 1H) 4.76 (br. s., 1H) 4.81-5.07 (m, 2H) 6.55 (s, 1H) 7.87 (br. s., 1H) 8.47 (br. s., 1H) 8.67 (d, J=8.08 Hz, 1H) 8.92 (br. s., 1H). HRMS m/z, (M+H)+: 588.3424.

164

Example 63

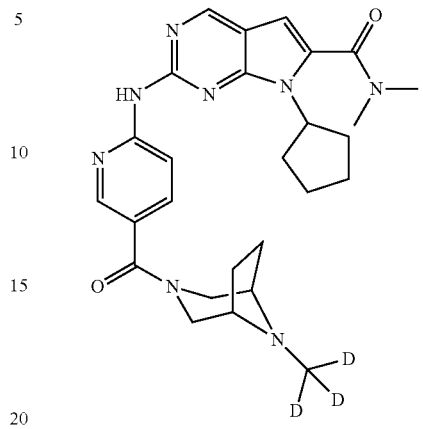

7-Cyclopentyl-2-[5-(8-methyl-d₃-3,8-diaza-bicyclo[3.2.1]octane-3-carbonyl)-pyridin-2-ylamino]-7H-pyrrolo[2,3-d]pyrimidine-6-carboxylic acid dimethylamide

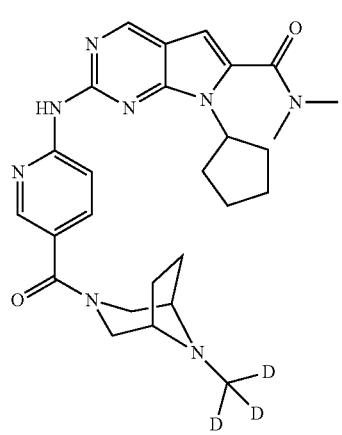 [SMILES: [2H]C([2H])([2H])N1C2CCC1CN(C(=O)c1ccc(Nc3ncc4cc(C(=O)N(C)C)n(C5CCCC5)c4n3)nc1)C2]

Preparation of 7-Cyclopentyl-2-[5-(8-methyl-d₃-3,8-diaza-bicyclo[3.2.1]octane-3-carbonyl)-pyridin-2-ylamino]-7H-pyrrolo[2,3-d]pyrimidine-6-carboxylic acid dimethylamide To a mixture of 7-Cyclopentyl-2-[5-(3,8-diaza-bicyclo[3.2.1]octane-3-carbonyl)-pyridin-2-ylamino]-7H-pyrrolo

[2,3-d]pyrimidine-6-carboxylic acid dimethylamide (111 mg, 0.227 mmol, 1.0 eq), Potassium Carbonate (37.7 mg, 0.273 mmol, 1.2 eq) in Acetonitrile (1 mL) was added Iodomethane-$d_3$ (0.021 mL, 0.341 mmol, 1.5 eq) and the mixture stirred at 23° C. for 5 hours. The reaction mixture was diluted with Ethyl Acetate and water and the organics collected and dried ($Na_2SO_4$), filtered, and concentrated. The residue was purified using chromatography (Ethyl Acetate/Heptane) which gave desired product (15 mg) in 12% yield. 1H NMR (400 MHz, CHLOROFORM-d δ ppm 1.61-1.83 (m, 3H) 2.02-2.18 (m, 7H) 2.46-2.68 (m, 2H) 3.18 (s, 7H) 3.35 (br. s., 1H) 3.42 (br. s., 2H) 3.60 (d, J=7.58 Hz, 1H) 3.71 (br. s., 1H) 3.79 (br. s., 1H) 4.57 (br. s., 1H) 4.83 (quin, J=8.84 Hz, 1H) 6.51 (s, 1H) 7.83 (dd, J=8.84, 2.27 Hz, 1H) 8.50 (d, J=2.02 Hz, 1H) 8.60 (d, J=9.09 Hz, 1H) 8.85 (s, 2H). HRMS m/z, (M+H)$^+$: 506.3029.

Example 64

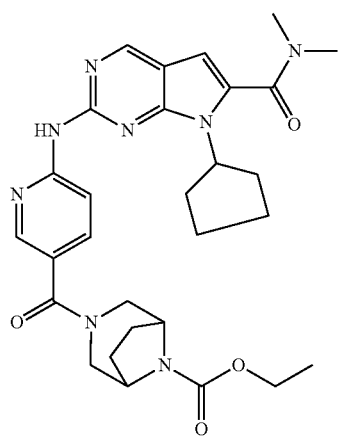 [SMILES: CCOC(=O)N1C2CCC1CN(C(=O)c1ccc(Nc3ncc4cc(C(=O)N(C)C)n(C5CCCC5)c4n3)nc1)C2]

3-[6-(7-Cyclopentyl-6-dimethylcarbamoyl-7H-pyrrolo[2,3-d]pyrimidin-2-ylamino)-pyridine-3-carbonyl]-3,8-diaza-bicyclo[3.2.1]octane-8-carboxylic acid ethyl ester

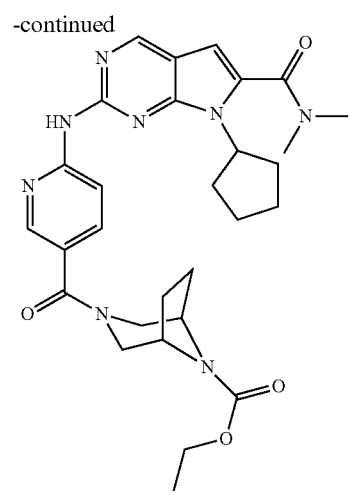

Preparation of 3-[6-(7-Cyclopentyl-6-dimethylcarbamoyl-7H-pyrrolo[2,3-d]pyrimidin-2-ylamino)-pyridine-3-carbonyl]-3,8-diaza-bicyclo[3.2.1]octane-8-carboxylic acid ethyl ester To a solution of 7-cyclopentyl-2-[5-(3,8-diaza-bicyclo[3.2.1]octane-3-carbonyl)-pyridin-2-ylamino]-7H-pyrrolo[2,3-d]pyrimidine-6-carboxylic acid dimethylamide (100 mg, 0.205 mmol, 1.0 eq) and Diisopropylethylamine (0.071 mL, 0.409 mmol, 2.0 eq) in $CH_2Cl_2$ (5 mL) was added Ethyl Chloroformate (0.022 mL, 0.225 mmol, 1.1 eq) diluted in 3.0 mL of $CH_2Cl_2$. The reaction mixture was stirred at 23° C. for 1 hour then diluted with water. The organic was collected and dried over $Na_2SO_4$, filtered, and concentrated. The crude reaction was purified using silica gel chromatography which gave 3-[6-(7-Cyclopentyl-6-dimethylcarbamoyl-7H-pyrrolo[2,3-d]pyrimidin-2-ylamino)-pyridine-3-carbonyl]-3,8-diaza-bicyclo[3.2.1]octane-8-carboxylic acid ethyl ester (25 mg) in 21% yield. 1H NMR (400 MHz, CHLOROFORM-d) δ ppm 1.22-1.37 (m, 4H) 1.60 (br. s., 2H) 1.69-1.82 (m, 3H) 1.97 (br. s., 3H) 2.04-2.20 (m, 4H) 2.56 (d, J=8.59 Hz, 2H) 3.19 (s, 6H) 3.60 (br. s., 2H) 4.21 (q, J=7.07 Hz, 2H) 4.36 (br. s., 2H) 4.56 (br. s., 1H) 4.83 (t, J=8.59 Hz, 1H) 6.52 (s, 1H) 7.82 (dd, J=8.59, 2.02 Hz, 1H) 8.39 (d, J=2.02 Hz, 1H) 8.59 (d, J=8.59 Hz, 1H) 8.77 (s, 1H). HRMS m/z, (M+H)$^+$: 561.2946.

Example 65

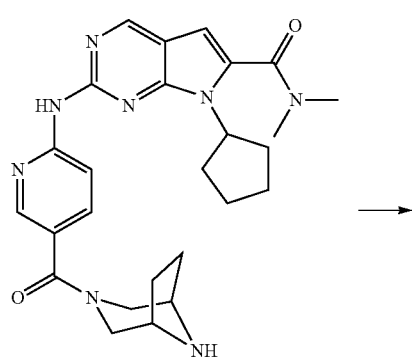

→

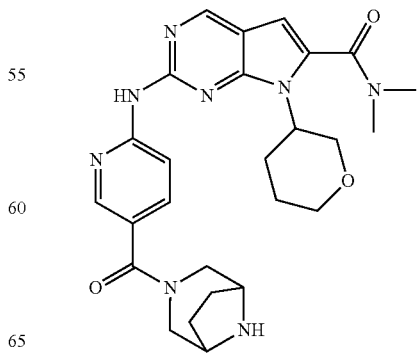

167

2-(5-(3,8-diazabicyclo[3.2.1]octane-3-carbonyl)pyridin-2-ylamino)-N,N-dimethyl-7-(tetrahydro-2H-pyran-3-yl)-7H-pyrrolo[2,3-d]pyrimidine-6-carboxamide Step 1

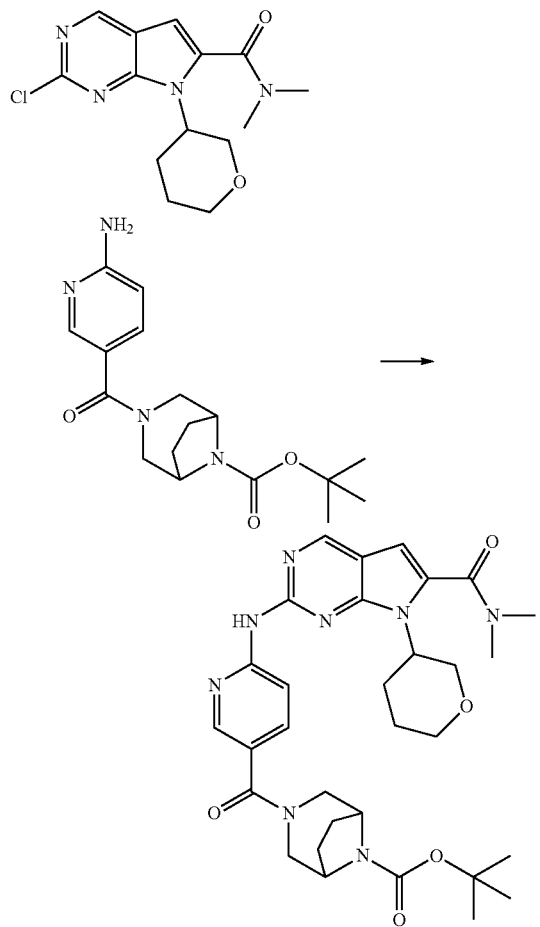

Preparation of tert-Butyl 3-(6-(6-(dimethylcarbamoyl)-7-(tetrahydro-2H-pyran-3-yl)-7H-pyrrolo[2,3-d]pyrimidin-2-ylamino)nicotinoyl)-3,8-diazabicyclo[3.2.1]octane-8-carboxylate Following general N—C coupling procedure 1, 2-chloro-N,N-dimethyl-7-(tetrahydro-2H-pyran-3-yl)-7H-pyrrolo[2,3-d]pyrimidine-6-carboxamide (80 mg, 0.26 mmole) was combined with tert-butyl 3-(6-aminonicotinoyl)-3,8-diazabicyclo[3.2.1]octane-8-carboxylate (82 mg, 0.26 mmole) which gave tert-butyl 3-(6-(6-(dimethylcarbamoyl)-7-(tetrahydro-2H-pyran-3-yl)-7H-pyrrolo[2,3-d]pyrimidin-2-ylamino)nicotinoyl)-3,8-diazabicyclo[3.2.1]octane-8-carboxylate (40 mg) in 25% yield. 1H NMR (400 MHz, CD$_2$Cl$_2$) δ 8.84 (s, 1H), 8.72-8.65 (m, 1H), 8.42 (m, 1H), 7.89-7.82 (m, 1H), 6.56 (s, 1H), 4.63-4.52 (m, 1H), 4.52-4.41 (m, 1H), 4.26 (br, 2H), 4.08-3.96 (m, 2H), 3.70-3.49 (m, 3H), 3.16 (S, 6H), 3.23-3.02 (m, 1H), 3.03-2.88 (m, 1H), 2.18-2.07 (m, 1H), 2.02-1.57 (m, 7H), 1.51 (s, 9H). HR-MS m/z 605.3201 (M+H)$^+$

168

Step 2

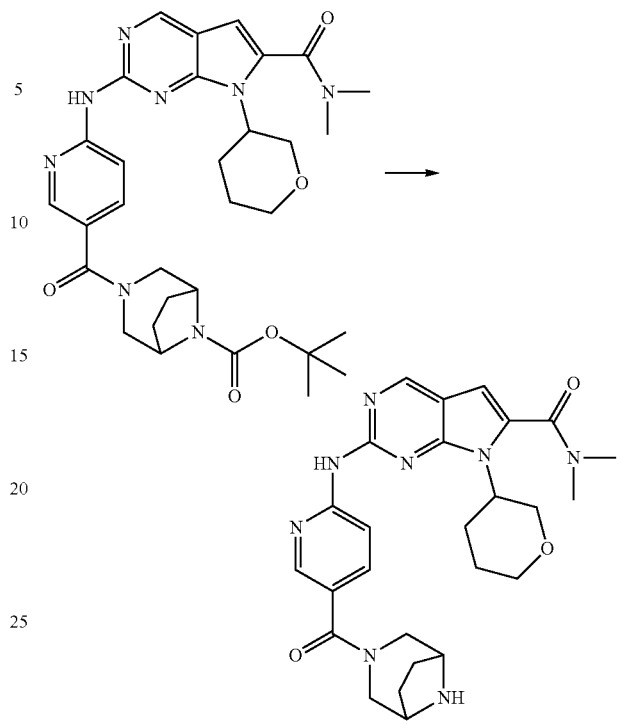

Preparation of 2-(5-(3,8-diazabicyclo[3.2.1]octane-3-carbonyl)pyridin-2-ylamino)-N,N-dimethyl-7-(tetrahydro-2H-pyran-3-yl)-7H-pyrrolo[2,3-d]pyrimidine-6-carboxamide Following deprotection method 1, tert-Butyl 3-(6-(6-(dimethylcarbamoyl)-7-(tetrahydro-2H-pyran-3-yl)-7H-pyrrolo[2,3-d]pyrimidin-2-ylamino)nicotinoyl)-3,8-diazabicyclo[3.2.1]octane-8-carboxylate (35 mg, 0.058 mmole) was converted to 2-(5-(3,8-diazabicyclo[3.2.1]octane-3-carbonyl)pyridin-2-ylamino)-N,N-dimethyl-7-(tetrahydro-2H-pyran-3-yl)-7H-pyrrolo[2,3-d]pyrimidine-6-carboxamide as a free base form (11 mg) in 37% yield. 1H NMR (400 MHz, CD$_3$OD) δ 8.80 (s, 1H), 8.60-8.55 (m, 1H), 8.48-8.35 (m, 1H), 7.99-7.85 (m, 1H), 6.93-6.71 (m, 1H), 4.59-4.35 (m, 2H), 4.04-3.95 (m, 2H), 3.63-3.50 (m, 3H), 3.50-3.39 (m, 2H), 3.20 (s, 3H), 3.17 (s, 3H), 2.97-2.77 (m, 2H), 2.15-1.96 (m, 2H), 1.93-1.74 (m, 5H), 1.70-1.56 (m, 1H); HR-MS m/z 505.2657 (M+H)$^+$ Example 66

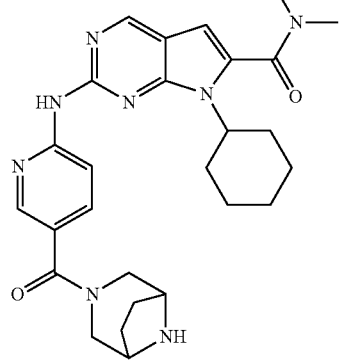

7-Cyclohexyl-2-[5-(3,8-diaza-bicyclo[3.2.1]octane-3-carbonyl)-pyridin-2-ylamino]-7H-pyrrolo[2,3-d]pyrimidine-6-carboxylic acid dimethylamide Step 1

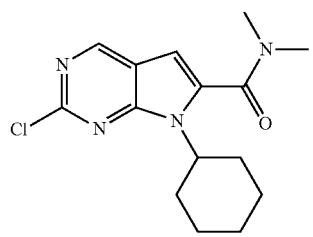

Preparation of 2-chloro-7-cyclohexyl-7H-pyrrolo[2,3-d]pyrimidine-6-carboxylic acid dimethylamide Following General Procedure A, 2-chloro-7-cyclohexyl-7H-pyrrolo[2,3-d]pyrimidine-6-carboxylic acid dimethylamide was synthesized (2.4 gm, 17% Overall Yield)

MS m/z 307.5 (M+H)$^+$.

Step 2

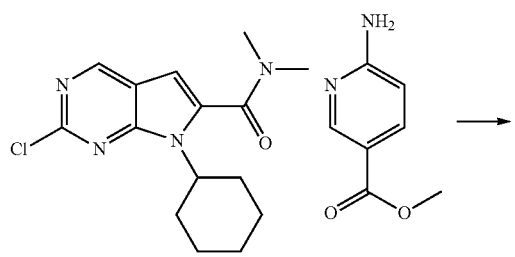

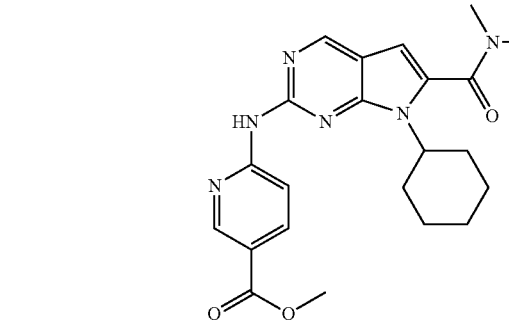

Preparation of 6-(7-Cyclohexyl-6-dimethylcarbamoyl-7H-pyrrolo[2,3-d]pyrimidin-2-ylamino)-nicotinic acid methyl ester Following general N—C coupling procedure 1, 2-chloro-7-cyclohexyl-7H-pyrrolo[2,3-d]pyrimidine-6-carboxylic acid dimethylamide (800 mg, 2.61 mmol), was combined with 6-amino-nicotinic acid methyl ester (397 mg, 2.61 mmol) which gave 6-(7-cyclohexyl-6-dimethylcarbamoyl-7H-pyrrolo[2,3-d]pyrimidin-2-ylamino)-nicotinic acid methyl ester (720 mg, 1.70 mmol) in 65% yield. MS m/z 423.6 (M+H)$^+$.

Step 3

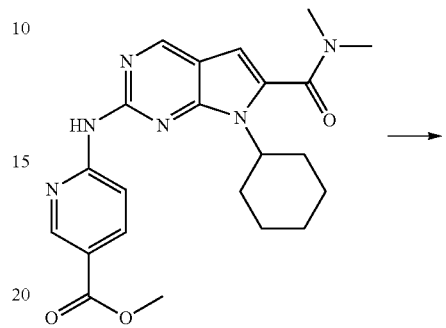

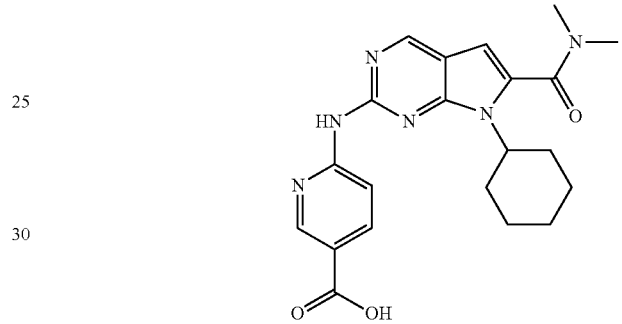

Preparation of 6-(7-Cyclohexyl-6-dimethylcarbamoyl-7H-pyrrolo[2,3-d]pyrimidin-2-ylamino)-nicotinic acid. To a 25 mL solution of THF, water and MeOH (2:2:1) containing 6-(7-cyclohexyl-6-dimethylcarbamoyl-7H-pyrrolo[2,3-d]pyrimidin-2-ylamino)-nicotinic acid methyl ester (860 mg, 2.04 mmol) was added solid LiOH (244 mg, 10.2 mmol). After stirring at 50° C. for 90 m, reaction was acidified to pH 6 with 1M HCl and then partitioned into two phases with a mixture of water, isopropyl alcohol and chloroform. The organic layer was removed and concentrated to yield 6-(7-cyclohexyl-6-dimethylcarbamoyl-7H-pyrrolo[2,3-d]pyrimidin-2-ylamino)-nicotinic acid (805 mg, 1.97 mmol) in 97% yield. MS m/z 409.6 (M+H)$^+$ Step 4

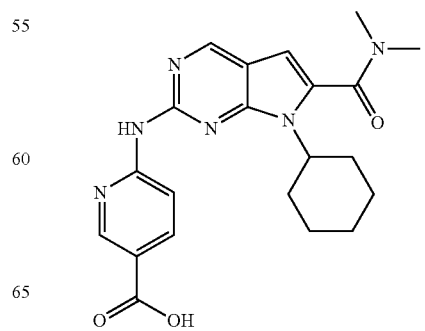

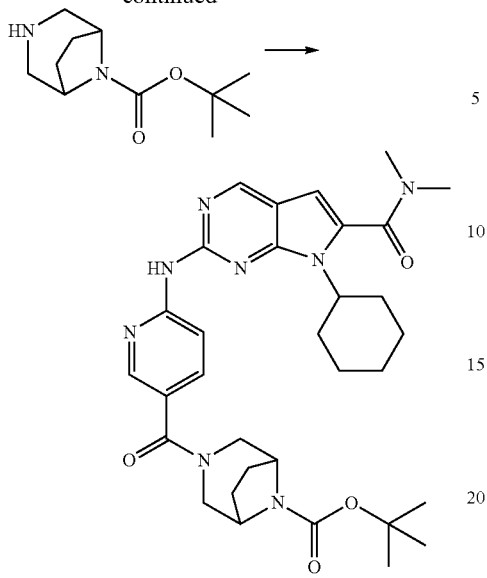

Preparation of 3-[6-(7-Cyclohexyl-6-dimethylcarbamoyl-7H-pyrrolo[2,3-d]pyrimidin-2-ylamino)-pyridine-3-carbonyl]-3,8-diaza-bicyclo[3.2.1]octane-8-carboxylic acid tert-butyl ester To a 1 mL DMF solution of 6-(7-cyclohexyl-6-dimethylcarbamoyl-7H-pyrrolo[2,3-d]pyrimidin-2-ylamino)-nicotinic acid (50 mg, 0.122 mmol) was added DIPEA (32 mg, 0.043 mmol) and HBTU (49 mg, 0.129 mmol). After stirring for 15 m at room temperature 3,8-diaza-bicyclo[3.2.1]octane-8-carboxylic acid tert-butyl ester (31.2 mg, 0.147 mmol) was added and the reaction mixture was left to stir at room temperature for 4 h. The reaction was quenched by pouring into brine and extracted with EtOAc. The organic extracts were dried with $Na_2SO_4$, filtered and concentrated. The crude product was purified by NP-LC (Analogix, 10% MeOH in EtOAc) to yield 3-[6-(7-cyclohexyl-6-dimethylcarbamoyl-7H-pyrrolo[2,3-d]pyrimidin-2-ylamino)-pyridine-3-carbonyl]-3,8-diaza-bicyclo[3.2.1]octane-8-carboxylic acid tert-butyl ester (60 mg, 0.10 mmol). MS m/z 603.5 (M+H)$^+$.

Step 5

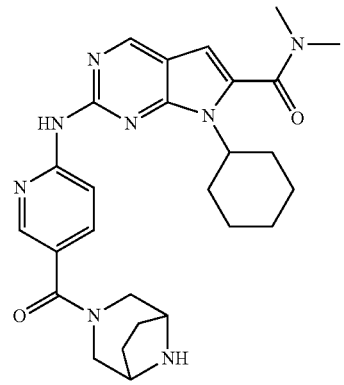 [SMILES: CN(C)C(=O)c1cc2cnc(Nc3ccc(C(=O)N4CC5CCC(C4)N5)cn3)nc2n1C1CCCCC1]

Preparation of 7-Cyclohexyl-2-[5-(3,8-diaza-bicyclo[3.2.1]octane-3-carbonyl)-pyridin-2-ylamino]-7H-pyrrolo[2,3-d]pyrimidine-6-carboxylic acid dimethylamide Following deprotection method 2, 3-[6-(7-Cyclohexyl-6-dimethylcarbamoyl-7H-pyrrolo[2,3-d]pyrimidin-2-ylamino)-pyridine-3-carbonyl]-3,8-diaza-bicyclo[3.2.1]octane-8-carboxylic acid tert-butyl ester (105 mg, 0.174 mmol) was converted to 7-cyclohexyl-2-[5-(3,8-diaza-bicyclo[3.2.1]octane-3-carbonyl)-pyridin-2-ylamino]-7H-pyrrolo[2,3-d]pyrimidine-6-carboxylic acid dimethylamide (78 mg, 0.155 mmol) in 89% yield. 1H NMR (400 MHz, DMSO-$d_6$) δ ppm 10.10 (s, 1H), 8.85 (s, 1H), 8.47 (d, J=9.03 Hz, 1H), 8.33 (d, J=2.01 Hz, 1H), 7.80 (dd, J=8.78, 2.26 Hz, 1H), 6.66 (s, 1H), 4.28 (m, 1H), 3.36 (br. s., 10H), 3.07 (d, J=14.56 Hz, 6H), 2.56 (m, 1H), 1.85 (m, 3H), 1.74 (d, J=9.54 Hz, 1H), 1.65 (br. s., 4H), 1.33 (m, 2H). MS m/z 503.5 (M+H)$^+$.

Example 67

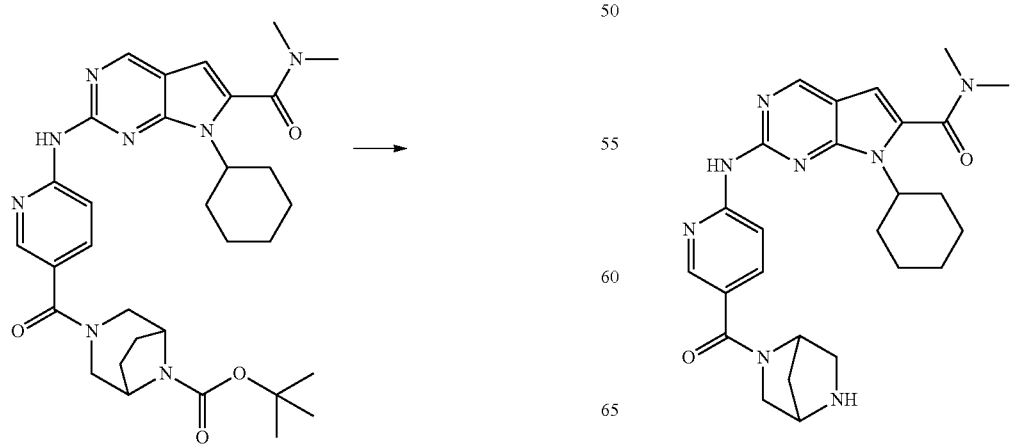

173

7-Cyclohexyl-2-[5-(2,5-diaza-bicyclo[2.2.1]heptane-2-carbonyl)-pyridin-2-ylamino]-7H-pyrrolo[2,3-d]pyrimidine-6-carboxylic acid dimethylamide Step 1

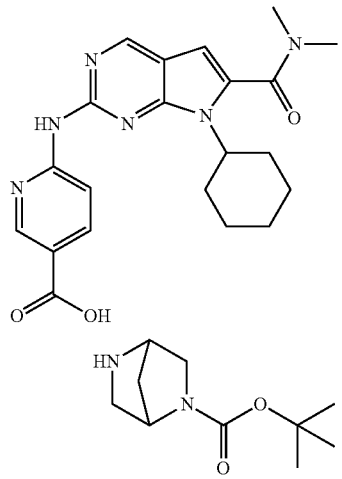

174

Step 2

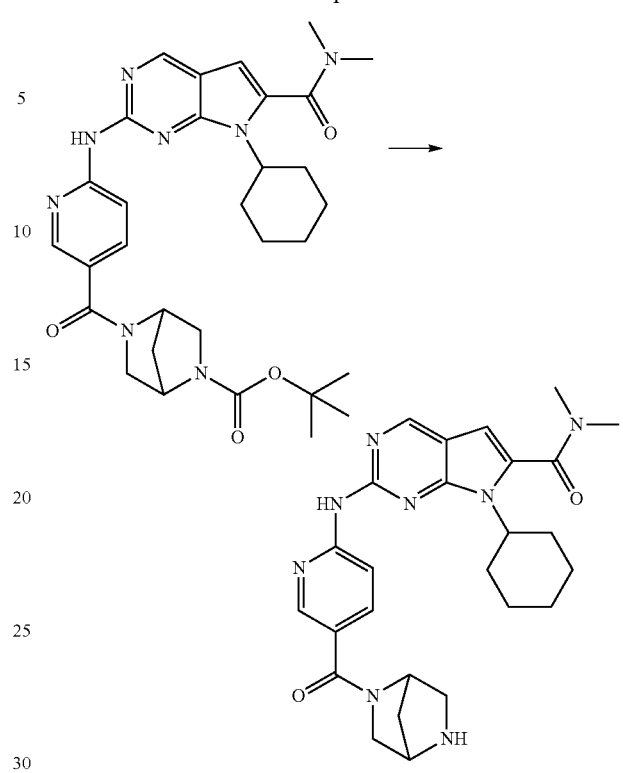

Preparation of 7-Cyclohexyl-2-[5-(2,5-diaza-bicyclo[2.2.1]heptane-2-carbonyl)-pyridin-2-ylamino]-7H-pyrrolo[2,3-d]pyrimidine-6-carboxylic acid dimethylamide Following deprotection method 2, 5-[2-(7-cyclohexyl-6-dimethylcarbamoyl-7H-pyrrolo[2,3-d]pyrimidin-2-ylamino)-pyrimidine-5-carbonyl]-2,5-diaza-bicyclo[2.2.1]heptane-2-carboxylic acid tert-butyl ester (110 mg, 0.187 mmol) was converted to 7-cyclohexyl-2-[5-(2,5-diaza-bicyclo[2.2.1]heptane-2-carbonyl)-pyridin-2-ylamino]-7H-pyrrolo[2,3-d]pyrimidine-6-carboxylic acid dimethylamide (78 mg, 0.160 mmol) in 86% yield. 1H NMR (400 MHz, DMSO-$d_6$) δ ppm 10.10 (s, 1H), 8.85 (s, 1H), 8.47 (d, J=9.03 Hz, 1H), 8.33 (d, J=2.01 Hz, 1H), 7.80 (dd, J=8.78, 2.26 Hz, 1H), 6.76 (m, 0H), 6.66 (s, 1H), 4.27 (m, 2H), 3.36 (br. s., 8H), 3.07 (d, J=14.56 Hz, 7H), 1.85 (m, 5H), 1.71 (m, 6H), 1.33 (m, 4H). MS m/z 489.5 (M+H)$^+$.

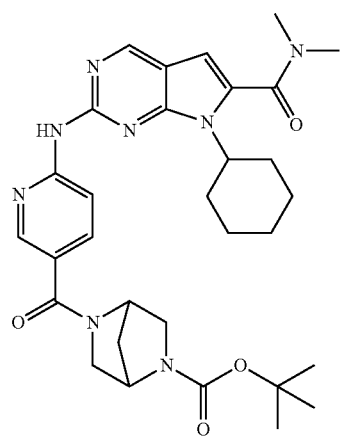

Preparation of 5-[2-(7-Cyclohexyl-6-dimethylcarbamoyl-7H-pyrrolo[2,3-d]pyrimidin-2-ylamino)-pyrimidine-5-carbonyl]-2,5-diaza-bicyclo[2.2.1]heptane-2-carboxylic acid tert-butyl ester Following general amide formation method 1, 6-(7-cyclohexyl-6-dimethylcarbamoyl-7H-pyrrolo[2,3-d]pyrimidin-2-ylamino)-nicotinic acid (50 mg, 0.122 mmol) was combined with 2,5-diaza-bicyclo[2.2.1]heptane-2-carboxylic acid tert-butyl ester (29.1 mg, 0.147 mmol) which gave 5-[2-(7-cyclohexyl-6-dimethylcarbamoyl-7H-pyrrolo[2,3-d]pyrimidin-2-ylamino)-pyrimidine-5-carbonyl]-2,5-diaza-bicyclo[2.2.1]heptane-2-carboxylic acid tert-butyl ester (60 mg, 0.102 mmol) in 84% yield. MS m/z 589.5 (M+H)$^+$.

Example 68

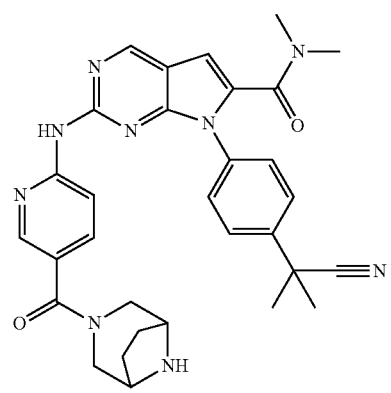 [SMILES: CN(C)C(=O)c1cc2cnc(Nc3ccc(C(=O)N4CC5CCC(C4)N5)cn3)nc2n1-c1ccc(C(C)(C)C#N)cc1]

7-[4-(Cyano-dimethyl-methyl)-phenyl]-2-[5-(3,8-diaza-bicyclo[3.2.1]octane-8-carbonyl)-pyridin-2-ylamino]-7H-pyrrolo[2,3-d]pyrimidine-6-carboxylic acid dimethylamide

Step 1

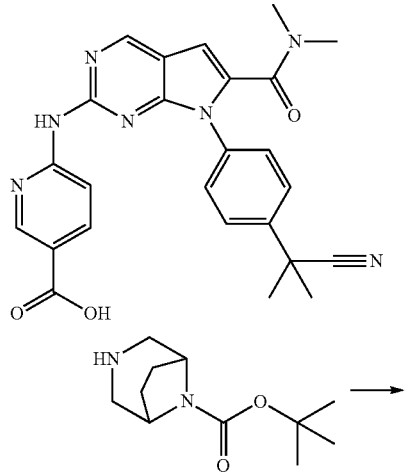

Step 2

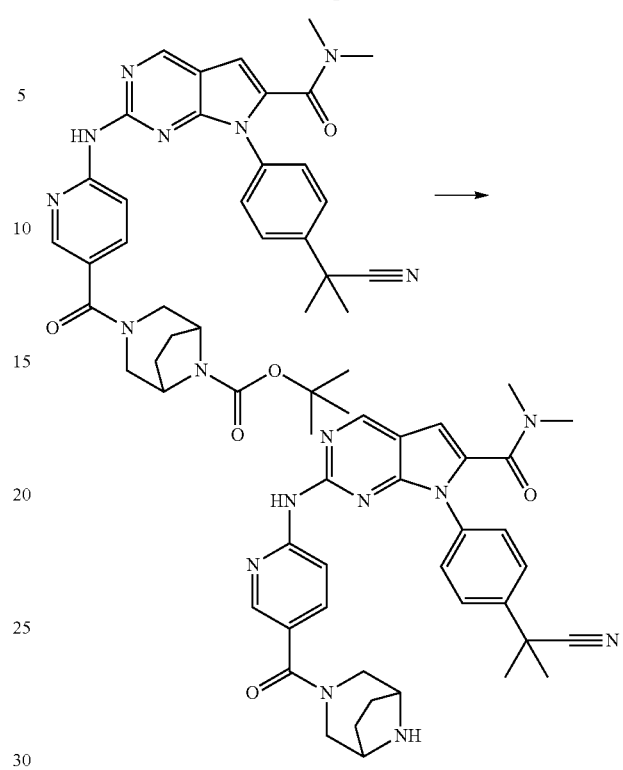

Preparation of 3-(6-{7-[4-(Cyano-dimethyl-methyl)-phenyl]-6-dimethylcarbamoyl-7H-pyrrolo[2,3-d]pyrimidin-2-ylamino}-pyridine-3-carbonyl)-3,8-diaza-bicyclo[3.2.1]octane-8-carboxylic acid tert-butyl ester

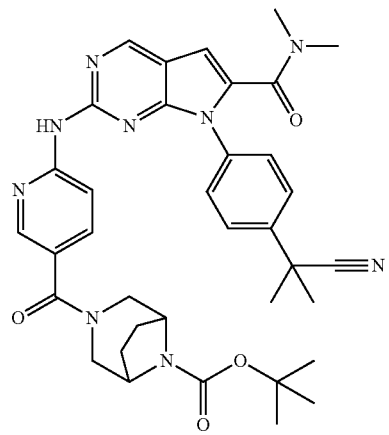

Following general N—C coupling procedure 1, 2-chloro-7-[4-(cyano-dimethyl-methyl)-phenyl-7H-pyrrolo[2,3-d]pyrimidine-6-carboxylic acid dimethylamide (70 mg, 0.190 mmol) was combined with 3-(6-amino-pyridine-3-carbonyl)-3,8-diazabicyclo[3.2.1]octane-8-carboxylic acid tert-butyl ester (63.3 mg, 0.190 mmol) which gave 3-(6-{7-[4-(cyano-dimethyl-methyl)-phenyl]-6-dimethylcarbamoyl-7H-pyrrolo[2,3-d]pyrimidin-2-ylamino}-pyridine-3-carbonyl)-3,8-diaza-bicyclo[3.2.1]octane-8-carboxylic acid tert-butyl ester (63 mg, 0.095 mmol) in 50% yield. MS m/z 664.2 (M+H)$^+$.

Preparation of 7-[4-(Cyano-dimethyl-methyl)-phenyl]-2-[5-(3,8-diaza-bicyclo[3.2.1]octane-8-carbonyl)-pyridin-2-ylamino]-7H-pyrrolo[2,3-d]pyrimidine-6-carboxylic acid dimethylamide Following deprotection method 2, 3-(6-{7-[4-(cyano-dimethyl-methyl)-phenyl]-6-dimethylcarbamoyl-7H-pyrrolo[2,3-d]pyrimidin-2-ylamino}-pyridine-3-carbonyl)-3,8-diaza-bicyclo[3.2.1]octane-8-carboxylic acid tert-butyl ester (63 mg, 0.095 mmol) was converted to 7-[4-(cyano-dimethyl-methyl)-phenyl]-2-[5-(3,8-diaza-bicyclo[3.2.1]octane-8-carbonyl)-pyridin-2-ylamino]-7H-pyrrolo[2,3-d]pyrimidine-6-carboxylic acid dimethylamide. (48 mg, 0.085 mmol) in 89% yield. 1H NMR (400 MHz, DMSO-d$_6$) δ ppm 10.08 (s, 1H), 8.97 (s, 1H), 8.28 (m, 2H), 7.73 (d, J=8.59 Hz, 2H), 7.68 (dd, J=8.59, 2.53 Hz, 1H), 7.56 (d, J=8.59 Hz, 2H), 6.97 (s, 1H), 3.41 (m, 4H), 3.01 (m, 8H), 1.77 (m, 5H), 1.63 (d, J=4.04 Hz, 4H), 1.26 (m, 1H), 0.86 (s, 1H). MS m/z 564.5 (M+H)$^+$.

Example 69

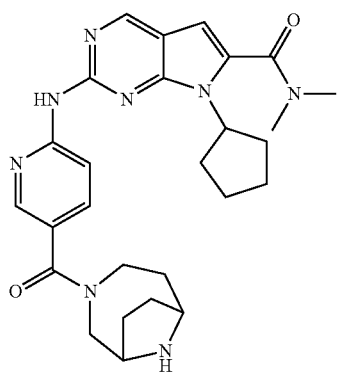 [SMILES: CN(C)C(=O)c1cc2cnc(Nc3ccc(C(=O)N4CCC5CCC(C4)N5)cn3)nc2n1C1CCCC1]

7-Cyclopentyl-2-[5-(3,9-diaza-bicyclo[4.2.1]nonane-3-carbonyl)-pyridin-2-ylamino]-7H-pyrrolo[2,3-d]pyrimidine-6-carboxylic acid dimethylamide Step 1

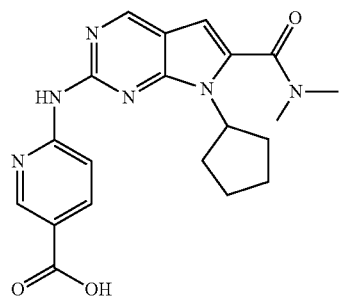

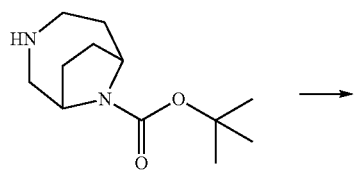

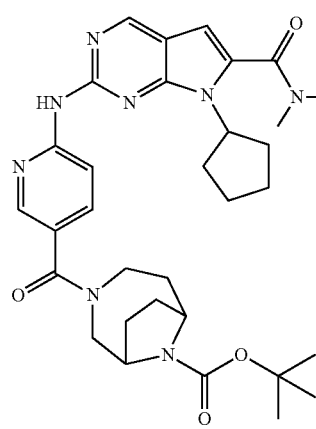

Preparation of 3-[6-(7-Cyclopentyl-6-dimethylcarbamoyl-7H-pyrrolo[2,3-d]pyrimidin-2-ylamino)-pyridine-3-carbonyl]-3,9-diaza-bicyclo[4.2.1]nonane-9-carboxylic acid tert-butyl ester Following general amide formation method 3, 6-(7-cyclopentyl-6-(dimethylcarbamoyl)-7H-pyrrolo[2,3-d]pyrimidin-2-ylamino)nicotinic acid (0.2 g, 0.507 mmol) was combined with 3,9-diaza-bicyclo[4.2.1]nonane-9-carboxylic acid tert-butyl ester (0.136 g, 0.6 mmol) which gave 3-[6-(7-Cyclopentyl-6-dimethylcarbamoyl-7H-pyrrolo[2,3-d]pyrimidin-2-ylamino)-pyridine-3-carbonyl]-3,9-diaza-bicyclo[4.2.1]nonane-9-carboxylic acid tert-butyl ester (0.269 g, 0.433 mmol) in 85% yield. MS m/z 602.7 (M+H)⁺.

Step 2

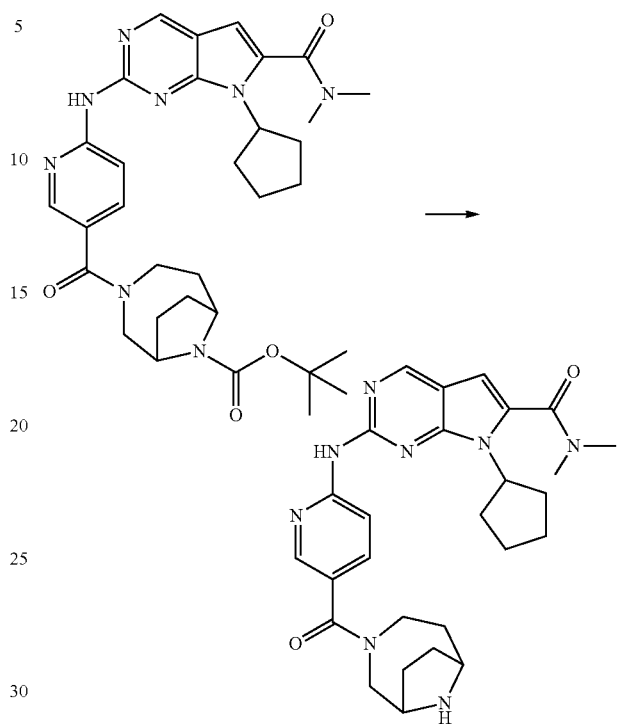

Preparation of 7-Cyclopentyl-2-[5-(3,9-diaza-bicyclo[4.2.1]nonane-3-carbonyl)-pyridin-2-ylamino]-7H-pyrrolo[2,3-d]pyrimidine-6-carboxylic acid dimethylamide Following deprotection method 1, 3-[6-(7-Cyclopentyl-6-dimethylcarbamoyl-7H-pyrrolo[2,3-d]pyrimidin-2-ylamino)-pyridine-3-carbonyl]-3,9-diaza-bicyclo[4.2.1]nonane-9-carboxylic acid tert-butyl ester (0.24 g, 0.398 mmol) was converted to 7-Cyclopentyl-2-[5-(3,9-diaza-bicyclo[4.2.1]nonane-3-carbonyl)-pyridin-2-ylamino]-7H-pyrrolo[2,3-d]pyrimidine-6-carboxylic acid dimethylamide (203 mg, 0.363 mmol) in 91.4% yield. 1H NMR (400 MHz, DMSO-d₆) δ ppm 11.7 (s, 1H), 10.18 (s, 1H), 9.05 (s, 1H), 8.52 (s, 1H), 8.13 (d, 1H), 7.8 (d, 1H), 6.85 (s, 1H), 4.8 (m, 2H), 4.1 (m. broad, 2H), 3.7 (m. broad, 2H), 3.06 (s, 3H), 3.05 (s, 3H), 2.3 (m. broad, 2H), 2.25-1.7 (m. broad, 8H), 1.65 (m. broad, 2H). MS m/z 502.7 (M+H)⁺.

Example 70

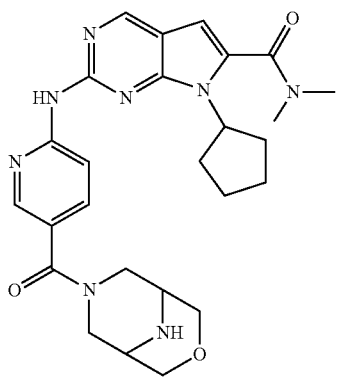 [SMILES: CN(C)C(=O)c1cc2cnc(Nc3ccc(C(=O)N4CC5COCC(C4)N5)cn3)nc2n1C1CCCC1]

7-Cyclopentyl-2-[5-(3-oxa-7,9-diaza-bicyclo[3.3.1]
nonane-7-carbonyl)-pyridin-2-ylamino]-7H-pyrrolo
[2,3-d]pyrimidine-6-carboxylic acid dimethylamide Step 1

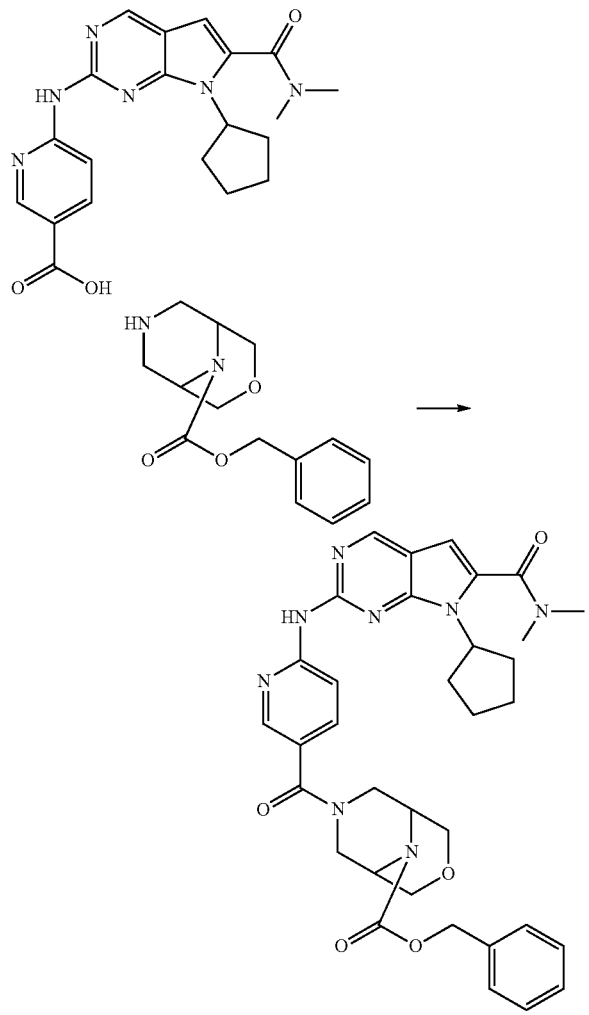

Preparation of 7-[6-(7-Cyclopentyl-6-dimethylcar-
bamoyl-7H-pyrrolo[2,3-d]pyrimidin-2-ylamino)-
pyridine-3-carbonyl]-3-oxa-7,9-diaza-bicyclo[3.3.1]
nonane-9-carboxylic acid benzyl ester Following general amide formation method 3, 6-(7-cyclo-pentyl-6-(dimethylcarbamoyl)-7H-pyrrolo[2,3-d]pyrimidin-2-ylamino)nicotinic acid (406 mg, 1.03 mmole) was combined with 3-Oxa-7,9-diaza-bicyclo[3.3.1]nonane-9-carboxylic acid benzyl ester (266 mg, 0.9 mmole) which gave 7-[6-(7-Cyclopentyl-6-dimethylcarbamoyl-7H-pyrrolo[2,3-d]pyrimidin-2-ylamino)-pyridine-3-carbonyl]-3-oxa-7,9-diaza-bicyclo[3.3.1]nonane-9-carboxylic acid benzyl ester (0.466 g, 0.723 mmol) in 80% yield. MS m/z 639.3 (M+H)+.

Step 2

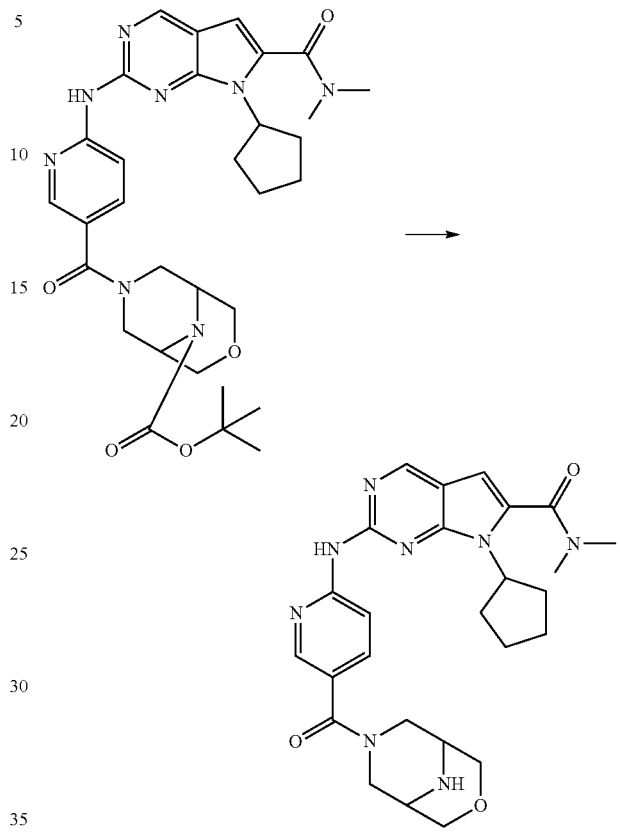

Preparation of 7-Cyclopentyl-2-[5-(3-oxa-7,9-diaza-
bicyclo[3.3.1]nonane-7-carbonyl)-pyridin-2-
ylamino]-7H-pyrrolo[2,3-d]pyrimidine-6-carboxylic
acid dimethylamide To a round bottom flask was combined 7-[6-(7-Cyclopentyl-6-dimethylcarbamoyl-7H-pyrrolo[2,3-d]pyrimidin-2-ylamino)-pyridine-3-carbonyl]-3-oxa-7,9-diaza-bicyclo[3.3.1]nonane-9-carboxylic acid benzyl ester (0.461 g, 0.722 mmol), methanol ethyl acetate (12 ml), THF (3 ml), methanol (3 ml), and Pd on C/10%. The mixture was put under a balloon of hydrogen and stirred over night. The mixture was purged with nitrogen followed by addition of methylene chloride. The resultant mixture was filtered through a pad of celite. The celite was washed with additional methylene chloride. The organics were combined and concentrated to a residue. The residue was purified by silica gel chromotography which gave 7-Cyclopentyl-2-[5-(3-oxa-7,9-diaza-bicyclo[3.3.1]nonane-7-carbonyl)-pyridin-2-ylamino]-7H-pyrrolo[2,3-d]pyrimidine-6-carboxylic acid dimethylamide (338 mg, 0.67 mmol) in 93% yield. $^1$H NMR (400 MHz, CDCl$_3$) δ ppm 8.82 (s, 1H), 8.63 (d, J=8.6 Hz, 1H), 8.56 (s, 1H), 8.47 (d, J=2.0 Hz, 1H), 7.87 (dd, J1=8.78 Hz, J2=2.26 Hz, 1H), 6.51 (s, 1H), 4.83 (m, 1H), 4.47 (s, 1H), 4.09 (m, 4H), 3.77 (s, 1H), 3.45-3.21 (m, 4H), 3.19 (s, 6H), 2.59 (m, 2H), 2.11 (m, 5H), 1.77 (m, 2H); HRMS m/z 505.2665 (M+H)+.

Examples 71-72

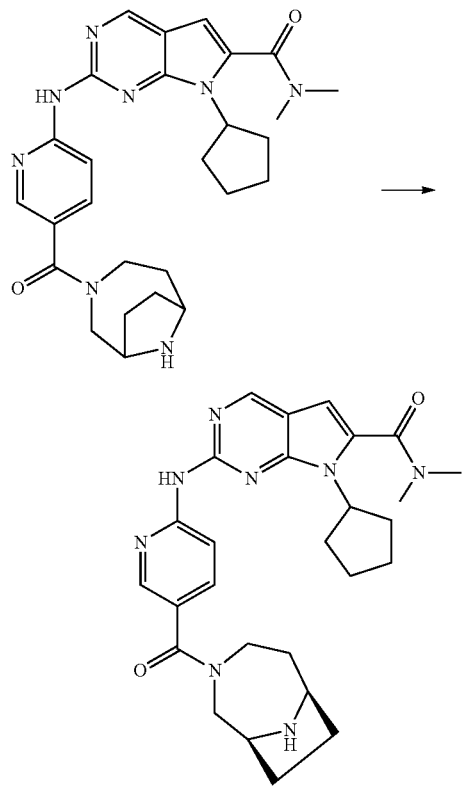

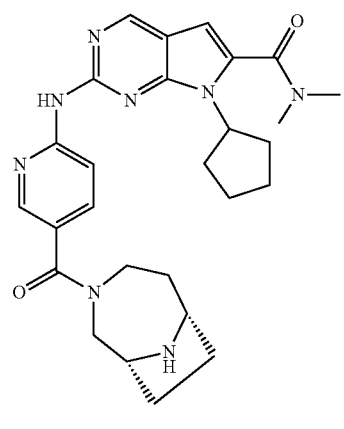

Racemic 7-Cyclopentyl-2-[5-(3,9-diaza-bicyclo[4.2.1]nonane-3-carbonyl)-pyridin-2-ylamino]-7H-pyrrolo[2,3-d]pyrimidine-6-carboxylic acid dimethylamide was chirally separated by SFC chromatography, Chiralpak AD-H (Chiral Technologies), 21.2×250 mm, 5 µm, 10% methanol, 100 mbar CO$_2$, 75 g/min flow, Thar SFC Prep-80 system, which gave Example 71, 7-Cyclopentyl-2-[5-((1S,6R)-3,9-diaza-bicyclo[4.2.1]nonane-3-carbonyl)-pyridin-2-ylamino]-7H-pyrrolo[2,3-d]pyrimidine-6-carboxylic acid dimethylamide which has a retention time ~2.5 min and Example 2, 7-cyclopentyl-2-[5-((1R,6S)-3,9-diaza-bicyclo[4.2.1]nonane-3-carbonyl)-pyridin-2-ylamino]-7H-pyrrolo[2,3-d]pyrimidine-6-carboxylic acid dimethylamide which has a retention time ~3.3 min

Example 71

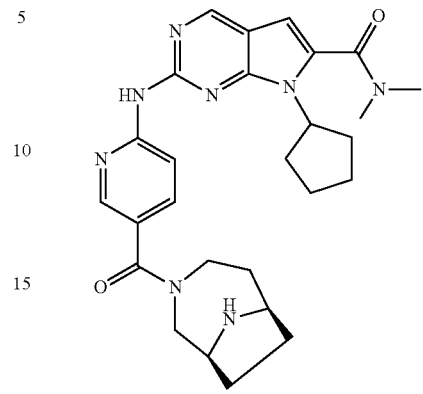

7-Cyclopentyl-2-[5-((1S,6R)-3,9-diaza-bicyclo[4.2.1]nonane-3-carbonyl)-pyridin-2-ylamino]-7H-pyrrolo[2,3-d]pyrimidine-6-carboxylic acid dimethylamide 1H NMR (400 MHz, DMSO-d$_6$) δ ppm 11.7 (s, 1H), 10.18 (s, 1H), 9.05 (s, 1H), 8.52 (s, 1H), 8.13 (d, 1H), 7.8 (d, 1H), 6.85 (s, 1H), 4.8 (m, 2H), 4.1 (m. broad, 2H), 3.7 (m. broad, 2H), 3.06 (s, 3H), 3.05 (s, 3H), 2.3 (m. broad, 2H), 2.25-1.7 (m. broad, 8H), 1.65 (m. broad, 2H). MS m/z 502.7 (M+H)$^+$.

Example 72

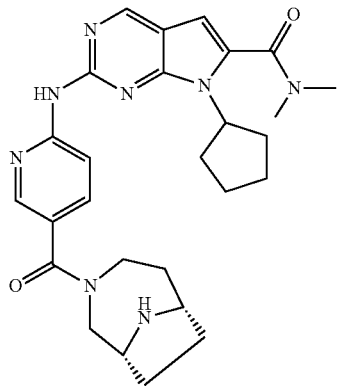 [SMILES: CN(C)C(=O)c1cc2cnc(Nc3ccc(C(=O)N4CC[C@@H]5CC[C@H](C4)N5)cn3)nc2n1C1CCCC1]

7-Cyclopentyl-2-[5-((1S,6R)-3,9-diaza-bicyclo[4.2.1]nonane-3-carbonyl)-pyridin-2-ylamino]-7H-pyrrolo[2,3-d]pyrimidine-6-carboxylic acid dimethylamide 1H NMR (400 MHz, DMSO-d$_6$) & ppm 11.7 (s, 1H), 10.18 (s, 1H), 9.05 (s, 1H), 8.52 (s, 1H), 8.13 (d, 1H), 7.8 (d, 1H), 6.85 (s, 1H), 4.8 (m, 2H), 4.1 (m. broad, 2H), 3.7 (m. broad, 2H), 3.06 (s, 3H), 3.05 (s, 3H), 2.3 (m. broad, 2H), 2.25-1.7 (m. broad, 8H), 1.65 (m. broad, 2H). MS m/z 502.7 (M+H)$^+$.

Example 73

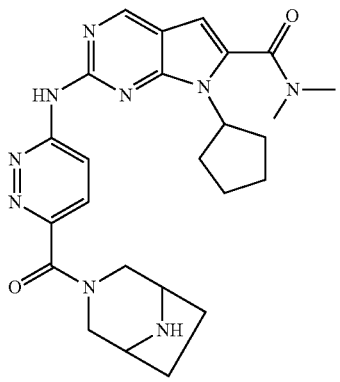 [SMILES: CN(C)C(=O)c1cc2cnc(Nc3ccc(C(=O)N4CC5CCC(C4)N5)nn3)nc2n1C1CCCC1]

7-Cyclopentyl-2-[6-(3,8-diaza-bicyclo[3.2.1]octane-3-carbonyl)-pyridazin-3-ylamino]-7H-pyrrolo[2,3-d]pyrimidine-6-carboxylic acid dimethylamide

Step 1

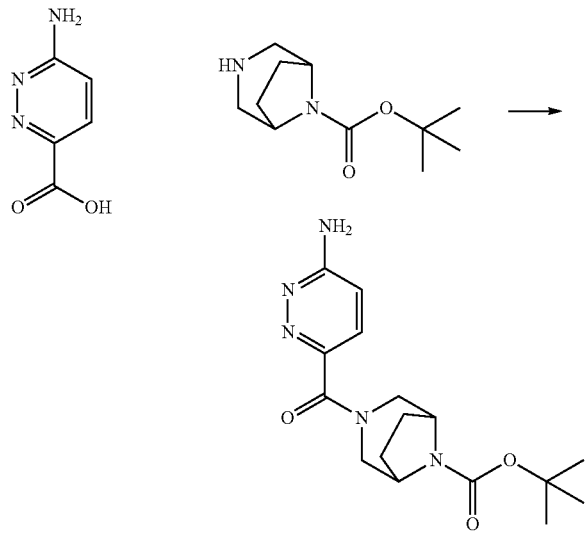

Preparation of 3-(6-Amino-pyridazine-3-carbonyl)-3,8-diaza-bicyclo[3.2.1]octane-8-carboxylic acid tert-butyl ester To a solution of 6-amino-pyridazine-3-carboxylic acid (212 mg, 1.0 mmol) in DMF (5 mL) was added 3,8-diaza-bicyclo[3.2.1]octane-8-carboxylic acid tert-butyl ester (139 mg, 1.0 mmol), HATU (456 mg, 1.2 mmol) and N,N-diisopropylethylamine (0.52 mL, 3.0 mmol). The mixture was stirred at room temperature overnight after which it was diluted with EtOAc, washed with brine, dried over $Na_2SO_4$, concentrated and purified over normal silica with 0-20% MeOH/DCM which gave a white solid (169 mg, 0.51 mmol). MS m/z 334.4 $(M+H)^+$.

Step 2

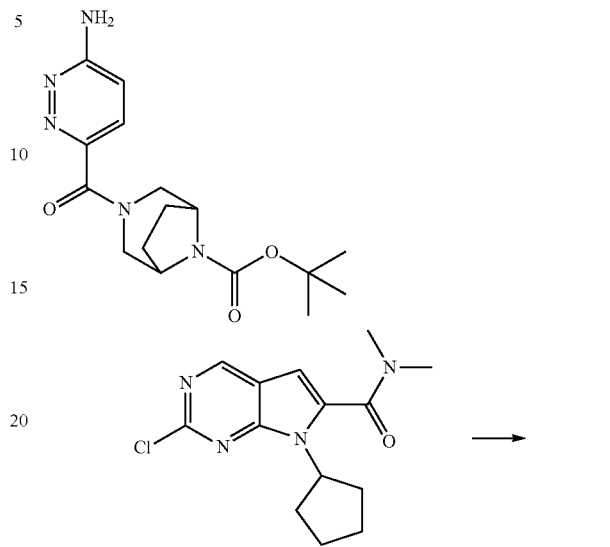

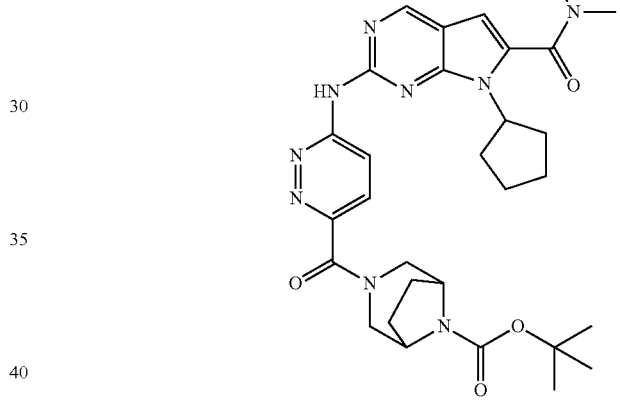

Preparation of 3-[6-(7-Cyclopentyl-6-dimethylcarbamoyl-7H-pyrrolo[2,3-d]pyrimidin-2-ylamino)-pyridazine-3-carbonyl]-3,8-diaza-bicyclo[3.2.1]octane-8-carboxylic acid tert-butyl ester In a 4 mL microwave vial 2-chloro-7-cyclopentyl-7H-pyrrolo[2,3-d]pyrimidine-6-carboxylic acid dimethylamide (98 mg, 0.336 mmol), 3-(6-amino-pyridazine-3-carbonyl)-3,8-diaza-bicyclo[3.2.1]octane-8-carboxylic acid tert-butyl ester (112 mg, 0.336 mmol), BINAP (10.5 mg, 0.017 mmol), $Cs_2CO_3$ (164 mg, 0.504 mmol) and $Pd(OAc)_2$ (3.8 mg, 0.017 mmol) were added together. The tube was capped and then purged with $N_2$ three times. Dioxane (1.68 mL) was added and the capped tube was heated to 120° C. for 20 min in a microwave reactor. After cooling the reaction mixture was diluted with heptane resulting in the crude product precipitating out. The crude product was isolated by filtration, resuspended in water and subjected to vigorous stirring and sonication. After re-isolating by filtration the product was purified by normal phase silica chromatography with a 0 to 20% MeOH/EtOAc gradient which gave a light tan solid (115 mg, 0.195 mmol). MS m/z 590.6 $(M+H)^+$.

Step 3

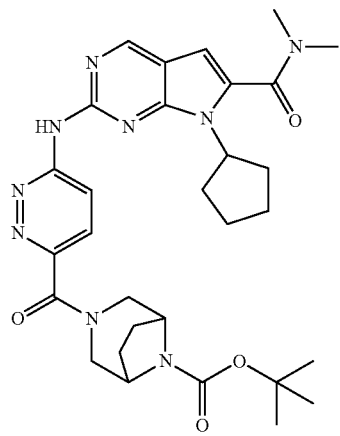

Example 74

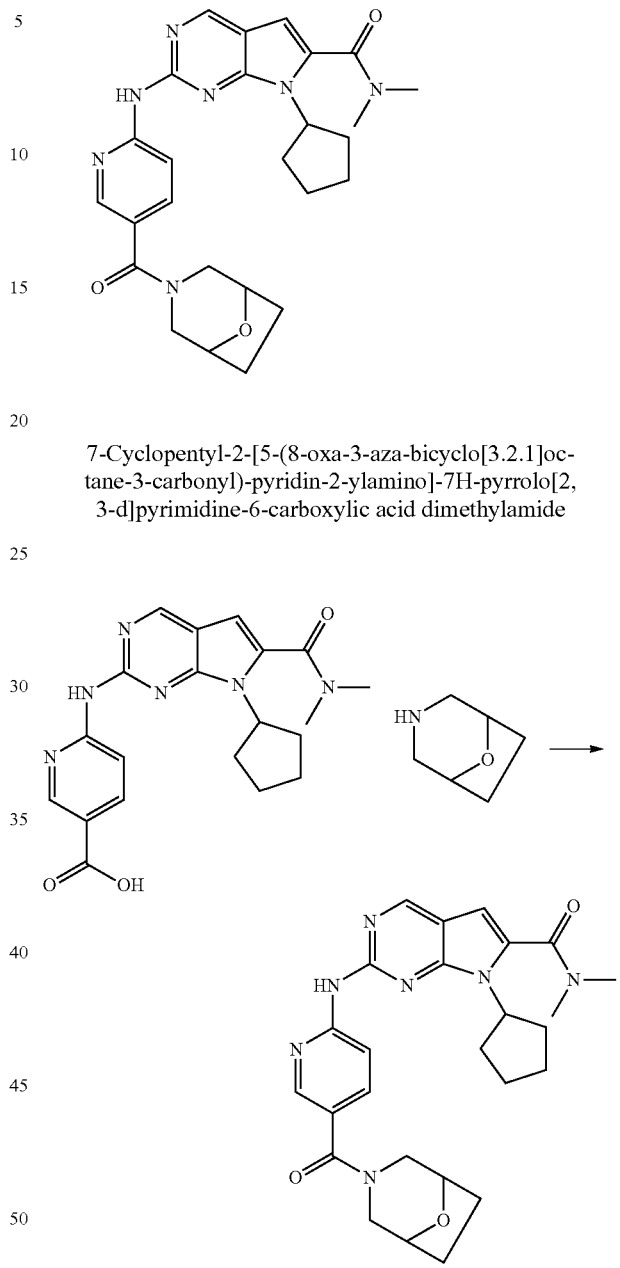

7-Cyclopentyl-2-[5-(8-oxa-3-aza-bicyclo[3.2.1]oc-tane-3-carbonyl)-pyridin-2-ylamino]-7H-pyrrolo[2, 3-d]pyrimidine-6-carboxylic acid dimethylamide Preparation of 7-Cyclopentyl-2-[6-(3,8-diaza-bicyclo [3.2.1]octane-3-carbonyl)-pyridazin-3-ylamino]-7H-pyrrolo[2,3-d]pyrimidine-6-carboxylic acid dimethylamide To a solution of 3-[6-(7-cyclopentyl-6-dimethylcarbamoyl-7H-pyrrolo[2,3-d]pyrimidin-2-ylamino)-pyridazine-3-carbonyl]-3,8-diaza-bicyclo[3.2.1]octane-8-carboxylic acid tert-butyl ester (110 mg, 0.187 mmol) in DCM (1 ml) at −78° C. was added TFA (1 mL, 13.0 mmol). After warming to room temperature and stirring for 1 h, the reaction was concentrated under reduced pressure. The resulting oily residue was dissolved in 2 mL MeOH, flushed through a PL-HCO3 MP-Resin cartridge to remove TFA, then purified by HPLC which gave a white solid (55 mg, 0.112 mmol). $^1$H NMR (400 MHz, DMSO): δ, 10.71 (s, 1H), 8.88 (s, 1H), 8.60 (d, J=8 Hz, 1H), 7.82 (d, J=8 Hz, 1H), 6.68 (s, 1H), 4.81-4.72 (m, 1H), 4.22 (d, J=12 Hz, 1H), 3.53 (d, J=12 Hz, 1H), 3.48 (br s, 1H), 3.29 (br s, 1H), 3.27 (d, J=12 Hz, 1H), 3.06 (s, 3H), 3.05 (s, 3H) 2.93 (d, J=12 Hz, 1H), 2.42-2.33 (m, 2H), 2.01-1.96 (m, 4H), 1.72-1.58 (m, 6H); HRMS calcd for C25H31N9O2. H$^+$ (M+H)$^+$ 490.2679. Found 490.2676 (M+H)$^+$.

Preparation of 7-Cyclopentyl-2-[5-(8-oxa-3-aza-bicyclo[3.2.1]octane-3-carbonyl)-pyridin-2-ylamino]-7H-pyrrolo[2,3-d]pyrimidine-6-carboxylic acid dimethylamide Following general amide formation method 3, 6-(7-cyclopentyl-6-(dimethylcarbamoyl)-7H-pyrrolo[2,3-d]pyrimidin-2-ylamino)nicotinic acid (528 mg, 1.34 mmole) was combined with 8-Oxa-3-aza-bicyclo[3.2.1]octane (199 mg, 1.34 mmol) which gave 7-Cyclopentyl-2-[5-(8-oxa-3-aza-bicyclo [3.2.1]octane-3-carbonyl)-pyridin-2-ylamino]-7H-pyrrolo [2,3-d]pyrimidine-6-carboxylic acid dimethylamide (213 mg, 0.435 mmol) in 32.5% yield. $^1$H NMR (400 MHz, CDCl₃) δ ppm 1.74 (m, 8H), 2.07 (m, 5H), 2.58 (m, 2H), 3.17 (s, 7H), 4.81 (dd, 1H), 6.48 (s, 1H), 7.79 (dd, 8.30 (s, 1H), 8.39 (d, 1H), 8.56 (d, 1H), 8.77 (s, 1H) MS m/z 490.5 (M+H)⁺.

Example 75

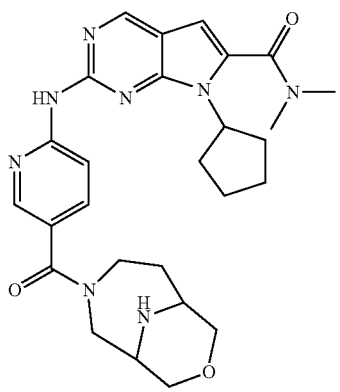 [SMILES: CN(C)C(=O)c1cc2cnc(Nc3ccc(C(=O)N4CCC5COCC(C4)N5)cn3)nc2n1C1CCCC1]

7-Cyclopentyl-2-[5-(8-oxa-3,10-diaza-bicyclo[4.3.1]
decane-3-carbonyl)-pyridin-2-ylamino]-7H-pyrrolo
[2,3-d]pyrimidine-6-carboxylic acid dimethylamide Step 1

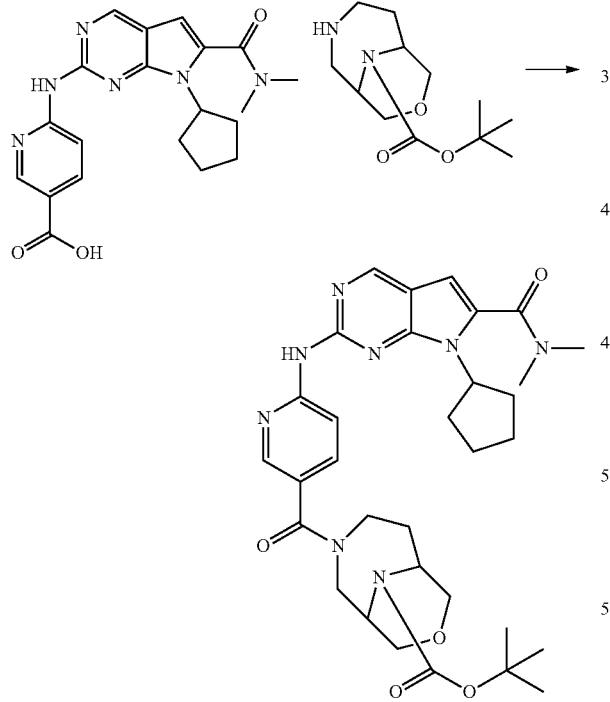

Preparation of 3-[6-(7-Cyclopentyl-6-dimethylcar-
bamoyl-7H-pyrrolo[2,3-d]pyrimidin-2-ylamino)-
pyridine-3-carbonyl]-8-oxa-3,10-diaza-bicyclo
[4.3.1]decane-10-carboxylic acid tert-butyl ester Following general amide formation method 3, 6-(7-cyclo-
pentyl-6-(dimethylcarbamoyl)-7H-pyrrolo[2,3-d]pyrimidin-2-ylamino)nicotinic acid (385 mg, 0.97 mmole) was combined with 8-Oxa-3,10-diaza-bicyclo[4.3.1]decane-10-carboxylic acid tert-butyl ester (215 mg, 0.887 mmol) which gave 3-[6-(7-Cyclopentyl-6-dimethylcarbamoyl-7H-pyrrolo[2,3-d]pyrimidin-2-ylamino)-pyridine-3-carbonyl]-8-oxa-3,10-diaza-bicyclo[4.3.1]decane-10-carboxylic acid tert-butyl ester (323 mg, 0.522 mmol) in 59% yield. MS 619.7 (M+H)⁺.

Step 2

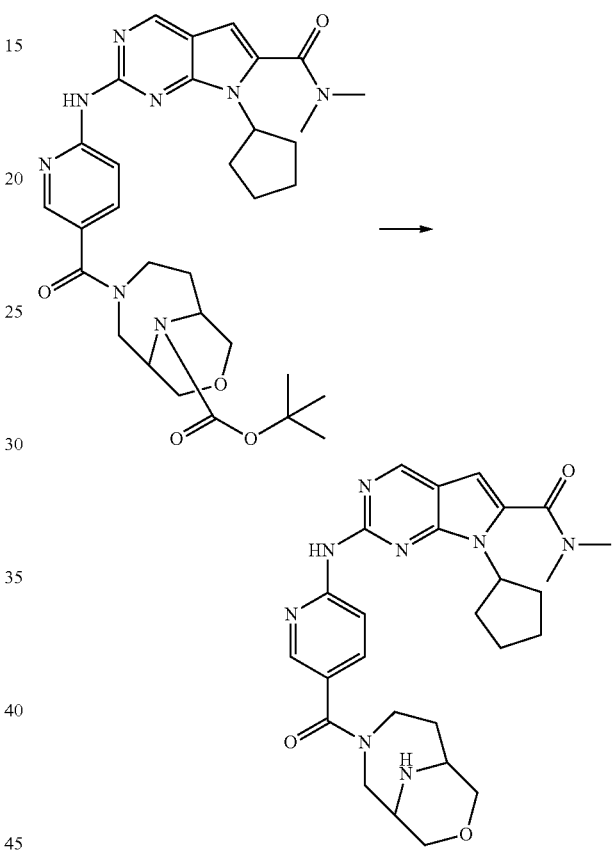

Preparation of 7-Cyclopentyl-2-[5-(8-oxa-3,10-
diaza-bicyclo[4.3.1]decane-3-carbonyl)-pyridin-2-
ylamino]-7H-pyrrolo[2,3-d]pyrimidine-6-carboxylic
acid dimethylamide Following deprotection method 1, 3-[6-(7-Cyclopentyl-6-dimethylcarbamoyl-7H-pyrrolo[2,3-d]pyrimidin-2-ylamino)-pyridine-3-carbonyl]-8-oxa-3,10-diaza-bicyclo[4.3.1]decane-10-carboxylic acid tert-butyl ester (313 mg, 0.506 mmol) was converted to 7-Cyclopentyl-2-[5-(8-oxa-3,10-diaza-bicyclo[4.3.1]decane-3-carbonyl)-pyridin-2-ylamino]-7H-pyrrolo[2,3-d]pyrimidine-6-carboxylic acid dimethylamide (187 mg, 0.35 mmol) in 69.1% yield. ¹H NMR (400 MHz, CDCl₃-d) δ ppm 1.75 (d, 3H) 2.06-2.18 (m, 5H) 2.49-2.66 (m, 2H) 3.03-3.14 (m, 2H) 3.18 (s, 6H) 3.42 (dd, 2.0 Hz, 2H) 3.63 (br. s., 1H) 3.81 (br. s., 2H) 4.83 (t, 1H) 6.50 (s, 1H) 7.85 (dd, 1H) 8.42 (br. s., 1H) 8.45-8.51 (m, 1H) 8.60 (d, 1H) 8.79 (s, 1H). MS 518.6 (M+H)⁺.

Example 76

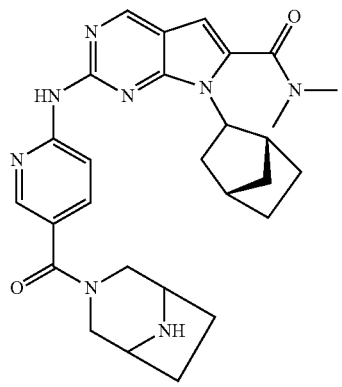 [SMILES: CN(C)C(=O)c1cc2cnc(Nc3ccc(C(=O)N4CC5CCC(C4)N5)cn3)nc2n1C1C[C@H]2CC[C@@H]1C2]

7-(1R,2R,4S)-Bicyclo[2.2.1]hept-2-yl-2-[5-(3,8-diaza-bicyclo[3.2.1]octane-3-carbonyl)-pyridin-2-ylamino]-7H-pyrrolo[2,3-d]pyrimidine-6-carboxylic acid dimethylamide

Step 1

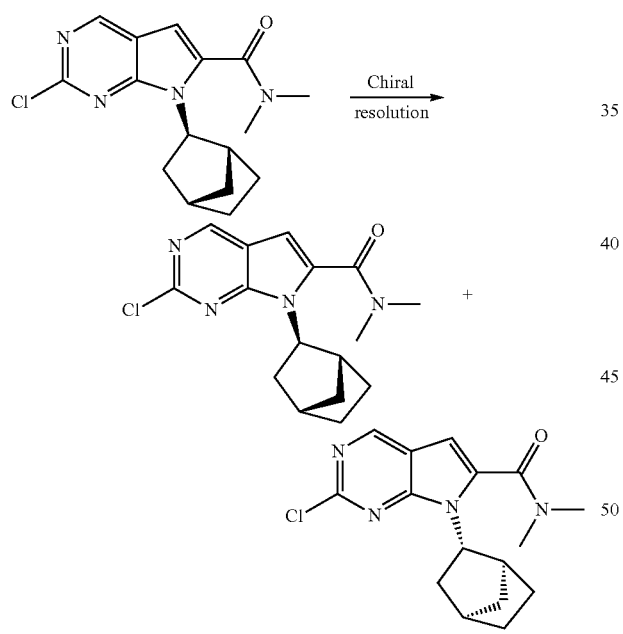

Racemic 7-exo-bicyclo[2.2.1]hept-2-yl-2-chloro-7H-pyrrolo[2,3-d]pyrimidine-6-carboxylic acid dimethylamide was chirally separated by SFC chromatography, Chiralpak AD-H (Chiral Technologies), 21.2×250 mm, 5 μm, 10% methanol, 100 mbar $CO_2$, 75 g/min flow, Thar SFC Prep-80 system, which gave enantiomer 1: 7-(1R,2R,4S)-Bicyclo[2.2.1]hept-2-yl-2-chloro-7H-pyrrolo[2,3-d]pyrimidine-6-carboxylic acid dimethylamide (enantiomer 1 retention time 1.9 min), and enantiomer 2: 7-(1S,2S,4R)-Bicyclo[2.2.1]hept-2-yl-2-chloro-7H-pyrrolo[2,3-d]pyrimidine-6-carboxylic acid dimethylamide (enantiomer 2 retention time 2.4 min)

Step 2

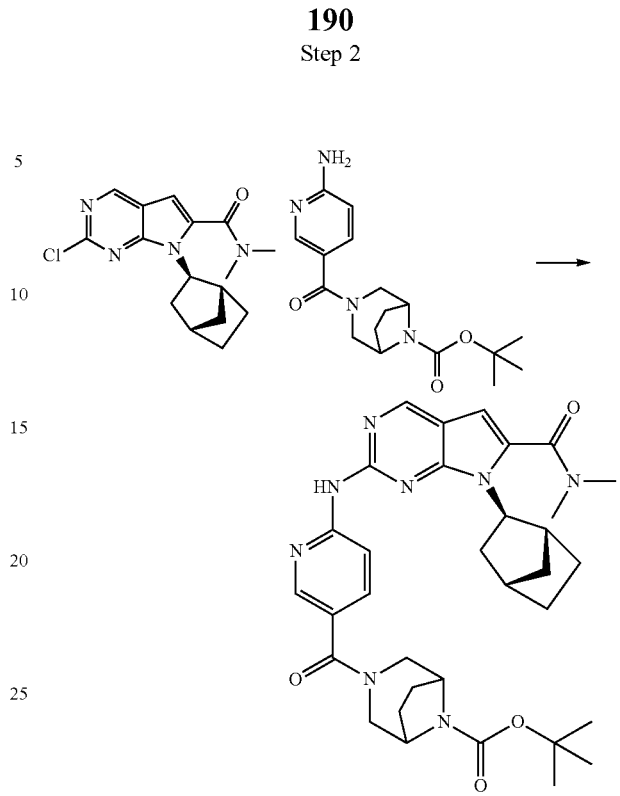

Preparation of 3-[6-((1R,2R,4S)-7-Bicyclo[2.2.1]hept-2-yl-6-dimethylcarbamoyl-7H-pyrrolo[2,3-d]pyrimidin-2-ylamino)-pyridine-3-carbonyl]-3,8-diaza-bicyclo[3.2.1]octane-8-carboxylic acid tert-butyl ester Following general N—C coupling procedure 1, 1 7-(1R,2R,4S)-Bicyclo[2.2.1]hept-2-yl-2-chloro-7H-pyrrolo[2,3-d]pyrimidine-6-carboxylic acid dimethylamide (90 mg, 0.28 mmol) with 3-(6-Amino-pyridine-3-carbonyl)-3,8-diaza-bicyclo[3.2.1]octane-8-carboxylic acid tert-butyl ester (99 mg, 0.30 mmol) which gave 3-[6-((1R,2R,4S)-7-Bicyclo[2.2.1]hept-2-yl-6-dimethylcarbarmyl-7H-pyrrolo[2,3-d]pyrimidin-2-ylamino)-pyridine-3-carbonyl]-3,8-diaza-bicyclo[3.2.1]octane-8-carboxylic acid tert-butyl ester and was used as is without further characterization.

Step 3

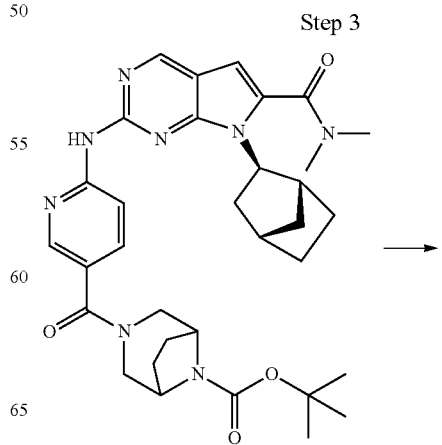

191
-continued

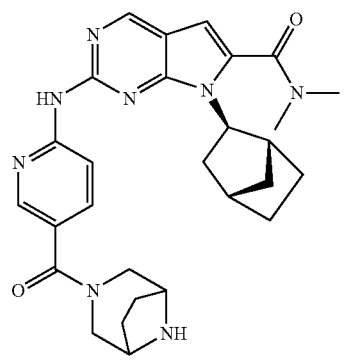

Preparation of 7-(1R,2R,4S)-Bicyclo[2.2.1]hept-2-yl-2-[5-(3,8-diazabicyclo[3.2.1]octane-3-carbonyl)-pyridin-2-ylamino]-7H-pyrrolo[2,3-d]pyrimidine-6-carboxylic acid dimethylamide Following deprotection method 2, 3-[6-((1R,2R,4S)-7-Bicyclo[2.2.1]hept-2-yl-6-dimethylcarbamoyl-7H-pyrrolo[2,3-d]pyrimidin-2-ylamino)-pyridine-3-carbonyl]-3,8-diaza-bicyclo[3.2.1]octane-8-carboxylic acid tert-butyl ester was converted to 7-(1R,2R,4S)-Bicyclo[2.2.1]hept-2-yl-2-[5-(3,8-diaza-bicyclo[3.2.1]octane-3-carbonyl)-pyridin-2-ylamino]-7H-pyrrolo[2,3-d]pyrimidine-6-carboxylic acid dimethylamide (15 mg) in 10% overall yield. ¹H NMR (400 MHz, DMSO-d6) δ 9.94 (s, 1H), 8.82 (s, 1H), 8.39 (s, 1H), 8.29 (d, J=8.6, 1H), 7.89 (d, J=8.6, 1H), 6.65 (s, 1H), 4.46 (m, 1H), 4.35 (m, 1H), 3.96 (m, 1H), 3.04 (s, 6H), 2.86 (m, 3H), 2.62 (m, 3H), 2.37 (m, 1H), 1.85-1.79 (m, 5H), 1.55 (m, 2H), 1.22 (m, 3H). MS m/z 515.7 (MH⁺)

Example 77

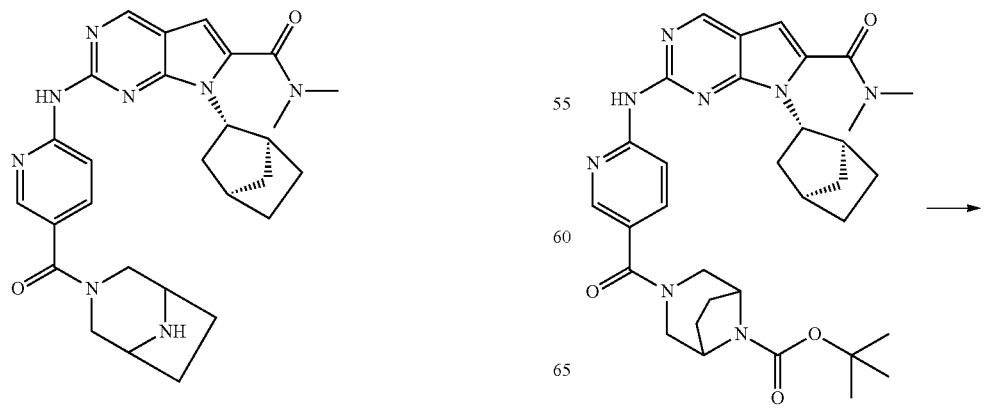

192

7-(1S,2S,4R)-Bicyclo[2.2.1]hept-2-yl-2-[5-(3,8-diaza-bicyclo[3.2.1]octane-3-carbonyl)-pyridin-2-ylamino]-7H-pyrrolo[2,3-d]pyrimidine-6-carboxylic acid dimethylamide Step 1

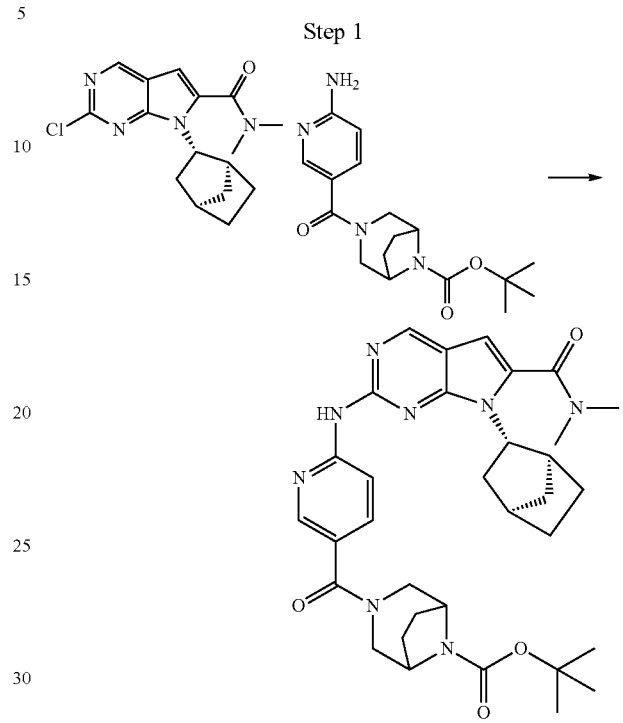

Preparation of 3-[6-((1S,2S,4R)-7-Bicyclo[2.2.1]hept-2-yl-6-dimethylcarbamoyl-7H-pyrrolo[2,3-d]pyrimidin-2-ylamino)-pyridine-3-carbonyl]-3,8-diaza-bicyclo[3.2.1]octane-8-carboxylic acid tert-butyl ester Following general N—C coupling procedure 1 as in example 76, 7-(1S,2S,4R)-Bicyclo[2.2.1]hept-2-yl-2-chloro-7H-pyrrolo[2,3-d]pyrimidine-6-carboxylic acid dimethylamide (90 mg, 0.28 mmol) was combined with 3-(6-Amino-pyridine-3-carbonyl)-3,8-diaza-bicyclo[3.2.1]octane-8-carboxylic acid tert-butyl ester which gave 3-[6-((1S,2S,4R)-7-Bicyclo[2.2.1]hept-2-yl-6-dimethylcarbamoyl-7H-pyrrolo[2,3-d]pyrimidin-2-ylamino)-pyridine-3-carbonyl]-3,8-diaza-bicyclo[3.2.1]octane-8-carboxylic acid tert-butyl ester and was used as is without further characterization.

Step 2

193

-continued

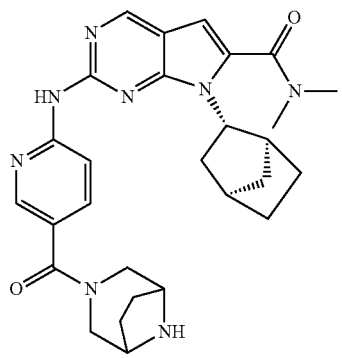

Preparation of 7-(1S,2S,4R)-Bicyclo[2.2.1]hept-2-yl-2-[5-(3,8-diaza-bicyclo[3.2.1]octane-3-carbonyl)-pyridin-2-ylamino]-7H-pyrrolo[2,3-d]pyrimidine-6-carboxylic acid dimethylamide Following deprotection method 2, 3-[6-((1S,2S,4R)-7-Bicyclo[2.2.1]hept-2-yl-6-dimethylcarbamoyl-7H-pyrrolo[2,3-d]pyrimidin-2-ylamino)-pyridine-3-carbonyl]-3,8-diaza-bicyclo[3.2.1]octane-8-carboxylic acid tert-butyl ester was converted to 7-(1S,2S,4R)-Bicyclo[2.2.1]hept-2-yl-2-[5-(3,8-diaza-bicyclo[3.2.1]octane-3-carbonyl)-pyridin-2-ylamino]-7H-pyrrolo[2,3-d]pyrimidine-6-carboxylic acid dimethylamide which after purification gave the title compound (5 mg) in 3% overall yield. $^1$H NMR (400 MHz, DMSO-d6) δ 9.94 (s, 1H), 8.82 (s, 1H), 8.39 (s, 1H), 8.29 (d, J=8.6, 1H), 7.89 (d, J=8.6, 1H), 6.65 (s, 1H), 4.46 (m, 1H), 4.35 (m, 1H), 3.96 (m, 1H), 3.04 (s, 6H), 2.86 (m, 3H), 2.62 (m, 3H), 2.37 (m, 1H), 1.85-1.79 (m, 5H), 1.55 (m, 2H), 1.22 (m, 3H). MS m/z 514.8 (MH+)

Example 78

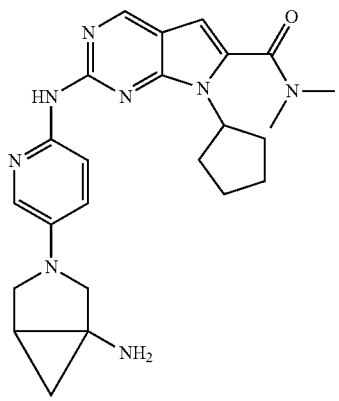 [SMILES: CN(C)C(=O)c1cc2cnc(Nc3ccc(N4CC5CC5(N)C4)cn3)nc2n1C1CCCC1]

194

2-[5-(1-Amino-3-aza-bicyclo[3.1.0]hex-3-yl)-pyridin-2-ylamino]-7-cyclopentyl-7H-pyrrolo[2,3-d]pyrimidine-6-carboxylic acid dimethylamide Step 1

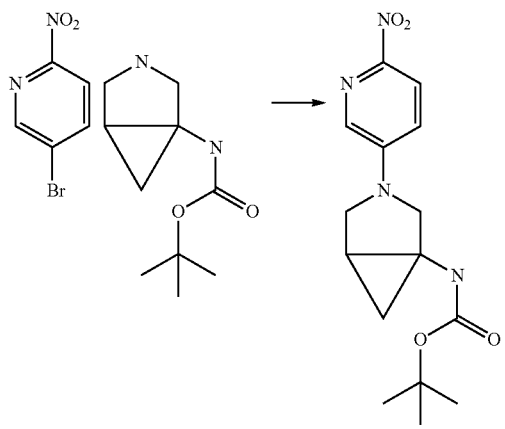

Preparation of [3-(6-Nitro-pyridin-3-yl)-3-aza-bicyclo[3.1.0]hex-1-yl]-carbamic acid tert-butyl ester Following general N—C coupling procedure 1, 5-bromo-2-nitropyridine (50 mg, 0.246 mmol), was combined with tert-butyl 3-azabicyclo[3.1.0]hexan-1-ylcarbamate (48.8 mg, 0.246 mmol), which gave 75 mg of [3-(6-Nitro-pyridin-3-yl)-3-aza-bicyclo[3.1.0]hex-1-yl]-carbamic acid tert-butyl ester in 95% yield. MS (ESI) m/e (M+H$^+$): 321.3

Step 2

Preparation of [3-(6-Amino-pyridin-3-yl)-3-aza-bicyclo[3.1.0]hex-1-yl]-carbamic acid tert-butyl ester To a solution of [3-(6-Nitro-pyridin-3-yl)-3-aza-bicyclo[3.1.0]hex-1-yl]-carbamic acid tert-butyl ester (150 mg, 0.468 mmol) in MeOH—CH2Cl2 (3:1) was added Pd/C (24.92 mg, 0.234 mmol). The resulting mixture was stirred under H2 balloon (H2/vacuum exchange three times) at r.t. for 4 h. LCMS showed complete conversion. The reaction mixture was then filtered through a pad of Celite with DCM and concentrated to give a black precipitate. This precipitate was diluted in ethyl acetate followed by filtration. The filtrate was then evaporated to give 120 mg of [3-(6-Amino-pyridin-3-yl)-3-aza-bicyclo[3.1.0]hex-1-yl]-carbamic acid tert-butyl ester in 88% yield. MS (ESI) m/e (M+H$^+$): 291.1

Step 3

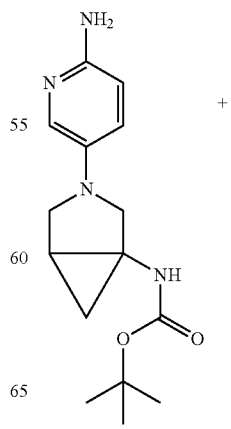

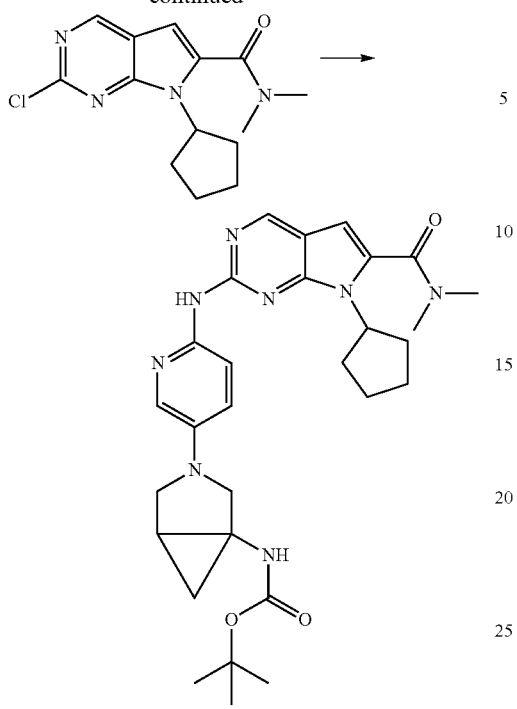

Preparation of {3-[6-(7-Cyclopentyl-6-dimethylcarbamoyl-7H-pyrrolo[2,3-d]pyrimidin-2-ylamino)-pyridin-3-yl]-3-aza-bicyclo[3.1.0]hex-1-yl}-carbamic acid tert-butyl ester Following general N—C coupling procedure 1, 3-(6-Amino-pyridin-3-yl)-3-aza-bicyclo[3.1.0]hex-1-yl]-carbamic acid tert-butyl ester (120 mg, 0.413 mmol) was combined with 2-Chloro-7-cyclopentyl-7H-pyrrolo[2,3-d]pyrimidine-6-carboxylic acid dimethylamide (121 mg, 0.413 mmol) which gave 200 mg {3-[6-(7-Cyclopentyl-6-dimethylcarbamoyl-7H-pyrrolo[2,3-d]pyrimidin-2-ylamino)-pyridin-3-yl]-3-aza-bicyclo[3.1.0]hex-1-yl}-carbamic acid tert-butyl ester in 89% yield. MS (ESI) m/e (M+H⁺): 547.0

Step 4

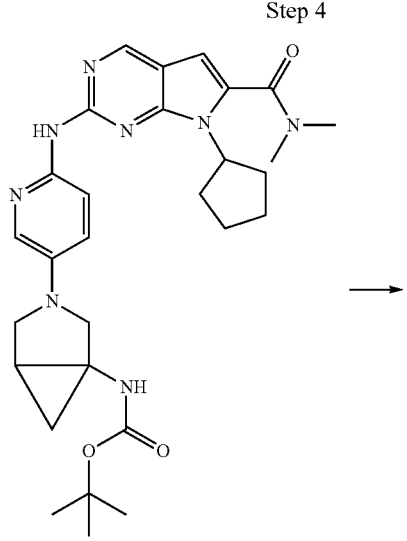

Preparation of 2-[5-(1-Amino-3-aza-bicyclo[3.1.0]hex-3-yl)-pyridin-2-ylamino]-7-cyclopentyl-7H-pyrrolo[2,3-d]pyrimidine-6-carboxylic acid dimethylamide Following deprotection method 1, {3-[6-(7-Cyclopentyl-6-dimethylcarbamoyl-7H-pyrrolo[2,3-d]pyrimidin-2-ylamino)-pyridin-3-yl]-3-aza-bicyclo[3.1.0]hex-1-yl}-carbamic acid tert-butyl ester 2-[5-(1-Amino-3-aza-bicyclo[3.1.0]hex-3-yl)-pyridin-2-ylamino]-7-cyclopentyl-7H-pyrrolo[2,3-d]pyrimidine-6-carboxylic acid dimethylamide, 20 mg.

MS (ESI) m/e (M+H⁺): 447.5; 1H NMR (400 MHz, DMSO-d$_6$) δ ppm 9.14 (1H, s), 8.72 (1H, s), 8.05 (1H, d), 7.65 (1H, d), 7.00 (1H, dd), 6.58 (1H, s), 4.67-4.76 (1H, quin.), 3.62 (1H, d), 3.35 (5H, s), 3.22 (1H, d), 3.05 (6H, d), 2.42 (2H, br. s.), 1.96-1.99 (4H, d), 1.63 (2H, br. s.), 0.85 (1H, m), 0.55 (1H, m).

Example 79

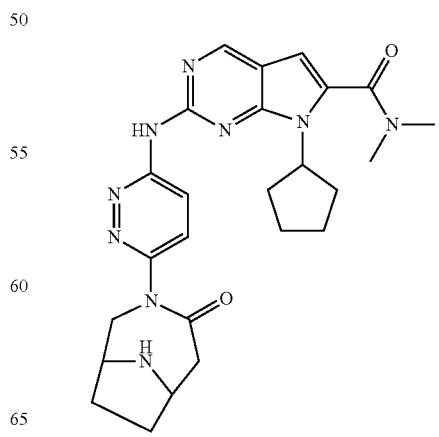

7-Cyclopentyl-2-[6-(4-oxo-3,9-diaza-bicyclo[4.2.1]non-3-yl)pyridazin-3-ylamino]-7H-pyrrolo[2,3-d]pyrimidine-6-carboxylic acid dimethylamide Step 1

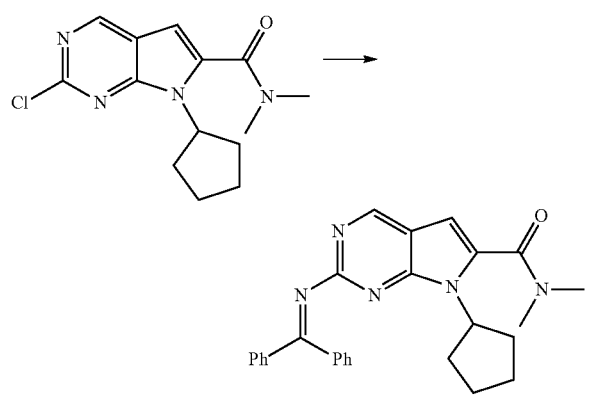

Preparation of 2-Amino-7-cyclopentyl-7H-pyrrolo[2,3-d]pyrimidine-6-carboxylic acid dimethylamide To a suspension of 2-chloro-7-cyclopentyl-7H-pyrrolo[2,3-d]pyrimidine-6-carboxylic acid dimethylamide (2.93 g, 10 mmol) in 50 mL Dioxane were added benzophenone imine (1.90 g, 10.5 mmol), Pd(OAc)$_2$ (0.11 g, 0.5 mmol), BINAP (0.31 g, 0.5 mmol) and Cs$_2$CO$_3$ (4.89 g, 15 mmol) and the flask was purged with N$_2$. Then the tube was sealed and the mixture was heated for 1 h at 120° C. Then the suspension was added with heptane and filtered. The precipitate was extracted with DCM and the extract was purified by SiO2 column chromatography to give 2-(benzhydrylidene-amino)-7-(1-ethyl-butyl)-7H-pyrrolo[2,3-d]pyrimidine-6-carboxylic acid dimethylamide (3.5 g, 8.0 mmol, 80% yield). MS m/z 438.5 (M+H)$^+$.

Step 2

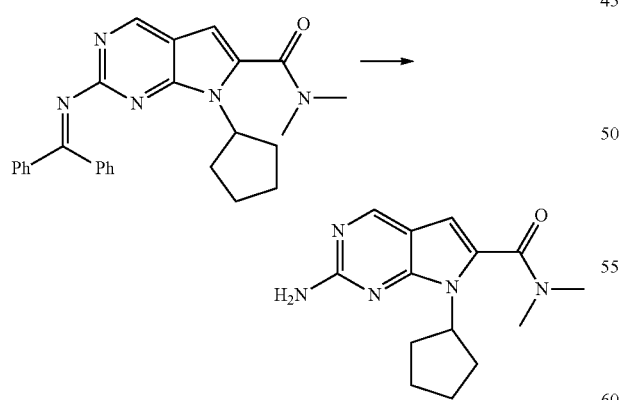

Preparation of 2-Amino-7-cyclopentyl-7H-pyrrolo[2,3-d]pyrimidine-6-carboxylic acid dimethylamide To a solution of 2-(benzhydrylidene-amino)-7-(1-ethyl-butyl)-7H-pyrrolo[2,3-d]pyrimidine-6-carboxylic acid dimethylamide (3.5 g, 8.0 mmol) in 26.7 mL THF was added aqueous 2M HCl (1.32 mL) and the mixture was stirred for 20 min. To this was added 60 mL heptane:EtOAc (4:1 v/v) and 60 mL aqueous 0.5N HCl and the layers were separated. The acidic aqueous layer was basified to pH 10 with aqueous 25% NaOH solution and extracted again with EtOAc. The organic extract was then washed with brine, dried (Na$_2$SO$_4$), concentrated and purified via SiO2 column chromatography (0-20% MeOH in EtOAc) to give 2-amino-7-cyclopentyl-7H-pyrrolo[2,3-d]pyrimidine-6-carboxylic acid dimethylamide as a white solid (1.68 g, 6.15 mmol, 77% yield). MS m/z 274.4 (M+H)$^+$.

Step 3

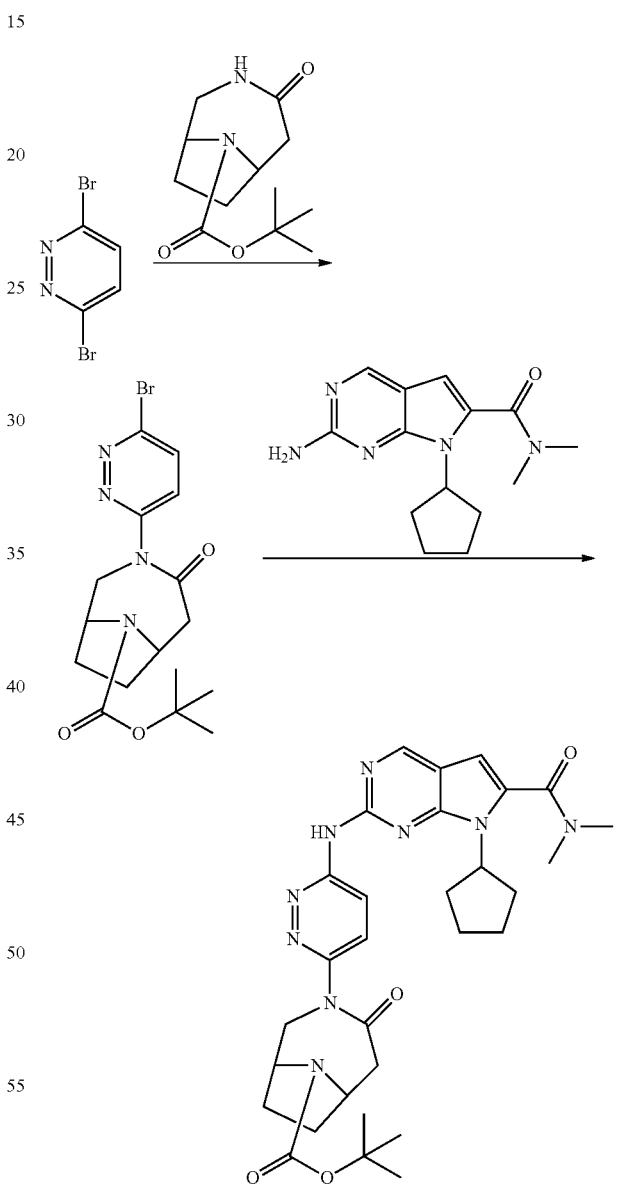

Synthesis of 3-[6-(7-Cyclopentyl-6-dimethylcarbamoyl-7H-pyrrolo[2,3-d]pyrimidin-2-ylamino)-pyridazin-3-yl]-4-oxo-3,9-diaza-bicyclo[4.2.1]nonane-9-carboxylic acid tert-butyl ester To a suspension of 3,6-dibromo-pyridazine (400 mg, 1.68 mmol) in 8 mL Toluene in a dry pressure tube were added 4-oxo-3,9-diaza-bicyclo[4.2.1]nonane-9-carbo-xylic acid tert-butyl ester (323 mg, 1.345 mmol), Pd$_2$(dba)$_3$ (154 mg, 0.168 mmol), xantphos (195 mg, 0.336 mmol) and NaOt-Bu (242 mg, 2.52 mmol) and the suspension was bubbled with N$^2$ for 3 min. Then the tube was sealed and the mixture was heated for 3 h at 100° C. Then the seal was open and the mixture was added with more of Pd$_2$(dba)$_3$ (41 mg, 0.045 mmol), xantphos (52 mg, 0.091 mmol), NaOt-Bu (65 mg, 0.680 mmol) and 2-amino-7-cyclopentyl-7H-pyrrolo[2,3-d]pyrimidine-6-carboxylic acid dimethylamide (124 mg, 0.453 mmol). The mixture was again heated at 10° C. for 16 h and the suspension was filtered through a celite plug and washed with 10% MeOH in DCM. The collective filtrates were combined and purified by two consecutive SiO$_2$ columns to give 3-[6-(7-cyclopentyl-6-dimethylcarbamoyl-7H-pyrrolo[2,3-d]pyrimidin-2-ylamino)pyridazin-3-yl]-4-oxo-3,9-diaza-bicyclo[4.2.1]nonane-9-carboxylic acid tert-butyl ester (66 mg, 0.112 mmol, 8% yield) as a white solid. MS m/z 590.6 (M+H)$^+$.

Step 4

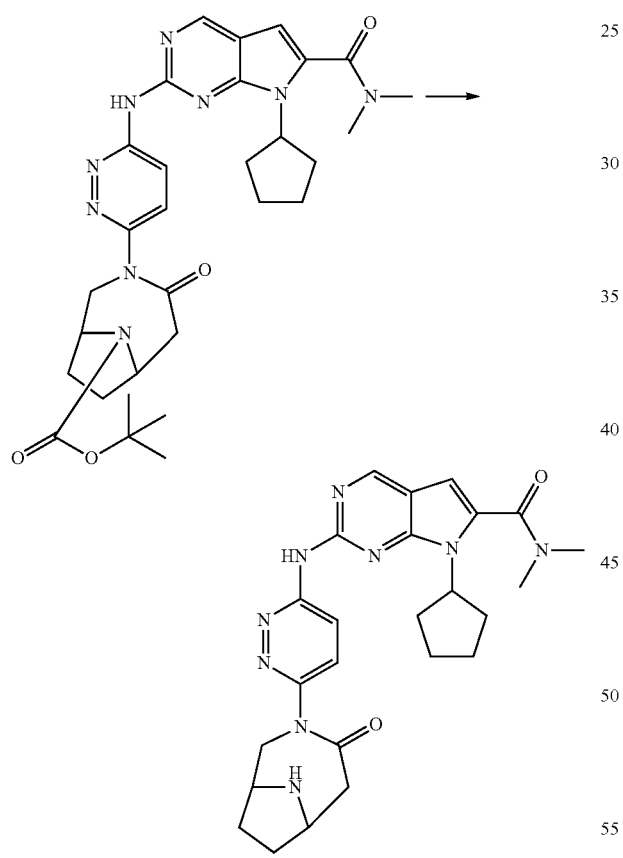

Preparation of Synthesis of 7-Cyclopentyl-2-[6-(4-oxo-3,9-diaza-bicyclo[4.2.1]non-3-yl)pyridazin-3-ylamino]-7H-pyrrolo[2,3-d]pyrimidine-6-carboxylic acid dimethylamide Following deprotection method 1, 3-[6-(7-cyclopentyl-6-dimethylcarbamoyl-7H-pyrrolo[2,3-d]pyrimidin-2-ylamino)-pyridazin-3-yl]-4-oxo-3,9-diaza-bicyclo[4.2.1]nonane-9-carboxylic acid tert-butyl ester (60 mg, 0.10 mmol) was converted to 7-Cyclopentyl-2-[6-(4-oxo-3,9-diaza-bicyclo[4.2.1]non-3-yl)pyridazin-3-ylamino]-7H-pyrrolo[2,3-d]pyrimidine-6-carboxylic acid dimethylamide (9 mg, 0.018 mmol) in 18% yield. 1H NMR (400 MHz, dichloromethane-d$_2$) δ ppm 8.69 (s, 1H), 8.63 (d, J=9.6 Hz, 1H), 8.44 (br. s., 1H), 7.68 (d, J=9.6 Hz, 1H), 6.39 (s, 1H), 4.72 (m, 1H), 4.36 (dd, J=15.2, 6.6 Hz, 1H), 3.88 (d, J=15.2 Hz, 1H), 3.72 (m, 1H), 3.59 (m, 1H), 3.02 (s, 6H), 2.87 (m, 1H), 2.75 (m, 1H), 2.42 (m, 2H), 1.98 (m, 5H), 1.78 (m, 3H), 1.65 (m, 2H); MS m/z 490.5 (M+H)$^+$; HRMS: m/z (M+H) calculated for C$_{25}$H$_{31}$N$_9$O$_2$: 490.2679. Found: 490.2693.

Example 80

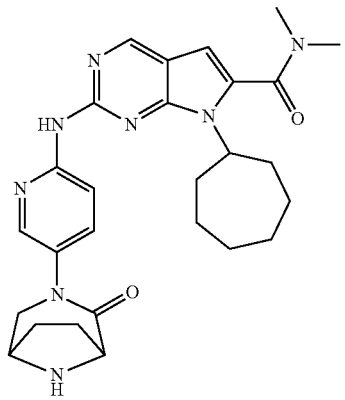 [SMILES: CN(C)C(=O)c1cc2cnc(Nc3ccc(N4CC5CCC(N5)C4=O)cn3)nc2n1C1CCCCCC1]

7-Cycloheptyl-2-[5-(2-oxo-3,8-diaza-bicyclo[3.2.1]oct-3-yl)-pyridin-2-ylamino]-7H-pyrrolo[2,3-d]pyrimidine-6-carboxylic acid dimethylamide

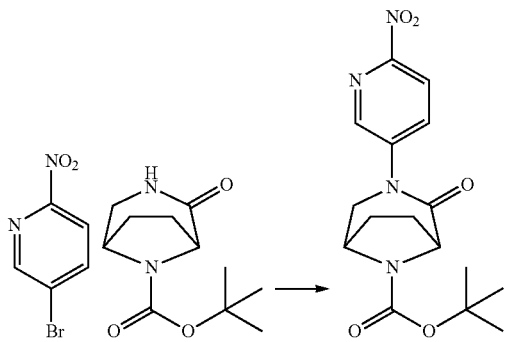

Step 1

Preparation of 3-(6-Nitro-pyridin-3-yl)-2-oxo-3,8-diaza-bicyclo[3.2.1]octane-8-carboxylic acid tert-butyl ester Following general N—C coupling procedure 1, 5-bromo-2-nitropyridine (110 mg, 0.542), was combined with 2-Oxo-3,8-diaza-bicyclo[3.2.1]octane-8-carboxylic acid tert-butyl ester (135 mg, 0.596 mg), which after purification silica gel chromatography gave 3-(6-Nitro-pyridin-3-yl)-2-oxo-3,8-diaza-bicyclo[3.2.1]octane-8-carboxylic acid tert-butyl ester (290 mg, 81%). MS m/z 349.0 (MH+), and was used directly as is without further characterization.

Step 2

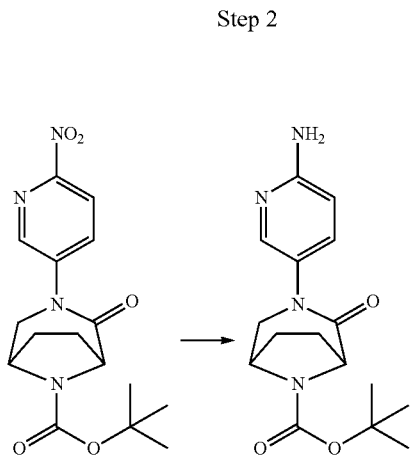

Preparation of 3-(6-Amino-pyridin-3-yl)-2-oxo-3,8-diaza-bicyclo[3.2.1]octane-8-carboxylic acid tert-butyl ester Following nitro group reduction procedure 1, 3-(6-Nitro-pyridin-3-yl)-2-oxo-3,8-diaza-bicyclo[3.2.1]octane-8-carboxylic acid tert-butyl ester (290 mg, 0.83 mmol) in methanol (10 mL) with nitrogen, then added 10% palladium on charcoal (200 mg, excess). Purged with hydrogen and allowed to stir under hydrogen atmosphere for 16 hours. Purged with nitrogen and filtered through a pad of celite, washing with methanol. Concentrated in vacuo which gave 3-(6-Amino-pyridin-3-yl)-2-oxo-3,8-diaza-bicyclo[3.2.1]octane-8-carboxylic acid tert-butyl ester (146 mg, 60%). Used without further purification. 1H NMR (400 MHz, DMSO-d6) δ 7.73 (d, J=2.6 Hz, 1H), 7.21 (dd, J=9.1, 2.6 Hz 1H), 6.43 (d, J=9.1 Hz, 1H), 6.01 (s, 2H), 4.38 (br. s, 1H), 4.26 (m, 1H), 3.77 (m, 1H), 3.30 (m, 1H), 2.17-2.07 (m, 2H), 2.02-1.95 (m, 2H), 1.43 (s, 9H); MS m/z 319.5 (MH+).

Step 3

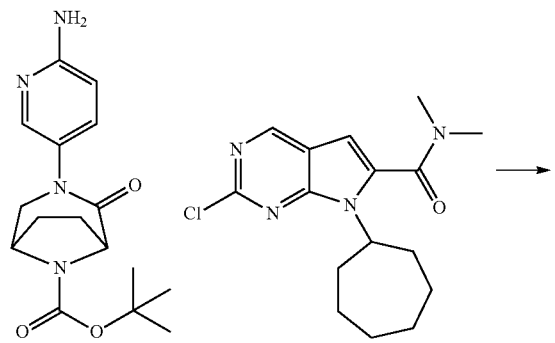

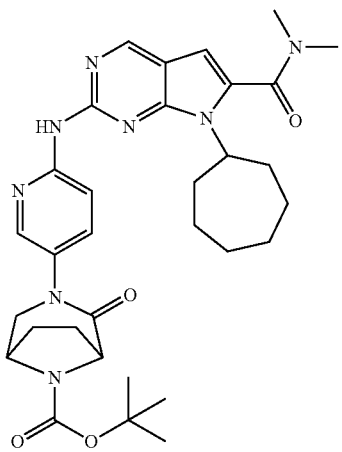

Preparation of 7-Cycloheptyl-2-[5-(2-oxo-3,8-diaza-bicyclo[3.2.1]oct-3-yl)-pyridin-2-ylamino]-7H-pyrrolo[2,3-d]pyrimidine-6-carboxylic acid dimethylamide tert butyl ester Following general N—C coupling procedure 1, 3-(6-Amino-pyridin-3-yl)-2-oxo-3,8-diaza-bicyclo[3.2.1]octane-8-carboxylic acid tert-butyl ester (146 mg, 0.46 mmol), was combined with 2-Chloro-7-cycloheptyl-7H-pyrrolo[2,3-d]pyrimidine-6-carboxylic acid dimethylamide (134 mg, 0.42 mmol), which after workup gave 7-Cycloheptyl-2-[5-(2-oxo-3,8-diaza-bicyclo[3.2.1]oct-3-yl)-pyridin-2-ylamino]-7H-pyrrolo[2,3-d]pyrimidine-6-carboxylic acid dimethylamide tert butyl ester and was used directly without further characterization Step 4

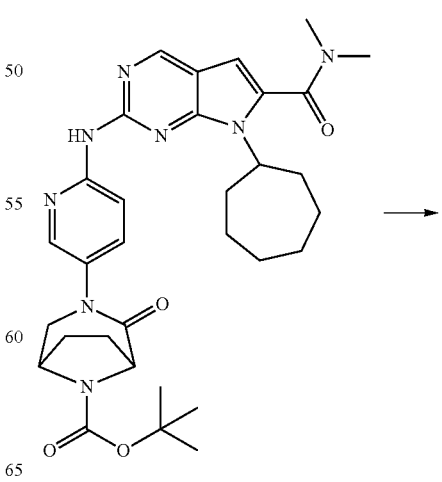

203
-continued

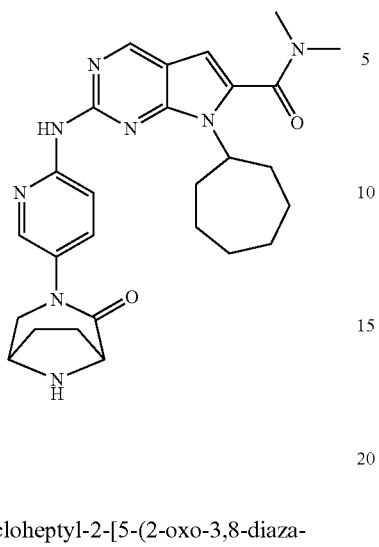

Preparation of 7-Cycloheptyl-2-[5-(2-oxo-3,8-diaza-bicyclo[3.2.1]oct-3-yl)-pyridin-2-ylamino]-7H-pyrrolo[2,3-d]pyrimidine-6-carboxylic acid dimethylamide Following deprotection method 2, 7-cycloheptyl-2-[5-(2-oxo-3,8-diaza-bicyclo[3.2.1]oct-3-yl)-pyridin-2-ylamino]-7H-pyrrolo[2,3-d]pyrimidine-6-carboxylic acid dimethylamide tert butyl ester was converted to 7-Cycloheptyl-2-[5-(2-oxo-3,8-diaza-bicyclo[3.2.1]oct-3-yl)-pyridin-2-ylamino]-7H-pyrrolo[2,3-d]pyrimidine-6-carboxylic acid dimethylamide (100 mg) in 48% yield. MS m/z 503.6 (MH$^+$); $^1$H NMR (400 MHz, DMSO-d6) δ 9.78 (s, 1H), 8.81 (s, 1H), 8.46 (d, J=9.1 Hz, 1H), 8.24 (d, J=2.5 Hz 1H), 7.70 (dd, J=9.1, 2.5 Hz 1H), 6.63 (s, 1H), 4.44 (m, 1H), 3.76-3.70 (m, 2H), 3.62 (m, 1H), 3.16 (s, 1H), 3.08 (s, 3H), 3.06 (s, 3H) 2.54 (m, 3H), 2.01-1.75 (m, 8H), 1.74-1.58 (m, 4H), 1.5-1.43 (m, 2H).

Example 81

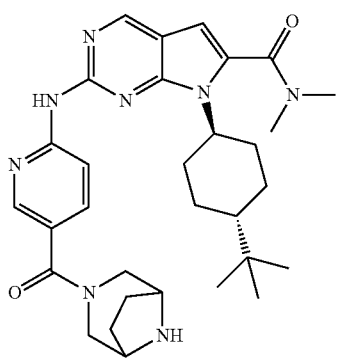 [SMILES: CN(C)C(=O)c1cc2cnc(Nc3ccc(C(=O)N4CC5CCC(C4)N5)cn3)nc2n1[C@H]1CC[C@H](C(C)(C)C)CC1]

204
7-Cycloheptyl-2-[5-(1-oxo-hexahydro-pyrrolo[3,4-c]pyrrol-2-yl)-pyridin-2-ylamino]-7H-pyrrolo[2,3-d]pyrimidine-6-carboxylic acid dimethylamide Step 1

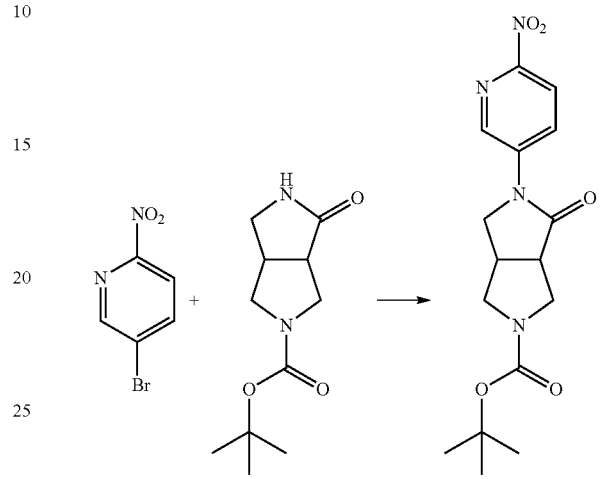

Preparation of Cis-tert-butyl 5-(6-nitropyridin-3-yl)-4-oxohexahydropyrrolo[3,4-c]pyrrole-2(1H)-carboxylate Following general N—C coupling procedure 1, 5-bromo-2-nitropyridine (4.71 g, 23.2 mmol, 1.05 eq) was combined with cis-tert-butyl 4-oxohexahydropyrrolo[3,4-c]pyrrole-2(1H)-carboxylate (5 g, 22.1 mmol, 1.0 eq), which after silica gel purification gave cis-tert-butyl 5-(6-nitropyridin-3-yl)-4-oxohexahydropyrrolo[3,4-c]pyrrole-2(1H)-carboxylate (6.3 g) in 81% yield. $^1$H NMR (400 MHz, CDCl$_3$) δ ppm 8.75 (m, 2H), 8.34 (d, J=9.09 Hz, 1H), 4.20 (dd, J1=9.85 Hz, J2=6.82 Hz, 1H), 4.02-3.85 (m, 2H), 3.80 (d, J=10.11 Hz, 1H), 3.68 (m, 1H), 1.52-1.43 (m, 3H).

Step 2

Preparation of cis-tert-butyl 5-(6-aminopyridin-3-yl)-4-oxohexahydropyrrolo[3,4-c]pyrrole-2(1H)-carboxylate Following nitro group reduction procedure 1, cis-tert-butyl 5-(6-nitropyridin-3-yl)-4-oxohexahydropyrrolo[3,4-c]pyrrole-2(1H)-carboxylate (1.05 g, 3.01 mmol.) was reduced to cis-tert-butyl 5-(6-aminopyridin-3-yl)-4-oxohexahydropyrrolo[3,4-c]pyrrole-2(1H)-carboxylate (1.0 g) in quantitative yield. $^1$H NMR (400 MHz, CDCl$_3$) δ ppm 8.09 (s, 1H), 7.95 (br s, 1H), 6.57 (d, J=9.6 Hz, 1H), 4.58 (br s, 2H), 4.04 (dd, J1=10.11 Hz, J2=6.57 Hz, 1H). 3.93 (dd, J1=11.62 Hz, J2=2.02 Hz, 1H) 3.86 (t, 1H), 3.69-3.55 (m, 2H), 3.24 (m, 2H), 3.11 (m, 1H), 1.48 (s, 9H); MS m/z 319.4 (M+H)$^+$.

Step 3

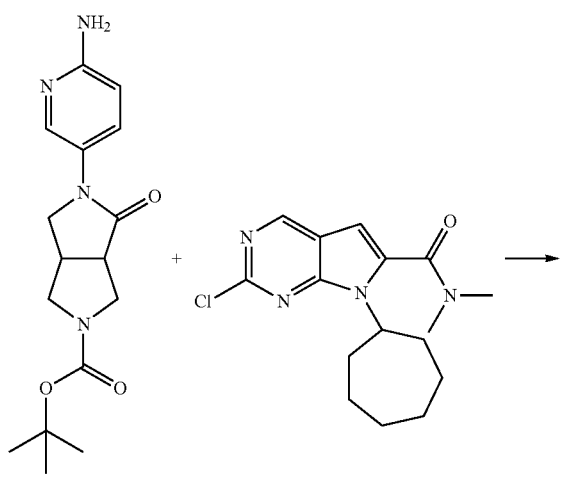

Preparation of cis-tert-butyl 5-(6-(7-cycloheptyl-6-(dimethylcarbamoyl)-7H-pyrrolo[2,3-d]pyrimidin-2-ylamino)pyridin-3-yl)-4-oxohexahydropyrrolo[3,4-c]pyrrole-2(1H)-carboxylate Following general N—C coupling procedure 1, 2-chloro-7-cycloheptyl-N,N-dimethyl-7H-pyrrolo[2,3-d]pyrimidine-6-carboxamide (50.4 mg, 0.157 mmol) was combined with cis-tert-butyl 5-(6-aminopyridin-3-yl)-4-oxohexahydropyrrolo[3,4-c]pyrrole-2(1H)-carboxylate (50 mg, 0.157 mmol, 1.0 eq), gave after silica gel chromatography, cis-tert-butyl 5-(6-(7-cycloheptyl-6-(dimethylcarbamoyl)-7H-pyrrolo[2, 3-d]pyrimidin-2-ylamino)pyridin-3-yl)-4-oxohexahydropyrrolo[3,4-c]pyrrole-2(1H)-carboxylate (90 mg) in 94% yield. $^1$H NMR (400 MHz, CDCl$_3$) δ ppm 8.76 (s, 1H), 8.65 (d, J=9.6 Hz, 1H), 8.54 (s, 1H), 8.34 (s, 1H), 8.18 (s, 1H), 6.46 (s, 1H), 4.54 (m, 1H), 4.13 (dd, J1=9.85 Hz, J2=6.82 Hz, 1H), 3.97 (d, J=10.61 Hz, 1H), 3.89 (t, J=9.85 Hz, 1H), 3.62-3.76 (m, 2H), 3.06-3.40 (m, 9H), 2.65 (q, J=10.95 Hz, 2H), 2.02 (m, 2H), 1.89 (m, 2H), 1.74 (m, 4H), 1.60 (m, 2H), 1.49 (m, 9H). MS m/z 603.6 (M+H)$^+$.

Step 4

Preparation of 7-cycloheptyl-N,N-dimethyl-2-(5-(cis-1-oxohexahydropyrrolo[3,4-c]pyrrol-2(1H)-yl)pyridin-2-ylamino)-7H-pyrrolo[2, 3-d]pyrimidine-6-carboxamide Following deprotection method 2, 7-Cycloheptyl-N,N-dimethyl-2-(5-(cis-1-oxohexahydropyrrolo[3,4-c]pyrrol-2(1H)-yl)pyridin-2-ylamino)-7H-pyrrolo[2,3-d]pyrimidine-6-carboxamide was obtained after purification (64 mg) in 85% yield. $^1$H NMR (400 MHz, CDCl$_3$) δ ppm 8.73 (s, 1H), 8.62 (d, J=9.6 Hz, 1H), 8.42 (d, J=2.53 Hz, 1H), 8.26 (dd, J1=9.09, J2=3.03 Hz, 1H), 8.01 (s, 1H), 7.28 (s, 1H), 6.45 (s, 1H), 4.54 (m, 1H), 4.17 (m, 1H), 3.63 (dd, J1=9.60, J2=3.03 Hz, 1H), 3.53 (m, 1H), 3.31-3.12 (m, 8H), 3.11-2.92 (m, 2H), 2.64 (m, 2H), 2.02 (m, 2H), 1.88 (m, 2H), 1.81-1.67 (m, 5H), 1.59 (m, 2H); HRMS m/z 503.2889 (M+H)$^+$.

Step 5

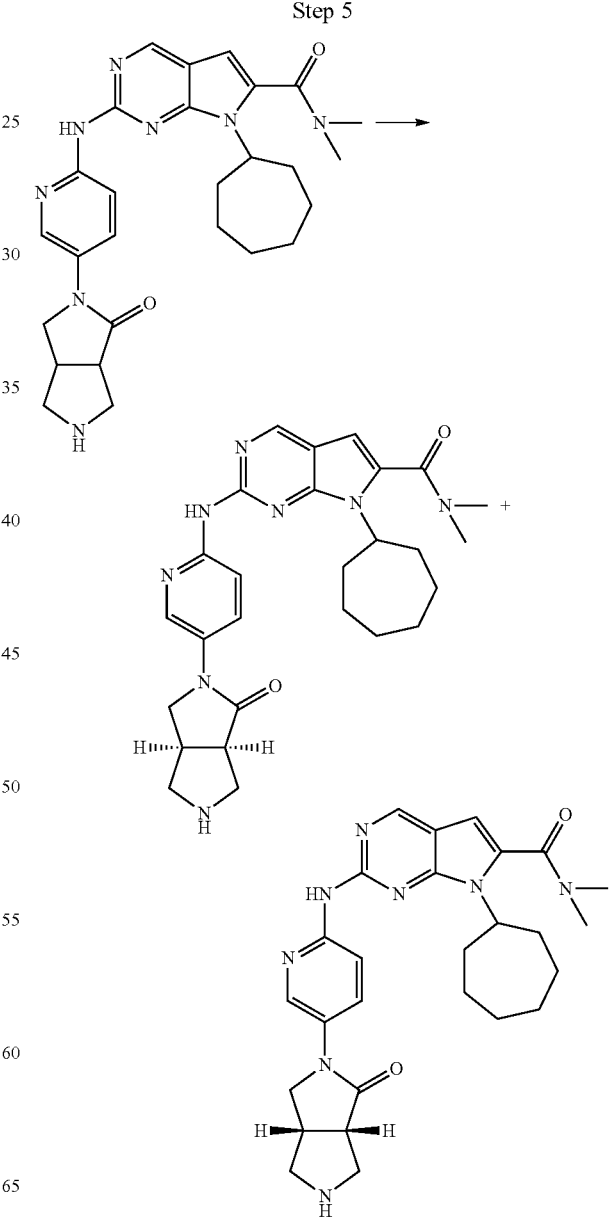

7-Cycloheptyl-N,N-dimethyl-2-(5-(cis-1-oxohexahydropyrrolo[3,4-c]pyrrol-2(1H)-yl)pyridin-2-ylamino)-7H-pyrrolo[2,3-d]pyrimidine-6-carboxamide (56 mg), a cis racemic compound was separated by CHIRALPAK® AS-H chiral column. The separation Mobil phase was 30% MeOH with 0.2% DEA. Two peaks were collected. The faster moving enantiomer was collected as enantiomer-1 (23 mg, 38% yield) and the slower moving enantiomer as enantiomer-2 (25 mg, 43% yield).

Example 82

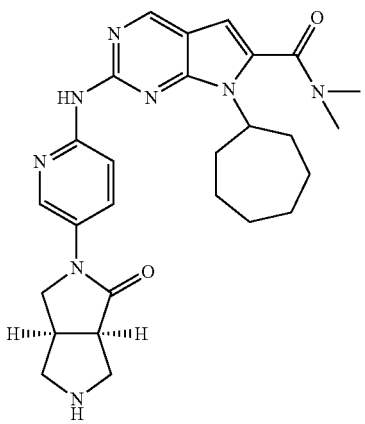 [SMILES: CN(C)C(=O)c1cc2cnc(Nc3ccc(N4C[C@@H]5CNC[C@@H]5C4=O)cn3)nc2n1C1CCCCCC1]

7-cycloheptyl-N,N-dimethyl-2-(5-((3aS,6aR)-1-oxo-hexahydropyrrolo[3,4-c]pyrrol-2(1H)-yl)pyridin-2-ylamino)-7H-pyrrolo[2,3-d]pyrimidine-6-carboxamide. Enantiomer-1

$^1$H NMR (400 MHz, CDCl$_3$) δ ppm 8.73 (s, 1H), 8.62 (d, J=9.09 Hz, 1H), 8.42 (d, J=2.53 Hz, 1H), 8.26 (dd, J1=9.35, J2=2.78 Hz, 1H), 8.02 (s, 1H), 7.28 (s, 1H), 6.45 (s, 1H), 4.54 (m, 1H), 4.17 (m, 1H), 3.63 (dd, J1=9.85, J2=2.78 Hz, 1H), 3.53 (m, 1H), 3.31-3.12 (m, 8H), 3.11-2.94 (m, 2H), 2.64 (m, 2H), 2.02 (m, 2H), 1.88 (m, 2H), 1.81-1.67 (m, 5H), 1.59 (m, 2H); HRMS m/z 503.2882 (M+H)$^+$.

Example 83

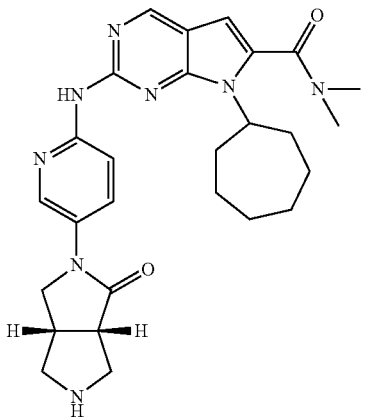 [SMILES: CN(C)C(=O)c1cc2cnc(Nc3ccc(N4C[C@H]5CNC[C@H]5C4=O)cn3)nc2n1C1CCCCCC1]

7-cycloheptyl-N,N-dimethyl-2-(5-((3aR,6aS)-1-oxo-hexahydropyrrolo[3,4-c]pyrrol-2(1H)-yl)pyridin-2-ylamino)-7H-pyrrolo[2,3-d]pyrimidine-6-carboxamide. Enantiomer-2

$^1$H NMR (400 MHz, CDCl$_3$) δ ppm 8.73 (s, 1H), 8.62 (d, J=9.09 Hz, 1H), 8.42 (d, J=2.53 Hz, 1H), 8.26 (dd, J1=8.84, J2=2.78 Hz, 1H), 8.00 (s, 1H), 7.28 (s, 1H), 6.45 (s, 1H), 4.54 (m, 1H), 4.17 (m, 1H), 3.63 (dd, J1=9.85, J2=2.78 Hz, 1H), 3.53 (m, 1H), 3.31-3.12 (m, 8H), 3.11-2.94 (m, 2H), 2.64 (m, 2H), 2.02 (m, 2H), 1.88 (m, 2H), 1.81-1.67 (m, 5H), 1.59 (m, 2H); HRMS m/z 503.2890 (M+H)$^+$.

Example 84

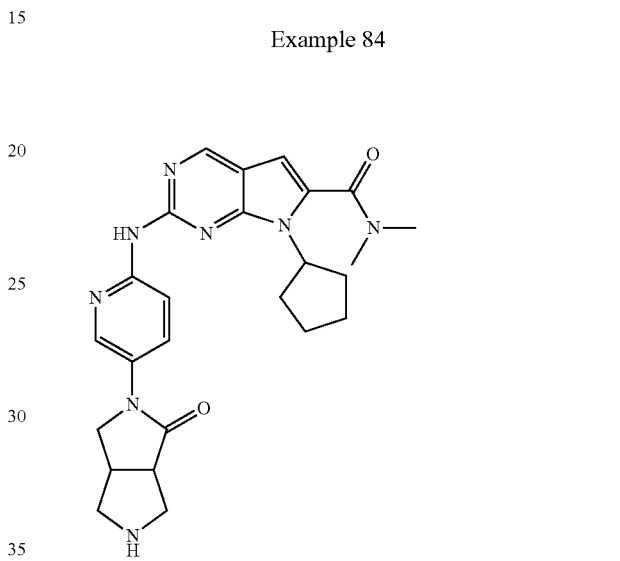

7-cyclopentyl-N,N-dimethyl-2-(5-cis-1-oxohexahydropyrrolo[3,4-c]pyrrol-2(1H)-yl)pyridin-2-ylamino)-7H-pyrrolo[2,3-d]pyrimidine-6-carboxamide Step 1

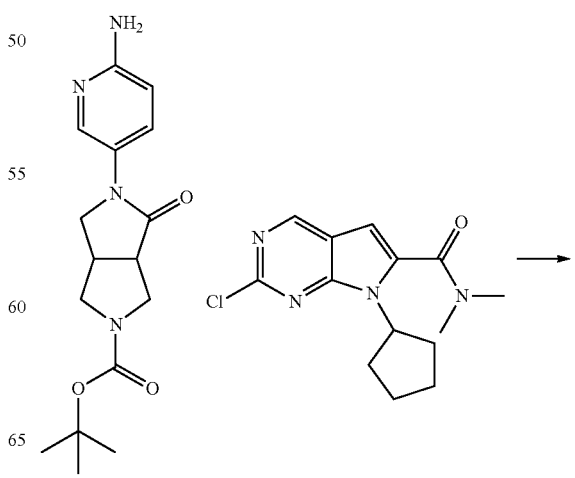

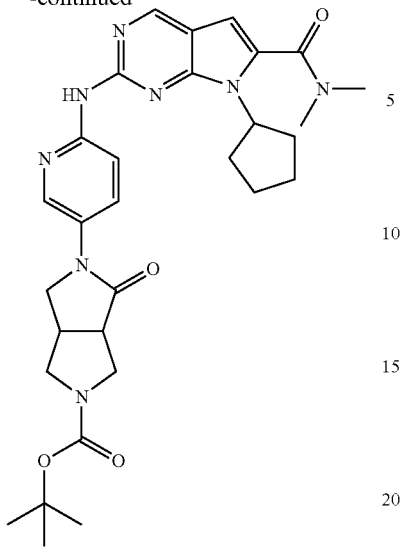

7-cyclopentyl-N,N-dimethyl-2-(5-cis-1-oxohexahydropyrrolo[3,4-c]pyrrol-2(1H)-yl)pyridin-2-ylamino)-7H-pyrrolo[2,3-d]pyrimidine-6-carboxamide Following general N—C coupling procedure 1, 2-chloro-7-cyclopentyl-N,N-dimethyl-7H-pyrrolo[2,3-d]pyrimidine-6-carboxamide and cis-tert-butyl 5-(6-aminopyridin-3-yl)-4-oxohexahydropyrrolo[3,4-c]pyrrole-2(1H)-carboxylate were combined to give after purification cis-tert-butyl 5-(6-(7-cyclopentyl-6-(dimethylcarbamoyl)-7H-pyrrolo[2,3-d]pyrimidin-2-ylamino)pyridin-3-yl)-4-oxohexahydropyrrolo[3,4-c]pyrrole-2(1H)-carboxylate carboxylate (82 mg) in 89% yield. $^1$H NMR (400 MHz, CDCl$_3$) δ ppm 8.74 (s, 1H), 8.52 (d, J=9.09 Hz, 1H), 8.40 (s, 1H), 8.17 (br s, 1H), 8.08 (s, 1H), 6.46 (s, 1H), 4.81 (m, 1H), 4.11 (dd, J1=10.11 Hz, J2=6.57 Hz, 1H), 3.96 (d, J=11.62 Hz, 1H), 3.88 (t, J=9.60 Hz, 1H), 3.67 (m, 2H), 3.28 (m, 2H), 3.14 (m, 7H), 2.58 (m, 2H), 2.08 (m, 4H), 1.74 (m, 2H), 1.48 (m, 9H). LCMS m/z 575.6 (M+H)$^+$.

Step 2

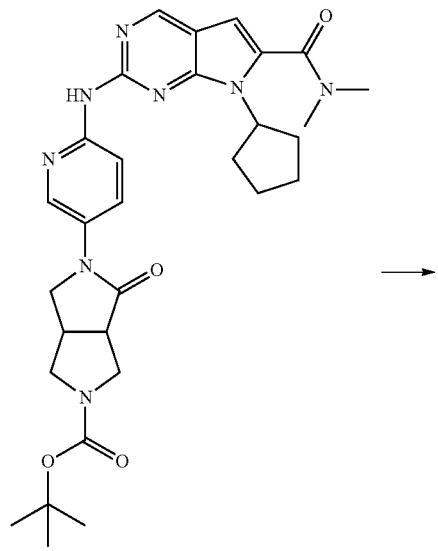

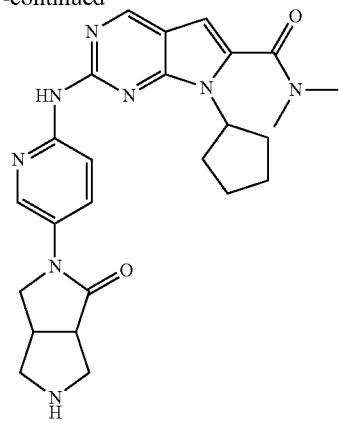

Following deprotection method 2, 7-cyclopentyl-N,N-dimethyl-2-(5-cis-1-oxohexahydropyrrolo[3,4-c]pyrrol-2(1H)-yl)pyridin-2-ylamino)-7H-pyrrolo[2,3-d]pyrimidine-6-carboxamide (61 mg) was obtained in 90% yield. $^1$H NMR (400 MHz, CDCl$_3$) δ ppm 8.75 (s, 1H), 8.51 (d, J=9.09 Hz, 1H), 8.44 (d, J=2.53 Hz, 1H), 8.23 (dd, J1=9.09, J2=2.53 Hz, 1H), 8.13 (s, 1H), 6.47 (s, 1H), 4.82 (m, 1H), 4.16 (m, 1H), 3.62 (dd, J1=10.11, J2=3.03 Hz, 1H), 3.53 (dd, J1=11.12, J2=2.02 Hz, 1H), 3.29-3.13 (m, 8H), 3.08-2.98 (m, 2H), 2.59 (m, 2H), 2.08 (m, 5H), 1.75 (m, 2H)

HRMS m/z 475.2591 (M+H)$^+$.

Step 3

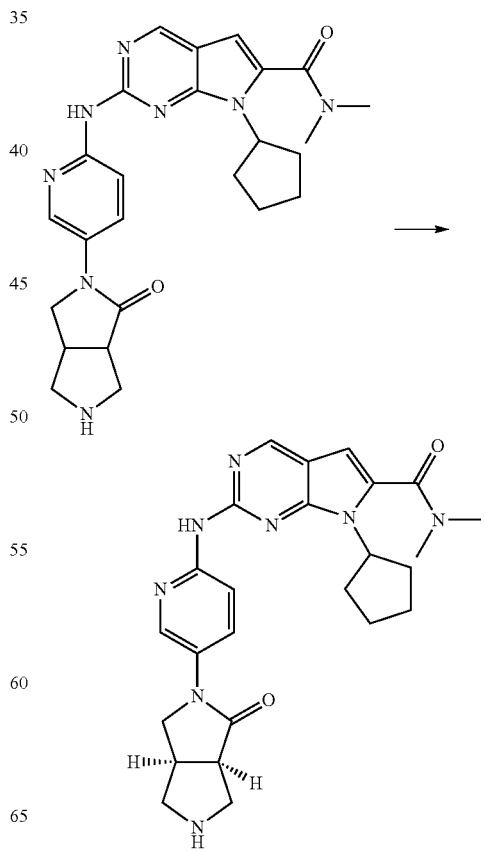

-continued

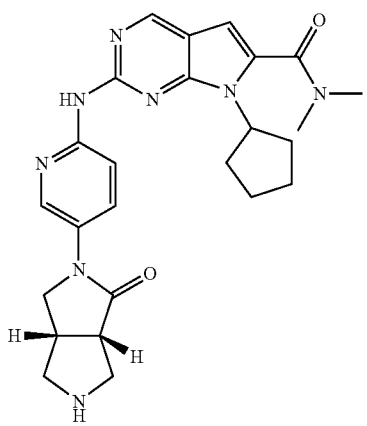

7-cyclopentyl-N,N-dimethyl-2-(5-cis-1-oxohexahydropyrrolo[3,4-c]pyrrol-2(1H)-yl)pyridin-2-ylamino)-7H-pyrrolo[2,3-d]pyrimidine-6-carboxamide (52 mg), was separated by CHIRALPAK® AS-H chiral column. The separation Mobil phase was 35% MeOH with 0.2% DEA. Two peaks were collected. The faster moving enantiomer was collected as enantiomer-1 (15 mg, 29% yield) and the slower moving enantiomer as enantiomer-2 (18 mg, 34% yield).

Example 85

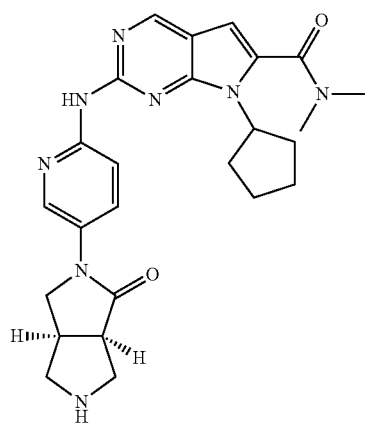 [SMILES: CN(C)C(=O)c1cc2cnc(Nc3ccc(N4C[C@@H]5CNC[C@@H]5C4=O)cn3)nc2n1C1CCCC1]

7-cyclopentyl-N,N-dimethyl-2-(5-((3aS,6aR)-1-oxo-hexahydropyrrolo[3,4-c]pyrrol-2(1H)-yl)pyridin-2-ylamino)-7H-pyrrolo[2,3-d]pyrimidine-6-carboxamide. Enantiomer-1

$^1$H NMR (400 MHz, CDCl$_3$) δ ppm 8.75 (s, 1H), 8.51 (d, J=9.09 Hz, 1H), 8.44 (d, J=2.53 Hz, 1H), 8.23 (dd, J=9.09, 3.03 Hz, 1H), 8.06 (s, 1H), 6.47 (s, 1H), 4.82 (m, 1H), 4.17 (m, 1H), 3.64 (dd, J1=9.85, J2=2.78 Hz, 1H), 3.55 (d, J=11.12, 1H), 3.29-3.13 (m, 8H), 3.08-2.98 (m, 2H), 2.59 (m, 2H), 2.09 (m, 5H), 1.75 (m, 2H)

HRMS m/z 475.2568 (M−1-H)$^+$.

Example 86

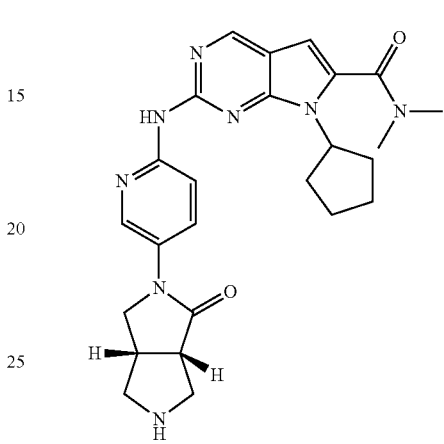

7-cyclopentyl-N,N-dimethyl-2-(5-((3aR,6aS)-1-oxo-hexahydropyrrolo[3,4-c]pyrrol-2(1H)-yl)pyridin-2-ylamino)-7H-pyrrolo[2,3-d]pyrimidine-6-carboxamide. Enantiomer-2

$^1$H NMR (400 MHz, CDCl$_3$) δ ppm 8.74 (s, 1H), 8.51 (d, J=9.09 Hz, 1H), 8.42 (d, J=2.53 Hz, 1H), 8.24 (dd, J1=9.09, J2=2.53 Hz, 1H), 8.01 (s, 1H), 6.47 (s, 1H), 4.82 (m, 1H), 4.17 (m, 1H), 3.62 (dd, J=9.85, 2.78 Hz, 1H), 3.53 (d, J=11.62, 1H), 3.29-3.13 (m, 8H), 3.08-2.98 (m, 2H), 2.59 (m, 2H), 2.09 (m, 5H), 1.75 (m, 2H)

HRMS m/z 475.2573 (M+H)$^+$.

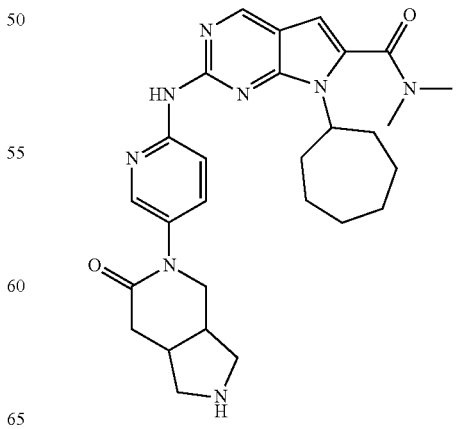

Example 87 cis-tert-butyl 5-(6-(7-cycloheptyl-6-(dimethylcarbamoyl)-7H-pyrrolo[2,3-d]pyrimidin-2-ylamino)pyridin-3-yl)-6-oxohexahydro-1H-pyrrolo[3,4-c]pyridine-2(3H)-carboxylate

Step 1

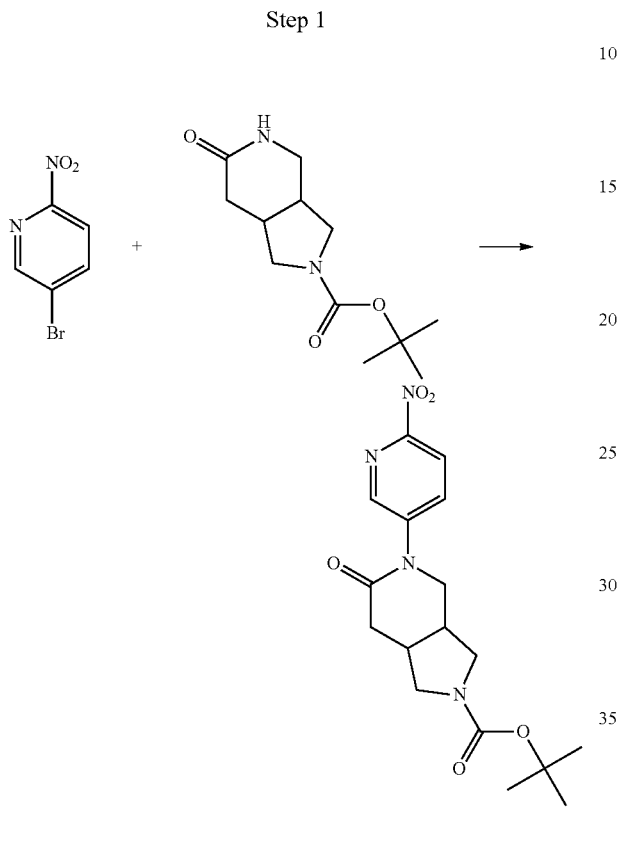

Cis-tert-butyl 5-(6-nitropyridin-3-yl)-6-oxohexahydro-1H-pyrrolo[3,4-c]pyridine-2(3H)-carboxylate Following general N—C coupling procedure 1, 5-bromo-2-nitropyridine and cis-tert-butyl 6-oxohexahydro-1H-pyrrolo[3,4-c]pyridine-2(3H)-carboxylate were combined and gave after purification cis-tert-butyl 5-(6-nitropyridin-3-yl)-6-oxohexahydro-1H-pyrrolo[3,4-c]pyridine-2(3H)-carboxylate (1.0 g) in 85% yield. $^1$H NMR (400 MHz, CDCl$_3$) δ ppm 8.58 (d, J=2.53 Hz, 1H), 8.28 (d, J=8.59 Hz, 1H), 8.07 (dd, J1=8.84, J2=2.27 Hz, 1H), 4.18-3.61 (m, 4H), 3.29 (m, 2H), 2.85 (m, 3H), 2.55 (m, 1H), 1.47 (s, 9H)

LCMS m/z 362.8 (M+H)$^+$.

Step 2

Preparation of cis-tert-butyl 5-(6-aminopyridin-3-yl)-6-oxohexahydro-1H-pyrrolo[3,4-c]pyridine-2(3H)-carboxylate Following nitro group reduction procedure 1, cis-tert-butyl 5-(6-aminopyridin-3-yl)-6-oxohexahydro-1H-pyrrolo[3,4-c]pyridine-2(3H)-carboxylate was obtained (300 mg) in 96% yield. $^1$H NMR (400 MHz, CDCl$_3$) δ ppm 7.93 (d, J=2.02 Hz, 1H), 7.45 (dd, J1=9.09, J2=2.53 Hz, 1H), 6.59 (d, J=9.09 Hz, 1H), 4.92 (br s, 2H), 3.83-3.00 (m, 6H), 2.91-2.66 (m, 3H), 2.48 (dd, J1=16.42, J2=5.81 Hz, 1H). LCMS m/z 332.8 (M+H)$^+$.

Step 3

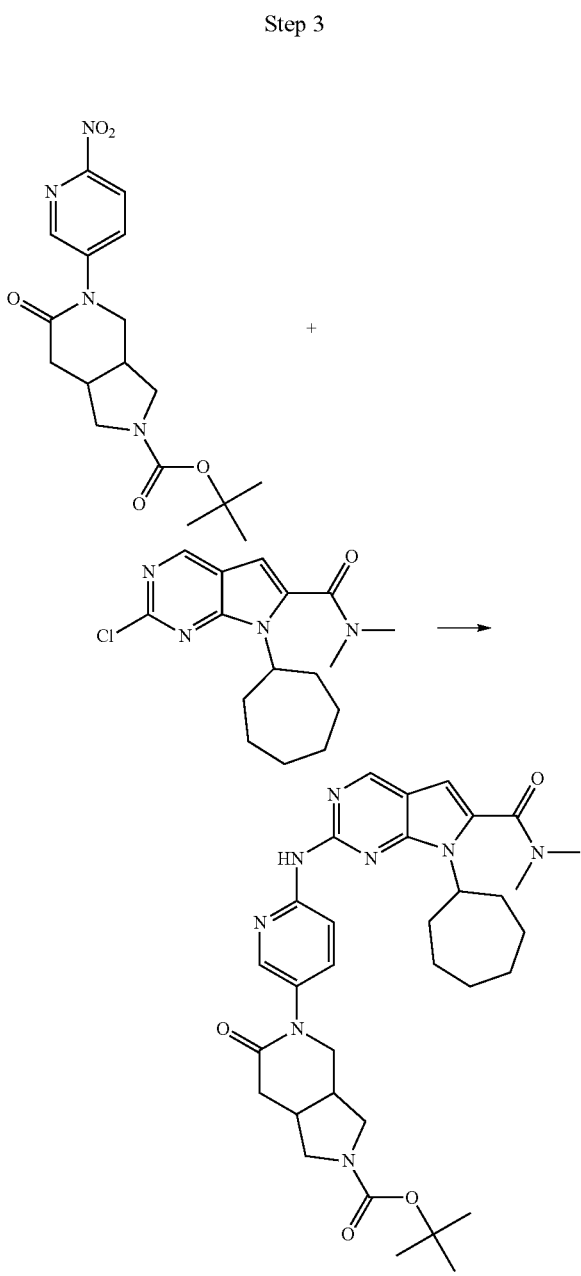

Preparation of 7-cycloheptyl-N,N-dimethyl-2-(5-(cis-6-oxotetrahydro-1H-pyrrolo[3,4-c]pyridin-5(6H,7H,7aH)-yl)pyridin-2-ylamino)-7H-pyrrolo[2,3-d]pyrimidine-6-carboxamide Following general N—C coupling procedure 1, 2-chloro-7-cycloheptyl-N,N-dimethyl-7H-pyrrolo[2,3-d]pyrimidine-6-carboxamide and cis-tert-butyl 5-(6-aminopyridin-3-yl)-6-oxohexahydro-1H-pyrrolo[3,4-c]pyridine-2(3H)-carboxylate were combined and gave after purification cis-tert-butyl 5-(6-(7-cycloheptyl-6-(dimethylcarbamoyl)-7H-pyrrolo[2,3-d]pyrimidin-2-ylamino)pyridin-3-yl)-6-oxohexahydro-1H-pyrrolo[3,4-c]pyridine-2(3H)- carboxylate (85 mg) in 86% yield. $^1$H NMR (400 MHz, CDCl$_3$) δ ppm 8.77 (s, 1H), 8.66 (d, J=9.09 Hz, 1H), 8.48 (br s, 1H), 8.24 (s, 1H), 7.64 (dd, J1=9.09 Hz, J2=2.53 Hz, 1H), 6.45 (s, 1H), 4.53 (m, 1H), 3.84 (dd, J1=13.14 Hz, J2=5.56 Hz, 1H), 3.70 (m, 3H), 3.31 (m, 2H), 3.17 (s, 6H), 2.82 (m, 3H), 2.63 (m, 2H), 2.51 (dd, J1=16.42 Hz, J2=5.81 Hz, 1H), 2.01 (m, 2H), 1.87 (m, 2H), 1.73 (m, 4H), 1.58 (m, 2H), 1.48 (s, 9H). LCMS m/z 617.7 (M+H)$^+$.

Step 4

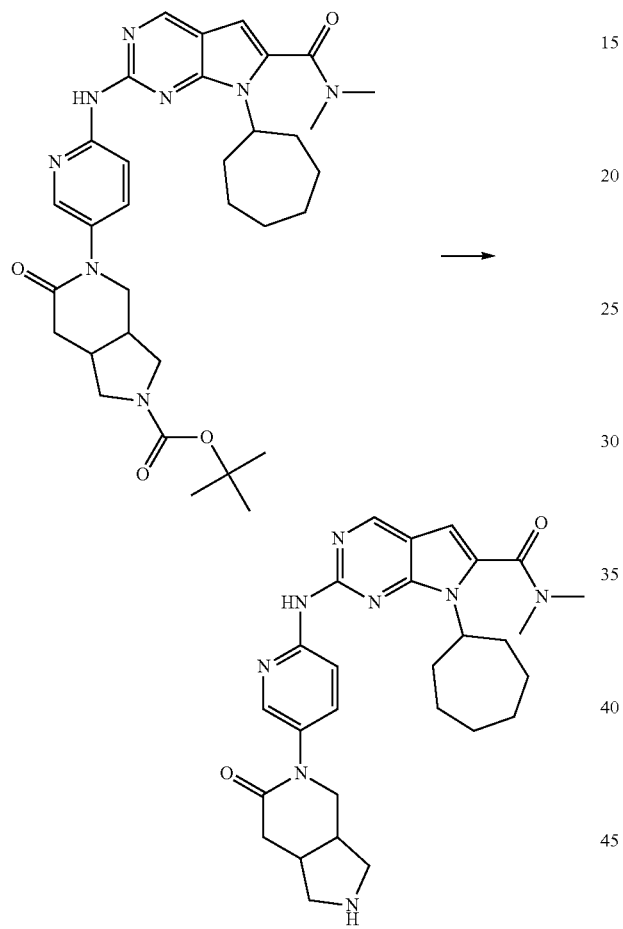

Preparation of 7-cycloheptyl-N,N-dimethyl-2-(5-(cis-6-oxotetrahydro-1H-pyrrolo[3,4-c]pyridin-5(6H,7H,7aH)-yl)pyridin-2-ylamino)-7H-pyrrolo[2,3-d]pyrimidine-6-carboxamide Following deprotection method 2, 7-cycloheptyl-N,N-dimethyl-2-(5-(cis-6-oxotetrahydro-1H-pyrrolo[3,4-c]pyridin-5(6H, 7H, 7aH)-yl)pyridin-2-ylamino)-7H-pyrrolo[2,3-d]pyrimidine-6-carboxamide (64 mg) was obtained in 89% yield. $^1$H NMR (400 MHz, CDCl$_3$) δ ppm 8.74 (s, 1H), 8.64 (d, J=9.09 Hz, 1H), 8.24 (d, J=2.53 Hz, 1H), 8.19 (s, 1H), 7.68 (dd, J1=8.84, J2=2.78 Hz, 1H), 6.46 (s, 1H), 4.54 (m, 1H), 3.88 (dd, J1=13.14, J2=4.04 Hz, 1H), 3.63 (dd, J1=13.14, J2=5.05 Hz, 1H), 3.29 (m, 2H), 3.18 (s, 6H), 2.84-2.50 (m, 7H), 2.02 (m, 2H), 1.93-1.66 (m, 7H), 1.58 (m, 2H). HRMS m/z 517.3062 (M+H)$^+$.

Step 5

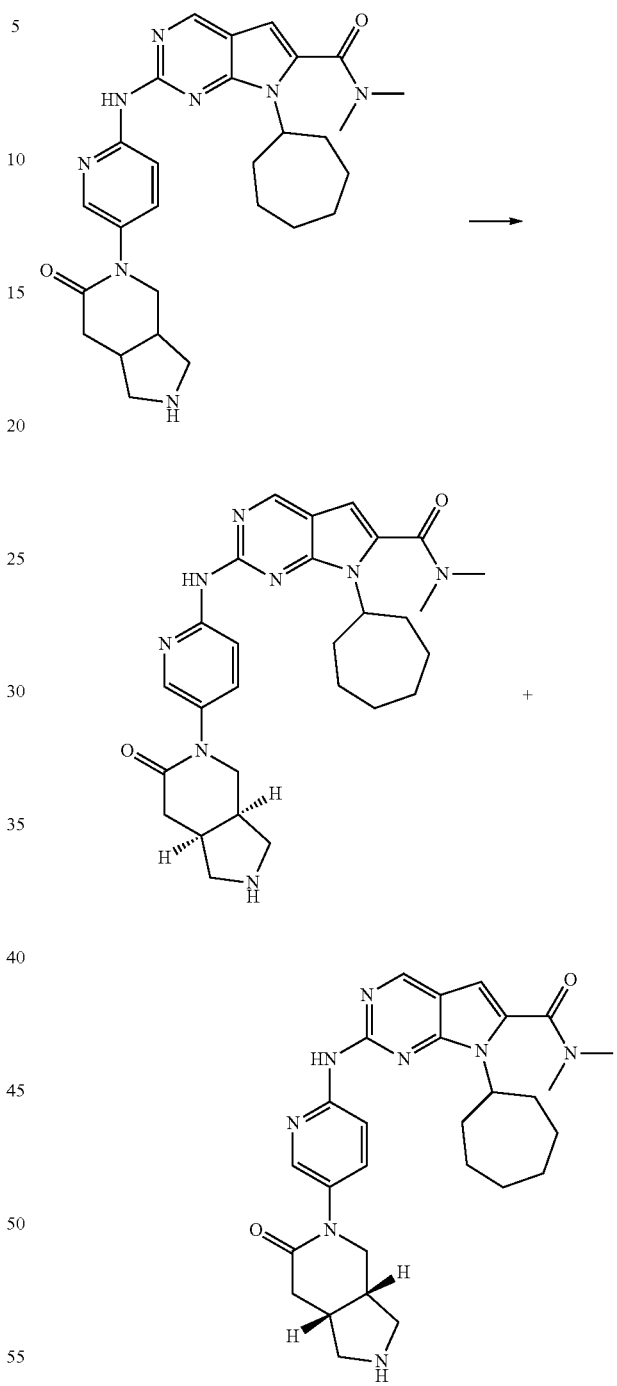

7-Cycloheptyl-N,N-dimethyl-2-(5-(cis-6-oxotetrahydro-1H-pyrrolo[3,4-c]pyridin-5(6H,7H,7aH)-yl)pyridin-2-ylamino)-7H-pyrrolo[2,3-d]pyrimidine-6-carboxamide (56 mg), a cis racemic compound was seperated by CHIRAL-PAK® AD-H chiral column. The separation Mobil phase was 35% MeOH with 0.2% DEA. Two peaks were collected. The faster moving enantiomer was collected as enantiomer-1 (16 mg, 28% yield) and the slower moving enantiomer as enantiomer-2 (16 mg, 28% yield). The absolute stereo configurations were not determined.

217

Example 88

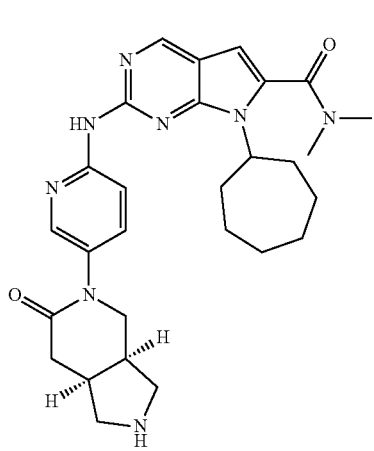 [SMILES: CN(C)C(=O)c1cc2cnc(Nc3ccc(N4C[C@H]5CNC[C@H]5CC4=O)cn3)nc2n1C1CCCCCC1]

7-cycloheptyl-N,N-dimethyl-2-(5-(cis-6-oxotetrahydro-1H-pyrrolo[3,4-c]pyridin-5(6H, 7H, 7a H)-yl)pyridin-2-ylamino)-7H-pyrrolo[2,3-d]pyrimidine-6-carboxamide. Enantiomer-1

$^1$H NMR (400 MHz, CDCl$_3$) δ ppm 8.78 (s, 1H), 8.66 (d, J=9.09 Hz, 1H), 8.46 (s, 1H), 8.29 (d, J=2.02 Hz, 1H), 8.19 (s, 1H), 7.68 (dd, J1=8.84, J2=2.78 Hz, 1H), 6.46 (s, 1H), 4.54 (m, 1H), 3.90 (dd, J1=12.63, J2=4.04 Hz, 1H), 3.71 (dd, J1=13.14, J2=4.55 Hz, 1H), 3.37 (m, 2H), 3.19 (s, 6H), 2.94-2.57 (m, 7H), 2.02 (m, 2H), 1.96-1.65 (m, 7H), 1.58 (m, 2H). HRMS m/z 517.3051 (M+H)$^+$.

Example 89

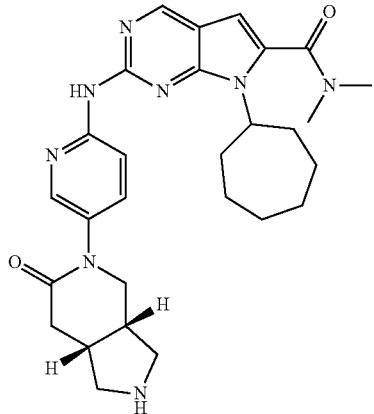 [SMILES: CN(C)C(=O)c1cc2cnc(Nc3ccc(N4C[C@@H]5CNC[C@@H]5CC4=O)cn3)nc2n1C1CCCCCC1]

7-cycloheptyl-N,N-dimethyl-2-(5-(cis-6-oxotetrahydro-1H-pyrrolo[3,4-c]pyridin-5(6H,7H,7aH)-yl)pyridin-2-ylamino)-7H-pyrrolo[2,3-d]pyrimidine-6-carboxamide. Enantiomer-2. $^1$H NMR (400 MHz, CDCl$_3$) δ ppm 8.75 (s, 1H), 8.63 (d, J=9.09 Hz, 1H), 8.35 (s, 1H), 8.25 (d, J=2.53 Hz, 1H), 7.66 (dd, J1=9.09, J2=2.53 Hz, 1H), 6.44 (s, 1H), 4.53 (m, 1H), 3.87 (dd, J1=13.39, J2=4.29 Hz, 1H), 3.64 (dd, J1=13.14, J2=5.56 Hz, 1H), 3.30 (m, 2H), 3.17 (s, 6H), 2.87-2.50 (m, 7H), 2.04 (m, 2H), 1.86 (m, 2H), 1.73 (m, 3H), 1.58 (m, 2H). HRMS m/z 517.3044 (M+H)$^+$.

218

Example 90

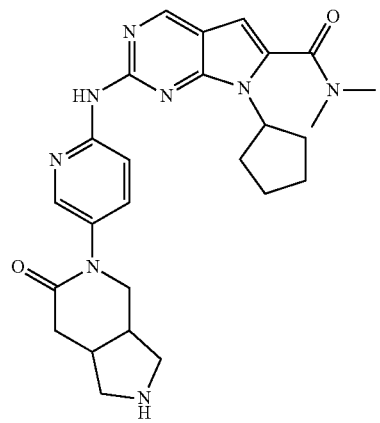 [SMILES: CN(C)C(=O)c1cc2cnc(Nc3ccc(N4CC5CNCC5CC4=O)cn3)nc2n1C1CCCC1]

Step 1

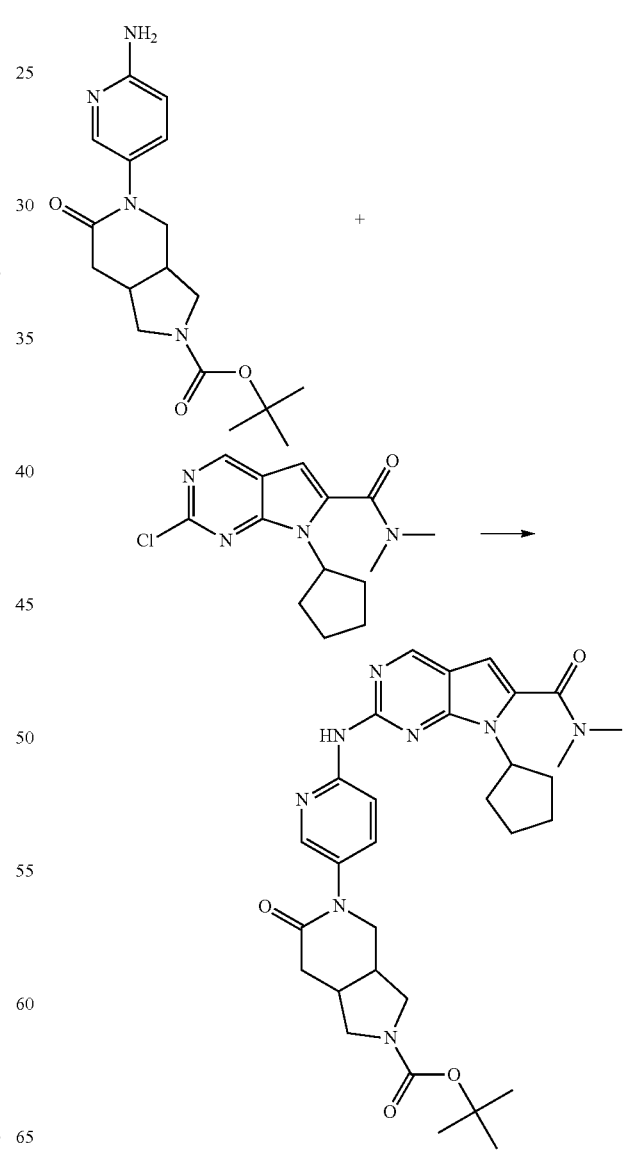

7-cyclopentyl-N,N-dimethyl-2-(5-(cis-6-oxotetrahydro-1H-pyrrolo[3,4-c]pyridin-5(6H,7H,7aH)-yl)pyridin-2-ylamino)-7H-pyrrolo[2,3-d]pyrimidine-6-carboxamide Following general N—C coupling procedure 1, 2-chloro-7-cyclopentyl-N,N-dimethyl-7H-pyrrolo[2,3-d]pyrimidine-6-carboxamide and cis-tert-butyl 5-(6-aminopyridin-3-yl)-6-oxohexahydro-1H-pyrrolo[3,4-c]pyridine-2(3H)-carboxylate were combined and gave after purification cis-tert-butyl 5-(6-(7-cyclopentyl-6-(dimethylcarbamoyl)-7H-pyrrolo[2,3-d]pyrimidin-2-ylamino)pyridin-3-yl)-6-oxohexahydro-1H-pyrrolo[3,4-c]pyridine-2(3H)-carboxylate (81 mg) in 86% yield. $^1$H NMR (400 MHz, CDCl$_3$) δ ppm 8.79 (s, 1H), 8.56 (s, 1H), 8.53 (s, 1H), 8.24 (d, J=2.53 Hz, 1H), 7.63 (dd, J1=9.09 Hz, J2=2.53 Hz, 1H), 6.46 (s, 1H), 4.81 (m, 1H), 3.84 (dd, J1=13.14 Hz, J2=5.56 Hz, 1H), 3.78-3.63 (m, 3H), 3.49-3.21 (m, 2H), 3.16 (s, 6H), 2.79 (m, 3H), 2.55 (m, 3H), 2.07 (m, 4H), 1.72 (m, 2H), 1.48 (s, 9H). LCMS m/z 589.6 (M+H)$^+$.

Step 2

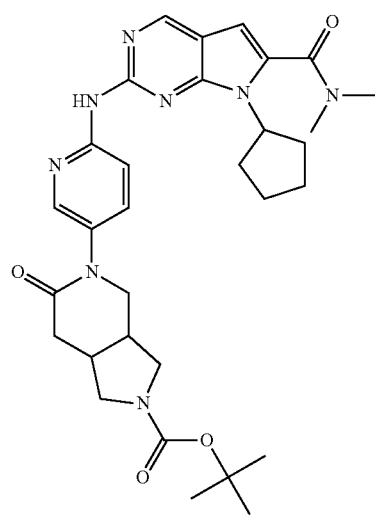

Following deprotection method 2, 7-cyclopentyl-N,N-dimethyl-2-(5-(cis-6-oxotetrahydro-1H-pyrrolo[3,4-c]pyridin-5(6H,7H,7aH)-yl)pyridin-2-ylamino)-7H-pyrrolo[2,3-d]pyrimidine-6-carboxamide (64 mg) was obtained in 86% yield. $^1$H NMR (400 MHz, CDCl$_3$) δ ppm 8.74 (s, 1H), 8.52 (d, J=8.59 Hz, 1H), 8.22 (d, J=2.53 Hz, 1H), 8.09 (s, 1H), 7.66 (dd, J1=8.84 Hz, 0.12=2.78 Hz, 1H), 6.46 (s, 1H), 4.81 (m, 1H), 3.87 (dd, J1=12.88 Hz, J2=4.29 Hz, 1H), 3.63 (dd, J1=12.88 Hz, J2=5.31 Hz, 1H), 3.30 (m, 2H), 3.17 (m, 6H), 2.87-2.49 (m, 7H), 2.07 (m, 5H), 1.73 (m, 2H); HRMS m/z 489.2727 (M+H)$^+$.

Step 3

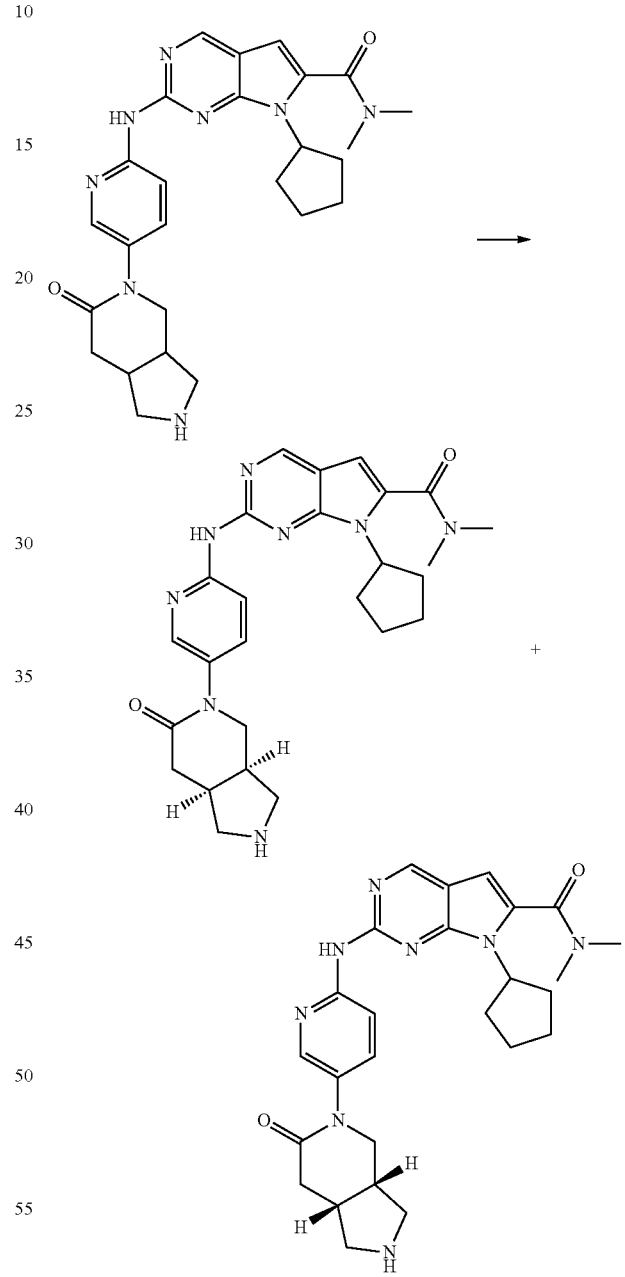

7-Cyclopentyl-N,N-dimethyl-2-(5-(cis-6-oxotetrahydro-1H-pyrrolo[3,4-c]pyridin-5(6H,7H, 7aH)-yl)pyridin-2-ylamino)-7H-pyrrolo[2,3-d]pyrimidine-6-carboxamide (56 mg), a cis racemic compound was chirally separated by CHIRALPAK® AD-H chiral column. The separation Mobil phase was 40% IPA with 0.2% DEA. Two peaks were collected. The faster moving enantiomer was collected as enantiomer-1 (16 mg, 28% yield) and the slower moving enantiomer was as enantiomer-2 (17 mg, 30% yield). The absolute stereo configurations were not determined.

Example 91

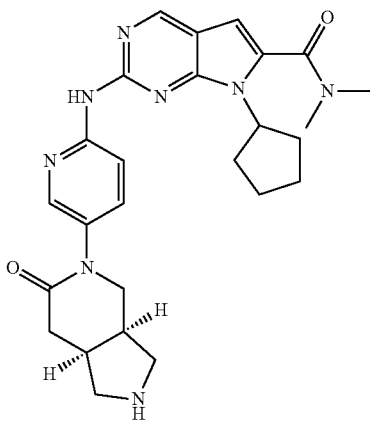 [SMILES: CN(C)C(=O)c1cc2cnc(Nc3ccc(N4C[C@H]5CNC[C@H]5CC4=O)cn3)nc2n1C1CCCC1]

7-cyclopentyl-N,N-dimethyl-2-(5-(cis-6-oxotetrahydro-1H-pyrrolo[3,4-c]pyridin-5(6H,7H,7aH)-yl)pyridin-2-ylamino)-7H-pyrrolo[2,3-d]pyrimidine-6-carboxamide $^1$H NMR (400 MHz, CDCl$_3$) δ ppm 8.76 (s, 1H), 8.53 (d, J=9.09 Hz, 1H), 8.27 (m, 2H), 7.66 (dd, J1=9.09 Hz, J2=2.53 Hz, 1H), 6.47 (s, 1H), 4.81 (m, 1H), 3.88 (d, J=13.64 Hz, 1H), 3.66 (dd, J1=13.14 Hz, J2=5.05 Hz, 1H), 3.34 (m, 2H), 3.17 (m, 6H), 2.91-2.53 (m, 7H), 2.07 (m, 5H), 1.73 (m, 2H); HRMS m/z 489.2726 (M+H)$^+$.

Example 92

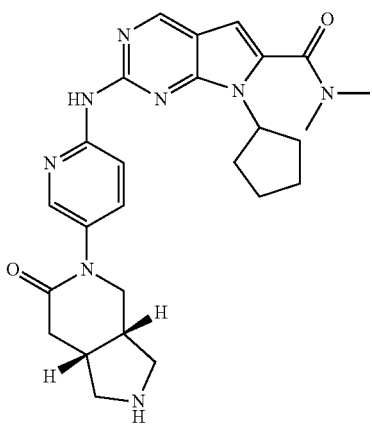 [SMILES: CN(C)C(=O)c1cc2cnc(Nc3ccc(N4C[C@@H]5CNC[C@@H]5CC4=O)cn3)nc2n1C1CCCC1]

7-cyclopentyl-N,N-dimethyl-2-(5-(cis-6-oxotetrahydro-1H-pyrrolo[3,4-c]pyridin-5(6H,7H,7aH)-yl)pyridin-2-ylamino)-7H-pyrrolo[2,3-d]pyrimidine-6-carboxamide $^1$H NMR (400 MHz, CDCl$_3$) δ ppm 8.75 (s, 1H), 8.52 (d, J=9.09 Hz, 1H), 8.24 (m, 2H), 7.66 (dd, J1=9.09 Hz, J2=2.53 Hz, 1H), 6.46 (s, 1H), 4.81 (m, 1H), 3.88 (dd, J1=13.14 Hz, J2=4.55 Hz, 1H), 3.65 (dd, J1=13.39 Hz, J2=4.80 Hz, 1H), 3.32 (m, 2H), 3.17 (m, 6H), 2.89-2.52 (m, 7H), 2.07 (m, 5H), 1.74 (m, 2H); HRMS m/z 489.2726 (M+H)$^+$.

Example 93

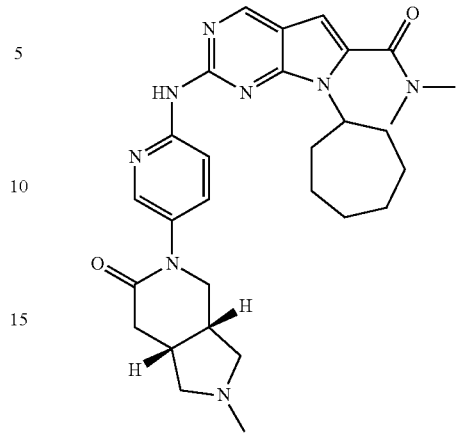

Preparation of 7-cycloheptyl-N,N-dimethyl-2-(5-((3aS,7aR)-2-methyl-6-oxotetrahydro-1H-pyrrolo[3,4-c]pyridin-5(6H,7H,7aH)-yl)pyridin-2-ylamino)-7H-pyrrolo[2,3-d]pyrimidine-6-carboxamide To a solution of 7-cycloheptyl-N,N-dimethyl-2-(5-((3aS,7aR)-6-oxotetrahydro-1H-pyrrolo[3,4-c]pyridin-5(6H,7H,7aH)-yl)pyridin-2-ylamino)-7H-pyrrolo[2,3-d]pyrimidine-6-carboxamide (from example 89, enantiomer-2) (66 mg, 0.128 mmol, 1 eq) in THF (2.0 mL) was added 37% aqueous solution of formaldehyde (0.048 mL, 0.639 mmol, 5 eq). The reaction mixture was stirred at room temperature for 5 minutes. Solid sodium triacetoxyhydroborate (81 mg, 0.383 mmol, 3 eq was added into the mixture. The reaction was stirred for 10 more minutes and quenched with a drop of TFA and naturalized with ammonia in methanol. The residue was concentrated under vacuum and purified by column chromatography (NH3/MeOH/CH$_2$Cl$_2$) to provide 7-cycloheptyl-N,N-dimethyl-2-(5-((3aS,7aR)-2-methyl-6-oxotetrahydro-1H-pyrrolo[3,4-c]pyridin-5(6H,7H,7aH)-yl)pyridin-2-ylamino)-7H-pyrrolo[2,3-d]pyrimidine-6-carboxamide (67 mg) in quantitative yield. $^1$H NMR (400 MHz, CDCl$_3$) δ ppm 8.74 (s, 1H), 8.63 (d, J=9.09 Hz, 1H), 8.27 (s, 1H), 8.24 (d, J=2.53 Hz, 1H), 7.67 (dd, J1=9.09, J2=2.53 Hz, 1H), 6.44 (s, 1H), 4.73 (s, 3H), 4.52 (m, 1H), 3.83 (dd, J1=13.14, J2=4.04 Hz, 1H), 3.65 (dd, J1=13.14, J2=4.04 Hz, 1H), 3.17 (s, 6H), 2.91-2.51 (m, 7H), 2.36 (m, 4H), 2.01 (m, 2H), 1.87 (m, 2H), 1.79-1.51 (m, 5H); HRMS m/z 531.3219 (M+H)$^+$.

Example 94

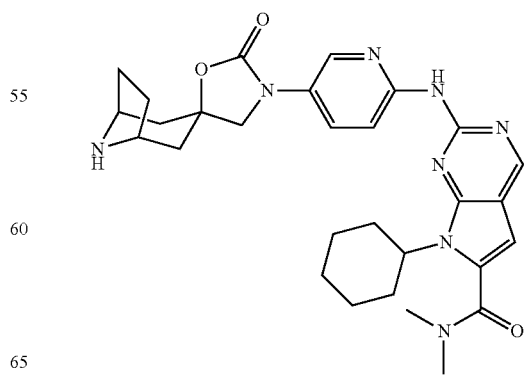

7-cyclohexyl-N,N-dimethyl-2-(5-((1R,3r,5S)-2'-oxo-8-azaspiro[bicyclo[3.2.1]octane-3,5'-oxazolidine]-3'-yl)pyridin-2-ylamino)-7H-pyrrolo[2,3-d]pyrimidine-6-carboxamide Step 1

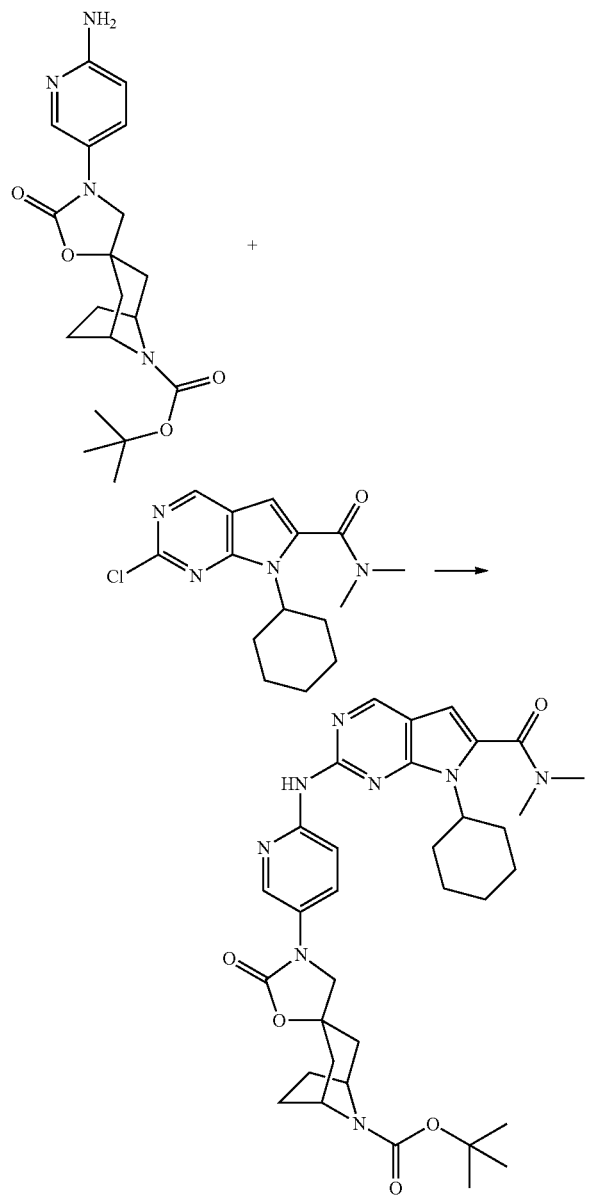

Preparation of (1R,3r,5S)-tert-butyl 3'-(6-(7-cyclohexyl-6-(dimethylcarbamoyl)-7H-pyrrolo[2,3-d]pyrimidin-2-ylamino)pyridin-3-yl)-2'-oxo-8-azaspiro[bicyclo[3.2.1]octane-3,5'-oxazolidine]-8-carboxylate Following general N—C coupling procedure 1, (1R,3r, 5S)-3'-(6-aminopyridin-3-yl)-8-azaspiro[bicyclo[3.2.1]octane-3,5'-oxazolidin]-2'-one (0.350 g, 0.935 mmol, 1.0 eq) was combined with 2-Chloro-7-cyclohexyl-7H-pyrrolo[2,3-d]pyrimidine-6-carboxylic acid dimethylamide (0.287 g, 0.935 mmol, 1.0 eq) which gave (1R,3r,5S)-tert-butyl 3'-(6-(7-cyclohexyl-6-(dimethylcarbamoyl)-7H-pyrrolo[2,3-d]pyrimidin-2-ylamino)pyridin-3-yl)-2'-oxo-8-azaspiro[bicyclo[3.2.1]octane-3,5'-oxazolidine]-8-carboxylate (0.454 g) in 75% yield. 1H NMR (400 MHz, CHLOROFORM-d) δ ppm 1.26-1.45 (m, 3H) 1.49 (s, 9H) 1.81 (d, J=11.62 Hz, 1H) 1.87-2.05 (m, 7H) 2.05-2.22 (m, 4H) 2.22-2.32 (m, 2H) 2.52-2.73 (m, 2H) 3.16 (s, 6H) 3.72 (s, 2H) 4.22-4.47 (m, 3H) 6.44 (s, 1H) 8.06 (dd, J=9.35, 2.78 Hz, 1H) 8.32 (d, J=2.53 Hz, 1H) 8.43 (s, 1H) 8.60 (d, J=9.09 Hz, 1H) 8.76 (s, 1H). MS m/z 645.7 (M+H)$^+$ Step 2

Preparation of 7-cyclohexyl-N,N-dimethyl-2-(5-((1R,3r,5S)-2'-oxo-8-azaspiro[bicyclo[3.2.1]octane-3,5'-oxazolidine]-3'-yl)pyridin-2-ylamino)-7H-pyrrolo[2,3-d]pyrimidine-6-carboxamide Following deprotection method 1, (1R,3r,5S)-tert-butyl 3'-(6-(7-cyclohexyl-6-(dimethylcarbamoyl)-7H-pyrrolo[2,3-d]pyrimidin-2-ylamino)pyridin-3-yl)-2'-oxo-8-azaspiro[bicyclo[3.2.1]octane-3,5'-oxazolidine]-8-carboxylate (0.450 g, 0.713 mmol) was converted to 7-cyclohexyl-N,N-dimethyl-2-(5-((1R,3r,5S)-2'-oxo-8-azaspiro[bicyclo[3.2.1]octane-3, 5'-oxazolidine]-3'-yl)pyridin-2-ylamino)-7H-pyrrolo[2,3-d]pyrimidine-6-carboxamide (0.286 g, 0.517 mmol) in 73% yield. 1H NMR (400 MHz, CHLOROFORM-d) δ ppm 1.28-1.51 (m, 3H) 1.62 (br. s., 1H) 1.71-1.87 (m, 3H) 1.87-1.99 (m, 5H) 2.01 (d, J=3.01 Hz, 1H) 2.20 (d, J=14.05 Hz, 2H) 2.25-2.37 (m, 2H) 2.52-2.71 (m, 2H) 3.16 (s, 6H) 3.65 (br. s., 2H) 3.71 (s, 2H) 4.27-4.43 (m, 1H) 6.44 (s, 1H) 7.91 (s, 1H) 8.10 (dd, J=9.29, 2.76 Hz, 1H) 8.22 (d, J=2.51 Hz, 1H) 8.58 (d, J=9.03 Hz, 1H) 8.70 (s, 1H); HRMS calc for m/z=545.2994. Found m/z=545.2989 (M+H)

Example 95

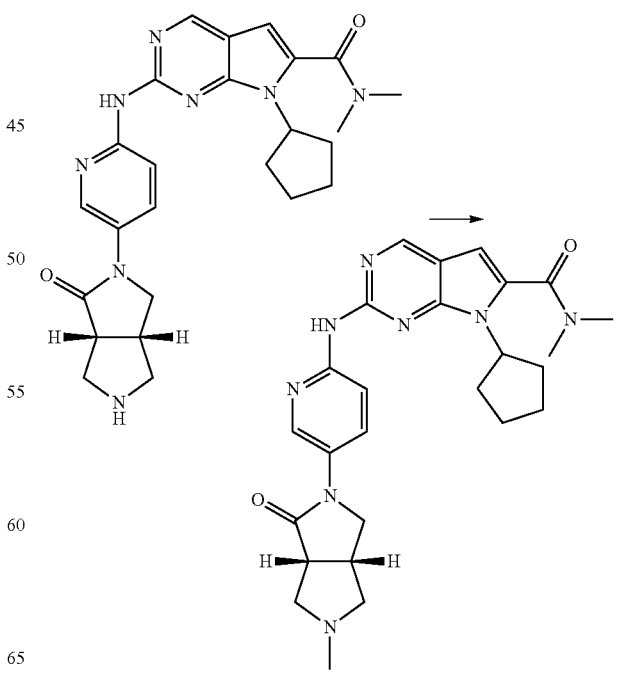

Preparation of 7-cyclopentyl-N,N-dimethyl-2-(5-((3aR,6aS)-5-methyl-1-oxohexahydropyrrolo[3,4-c]pyrrol-2(1H)-yl)pyridin-2-ylamino)-7H-pyrrolo[2,3-d]pyrimidine-6-carboxamide Following general reductive alkylation method 1, 7-cyclopentyl-N,N-dimethyl-2-(5-((3 as,6ar)-5-methyl-1-oxohexahydropyrrolo[3,4-c]pyrrol-2(1H)-yl)pyridin-2-ylamino)-7H-pyrrolo[2,3-d]pyrimidine-6-carboxamide was prepared.

Example 96

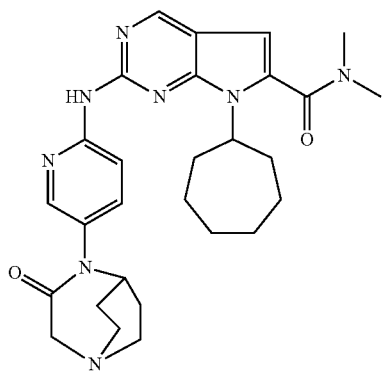 [SMILES: CN(C)C(=O)c1cc2cnc(Nc3ccc(N4C(=O)CN5CCC4CC5)cn3)nc2n1C1CCCCCC1]

Step 1

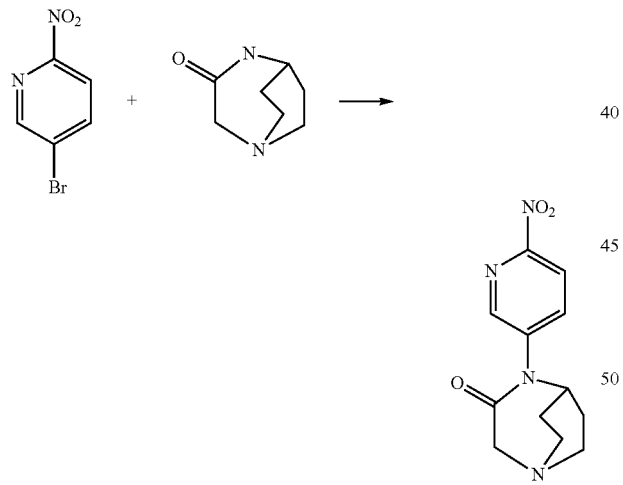

4-(6-nitropyridin-3-yl)-1,4-diazabicyclo[3.2.2]nonan-3-one

Following general N—C coupling procedure 1, 5-bromo-2-nitropyridine and 1,4-diazabicyclo[3.2.2]nonan-3-one were combined and gave 4-(6-nitropyridin-3-yl)-1,4-diazabicyclo[3.2.2]nonan-3-one (418 mg) in 64% yield.
$^1$H NMR (400 MHz, CDCl$_3$) δ ppm 8.53 (d, J=2.53 Hz, 1H), 8.30 (d, J=8.59 Hz, 1H), 7.94 (dd, J1=8.59, J2=2.53 Hz, 1H), 4.00-3.93 (m, 3H), 3.19 (m, 4H), 2.38 (m, 2H), 2.13 (m, 2H); LCMS m/z 263.4 (M+H)$^+$.

Step 2

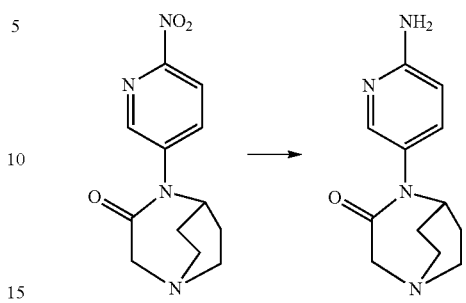

4-(6-aminopyridin-3-yl)-1,4-diazabicyclo[3.2.2]nonan-3-one

Following nitro group reduction procedure 1, 4-(6-aminopyridin-3-yl)-1,4-diazabicyclo[3.2.2]nonan-3-one, (322 mg) was obtained in 88% yield.
$^1$H NMR (400 MHz, DMSO-d6) δ ppm 7.73 (d, J=2.53 Hz, 1H), 7.22 (dd, J1=8.84, J2=2.78 Hz, 1H), 6.44 (d, J=8.59 Hz, 1H), 5.98 (br s, 2H), 3.73 (s, 2H), 3.62 (m, 1H), 3.05 (d, J=7.33 Hz, 4H) 2.25 (m, 2H), 1.94 (m, 2H)
LCMS m/z 233.4 (M+H)$^+$.

Step 3

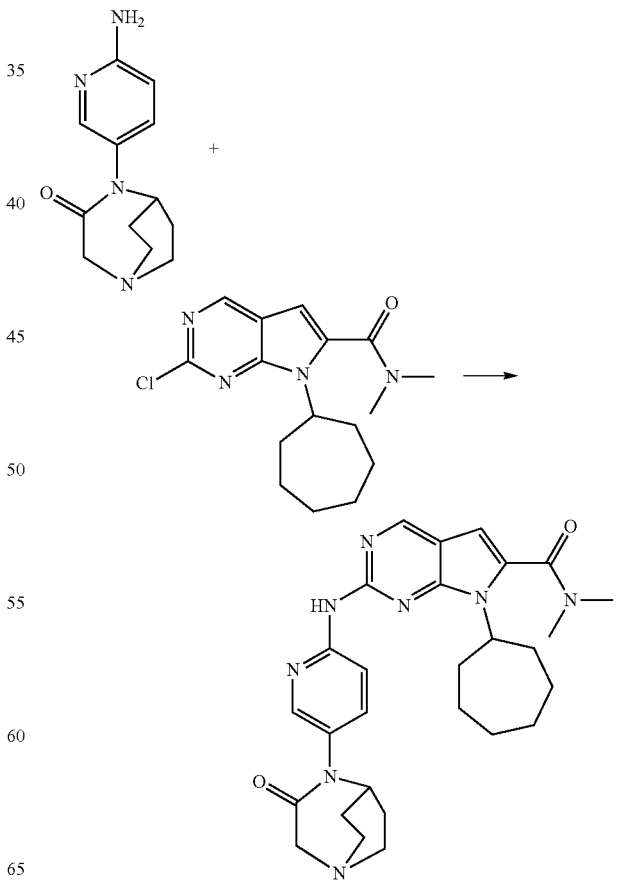

7-cyclopentyl-N,N-dimethyl-2-(5-(3-oxo-1,4-diazabicyclo[3.2.2]nonan-4-yl)pyridin-2-ylamino)-7H-pyrrolo[2,3-d]pyrimidine-6-carboxamide Following general N—C coupling procedure 1, 4-(6-aminopyridin-3-yl)-1,4-diazabicyclo[3.2.2]nonan-3-one was combined with 2-chloro-7-cyclopentyl-N,N-dimethyl-7H-pyrrolo[2,3-d]pyrimidine-6-carboxamide and gave 7-cyclopentyl-N,N-dimethyl-2-(5-(3-oxo-1,4-diazabicyclo[3.2.2]nonan-4-yl)pyridin-2-ylamino)-7H-pyrrolo[2,3-d]pyrimidine-6-carboxamide, 99 mg in 86% yield. $^1$H NMR (400 MHz, CDCl$_3$) δ ppm 8.74 (s, 1H), 8.55 (d, J=9.09 Hz, 1H), 8.16 (d, J=2.02 Hz, 1H), 8.09 (s, 1H), 7.55 (dd, J1=9.09 Hz, J2=2.53 Hz, 1H), 6.47 (s, 1H), 4.81 (m, 1H), 3.93 (s, 2H), 3.82 (m, 1H), 3.19 (m, 10H), 2.59 (m, 2H), 2.41 (m, 2H), 2.07 (m, 6H), 1.74 (m, 2H); HRMS m/z 489.2740 (M+H)$^+$.

Example 97

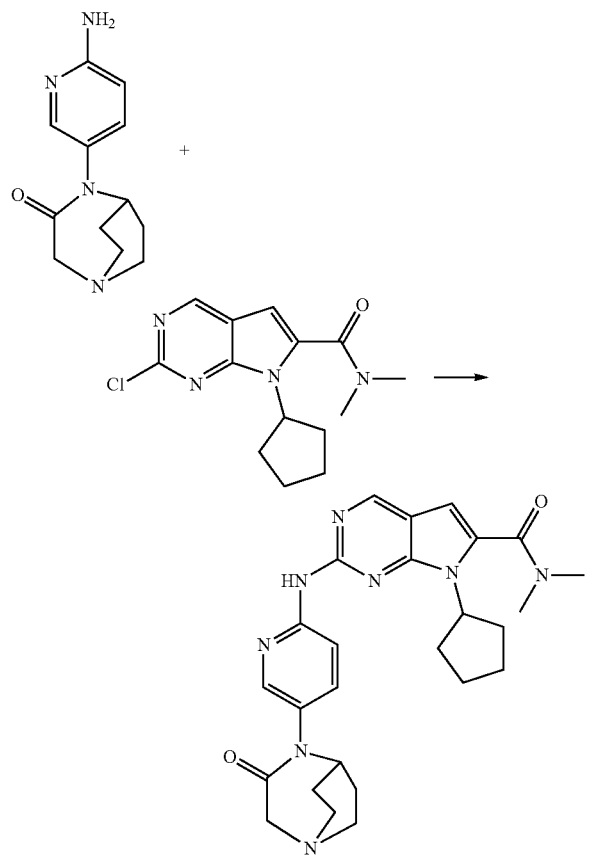

7-cycloheptyl-N,N-dimethyl-2-(5-(3-oxo-1,4-diazabicyclo[3.2.2]nonan-4-yl)pyridin-2-ylamino)-7H-pyrrolo[2,3-d]pyrimidine-6-carboxamide Following general N—C coupling procedure 1, 2-chloro-7-cycloheptyl-N,N-dimethyl-7H-pyrrolo[2,3-d]pyrimidine-6-carboxamide was combined with 4-(6-aminopyridin-3-yl)-1,4-diazabicyclo[3.2.2]nonan-3-one and gave 7-cycloheptyl-N,N-dimethyl-2-(5-(3-oxo-1,4-diazabicyclo[3.2.2]nonan-4-yl)pyridin-2-ylamino)-7H-pyrrolo[2,3-d]pyrimidine-6-carboxamide (103 mg) in 77% yield. $^1$H NMR (400 MHz, CDCl$_3$) δ ppm 8.73 (s, 1H), 8.66 (d, J=9.09 Hz, 1H), 8.17 (d, J=2.02 Hz, 1H), 8.14 (s, 1H), 7.55 (dd, J1=9.09 Hz, J2=2.53 Hz, 1H), 6.45 (s, 1H), 4.53 (m, 1H), 3.95 (s, 2H), 3.83 (m, 1H), 3.21 (m, 10H), 2.64 (m, 2H), 2.42 (m, 2H), 2.14-1.54 (m, 12H); HRMS m/z 517.3049 (M+H)$^+$.

Example 98

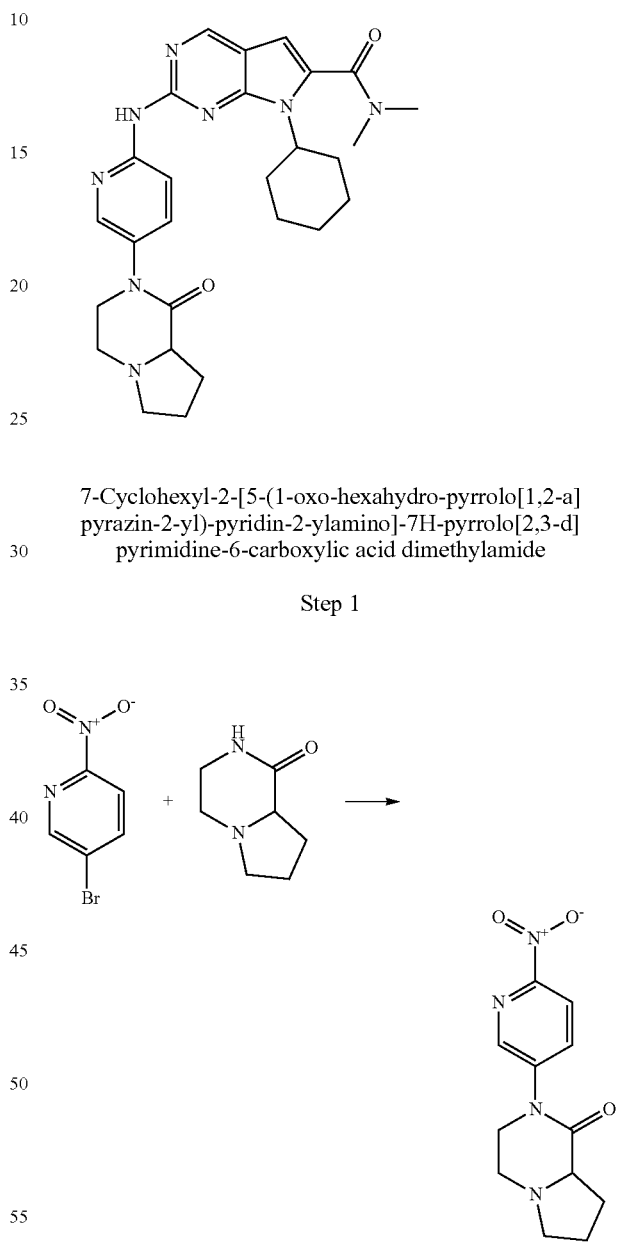

7-Cyclohexyl-2-[5-(1-oxo-hexahydro-pyrrolo[1,2-a]pyrazin-2-yl)-pyridin-2-ylamino]-7H-pyrrolo[2,3-d]pyrimidine-6-carboxylic acid dimethylamide Step 1

Preparation of 2-(6-Nitro-pyridin-3-yl)-hexahydro-pyrrolo[1,2-a]pyrazin-1-one Following general N—C coupling procedure 1, hexahydro-pyrrolo[1,2-a]pyrazin-1-one (0.202 g, 1.44 mmol), was combined with 5-bromo-2-nitropyridine (0.293 g, 1.44 mmol, 1.0 eq) which gave 2-(6-Nitro-pyridin-3-yl)hexahydro-pyrrolo[1,2-a]pyrazin-1-one as a tan solid (0.170 g, 0.616 mmol) in 43% yield. $^1$H NMR (400 MHz, CDCl$_3$) δ ppm 1.79-2.19 (m, 1H) 2.31 (br. s., 1H) 2.77 (br. s., 1H) 2.98-3.16 (m, 1H) 3.26 (dt, J=12.05, 4.52 Hz, 1H) 3.47 (br. s., 1H) 3.80 (br. s., 1H) 3.95-4.23 (m, 1H) 8.15 (dd, J=8.53, 2.51 Hz, 1H) 8.32 (d, J=8.53 Hz, 1H) 8.70 (d, J=2.51 Hz, 1H). MS m/z 263.1 (M+H)+.

Step 2

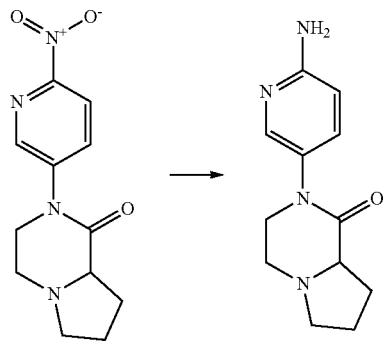

2-(6-Amino-pyridin-3-yl)-hexahydro-pyrrolo[1,2-a]pyrazin-1-one

Following nitro group reduction procedure 1, 2-(6-Nitro-pyridin-3-yl)-hexahydro-pyrrolo[1,2-a]pyrazin-1-one (0.170 g, 0.648 mmol) was converted to 2-(6-Amino-pyridin-3-yl)-hexahydro-pyrrolo[1,2-a]pyrazin-1-one and isolated as a yellow solid (0.126 g, 0.542) in 84% yield. $^1$H NMR (400 MHz, MeOD) δ ppm 1.78-2.11 (m, 1H) 2.16-2.35 (m, 1H) 2.80 (ddd, J=10.04, 8.03, 6.02 Hz, 1H) 2.97-3.11 (m, 1H) 3.11-3.25 (m, 1H) 3.42-3.52 (m, 1H) 3.59 (ddd, J=12.42, 4.39, 4.27 Hz, 1H) 3.85 (ddd, J=12.55, 8.53, 4.52 Hz, 1H) 6.60 (d, J=8.03 Hz, 1H) 7.39 (dd, J=9.03, 2.51 Hz, 1H) 7.83 (d, J=2.01 Hz, 1H) MS m/z 233.2 (M+H)+.

Step 3

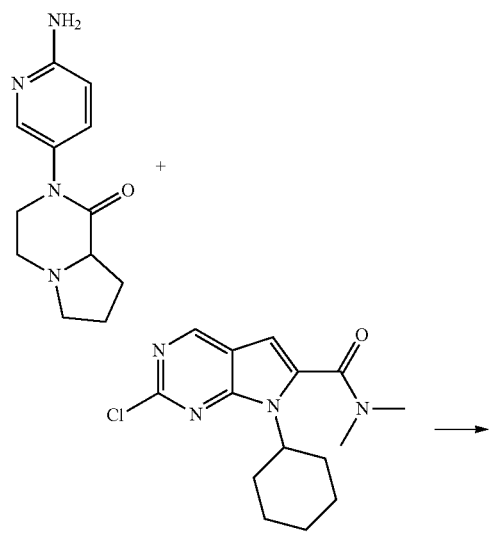

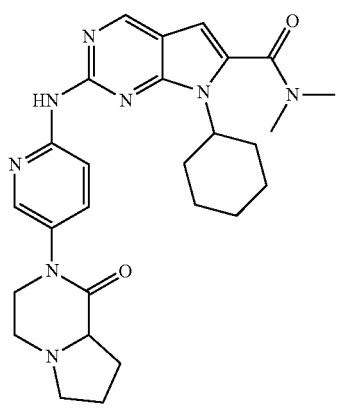 [SMILES: CN(C)C(=O)c1cc2cnc(Nc3ccc(N4CCN5CCCC5C4=O)cn3)nc2n1C1CCCCC1]

7-Cyclohexyl-2-[5-(1-oxo-hexahydro-pyrrolo[1,2-a]pyrazin-2-yl)-pyridin-2-ylamino]-7H-pyrrolo[2,3-d]pyrimidine-6-carboxylic acid dimethylamide Following general N—C coupling procedure 1, 2-(6-amino-pyridin-3-yl)-hexahydro-pyrrolo[1,2-a]pyrazin-1-one (0.050 g, 0.215 mmol) was combined with 2-chloro-7-cyclohexyl-7H-pyrrolo[2,3-d]pyrimidine-6-carboxylic acid dimethylamide (0.066 g, 0.215 mmol, 1.0 eq), and gave 7-Cyclohexyl-2-[5-(1-oxo-hexahydro-pyrrolo[1,2-a]pyrazin-2-yl)-pyridin-2-ylamino]-7H-pyrrolo[2,3-d]pyrimidine-6-carboxylic acid dimethylamide as a beige solid (75 mg, 0.139 mmol), in 65% yield. $^1$H NMR (400 MHz, CDCl$_3$) δ ppm 1.23-1.52 (m, 4H) 1.72-1.90 (m, 2H) 1.90-2.00 (m, 6H) 2.00-2.18 (m, 2H) 2.21-2.39 (m, 1H) 2.52-2.82 (m, 3H) 2.95-3.14 (m, 3H) 3.15-3.27 (m, 8H) 3.42 (t, J=8.28 Hz, 1H) 3.66 (dt, J=11.54, 4.02 Hz, 1H) 3.95 (ddd, J=11.80, 9.29, 4.52 Hz, 1H) 4.27-4.41 (m, 1H) 6.45 (s, 1H) 7.69 (dd, J=9.03, 2.51 Hz, 1H) 8.11 (5, 1H) 8.25 (d, J=2.51 Hz, 1H) 8.65 (d, J=9.03 Hz, 1H) 8.73 (s, 1H); HRMS calc for m/z=503.2883. Found m/z=503.2892 (M+H).

Example 99

7-Cyclopentyl-2-[5-(1-oxo-octahydro-pyrido[1,2-a]pyrazin-2-yl)-pyridin-2-ylamino]-7H-pyrrolo[2,3-d]pyrimidine-6-carboxylic acid dimethylamide

Step 1

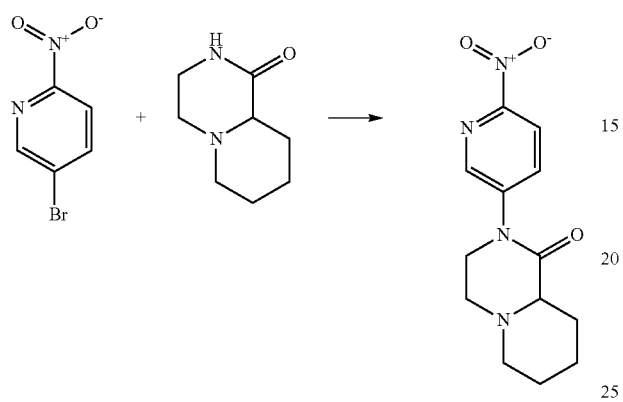

Preparation of 2-(6-Nitro-pyridin-3-yl)hexahydro-pyrido[1,2-a]pyrazin-1-one

Following general N—C coupling procedure 1, hexahydro-pyrido[1,2-a]pyrazin-1-one (0.300 g, 1.945 mmol), was combined with 5-bromo-2-nitropyridine (0.395 g, 1.945 mmol, 1.0 eq), and gave 2-(6-Nitro-pyridin-3-yl)-hexahydro-pyrido[1,2-a]pyrazin-1-one (0.481 g, 1.567 mmol) in 81% yield. $^1$H NMR (400 MHz, CDCl$_3$) δ ppm 1.27-1.53 (m, 2H) 1.54-1.61 (m, 4H) 1.66-1.81 (m, 1H) 1.94 (d, J=12.55 Hz, 1H) 2.22 (td, J=11.80, 3.01 Hz, 1H) 2.39 (d, J=12.55 Hz, 1H) 2.68-2.83 (m, 2H) 2.96-3.12 (m, 2H) 3.49 (d, J=3.51 Hz, 1H) 3.56 (dd, J=10.79, 2.26 Hz, 1H) 4.16 (td, J=11.29, 4.52 Hz, 1H) 8.13 (dd, J=8.53, 2.51 Hz, 1H) 8.29 (d, J=8.53 Hz, 1H) 8.68 (d, J=2.51 Hz, 1H); MS m/z 277.2 (M+H)$^+$.

Step 2

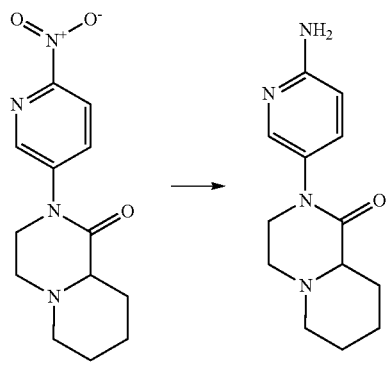 [SMILES: O=C1C2CCCCN2CCN1c1ccc([N+](=O)[O-])nc1 ; Nc1ccc(N2CCN3CCCCC3C2=O)cn1]

Preparation of 2-(6-Amino-pyridin-3-yl)-hexahydro-pyrido[1,2-a]pyrazin-1-one

Following nitro group reduction procedure 1, 2-(6-Nitro-pyridin-3-yl)-hexahydro-pyrido[1,2-a]pyrazin-1-one (0.200 g, 0.724 mmol), was converted to 2-(6-Amino-pyridin-3-yl)-hexahydro-pyrido[1,2-a]pyrazin-1-one (0.170 g, 0.690 mmol) in 95% yield. $^1$H NMR (400 MHz, CDCl$_3$) δ ppm 1.28-1.55 (m, 1H) 1.53-1.77 (m, 1H) 1.91 (d, J=12.05 Hz, 1H) 2.19 (td, J=11.42, 3.26 Hz, 1H) 2.33-2.48 (m, 1H) 2.60-2.75 (m, 1H) 2.89-3.06 (m, 1H) 3.39 (dd, J=11.54, 3.01 Hz, 1H) 3.93 (td, J=11.80, 4.52 Hz, 1H) 4.46 (br. s., 1H) 6.51 (d, J=8.53 Hz, 1H) 7.37 (dd, J=8.53, 2.51 Hz, 1H) 7.99 (d, J=2.51 Hz, 1H) MS m/z 247.2 (M+H)$^+$.

Step 3

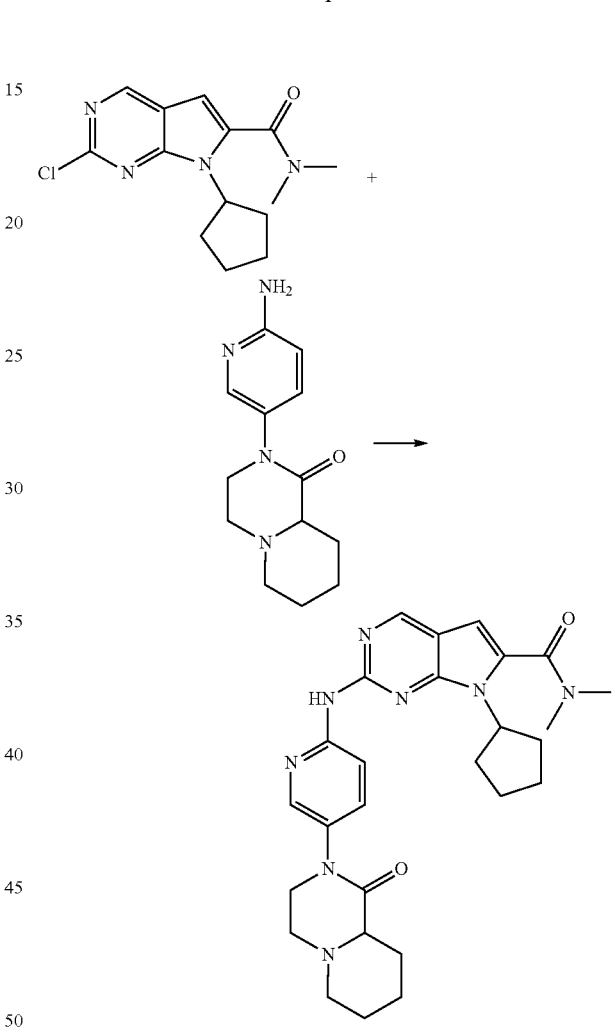

Preparation of 7-Cyclopentyl-2-[5-(1-oxo-octahydro-pyrido[1,2-a]pyrazin-2-yl)-pyridin-2-ylamino]-7H-pyrrolo[2,3-d]pyrimidine-6-carboxylic acid dimethylamide Following general N—C coupling procedure 1, 2-(6-Amino-pyridin-3-yl)-hexahydro-pyrido[1,2-a]pyrazin-1-one (0.060 g, 0.244 mmol) was combined with 2-Chloro-7-cyclopentyl-7H-pyrrolo[2,3-d]pyrimidine-6-carboxylic acid dimethylamide (0.072 g, 0.246 mmol, 1.01 eq) which gave 7-Cyclopentyl-2-[5-(1-oxo-octahydro-pyrido[1,2-a]pyrazin-2-yl)-pyridin-2-ylamino]-7H-pyrrolo[2,3-d]pyrimidine-6-carboxylic acid dimethylamide, (0.070 g, 0.136 mmol) in 56% yield. $^1$H NMR (400 MHz, CDCl$_3$) δ ppm 1.31-1.50 (m, 2H) 1.66-1.82 (m, 4H) 1.91 (br. s., 1H) 1.98-2.14 (m, 5H)

2.21 (td, J=11.42, 3.26 Hz, 1H) 2.40 (br. s., 1H) 2.58 (dd, J=12.30, 8.78 Hz, 2H) 2.67-2.81 (m, 2H) 2.93-3.07 (m, 2H) 3.16 (s, 7H) 3.47 (dd, J=11.29, 3.26 Hz, 1H) 4.02 (td, J=11.67, 4.77 Hz, 1H) 4.79 (dq, J=9.03, 8.87 Hz, 1H) 6.46 (s, 1H) 7.66 (dd, J=9.03, 2.51 Hz, 1H) 7.94 (s, 1H) 8.23 (d, J=2.01 Hz, 1H) 8.54 (d, J=9.03 Hz, 1H) 8.71 (s, 1H)

HRMS calc for m/z=503.2883. Found m/z=503.2908 (M+H)

Example 100

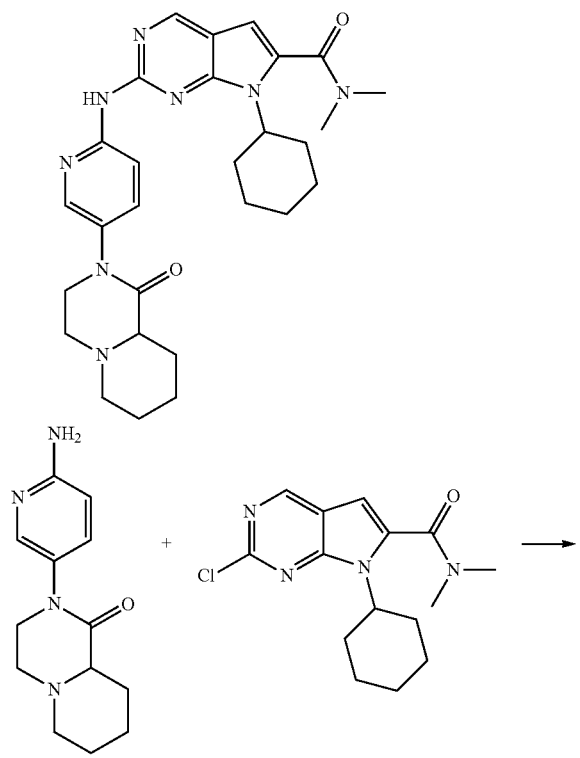

Preparation of 7-Cyclohexyl-2-[5-(1-oxo-octahydro-pyrido[1,2-a]pyrazin-2-yl)-pyridin-2-ylamino]-7H-pyrrolo[2,3-d]pyrimidine-6-carboxylic acid dimethylamide Following general N—C coupling procedure 1, 2-(6-Amino-pyridin-3-yl)-hexahydro-pyrido[1,2-a]pyrazin-1-one (0.060 g, 0.244 mmol) was combined with 2-Chloro-7-cyclohexyl-7H-pyrrolo[2,3-d]pyrimidine-6-carboxylic acid dimethylamide (0.075 g, 0.244 mmol, 1.0 eq) which gave 7-Cyclohexyl-2-[5-(1-oxo-octahydro-pyrido[1,2-a]pyrazin-2-yl)-pyridin-2-ylamino]-7H-pyrrolo[2,3-d]pyrimidine-6-carboxylic acid dimethylamide (0.020 g, 0.039 mmol) in 16% yield. $^1$H NMR (400 MHz, CDCl$_3$) δ ppm 1.19-1.41 (m, 6H) 1.41-1.52 (m, 5H) 1.61-1.75 (m, 4H) 1.93 (br. s., 9H) 2.21 (td, J=11.37, 3.54 Hz, 2H) 2.40 (br. s., 2H) 2.52-2.81 (m, 7H) 2.93-3.05 (m, 4H) 3.16 (s, 11H) 3.47 (dd, J=11.37, 2.78 Hz, 2H) 3.93-4.09 (m, 2H) 4.26-4.42 (m, 2H) 6.44 (s, 2H) 7.68 (dd, J=8.84, 2.78 Hz, 2H) 8.00 (s, 2H) 8.23 (d, J=2.02 Hz, 2H) 8.63 (d, J=9.09 Hz, 2H) 8.71 (s, 2H) HRMS calc for m/z=517.3039. Found m/z=517.3046 (M+H)

Example 101

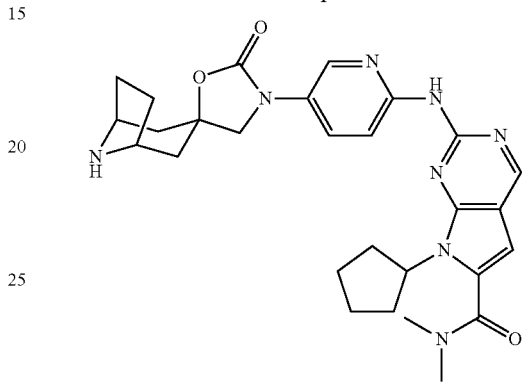

7-cyclopentyl-N,N-dimethyl-2-(5-((1R,3r,5S)-2'-oxo-8-azaspiro[bicyclo[3.2.1]octane-3,5'-oxazolidine]-3'-yl)pyridin-2-ylamino)-7H-pyrrolo[2,3-d]pyrimidine-6-carboxamide Step 1

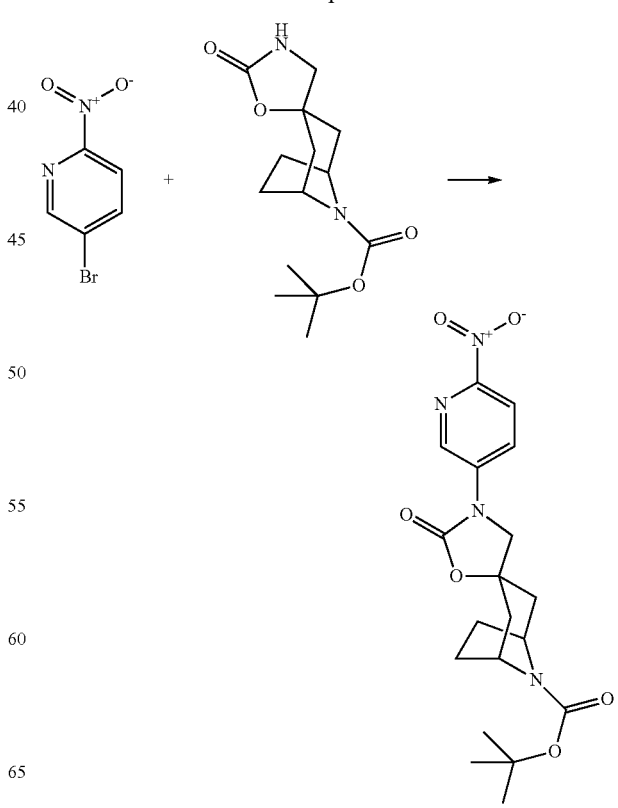

Preparation of (1R,3r,5S)-3'-(6-nitropyridin-3-yl)-8-azaspiro[bicyclo[3.2.1]octane-3,5'-oxazolidin]-2'-one Following general N—C coupling procedure 1, (1R,3r,5S)-8-azaspiro[bicyclo[3.2.1]octane-3,5'-oxazolidin]-2'-one (0.488 g, 1.728 mmol) (Reference: German Patent DE10 2005 030051A1 (Dec. 28, 2006)) was combined with 5-bromo-2-nitropyridine (0.351 g, 1.728, 1.0 eq) which gave (1R,3r,5S)-3'-(6-nitropyridin-3-yl)-8-azaspiro[bicyclo[3.2.1]octane-3,5'-oxazolidin]-2'-one (0.615 g, 1.521 mmol) 88% yield. $^1$H NMR (400 MHz, CDCl$_3$) δ ppm 1.49 (s, 9H) 1.91-2.10 (m, 4H) 2.10-2.33 (m, 6H) 3.81 (s, 2H) 4.32 (br. s., 1H) 4.37 (br. s., 1H) 8.32 (d, J=8.53 Hz, 1H) 8.47-8.57 (m, 2H); MS m/z 405.2 (M+H)$^+$.

Step 2

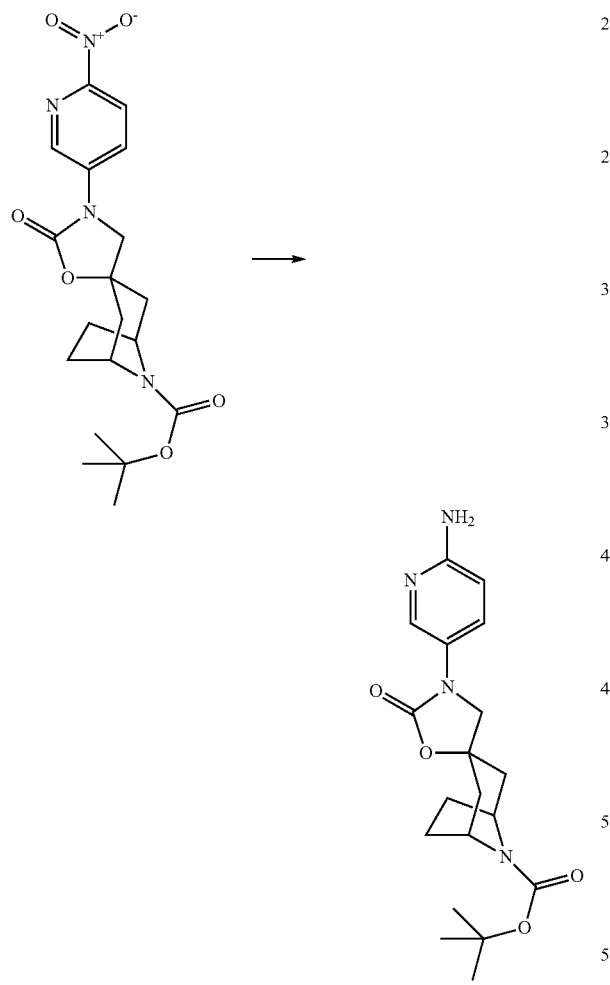

Preparation of (1R,3r,5S)-3'-(6-aminopyridin-3-yl)-8-azaspiro[bicyclo[3.2.1]octane-3,5'-oxazolidin]-2'-one Following nitro group reduction procedure 1, (1R,3R,5S)-3'-(6-nitropyridin-3-yl)-8-azaspiro[bicyclo[3.2.1]octane-3,5'-oxazolidin]-2'-one (0.705 g, 1.743 mmol) was converted to (1R,3r,5S)-3'-(6-aminopyridin-3-yl)-8-azaspiro[bicyclo[3.2.1]octane-3,5'-oxazolidin]-2'-one as an off-white solid (0.356 g, 0.951 mmol) 55% yield. $^1$H NMR (400 MHz, CDCl$_3$) δ ppm 1.48 (s, 9H) 1.99 (br. s., 4H) 2.07-2.19 (m, 3H) 2.23 (d, J=6.02 Hz, 2H) 3.63 (s, 2H) 4.27 (br. s., 1H) 4.35 (br. s., 1H) 4.43 (br. s., 2H) 6.55 (d, J=9.03 Hz, 1H) 7.27 (s, 1H) 7.85-7.91 (m, 1H) 7.93 (d, J=2.51 Hz, 1H)

MS m/z 375.2 (M-1-H)$^+$.

Step 3

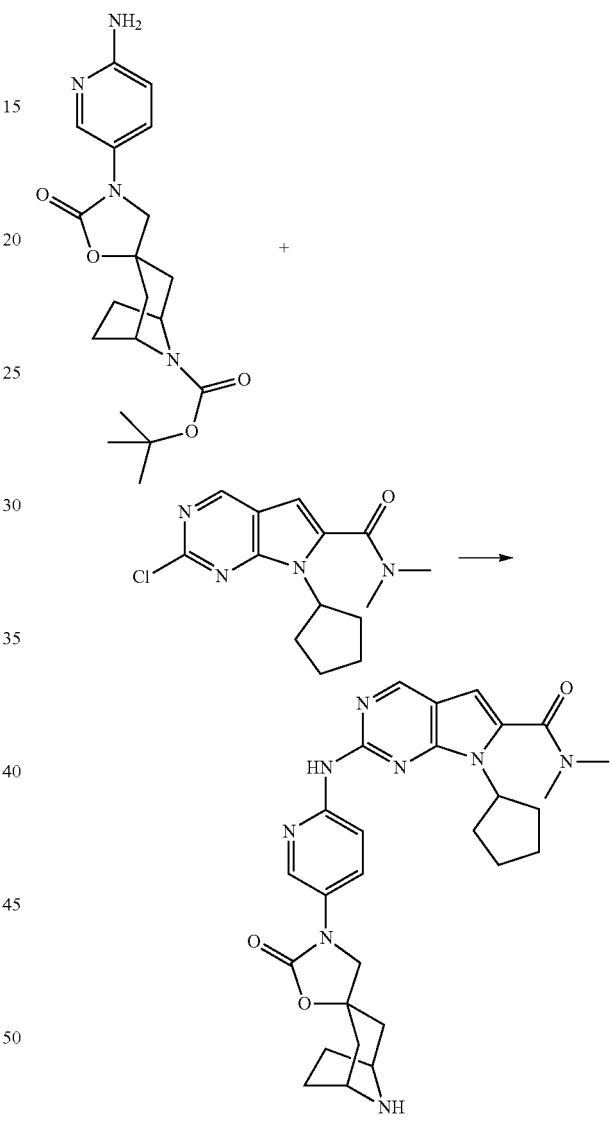

Preparation of (1R,3r,5S)-tert-butyl 3'-(6-(7-cyclopentyl-6-(dimethylcarbamoyl)-7H-pyrrolo[2,3-d]pyrimidin-2-ylamino)pyridin-3-yl)-2'-oxo-8-azaspiro[bicyclo[3.2.1]octane-3,5'-oxazolidine]-8-carboxylate Following general N—C coupling procedure 1, (1R,3r,5S)-3'-(6-aminopyridin-3-yl)-8-azaspiro[bicyclo[3.2.1]octane-3,5'-oxazolidin]-Z-one was combined with 2-Chloro-7-cyclopentyl-7H-pyrrolo[2,3-d]pyrimidine-6-carboxylic acid dimethylamide which gave (1R,3r,5S)-tert-butyl 3'-(6-(7-cyclopentyl-6-(dimethylcarbamoyl)-7H-pyrrolo[2,3-d]pyrimidin-2-ylamino)pyridin-3-yl)-2'-oxo-8-azaspiro[bicyclo[3.2.1]octane-3,5'-oxazolidine]-8-carboxylate as a dark solid (0.458 g, 0.726 mmol) in 78% yield and used in next step without purification. ¹H NMR (400 MHz, CDCl₃) δ ppm 1.49 (s, 9H) 1.66-1.81 (m, 2H) 1.98-2.27 (m, 12H) 2.48-2.67 (m, 2H) 3.16 (s, 6H) 3.72 (s, 2H) 4.36 (br. s., 2H) 4.80 (dq, J=9.03, 8.87 Hz, 1H) 6.46 (5, 1H) 8.03-8.11 (m, 2H) 8.26 (d, J=3.01 Hz, 1H) 8.51 (d, J=9.03 Hz, 1H) 8.74 (s, 1H). MS m/z 631.4 (M+H)⁺.

Step 4

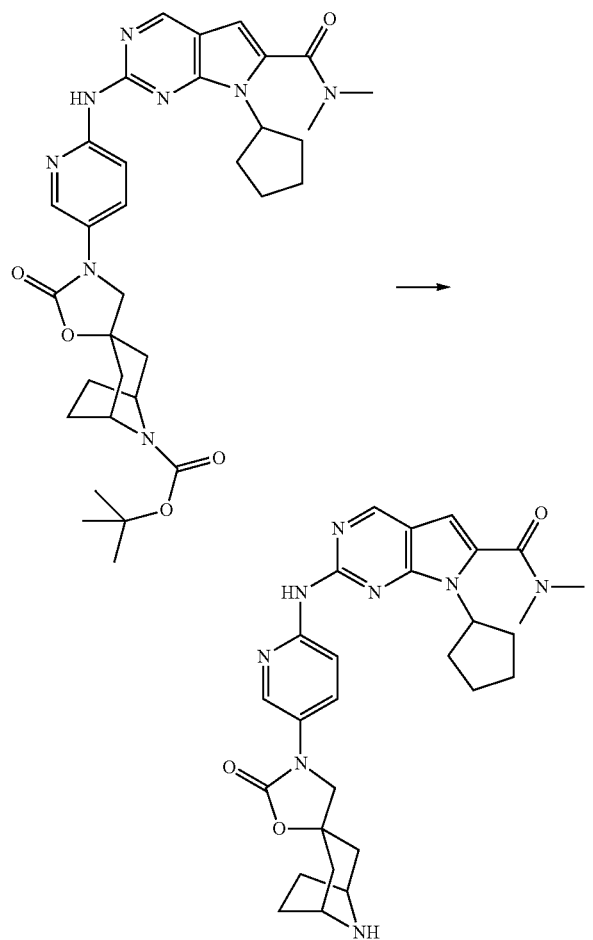

Preparation of 7-cyclopentyl-N,N-dimethyl-2-(5-((1R,3r,5S)-2'-oxo-8-azaspiro[bicyclo[3.2.1]octane-3,5'-oxazolidine]-3'-yl)pyridin-2-ylamino)-7H-pyrrolo[2,3-d]pyrimidine-6-carboxamide Following deprotection method 1, (1R,3r,5S)-tert-butyl 3'-(6-(7-cyclopentyl-6-(dimethylcarbamoyl)-7H-pyrrolo[2,3-d]pyrimidin-2-ylamino)pyridin-3-yl)-2'-oxo-8-azaspiro[bicyclo[3.2.1]octane-3,5'-oxazolidine]-8-carboxylate (0.450 g, 0.713 mmol) was converted to 7-cyclopentyl-N,N-dimethyl-2-(5-((1R,3r,5S)-2'-oxo-8-azaspiro[bicyclo[3.2.1]octane-3,5'-oxazolidine]-3'-yl)pyridin-2-ylamino)-7H-pyrrolo[2,3-d]pyrimidine-6-carboxamide (0.286 g, 0.517 mmol) in 73% yield. ¹H NMR (400 MHz, CDCl₃) δ ppm 1.62 (br. s., 1H) 1.66-1.84 (m, 4H) 1.93-2.14 (m, 7H) 2.20 (d, J=14.56 Hz, 2H) 2.24-2.37 (m, 2H) 2.47-2.68 (m, 2H) 3.16 (s, 6H) 3.65 (br. 5., 2 H) 3.71 (s, 2H) 4.80 (quin, J=8.78 Hz, 1H) 6.46 (s, 1H) 8.08 (dd, J=9.03, 2.51 Hz, 1H) 8.19-8.32 (m, 2H) 8.50 (d, J=9.03 Hz, 1H) 8.75 (s, 1H); HRMS calc for m/z=531.2832. Found m/z=531.2858 (M+H)⁺.

Example 102

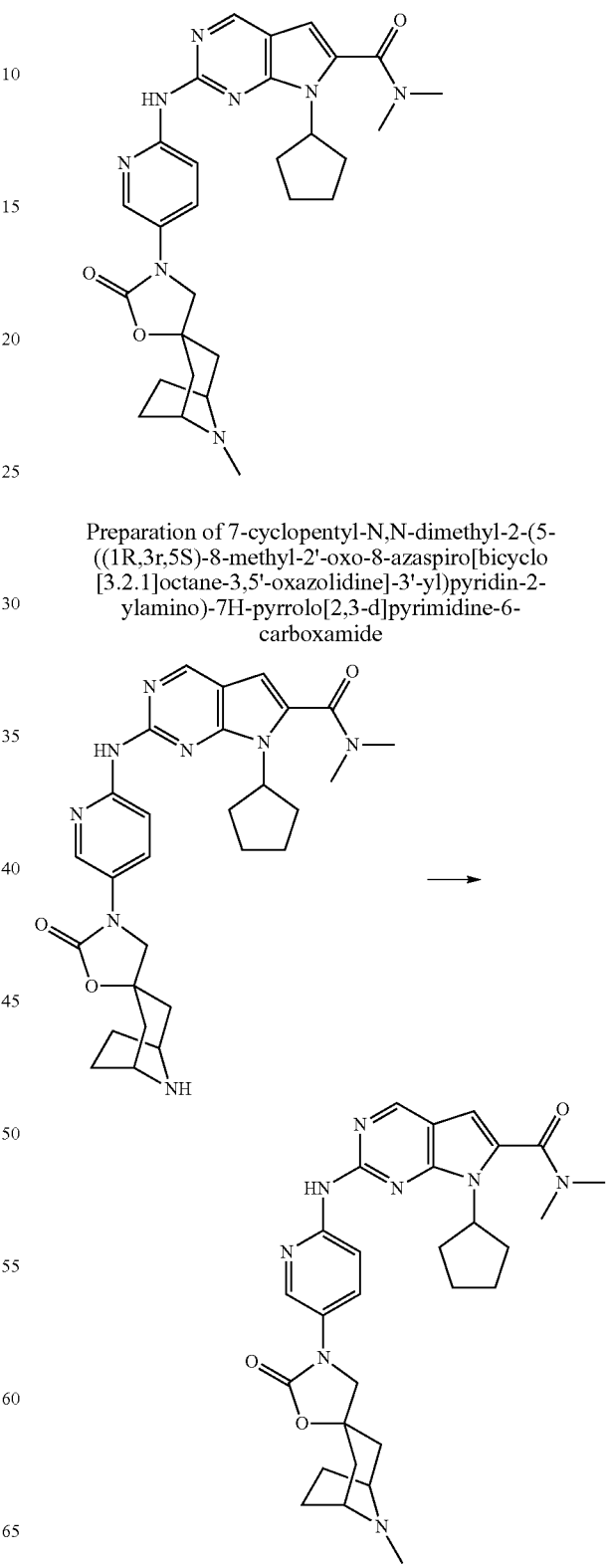

Preparation of 7-cyclopentyl-N,N-dimethyl-2-(5-((1R,3r,5S)-8-methyl-2'-oxo-8-azaspiro[bicyclo[3.2.1]octane-3,5'-oxazolidine]-3'-yl)pyridin-2-ylamino)-7H-pyrrolo[2,3-d]pyrimidine-6-carboxamide Preparation of 7-cyclopentyl-N,N-dimethyl-2-(5-((1R,3r,5S)-8-methyl-2'-oxo-8-azaspiro[bicyclo[3.2.1]octane-3,5'-oxazolidine]-3'-yl)pyridin-2-ylamino)-7H-pyrrolo[2,3-d]pyrimidine-6-carboxamide Following general reductive alkylation method 1, 7-cyclopentyl-N,N-dimethyl-2-(5-((1R,3r,5S)—Z-oxo-8-azaspiro[bicyclo[3.2.1]octane-3,5-oxazolidine]-3-yl)pyridin-2-ylamino)-7H-pyrrolo[2,3-d]pyrimidine-6-carboxamide (0.216 g, 0.407 mmol) was converted to 7-cyclopentyl-N,N-dimethyl-2-(5-((1R,3r,5S)-8-methyl-2'-oxo-8-azaspiro[bicyclo[3.2.1]octane-3,5'-oxazolidine]-3'-yl)pyridin-2-ylamino)-7H-pyrrolo[2,3-d]pyrimidine-6-carboxamide as an white solid (0.120 g, 0.220 mmol) in 54% yield. $^1$H NMR (400 MHz, CDCl$_3$) δ ppm 1.52-1.82 (m, 4H) 1.93-2.11 (m, 7H) 2.11-2.25 (m, 6H) 2.34 (br. s., 4H) 2.48-2.68 (m, 2H) 3.16 (s, 6H) 3.25 (br. s., 2H) 3.71 (s, 2H) 4.80 (qd, J=8.95, 8.78 Hz, 1H) 6.46 (s, 1H) 7.98 (s, 1H) 8.07 (dd, J=9.29, 2.76 Hz, 1H) 8.23 (d, J=2.51 Hz, 1H) 8.49 (d, J=9.54 Hz, 1H) 8.72 (s, 1H)

HRMS calc for m/z=545.2989. Found m/z=545.2988 (M+H)$^+$.

Example 103

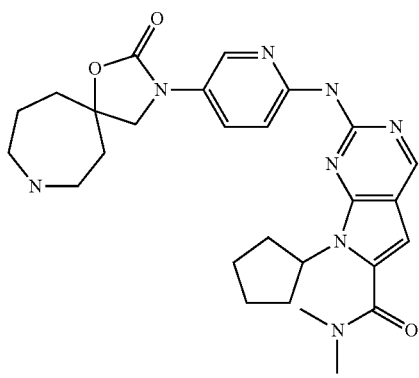 [SMILES: CN(C)C(=O)c1cc2cnc(Nc3ccc(N4CC5(CCCNCC5)OC4=O)cn3)nc2n1C1CCCC1]

7-cyclopentyl-N,N-dimethyl-2-(5-(2-oxo-1-oxa-3,8-diazaspiro[4.6]undecan-3-yl)pyridin-2-ylamino)-7H-pyrrolo[2,3-d]pyrimidine-6-carboxamide Step 1

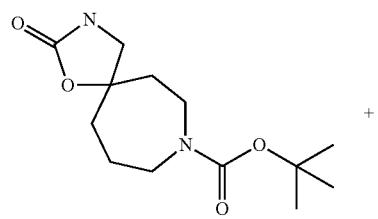

+

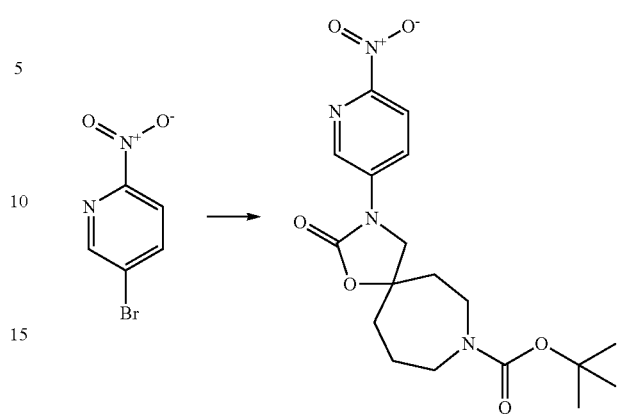

Preparation of 3-(6-Nitro-pyridin-3-yl)-2-oxo-1-oxa-3,8-diaza-spiro[4.6]undecane-8-carboxylic acid tert-butyl ester Following general N—C coupling procedure 1, 2-oxo-1-oxa-3,8-diaza-spiro[4.6]undecane-8-carboxylic acid tert-butyl ester (0.510 g, 1.887 mmol) (Reference: German Patent DE10 2005 030051A1 (Dec. 28, 2006)) was combined with 5-bromo-2-nitropyridine (0.400 g, 1.971 mmol, 1.05 eq) which gave 3-(6-Nitro-pyridin-3-yl)-2-oxo-1-oxa-3,8-diaza-spiro[4.6]undecane-8-carboxylic acid tert-butyl ester as a brown solid (0.684 g, 1.743 mmol) in 92% yield. $^1$H NMR (400 MHz, CDCl$_3$) δ ppm 1.45 (br. s., 9H) 1.54-1.72 (m, 1H) 1.86-2.16 (m, 3H) 3.30 (d, J=8.03 Hz, 1H) 3.66 (br. s., 2H) 3.81 (d, J=9.03 Hz, 1H) 3.94 (d, J=7.53 Hz, 1H) 8.33 (d, J=9.03 Hz, 1H) 8.52 (br. s., 1H) 8.60 (dd, J=9.03, 3.01 Hz, 1H). MS m/z 337.1 (M+H)$^+$ Step 2

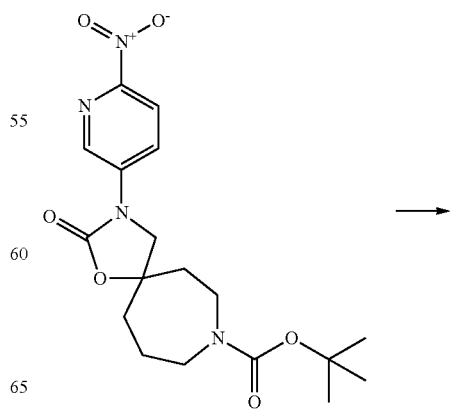

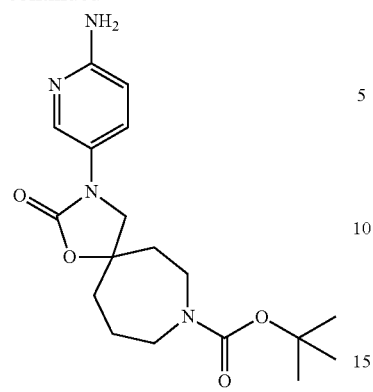

Preparation of 3-(6-Amino-pyridin-3-yl)-2-oxo-1-oxa-3,8-diaza-spiro[4.6]undecane-8-carboxylic acid tert-butyl ester Following nitro group reduction procedure 1, 3-(6-Nitro-pyridin-3-yl)-1-oxa-3,8-diaza-spiro[4.6]undecan-2-one (0.620 g, 1.580 mmol) was converted to 3-(6-Amino-pyridin-3-yl)-2-oxo-1-oxa-3,8-diaza-spiro[4.6]undecane-8-carboxylic acid tert-butyl ester as an off-white solid (0.532 g, 1.47 mmol) 93% yield. $^1$H NMR (400 MHz, CDCl$_3$) δ ppm 1.47 (s, 9H) 1.80 (dd, J=13.55, 9.54 Hz, 2H) 1.86-2.01 (m, 1H) 2.06-2.24 (m, 3H) 3.18-3.34 (m, 2H) 3.58-3.80 (m, 4H) 4.40 (br. s., 2 H) 6.54 (d, J=8.53 Hz, 1H) 7.87-7.97 (m, 2H). MS m/z 363.2 (M+H)$^+$.

Step 3

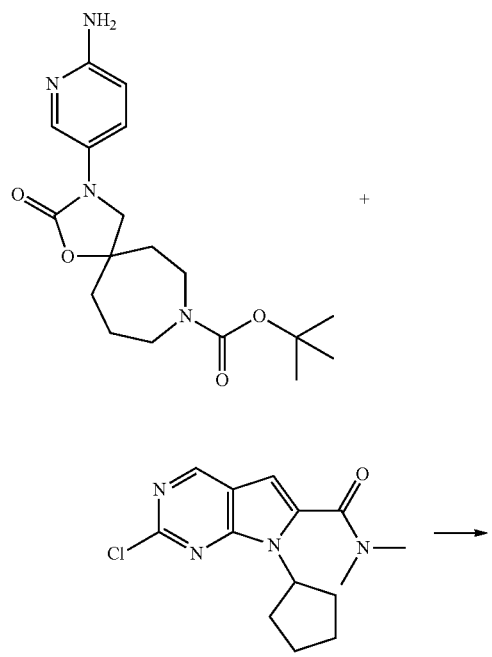

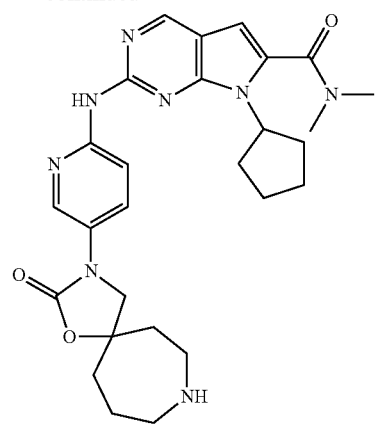

Preparation of 7-cyclopentyl-N,N-dimethyl-2-(5-(2-oxo-1-oxa-3,8-diazaspiro[4.6]undecan-3-yl)pyridin-2-ylamino)-7H-pyrrolo[2,3-d]pyrimidine-6-carboxamide Following general N—C coupling procedure 1, 3-(6-Amino-pyridin-3-yl)-1-oxa-3,8-diaza-spiro[4.6]undecan-2-one (0.100 g, 0.276 mmol) was combined with 2-Chloro-7-cyclopentyl-7H-pyrrolo[2,3-d]pyrimidine-6-carboxylic acid dimethylamide (0.081 g, 0.276 mmol, 1.0 eq) which gave 7-cyclopentyl-N,N-dimethyl-2-(5-(2-oxo-1-oxa-3,8-diazaspiro[4.6]undecan-3-yl)pyridin-2-ylamino)-7H-pyrrolo[2,3-d]pyrimidine-6-carboxamide as white solid (0.075 g, 0.139 mmol) in 50% yield. $^1$H NMR (400 MHz, CDCl$_3$) δ ppm 1.58-1.82 (m, 4H) 1.97-2.27 (m, 14H) 2.47-2.65 (m, 2H) 2.86-3.11 (m, 4H) 3.16 (s, 7H) 3.80-3.88 (m, 2H) 4.80 (qd, J=8.95, 8.78 Hz, 1H) 6.46 (s, 1H) 8.06 (s, 1H) 8.13 (dd, J=9.03, 3.01 Hz, 1H) 8.21-8.32 (m, 1H) 8.50 (d, J=9.03 Hz, 1H) 8.72 (s, 1H); HRMS calc for m/z=531.2832. Found m/z=531.2858 (M+H)$^+$.

Example 104

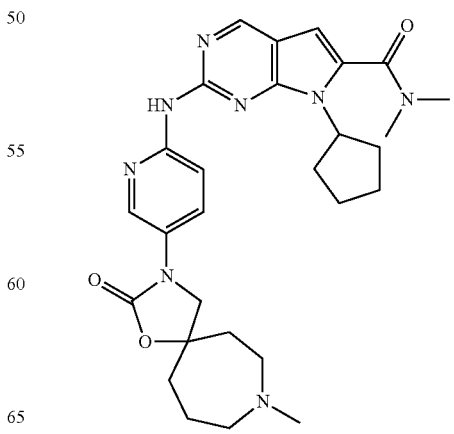

243

7-Cyclopentyl-2-[5-(8-methyl-2-oxo-1-oxa-3,8-diaza-spiro[4.6]undec-3-yl)-pyridin-2-ylamino]-7H-pyrrolo[2,3-d]pyrimidine-6-carboxylic acid dimethylamide

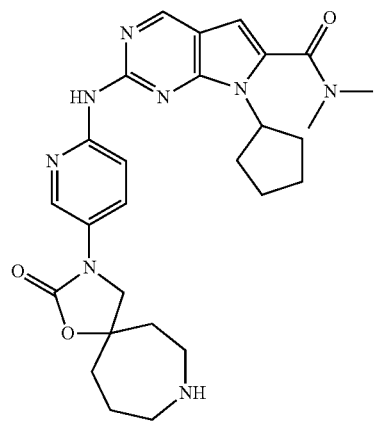

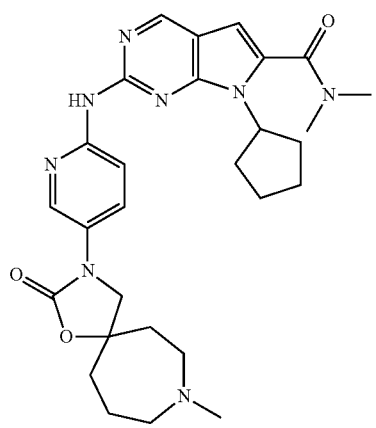 [SMILES: CN1CCCC2(CC1)CN(c1ccc(Nc3ncc4cc(C(=O)N(C)C)n(C5CCCC5)c4n3)nc1)C(=O)O2]

Step 1

7-cyclopentyl-N,N-dimethyl-2-(5-(8-methyl-2-oxo-1-oxa-3,8-diazaspiro[4.6]undecan-3-yl)pyridin-2-ylamino)-7H-pyrrolo[2,3-d]pyrimidine-6-carboxamide Following general reductive alkylation method 1, 7-cyclopentyl-N,N-dimethyl-2-(5-(2-oxo-1-oxa-3,8-diazaspiro[4.6]undecan-3-yl)pyridin-2-ylamino)-7H-pyrrolo[2,3-d]pyrimidine-6-carboxamide was converted to 7-cyclopentyl-N,N-dimethyl-2-(5-(8-methyl-2-oxo-1-oxa-3,8-diazaspiro[4.6]undecan-3-yl)pyridin-2-ylamino)-7H-pyrrolo[2,3-d]pyrimidine-6-carboxamide (0.062 g, 0.112 mmol) in 77% yield. $^1$H NMR (400 MHz, DMSO-d$_6$) δ ppm 1.52-1.79 (m, 5H) 1.84-2.05 (m, 8H) 2.07 (t, J=5.27 Hz, 2H) 2.28 (s, 3H) 3.06 (d, J=10.54 Hz, 7H) 3.90 (s, 2H) 4.68-4.84 (m, 1H) 6.63 (s, 1H) 7.99 (dd, J=9.03, 2.51 Hz, 1H) 8.33 (d, J=9.03 Hz, 1H) 8.43 (d, J=2.51 Hz, 1H) 8.80 (s, 1H) 9.73 (s, 1H);

HRMS calc for m/z=533.2989. Found m/z=533.3009 (M+H)$^+$.

244

Example 105

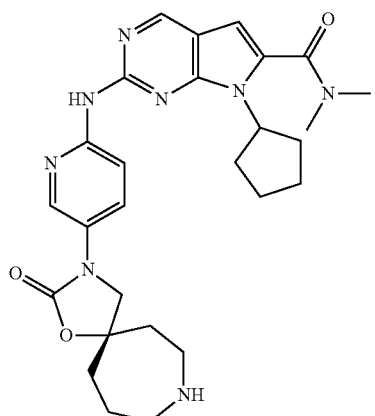

7-Cyclopentyl-2-[5-((S)-2-oxo-1-oxa-3,8-diaza-spiro[4.6]undec-3-yl)-pyridin-2-ylamino]-7H-pyrrolo[2,3-d]pyrimidine-6-carboxylic acid dimethylamide

Step 1

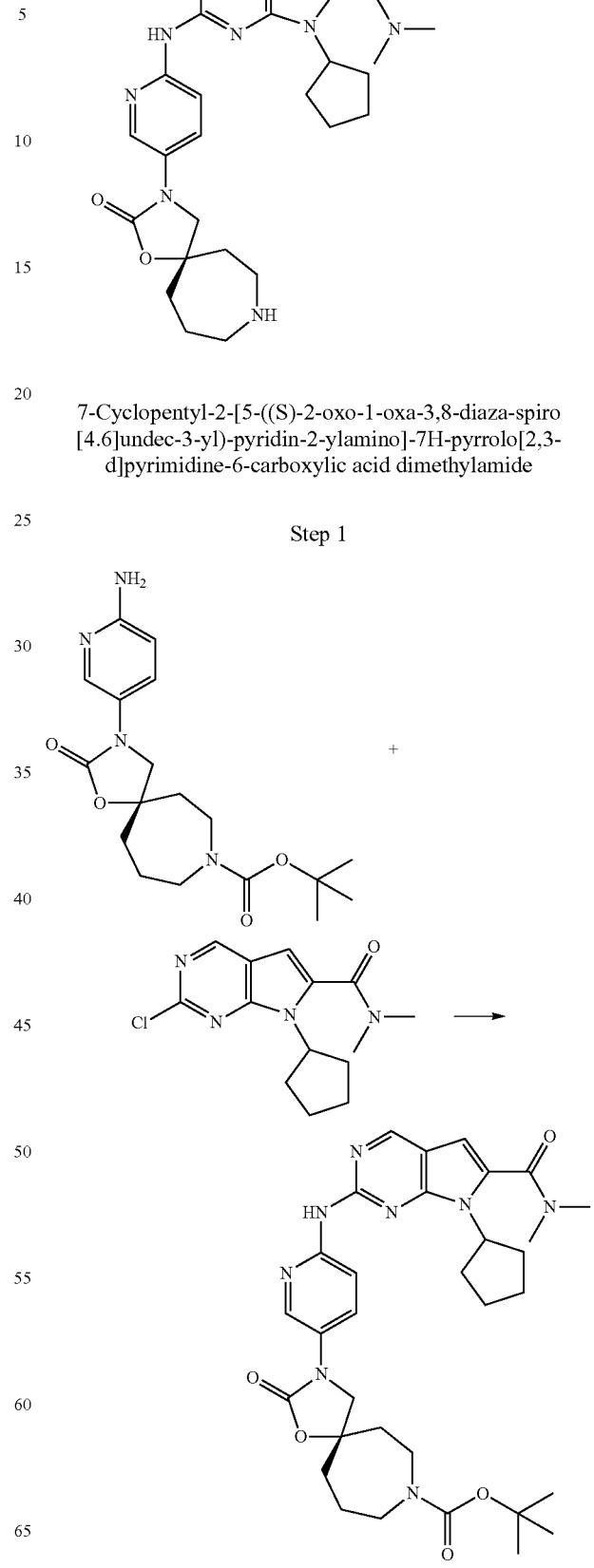

Preparation of (S)-3-[6-(7-Cyclopentyl-6-dimethyl-carbamoyl-7H-pyrrolo[2,3-d]pyrimidin-2-ylamino)-pyridin-3-yl]-2-oxo-1-oxa-3,8-diaza-spiro[4.6]undecane-8-carboxylic acid tert-butyl ester Following general N—C coupling procedure 1, (S)-3-(6-Amino-pyridin-3-yl)-2-oxo-1-oxa-3,8-diaza-spiro[4.6]undecane-8-carboxylic acid tert-butyl ester was combined with 2-Chloro-7-cyclopentyl-7H-pyrrolo[2,3-d]pyrimidine-6-carboxylic acid dimethylamide which gave (S)-3-[6-(7-Cyclopentyl-6-dimethylcarbamoyl-7H-pyrrolo[2,3-d]pyrimidin-2-ylamino)-pyridin-3-yl]-2-oxo-1-oxa-3,8-diaza-spiro[4.6]undecane-8-carboxylic acid tert-butyl ester as a white solid (0.075 g, 0.115 mmol) in 35% yield. MS m/z 619.5 (M+H)+.

Step 2

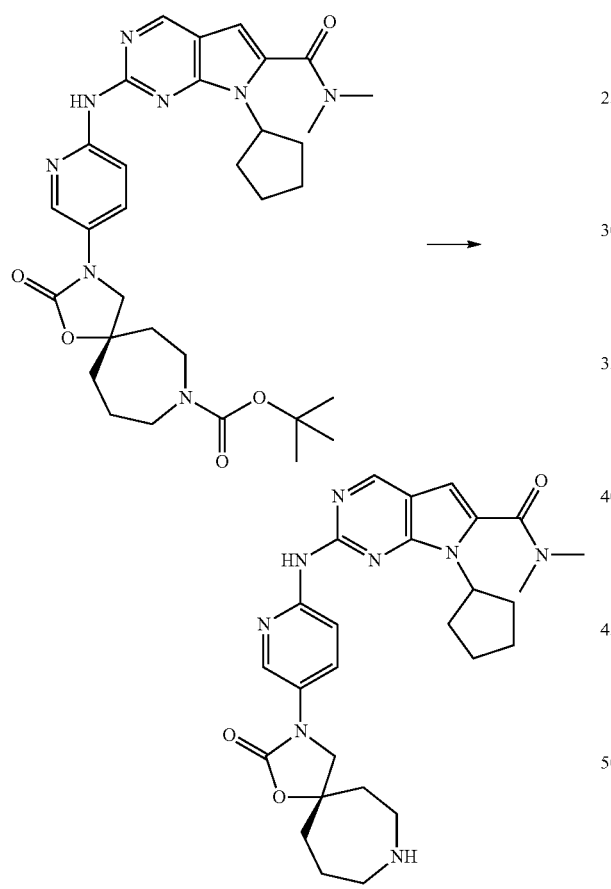

Preparation of 7-Cyclopentyl-2-[5-((S)-2-oxo-1-oxa-3,8-diaza-spiro[4.6]undec-3-yl)-pyridin-2-ylamino]-7H-pyrrolo[2,3-d]pyrimidine-6-carboxylic acid dimethylamide Following deprotection method 1, (S)-3-[6-(7-Cyclopentyl-6-dimethylcarbamoyl-7H-pyrrolo[2,3-d]pyrimidin-2-ylamino)-pyridin-3-yl]-2-oxo-1-oxa-3,8-diaza-spiro[4.6]undecane-8-carboxylic acid tert-butyl ester was converted to 7-Cyclopentyl-2-[5-((S)-2-oxo-1-oxa-3,8-diaza-spiro[4.6]undec-3-yl)-pyridin-2-ylamino]-7H-Pyrrolo[2,3-d]pyrimidine-6-carboxylic acid dimethylamide as a white solid (0.040 g, 0.076 mmol) in 67% yield. $^1$H NMR (400 MHz, MeOD) δ ppm 1.67-1.86 (m, 3H) 1.91-2.17 (m, 8H) 2.19-2.28 (m, 2H) 2.49-2.65 (m, 2H) 2.86-3.09 (m, 4H) 3.11-3.21 (m, 7H) 3.95 (s, 2H) 4.78 (dq, J=9.03, 8.87 Hz, 1H) 8.05 (dd, J=9.03, 3.01 Hz, 1H) 8.40-8.49 (m, 2H) 8.75 (5, 1H); HRMS calc for m/z=519.2832. Found m/z=519.2842 (M+H)+.

Example 106

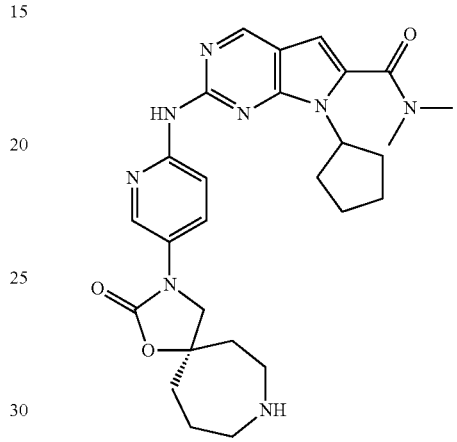

7-Cyclopentyl-2-[5-((R)-2-oxo-1-oxa-3,8-diaza-spiro[4.6]undec-3-yl)-pyridin-2-ylamino]-7H-pyrrolo[2,3-d]pyrimidine-6-carboxylic acid dimethylamide Step 1

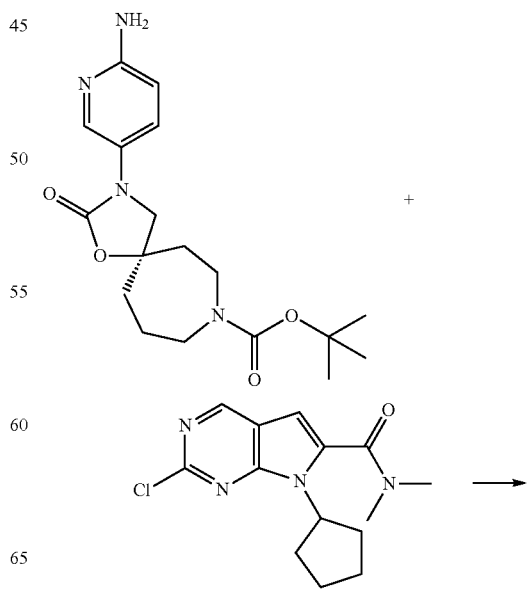

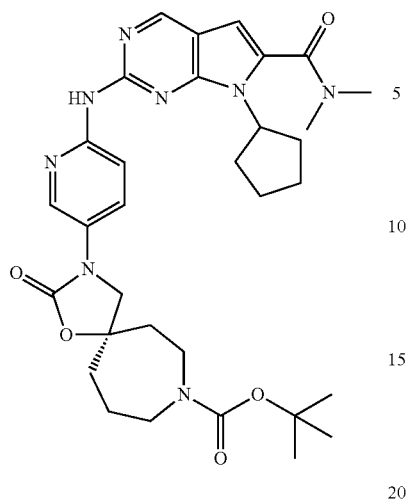

Preparation of (R)-3-[6-(7-Cyclopentyl-6-dimethyl-carbamoyl-7H-pyrrolo[2,3-d]pyrimidin-2-ylamino)-pyridin-3-yl]-2-oxo-1-oxa-3,8-diaza-spiro[4.6]undecane-8-carboxylic acid tert-butyl ester Following general N—C coupling procedure 1, (R)-3-(6-Amino-pyridin-3-yl)-2-oxo-1-oxa-3,8-diaza-spiro[4.6]undecane-8-carboxylic acid tert-butyl ester was combined with 2-Chloro-7-cyclopentyl-7H-pyrrolo[2,3-d]pyrimidine-6-carboxylic acid dimethylamide which gave (R)-3-[6-(7-Cyclopentyl-6-dimethylcarbamoyl-7H-pyrrolo[2,3-d]pyrimidin-2-ylamino)-pyridin-3-yl]-2-oxo-1-oxa-3,8-diaza-spiro[4.6]undecane-8-carboxylic acid tert-butyl ester as a white solid (0.175 g, 0.272 mmol) in 66% yield. $^1$H NMR (400 MHz, DMSO-$d_6$) δ ppm 1.42 (s, 9H) 1.61-1.78 (m, 3H) 1.79-1.96 (m, 3H) 1.96-2.14 (m, 7H) 2.38-2.48 (m, 2H) 3.06 (d, J=10.54 Hz, 6H) 3.20-3.33 (m, 2H) 3.36-3.63 (m, 2H) 3.82-3.97 (m, 2H) 4.75 (quin, J=8.78 Hz, 1H) 6.63 (5, 1H) 7.98 (d, J=9.03 Hz, 1H) 8.34 (d, J=9.54 Hz, 1H) 8.44 (s, 1H) 8.81 (s, 1H) 9.78 (s, 1H). MS m/z 619.5 (M+H)$^+$.

Step 2

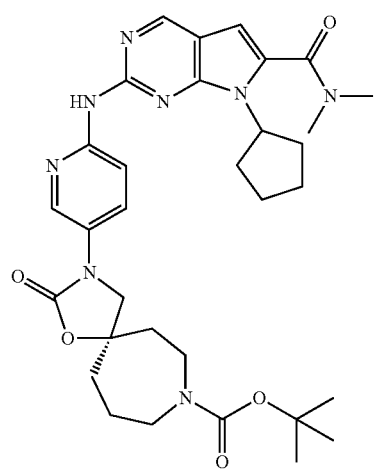

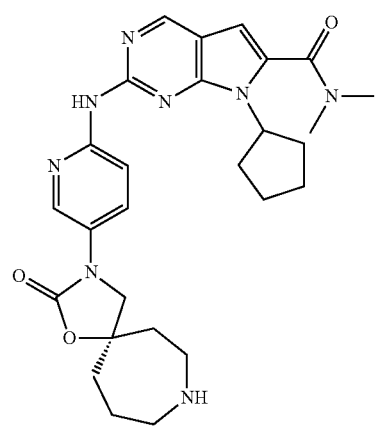 [SMILES: CN(C)C(=O)c1cc2cnc(Nc3ccc(N4C[C@]5(CCCNCC5)OC4=O)cn3)nc2n1C1CCCC1]

Preparation of 7-Cyclopentyl-2-[5-((R)-2-oxo-1-oxa-3,8-diaza-spiro[4.6]undec-3-yl)-pyridin-2-ylamino]-7H-pyrrolo[2,3-d]pyrimidine-6-carboxylic acid dimethylamide Following deprotection method 1, (R)-3-[6-(7-Cyclopentyl-6-dimethylcarbamoyl-7H-pyrrolo[2,3-d]pyrimidin-2-ylamino)-pyridin-3-yl]-2-oxo-1-oxa-3,8-diaza-spiro[4.6]undecane-8-carboxylic acid tert-butyl ester was converted to 7-Cyclopentyl-2-[5-((R)-2-oxo-1-oxa-3,8-diaza-spiro[4.6]undec-3-yl)-pyridin-2-ylamino]-7H-pyrrolo[2,3-d]pyrimidine-6-carboxylic acid dimethylamide as a white solid (0.090 g, 0.167 mmol) in 70% yield. $^1$H NMR (400 MHz, MeOD) δ ppm 1.65-1.86 (m, 3H) 1.97 (dd, J=10.79, 4.27 Hz, 1H) 2.01-2.29 (m, 9H) 2.46-2.64 (m, 2H) 2.88-3.11 (m, 4H) 3.13-3.22 (m, 6H) 3.94 (s, 2H) 4.77 (dq, J=9.03, 8.87 Hz, 1H) 6.63 (s, 1H) 8.04 (dd, J=9.29, 2.76 Hz, 1H) 8.40-8.49 (m, 2H) 8.76 (s, 1H). HRMS calc for m/z=519.2832. Found m/z=519.2834 (M+H)$^+$.

Example 107

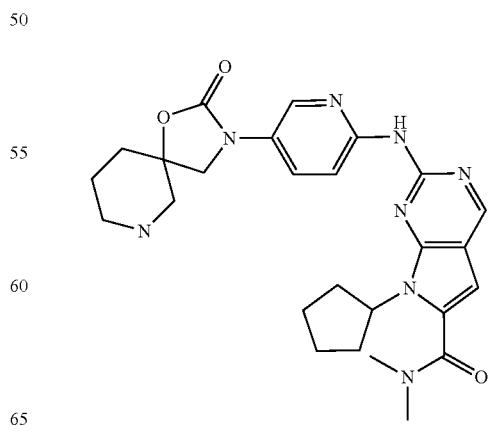

7-cyclopentyl-N,N-dimethyl-2-(5-(2-oxo-1-oxa-3,7-diazaspiro[4.5]decan-3-yl)pyridin-2-ylamino)-7H-pyrrolo[2,3-d]pyrimidine-6-carboxamide Step 1

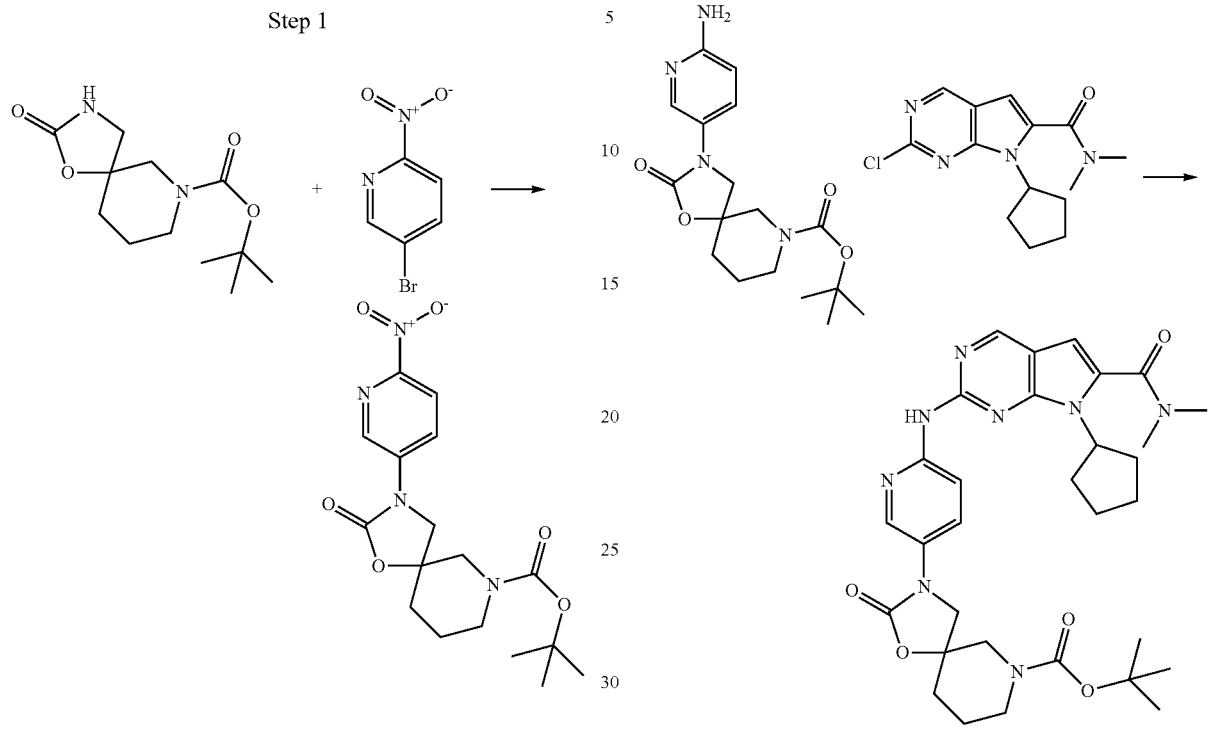

Preparation of 3-(6-Nitro-pyridin-3-yl)-2-oxo-1-oxa-3,7-diaza-spiro[4.5]decane-7-carboxylic acid tert-butyl ester Following general N—C coupling procedure 1, 2-oxo-1-oxa-3,7-diaza-spiro[4.5]decane-7-carboxylic acid tert-butyl ester (0.546 g, 2.130 mmol) (Reference: German Patent DE10 2005 030051A1 (Dec. 28, 2006)), was combined with 5-bromo-2-nitropyridine (0.432 g, 2.130 mmol, 1.0 eq) which gave 3-(6-Nitro-pyridin-3-yl)-2-oxo-1-oxa-3,7-diaza-spiro[4.5]decane-7-carboxylic acid tert-butyl ester as a brown solid (0.709 g, 1.735 mmol) in 81% yield. $^1$H NMR (400 MHz, CDCl$_3$) δ ppm 1.46 (br. s., 9H) 1.55-1.73 (m, 2H) 1.89-2.17 (m, 3H) 3.41 (br. s., 2H) 3.65 (br. s., 2H) 3.78-3.88 (m, 1H) 3.95 (d, J=8.03 Hz, 1H) 8.34 (d, J=9.03 Hz, 1H) 8.54 (br. s., 1H) 8.61 (dd, J=9.03, 3.01 Hz, 1H) MS m/z 379.1 (M+H)$^+$.

Step 2

Preparation of 3-(6-Amino-pyridin-3-yl)-2-oxo-1-oxa-3,7-diaza-spiro[4.5]decane-7-carboxylic acid tert-butyl ester Following nitro group reduction procedure 1, 3-(6-Nitro-pyridin-3-yl)-2-oxo-1-oxa-3,7-diaza-spiro[4.5]decane-7-carboxylic acid tert-butyl ester (0.605 g, 1.599 mmol) was converted to 3-(6-Amino-pyridin-3-yl)-2-oxo-1-oxa-3,7-diaza-spiro[4.5]decane-7-carboxylic acid tert-butyl ester (0.549 g, 1.45 mmol) in 92% yield. $^1$H NMR (400 MHz, CDCl$_3$) δ ppm 1.45 (s, 1H) 1.50-1.70 (m, 1H) 1.79-2.08 (m, 1H) 3.21 (t, J=10.04 Hz, 1H) 3.31-3.47 (m, 1H) 3.65 (d, J=9.03 Hz, 1H) 3.70-3.85 (m, 1H) 4.41 (br. s., 1H) 6.55 (d, J=8.53 Hz, 1H) 7.91 (dd, J=8.78, 2.76 Hz, 1H) 7.96 (d, J=2.51 Hz, 1H). MS m/z 349.1 (M+H)$^+$.

Step 3

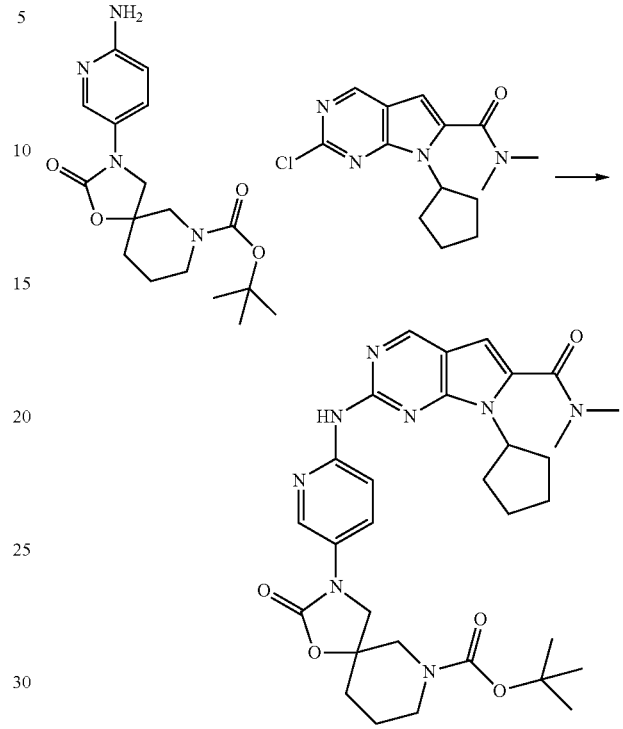

Preparation of 3-[6-(7-Cyclopentyl-6-dimethylcarbamoyl-7H-pyrrolo[2,3-d]pyrimidin-2-ylamino)-pyridin-3-yl]-2-oxo-1-oxa-3,7-diaza-spiro[4.5]decane-7-carboxylic acid tert-butyl ester Following general N—C coupling procedure 1, 3-(6-Amino-pyridin-3-yl)-2-oxo-1-oxa-3,7-diaza-spiro[4.5]decane-7-carboxylic acid tert-butyl ester was combined with 2-Chloro-7-cyclopentyl-7H-pyrrolo[2,3-d]pyrimidine-6-carboxylic acid dimethylamide (0.084 g, 0.287 mmol, 1.0 eq) and gave 3-[6-(7-Cyclopentyl-6-dimethylcarbamoyl-7H-pyrrolo[2,3-d]pyrimidin-2-ylamino)-pyridin-3-yl]-2-oxo-1-oxa-3,7-diaza-spiro[4.5]decane-7-carboxylic acid tert-butyl ester which was used directly in the following BOC deprotection.

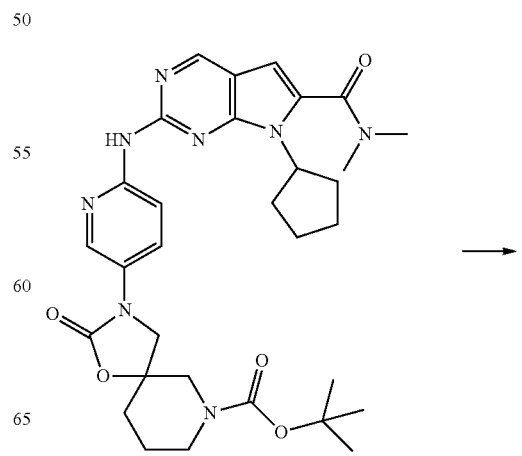

-continued

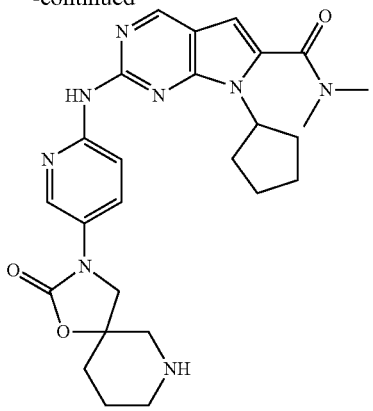

Step 4

Preparation of 7-cyclopentyl-N,N-dimethyl-2-(5-(2-oxo-1-oxa-3,7-diazaspiro[4.5]decan-3-yl)pyridin-2-ylamino)-7H-pyrrolo[2,3-d]pyrimidine-6-carboxamide Following deprotection method 1, 3-[6-(7-Cyclopentyl-6-dimethylcarbamoyl-7H-pyrrolo[2,3-d]pyrimidin-2-ylamino)-pyridin-3-yl]-2-oxo-1-oxa-3,7-diaza-spiro[4.5]decane-7-carboxylic acid tert-butyl ester was converted to 7-cyclopentyl-N,N-dimethyl-2-(5-(2-oxo-1-oxa-3,7-diazaspiro[4.5]decan-3-yl)pyridin-2-ylamino)-7H-pyrrolo[2,3-d]pyrimidine-6-carboxamide which gave a white solid (0.070 g, 0.135 mmol in 47% yield.

$^1$H NMR (400 MHz, CDCl$_3$) δ ppm 1.54-1.68 (m, 1H) 1.68-1.81 (m, 2H) 1.81-1.98 (m, 4H) 1.98-2.14 (m, 6H) 2.46-2.69 (m, 2H) 2.77-2.91 (m, 2H) 2.91-3.12 (m, 2H) 3.16 (s, 6H) 3.75 (d, J=8.53 Hz, 1H) 3.91 (d, J=8.53 Hz, 1H) 4.80 (dq, J=9.03, 8.87 Hz, 1H) 6.46 (s, 1H) 8.13 (dd, J=9.03, 3.01 Hz, 1H) 8.33 (br. s., 1H) 8.36 (d, J=2.51 Hz, 1H) 8.51 (d, J=9.03 Hz, 1H) 8.76 (s, 1H). HRMS calc for m/z=505.2676. Found m/z=505.2676 (M+H)$^+$.

Example 108

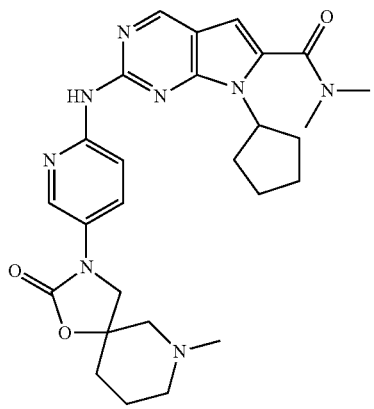 [SMILES: CN1CCCC2(C1)CN(c1ccc(Nc3ncc4cc(C(=O)N(C)C)n(C5CCCC5)c4n3)nc1)C(=O)O2]

Preparation of 7-cyclopentyl-N,N-dimethyl-2-(5-(7-methyl-2-oxo-1-oxa-3,7-diazaspiro[4.5]decan-3-yl)pyridin-2-ylamino)-7H-pyrrolo[2,3-d]pyrimidine-6-carboxamide Following general reductive alkylation method 1, 7-cyclopentyl-N,N-dimethyl-2-(5-(2-oxo-1-oxa-3,7-diazaspiro[4.5]decan-3-yl)pyridin-2-ylamino)-7H-pyrrolo[2,3-d]pyrimidine-6-carboxamide (0.116 mmol) was converted to 7-cyclopentyl-N,N-dimethyl-2-(5-(7-methyl-2-oxo-1-oxa-3,7-diazaspiro[4.5]decan-3-yl)pyridin-2-ylamino)-7H-pyrrolo[2,3-d]pyrimidine-6-carboxamide which was isolated as an off-white solid (0.052 g, 0.098 mmol) in 85% yield. $^1$H NMR (400 MHz, DMSO-d$_6$) δ ppm 1.51-1.79 (m, 6H) 1.85 (br. s., 1H) 1.99 (s, 5H) 2.09 (br. s., 1H) 2.22 (s, 4H) 2.37-2.48 (m, 3H) 2.68 (d, J=8.03 Hz, 1H) 3.06 (d, J=11.04 Hz, 7H) 3.86-3.98 (m, 2H) 4.69-4.83 (m, 1H) 6.63 (s, 1H) 8.03 (dd, J=9.29, 2.76 Hz, 1H) 8.34 (d, J=9.03 Hz, 1H) 8.48 (d, J=3.01 Hz, 1H) 8.81 (s, 1H) 9.74 (s, 1H). HRMS calc for m/z=519.2832. Found m/z=519.2834 (M+H)$^+$.

Example 109

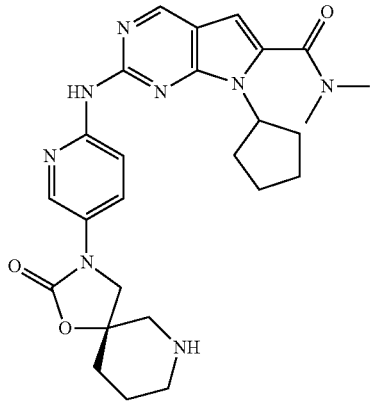 [SMILES: CN(C)C(=O)c1cc2cnc(Nc3ccc(N4C[C@@]5(CCCNC5)OC4=O)cn3)nc2n1C1CCCC1]

7-Cyclopentyl-2-[5-((S)-2-oxo-1-oxa-3,7-diaza-spiro[4.5]dec-3-yl)-pyridin-2-ylamino]-7H-pyrrolo[2,3-d]pyrimidine-6-carboxylic acid dimethylamide Step 1

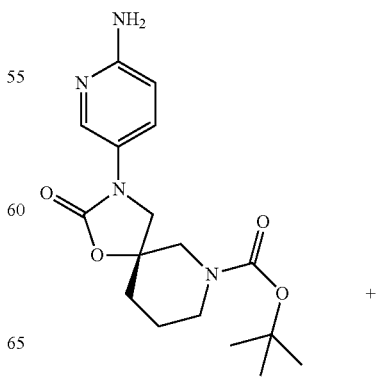

+

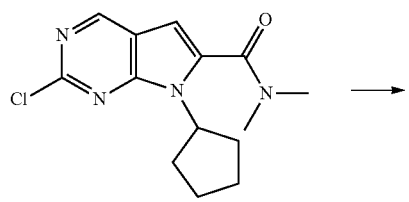

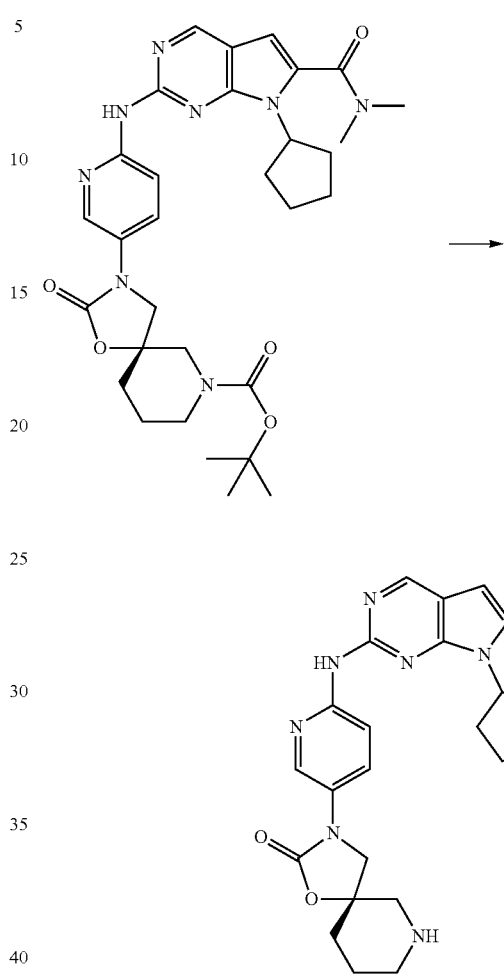

Preparation of (S)-3-[6-(7-Cyclopentyl-6-dimethyl-carbamoyl-7H-pyrrolo[2,3-d]pyrimidin-2-ylamino)-pyridin-3-yl]-2-oxo-1-oxa-3,7-diaza-spiro[4.5]decane-7-carboxylic acid tert-butyl ester Following general N—C coupling procedure 1, (S)-3-(6-Amino-pyridin-3-yl)-2-oxo-1-oxa-3,7-diaza-spiro[4.5]decane-7-carboxylic acid tert-butyl ester was combined with 2-Chloro-7-cyclopentyl-7H-pyrrolo[2,3-d]pyrimidine-6-carboxylic acid dimethylamide which gave (S)-3-[6-(7-Cyclopentyl-6-dimethylcarbamoyl-7H-pyrrolo[2,3-d]pyrimidin-2-ylamino)-pyridin-3-yl]-2-oxo-1-oxa-3,7-diaza-spiro[4.5]decane-7-carboxylic acid tert-butyl ester as a white solid (0.115 g, 0.190 mmol in 43% yield. $^1$H NMR (400 MHz, CDCl$_3$) δ ppm 1.37-1.51 (m, 13H) 1.51-1.69 (m, 3H) 1.69-1.84 (m, 2H) 1.85-2.15 (m, 11H) 2.47-2.68 (m, 2H) 3.10-3.19 (m, 6H) 3.19-3.33 (m, 2H) 3.43 (d, J=14.05 Hz, 1H) 3.58-3.71 (m, 2H) 3.71-3.80 (m, 2H) 3.85 (d, J=9.03 Hz, 2H) 4.12 (q, J=7.03 Hz, 1H) 4.44 (br. s., 1H) 4.80 (quin, J=8.78 Hz, 1H) 6.46 (s, 1H) 7.87-7.99 (m, 1H) 8.11 (dd, J=9.29, 2.76 Hz, 1H) 8.21 (br. s., 1H) 8.30 (br. s., 1H) 8.52 (d, J=9.03 Hz, 1H) 8.75 (s, 1H). MS m/z 605.5 (M+H)$^+$.

Step 2

Preparation of 7-Cyclopentyl-2-[5-((S)-2-oxo-1-oxa-3,7-diaza-spiro[4.5]dec-3-yl)-pyridin-2-ylamino]-7H-pyrrolo[2,3-d]pyrimidine-6-carboxylic acid dimethylamide Following deprotection method 1, (S)-3-[6-(7-Cyclopentyl-6-dimethylcarbamoyl-7H-pyrrolo[2,3-d]pyrimidin-2-ylamino)-pyridin-3-yl]-2-oxo-1-oxa-3,7-diaza-spiro[4.5]decane-7-carboxylic acid tert-butyl ester was converted to 7-Cyclopentyl-2-[5-((S)-2-oxo-1-oxa-3,7-diaza-spiro[4.5]dec-3-yl)-pyridin-2-ylamino]-7H-pyrrolo[2,3-d]pyrimidine-6-carboxylic acid dimethylamide (0.062 g, 0.123 mmol) in 71% yield. $^1$H NMR (400 MHz, MeOD) δ ppm 1.66 (ddd, J=9.66, 6.65, 3.26 Hz, 1H) 1.70-1.81 (m, 2H) 1.81-2.00 (m, 2H) 2.00-2.16 (m, 5H) 2.47-2.64 (m, 2H) 2.66-2.80 (m, 1H) 2.80-2.90 (m, 1H) 2.90-2.99 (m, 1H) 2.99-3.10 (m, 1H) 3.16 (d, J=4.52 Hz, 7H) 3.83-3.90 (m, 1H) 3.90-3.99 (m, 1H) 4.78 (dq, J=9.03, 8.87 Hz, 1H) 8.07 (dd, J=9.29, 2.76 Hz, 1H) 8.44 (s, 1H) 8.46 (d, J=5.02 Hz, 1H) 8.75 (s, 1H). HRMS calc for m/z=505.2676. Found m/z=505.2683 (M+H)$^+$.

Example 110

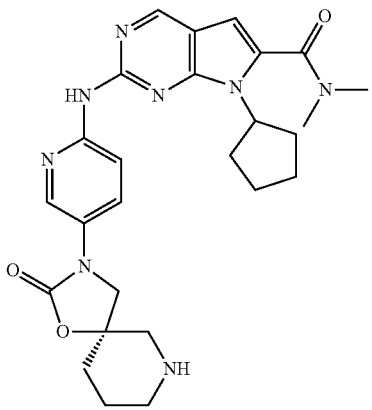 [SMILES: CN(C)C(=O)c1cc2cnc(Nc3ccc(N4C[C@]5(CCCNC5)OC4=O)cn3)nc2n1C1CCCC1]

7-Cyclopentyl-2-[5-((R)-2-oxo-1-oxa-3,7-diaza-spiro[4.5]dec-3-yl)-pyridin-2-ylamino]-7H-pyrrolo[2,3-d]pyrimidine-6-carboxylic acid dimethylamide

Step 1

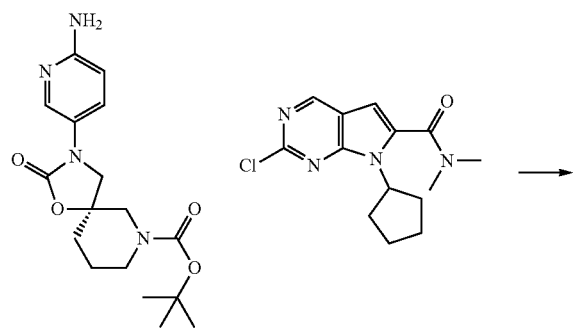

Preparation of (R)-3-[6-(7-Cyclopentyl-6-dimethyl-carbamoyl-7H-pyrrolo[2,3-d]pyrimidin-2-ylamino)-pyridin-3-yl]-2-oxo-1-oxa-3,7-diaza-spiro[4.5]decane-7-carboxylic acid tert-butyl ester Following general N—C coupling procedure 1, (R)-3-(6-amino-pyridin-3-yl)-2-oxo-1-oxa-3,7-diaza-spiro[4.5]decane-7-carboxylic acid tert-butyl ester was combined with 2-Chloro-7-cyclopentyl-7H-pyrrolo[2,3-d]pyrimidine-6-carboxylic acid dimethylamide which gave (R)-3-[6-(7-Cyclopentyl-6-dimethylcarbamoyl-7H-pyrrolo[2,3-d]pyrimidin-2-ylamino)-pyridin-3-yl]-2-oxo-1-oxa-3,7-diaza-spiro[4.5]decane-7-carboxylic acid tert-butyl ester as a white solid (0.175 g, 0.275 mmol) in 64% yield. $^1$H NMR (400 MHz, CDCl$_3$) δ ppm 1.47 (s, 9H) 1.55-1.68 (m, 2H) 1.68-1.85 (m, 3H) 1.88-2.18 (m, 8H) 2.50-2.68 (m, 2H) 3.13-3.21 (m, 6H) 3.21-3.32 (m, 1H) 3.37-3.58 (m, 1H) 3.61-3.72 (m, 1H) 3.75 (d, J=8.53 Hz, 2H) 3.86 (d, J=8.53 Hz, 2H) 4.72-4.95 (m, J=8.91, 8.91, 8.78, 8.53 Hz, 1H) 6.48 (s, 1H) 8.14 (dd, J=9.29, 2.76 Hz, 1H) 8.31 (br. s., 1H) 8.53 (d, J=9.54 Hz, 1H) 8.76 (s, 1H). MS m/z 605.5 (M+H)$^+$.

Step 2

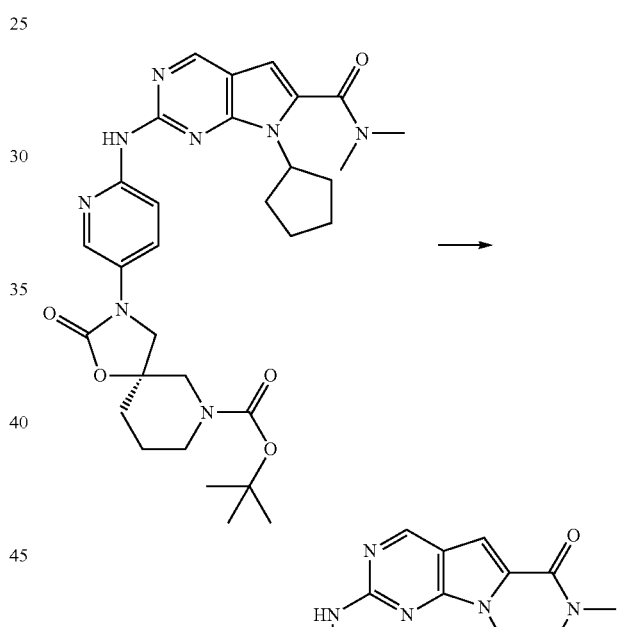

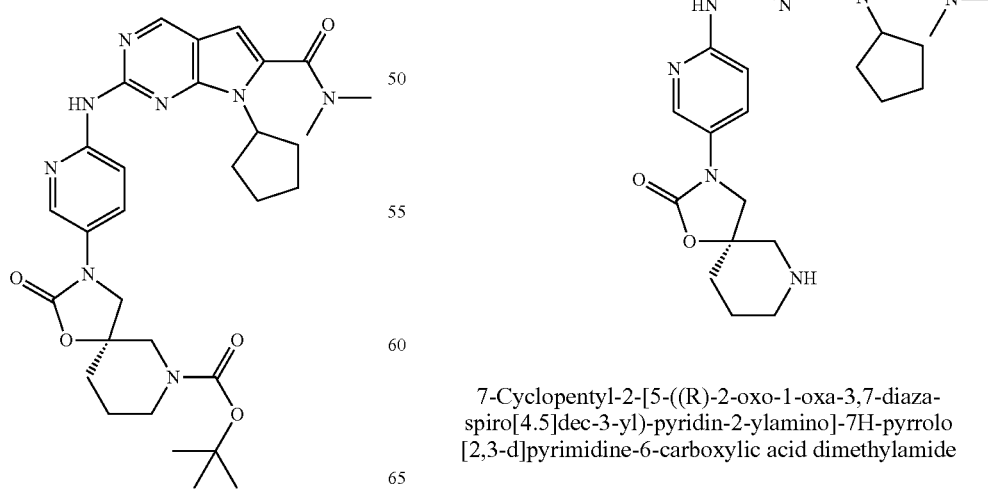

7-Cyclopentyl-2-[5-((R)-2-oxo-1-oxa-3,7-diaza-spiro[4.5]dec-3-yl)-pyridin-2-ylamino]-7H-pyrrolo[2,3-d]pyrimidine-6-carboxylic acid dimethylamide Following deprotection method 1, (R)-3-[6-(7-Cyclopentyl-6-dimethylcarbamoyl-7H-pyrrolo[2,3-d]pyrimidin-2- ylamino)-pyridin-3-yl]-2-oxo-1-oxa-3,7-diaza-spiro[4.5]decane-7-carboxylic acid tert-butyl ester was converted to 7-Cyclopentyl-2-[5-((R)-2-oxo-1-oxa-3,7-diaza-spiro[4.5]dec-3-yl)-pyridin-2-ylamino]-7H-pyrrolo[2,3-d]pyrimidine-6-carboxylic acid dimethylamide as a white solid (0.120 g, 0.238 mmol) in 85% yield.

$^1$H NMR (400 MHz, MeOD) δ ppm 1.66 (ddd, J=9.79, 6.53, 3.26 Hz, 1H) 1.70-1.81 (m, 2H) 1.81-2.01 (m, 2H) 2.01-2.18 (m, 5H) 2.47-2.64 (m, 2H) 2.69-2.82 (m, 1H) 2.85 (d, J=6.02 Hz, 1H) 2.91-2.99 (m, 1H) 2.99-3.09 (m, 1H) 3.10-3.20 (m, 6H) 3.82-3.90 (m, 1H) 3.90-3.99 (m, 1H) 4.78 (qd, J=8.95, 8.78 Hz, 1H) 6.63 (s, 1H) 8.07 (dd, J=9.54, 2.51 Hz, 1H) 8.44 (s, 1H) 8.46 (d, J=5.02 Hz, 1H) 8.75 (s, 1H)

HRMS talc for m/z=505.2676. Found m/z=505.2676 (M+H)$^+$.

Example 111

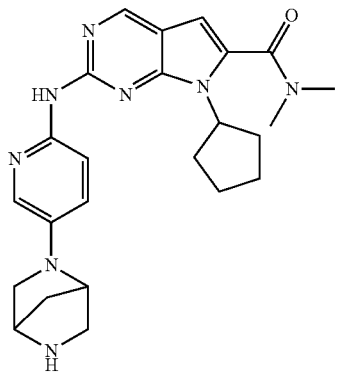 [SMILES: CN(C)C(=O)c1cc2cnc(Nc3ccc(N4CC5CC4CN5)cn3)nc2n1C1CCCC1]

7-Cyclopentyl-2-[5-(2,5-diaza-bicyclo[2.2.1]hept-2-yl)-pyridin-2-ylamino]-7H-pyrrolo[2,3-d]pyrimidine-6-carboxylic acid dimethylamide Step 1

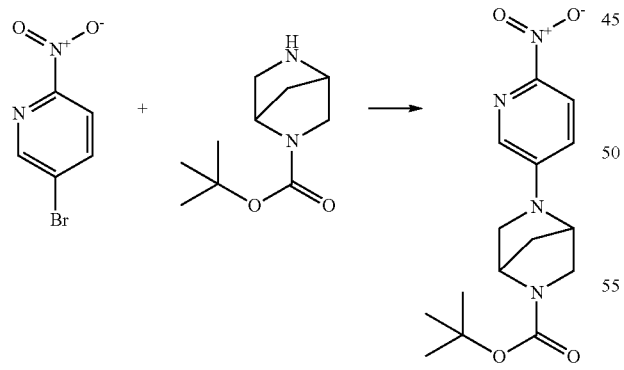

Preparation of 5-(6-Nitro-pyridin-3-yl)-2,5-diaza-bicyclo[2.2.1]heptane-2-carboxylic acid tert-butyl ester 2-Bromo-5-Nitropyridine (4.75 g, 23.4 mmol, 1.0 eq) and (R,R)-2,5-Diaza-bicyclo[2.2.1]heptane-2-carboxylic acid tert-butyl ester (5.04 g, 25.4 mmol, 1.1 eq) were combined in DMF (60 mL) and heated to 100° C. The reaction was cooled and diluted with Ethyl Acetate, washed with water several times followed by brine, the organic layer dried (Na$_2$SO$_4$), filtered, and the organic concentrated. Crude was purified using chromatography eluting with MeOH/DCM mixtures giving the desired product (4.3 g, 57%). MS m/z 278.4 (M-C$_4$H$_9$).

Step 2

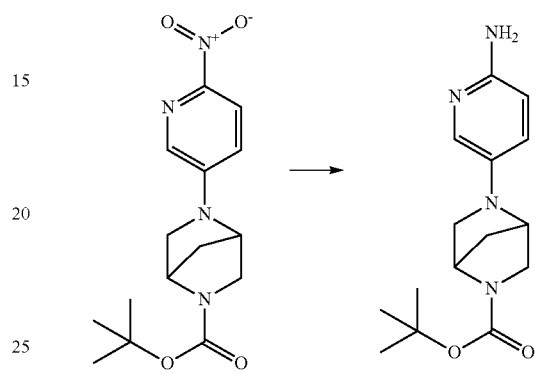

5-(6-Amino-pyridin-3-yl)-2,5-diaza-bicyclo[2.2.1]heptane-2-carboxylic acid tert-butyl ester 5-(6-Nitro-pyridin-3-yl)-2,5-diaza-bicyclo[2.2.1]heptane-2-carboxylic acid tert-butyl ester (1.00 g, 3.12, ol, 1.0 eq) was hydrogenated in a parr flask at 50 psi using Pd/C (0.250 g) in Ethyl Acetate (25 mL) for 16 hr. The reaction contents were filtered through Celite was washed with MeOH and the filtrate was concentrated. The crude was purified chromatographically using (MeOH/CH$_2$Cl$_2$) mixtures giving a purple solid (0.648 g, 68%). 1H NMR (400 MHz, CHLOROFORM-d) δ ppm 1.44 (d, J=19.71 Hz, 12H) 1.84-2.07 (m, 3H) 3.11 (d, J=8.59 Hz, 1H) 3.29-3.51 (m, 3H) 3.52-3.60 (m, 1H) 4.02 (br. s., 2H) 4.29 (s, 1H) 6.46-6.55 (m, 1H) 6.84 (dd, J=8.59, 2.53 Hz, 1H) 7.50 (br. s., 1H); MS m/z 291.6 (M+H)$^+$.

Step 3

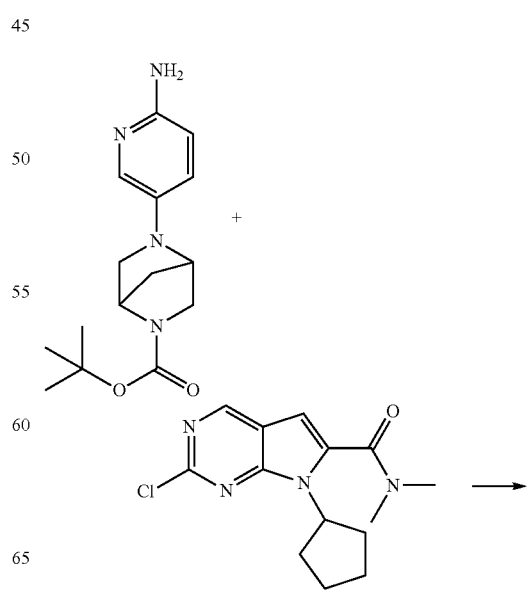

259

-continued

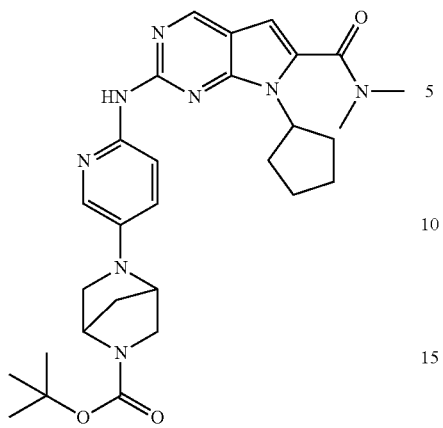

Preparation of 4-[6-(7-Cyclopentyl-6-dimethylcarbamoyl-7H-pyrrolo[2,3-d]pyrimidin-2-ylamino)-pyridin-3-yl]-piperazine-1-carboxylic acid tert-butyl ester Using General Buchwald method 1, 2-Chloro-7-cyclopentyl-7H-pyrrolo[2,3-d]pyrimidine-6-carboxylic acid dimethylamide (200 mg, 0.683 mmol, 1.0 eq) was combined with 5-(6-Amino-pyridin-3-yl)-2,5-diaza-bicyclo[2.2.1]heptane-2-carboxylic acid tert-butyl ester (218 mg, 0.751 mmol, 1.1 eq) to give 4-[6-(7-Cyclopentyl-6-dimethylcarbamoyl-7H-pyrrolo[2,3-d]pyrimidin-2-ylamino)-pyridin-3-yl]-piperazine-1-carboxylic acid tert-butyl ester (350 mg, 94% yield). 1H NMR (400 MHz, DMSO-$d_6$) δ ppm 1.32 (s, 6H) 1.39 (s, 6H) 1.62 (br. s., 3H) 1.94 (br. s., 8H) 2.41 (br. s., 3H) 2.92-3.02 (m, 2H) 3.05 (br. s., 7H) 3.26 (d, J=11.12 Hz, 3H) 3.34 (br. s., 3H) 3.51-3.64 (m, 1H) 4.39 (s, 1H) 4.45 (br. s., 1H) 4.55 (br. s., 1H) 4.72 (t, J=8.59 Hz, 1H) 6.58 (s, 1H) 7.12 (dd, J=9.09, 3.03 Hz, 1H) 7.74 (d, J=2.53 Hz, 1H) 8.02 (t, J=8.08 Hz, 1H) 8.72 (s, 1H) 9.15 (s, 1H); MS m/z 547.1 (M+H)$^+$.

Step 4

260

-continued

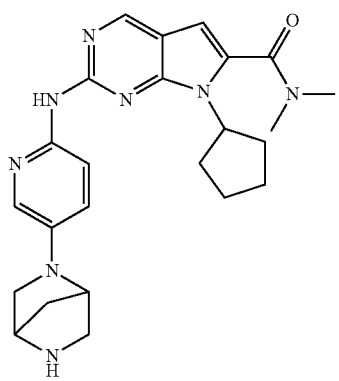

Preparation of 7-Cyclopentyl-2-[5-(2,5-diaza-bicyclo[2.2.1]hept-2-yl)-pyridin-2-ylamino]-7H-yrrolo[2,3-d]pyrimidine-6-carboxylic acid dimethylamide Treatment of 4-[6-(7-Cyclopentyl-6-dimethylcarbamoyl-7H-pyrrolo[2,3-d]pyrimidin-2-ylamino)-pyridin-3-yl]-piperazine-1-carboxylic acid tert-butyl ester with TFA using general deprotection method 2 for removal of the BOC group gave 7-Cyclopentyl-2-[5-(2,5-diaza-bicyclo[2.2.1]hept-2-yl)-pyridin-2-ylamino]-7H-yrrolo[2,3-d]pyrimidine-6-carboxylic acid dimethylamide (117 mg, 47%). 1H NMR (400 MHz, DMSO-$d_6$) δ ppm 1.65 (br. s., 3H) 1.79 (s, 1H) 1.90 (s, 1H) 1.93-2.02 (m, 5H) 2.43 (br. s., 3H) 2.82-2.91 (m, 3H) 3.05 (br. s., 6H) 3.49-3.57 (m, 1H) 3.64 (br. s., 1H) 4.37 (s, 1H) 4.67-4.79 (m, 1H) 6.57 (s, 1H) 7.04 (dd, J=9.09, 3.03 Hz, 1H) 7.68 (d, J=3.03 Hz, 1H) 8.03 (d, J=9.09 Hz, 1H) 8.71 (s, 1H) 9.07 (s, 1H); MS m/z 447.2 (M+H)$^+$.

Example 112

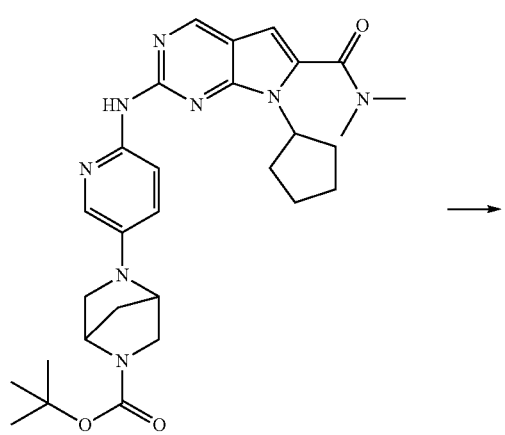 → 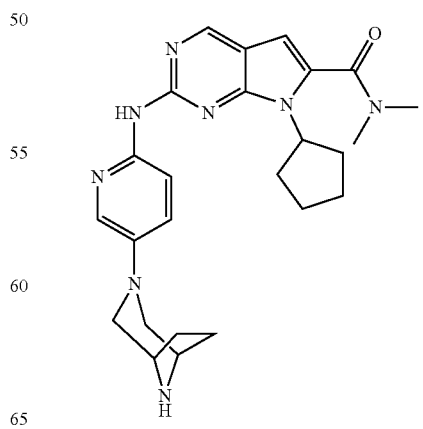

261

7-Cyclopentyl-2-[5-(3,8-diaza-bicyclo[3.2.1]oct-3-yl)pyridin-2-ylamino]-7H-pyrrolo[2,3-d]pyrimidine-6-carboxylic acid dimethylamide Step 1

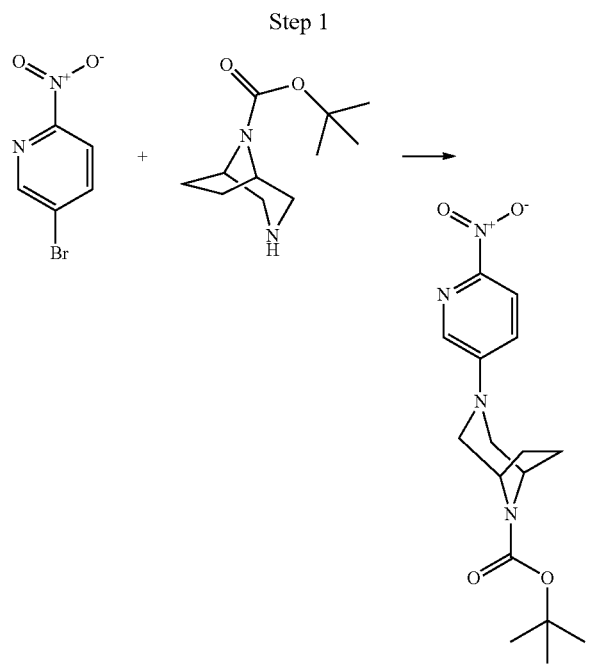

Preparation of 3-(6-Nitro-pyridin-3-yl)-3,8-diaza-bicyclo[3.2.1]octane-8-carboxylic acid tert-butyl ester Following Example 78 Step 1 using 5-bromo-2-nitropyridine (200 mg, 0.985 mmol, 1.0 eq) and (3,8-Diaza-bicyclo[3.2.1]octane-8-carboxylic acid tert-butyl ester (934 mg, 4.40 mmol, 4.5 eq) gave 3-(6-Nitro-pyridin-3-yl)-3,8-diaza-bicyclo[3.2.1]octane-8-carboxylic acid tert-butyl ester (242 mg, 74%). $^1$H NMR (400 MHz, CHLOROFORM-d) δ ppm 1.51 (s, 10H) 1.75-1.89 (m, 2H) 2.01-2.12 (m, 2H) 3.27 (d, J=11.12 Hz, 2H) 3.59 (d, J=11.62 Hz, 2H) 4.48 (br. s., 2H) 7.17 (dd, J=9.09, 3.03 Hz, 1H) 8.10 (d, J=3.03 Hz, 1H) 8.19 (d, J=9.09 Hz, 1H); MS m/z 335.1 (M+H)$^+$.

Step 2

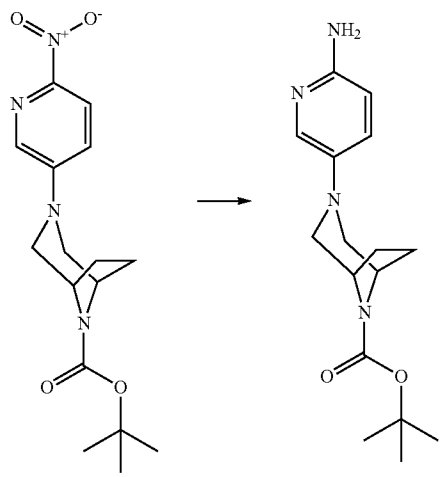

262

Preparation of 3-(6-Amino-pyridin-3-yl)-3,8-diaza-bicyclo[3.2.1]octane-8-carboxylic acid tert-butyl ester Following Example 78 Step 2 using 5-(6-Nitro-pyridin-3-yl)-2,5-diaza-bicyclo[2.2.1]heptane-2-carboxylic acid tert-butyl ester (240 mg, 0.718 mmol, 1.0 eq) and Pd/C (76 mg) gave 3-(6-Amino-pyridin-3-yl)-3,8-diaza-bicyclo[3.2.1]octane-8-carboxylic acid tert-butyl ester (205 mg, 94%). MS m/z 305.2 (M+H)$^+$.

Step 3

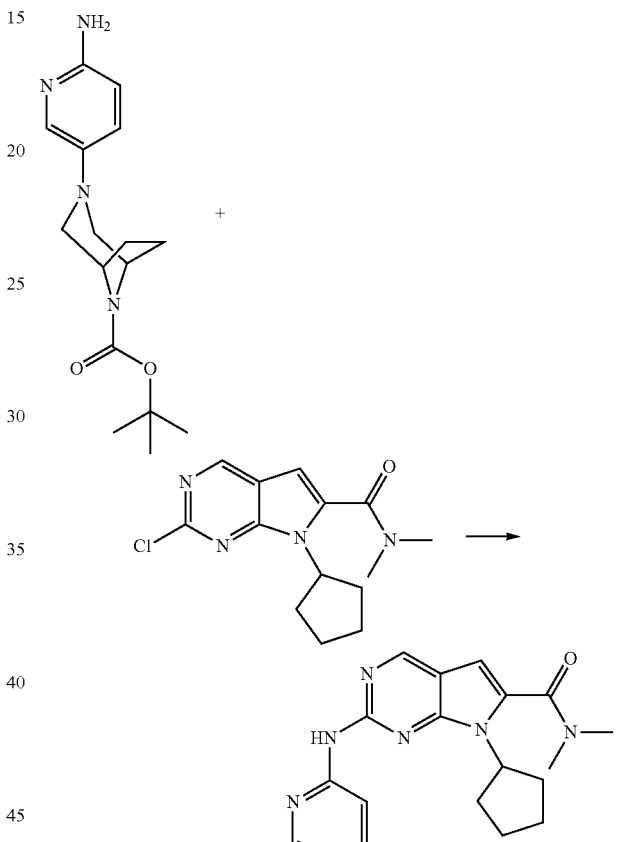

Preparation of 3-[6-(7-Cyclopentyl-6-dimethylcarbamoyl-7H-pyrrolo[2,3-d]pyrimidin-2-ylamino)-pyridin-3-yl]-3,8-diaza-bicyclo[3.2.1]octane-8-carboxylic acid tert-butyl ester Using General Buchwald method 1, 2-Chloro-7-cyclopentyl-7H-pyrrolo[2,3-d]pyrimidine-6-carboxylic acid dimethylamide (139 mg, 0.476 mmol, 1.0 eq) was combined with 3-(6-Amino-pyridin-3-yl)-3,8-diaza-bicyclo[3.2.1]octane-8-carboxylic acid tert-butyl ester (145 mg, 0.476 mmol, 1.0 eq) to give 3-[6-(7-Cyclopentyl-6-dimethylcarbamoyl-7H-pyrrolo[2,3-d]pyrimidin-2-ylamino)-pyridin-3-yl]-3,8-diaza-bicyclo[3.2.1]octane-8-carboxylic acid tert-butyl ester (143 mg, 51% yield). 1H NMR (400 MHz, DMSO-$d_6$) δ ppm 1.42 (s, 9H) 1.57-1.70 (m, 2H) 1.74-1.92 (m, 4H) 1.98 (br. s., 4H) 2.36-2.48 (m, 2H) 2.78 (d, J=10.11 Hz, 2H) 3.05 (br. s., 6H) 3.48 (d, J=10.11 Hz, 2H) 4.24 (br. s., 2H) 4.73 (qd, J=8.76, 8.59 Hz, 1H) 6.59 (s, 1H) 7.37 (dd, J=9.09, 3.03 Hz, 1H) 7.94 (d, J=3.03 Hz, 1H) 8.13 (d, J=9.09 Hz, 1H) 8.75 (s, 1H) 9.24 (s, 1H); MS m/z 561.3 (M+H).

Step 4

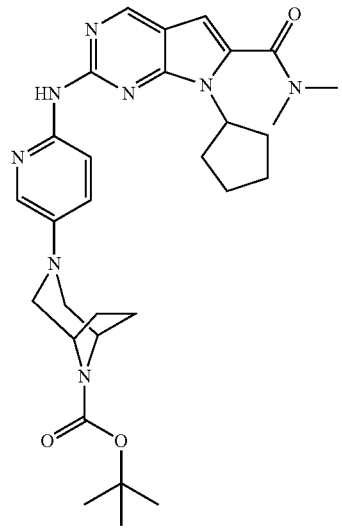

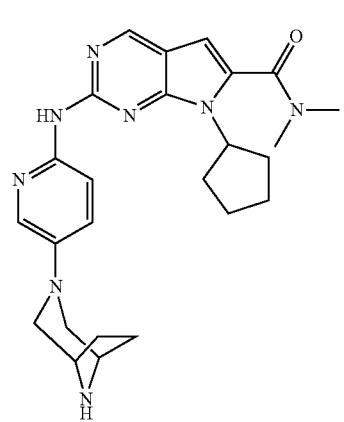 [SMILES: CN(C)C(=O)c1cc2cnc(Nc3ccc(N4CC5CCC(C4)N5)cn3)nc2n1C1CCCC1]

7-Cyclopentyl-2-[5-(3,8-diaza-bicyclo[3.2.1]oct-3-yl)-pyridin-2-ylamino]-7H-pyrrolo[2,3-d]pyrimidine-6-carboxylic acid dimethylamide Treatment of 3-[6-(7-Cyclopentyl-6-dimethylcarbamoyl-7H-pyrrolo[2,3-d]pyrimidin-2-ylamino)-pyridin-3-yl]-3,8-diaza-bicyclo[3.2.1]octane-8-carboxylic acid tert-butyl ester with TFA using general deprotection method 2 for removal of the BOC group gave 7-Cyclopentyl-2-[5-(3,8-diaza-bicyclo [3.2.1]oct-3-yl)-pyridin-2-ylamino]-7H-pyrrolo[2,3-d]pyrimidine-6-carboxylic acid dimethylamide (83 mg, 76%). 1H NMR (400 MHz, DMSO-$d_6$) δ ppm 1.54-1.72 (m, 2H) 1.86-2.04 (m, 8H) 2.36-2.48 (m, 2H) 2.93-3.11 (m, 8H) 3.59 (d, J=10.11 Hz, 2H) 4.06 (br. s., 2H) 4.74 (qd, J=8.76, 8.59 Hz, 1H) 6.60 (s, 1H) 7.41 (dd, J=9.35, 2.78 Hz, 1H) 7.97 (d, J=2.53 Hz, 1H) 8.16 (d, J=9.09 Hz, 1H) 8.36 (br. s., 1H) 8.75 (s, 1H) 9.30 (s, 1H); MS m/z 461.2 (M+H)

Example 113

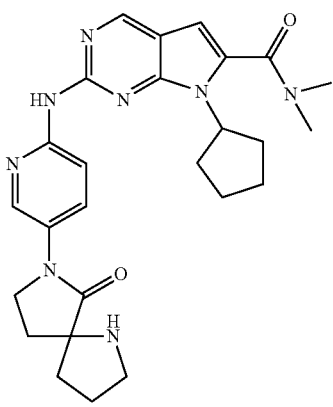 [SMILES: CN(C)C(=O)c1cc2cnc(Nc3ccc(N4CCC5(CCCN5)C4=O)cn3)nc2n1C1CCCC1]

Step 1

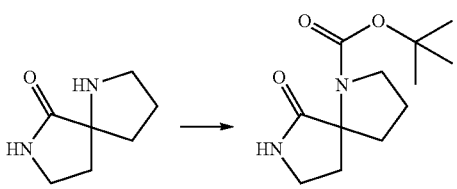 [SMILES: O=C1NCCC12CCCN2 ; CC(C)(C)OC(=O)N1CCCC12CCNC2=O]

Preparation of
6-Oxo-1,7-diaza-spiro[4,4]nonan-1-carboxylic acid tert-butyl ester 1

To a solution of 1,7-diazaspiro[4,4]nonan-6-one hydrochloride (0.98 g, 5.4 mmol) in dichloromethane were added tert-butyldicarbonate (1.41 g, 6.48 mmol) and triethylamine (1.3 g, 13.5 mmol). The resulting solution was stirred overnight at room temperature. The solution was diluted with water and extracted with dichloromethane. The organic phase was separated, dried, filtered and concentrated to afford 6-oxo-1,7-diaza-spiro[4,4]nonan-1-carboxylic acid tert-butyl ester product as white powder (1.3 g) in 100% yield and used directly without further purification. $^1$H NMR (400 MHz, CD$_2$Cl$_2$) δ 6.13-5.74 (br, 1H), 3.59-3.20 (m, 4H), 2.75-2.49 (m, 1H), 2.16-1.76 (m, 5H), 1.43 (s, 3H), 1.42 (s, 6H). MS m/z 241.2 (M+H)$^+$

Step 2

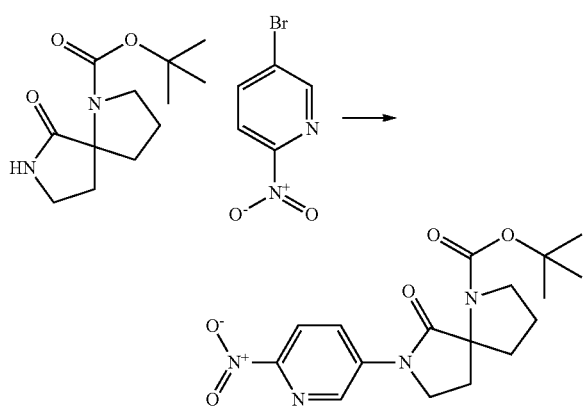

Preparation of 7-(6-Nitro-pyridin-3-yl)-6-oxo-1,7-diaza-spiro[4,4]nonane-1-carboxylic acid tert-butyl ester Following general N—C coupling procedure 1, 6-oxo-1,7-diaza-spiro[4,4]nonan-1-carboxylic acid tert-butyl ester (1.3 g, 5.41 mmol) was combined with 5-bromo-2-nitropyridine (1.10 g, 5.41 mmol) which gave 7-(6-nitro-pyridin-3-yl)-6-oxo-1,7-diaza-spiro[4,4]nonane-1-carboxylic acid tert-butyl ester (1.55 g) in 79% yield.
$^1$H NMR (400 MHz, CD$_2$Cl$_2$) δ 8.94-8.81 (m, 1H), 8.68-8.59 (m, 1H), 8.38-8.27 (m, 1H), 4.17-3.74 (m 2H), 3.66-3.45 (m, 2H), 2.88-2.58 (m, 1H), 2.26-1.87 (m, 5H), 1.46 gs, 3H), 1.32 (s, 6H). HR-MS m/z 368.1620 (M+H)$^+$

Step 2

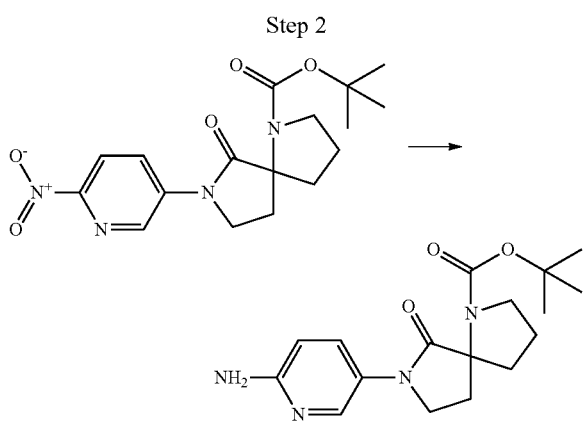

Preparation of 7-(6-Amino-pyridin-3-yl)-6-oxo-1,7-diaza-spiro[4,4]nonane-1-carboxylic acid tert-butyl ester Following nitro group reduction procedure 1, (7-(6-nitro-pyridin-3-yl)-6-oxo-1,7-diaza-spiro[4,4]nonane-1-carboxylic acid tert-butyl ester (1.55 g, 4.28 mmol) was converted to 7-(6-Amino-pyridin-3-yl)-6-oxo-1,7-diaza-spiro[4,4]nonane-1-carboxylic acid tert-butyl ester (1 g) in 70% yield.
$^1$H NMR (400 MHz, CD$_3$OD) δ 8.21-8.05 (m, 1H), 6.68-6.57 (m, 1H), 3.85-3.72 (m 2H), 3.60-3.40 (m, 2H), 2.67-2.47 (m, 1H), 2.23-1.83 (m, 5H), 1.46 9s, 3H), 1.39 (s, 6H). HR-MS m/z 333.1933 (M+H)$^+$

Step 3

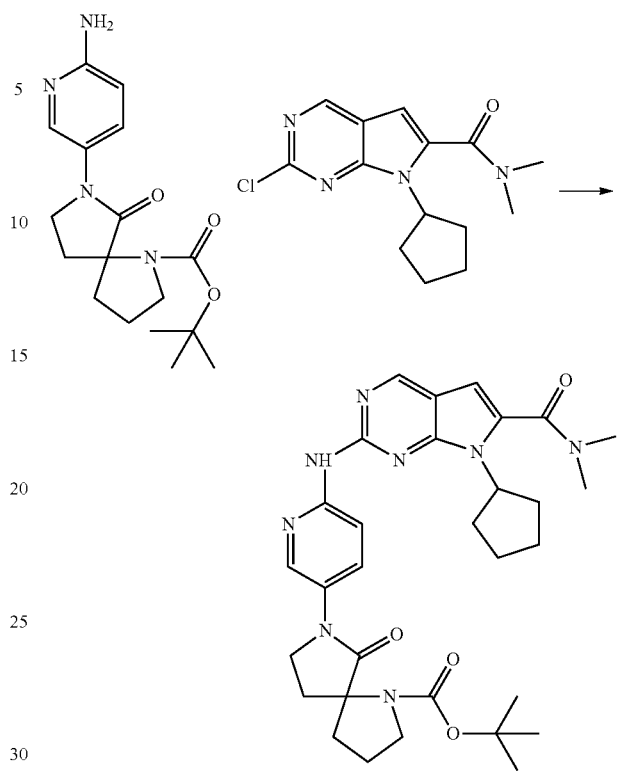

Preparation of 7-(6-(7-Cyclopentyl-6-dimethylcarbamoyl-7H-pyrrolo[2,3-d]pyrimidin-2-yl-amino-pyridin-3-yl)-6-oxo-1,7-diaza-spiro[4,4]nonane-1-carboxylic acid tert-butyl ester Following general N—C coupling procedure 1, 7-(6-amino-pyridin-3-yl)-6-oxo-1,7-diaza-spiro[4,4]nonane-1-carboxylic acid tert-butyl ester (114 mg, 0.34 mmol) was combined with 2-chloro-7-cyclopentyl-7H-pyrrolo[2,3-d]pyrimidine-6-carboxylic acid dimethylamide (100 mg, 0.34 mmol), which after silica gel column chromatography gave 7-(6-(7-cyclopentyl-6-dimethylcarbamoyl-7H-pyrrolo[2,3-d]pyrimidin-2-yl-amino-pyridin-3-yl)-6-oxo-1,7-diaza-spiro[4,4]nonane-1-carboxylic acid tert-butyl ester (100 mg) in 49% yield. MS m/z 589.5 (M+H)$^+$

Step 4

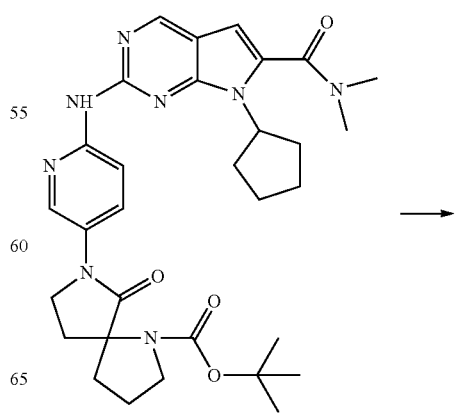

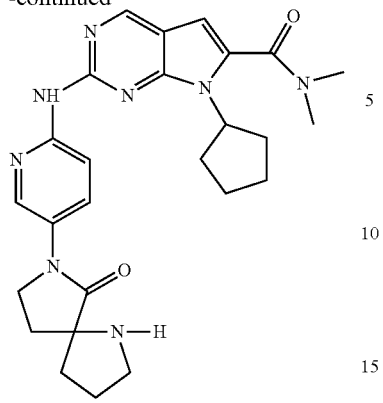

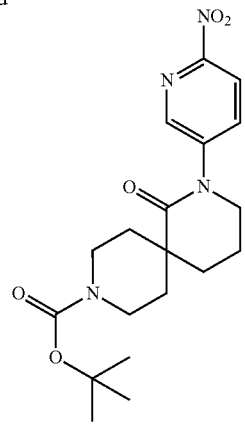

Preparation of 7-Cyclopentyl-2-[5-(6-oxo-1,7-diaza-spiro[4,4]non-7-yl)-pyridin-2-ylamino]-7H-pyrrolo[2,3-d]pyrimidin-6-carboxylic acid dimethylamide Following deprotection method 1, 7-(6-(7-cyclopentyl-6-dimethylcarbamoyl-7H-pyrrolo[2,3-d]pyrimidin-2-ylamino-pyridin-3-yl)-6-oxo-1,7-diaza-spiro[4,4]nonane-1-carboxylic acid tert-butyl ester (100 mg, 0.17 mmol) was converted to 7-cyclopentyl-2-[5-(6-oxo-1,7-diaza-spiro[4,4]non-7-yl)-pyridin-2-ylamino]-7H-pyrrolo[2,3-d]pyrimidin-6-carboxylic acid dimethylamide (80 mg) in 96% yield. $^1$H NMR (400 MHz, CD$_3$OD) δ 8.77 (s, 1H), 8.60-8.53 (m, 1H), 8.50-8.42 (m, 1H), 8.18-8.16 (m, 1H), 6.63 (s, 1H), 4.83-4.67 (m, 1H), 3.93-3.78 (m 2H), 3.25-3.11 (m, 1H), 3.15 (s, 6H), 3.06-2.95 (m, 1H), 2.65-2.46 (m, 2H), 2.32-1.83 (m, 10H), 1.83-1.68 (m, 2H). HR-MS m/z 489.2727 (M+H)$^+$

Preparation of 2-(6-Nitro-pyridin-3-yl)-1-oxo-2,9-diaza-spiro[5,5]undecane-9-carboxylic acid tert-butyl ester Following general N—C coupling procedure 1, 1-oxo-2,9-diaza-spiro[5,5]undercane-9-carboxylic acid tert-butyl ester (200 mg, 0.74 mmol) in dioxane was combined with 5-bromo-2-nitropyridine (150 mg, 0.74 mmol) which after purification gave 2-(6-nitro-pyridin-3-yl)-1-oxo-2,9-diaza-spiro[5,5]undecane-9-carboxylic acid tert-butyl ester (100 mg) in 34% yield. 1H NMR (400 MHz, CD$_2$Cl$_2$) 8.56 (d, J=2.51 Hz, 1H), δ 8.28 (d, J=8.53 Hz, 1H), 8.03-7.98 (m, 1H), 3.91-3.75 (m 4H), 3.29-3.16 (m, 2H), 2.23-1.94 (m, 6H), 1.65-1.55 (m, 2H), 1.47 (s, 9H). MS m/z 391.2 (M+H)$^+$ Step 2

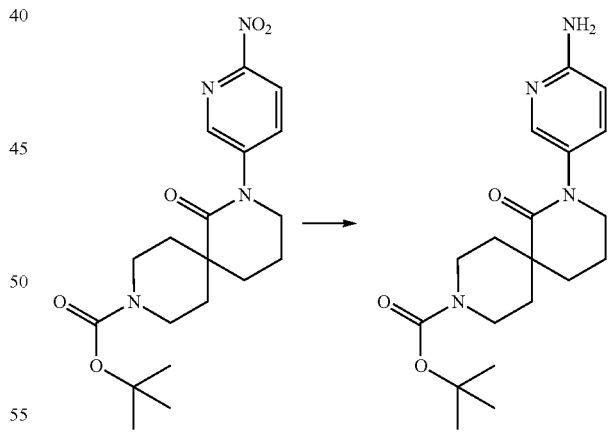

Preparation of 2-(6-Amino-pyridin-3-yl)-1-oxo-2,9-diaza-spiro[5,5]undecane-9-carboxylic acid tert-butyl ester Following nitro group reduction procedure 1, 2-(6-nitro-pyridin-3-yl)-1-oxo-2,9-diaza-spiro[5,5]undecane-9-carboxylic acid tert-butyl ester (100 mg, 0.26 mmol) was converted to 2-(6-amino-pyridin-3-yl)-1-oxo-2,9-diaza-spiro[5,5]undecane-9-carboxylic acid tert-butyl ester (92 mg) in Example 114

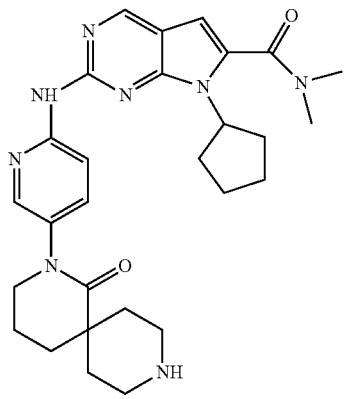 [SMILES: CN(C)C(=O)c1cc2cnc(Nc3ccc(N4CCCC5(CCNCC5)C4=O)cn3)nc2n1C1CCCC1]

Step 1

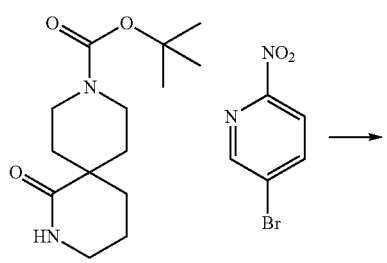

2100% yield. 1H NMR (400 MHz, CD₃OD) δ 7.75 (d, J=2.51 Hz, 1H), 7.34-7.28 (m, 1H), 6.59 (d, J=9.54 Hz, 1H), 3.89-3.74 (m, 3H), 3.67-3.54 (m, 3H), 2.11-1.92 (m, 6H), 1.65-1.52 (m, 2H), 1.45 (s, 9H). MS m/z 361.5 (M+H)⁺

Step 3

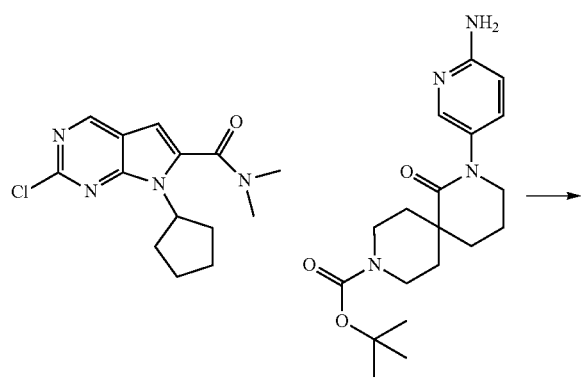

Step 4

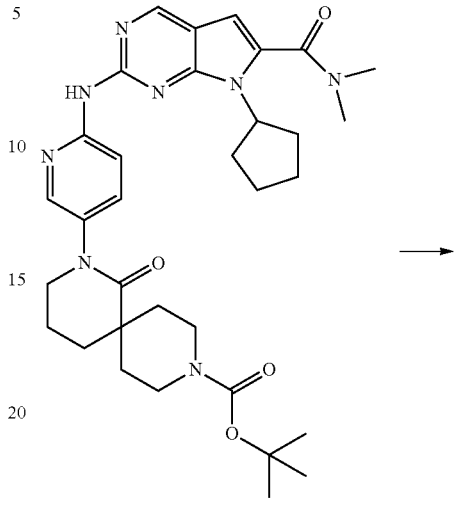

Preparation of 2[6-(7-Cyclopentyl-6-dimethylcarbamoyl-7H-pyrrolo[2,3-d]pyrimidin-2-ylamino)-pyridin-3-yl]-1-oxo-2,9-diaza-spiro[5,5]undecane-9-carboxylic acid tert-butyl ester Following general N—C coupling procedure 1, 2-(6-amino-pyridin-3-yl)-1-oxo-2,9-diaza-spiro[5,5]undecane-9-carboxylic acid tert-butyl ester (98 mg, 0.27 mmol) was combined with 2-chloro-7-cyclopentyl-7H-pyrrolo[2,3-d]pyrimidine-6-carboxylic acid dimethylamide (80 mg, 0.27 mmol) which gave 2[6-(7-cyclopentyl-6-dimethylcarbamoyl-7H-pyrrolo[2,3-d]pyrimidin-2-ylamino)-pyridin-3-yl]-1-oxo-2,9-diaza-spiro[5,5]undecane-9-carboxylic acid tert-butyl ester (155 mg) in 92% yield. 1H NMR (400 MHz, CD₂Cl₂) δ 8.92-8.70 (m, 1H), 8.63-8.53 (m, 1H), 8.25-8.13 (m, 1H), 7.75-7.36 (m, 1H), 6.59-6.46 (m, 1H), 4.93-4.70 (m, 1H), 3.93-3.78 (m 2H), 3.74-3.65 (m, 2H), 3.28-3.18 (m, 2H), 3.14 (s, 6H), 2.65-2.49 (m, 2H), 2.24-1.88 (m, 9H), 1.85-1.71 (m, 2H), 1.65-1.50 (m, 3H), 1.47 (s, 9H); HR-MS m/z 617.3583 (M+H)⁺

Preparation of 7-Cyclopentyl-2-[5-(1-oxo-2,9-diaza-spiro[5,5]undec-2-yl)-pyridin-2-ylamino]-7H-pyrrolo[2,3-d]pyrimidine-6-carboxylic acid dimethylamide Following deprotection method 1, 2[6-(7-cyclopentyl-6-dimethylcarbamoyl-7H-pyrrolo[2,3-d]pyrimidin-2-ylamino)-pyridin-3-yl]-1-oxo-2,9-diaza-spiro[5,5]undecane-9-carboxylic acid tert-butyl ester (45 mg, 0.07 mmol) was converted to 7-Cyclopentyl-2-[5-(1-oxo-2,9-diaza-spiro[5,5]undec-2-yl)-pyridin-2-ylamino]-7H-pyrrolo[2,3-d]pyrimidine-6-carboxylic acid dimethylamide (30 mg) in 80% yield. 1H NMR (400 MHz, CD₃OD) δ 8.77 (s, 1H), 8.51 (d, J=9.03 Hz, 1H), 8.18-8.12 (m, 1H), 7.73-7.64 (m, 1H), 6.64 (s, 1H), 4.85-4.71 (m, 1H), 3.74-3.64 (m 2H), 3.15 (s, 6H), 3.08-2.96 (m, 2H), 2.92-2.81 (m, 2H), 2.64-2.48 (m, 2H), 2.21-1.98 (m, 10H), 1.81-1.69 (m, 2H), 1.68-1.58 (m, 2H). HR-MS m/z 517.3040 (M+H)⁺

Example 115

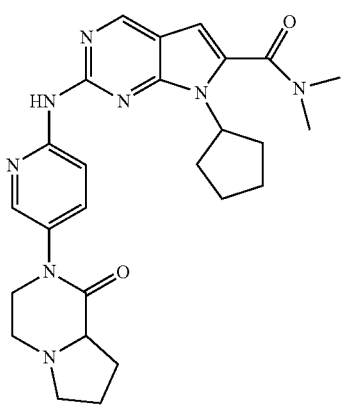 [SMILES: CN(C)C(=O)c1cc2cnc(Nc3ccc(N4CCN5CCCC5C4=O)cn3)nc2n1C1CCCC1]

7-Cyclopentyl-2[5-(1-oxo-hexahydro-pyrrolo[1,2-a]pyrazin-2-yl)-pyridin-2-ylamino]-7H-pyrrolo[2,3-d]pyrimidine-6-carboxylic acid dimethylamide

Step 1

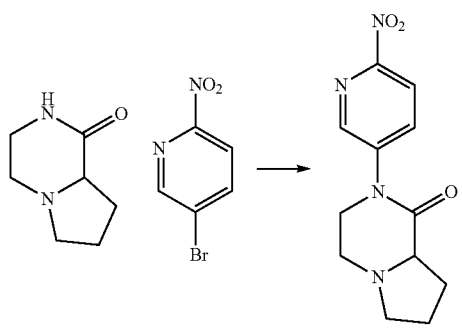

Preparation of 2-(6-Nitro-pyridin-3-yl)-hexahydro-pyrrolo[1,2-a]pyrazin-1-1one

Following general N—C coupling procedure 1, hexahydro-pyrrolo[1,2-a]pyrazin-1-one was combined with 5-bromo-2-nitropyridine which gave 2-(6-Nitro-pyridin-3-yl)-hexahydro-pyrrolo[1,2-a]pyrazin-1-1one (250 mg) in 66% yield. 1H NMR (400 MHz, CD$_2$Cl$_2$) δ 8.73 (d, J=2.51 Hz, 1H), 8.37 (d, J=8.53 Hz, 1H), 8.29-8.19 (m, 1H), 4.17-4.15 (m 1H), 3.86-3.76 (m, 1H), 3.65-3.56 (m, 1H), 3.27-3.02 (m, 3H), 2.89-2.78 (m, 1H), 2.34-2.20 (m, 1H), 2.13-1.79 (m, 3H). HR-MS m/z 263.1146 (M+H)$^+$.

Step 2

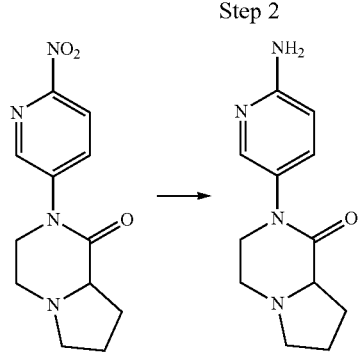

Preparation of 2-(6-Amino-pyridin-3-yl)-hexahydro-pyrrolo[1,2-a]pyrazin-1-1one

Following nitro group reduction procedure 1 2-(6-Nitro-pyridin-3-yl)-hexahydro-pyrrolo[1,2-a]pyrazin-1-1one was converted to 2-(6-Amino-pyridin-3-yl)-hexahydro-pyrrolo[1,2-a]pyrazin-1-1one (220 mg) in 99% yield. 1H NMR (400 MHz, CD$_3$OD) δ 8.07-7.78 (m, 1H), 7.65-7.33 (m, 1H), 7.06-6.55 (m, 1H), 3.98-3.78 (m 1H), 3.69-3.55 (m, 1H), 3.55-3.44 (m, 1H), 3.23-2.96 (m, 3H), 2.87-2.72 (m, 1H), 2.30-2.12 (m, 1H), 2.07-1.75 (m, 3H). HR-MS m/z 233.1408 (M+H)$^+$

Step 3

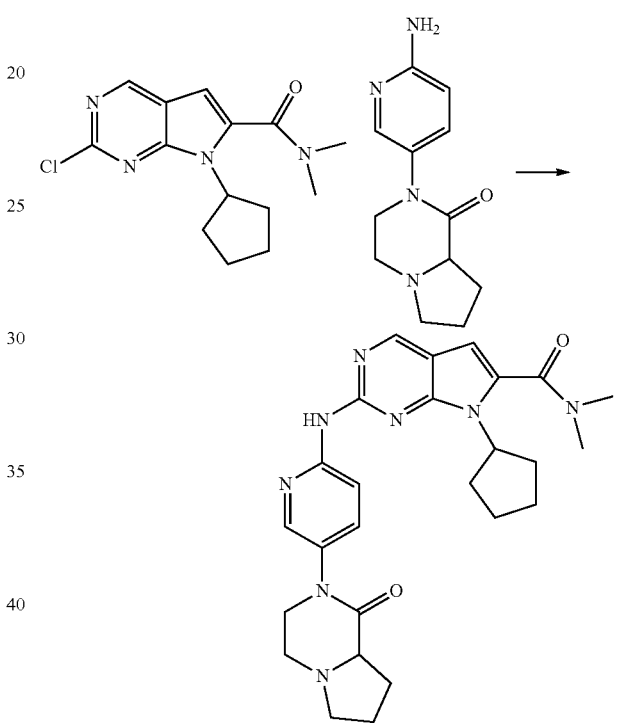

Preparation of 7-Cyclopentyl-2[5-(1-oxo-hexahydro-pyrrolo[1,2-a]pyrazin-2-yl)-pyridin-2-ylamino]-7H-pyrrolo[2,3-d]pyrimidine-6-carboxylic acid dimethylamide Following general N—C coupling procedure 1, 2-(6-Amino-pyridin-3-yl)-hexahydro-pyrrolo[1,2-a]pyrazin-1-1one was combined with 2-chloro-7-cyclopentyl-7H-pyrrolo[2,3-d]pyrimidine-6-carboxylic acid dimethylamide which gave 7-Cyclopentyl-2[5-(1-oxo-hexahydro-pyrrolo[1,2-a]pyrazin-2-yl)-pyridin-2-ylamino]-7H-pyrrolo[2,3-d]pyrimidine-6-carboxylic acid dimethylamide (67 mg) in 31% yield. 1H NMR (400 MHz, CD$_3$OD) δ 8.77 (s, 1H), 8.52 (d, J=9.03 Hz, 1H), 8.24 (d, J=2.51 Hz, 1H), 7.76-7.64 (m, 1H), 6.64 (s, 1H), 4.84-4.70 (m, 1H), 4.01-3.92 (m, 1H), 3.74-3.64 (m, 1H), 3.57-3.51 (m, 1H), 3.16 (s, 6H), 3.25-3.05 (m, 3H), 2.87-2.79 (m, 1H), 2.62-2.50 (m, 2H), 2.31-2.22 (m, 1H), 2.16-1.92 (m, 6H), 1.91-1.82 (m, 1H), 1.80-1.70 (m, 2H). HR-MS m/z 489.2734 (M+H)$^+$

Example 116

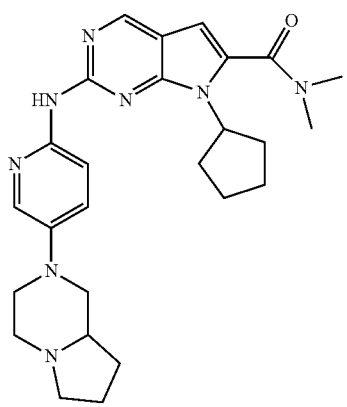 [SMILES: CN(C)C(=O)c1cc2cnc(Nc3ccc(N4CCN5CCCC5C4)cn3)nc2n1C1CCCC1]

7-cyclopentyl-2-(5-(hexahydropyrrolo[1,2-a]pyrazin-2(1H)-yl)pyridin-2-ylamino)-N,N-dimethyl-7H-pyrrolo[2,3-d]pyrimidine-6-carboxamide

Step 1

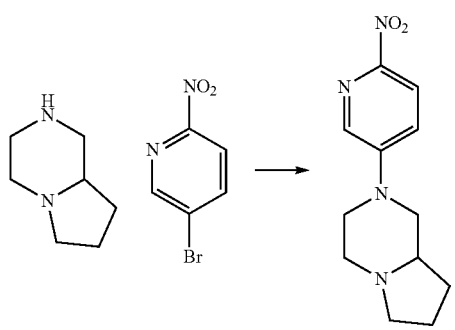

Preparation of 2-(6-nitro-pyridin-3-yl)-octahydropyrrolo[1,2-a]pyrazine

Following general N—C coupling procedure 1, 5-bromo-2-nitropyridine (483 mg, 2.38 mmole) was combined with octahydropyrrolo[1,2-c]pyrimidine (300 mg, 2.38 mmole) which gave 2-(6-nitro-pyridin-3-yl)-octahydro-pyrrolo[1,2-a]pyrazine (270 mg) in 45% yield. 1H NMR (400 MHz, CD$_2$Cl$_2$) δ 8.19-8.09 (m, 2H), 7.26-7.14 (m, 1H), 4.05-3.96 (m 1H), 3.92-3.80 (m, 1H), 3.25-3.08 (m, 3H), 2.87-2.74 (m, 1H), 2.44-2.32 (m, 1H), 2.28-2.08 (m, 2H), 2.02-1.72 (m, 3H), 1.61-1.44 (m, 1H)
MS m/z 249.2 (M+H)$^+$

Step 2

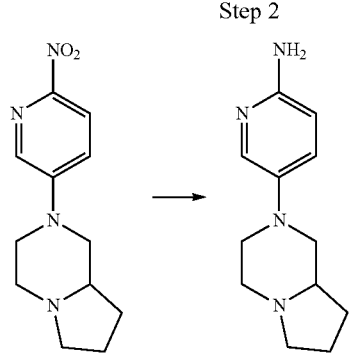

Preparation of 5-(hexahydropyrrolo[1,2-a]pyrazin-2(1H)-yl)pyridin-2-amine

Following nitro group reduction procedure 1, 2-(6-Nitro-pyridin-3-yl)-octahydro-pyrrolo[1,2-a]pyrazine (270 mg, 1.09 mmole) was converted to 5-(hexahydropyrrolo[1,2-a]pyrazin-2(1H)-yl)pyridin-2-amine (223 mg) in 94% yield. 1H NMR (400 MHz, CD$_2$Cl$_2$) δ 7.57 (s, 1H), 7.29 (d, J=9.03 Hz, 1H), 6.54 (d, J=9.02 Hz, 1H), 3.50-3.41 (m 1H), 3.36-3.24 (m, 1H), 3.13-3.03 (m, 2H), 2.81-2.71 (m, 1H), 2.48-2.34 (m, 2H), 2.30-2.15 (m, 2H), 1.95-1.73 (m, 3H), 1.52-1.37 (m, 1H) HR-MS m/z 219.1612 (M+H)$^+$

Step 3

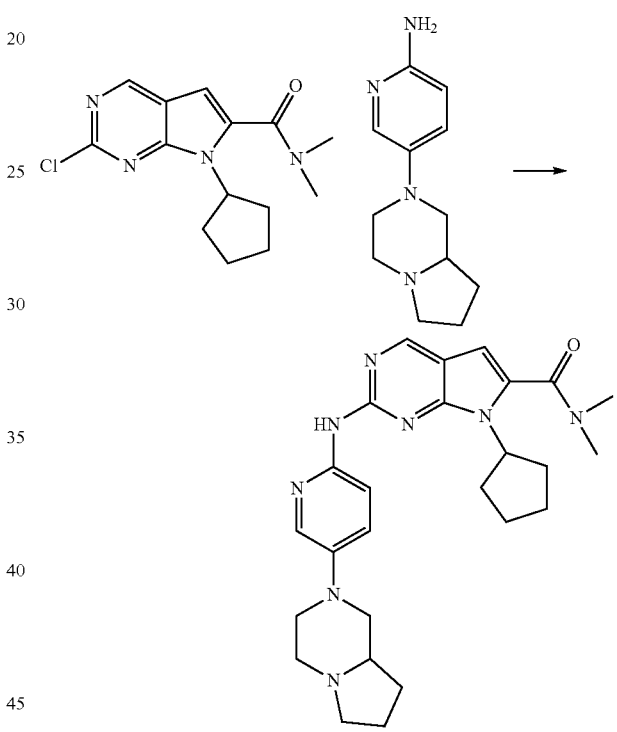

Preparation of 7-cyclopentyl-2-(5-(hexahydropyrrolo[1,2-a]pyrazin-2(1H)-yl)pyridin-2-ylamino)-N,N-dimethyl-7H-pyrrolo[2,3-d]pyrimidine-6-carboxamide Following general N—C coupling procedure 1, 2-chloro-7-cyclopentyl-N,N-dimethyl-7H-pyrrolo[2,3-d]pyrimidine-6-carboxamide (100 mg, 0.34 mmole) was combined with 5-(hexahydropyrrolo[1,2-a]pyrazin-2(1H)-yl)pyridin-2-amine (74.6 mg, 0.34 mmole) which gave 7-cyclopentyl-2-(5-(hexahydropyrrolo[1,2-a]pyrazin-2(1H)-yl)pyridin-2-ylamino)-N,N-dimethyl-7H-pyrrolo[2,3-d]pyrimidine-6-carboxamide (60 mg) in 37% yield.

1H NMR (400 MHz, DMSO) δ 9.30 (s, 1H). 8.77 (s, 1H), 8.18-8.12 (m, 1H), 8.02-7.98 (m, 1H), 7.48-7.40 (m, 1H), 6.59 (s, 1H), 4.78-4.68 (m, 1H), 3.77-3.72 (m, 1H), 3.62-3.55 (m, 1H), 3.08 (s, 3H), 3.04 (s, 3H), 2.77-2.63 (m, 2H), 2.51-

2.31 (m, 4H), 2.30-2.21 (m, 1H), 2.13-1.91 (m, 6H), 1.88-1.58 (m, 5H), 1.43-1.33 (m, 1H) HR-MS m/z 475.2941 (M+H)+

Example 117

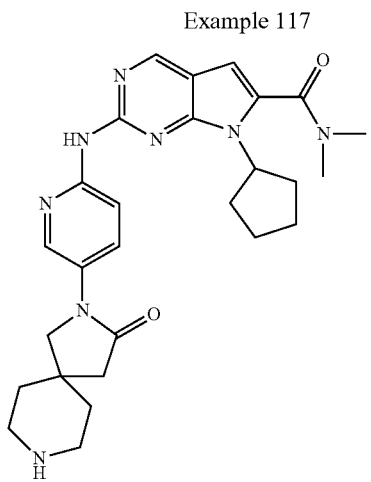

7-cyclopentyl-N,N-dimethyl-2-(5-(1-oxo-2,8-diaza-spiro[4.5]decan-2-yl)pyridin-2-ylamino)-7H-pyrrolo[2,3-d]pyrimidine-6-carboxamide Step 1

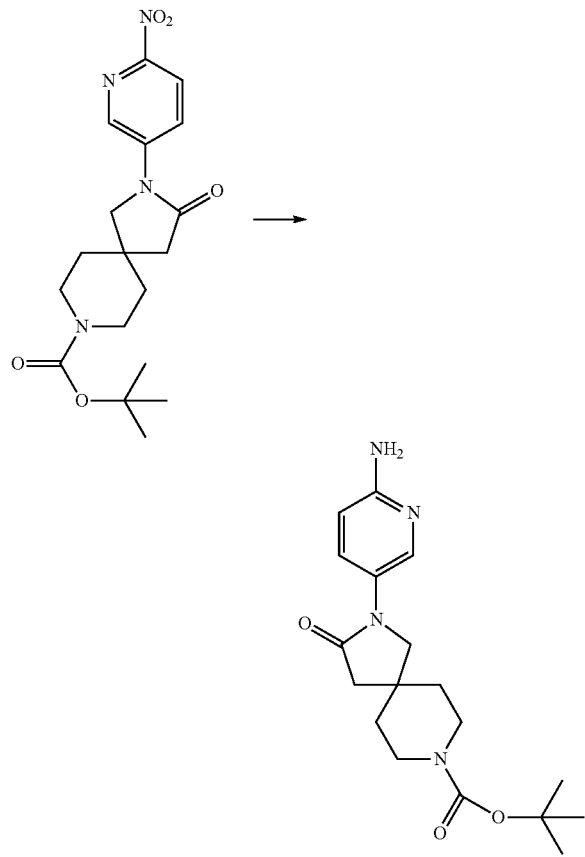

Preparation of tert-butyl 2-(6-aminopyridin-3-yl)-3-oxo-2,8-diazaspiro[4.5]decane-8-carboxylate Following nitro group reduction procedure 1, tert-butyl 2-(6-nitropyridin-3-yl)-3-oxo-2,8-diazaspiro[4.5]decane-8-carboxylate (400 mg, 1.06 mmole) was converted to tert-butyl 2-(6-aminopyridin-3-yl)-3-oxo-2,8-diazaspiro[4.5]decane-8-carboxylate (250 mg) in 67% yield. 1H NMR (400 MHz, CD3OD) δ 8.03 (s, 1H), 7.73-7.63 (m, 1H), 6.64-6.56 (m, 1H), 3.68 (s, 2H), 3.61-3.48 (m, 2H), 3.45-3.34 (m, 2H), 2.51 (s, 2H), 1.73-1.62 (m, 4H), 1.45 (s, 9H); HR-MS m/z 347.2092 (M+H)+

Step 2

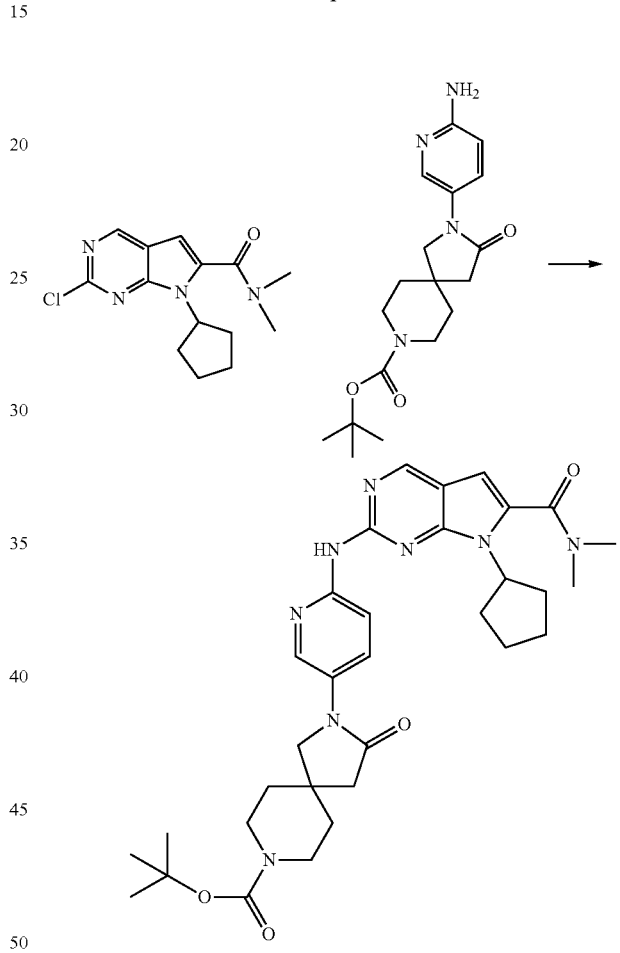

Preparation of 2-(6-(7-cyclopentyl-6-(dimethylcarbamoyl)-7H-pyrrolo[2,3-d]pyrimidin-2-ylamino)pyridin-3-yl)-1-oxo-2,8-diazaspiro[4.5]decane-8-carboxylate Following general N—C coupling procedure 1, 2-chloro-7-cyclopentyl-N,N-dimethyl-7H-pyrrolo[2,3-d]pyrimidine-6-carboxamide (135 mg, 0.46 mmole) was combined with tert-butyl 2-(6-aminopyridin-3-yl)-3-oxo-2,8-diazaspiro[4.5]decane-8-carboxylate (160 mg, 0.46 mmole) which gave tert-butyl 2-(6-(7-cyclopentyl-6-(dimethylcarbamoyl)-7H-pyrrolo[2,3-d]pyrimidin-2-ylamino)pyridin-3-yl)-1-oxo-2,8-diazaspiro[4.5]decane-8-carboxylate (270 mg) in 97% yield. 1H NMR (400 MHz, CD2Cl2) δ 8.70 (s, 1H), 8.47-8.36 (m, 2H), 8.29 (s, 1H), 8.02-7.94 (m, 1H), 6.38 (s, 1H), 4.79-

4.66 (m, 1H), 3.58 (s, 2H), 3.54-3.45 (m, 2H), 3.28-3.18 (m, 2H), 3.02 (s, 6H), 2.55-2.40 (m, 2H), 2.42 (s, 2H), 2.04-1.90 (m, 4H), 1.73-1.49 (m, 6H), 1.36 (s, 9H); HR-MS m/z 603.3406 (M+H)+

Step 3

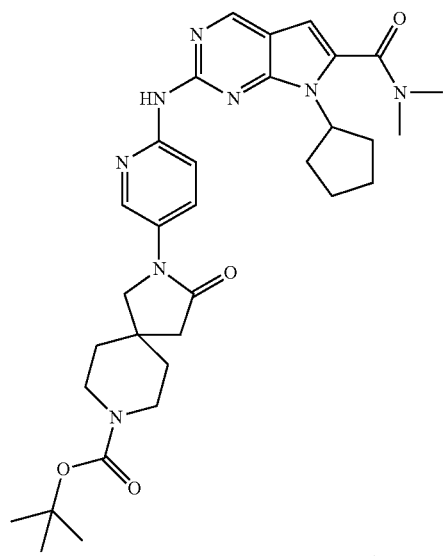

Preparation of 7-cyclopentyl-N,N-dimethyl-2-(5-(1-oxo-2,8-diazaspiro[4.5]decan-2-yl)pyridin-2-ylamino)-7H-pyrrolo[2,3-d]pyrimidine-6-carboxamide Following de protection method 1, tert-Butyl 2-(6-(7-cyclopentyl-6-(dimethylcarbamoyl)-7H-pyrrolo[2,3-d]pyrimidin-2-ylamino)pyridin-3-yl)-1-oxo-2,8-diazaspiro[4.5]decane-8-carboxylate (270 mg, 0.45 mmole) was converted to 7-cyclopentyl-N,N-dimethyl-2-(5-(1-oxo-2,8-diazaspiro [4.5]decan-2-yl)pyridin-2-ylamino)-7H-pyrrolo[2,3-d]pyrimidine-6-carboxamide (86 mg) in 38% yield. 1H NMR (400 MHz, CD₃OD) δ 8.76 (s, 1H), 8.53-8.50 (m, 1H), 8.48-8.42 (m, 1H), 8.11-8.05 (m, 1H), 6.64 (s, 1H), 4.84-4.71 (m, 1H), 3.79 (s, 2H), 3.21-3.10 (m, 6H), 2.96-2.82 (m, 4H), 2.62-2.50 (m, 4H), 2.16-2.01 (m, 4H), 1.82-1.67 (m, 6H). HR-MS m/z 503.2882 (M+H)+

Example 118

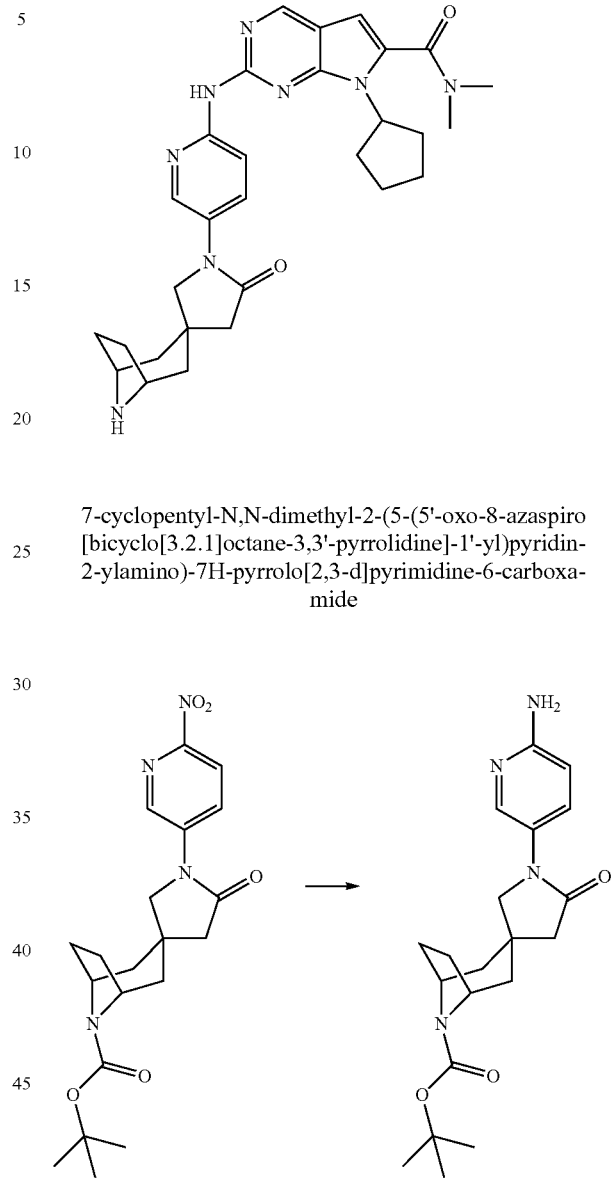

7-cyclopentyl-N,N-dimethyl-2-(5-(5'-oxo-8-azaspiro [bicyclo[3.2.1]octane-3,3'-pyrrolidine]-1'-yl)pyridin-2-ylamino)-7H-pyrrolo[2,3-d]pyrimidine-6-carboxamide Step 1

Preparation of tert-butyl 1'-(6-aminopyridin-3-yl)-5'-oxo-8-azaspiro[bicyclo[3.2.1]octane-3,3'-pyrrolidine]-8-carboxylate Following nitro group reduction procedure 1, tert-Butyl 1'-(6-nitropyridin-3-yl)-5'-oxo-8-azaspiro[bicyclo[3.2.1]octane-3,3'-pyrrolidine]-8-carboxylate (400 mg, 0.99 mmole) was converted to tert-butyl 1'-(6-aminopyridin-3-yl)-5'-oxo-8-azaspiro[bicyclo[3.2.1]octane-3,3'-pyrrolidine]-8-carboxylate (150 mg) in 40% yield. 1H NMR (400 MHz, CD₃OD) δ 8.01 (s, 1H), 7.69-7.62 (m, 1H), 6.63-6.55 (m, 1H), 4.32-4.21 (m, 2H), 3.52 (s, 2H), 2.81 (s, 2H), 2.07-1.83 (m, 8H), 1.49 (s, 9H)

HR-MS m/z 373.2239 (M+H)+

279
Step 2

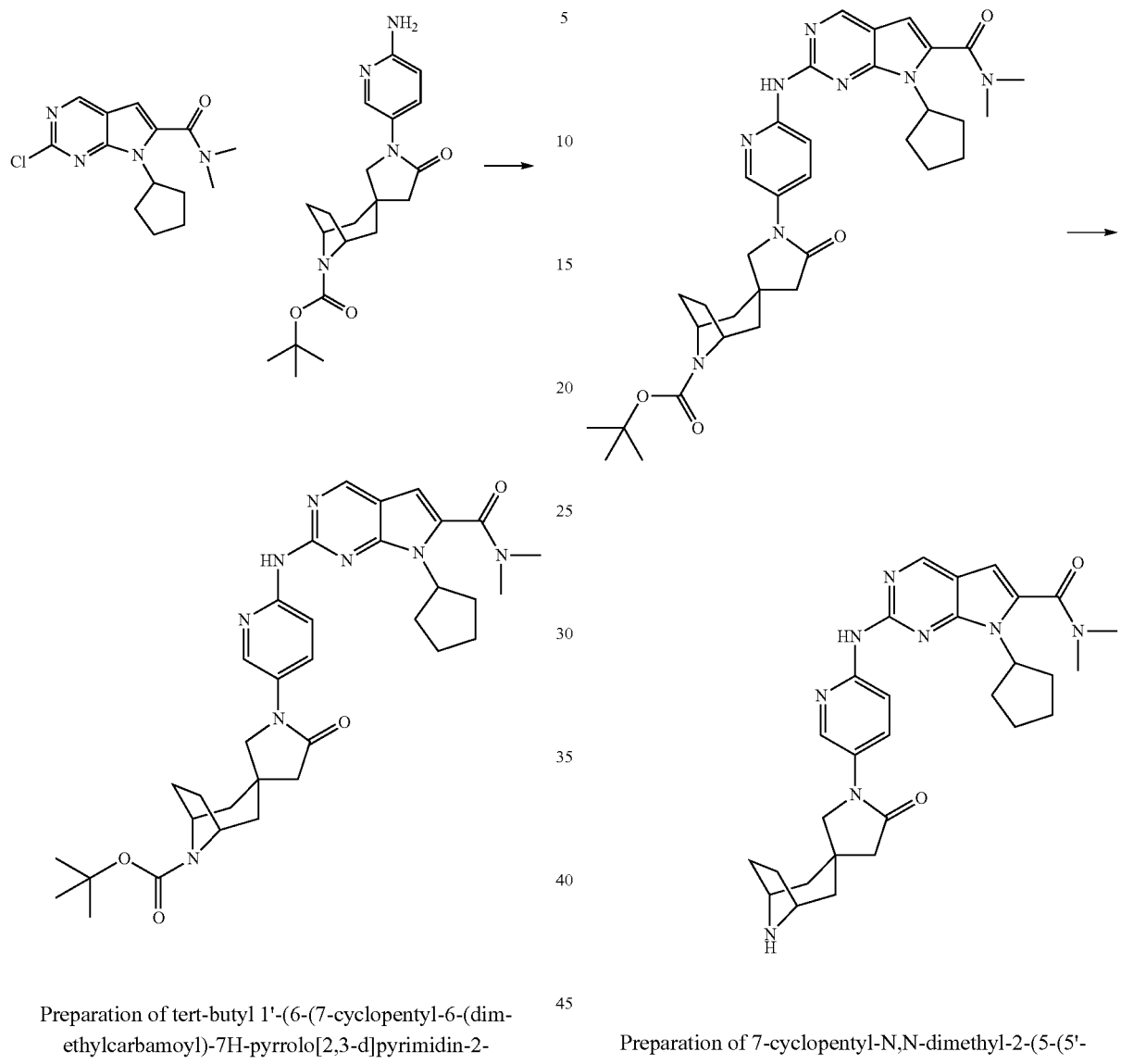

Preparation of tert-butyl 1'-(6-(7-cyclopentyl-6-(dimethylcarbamoyl)-7H-pyrrolo[2,3-d]pyrimidin-2-ylamino)pyridin-3-yl)-5'-oxo-8-azaspiro[bicyclo[3.2.1]octane-3,3'-pyrrolidine]-8-carboxylate Following general N—C coupling procedure 1, 2-chloro-7-cyclopentyl-N,N-dimethyl-7H-pyrrolo[2,3-d]pyrimidine-6-carboxamide (162 mg, 0.55 mmole) was combined with tert-Butyl 1'-(6-aminopyridin-3-yl)-5'-oxo-8-azaspiro[bicyclo[3.2.1]octane-3,3'-pyrrolidine]-8-carboxylate (150 mg, 0.55 mmole) which gave tert-butyl 1'-(6-(7-cyclopentyl-6-(dimethylcarbamoyl)-7H-pyrrolo[2,3-d]pyrimidin-2-ylamino)pyridin-3-yl)-5'-oxo-8-azaspiro[bicyclo[3.2.1]octane-3,3'-pyrrolidine]-8-carboxylate (250 mg) in 86% yield. 1H NMR (400 MHz, $CD_2Cl_2$) δ 8.76 (s, 1H), 8.56-8.49 (m, 1H), 8.41 (s, 1H), 8.08-7.99 (m, 2H), 6.49 (s, 1H), 4.88-4.77 (m, 1H), 4.31 (s, 2H), 3.62-3.49 (m, 2H), 3.14 (s, 6H), 2.82 (s, 2H), 2.65-2.51 (m, 2H), 2.16-1.53 (m, 14H), 1.49 (s, 9H) HR-MS m/z 629.3568 $(M+H)^+$

280
Step 3

Preparation of 7-cyclopentyl-N,N-dimethyl-2-(5-(5'-oxo-8-azaspiro[bicyclo[3.2.1]octane-3,3'-pyrrolidine]-1'-yl)pyridin-2-ylamino)-7H-pyrrolo[2,3-d]pyrimidine-6-carboxamide Following general amide formation method 1, tert-Butyl 1'-(6-(7-cyclopentyl-6-(dimethylcarbamoyl)-7H-pyrrolo[2,3-d]pyrimidin-2-ylamino)pyridin-3-yl)-5'-oxo-8-azaspiro[bicyclo[3.2.1]octane-3,3'-pyrrolidine]-8-carboxylate (250 mg, 0.47 mmole) was converted to 7-cyclopentyl-N,N-dimethyl-2-(5-(5'-oxo-8-azaspiro[bicyclo[3.2.1]octane-3,3'-pyrrolidine]-1'-yl)pyridin-2-ylamino)-7H-pyrrolo[2,3-d]pyrimidine-6-carboxamide (56 mg) in 22% yield. 1H NMR (400 MHz, $CD_3OD$) δ 8.76 (s, 1H), 8.50-8.41 (m, 2H), 8.06-8.00 (m, 1H), 6.64 (s, 1H), 4.83-4.72 (m, 1H), 3.73 (br, 2H), 3.66 (s, 2H), 3.16 (s, 6H), 2.82 (s, 2H), 2.64-2.49 (m, 2H), 2.16-1.89 (m, 12H), 1.83-1.69 (m, 2H). HR-MS m/z 529.3035 $(M+H)^+$

Example 119

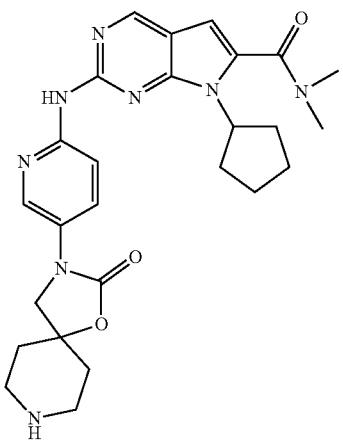 [SMILES: CN(C)C(=O)c1cc2cnc(Nc3ccc(N4CC5(CCNCC5)OC4=O)cn3)nc2n1C1CCCC1]

7-cyclopentyl-N,N-dimethyl-2-(5-(2-oxo-1-oxa-3,8-diazaspiro[4.5]decan-3-yl)pyridin-2-ylamino)-7H-pyrrolo[2,3-d]pyrimidine-6-carboxamide

Step 1

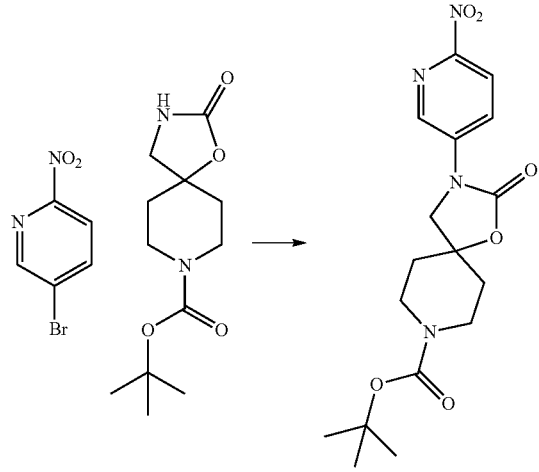 [SMILES: O=[N+]([O-])c1ccc(Br)cn1 ; CC(C)(C)OC(=O)N1CCC2(CC1)CNC(=O)O2 ; CC(C)(C)OC(=O)N1CCC2(CC1)CN(c1ccc([N+](=O)[O-])nc1)C(=O)O2]

Preparation of tert-butyl 3-(6-nitropyridin-3-yl)-2-oxo-1-oxa-3,8-diazaspiro[4.5]decane-8-carboxylate ester Following general N—C coupling procedure 1, 5-bromo-2-nitropyridine (238 mg, 1.17 mmole) was combined with tert-butyl 2-oxo-1-oxa-3,8-diazaspiro[4.5]decane-8-carboxylate (300 mg, 1.17 mmole) which gave tert-butyl 3-(6-nitropyridin-3-yl)-2-oxo-1-oxa-3,8-diazaspiro[4.5]decane-8-carboxylate ester (400 mg) in 90% yield.

1H NMR (400 MHz, CD$_2$Cl$_2$) δ 8.66 (s, 1H), 8.51-8.44 (m, 1H), 8.37-8.31 (m, 1H), 4.00-3.86 (m, 1H), 3.74-3.65 (m, 1H), 3.44-3.28 (m, 2H), 3.22-3.08 (m, 2H), 2.08-1.99 (m, 2H), 1.93-1.81 (m, 2H), 1.49 (s, 9H). MS m/z 379.1616 (M+H)$^+$

Step 2

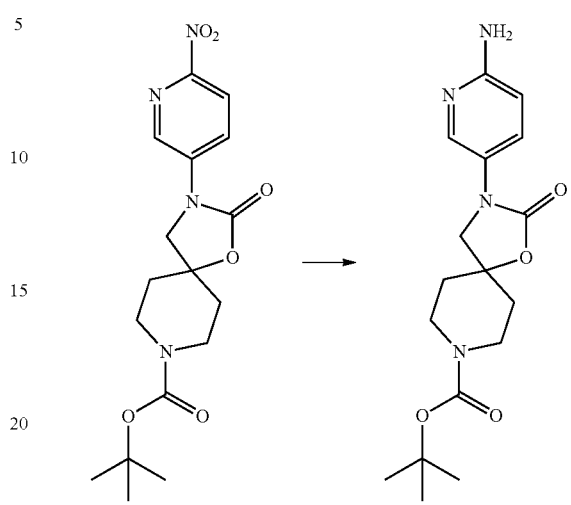

Preparation of tert-butyl 3-(6-aminopyridin-3-yl)-2-oxo-1-oxa-3,8-diazaspiro[4.5]decane-8-carboxylate Following nitro group reduction procedure 1, tert-Butyl 3-(6-nitropyridin-3-yl)-2-oxo-1-oxa-3,8-diazaspiro[4.5]decane-8-carboxylate ester (400 mg, 1.06 mmole) was converted to tert-butyl 3-(6-aminopyridin-3-yl)-2-oxo-1-oxa-3,8-diazaspiro[4.5]decane-8-carboxylate (370 mg) in 100% yield. 1H NMR (400 MHz, CD$_3$OD) δ 8.00 (s, 1H), 7.77 (d, J=9.03 Hz, 1H), 6.64 (d, J=9.03 Hz, 1H), 3.88-3.75 (m, 2H), 3.44-3.33 (m, 2H), 3.31 (s, 2H), 2.01-1.93 (m, 2H), 1.89-1.78 (m, 2H), 1.46 (s, 9H). MS m/z 349.1879 (M H)$^+$

Step 3

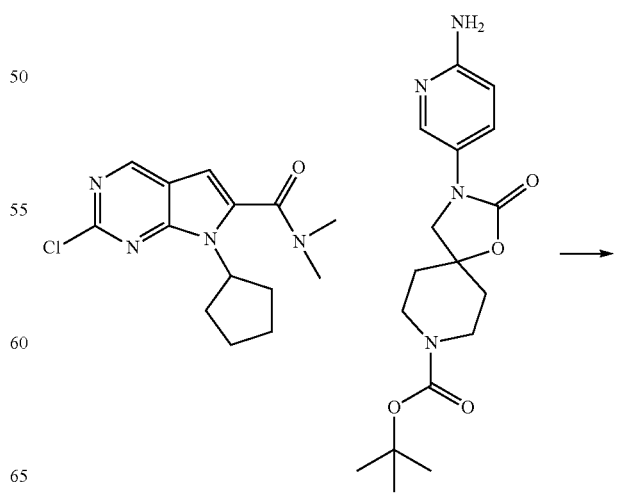

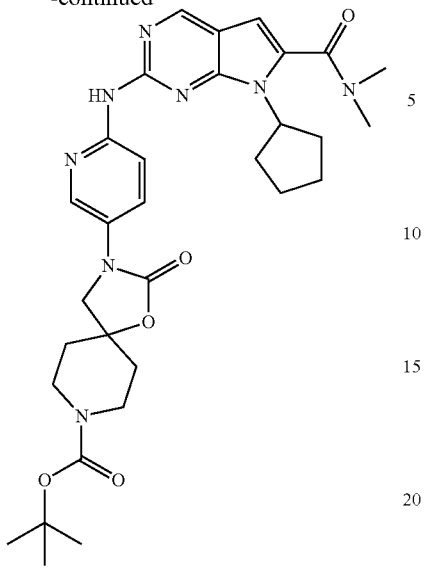

Preparation of tert-butyl 3-(6-(7-cyclopentyl-6-(dimethylcarbamoyl)-7H-pyrrolo[2,3-d]pyrimidin-2-ylamino) pyridin-3-yl)-2-oxo-1-oxa-3,8-diazaspiro[4.5]decane-8-carboxylate Following general N—C coupling procedure 1, 2-chloro-7-cyclopentyl-N,N-dimethyl-7H-pyrrolo[2,3-d]pyrimidine-6-carboxamide (133 mg, 0.45 mmole) was combined with tert-butyl 3-(6-aminopyridin-3-yl)-2-oxo-1-oxa-3,8-diazaspiro[4.5]decane-8-carboxylate (158 mg, 0.45 mmole) which gave tert-butyl 3-(6-(7-cyclopentyl-6-(dimethylcarbamoyl)-7H-pyrrolo[2,3-d]pyrimidin-2-ylamino) pyridin-3-yl)-2-oxo-1-oxa-3,8-diazaspiro[4.5]decane-8-carboxylate (170 mg) in 62% yield. 1H NMR (400 MHz, CD$_2$Cl$_2$) δ 8.89 (s, 1H), 8.76 (s, 1H), 8.46 (d, J=9.03 Hz, 1H), 8.38 (d, J=2.51 Hz, 1H), 7.97-7.92 (m, 1H), 6.40 (s, 1H), 4.78-4.68 (m, 1H), 3.83-3.73 (m, 2H), 3.71 (s, 2H), 3.33-3.21 (m, 2H), 3.02 (s, 6H), 2.54-2.40 (m, 2H), 2.05-1.86 (m, 6H), 1.78-1.58 (m, 4H), 1.38 (s, 9H)

HR-MS m/z 605.3221 (M+H)$^+$

Step 4

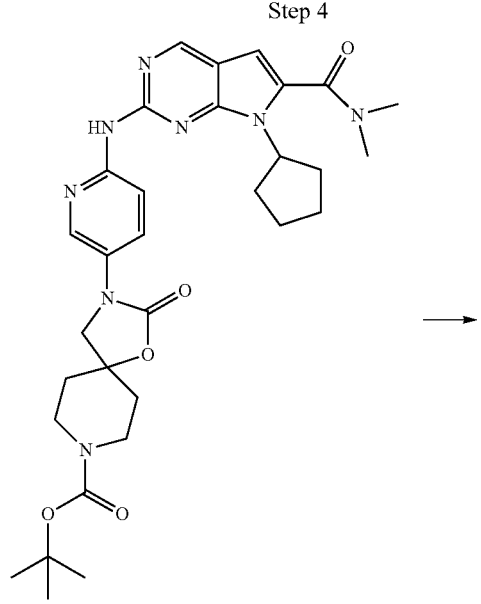

→

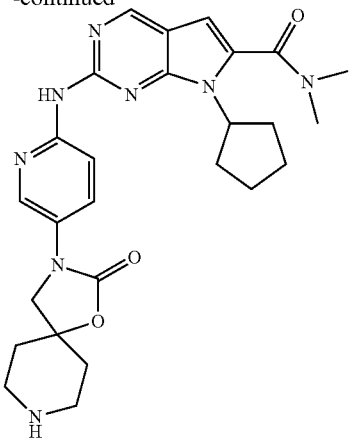

Preparation of 7-cyclopentyl-N,N-dimethyl-2-(5-(2-oxo-1-oxa-3,8-diazaspiro[4.5]decan-3-yl)pyridin-2-ylamino)-7H-pyrrolo[2,3-d]pyrimidine-6-carboxamide Following deprotection method 1, tert-Butyl 3-(6-(7-cyclopentyl-6-(dimethylcarbamoyl)-7H-pyrrolo[2,3-d]pyrimidin-2-ylamino) pyridin-3-yl)-2-oxo-1-oxa-3,8-diazaspiro[4.5]decane-8-carboxylate (150 mg, 0.25 mmole) was converted to 7-cyclopentyl-N,N-dimethyl-2-(5-(2-oxo-1-oxa-3,8-diazaspiro[4.5]decan-3-yl)pyridin-2-ylamino)-7H-pyrrolo[2,3-d]pyrimidine-6-carboxamide (170 mg) in 62% yield.

1H NMR (400 MHz, DMSO) δ 9.72 (s, 1H), 8.80 (s, 1H), 8.49-8.43 (m, 1H), 8.37-8.31 (m, 1H), 8.05-8.00 (m, 1H), 6.40 (s, 1H), 4.81-4.67 (m, 1H), 3.91 (s, 2H), 3.35-3.30 (m, 1H), 3.07 (s, 3H), 3.04 (s, 3H), 2.91-2.79 (m, 2H), 2.75-2.64 (m, 2H), 2.55-2.36 (m, 2H), 2.09-1.90 (m, 4H), 1.83-1.73 (m, 4H), 1.72-1.59 (m, 2H)

HR-MS m/z 505.2694 (M+H)$^+$

Example 120

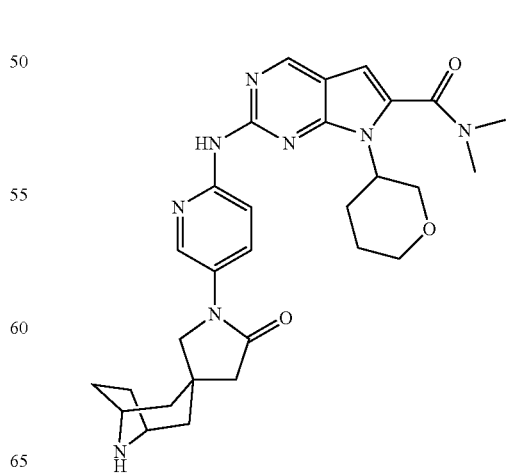

285

N,N-dimethyl-2-(5-(5'-oxo-8-azaspiro[bicyclo[3.2.1]
octane-3,3'-pyrrolidine]-1'-yl)pyridin-2-ylamino)-7-
(tetrahydro-2H-pyran-3-yl)-7H-pyrrolo[2,3-d]pyri-
midine-6-carboxamide Step 1

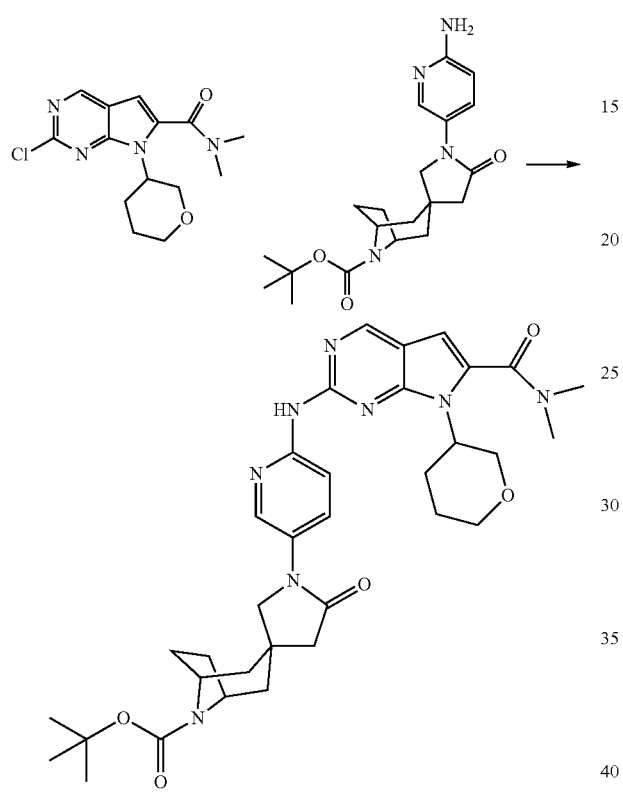

Preparation of tert-butyl 1'-(6-(6-(dimethylcarbam-
oyl)-7-(tetrahydro-2H-pyran-3-yl)-7H-pyrrolo[2,3-d]
pyrimidin-2-ylamino)pyridin-3-yl)-5'-oxo-8-azaspiro
[bicyclo[3.2.1]octane-3,3'-pyrrolidine]-8-carboxylate Following general N—C coupling procedure 1, 2-chloro-N,N-dimethyl-7-(tetrahydro-2H-pyran-3-yl)-7H-pyrrolo[2,3-d]pyrimidine-6-carboxamide (70.6 mg, 0.23 mmole) was combined with tert-butyl 1'-(6-aminopyridin-3-yl)-5'-oxo-8-azaspiro[bicyclo[3.2.1]octane-3,3'-pyrrolidine]-8-carboxylate (62 mg, 0.23 mmole) which gave tert-butyl(dimethylcarbamoyl)-7-(tetrahydro-2H-pyran-3-yl)-7H-pyrrolo[2,3-d]pyrimidin-2-ylamino)pyridin-3-yl)-5'-oxo-8-azaspiro[bicyclo[3.2.1]octane-3,3'-pyrrolidine]-8-carboxylate (71 mg) in 57% yield. 1H NMR (400 MHz, CD$_2$Cl$_2$) δ 8.77 (s, 1H), 8.65-8.57 (m, 1H), 8.49 (m, 1H), 8.15-8.08 (m, 1H), 6.56 (s, 1H), 4.63-4.52 (m, 1H), 4.30 (br, 2H), 4.08-3.96 (m, 2H), 3.64-3.51 (m, 3H), 3.18 (S, 6H), 2.96-2.86 (m, 1H), 2.83 (s, 2H), 2.16-1.99 (m, 3H), 1.96-1.79 (m, 5H), 1.77-1.52 (m, 4H), 1.51 (s, 9H). HR-MS m/z 645.3527 (M+H)$^+$

286

Step 2

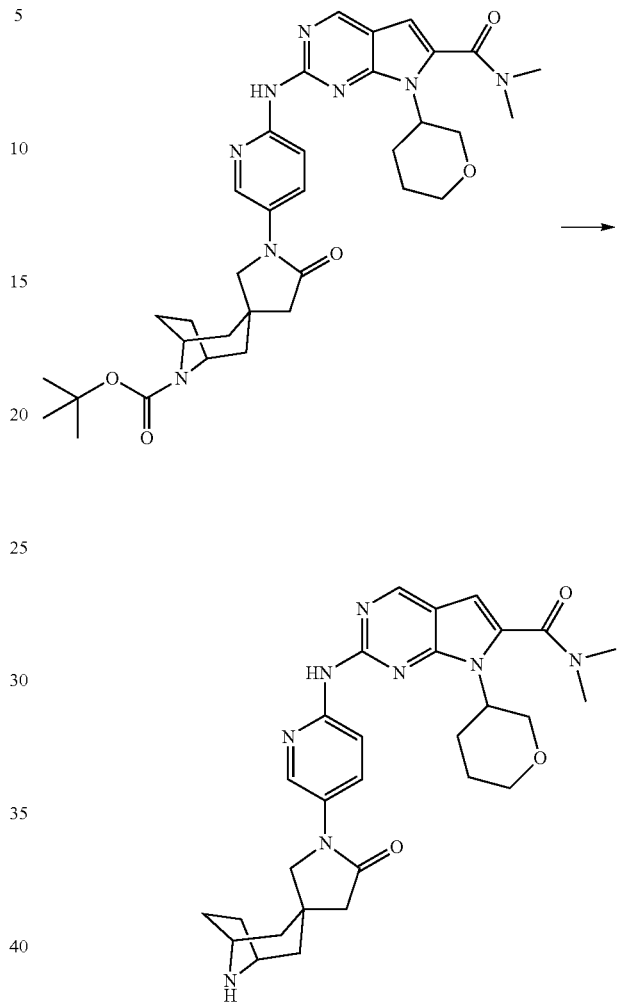

Preparation of N,N-dimethyl-2-(5-(5'-oxo-8-azaspiro
[bicyclo[3.2.1]octane-3,3'-pyrrolidine]-1'-yl)pyridin-
2-ylamino)-7-(tetrahydro-2H-pyran-3-yl)-7H-pyrrolo
[2,3-d]pyrimidine-6-carboxamide Following deprotection method 1, tert-Butyl 1'-(6-(6-(dimethylcarbamoyl)-7-(tetrahydro-2H-pyran-3-yl)-7H-pyrrolo[2,3-d]pyrimidin-2-ylamino)pyridin-3-yl)-5'-oxo-8-azaspiro[bicyclo[3.2.1]octane-3,3'-pyrrolidine]-8-carboxylate (68 mg, 0.125 mmole) was converted to N,N-dimethyl-2-(5-(5'-oxo-8-azaspiro[bicyclo[3.2.1]octane-3,3'-pyrrolidine]-1'-yl)pyridin-2-ylamino)-7-(tetrahydro-2H-pyran-3-yl)-7H-pyrrolo[2,3-d]pyrimidine-6-carboxamide (17 mg) in 25% yield. 1H NMR (400 MHz, CD$_3$OD) δ 8.77 (s, 1H), 8.52-8.46 (m, 2H), 8.08-8.03 (m, 1H), 6.68 (s, 1H), 4.57-4.39 (m, 1H), 4.04-3.96 (m, 2H), 3.65 (s, 2H), 3.64-3.46 (m, 3H), 3.20 (s, 3H), 3.15 (s, 3H), 2.94-2.84 (m, 1H), 2.83 (s, 2H), 2.14-2.04 (m, 1H), 1.98-1.77 (m, 11H). HR-MS m/z 545.2991 (M+H)$^+$

Example 121

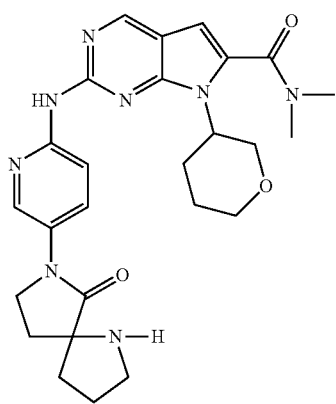 [SMILES: CN(C)C(=O)c1cc2cnc(Nc3ccc(N4CCC5(CCCN5)C4=O)cn3)nc2n1C1CCCOC1]

N,N-dimethyl-2-(5-(6-oxo-1,7-diazaspiro[4.4]nonan-7-yl)pyridin-2-ylamino)-7-(tetrahydro-2H-pyran-3-yl)-7H-pyrrolo[2,3-d]pyrimidine-6-carboxamide

Step 1

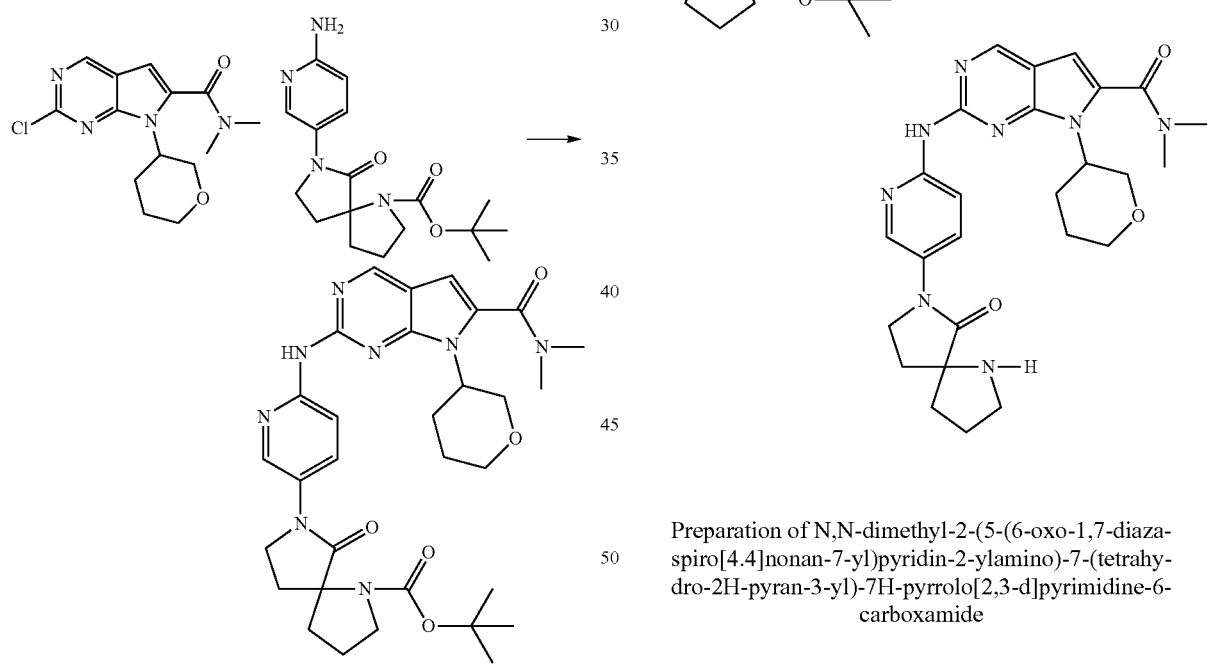

Preparation of tert-butyl 7-(6-(6-(dimethylcarbamoyl)-7-(tetrahydro-2H-pyran-3-yl)-7H-pyrrolo[2,3-d]pyrimidin-2-ylamino)pyridin-3-yl)-6-oxo-1,7-diazaspiro[4.4]nonane-1-carboxylate Following general N—C coupling procedure 1, 2-chloro-N,N-dimethyl-7-(tetrahydro-2H-pyran-3-yl)-7H-pyrrolo[2,3-d]pyrimidine-6-carboxamide (76 mg, 0.246 mmole) was combined with tert-butyl 7-(6-aminopyridin-3-yl)-6-oxo-1,7-diazaspiro[4.4]nonane-1-carboxylate (82 mg, 0.246 mmole) which gave tert-butyl 7-(6-(6-(dimethylcarbamoyl)-7-(tetrahydro-2H-pyran-3-yl)-7H-pyrrolo[2,3-d]pyrimidin-2-ylamino)pyridin-3-yl)-6-oxo-1,7-diazaspiro[4.4]nonane-1-carboxylate (107 mg) in 72% yield. 1H NMR (400 MHz, CD$_2$Cl$_2$) δ 8.80 (s, 1H), 8.69-8.57 (m, 2H), 8.35-8.25 (m, 1H), 6.54 (s, 1H), 4.63-4.52 (m, 1H), 4.06-3.88 (m, 2H), 3.86-3.70 (m, 2H), 3.64-3.46 (m, 2H), 3.18 (S, 6H), 3.02-2.84 (m, 1H), 2.84-2.59 (m, 1H), 2.24-1.99 (m, 6H), 1.96-1.79 (m, 3H), 1.77-1.52 (m, 1H), 1.48 (s, 4H), 1.39 (s, 5H). HR-MS m/z 605.3210 (M+H)$^+$

Step 2

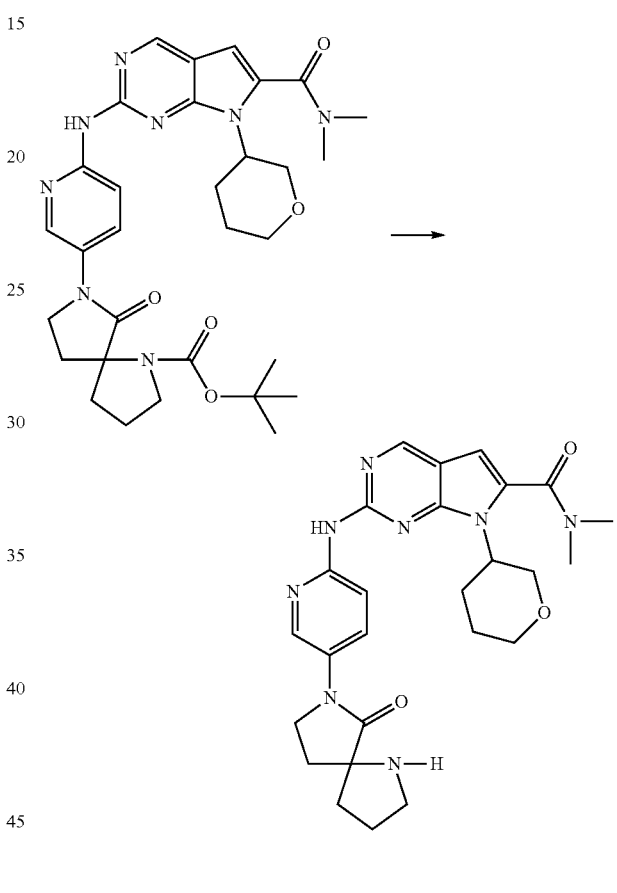

Preparation of N,N-dimethyl-2-(5-(6-oxo-1,7-diazaspiro[4.4]nonan-7-yl)pyridin-2-ylamino)-7-(tetrahydro-2H-pyran-3-yl)-7H-pyrrolo[2,3-d]pyrimidine-6-carboxamide Following deprotection method 1, tert-Butyl 7-(6-(6-(dimethylcarbamoyl)-7-(tetrahydro-2H-pyran-3-yl)-7H-pyrrolo[2,3-d]pyrimidin-2-ylamino)pyridin-3-yl)-6-oxo-1,7-diazaspiro[4.4]nonane-1-carboxylate (100 mg, 0.165 mmole) was converted to N,N-dimethyl-2-(5-(6-oxo-1,7-diazaspiro[4.4]nonan-7-yl)pyridin-2-ylamino)-7-(tetrahydro-2H-pyran-3-yl)-7H-pyrrolo[2,3-d]pyrimidine-6-carboxamide (62 mg) in 74% yield. 1H NMR (400 MHz, CD$_3$OD) δ 8.76 (s, 1H), 8.58-8.56 (m, 1H), 8.53 (s, 1H), 8.50 (s, 1H), 8.20-8.14 (m, 1H), 4.57-4.42 (m, 1H), 4.04-3.93 (m, 2H), 3.90-3.83 (m, 2H), 3.61-3.51 (m, 1H), 3.49-3.46 (m, 1H), 3.21 (S, 3H), 3.16 (s, 3H), 3.03-2.96 (m, 1H), 2.93-2.84 (m, 1H), 2.24-2.14 (m, 2H), 2.13-1.77 (m, 7H). HR-MS m/z 505.2693 (M+H)$^+$

Example 122

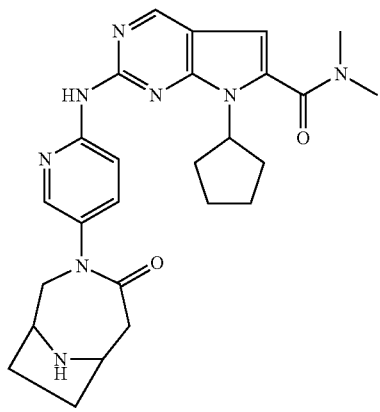 [SMILES: CN(C)C(=O)c1cc2cnc(Nc3ccc(N4CC5CCC(CC4=O)N5)cn3)nc2n1C1CCCC1]

7-Cyclopentyl-2-[5-(4-oxo-3,9-diaza-bicyclo[4.2.1]non-3-yl)-pyridin-2-ylamino]-7H-pyrrolo[2,3-d]pyrimidine-6-carboxylic acid dimethylamide

Step 1

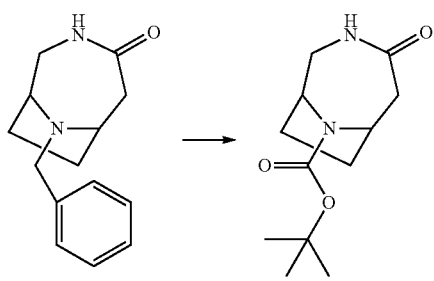 [SMILES: O=C1CC2CCC(CN1)N2Cc1ccccc1 ; CC(C)(C)OC(=O)N1C2CCC1CC(=O)NC2]

Preparation of 4-Oxo-3,9-diaza-bicyclo[4.2.1]nonane-9-carboxylic acid tert-butyl ester To a 500 ml Parr shaker bottle was added 10.53 grams (45.7 mmoles) of racemic 9-Benzyl-3,9-diaza-bicyclo[4.2.1]nonan-4-one 100 mls of methanol and 20 mls of tetrahydrofuran. In a single portion, 11 g (50.4 mmoles) of di-tertbutyl di-carbonate was added. The mixture was then put under nitrogen and about 0.5 grams of 10% palladium on carbon was added. The resultant mixture was hydrogenated with shaking at about 50 psi hydrogen for 36 hours. The mixture was removed from the Parr shaker and about 100 mls of dichloromethane and 25 grams of celite was added and stirred. The mixture was filtered through a pad of celite. The pad was washed with excess dichloromethane. The organics were combined and concentrated to a thick residue which solidified under vacuum. The solid was re-crystallized from dichloromethane/heptanes, the white solid was dried under vacuum which gave 4-Oxo-3,9-diaza-bicyclo[4.2.1]nonane-9-carboxylic acid tert-butyl ester 10.63 grams in 98% yield.

MS m/z 241 (M+H)$^+$.

Step 2

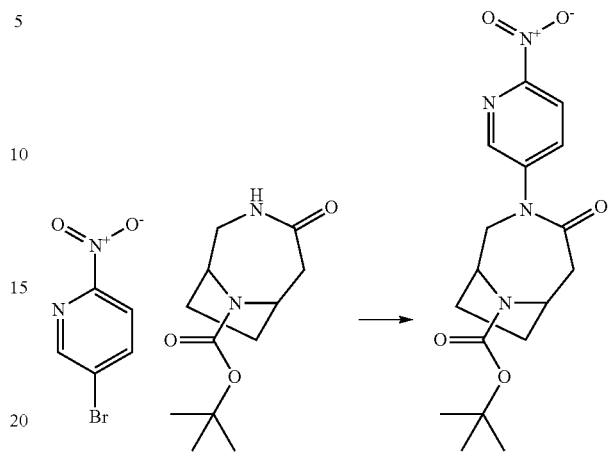

Preparation of 3-(6-Nitro-pyridin-3-yl)-4-oxo-3,9-diaza bicyclo[4.2.1]nonane-9-carboxylic acid tert-butyl ester Following general N—C coupling procedure 1, 4-oxo-3,9-diaza-bicyclo[4.2.1]nonane-9-carboxylic acid tert-butyl ester, 1.86 g (7.72 mmoles) was combined with 5-Bromo-2-nitro-pyridine, 1.51 g (7.42 mmoles), which after recrystallized from CH$_2$Cl$_2$-Heptanes gave 3-(6-Nitro-pyridin-3-yl)-4-oxo-3,9-diaza bicyclo[4.2.1]nonane-9-carboxylic acid tea-butyl ester, (1.59 g) in 58% yield. TLC Rf ~0.45 (75% Ethyl acetate-Heptane)

MS m/z 363 (M+H)$^+$

Step 3

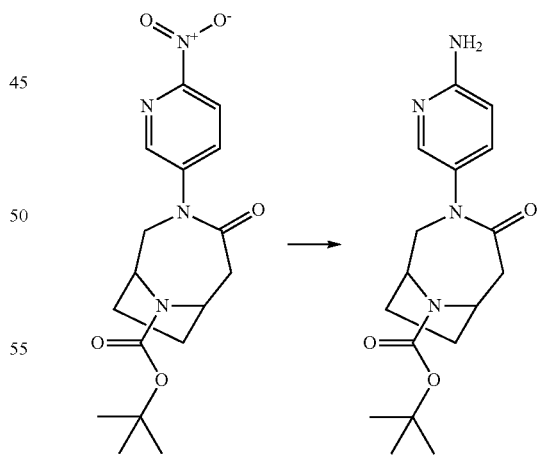

Preparation of 3-(6-Amino-pyridin-3-yl)-4-oxo-3,9-diaza-bicyclo[4.2.1]nonane-9-carboxylic acid tert-butyl ester Following nitro group reduction procedure 1 3-(6-Nitro-pyridin-3-yl)-4-oxo-3,9-diaza bicyclo[4.2.1]nonane-9-carboxylic acid tert-butyl ester 1.59 grams (4.24 mmoles) was converted to 3-(6-Amino-pyridin-3-yl)-4-oxo-3,9-diaza-bicyclo[4.2.1]nonane-9-carboxylic acid tert-butyl ester (1.41 grams) in 98% yield.

MS m/z 333 (M+H)⁺.

Step 4

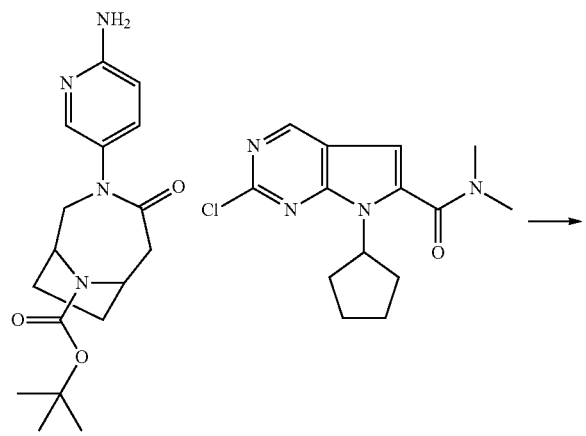

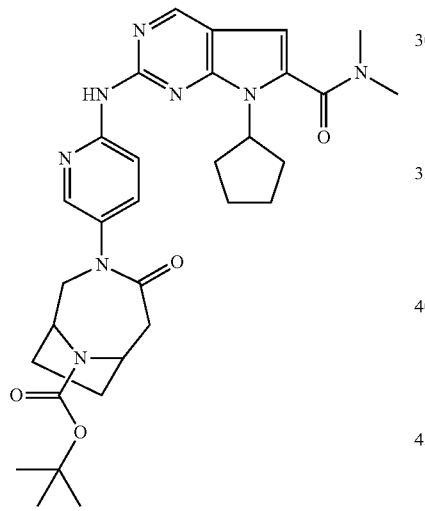

Preparation of 3-[6-(7-Cyclopentyl-6-dimethylcarbamoyl-7H-pyrrolo[2,3-d]pyrimidin-2-ylamino)-pyridin-3-yl]-4-oxo-3,9-diaza-bicyclo[4.2.1]nonane-9-carboxylic acid tert-butyl ester Following general Scheme 5 on a 1.023 mmole scale, 3-(6-Amino-pyridin-3-yl)-4-oxo-3,9-diaza-bicyclo[4.2.1] nonane-9-carboxylic acid tert-butyl ester was combined with 2-chloro-7-cyclopentyl-N,N-dimethyl-7H-pyrrolo[2,3-d] pyrimidine-6-carboxamide which yielded after SiO₂ gel Chromatograped (5-8% CH₃OH-ethyl acetate), 0.57 grams (95% yield) of 3-[6-(7-Cyclopentyl-6-dimethylcarbamoyl-7H-pyrrolo[2,3-d]pyrimidin-2-ylamino)-pyridin-3-yl]-4-oxo-3,9-diaza-bicyclo[4.2.1]nonane-9-carboxylic acid tert-butyl ester, TLC RF 0.4 in 5% CH₃OH-ethyl acetate, MS m/z 589 (M+H)⁺

Step 5

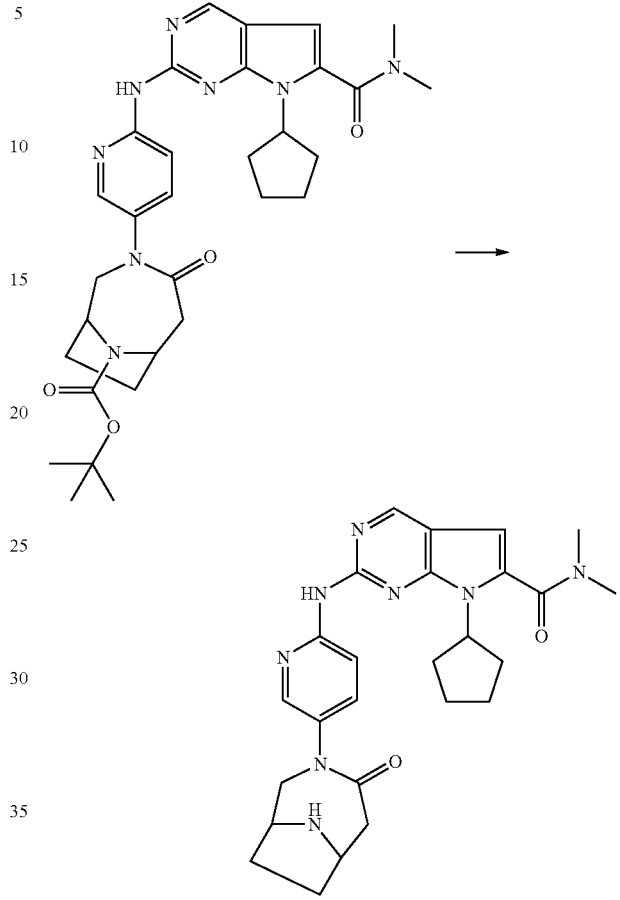

Preparation of 7-Cyclopentyl-2-[5-(4-oxo-3,9-diaza-bicyclo[4.2.1]non-3-yl)-pyridin-2-ylamino]-7H-pyrrolo[2,3-d]pyrimidine-6-carboxylic acid dimethylamide di-hydrochloride salt To 0.55 grams (0.96 mmoles) of 3-[6-(7-Cyclopentyl-6-dimethylcarbamoyl-7H-pyrrolo[2,3-d]pyrimidin-2-ylamino)-pyridin-3-yl]-4-oxo-3,9-diaza-bicyclo[4.2.1] nonane-9-carboxylic acid tert-butyl ester was added 15 ml of ethyl acetate. The mixture was stirred at room temperature under N₂ and cooled to ice bath temperature. To this mixture was added 5 mls 4N HCl in dioxane. The resultant mixture was allowed to stir until all starting material was consumed. The resultant mixture was stirred until all starting material was consumed as determined by HPLC-MS. To this mixture was added 50 ml of a 1:1 mixture of ethyl acetate/diethyl ether to precipitate solids. The solids were filtered and washed with excess 1:1 mixture of ethyl acetate/diethyl ether and dried under vacuum to a constant weight to yield 7-Cyclopentyl-2-[5-(4-oxo-3,9-diaza-bicyclo[4.2.1]non-3-yl)-pyridin-2-ylamino]-7H-pyrrolo[2,3-d]pyrimidine-6-carboxylic acid dimethylamide as the di-hydrochloride salt, 0.213 grams (45% yield). MS m/z 489 (M+H)⁺. ¹H NMR (400 MHz, D6 DMSO) δ 10.2 (s, 1H, broad), 9.05 (s, 1H, broad), 8.35 (s, 1H), 8.0 (d, 1H), 7.7 (d, 1H), 6.9 (s, 1H), 4.82 (m, 1H, broad), 4.6 (d, 1H), 4.25 (s, 1H, broad), 4.15 (s, 1H, broad), 3.82 (m, 1H, broad), 3.5 (d, 1H), 3.05 (s, 6H), 2.82 (m, 1H), 2.3 (m, 2H), 2.2-1.95 (m, 10H, broad), 1.89 (m, 1H), 1.65 (m, 2H).

Example 123

Preparation of 7-Cyclopentyl-2-[5-((1R,6S)-4-oxo-3, 9-diaza-bicyclo[4.2.1]non-3-yl)-pyridin-2-ylamino]-7H-pyrrolo[2,3-d]pyrimidine-6-carboxylic acid dimethylamide

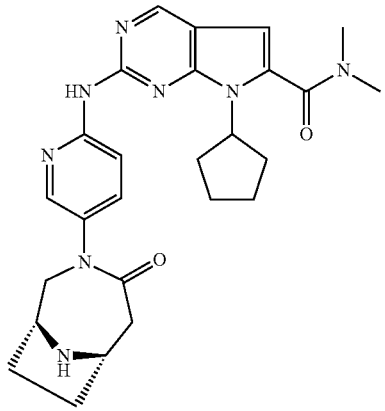

Chiral Separation of racemic 7-Cyclopentyl-2-[5-(4-oxo-3,9-diaza-bicyclo[4.2.1]non-3-yl)-pyridin-2-ylamino]-7H-pyrrolo[2,3-d]pyrimidine-6-carboxylic acid dimethylamide (235 mg) gave approximately equal amounts of the plus and minus enantiomer.

7-Cyclopentyl-2-[5-((1R,6S)-4-oxo-3,9-diaza-bicyclo [4.2.1]non-3-yl)-pyridin-2-ylamino]-7H-pyrrolo[2,3-d]pyrimidine-6-carboxylic acid dimethylamide. MS m/z 489 (M+H)$^{+1}$H NMR (400 MHz, D6 DMSO) δ 10.2 (s, 1H, broad), 9.05 (s, 1H, broad), 8.35 (s, 1H), 8.0 (d, 1H), 7.7 (d, 1H), 6.9 (s, 1H), 4.82 (m, 1H, broad), 4.6 (d, 1H), 4.25 (s, 1H, broad), 4.15 (s, 1H, broad), 3.82 (m, 1H), 3.5 (d, 1H), 3.05 (s, 6H), 2.82 (m, 1H), 2.3 (m, 2H), 2.2-1.95 (m, 10H, broad), 1.89 (m, 1H), 1.65 (m, 2H)

Example 123

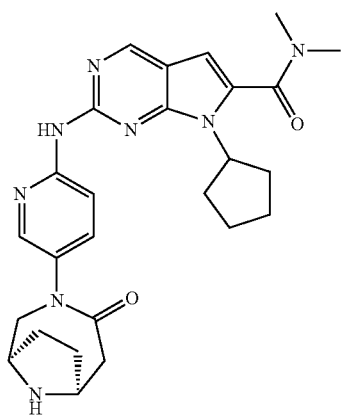 [SMILES: CN(C)C(=O)c1cc2cnc(Nc3ccc(N4C[C@H]5CC[C@@H](CC4=O)N5)cn3)nc2n1C1CCCC1]

7-Cyclopentyl-2-[5-((1R,6S)-4-oxo-3,9-diaza-bicyclo[4.2.1]non-3-yl)-pyridin-2-ylamino]-7H-pyrrolo[2,3-d]pyrimidine-6-carboxylic acid dimethylamide Step 1

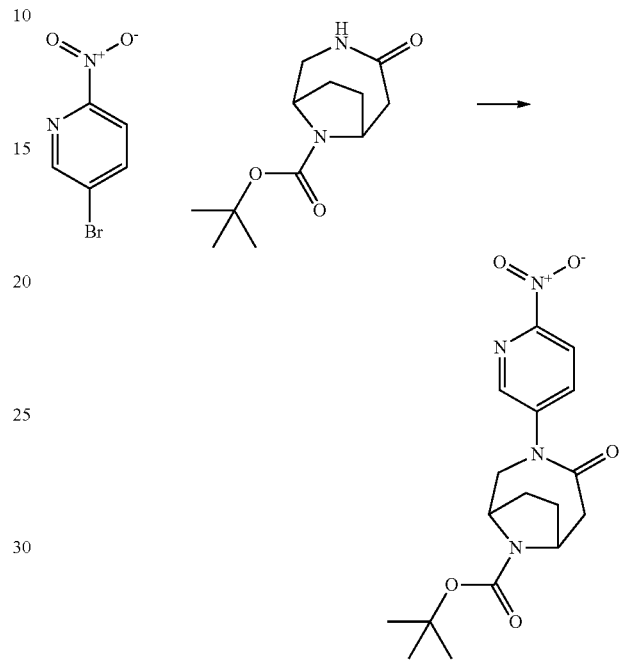

Preparation of 3-(6-Nitro-pyridin-3-yl)-4-oxo-3,9-diaza-bicyclo[4.2.1]nonane-9-carboxylic acid tert-butyl ester Following general N—C coupling procedure 1, 5-Bromo-2-nitropyridine (1 gm, 4.93 mmol) was combined with tert-butyl 4-oxo-3,9-diazabicyclo[4.2.1]nonane-9-carboxylate (1.18 gm, 4.93 mmol) which gave tert-butyl 3-(6-nitropyridin-3-yl)-4-oxo-3,9-diazabicyclo[4.2.1]nonane-9-carboxylate (1.4 gm) in 78% yield.

Step 2

Separation of 1 gm of the racemate 3-(6-Nitro-pyridin-3-yl)-4-oxo-3,9-diaza-bicyclo[4.2.1]nonane-9-carboxylic acid tert-butyl ester using the following conditions: 20×250 mm 5 µm prep IA column with a mobile phase of 30% MeOH/70% CO2 gave approximately 320 mg of (1S,6R)-tert-butyl 3-(6-nitropyridin-3-yl)-4-oxo-3,9-diazabicyclo[4.2.1]nonane-9-carboxylate. MS m/z 363.4 (M+H)

Enantiomer 2, (1R,6S)-tert-butyl 3-(6-nitropyridin-3-yl)-4-oxo-3,9-diazabicyclo[4.2.1]nonane-9-carboxylate and (1S,6R)-tert-butyl 3-(6-nitropyridin-3-yl)-4-oxo-3,9-diazabicyclo[4.2.1]nonane-9-carboxylate (320 mg). MS m/z 363.4 (M+H)

Step 3

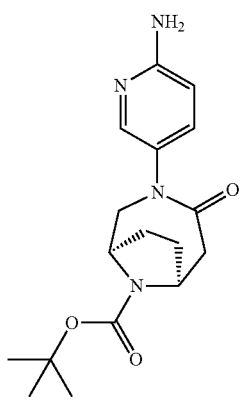 [SMILES: CC(C)(C)OC(=O)N1[C@@H]2CC[C@H]1CC(=O)N(c1ccc(N)nc1)C2]

Preparation of (1R,6S)-3-(6-Amino-pyridin-3-yl)-4-oxo-3,9-diazabicyclo[4.2.1]nonane-9-carboxylic acid tert-butyl ester Following nitro group reduction procedure 1, (1R,6S)-tert-butyl 3-(6-nitropyridin-3-yl)-4-oxo-3,9-diazabicyclo[4.2.1]nonane-9-carboxylate (360 mg, 0.96 mmol) was converted to (1R,6S)-3-(6-amino-pyridin-3-yl)-4-oxo-3,9-diaza-bicyclo[4.2.1]nonane-9-carboxylic acid tert-butyl ester (293 mg) in 92% yield
MS m/z 332.9 (M+H)

Step 4

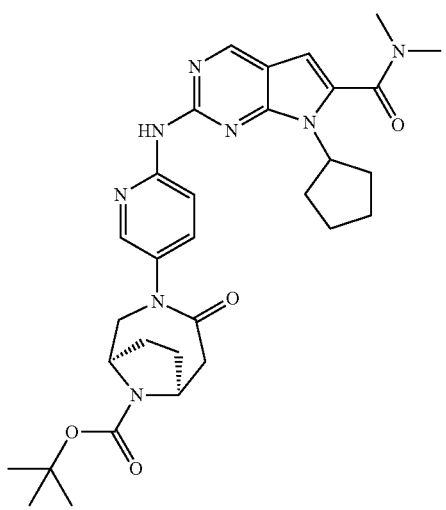 [SMILES: CN(C)C(=O)c1cc2cnc(Nc3ccc(N4C[C@H]5CC[C@@H](CC4=O)N5C(=O)OC(C)(C)C)cn3)nc2n1C1CCCC1]

Preparation of (1R,6S)-tert-butyl 3-(6-(7-cyclopentyl-6-(dimethylcarbamoyl)-7H-pyrrolo[2,3-d]pyrimidin-2-ylamino)pyridin-3-yl)-4-oxo-3,9-diazabicyclo[4.2.1]nonane-9-carboxylate Following general N—C coupling procedure 1, (1R,6S)-3-(6-Amino-pyridin-3-yl)-4-oxo-3,9-diaza-bicyclo[4.2.1]nonane-9-carboxylic acid tert-butyl ester (0.548 gm, 1.65 mmol) was combined with 2-chloro-7-cyclopentyl-N,N-dimethyl-7H-pyrrolo[2,3-d]pyrimidine-6-carboxamide (483 mg, 1.65 mmol) which gave (1R,6S)-tert-butyl 3-(6-(7-cyclopentyl-6-(dimethylcarbamoyl)-7H-pyrrolo[2,3-d]pyrimidin-2-ylamino)pyridin-3-yl)-4-oxo-3,9-diazabicyclo[4.2.1]nonane-9-carboxylate (858 mg) in 88% yield.
MS m/z 588.7 (M+H)

Step 5

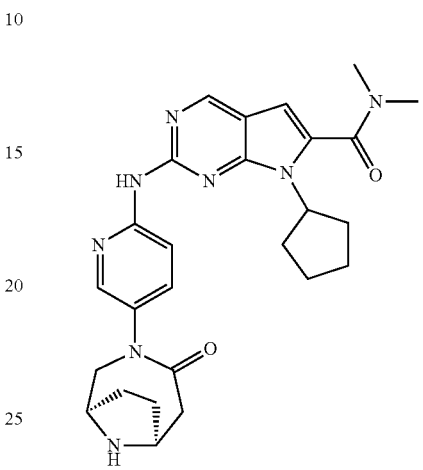

Preparation of 7-Cyclopentyl-2-[5-((1R,6S)-4-oxo-3,9-diaza-bicyclo[4.2.1]non-3-yl)-pyridin-2-ylamino]-7H-pyrrolo[2,3-d]pyrimidine-6-carboxylic acid dimethylamide Following deprotection method 1, (1R,6S)-tert-butyl 3-(6-(7-cyclopentyl-6-(dimethylcarbamoyl)-7H-pyrrolo[2,3-d]pyrimidin-2-ylamino)pyridin-3-yl)-4-oxo-3,9-diazabicyclo[4.2.1]nonane-9-carboxylate (858 mg, 1.46 mmol) was converted to 7-cyclopentyl-2-[5-((1R,6S)-4-oxo-3,9-diaza-bicyclo[4.2.1]non-3-yl)-pyridin-2-ylamino]-7H-pyrrolo[2,3-d]pyrimidine-6-carboxylic acid dimethylamide (700 mg) in 98% yield.
MS m/z 488.7 (M+H)$^+$.

Example 124

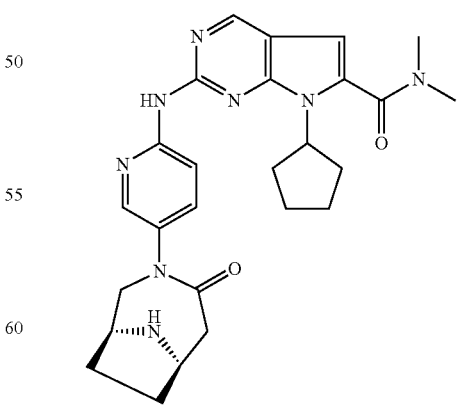

7-Cyclopentyl-2-[5-((1S,6R)-4-oxo-3,9-diaza-bicyclo[4.2.1]non-3-yl)-pyridin-2-ylamino]-7H-pyrrolo[2,3-d]pyrimidine-6-carboxylic acid dimethylamide was prepared from the chiral separation of racemate from example 122 to what has been done before. ¹H NMR (400 MHz, D6 DMSO) δ 10.2 (s, 1H, broad), 9.05 (s, 1H, broad), 8.35 (s, 1H), 8.0 (d, 1H), 7.7 (d, 1H), 6.9 (s, 1H), 4.82 (m, 1H, broad), 4.6 (d, 1H), 4.25 (s, 1H, broad), 4.15 (s, 1H, broad), 3.82 (m, 1H), 3.5 (d, 1H), 3.05 (s, 6H), 2.82 (m, 1H), 2.3 (m, 2H), 2.2-1.95 (m, 10H, broad), 1.89 (m, 1H), 1.65 (m, 2H)

MS m/z 489 (M+H)⁺

Example 125

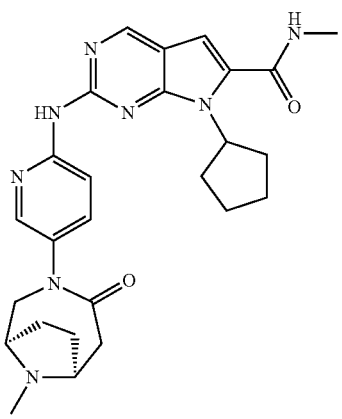 [SMILES: CNC(=O)c1cc2cnc(Nc3ccc(N4C[C@H]5CC[C@@H](CC4=O)N5C)cn3)nc2n1C1CCCC1]

7-cyclopentyl-2-[5-((1R,6S)-9-methyl-4-oxo-3,9-diaza-bicyclo[4.2.1]non-3-yl)-pyridin-2-ylamino]-7H-pyrrolo[2,3-c]pyrimidine-6-carboxylic acid methylamide Step 1

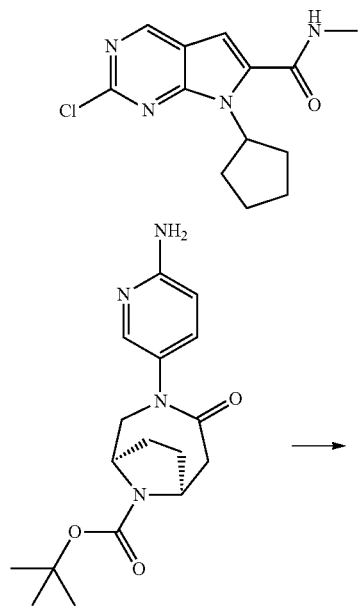

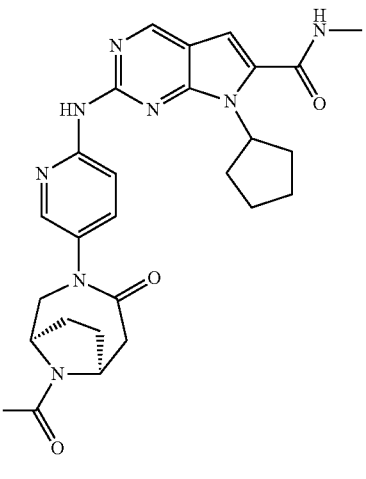

Preparation of (1R,6S)-3-[6-(7-Cyclopentyl-6-methylcarbamoyl-7H-pyrrolo[2,3-d]pyrimidin-2-ylamino)-pyridin-3-yl]-4-oxo-3,9-diaza-bicyclo[4.2.1]nonane-9-carboxylic acid tert-butyl ester Following general N—C coupling procedure 1, 2-chloro-7-cyclopentyl-N-methyl-7H-pyrrolo[2,3-d]pyrimidine-8-carboxamide was combined with (1R,6S)-tert-butyl 3-(6-aminopyridin-3-yl)-4-oxo-3,9-diazabicyclo[4.2.1]nonane-9-carboxylate which gave (1R,6S)-3-[6-(7-cyclopentyl-6-methylcarbamoyl-7H-pyrrolo[2,3-d]pyrimidin-2-ylamino)-pyridin-3-yl]-4-oxo-3,9-diaza-bicyclo[4.2.1]nonane-9-carboxylic acid tert-butyl ester (200 mg) in 78% yield. MS 575.8 m/z (M+H)

Step 2

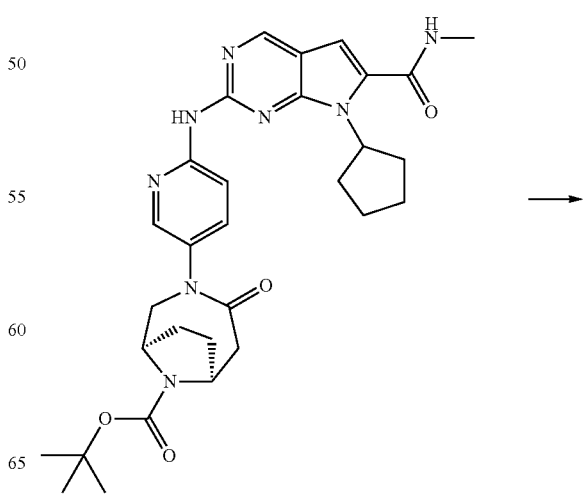

299
-continued

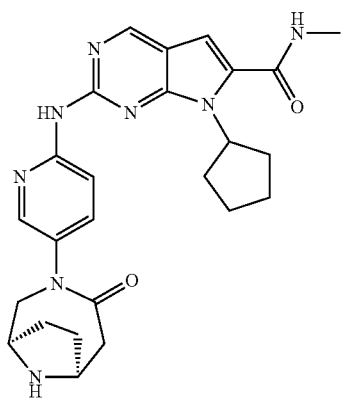

Preparation of 7-Cyclopentyl-2-[5-((1R,6S)-4-oxo-3,9-diaza-bicyclo[4.2.1]non-3-yl)-pyridin-2-ylamino]-7H-pyrrolo[2,3-d]pyrimidine-6-carboxylic acid methylamide Following deprotection method 1, (1R,6S)-3-[6-(7-Cyclopentyl-6-methylcarbamoyl-7H-pyrrolo[2,3-d]pyrimidin-2-ylamino)-pyridin-3-yl]-4-oxo-3,9-diaza-bicyclo[4.2.1]nonane-9-carboxylic acid tert-butyl ester was converted to 7-cyclopentyl-2-[5-((1R,6S)-4-oxo-3,9-diaza-bicyclo[4.2.1]non-3-yl)-pyridin-2-ylamino]-7H-pyrrolo[2,3-d]pyrimidine-6-carboxylic acidmethylamide (550 mg) in 52% yield. MS 475.6 m/z (M+H)

Step 3

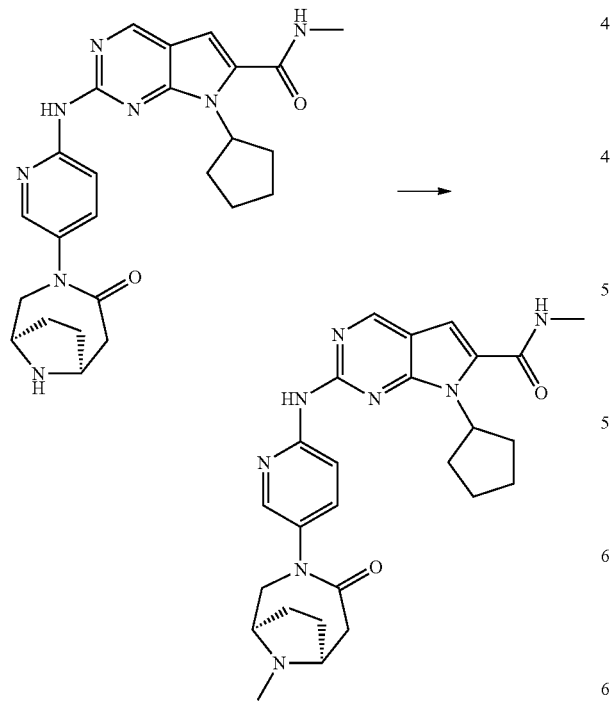

Preparation of 7-Cyclopentyl-2-[5-((1R,6S)-9-methyl-4-oxo-3,9-diaza-bicyclo[4.2.1]non-3-yl)-pyridin-2-ylamino]-7H-pyrrolo[2,3-d]pyrimidine-6-carboxylic acid methylamide Following general reductive alkylation method 1, 7-cyclopentyl-2-[5-((1R,6S)-4-oxo-3,9-diaza-bicyclo[4.2.1]non-3-yl)-pyridin-2-ylamino]-7H-pyrrolo[2,3-d]pyrimidine-6-carboxylic acid methylamide was combined with formaldehyde which gave 7-cyclopentyl-2-[5-((1R,6S)-9-methyl-4-oxo-3,9-diaza-bicyclo[4.2.1]non-3-yl)-pyridin-2-ylamino]-7H-pyrrolo[2,3-d]pyrimidine-6-carboxylic acid methylamide (100 mg) in 98% yield.

1H NMR (400 MHz, CDCl$_3$-d) δ ppm 8.75 (s, 1H), 8.49 (d, J=9.09 Hz, 1H), 8.21 (s, 1H), 8.16 (d, J=2.53 Hz, 1H), 7.53 (dd, J=8.84, 2.78 Hz, 1H), 6.66 (s, 1H), 6.21 (d, J=4.55 Hz, 1H), 5.48 (t, J=8.84 Hz, 1H), 4.22 (d, J=14.65 Hz, 1H), 3.41 (m, 1H), 3.32 (ddd, J=17.43, 6.57, 6.32 Hz, 2H), 3.01 (d, J=5.05 Hz, 6H), 2.76 (dd, J=15.66, 7.07 Hz, 1H), 2.59 (m, 2H), 2.45 (s, 3H), 2.20 (m, 2H), 2.06 (br. s., 4H), 1.94 (m, 2H)
MS 489.1 m/z (M+H)

Example 126

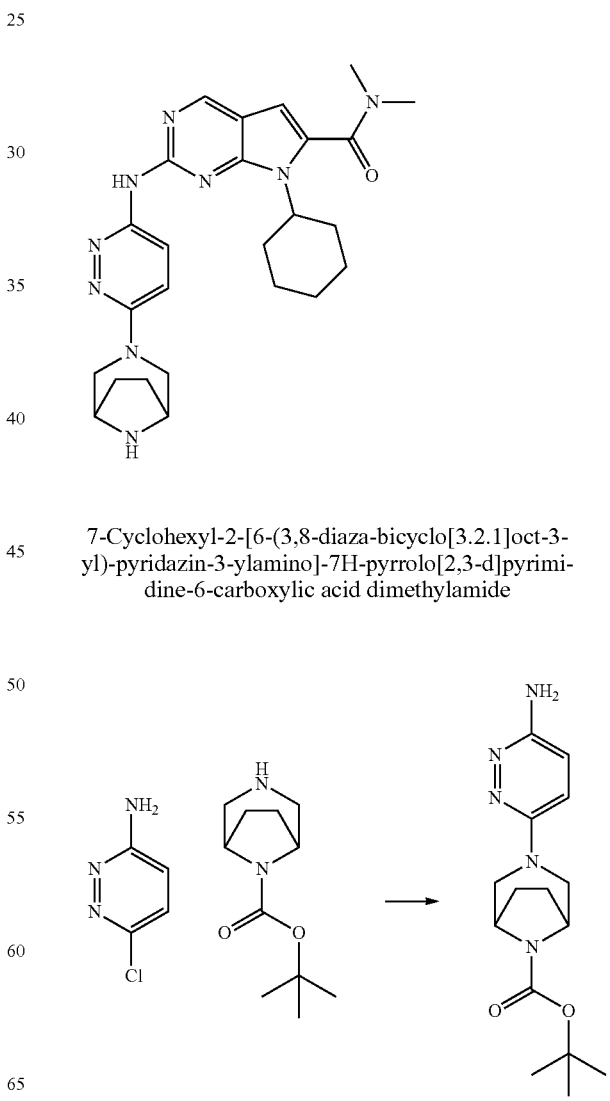

7-Cyclohexyl-2-[6-(3,8-diaza-bicyclo[3.2.1]oct-3-yl)-pyridazin-3-ylamino]-7H-pyrrolo[2,3-d]pyrimidine-6-carboxylic acid dimethylamide

301

Step 1

Preparation of 3-(6-Amino-pyridazin-3-yl)-3,8-diaza-bicyclo[3.2.1]octane-8-carboxylic acid tert-butyl ester In a mortar and pestle 6-chloro-pyridazin-3-ylamine (100 mg, 0.772 mmol) and 3,8-diaza-bicyclo[3.2.1]octane-8-carboxylic acid tert-butyl ester (180 mg, 0.849 mmol) were grounded together, placed in a sealed tube and heated to 130° C. for 16 h. The reaction was allowed to cool to room temperature and then the contents were dissolved in a minimal amount of dichloromethane. The crude product was purified by silica gel chromatography using a 0-50% ethyl acetate heptane gradient which gave 3-(6-amino-pyridazin-3-yl)-3,8-diaza-bicyclo[3.2.1]octane-8-carboxylic acid tert-butyl ester (70.7 mg, 0.232 mmol) in 30% yield.

MS m/z 306.1 (M+FI)$^+$.

Step 2

302

Preparation of 3-[6-(7-Cyclohexyl-6-dimethylcarbamoyl-7H-pyrrolo[2,3-d]pyrimidin-2-ylamino)-pyridazin-3-yl]-3,8-diaza-bicyclo[3.2.1]octane-8-carboxylic acid tert-butyl ester Following general N—C coupling procedure 1, 2-chloro-7-cyclohexyl-7H-pyrrolo[2,3-d]pyrimidine-6-carboxylic acid dimethylamide (25.2 mg, 0.082 mmol), was combined with 3-(6-amino-pyridazin-3-yl)-3,8-diaza-bicyclo[3.2.1] which after silica gel purification (0-10% methano ethyl acetate gradient) gave 3-[6-(7-cyclohexyl-6-dimethylcarbamoyl-7H-pyrrolo[2,3-d]pyrimidin-2-ylamino)-pyridazin-3-yl]-3,8-diaza-bicyclo[3.2.1]octane-8-carboxylic acid tert-butyl ester (25 mg, 0.043 mmol) in MS m/z 576.3 (M+H)$^+$.

Step 3

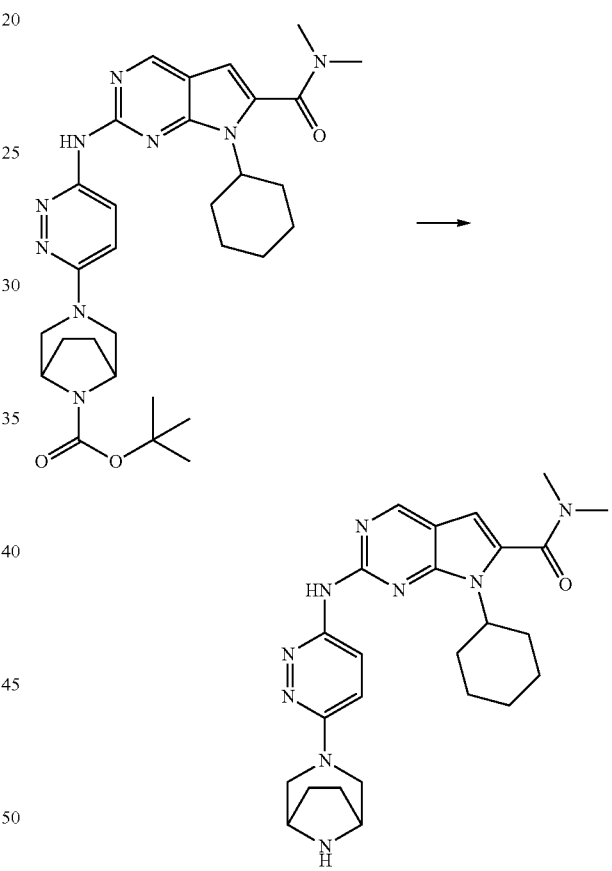

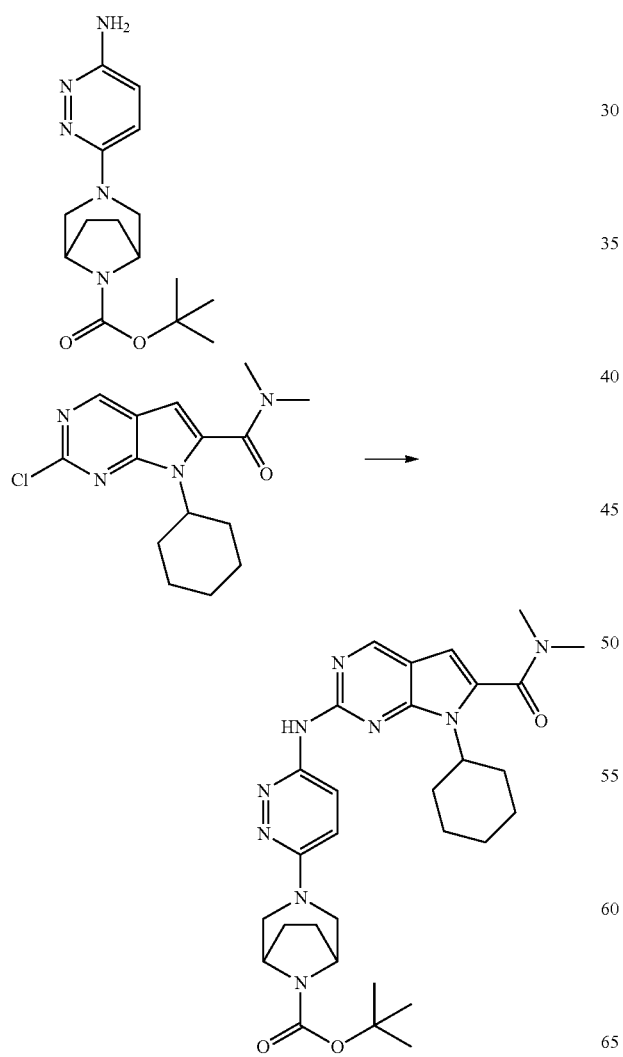

Preparation of 7-Cyclohexyl-2-[6-(3,8-diaza-bicyclo[3.2.1]oct-3-yl)-pyridazin-3-ylamino]-7H-pyrrolo[2,3-d]pyrimidine-6-carboxylic acid dimethylamide Following deprotection method 2, 3-[6-(7-cyclohexyl-6-dimethylcarbamoyl-7H-pyrrolo[2,3-d]pyrimidin-2-ylamino)-pyridazin-3-yl]-3,8-diaza-bicyclo[3.2.1]octane-8-carboxylic acid tert-butyl ester (25 mg, 0.043 mmol) was converted to 7-cyclohexyl-2-[6-(3,8-diaza-bicyclo[3.2.1]oct-3-yl)-pyridazin-3-ylamino]-7H-pyrrolo[2,3-d]pyrimidine-6-carboxylic acid dimethylamide (18 mg, 0.038 mmol) in 88% yield. 1H NMR (400 MHz, DMSO-d$_6$) δ ppm 9.66 (m, 1H), 8.74 (s, 1H), 8.21 (d, J=9.60 Hz, 1H), 7.21 (d, J=10.11 Hz, 1H), 6.59 (s, 1H), 4.23 (m, 1H), 3.81 (m, 2H), 3.52 (br. s., 2H), 3.05 (br. s., 6H), 2.92 (m, 2H), 2.42 (m, 2H), 1.82 (t, J=13.39 Hz, 5H), 1.67 (m, 5H), 1.27 (m, 3H). MS m/z 476.2 (M+H)$^+$.

Example 127

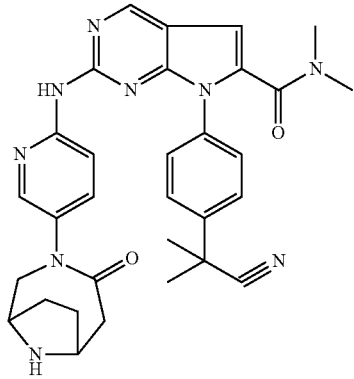 [SMILES: CN(C)C(=O)c1cc2cnc(Nc3ccc(N4CC5CCC(CC4=O)N5)cn3)nc2n1-c1ccc(C(C)(C)C#N)cc1]

7-(4-(2-cyanopropan-2-yl)phenyl)-N,N-dimethyl-2-(5-(4-oxo-3,9-diazabicyclo[4.2.1]nonan-3-yl)pyridin-2-ylamino)-7H-pyrrolo[2,3-d]pyrimidine-6-carboxamide Step 1

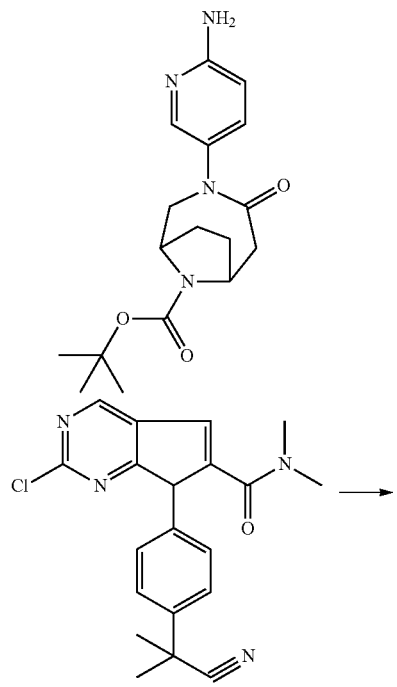

-continued

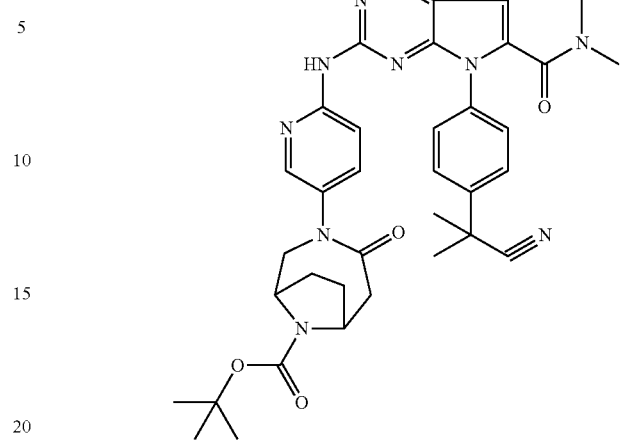

Preparation of tert-butyl 3-(6-(7-(4-(2-cyanopropan-2-yl)phenyl)-6-(dimethylcarbamoyl)-7H-pyrrolo[2,3-d]pyrimidin-2-ylamino)pyridin-3-yl)-4-oxo-3,9-diazabicyclo[4.2.1]nonane-9-carboxylate Following general N—C coupling procedure 1, 3-(6-Amino-pyridin-3-yl)-4-oxo-3,9-diaza-bicyclo[4.2.1]nonane-9-carboxylic acid tert-butyl ester was combined with 2-Chloro-7-[4-(cyano-dimethyl-methyl)-phenyl]-7H-pyrrolo[2,3-d]pyrimidine-6-carboxylic acid dimethylamide which gave tert-butyl 3-(6-(7-(4-(2-cyanopropan-2-yl)phenyl)-6-(dimethylcarbamoyl)-7H-pyrrolo[2,3-d]pyrimidin-2-ylamino) pyridin-3-yl)-4-oxo-3,9-diazabicyclo[4.2.1]nonane-9-carboxylate (160 mg) in 89% yield. MS m/z 664.7

Step 2

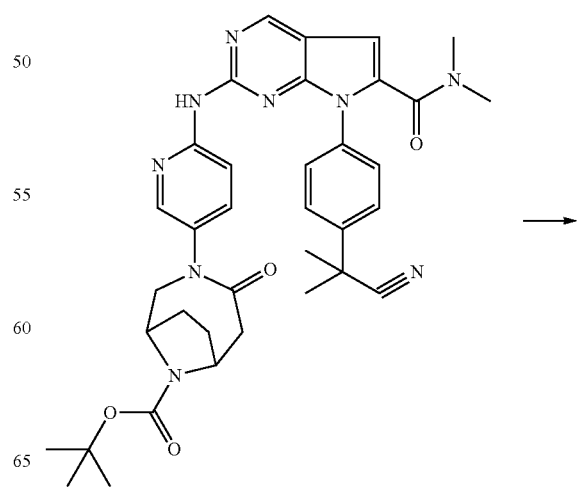

305
-continued

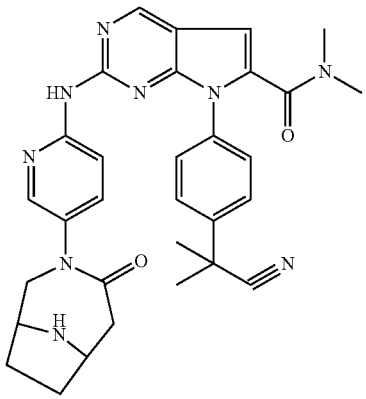

Preparation of 7-(4-(2-cyanopropan-2-yl)phenyl)-N,
N-dimethyl-2-(5-(4-oxo-3,9-diaza bicyclo[4.2.1]
nonan-3-yl)pyridin-2-ylamino)-7H-pyrrolo[2,3-d]
pyrimidine-6-carboxamide Following deprotection method 1, tert-butyl 3-(6-(7-(4-(2-cyanopropan-2-yl)phenyl)-6-(dimethylcarbamoyl)-7H-pyrrolo[2,3-d]pyrimidin-2-ylamino)pyridin-3-yl)-4-oxo-3,9-diazabicyclo[4.2.1]nonane-9-carboxylate was converted to 7-(4-(2-cyanopropan-2-yl)phenyl)-N,N-dimethyl-2-(5-(4-oxo-3,9-diazabicyclo[4.2.1]nonan-3-yl)pyridin-2-ylamino)-7H-pyrrolo[2,3-d]pyrimidine-6-carboxamide (72 mg) in 53% yield. 1H NMR (400 MHz, DMSO-$d_6$) δ ppm 9.91 (br. s., 1H), 9.63 (br. s., 2H), 8.94 (s, 1H), 8.23 (d, J=8.59 Hz, 1H), 8.16 (br. s., 1H), 7.72 (d, J=8.59 Hz, 1H), 7.54 (m, 1H), 6.95 (s, 1H), 4.40 (d, J=16.17 Hz, 1H), 4.16 (m, 2H), 3.73 (dd, J=16.17, 6.57 Hz, 1H), 3.31 (m, 3H), 3.02 (m, 6H), 2.80 (dd, J=16.67, 7.58 Hz, 1H), 2.08 (m, 3H), 1.89 (br. s., 1H), 1.77 (s, 6H). MS m/z 546.0 (M+H)

Example 128

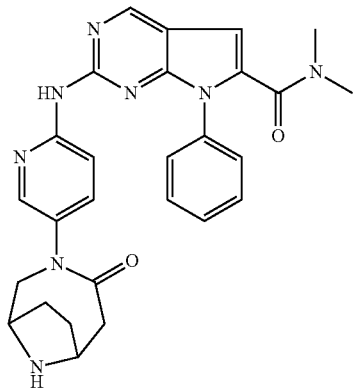 [SMILES: CN(C)C(=O)c1cc2cnc(Nc3ccc(N4CC5CCC(CC4=O)N5)cn3)nc2n1-c1ccccc1]

306

2-[5-(4-oxo-3,9-diaza-bicyclo[4.2.1]non-3-yl)-pyridin-2-ylamino]-7-phenyl-7H-pyrrolo[2,3-d]pyrimidine-6-carboxylic acid dimethylamide Step 1

Preparation of 3-[6-(6-Dimethylcarbamoyl-7-phenyl-7H-pyrrolo[2,3-d]pyrimidin-2-ylamino)-pyridin-3-yl]-4-oxo-3,9-diaza-bicyclo[4.2.1]nonane-9-carboxylic acid tert-butyl ester Following general N—C coupling procedure 1, 2-chloro-7-phenyl-7H-pyrrolo[2,3-d]pyrimidine-6-carboxylic acid dimethylamide (181 mg, 0.602 mmol) was combined with 3-(6-amino-pyridin-3-yl)-4-oxo-3,9-diaza-bicyclo[4.2.1]nonane-9-carboxylic acid tert-butyl ester (200 mg, 0.602 mmol), which gave 3-[6-(6-dimethylcarbamoyl-7-phenyl-7H-pyrrolo[2,3-d]pyrimidin-2-ylamino)-pyridin-3-yl]-4-oxo-3,9-diaza-bicyclo[4.2.1]nonane-9-carboxylic acid tert-butyl ester (320 mg, 0.536 mmol) in 86% yield.
MS m/z 597.6 (M+H)⁺.

Step 2

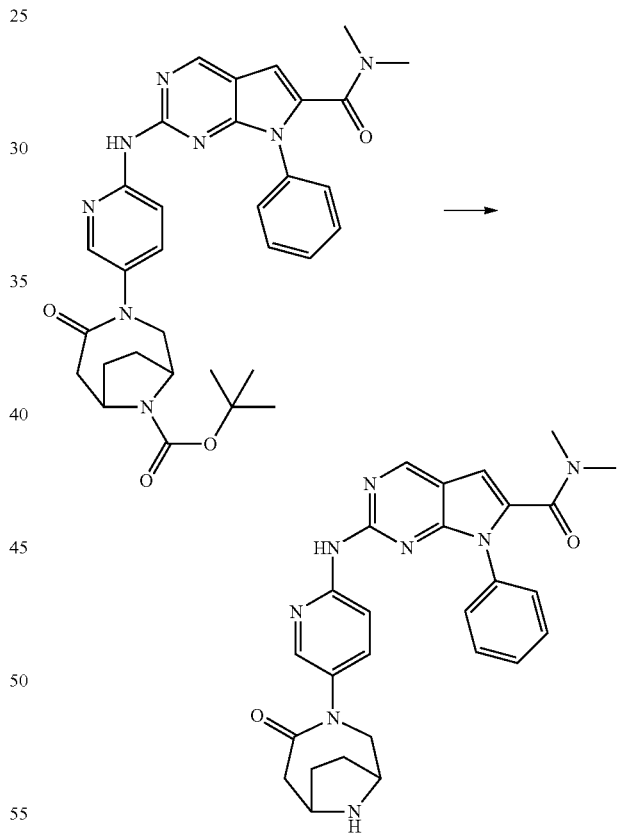

Preparation of 2-[5-(4-oxo-3,9-diaza-bicyclo[4.2.1]non-3-yl)-pyridin-2-ylamino]-7-phenyl-7H-pyrrolo[2,3-d]pyrimidine-6-carboxylic acid dimethylamide Following deprotection method 1, 3-[6-(6-dimethylcarbamoyl-7-phenyl-7H-pyrrolo[2,3-d]pyrimidin-2-ylamino)-pyridin-3-yl]-4-oxo-3,9-diaza-bicyclo[4.2.1]nonane-9-carboxylic acid tert-butyl ester (320 mg, 0.536 mmol) was converted to the hydrochloride salt of 2-[5-(4-oxo-3,9-diaza-bicyclo[4.2.1]non-3-yl)-pyridin-2-ylamino]-7-phenyl-7H- pyrrolo[2,3-d]pyrimidine-6-carboxylic acid dimethylamide (200 mg, 0.403 mmol). $^1$H NMR (400 MHz, DMSO-d$_6$) δ ppm 9.74 (m, 2H), 9.02 (s, 1H), 8.22 (d, J=2.53 Hz, 1H), 8.05 (d, J=8.08 Hz, 1H), 7.70 (d, J=7.58 Hz, 1H), 7.58 (t, J=7.83 Hz, 2H), 7.48 (m, 3H), 6.99 (s, 1H), 4.44 (d, J=16.17 Hz, 1H), 4.22 (br. s., 2H), 3.76 (dd, J=16.17, 6.57 Hz, 1H), 3.57 (s, 0H), 2.91 (m, 8H), 2.10 (m, 3H), 1.90 (m, 1H).

MS m/z 496.8 (M+H)$^+$.

Step 3

The enantiomers of 2-[5-(4-oxo-3,9-diaza-bicyclo[4.2.1] non-3-yl)-pyridin-2-ylamino]-7-phenyl-7H-pyrrolo[2,3-d] pyrimidine-6-carboxylic acid dimethylamide were separated using chiral chromatography (AD-H column, 21×250 mm column, 40% isopropyl alcohol with 0.2% diethylamine/60% CO$_2$) which gave the following.

Example 129

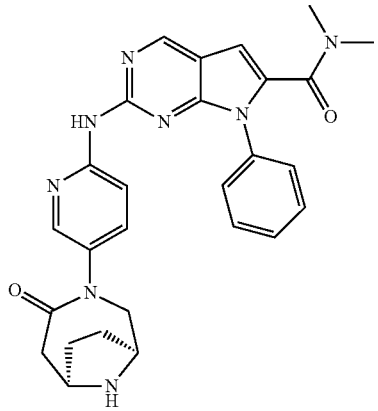 [SMILES: CN(C)C(=O)c1cc2cnc(Nc3ccc(N4C[C@@H]5CC[C@H](CC4=O)N5)cn3)nc2n1-c1ccccc1]

2-[5-((1S,6R)-4-Oxo-3,9-diaza-bicyclo[4.2.1]non-3-yl)-pyridin-2-ylamino]-7-phenyl-7H-pyrrolo[2,3-d]pyrimidine-6-carboxylic acid dimethylamide 1H NMR (400 MHz, DMSO-d$_6$) δ ppm 9.74 (m, 2H), 9.02 (s, 1H), 8.22 (d, J=2.53 Hz, 1H), 8.05 (d, J=8.08 Hz, 1H), 7.70 (d, J=7.58 Hz, 1H), 7.58 (t, J=7.83 Hz, 2H), 7.48 (m, 3H), 6.99 (s, 1H), 4.44 (d, J=16.17 Hz, 1H), 4.22 (br. s., 2H), 3.76 (dd, J=16.17, 6.57 Hz, 1H), 3.57 (s, 0H), 2.91 (m, 8H), 2.10 (m, 3H), 1.90 (m, 1H). MS m/z 497 (M+H)$^+$. Retention time of 1.88

Example 130

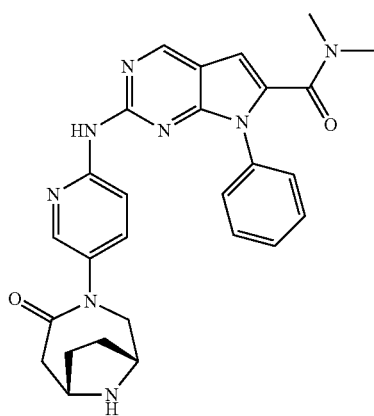 [SMILES: CN(C)C(=O)c1cc2cnc(Nc3ccc(N4C[C@H]5CC[C@@H](CC4=O)N5)cn3)nc2n1-c1ccccc1]

2-[5-((1R,6S)-4-oxo-3,9-diaza-bicyclo[4.2.1]non-3-yl)-pyridin-2-ylamino]-7-phenyl-7H-pyrrolo[2,3-d]pyrimidine-6-carboxylic acid dimethylamide. 1H NMR (400 MHz, DMSO-d$_6$) δ ppm 9.74 (m, 2H), 9.02 (s, 1H), 8.22 (d, J=2.53 Hz, 1H), 8.05 (d, J=8.08 Hz, 1H), 7.70 (d, J=7.58 Hz, 1H), 7.58 (t, J=7.83 Hz, 2H), 7.48 (m, 3H), 6.99 (s, 1H), 4.44 (d, J=16.17 Hz, 1H), 4.22 (br. s., 2H), 3.76 (dd, J=16.17, 6.57 Hz, 1H), 3.57 (s, 0H), 2.91 (m, 8H), 2.10 (m, 3H), 1.90 (m, 1H).
MS m/z 497 (M+H)$^\#$. Retention time of 2.61 minutes.

Example 131

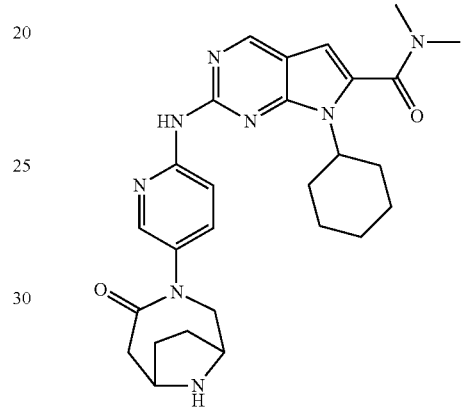

7-cyclohexyl-N,N-dimethyl-2-(5-(4-oxo-3,9-diazabicyclo[4.2.1]nonan-3-yl)pyridin-2-ylamino)-7H-pyrrolo[2,3-d]pyrimidine-6-carboxamide Step 1

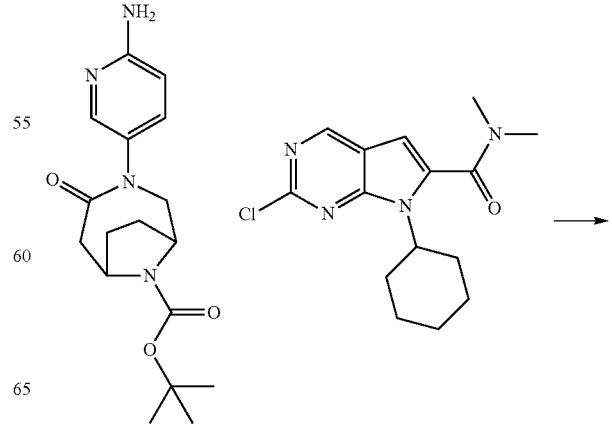

309

-continued

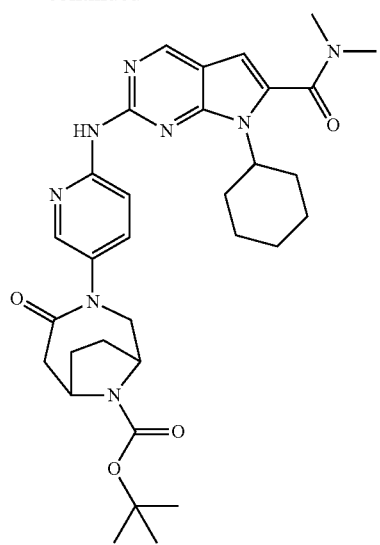

Preparation of tert-butyl 3-(6-(7-cyclohexyl-6-(dimethylcarbamoyl)-7H-pyrrolo[2,3-d]pyrimidin-2-ylamino)pyridin-3-yl)-4-oxo-3,9-diazabicyclo[4.2.1]nonane-9-carboxylate Following general N—C coupling procedure 1, tert-butyl 3-(6-aminopyridin-3-yl)-4-oxo-3,9-diazabicyclo[4.2.1]nonane-9-carboxylate (120 mg, 0.361 mmol) was combined with 2-chloro-7-cyclohexyl-N,N-dimethyl-7H-pyrrolo[2,3-d]pyrimidine-6-carboxamide (111 mg, 0.361 mmol) which gave tert-butyl 3-(6-(7-cyclohexyl-6-(dimethylcarbamoyl)-7H-pyrrolo[2,3-d]pyrimidin-2-ylamino)pyridin-3-yl)-4-oxo-3,9-diazabicyclo[4.2.1]nonane-9-carboxylate (120 mg) in 55.1% yield. MS m/z 603.6 (M+H)$^+$.

Step 2

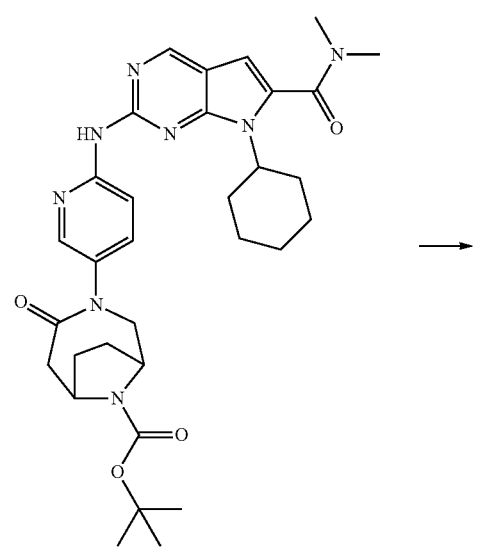

310

-continued

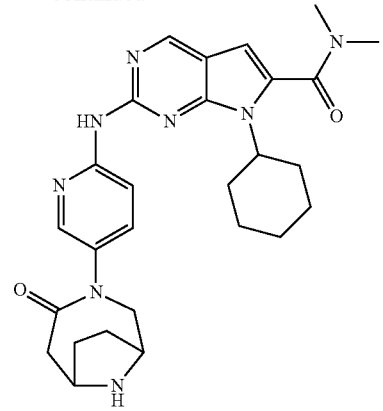 [SMILES: CN(C)C(=O)c1cc2cnc(Nc3ccc(N4CC5CCC(CC4=O)N5)cn3)nc2n1C1CCCCC1]

Preparation of 7-cyclohexyl-N,N-dimethyl-2-(5-(4-oxo-3,9-diazabicyclo[4.2.1]nonan-3-yl)pyridin-2-ylamino)-7H-pyrrolo[2,3-d]pyrimidine-6-carboxamide Following deprotection method 1, tert-butyl 3-(6-(7-cyclohexyl-6-(dimethylcarbamoyl)-7H-pyrrolo[2,3-d]pyrimidin-2-ylamino)pyridin-3-yl)-4-oxo-3,9-diazabicyclo[4.2.1]nonane-9-carboxylate (120 mg, 0.199 mmol) was converted to the hydrochloride salt of 7-cyclohexyl-N,N-dimethyl-2-(5-(4-oxo-3,9-diazabicyclo[4.2.1]nonan-3-yl)pyridin-2-ylamino)-7H-pyrrolo[2,3-d]pyrimidine-6-carboxamide (90 mg) in 90% yield. $^1$H NMR (400 MHz, CDCl$_3$) δ ppm 8.75 (s, 1H), 8.63 (d, J=9.03 Hz, 1H), 8.18 (d, J=2.51 Hz, 2H), 7.58 (d, J=7.53 Hz, 1H), 6.47 (s, 1H), 4.37 (t, J=3.51 Hz, 1H), 4.13 (d, J=14.56 Hz, 1H), 3.75 (m, 2H), 3.62 (dd, J=14.56, 6.53 Hz, 1H), 3.18 (s, 6H), 2.97 (m, 2H), 2.63 (d, J=11.04 Hz, 2H), 2.03 (m, 7H), 1.82 (d, J=11.54 Hz, 2H), 1.40 (m, 4H).
MS m/z 502.9 (M+H)$^+$.

Example 132

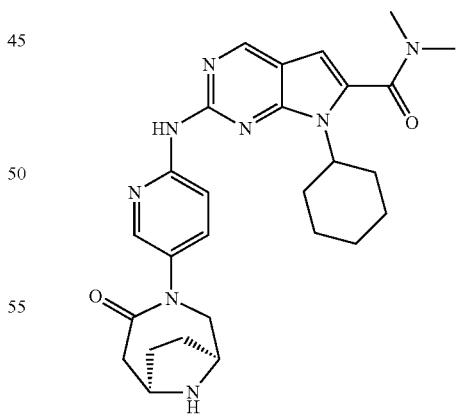

7-Cyclohexyl-2-[5-((1S,6R)-4-oxo-3,9-diaza-bicyclo[4.2.1]non-3-yl)-pyridin-2-ylamino]-7H-pyrrolo[2,3-d]pyrimidine-6-carboxylic acid dimethylamide Enantiomers were separated using chiral chromatography (AD-H column, 21×250 mm column, 40% isopropyl alcohol with 0.2% diethylamine 160% $CO_2$: Enantiomer 1 had a retention time of 1.75 minutes and

Example 133

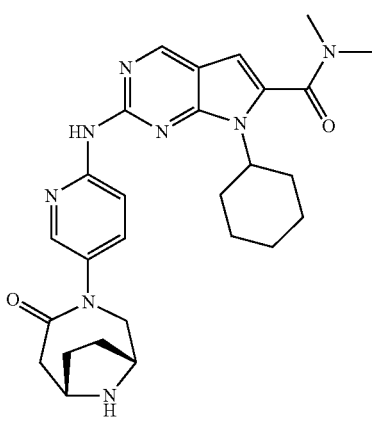 [SMILES: CN(C)C(=O)c1cc2cnc(Nc3ccc(N4C[C@H]5CC[C@@H](CC4=O)N5)cn3)nc2n1C1CCCCC1]

7-Cyclohexyl-2-[5-((1R,6S)-4-oxo-3,9-diaza-bicyclo[4.2.1]non-3-yl)-pyridin-2-ylamino]-7H-pyrrolo[2,3-d]pyrimidine-6-carboxylic acid dimethylamide Enantiomer 2 had a retention time of 2.21 minutes.

Example 134

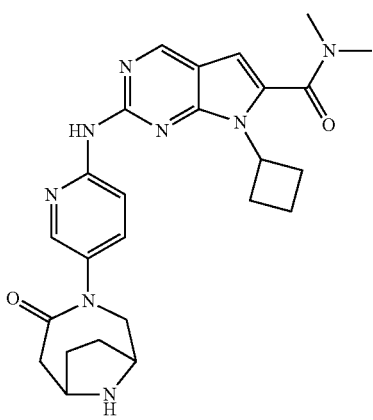 [SMILES: CN(C)C(=O)c1cc2cnc(Nc3ccc(N4CC5CCC(CC4=O)N5)cn3)nc2n1C1CCC1]

7-Cyclobutyl-2-[5-(4-oxo-3,9-diaza-bicyclo[4.2.1]non-3-yl)-pyridin-2-ylamino]-7H-pyrrolo[2,3-d]pyrimidine-6-carboxylic acid dimethylamide Step 1

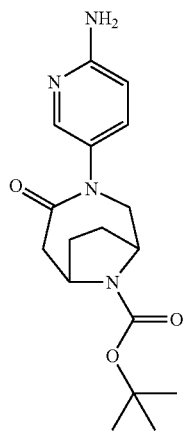 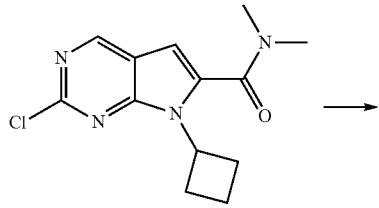

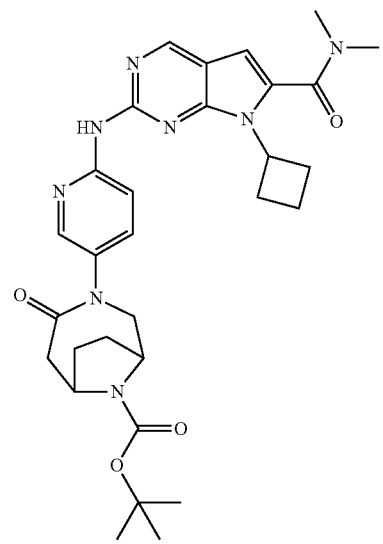

Preparation of tert-butyl 3-(6-(7-cyclobutyl-6-(dimethylcarbamoyl)-7H-pyrrolo[2,3-d]pyrimidin-2-ylamino)pyridin-3-yl)-4-oxo-3,9-diazabicyclo[4.2.1]nonane-9-carboxylate Following general N—C coupling procedure 1, tert-butyl-3-(6-aminopyridin-3-yl)-4-oxo-3,9-diazabicyclo[4.2.1]nonane-9-carboxylate (119 mg, 0.359 mmol) was combined with 2-chloro-7-cyclobutyl-N,N-dimethyl-7H-pyrrolo[2,3-d]pyrimidine-6-carboxamide (100 mg, 0.359 mmol) which gave tert-butyl 3-(6-(7-cyclobutyl-6-(dimethylcarbamoyl)-7H-pyrrolo[2,3-d]pyrimidin-2-ylamino)pyridin-3-yl)-4-oxo-3,9-diazabicyclo[4.2.1]nonane-9-carboxylate (150 mg) in 73% yield. MS m/z 575.2 (M+H)$^+$.

Step 2

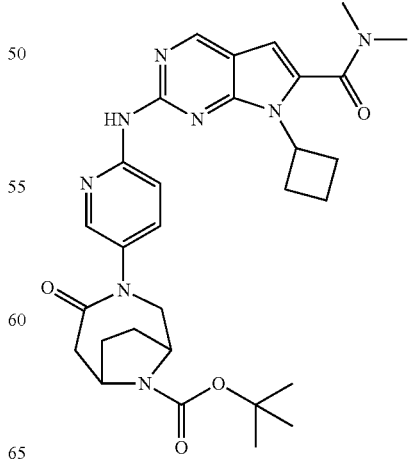

313

-continued

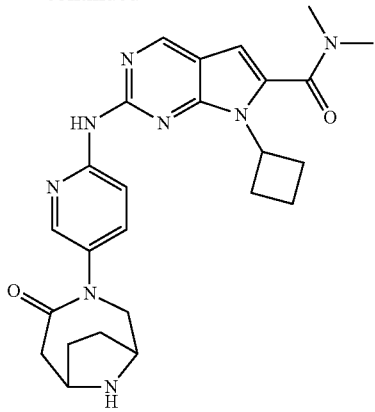

Preparation of 7-Cyclobutyl-2-[5-(4-oxo-3,9-diaza-bicyclo[4.2.1]non-3-yl)-pyridin-2-ylamino]-7H-pyrrolo[2,3-d]pyrimidine-6-carboxylic acid dimethylamide Following deprotection method 1, tert-butyl 3-(6-(7-cyclobutyl-6-(dimethylcarbamoyl)-7H-pyrrolo[2,3-d]pyrimidin-2-ylamino)pyridin-3-yl)-4-oxo-3,9-diazabicyclo[4.2.1]nonane-9-carboxylate (153 mg, 0.266 mmol) was converted to the HCl salt of 7-Cyclobutyl-2-[5-(4-oxo-3,9-diaza-bicyclo[4.2.1]non-3-yl)-pyridin-2-ylamino]-7H-pyrrolo[2,3-d]pyrimidine-6-carboxylic acid dimethylamide (76 mg) in 60% yield. 1H NMR (400 MHz, CDCl$_3$-d) δ ppm 8.75 (s, 1H), 8.63 (d, J=9.09 Hz, 1H), 8.17 (m, 2H), 7.59 (dd, J=8.59, 2.53 Hz, 1H), 6.47 (s, 1H), 5.00 (t, J=8.59 Hz, 1H), 4.12 (d, J=14.65 Hz, 1H), 3.75 (m, 2H), 3.62 (dd, J=14.91, 6.32 Hz, 1H), 3.24 (dd, 2H), 3.17 (s, 6H), 2.94 (m, 2H), 2.50 (m, 2H), 1.98 (m, 7H). MS m/z 475.4 (M+H)$^+$.

Example 135

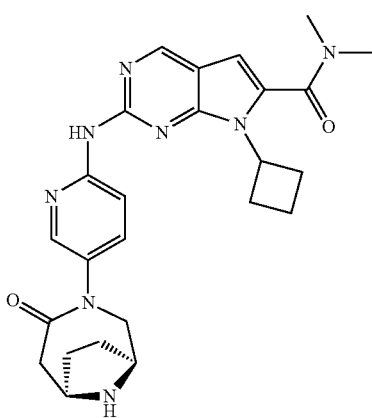 [SMILES: CN(C)C(=O)c1cc2cnc(Nc3ccc(N4C[C@@H]5CC[C@H](CC4=O)N5)cn3)nc2n1C1CCC1]

7-Cyclobutyl-2-[5-((1S,6R)-4-oxo-3,9-diaza-bicyclo[4.2.1]non-3-yl)-pyridin-2-ylamino]-7H-pyrrolo[2,3-d]pyrimidine-6-carboxylic acid dimethylamide Using chiral chromatography (IA column, 21×250 mm column, 40% isopropyl alcohol with 0.2% diethylamine/60% CO$_2$, the enantiomers of 7-Cyclobutyl-2-[5-(4-oxo-3,9-diaza-bicyclo[4.2.1]non-3-yl)-pyridin-2-ylamino]-7H-pyrrolo[2,3-d]pyrimidine-6-carboxylic acid dimethylamide were separated.

314

Enantiomer 1, 7-Cyclobutyl-2-[5-((1S,6R)-4-oxo-3,9-diaza-bicyclo[4.2.1]non-3-yl)-pyridin-2-ylamino]-7H-pyrrolo[2,3-d]pyrimidine-6-carboxylic acid dimethylamide, had a retention time of 1.98 minutes. 1H NMR (400 MHz, CDCl$_3$-d) δ ppm 8.75 (s, 1H), 8.63 (d, J=9.09 Hz, 1H), 8.17 (m, 2H), 7.59 (dd, J=8.59, 2.53 Hz, 1H), 6.47 (s, 1H), 5.00 (t, J=8.59 Hz, 1H), 4.12 (d, J=14.65 Hz, 1H), 3.75 (m, 2H), 3.62 (dd, J=14.91, 6.32 Hz, 1H), 3.24 (dd, 2H), 3.17 (s, 6H), 2.94 (m, 2H), 2.50 (m, 2H), 1.98 (m, 7H). MS m/z 475.4 (M+H)$^+$.

Example 136

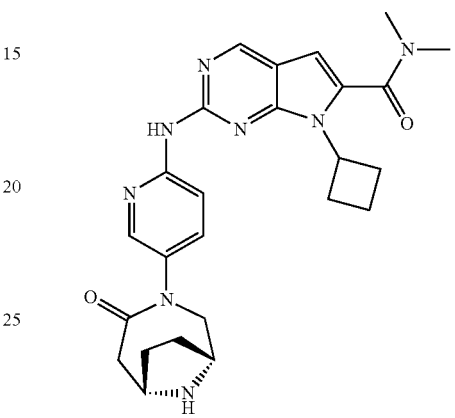

7-Cyclobutyl-2-[5-((1R,6S)-4-oxo-3,9-diaza-bicyclo[4.2.1]non-3-yl)-pyridin-2-ylamino]-7H-pyrrolo[2,3-d]pyrimidine-6-carboxylic acid dimethylamide Enantiomer 2, 7-Cyclobutyl-2-[5-((1R,6 S)-4-oxo-3,9-diaza-bicyclo[4.2.1]non-3-yl)-pyridin-2-ylamino]-7H-pyrrolo[2,3-d]pyrimidine-6-carboxylic acid dimethylamide, had a retention time of 2.72 minutes. $^1$H NMR (400 MHz, CDCl$_3$-d) δ ppm 8.75 (s, 1H), 8.63 (d, J=9.09 Hz, 1H), 8.17 (m, 2H), 7.59 (dd, J=8.59, 2.53 Hz, 1H), 6.47 (s, 1H), 5.00 (1, J=8.59 Hz, 1H), 4.12 (d, J=14.65 Hz, 1H), 3.75 (m, 2H), 3.62 (dd, J=14.91, 6.32 Hz, 1H), 3.24 (dd, 2H), 3.17 (s, 6H), 2.94 (m, 2H), 2.50 (m, 2H), 1.98 (m, 7H).
MS m/z 475.4 (M+H)$^+$.

Example 137

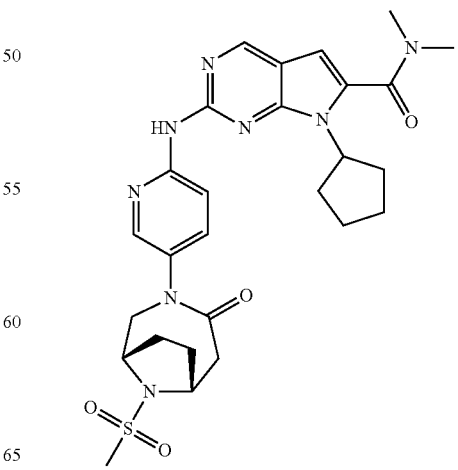

315

7-cyclopentyl-N,N-dimethyl-2-(5-((1S,6R)-9-(methylsulfonyl)-4-oxo-3,9-diazabicyclo[4.2.1]nonan-3-yl)pyridin-2-ylamino)-7H-pyrrolo[2,3-d]pyrimidine-6-carboxamide

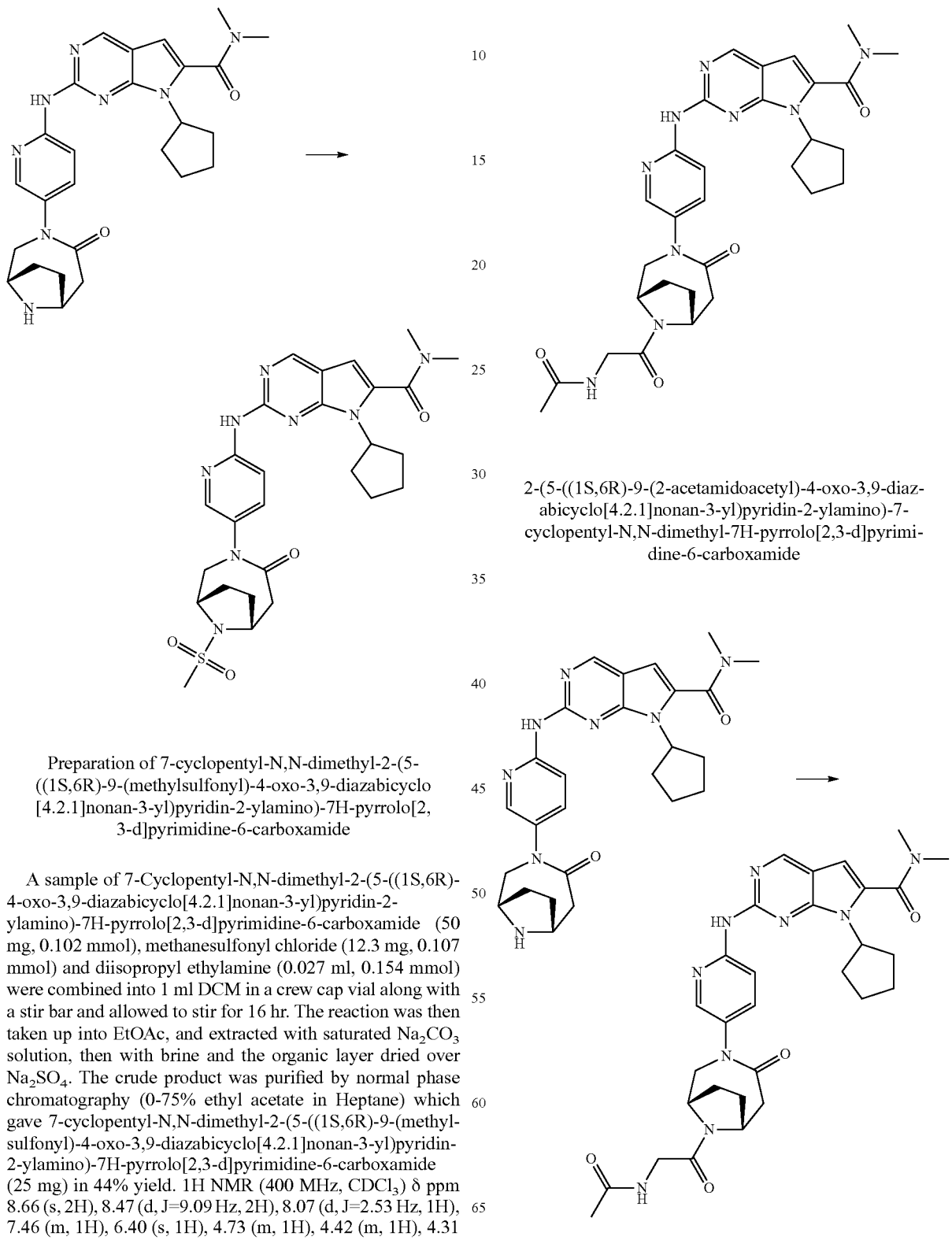

Preparation of 7-cyclopentyl-N,N-dimethyl-2-(5-((1S,6R)-9-(methylsulfonyl)-4-oxo-3,9-diazabicyclo[4.2.1]nonan-3-yl)pyridin-2-ylamino)-7H-pyrrolo[2,3-d]pyrimidine-6-carboxamide A sample of 7-Cyclopentyl-N,N-dimethyl-2-(5-((1S,6R)-4-oxo-3,9-diazabicyclo[4.2.1]nonan-3-yl)pyridin-2-ylamino)-7H-pyrrolo[2,3-d]pyrimidine-6-carboxamide (50 mg, 0.102 mmol), methanesulfonyl chloride (12.3 mg, 0.107 mmol) and diisopropyl ethylamine (0.027 ml, 0.154 mmol) were combined into 1 ml DCM in a crew cap vial along with a stir bar and allowed to stir for 16 hr. The reaction was then taken up into EtOAc, and extracted with saturated Na$_2$CO$_3$ solution, then with brine and the organic layer dried over Na$_2$SO$_4$. The crude product was purified by normal phase chromatography (0-75% ethyl acetate in Heptane) which gave 7-cyclopentyl-N,N-dimethyl-2-(5-((1S,6R)-9-(methylsulfonyl)-4-oxo-3,9-diazabicyclo[4.2.1]nonan-3-yl)pyridin-2-ylamino)-7H-pyrrolo[2,3-d]pyrimidine-6-carboxamide (25 mg) in 44% yield. 1H NMR (400 MHz, CDCl$_3$) δ ppm 8.66 (s, 2H), 8.47 (d, J=9.09 Hz, 2H), 8.07 (d, J=2.53 Hz, 1H), 7.46 (m, 1H), 6.40 (s, 1H), 4.73 (m, 1H), 4.42 (m, 1H), 4.31 (m, 1H), 4.20 (d, 1H), 3.64 (s, 2H), 3.09 (s, 6H), 3.00 (d, J=4.04 Hz, 1H), 2.90 (s, 3H), 2.49 (m, 2H), 2.00 (m, 4H), 1.66 (br. s., 4H). MS m/z 566.9 (M+H).

Example 138

2-(5-((1S,6R)-9-(2-acetamidoacetyl)-4-oxo-3,9-diazabicyclo[4.2.1]nonan-3-yl)pyridin-2-ylamino)-7-cyclopentyl-N,N-dimethyl-7H-pyrrolo[2,3-d]pyrimidine-6-carboxamide Preparation of 2-(5-((1S,6R)-9-(2-acetamidoacetyl)-4-oxo-3,9-diazabicyclo[4.2.1]nonan-3-yl)pyridin-2-ylamino)-7-cyclopentyl-N,N-dimethyl-7H-pyrrolo[2,3-d]pyrimidine-6-carboxamide 2-Acetamidoacetic acid (12 mg, 0.102 mmol) was combined with diisopropylethylamine (0.018 ml, 0.102 mmol) and HBTU (38.8 mg, 0.102 mmol) in DMF (1 ml) for 15 min. 7-Cyclopentyl-N,N-dimethyl-2-(5-((1S,6R)-4-oxo-3,9-diazabicyclo[4.2.1]nonan-3-yl)pyridin-2-ylamino)-7H-pyrrolo[2,3-d]pyrimidine-6-carboxamide (50 mg, 0.102 mmol) was then added and the reaction allowed to stir for 4 hrs. The reaction was then poured into brine and extracted with ethyl acetate. The combined ethyl acetate extracts were dried with sodium sulfate, filtered, concentrated and the resulting residue purified by silica gel chromatography which gave 2-(5-((1S,6R)-9-(2-acetamidoacetyl)-4-oxo-3,9-diazabicyclo[4.2.1]nonan-3-yl)pyridin-2-ylamino)-7-cyclopentyl-N,N-dimethyl-7H-pyrrolo[2,3-d]pyrimidine-6-carboxamide (45 mg) in 77% yield. $^1$H NMR (400 MHz, DMSO-d$_6$) δ ppm 9.71 (d, J=8.08 Hz, 2H), 8.82 (s, 1H), 8.14 (d, J=2.53 Hz, 1H), 8.07 (d, J=6.06 Hz, 1H), 7.61 (d, J=9.09 Hz, 2H), 6.63 (s, 2H), 4.76 (m, 2H), 4.53 (br. s., 1H), 4.44 (br. s., 0H), 4.21 (d, J=14.65 Hz, 0H), 3.95 (m, 2H), 3.61 (dd, J=14.91, 5.81 Hz, 1H), 3.04 (m, 6H), 2.78 (m, 1H), 2.40 (m, 3H), 2.00 (m, 6H), 1.89 (s, 3H), 1.66 (m, 3H). MS ink 588.6 (M+H)

Example 139

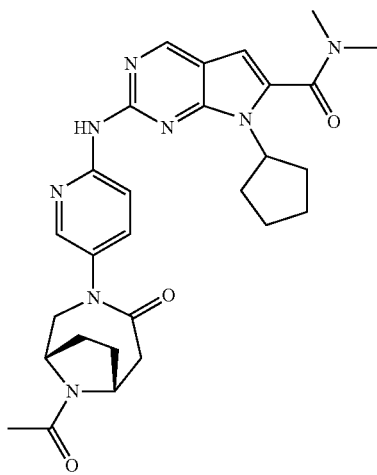 [SMILES: CC(=O)N1[C@@H]2CC[C@H]1CN(c1ccc(Nc3ncc4cc(C(=O)N(C)C)n(C5CCCC5)c4n3)nc1)C(=O)C2]

2-(5-((1S,6R)-9-acetyl-4-oxo-3,9-diazabicyclo[4.2.1]nonan-3-yl)pyridin-2-ylamino)-7-cyclopentyl-N,N-dimethyl-7H-pyrrolo[2,3-d]pyrimidine-6-carboxamide

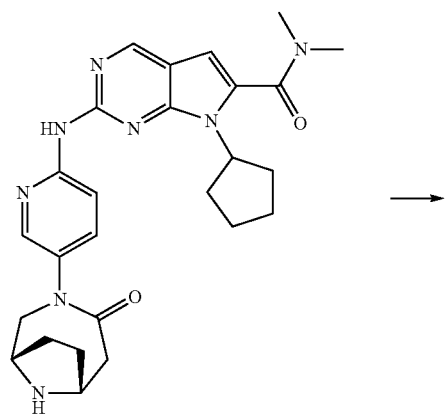

→

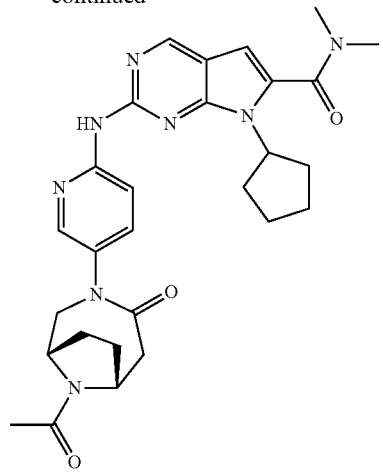

Preparation of 2-(5-((1S,6R)-9-acetyl-4-oxo-3,9-diazabicyclo[4.2.1]nonan-3-yl)pyridin-2-ylamino)-7-cyclopentyl-N,N-dimethyl-7H-pyrrolo[2,3-d]pyrimidine-6-carboxamide A sample of 7-Cyclopentyl-N,N-dimethyl-2-(5-((1S,6R)-4-oxo-3,9-diazabicyclo[4.2.1]nonan-3-yl)pyridin-2-ylamino)-7H-pyrrolo[2,3-d]pyrimidine-6-carboxamide (50 mg, 0.102 mmol), acetic anhydride (0.020 ml, 0.113 mmol) and diisopropylethylamine (0.014 ml, 0.154 mmol) were combined with 1 ml DCM. The mixture was allowed to stir for 16 hr and then taken up into EtOAc, washed with brine, dried over Na$_2$SO$_4$ filtered and concentrated. The crude product was purified by silica gel chromatography which gave 2-(5-((1S,6R)-9-acetyl-4-oxo-3,9-diazabicyclo[4.2.1]nonan-3-yl)pyridin-2-ylamino)-7-cyclopentyl-N,N-dimethyl-7H-pyrrolo[2,3-d]pyrimidine-6-carboxamide (32 mg) 52% yield. 1H NMR (400 MHz, DMSO-d$_6$) δ ppm 9.70 (d, J=8.08 Hz, 1H), 8.82 (s, 1H), 8.33 (dd, J=9.09, 6.06 Hz, 1H), 8.13 (d, J=2.53 Hz, 1H), 7.60 (dd, J=9.09, 2.53 Hz, 1H), 6.63 (s, 1H), 4.76 (t, J=8.84 Hz, 1H), 4.70 (br. s., 0H), 4.55 (m, 0H), 4.43 (s, 0H), 4.34 (br. s., 0H), 4.18 (d, J=14.65 Hz, 0H), 4.06 (d, J=14.15 Hz, 0H), 3.59 (m, 1H), 3.06 (br. s., 6H), 2.98 (d, J=16.17 Hz, 1H), 2.87 (d, J=14.65 Hz, 0H), 2.73 (m, 1H), 2.44 (br. s., 2H), 2.19 (m, 1H), 2.05 (d, J=4.55 Hz, 3H), 1.98 (m, 6H), 1.82 (m, 2H), 1.66 (d, J=5.56 Hz, 3H), 1.23 (br. s., 1H). MS m/z 531.6 (M+H).

Example 140

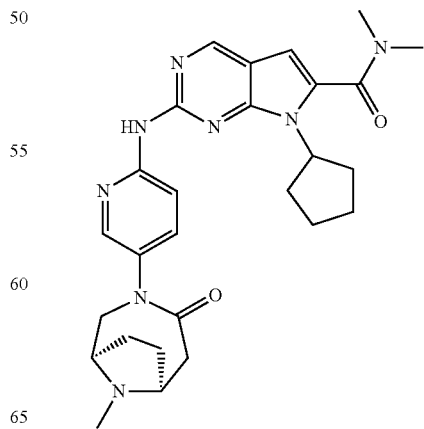

7-cyclopentyl-N,N-dimethyl-2-(5-((1R,6S)-9-methyl-4-oxo-3,9-diazabicyclo[4.2.1]nonan-3-yl)pyridin-2-ylamino)-7H-pyrrolo[2,3-d]pyrimidine-6-carboxamide

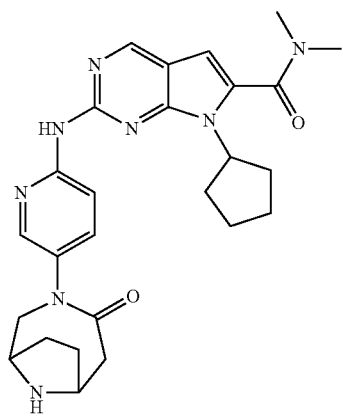

→

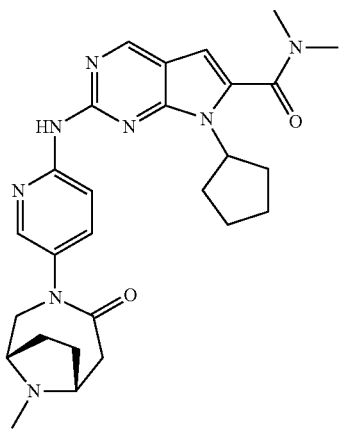 [SMILES: CN(C)C(=O)c1cc2cnc(Nc3ccc(N4C[C@@H]5CC[C@H](CC4=O)N5C)cn3)nc2n1C1CCCC1]

Example 141

7-Cyclopentyl-2-[5-((1S,6R)-9-methyl-4-oxo-3,9-diaza-bicyclo[4.2.1]non-3-yl)-pyridin-2-ylamino]-7H-pyrrolo[2,3-d]pyrimidine-6-carboxylic acid dimethylamide

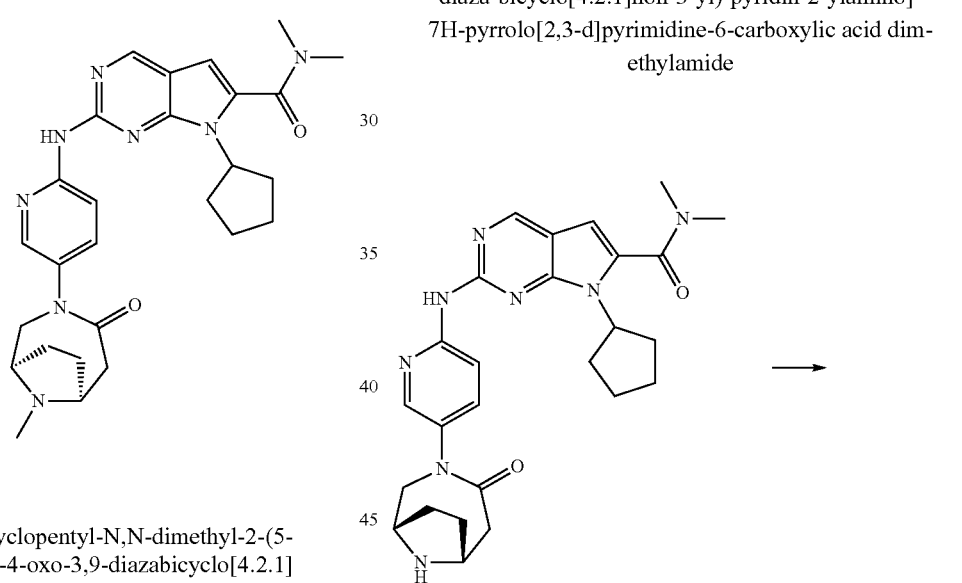

Preparation of 7-cyclopentyl-N,N-dimethyl-2-(5-((1R,6S)-9-methyl-4-oxo-3,9-diazabicyclo[4.2.1]nonan-3-yl)pyridin-2-ylamino)-7H-pyrrolo[2,3-d]pyrimidine-6-carboxamide Following general reductive alkylation method 1, 7-cyclopentyl-N,N-dimethyl-2-(5-((1R,6S)-4-oxo-3,9-diazabicyclo[4.2.1]nonan-3-yl)pyridin-2-ylamino)-7H-pyrrolo[2,3-d]pyrimidine-6-carboxamide (90 mg, 0.184 mmol) was combined with formaldehyde (37% solution in water, 0.041 ml, 1.474 mmol) which after silica gel chromatography gave 7-cyclopentyl-N,N-dimethyl-2-(5-((1R,6S)-9-methyl-4-oxo-3,9-diazabicyclo[4.2.1]nonan-3-yl)pyridin-2-ylamino)-7H-pyrrolo[2,3-d]pyrimidine-6-carboxamide (90 mg) in 97% yield. 1H NMR (400 MHz, DMSO-$d_6$) δ ppm 9.69 (s, 1H), 8.81 (s, 1H), 8.31 (d, J=9.09 Hz, 1H), 8.12 (d, J=2.53 Hz, 1H), 7.58 (dd, J=9.09, 2.53 Hz, 1H), 6.63 (s, 1H), 4.76 (m, 1H), 4.16 (d, J=14.65 Hz, 1H), 3.35 (m, 1H), 3.28 (m, 1H), 3.20 (t, J=6.57 Hz, 1H), 3.06 (br. s., 6H), 2.99 (m, 1H), 2.46 (m, 2H), 2.34 (s, 3H), 2.06 (m, 6H), 1.81 (m, 2H), 1.67 (m, 3H). MS m/z 503.6 (M+H)+.

Preparation of 7-Cyclopentyl-2-[5-((1S,6R)-9-methyl-4-oxo-3,9-diaza-bicyclo[4.2.1]non-3-yl)-pyridin-2-ylamino]-7H-pyrrolo[2,3-d]pyrimidine-6-carboxylic acid dimethylamide Following general reductive alkylation method 1, 7-Cyclopentyl-2-[5-((1S,6R)-4-oxo-3,9-diaza-bicyclo[4.2.1]non-3-yl)-pyridin-2-ylamino]-7H-pyrrolo[2,3-d]pyrimidine-6-carboxylic acid dimethylamide was combined with formaldehyde (37% solution in water) which after purification gave 7-cyclopentyl-2-[5-((1S,6R)-9-methyl-4-oxo-3,9-diaza-bicyclo[4.2.1]non-3-yl)-pyridin-2-ylamino]-7H-pyrrolo[2,3-d]pyrimidine-6-carboxylic acid dimethylamide (41 mg) in 80% yield. 1H NMR (400 MHz, DMSO-$d_6$) δ ppm 9.69 (s, 1H), 8.81 (s, 1H), 8.31 (d, J=9.09 Hz, 1H), 8.12 (d, J=2.53 Hz, 1H), 7.58 (dd, J=9.09, 2.53 Hz, 1H), 6.63 (s, 1H), 4.76 (m, 1H), 4.16 (d, J=14.65 Hz, 1H), 3.35 (m, 1H), 3.28 (m, 1H), 3.20 (t, J=6.57 Hz, 1H), 3.06 (br. s., 6H), 2.99 (m, 1H), 2.46 (m, 2H), 2.34 (s, 3H), 2.06 (m, 6H), 1.81 (m, 2H), 1.67 (m, 3H).
MS m/z 502.9 (M+H)$^+$.

Example 142

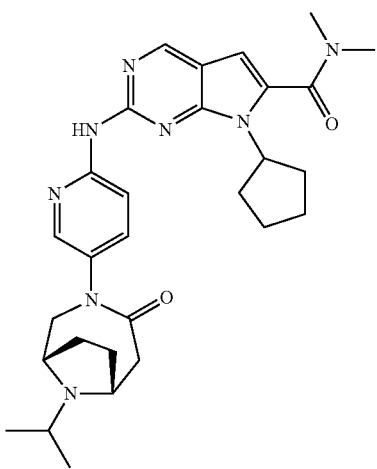 [SMILES: CC(C)N1[C@@H]2CC[C@H]1CN(c1ccc(Nc3ncc4cc(C(=O)N(C)C)n(C5CCCC5)c4n3)nc1)C(=O)C2]

7-Cyclopentyl-2-[5-((1S,6R)-9-isopropyl-4-oxo-3,9-diaza-bicyclo[4.2.1]non-3-yl)-pyridin-2-ylamino]-7H-pyrrolo[2,3-d]pyrimidine-6-carboxylic acid dimethylamide

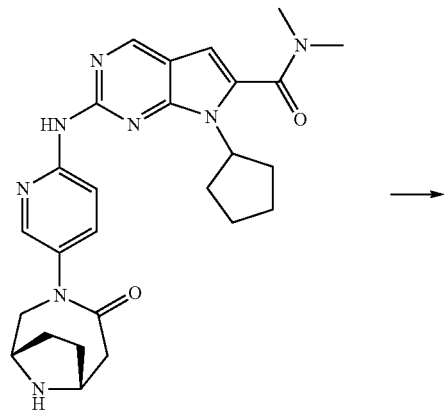

→

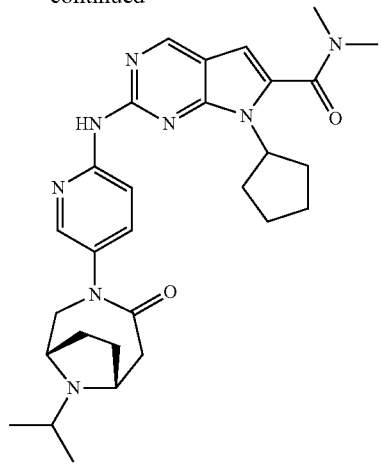

Preparation of 7-Cyclopentyl-2-[5-((1S,6R)-9-isopropyl-4-oxo-3,9-diaza-bicyclo[4.2.1]non-3-yl)-pyridin-2-ylamino]-7H-pyrrolo[2,3-d]pyrimidine-6-carboxylic acid dimethylamide Following general reductive alkylation method 1, 7-Cyclopentyl-N,N-dimethyl-2-(5-((1S,6R)-4-oxo-3,9-diazabicyclo[4.2.1]nonan-3-yl)pyridin-2-ylamino)-7H-pyrrolo[2,3-d]pyrimidine-6-carboxamide (65 mg, 0.133 mmol) was combined with acetone (0.05 mL, 0.665 mmol) which gave 7-cyclopentyl-2-[5-((1S,6R)-9-isopropyl-4-oxo-3,9-diaza-bicyclo[4.2.1]non-3-yl)-pyridin-2-ylamino]-7H-pyrrolo[2,3-d]pyrimidine-6-carboxylic acid dimethylamide (61 mg) in 86% yield. $^1$H NMR (400 MHz, CHLOROFORM-d) δ ppm 8.67 (s, 1H), 8.44 (d, J=8.59 Hz, 1H), 8.12 (s, 1H), 8.08 (d, J=2.53 Hz, 1H), 7.46 (dd, J=8.59, 2.53 Hz, 1H), 6.38 (s, 1H), 4.73 (t, J=9.09 Hz, 1H), 4.24 (d, J=14.65 Hz, 1H), 3.59 (m, 2H), 3.21 (br. s., 1H), 3.08 (m, 7H), 2.97 (br. s., 1H), 2.53 (m, 3H), 1.95 (m, 6H), 1.66 (m, 3H), 1.07 (t, J=5.81 Hz, 6H).
MS m/z 531.6 (M+H)

Example 143

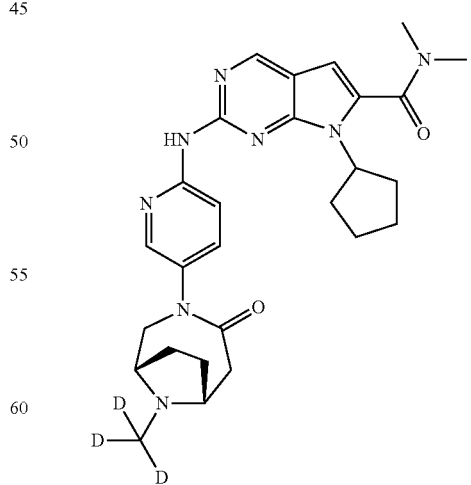

7-Cyclopentyl-2-[5-((1S,6R)-9-trideuteromethyl-4-oxo-3,9-diazabicyclo[4.2.1]non-3-yl)-pyridin-2-ylamino]-7H-pyrrolo[2,3-d]pyrimidine-6-carboxylic acid dimethylamide

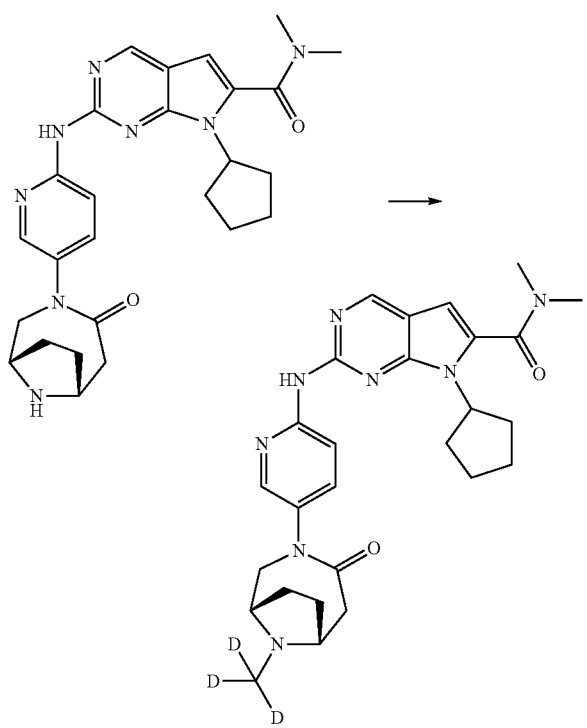

Preparation of 7-Cyclopentyl-2-[5-((1S,6R)-9-trideuteromethyl-4-oxo-3,9-diazabicyclo[4.2.1]non-3-yl)-pyridin-2-ylamino]-7H-pyrrolo[2,3-d]pyrimidine-6-carboxylic acid dimethylamide Following general reductive alkylation method 1, 7-Cyclopentyl-N,N-dimethyl-2-(5-((1S,6R)-4-oxo-3,9-diazabicyclo[4.2.1]nonan-3-yl)pyridin-2-ylamino)-7H-pyrrolo[2,3-d]pyrimidine-6-carboxamide (50 mg, 0.102 mmol) was combined with formaldehyde-d₂ (0.015 ml, 0.015 mL) which gave 7-cyclopentyl-2-[5-((1S,6R)-9-trideuteromethyl-4-oxo-3,9-diazabicyclo[4.2.1]non-3-yl)-pyridin-2-ylamino]-7H-pyrrolo[2,3-d]pyrimidine-6-carboxylic acid dimethylamide (43 mg) in 85% yield. 1H NMR (400 MHz, CDCl$_3$) δ ppm 8.75 (s, 1H), 8.53 (d, J=9.09 Hz, 1H), 8.16 (m, 1H), 7.56 (dd, J=9.09, 2.53 Hz, 1H), 6.48 (s, 1H), 4.82 (t, J=8.84 Hz, 1H), 4.26 (m, 1H), 3.41 (m, 6H), 3.16 (m, 2H), 2.79 (m, 3H), 2.59 (m, 2H), 2.24 (br. s., 2H), 2.08 (m, 6H), 1.75 (m, 3H). MS m/z 506.6 (M+H)

Example 144

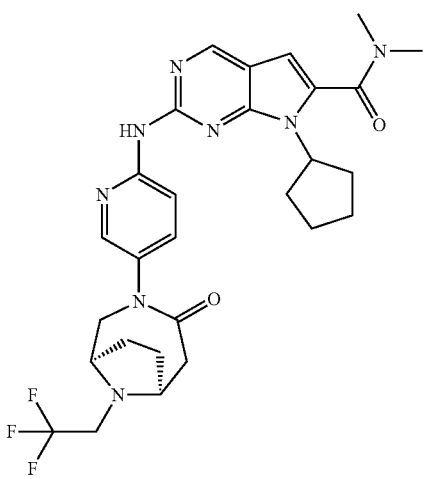 [SMILES: CN(C)C(=O)c1cc2cnc(Nc3ccc(N4C[C@H]5CC[C@@H](CC4=O)N5CC(F)(F)F)cn3)nc2n1C1CCCC1]

7-cyclopentyl-N, N-dimethyl-2-(5-((1R,6S)-4-oxo-9-(2,2,2-trifluoroethyl)-3,9-diazabicyclo[4.2.1]nonan-3-yl)pyridin-2-ylamino)-7H-pyrrolo[2,3-d]pyrimidine-6-carboxamide

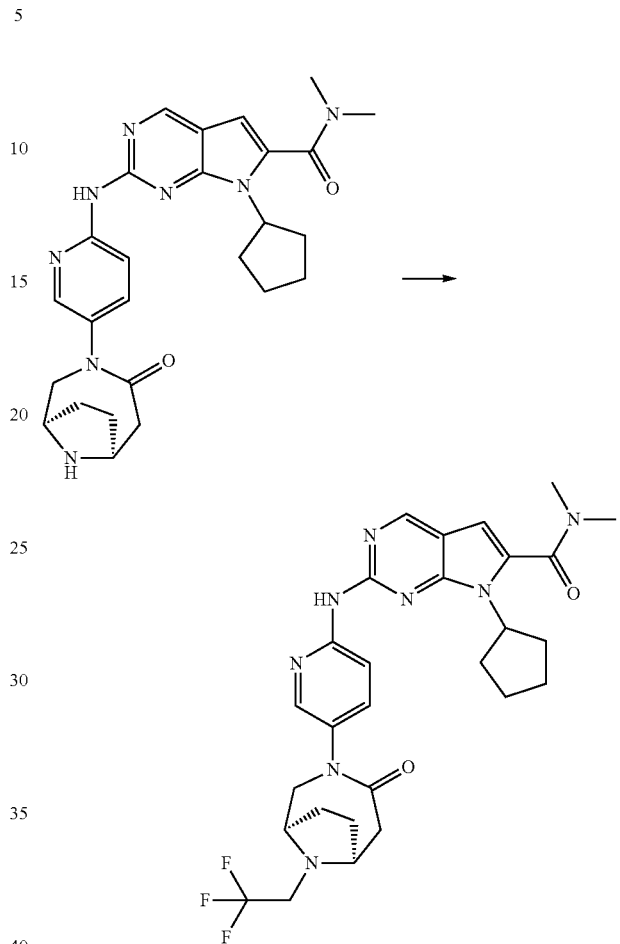

Preparation of 7-cyclopentyl-N,N-dimethyl-2-(5-((1R,6S)-4-oxo-9-(2,2,2-trifluoroethyl)-3,9-diazabicyclo[4.2.1]nonan-3-yl)pyridin-2-ylamino)-7H-pyrrolo[2,3-d]pyrimidine-6-carboxamide A sample of 7-Cyclopentyl-N,N-dimethyl-2-(5-((1S,6R)-4-oxo-3,9-diazabicyclo[4.2.1]nonan-3-yl)pyridin-2-ylamino)-7H-pyrrolo[2,3-d]pyrimidine-6-carboxamide (60 mg, 0.123 mmol) was combined with 2,2,2-trifluoroethyl trifluoromethanesulfonate (0.035 ml, 0.246 mmol) in dimethylformamide (1 mL) and heated to (80° C.) overnight. The reaction was then poured into water and extracted with ethyl acetate. The aqueous was washed with ethyl acetate. The organics were combined, dried over sodium sulfate, filtered and concentrated which gave a crude material that was purified by silica gel column chromatography which gave 7-cyclopentyl-N,N-dimethyl-2-(5-((1R,6S)-4-oxo-9-(2,2,2-trifluoroethyl)-3,9-diazabicyclo[4.2.1]nonan-3-yl)pyridin-2-ylamino)-7H-pyrrolo[2,3-d]pyrimidine-6-carboxamide (45 mg) in 64% yield. 1H NMR (400 MHz, CDCl$_3$) δ ppm 8.74 (s, 1H), 8.51 (d, J=9.09 Hz, 1H), 8.22 (s, 1H), 8.15 (d, J=2.53 Hz, 1H), 7.52 (dd, J=8.84, 2.78 Hz, 1H), 6.46 (s, 1H), 4.80 (t, J=8.59 Hz, 1H), 4.23 (d, J=13.64 Hz, 1H), 3.47 (m, 3H), 3.16 (s, 6H), 3.06 (m, 3H), 2.83 (dd, J=15.66, 7.07 Hz, 1H), 2.57 (dd, J=12.13, 8.59 Hz, 2H), 2.04 (m, 6H), 1.70 (m, 4H). MS m/z 571.6 (M+H)

Example 145

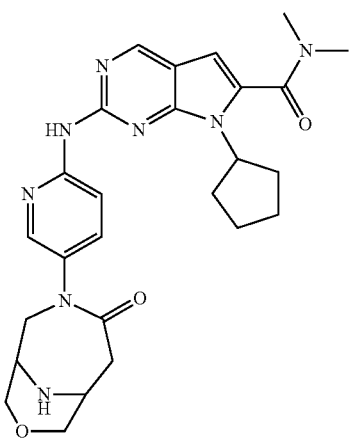 [SMILES: CN(C)C(=O)c1cc2cnc(Nc3ccc(N4CC5COCC(CC4=O)N5)cn3)nc2n1C1CCCC1]

7-Cyclopentyl-2-[5-(4-oxo-8-oxa-3,10-diaza-bicyclo[4.3.1]dec-3-yl)-pyridin-2-ylamino]-7H-pyrrolo[2,3-d]pyrimidine-6-carboxylic acid dimethylamide

Step 1

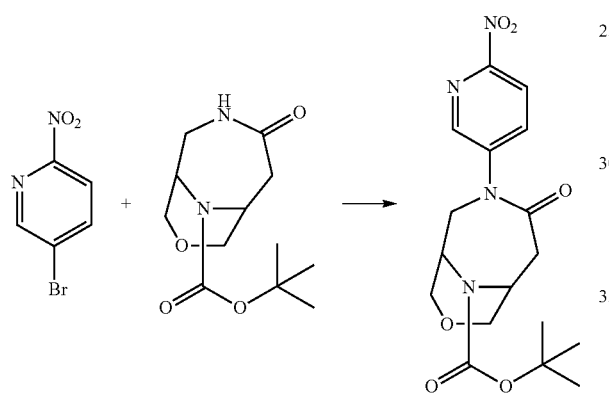

Preparation of 3-(6-Nitro-pyridin-3-yl)-4-oxo-8-oxa-3,10-diaza-bicyclo[4.3.1]decane-10-carboxylic acid tert-butyl ester Following general N—C coupling procedure 1, 4-Oxo-8-oxa-3,10-diaza-bicyclo[4.3.1]decane-10-carboxylic acid tert-butyl ester (0.776 g, 3.03 mmol) was combined with 5-Bromo-2-nitro-pyridine (0.676 g, 3.33 mmol) which gave 3-(6-Nitro-pyridin-3-yl)-4-oxo-8-oxa-3,10-diaza-bicyclo[4.3.1]decane-10-carboxylic acid tert-butyl ester (0.69 g, 1.732) in 57.2 yield. MS m/z 379.4 (M+H)

Step 2

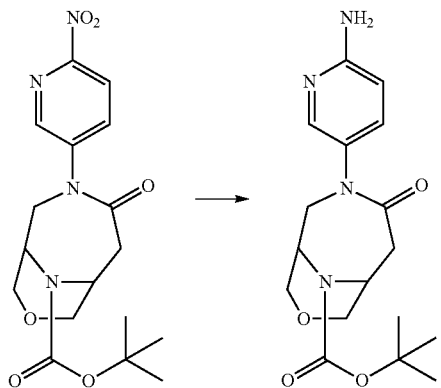 [SMILES: CC(C)(C)OC(=O)N1C2COCC1CN(c1ccc([N+](=O)[O-])nc1)C(=O)C2 ; CC(C)(C)OC(=O)N1C2COCC1CN(c1ccc(N)nc1)C(=O)C2]

Preparation of 3-(6-Amino-pyridin-3-yl)-4-oxo-8-oxa-3,10-diaza-bicyclo[4.3.1]decane-10-carboxylic acid tert-butyl ester Following general nitro reduction procedure 3-(6-niro-pyridin-3-yl)-4-oxo-8-oxa-3,10-diaza-bicyclo[4.3.1]decane-10-carboxylic acid tert-butyl ester (690 mg, 1.824 mmol) was converted to 3-(6-Amino-pyridin-3-yl)-4-oxo-8-oxa-3,10-diaza-bicyclo[4.3.1]decane-10-carboxylic acid tert-butyl ester (351 mg, 1.007 mmol) in 55.2% yield.

MS m/z 349.3 (M+H)

Step 3

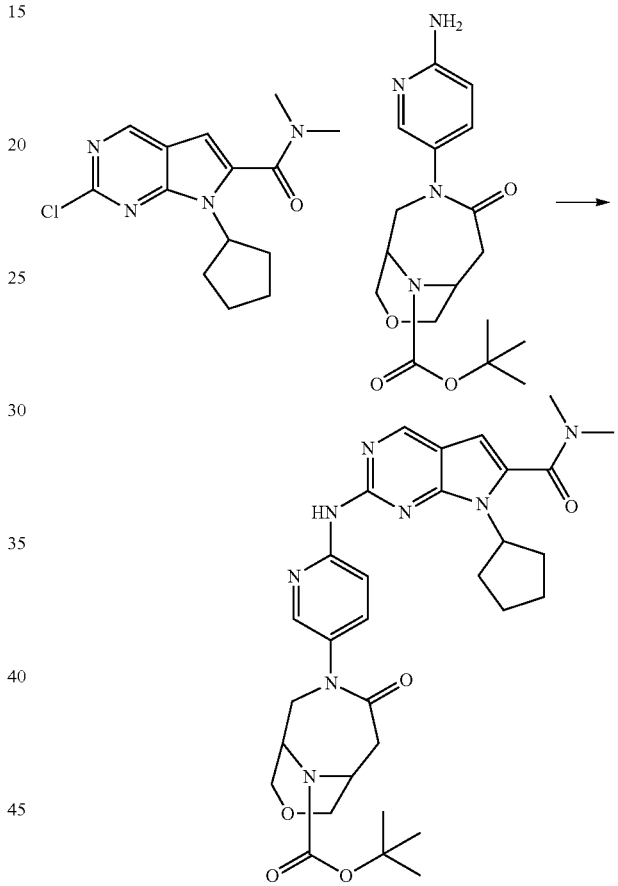

Preparation of 3-[6-(7-Cyclopentyl-6-dimethylcarbamoyl-7H-pyrrolo[2,3-d]pyrimidin-2-ylamino)-pyridin-3-yl]-4-oxo-8-oxa-3,10-diaza-bicyclo[4.3.1]decane-10-carboxylic acid tert-butyl ester Following general N—C coupling procedure 1, 3-(6-Amino-pyridin-3-yl)-4-oxo-8-oxa-3,10-diaza-bicyclo[4.3.1]decane-10-carboxylic acid tert-butyl ester (350 mg, 1.047 mmol) was combined with 2-Chloro-7-cyclopentyl-7H-pyrrolo[2,3-d]pyrimidine-6-carboxylic acid dimethylamide (337 mg, 1.151 mmol) which gave 3-[6-(7-Cyclopentyl-6-dimethylcarbamoyl-7H-pyrrolo[2,3-d]pyrimidin-2-ylamino)-pyridin-3-yl]-4-oxo-8-oxa-3,10-diaza-bicyclo[4.3.1]decane-10-carboxylic acid tert-butyl ester (476 mg, 0.787 mmol) in 75% yield.

MS m/z 604.6 (M+H)

Step 4

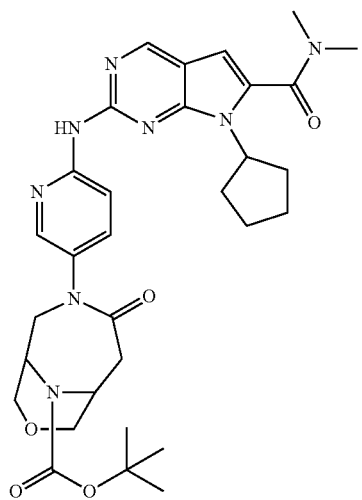
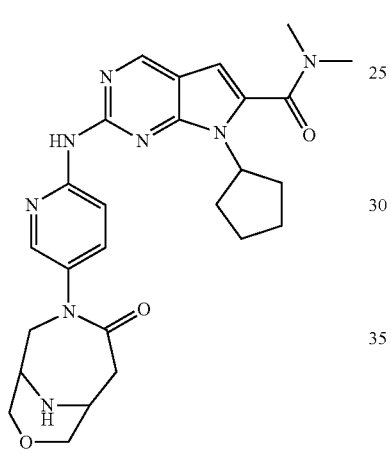

Preparation of 7-Cyclopentyl-2-[5-(4-oxo-8-oxa-3,10-diaza-bicyclo[4.3.1]dec-3-yl)-pyridin-2-ylamino]-7H-pyrrolo[2,3-d]pyrimidine-6-carboxylic acid dimethylamide Following deprotection method 1, 3-[6-(7-Cyclopentyl-6-dimethylcarbamoyl-7H-pyrrolo[2,3-d]pyrimidin-2-ylamino)-pyridin-3-yl]-4-oxo-8-oxa-3,10-diaza-bicyclo[4.3.1]decane-10-carboxylic acid tert-butyl ester (470 mg, 0.777 mmol) was converted to 7-Cyclopentyl-2-[5-(4-oxo-8-oxa-3,10-diaza-bicyclo[4.3.1]dec-3-yl)-pyridin-2-ylamino]-7H-pyrrolo[2,3-d]pyrimidine-6-carboxylic acid dimethylamide (231 mg, 0.457 mmol) in 58.8% yield. $^1$H NMR (400 MHz, D6 DMSO) δ 10.2 (s, 1H, broad), 9.05 (s, 1H, broad), 8.35 (s, 1H), 8.0 (d, 1H), 7.7 (d, 1H), 6.9 (s, 1H), 4.82 (m, 1H, broad), 4.6 (d, 1H), 4.25 (s, 1H, broad), 4.15 (s, 1H, broad), 3.82 (m, 1H, broad), 3.5 (d, 1H), 3.05 (s, 6H), 2.82 (m, 1H), 2.3 (m, 2H), 2.2-1.95 (m, 10H, broad), 1.89 (m, 1H), 1.65 (m, 2H) MS m/z 504.6 (M+H)

Example 146-147

A sample of 7-Cyclopentyl-2[5-(1-oxo-hexahydro-pyrrolo[1,2-a]pyrazin-2-yl)-pyridin-2-ylamino]-7H-pyrrolo[2,3-d]pyrimidine-6-carboxylic acid dimethylamide was chirally separated to give (enantiomer 1) 7-Cyclohexyl-2-[5-((S)-1-oxo-hexahydro-pyrrolo[1,2-a]pyrazin-2-yl)-pyridin-2-ylamino]-7H-pyrrolo[2,3-d]pyrimidine-6-carboxylic acid dimethylamide and (enantiomer 2) 7-Cyclohexyl-2-[5-((R)-1-oxo-hexahydro-pyrrolo[1,2-a]pyrazin-2-yl)-pyridin-2-ylamino]-7H-pyrrolo[2,3-d]pyrimidine-6-carboxylic acid dimethylamide.

Example 146

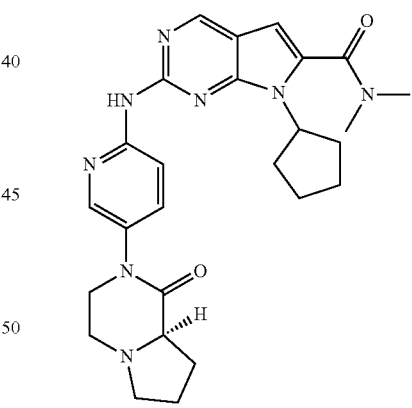

7-Cyclohexyl-2-[5-((S)-1-oxo-hexahydro-pyrrolo[1,2-a]pyrazin-2-yl)-pyridin-2-ylamino]-7H-pyrrolo[2,3-d]pyrimidine-6-carboxylic acid dimethylamide.
White Solid (4 mg) MS m/z 489.3 (M+H)$^+$.

Example 147

7-Cyclohexyl-2-[5-((R)-1-oxo-hexahydro-pyrrolo[1,2-a]pyrazin-2-yl)-pyridin-2-ylamino]-7H-pyrrolo[2,3-d]pyrimidine-6-carboxylic acid dimethylamide. White Solid (5 mg) MS m/z 489.3 (M+H)$^+$.

Biological Assays

CDK4/Cyclin D1 Enzymatic Activity Assay

An assay for monitoring CDK4/cyclin D1-catalyzed phosphorylation of pRb at the Ser780 site was performed using TR-FRET in a 384-well format, and was used for IC$_{50}$ determination and kinetic analysis. The reaction was carried out in a 30 μL volume containing 0.3 nM CDK4/cyclin D1, 150 nM biotin-pRb (773-924), 3 μM ATP, and 1.3% DMSO (or compound in DMSO) in the assay buffer (50 mM HEPES-Na, pH 7.5; 5 mM $MgCl_2$, 1 mM DTT, 0.02% Tween-20, and 0.05% BSA). 3 µM ATP was added last to initiate the reaction. The reaction was quenched with 10 µL of 240 mM EDTA-Na (pH 8.0) after 60 min incubation at 22° C. The signal was developed by the addition of 40 µL detection solution containing 40 nM SA-APC, 143 ng/mL anti-phospho-pRb (S780) antibody, and 1 nM Eu-W1024 anti-rabbit IgG antibody in the detection buffer (50 mM HEPES-Na, pH 7.5, 60 mM EDTA-Na, pH 8.0, 0.05% BSA, and 0.1% Triton X-100). After 60 min incubation in the dark, the plate was read on Envision (Perkin Elmer 2102-0010).

Human CDK4/cyclin D1 was expressed in Sf21 cells via baculovirus infection.

A CDK6/cyclin D3 enzymatic activity assay can be performed using the general procedures outlined in the CDK4/cyclin D1 enzymatic assay. CDK6/cyclin D3 enzyme complex can be purchased from a commercial source (CarnaBiosciences, Cat. No. 04-107)

CDK1/Cyclin B Enzymatic Activity Assay

A 384-well microtiter IMAP-FP™ (Molecular Devices Trade Mark Technology) endpoint assay was used for CDK1/cyclin B kinase activity measurements. The same assay was used for $IC_{50}$ determination of small molecule inhibitors. In general, the kinase reactions were carried out in 20 µL volumes in the reaction solution, which is composed of 2 µL compound (in 20% DMSO), 8 µL CDK1/cyclin B in the 1× Reaction Buffer (Molecular Devices, Cat. No. R8139), 10 µL substrate mixture of Tamra Histone-H1 peptide (Molecular Devices, Cat. No. R7384) and ATP (Amersham Pharmacia, Cat. No. 27-2056-01) in the 1× Reaction Buffer with 1 mM DTT freshly added. The final reaction mixture contains compound (inhibitor) with the concentration varying from 0.005-10 µM, 2% DMSO, 0.25 nM CDK1/cyclin B, 100 nM Tamra Histone-H1 peptide, and 20 µM ATP.

All reactions were run at room temperature in black 384-well flat-bottom Costar plates (Corning, Cat. No. 3710) for 120 min then were quenched by the addition of 60 µL 400-fold diluted 1× Progressive Binding Buffer A (Molecular Devices, Cat. No. R8139). The fluorescent polarization signals were read on the Evision Multilabel Reader (Perkin Elmer, Envision 2102-0010) after 2-hour incubation at room temperature. Note: $IC_{50}$<0.005 nM or $IC_{50}$>10 µM indicates the true $IC_{50}$ is out of detection range.

CDK4 Cellular Assays

Cell-based assay measuring phosphorylation levels of pRb at the Ser780 site using an enzyme-linked immunosorbent assay (ELISA) method (Table 6). JeKo-1, a mantle-cell lymphoma cell line, was selected for use in this assay due to its known translocation and subsequent overexpression of cyclin D1. [Ref: Amin, H. M.; McDonnell, T. J.; Medeiros, L. J.; Rassidakis, G. Z.; Leventaki, V.; O'Connor, S. L.; Keating, M. J.; Lai, R. Characterization of 4 mantle cell lymphoma cell lines—Establishment of an in vitro study model. *Arch. Pathol. Lab. Med.* 2003, 127, 424-431].

The pRb expressing JeKo-1 mantle cell lymphoma cell line was grown in complete media consisting of RPMI1640 (Gibco catalog no. 22400-071), 20% FBS (Gibco catalog no. 10082-131), 2 mM L-glutamine (Gibco catalog no. 25030-081), and 1% Penicillin/Streptomycin (Gibco catalog no. 15140-133). JeKo-1 cells were seeded in Biocoat Cell Environment Poly-D-Lysine 96-well tissue culture plates (Becton Dickinson catalog no. 356461) at 20,000 cells/well in 100 µL final volume of complete media. Cells were allowed to adhere overnight. Compounds were prepared as 10 mM stock solution in DMSO and diluted to a concentration of 110 µM in complete media in a 96 well tissue culture plate, and then serially diluted four fold, allowing a titration curve of 7 points with a final concentration of 26 nM. 10 µL of the dilution were then transferred to the cell culture plate, resulting in a final concentration range of 10 µM to 2 nM. The incubation was carried out at 37° C. with 5% $CO_2$. All compounds were tested in triplicates at each concentration. Following compound incubation, the media was removed and the cells were lysed in 35 µL of lysis buffer, consisting of 50 mM Tris.Cl, pH 7.2, 120 mM NaCl, 1 mM EDTA, 6 mM EGTA, 1% NP-40, complete protease inhibitor cocktail (Roche, catalog no. 11836170001) and a protease inhibitor cocktail from Calbiochem (catalog no. 524525). The plates were placed at 4° C. with vigorous shaking for 5 min to lyse the cells. The resulting lysates contained approximately 1 µg/µL of protein.

The 4H1 total pRb antibody from Cell signaling technology (catalog no. 9309) was added to clear MaxiSorp plates (Nunc catalog no. 442404) at a concentration of 50 ng per well in 50 µL Dulbecco's Phosphate Buffered Saline (DPBS) (Gibco catalog no. 14190-144). Plates were incubated overnight at 4° C. with rocking. After a 250 µL wash with TBST (Teknova catalog no. T9501) and blot-drying, 250 µL Superblock (Pierce catalog no. 37535) was added to each well. After shaking for 10 minutes, the Superblock solution was replaced with fresh Superblock and plates were incubated on a shaker for an additional 50 min. After blocking, 30 µL of JeKo-1 cell lysate, containing approximately 10 µg total protein, were added to wells in triplicate. 20 µL PBS (Gibco catalog no. 10010-023) containing 10% Superblock (Pierce catalog no. 37535) were added to each well for a final reaction volume of 50 µL. Plates were then sealed with Uniseal plate sealers (Whatman catalog no. 7704-0007), and incubated for 2 h at room temperature on a shaker. Plates were washed with 3×250 µL TBST. 50 µL of a 1:1000 dilution of anti-phospho Rb $Ser^{780}$ from Cell Signaling (catalog no. 9307) in PBS/10% Superblock were added and the plate was incubated on a shaker for 1 h at room temperature. For all incubation steps, plates were covered with Uniseal plate sealers. Following incubation, plates were washed with 3×250 µL TBST. Next, 50 µL of a 1:2500 dilution of donkey-anti-rabbit HRP (Promega catalog no. W401B) in PBS/10% Superblock were added, and plates were incubated for 30 min at room temperature on a shaker. Plates were again washed as described above. Finally, 50 µL Ultra TMB ELISA (Pierce catalog no. 34028) were added and plates incubated, unsealed, 5-15 min in the dark, until blue color developed. After incubation, 50 µL 2 M sulfuric acid were added to plates to top the reaction, and absorbance was determined on a SpectraMax (Molecular Devices, Sunnydale, Calif.) within 15 minutes at 450 nm. All washes were performed using a Bio-Tek plate washer.

The Total Rb ELISA kit (Invitrogen catalog no. KH00011) was used to determine the levels of total pRb. This kit uses wells precoated with a proprietary total pRb antibody for capture. All reagents listed, with the exception of cell lysate, were included in the kit. The nature of the antibodies used for capture and detection was labeled as proprietary and not disclosed. 10 µg of cell lysate was loaded into the wells and volume adjusted to 50 µL with standard dilution buffer. Plates were sealed with film included in the kit and incubated for 2 h at room temperature on a shaker. Plates are then manually washed three times with 250 µL wash buffer. 50 µL of proprietary primary antibody (pre-conjugated to biotin) was added to wells and incubated for 1 h at room temperature on a shaker. Then plates were again washed as noted above. The secondary antibody (HRP pre-conjugated to Streptavidin) was diluted 1:100 in Streptavidin-HRP diluent buffer and 50 µL was added to each well. Plates were then incubated for 30 min. Afterwards, plates were washed four times with buffer as outlined above. Finally, 50 µL stabilized Chromogen was added per well and plates were incubated for 15 min, at which point 50 µL of stop solution was added. Plates were then read on a Spectramax at 450 nm.

Upon quantitation of the pRb phosphorylation (p-pRb) levels, % inhibition values were derived for each concentration tested and used to determine 50% inhibitory concentrations ($IC_{50}$) for a particular compound (non-normalized). The total pRb levels were then used to adjust the p-pRb % inhibition values to account for any loss of signal due to the absence of the pRb protein itself, and the $IC_{50}$ values obtained from the adjusted % inhibitions represent normalized cellular p-pRb $IC_{50}$.

Automated Electrophysiology Studies (Q-Patch Clamp Assay)

Cell cultures: CHO cells constitutively expressing functional hERG channels were purchased from AVIVA Biosciences Corp. (San Diego, Calif.). Cells were grown in DMEM/F12 (Gibco Cat #11039-021), supplemented with 10% FBS (Gibco Cat #10082-142), 1% Penicillin-Streptomycin (Gibco Cat #15140-122) and 1% Geneticin (Gibco Cat #10131-027). Cells were split when they reach-70-90% confluence by aspirating the medium from the culture and rinsing the cell monolayer with Dulbecco's PBS (Gibco Cat #14190-136). After removing the rinse buffer, trypsin/EDTA (0.05%, Gibco Cat #25300-054) was added to cover the cell monolayer and incubated for 1 minute at room temperature. Aspirate the trypsin/EDTA and leave the cells for 1 more minute. Dislodge cells from the flask by tapping the flask. Add complete medium and pipette up and down several times to mix and dissociate cell clumps until cells were separated. Count the cells and re-seed cells in flasks in 37° C., 5.0% CO2, 100% humidity incubator for passaging cells and 30° C., 5.0% CO2, 100% humidity for compound screening. Before QPatch assay, growth media was removed from the culture flasks, and cells were gently rinsed with 12 ml D-PBS once. The cells were immersed in 10 ml Trypsin/EDTA (prepared freshly from 10× frozen stock with D-PBS) at room temperature for approximately 30 seconds before the solution was aspirated, then incubated for 3-4 min at 37° C. At the end the incubation, visibly rounded cells were easily dislodged from the bottom of the flask without any tap. QPatch modified storage media (CHO-S-SFM II, 25 mM HEPES, and 0.04 mg/ml soy bean trypsin inhibitor) was added and the cells were re-suspended gently by pipetting up and down 6-10 times. Cell density and viability were determined with Beckman Vicell. The cell density was adjusted to 2–3×106/ml in QPatch modified storage media. The cell suspension was applied to the storage container on QPatch platform immediately.

Solutions and Drugs: Cells were centrifuged (150 g, 2 min), the supernatant was removed, and the cell pellet was washed twice and finally resuspended in an extracellular solution (Na-Ringer) containing the following (in mM): 145 NaCl, 4 KCl, 2CaCl2, 1 MgCl2, 10 HEPES adjusted to pH 7.4. Aliquots (300 ul) of this suspension (3-10 3 106 cells/ml) were transferred to the chip. The intracellular solution consisted of the following (in mM): 120 KCl, 5.374 CaCl2, 1.75 MgCl2, 10 KOH/EGTA, 10HEPES, 5 K2-ATP adjusted to pH 7.2. Amitriptyline (reference control) was from Sigma. All compounds were prepared at 10 mM in 100% DMSO. Each concentration was made by five-fold serial dilution in 100% DMSO, in a 96-well plate in triplicate. Each dilution was then transferred and further diluted 333-fold (testing concentration: 0.2 to 30 µM) in extracellular solution in a 96-well glass coated plate. The final DMSO concentration was ≤0.3%.

Electrophysiology: All electrophysiological experiments were conducted on a single-channel QPatch test version. The Q-plate has 16 recording chambers and each chamber has a patch clamp amplifier operating in parallel. The amplifiers are controlled by a custom-made Digital Signal Processor (DSP) board by Sophion, which performs voltage clamp of a single cell in whole-cell mode. In the hERG assay the acquisition rate of the whole-cell current during voltage protocol execution was 10 kHz. This current signal was digitally filtered with a cut-off frequency of 3 kHz (Bessel filter, order=4). CHO-hERG Cells were held at −80 mV resting membrane potential for 100 msec and at −50 mV for 100 msec (leak subtraction), and depolarized to +20 mV for 4 sec (prepulse), followed by repolarization to −50 mV for 4 sec (test pulse) before returning to the holding potential, −80 mV. The protocol was repeated every 20 sec. During each baseline and increased dose application period approximately 10 voltage protocols were executed.

Fluidics: Cell suspension, compound samples, and Na-Ringer (wash) in volumes of 5-15 µl were pipetted to the chips.

Data analysis: IC50 and Hill coefficient were estimated from best fits to the experimental dose-response data by the Hill equation:

Remaining current(%)=Max$I$+((Min$I$−Max$I$)/(1+
((Conc./IC50)^Hill))) Where Max$I$=100,Min$I$=0

This fitting procedure returned values for the two variable parameters: an IC50 value and a Hill slope.

Certain Examples of the present invention were evaluated in the O-patch clamp assay.

Biological Data

The results of the CDK4 and CDK1 enzymatic activity assays and the CDK4 cellular assay are given in Table 1.

TABLE 1

| Example | Biochemical CDK4 enzyme IC50/uM | Cellular ppRb inhibition IC50/uM | Normalized cellular ppRb inhibition IC50/uM | Biochemical CDK1 enzyme IC50/uM |
|---|---|---|---|---|
| 1 | 0.017 | 0.364 | 0.538 | >15 |
| 2 | 0.005 | 0.066 | 0.084 | >15 |
| 3 | 0.001 | 0.019 to 0.026 | 0.029 to 0.033 | 4.2 to 5.143 |
| 4 | 0.004 | 0.009 | 0.01 | 7.065 |
| 5 | 0.008 to 0.016 | 0.115 | 0.117 | >15 |
| 6 | 0.187 | 0.148 | 0.889 | >15 |
| 7 | 0.021 | 0.127 | 0.288 | 17.59 |
| 8 | 0.039 | 0.072 | 0.259 | >15 |
| 9 | <0.004 | 0.055 | 0.12 | 7.101 |
| 10 | <0.005 to 0.005 | 0.021 | 0.025 | 4.137 |
| 11 | 0.009 | 0.039 | 0.068 | >15 |
| 12 | 0.049 | 0.255 | 0.724 | >15 |
| 13 | 0.006 | 0.065 | 0.145 | 8.439 |
| 14 | 0.019 | 0.133 | 0.371 | >15 |

TABLE 1-continued

| Example | Biochemical CDK4 enzyme IC50/uM | Cellular ppRb inhibition IC50/uM | Normalized cellular ppRb inhibition IC50/uM | Biochemical CDK1 enzyme IC50/uM |
|---|---|---|---|---|
| 15 | 0.018 | 0.043 | 0.264 | >15 |
| 16 | 0.015 | 0.092 | 0.233 | >15 |
| 17 | 0.065 | 0.281 | 0.643 | >15 |
| 18 | 0.008 to 0.024 | 0.012 to 0.037 | 0.026 to 0.09 | 13.206 |
| 19 | 0.005 to 0.008 | 0.054 to 0.055 | 0.064 to 0.116 | >15 |
| 20 | 0.064 | 0.267 | 0.452 | >15 |
| 21 | 0.047 | 0.187 | 0.401 | >15 |
| 22 | 0.062 to 0.083 | 0.086 to 0.513 | 0.086 to 0.817 | >15 |
| 23 | 1.63 | 6.77 | 6.77 | >15 |
| 24 | 0.049 | 0.266 | 0.272 | >15 |
| 25 | 0.008 | 0.02 | 0.022 | >15 |
| 26 | 0.038 | 0.325 | 0.388 | >15 |
| 27 | 0.046 | 0.194 | 0.201 | >15 |
| 28 | 0.022 | 0.063 | 0.069 | >15 |
| 29 | 0.014 to 0.017 | 0.024 to 0.034 | 0.02 to 0.048 | >15 |
| 30 | 0.088 to 0.114 | 0.422 to 0.542 | 0.344 to 0.582 | >15 |
| 31 | 0.069 to 0.081 | 0.252 to 0.352 | 0.497 to 0.591 | >15 |
| 32 | 0.015 to 0.021 | 0.131 | 0.212 | >15 |
| 33 | 0.094 to 0.144 | 0.377 to 0.919 | 0.43 to 1.3 | >15 |
| 34 | 0.022 | 0.075 | 0.14 | >15 |
| 35 | 0.026 | 0.069 | 0.197 | >15 |
| 36 | 0.003 | 0.023 | 0.028 | 12.965 |
| 37 | <0.005 to 0.006 | 0.121 to 0.301 | 0.288 to 0.438 | >15 |
| 38 | 0.045 to 0.084 | 0.075 to 0.259 | 0.139 to 0.783 | >15 |
| 39 | 0.077 | 0.079 | 0.136 | >15 |
| 40 | 0.036 to 0.052 | 0.04 to 0.099 | 0.051 to 0.222 | >15 |
| 41 | 0.015 to 0.017 | 0.112 to 0.228 | 0.132 to 0.415 | >15 |
| 42 | 0.015 | 0.086 | 0.241 | >15 |
| 43 | 0.176 to 0.198 | 0.461 to 0.745 | 0.469 to 1.28 | >15 |
| 44 | 0.177 to 0.351 | 0.72 to 1.493 | 0.778 to ND | >15 |
| 45 | 0.014 to 0.024 | 0.064 | 0.064 | 12.815 |
| 46 | 0.1 | 0.724 | 0.73 | >15 |
| 47 | 0.03 | 0.315 | 0.352 | >15 |
| 48 | 0.024 | 0.152 | 0.229 | >15 |
| 49 | 0.045 | 0.044 to 0.231 | 0.052 to 0.431 | >15 |
| 50 | 0.021 | 0.041 | 0.09 | >15 |
| 51 | 0.023 | 0.028 | 0.06 | >15 |
| 52 | 0.027 | 0.021 to 0.047 | 0.045 to 0.053 | >15 |
| 53 | 0.003 | 0.007 to 0.014 | 0.007 to 0.027 | >15 |
| 54 | 0.003 | 0.006 to 0.033 | 0.008 to 0.047 | 1.992 |
| 55 | 0.014 to 0.036 | 0.031 to 0.112 | 0.035 to 0.164 | >15 |
| 56 | 0.112 | 0.395 | 0.47 | >15 |
| 57 | 1.566 | >10 | >10 | >15 |
| 58 | 0.074 | 0.105 to 0.188 | 0.288 to 0.338 | >15 |
| 59 | 0.008 | 2.5 | >10 | >15 |
| 60 | 0.019 | 0.021 | 0.047 | >15 |
| 61 | 0.02 | 0.021 | 0.053 | >15 |
| 62 | 0.01 | 0.291 | 0.723 | 39.91 |
| 63 | 0.011 to 0.024 | 0.034 to 0.078 | 0.04 to 0.242 | >15 |
| 64 | 0.072 to 0.179 | 0.323 to 0.466 | 0.771 to 2.2 | >15 |
| 65 | 0.076 | 0.126 to 0.211 | 0.132 to 0.458 | >15 |
| 66 | 0.004 to 0.007 | 0.038 | 0.041 | >15 |
| 67 | 0.003 | 0.051 | 0.054 | 10.377 |
| 68 | <0.005 to 0.008 | 0.266 | 0.712 | >15 |
| 69 | <0.005 to 0.018 | 0.024 | 0.048 | >15 |
| 70 | 0.039 | 0.117 | 0.18 | >15 |
| 71 | <0.005 to 0.006 | 0.031 | 0.056 | 12.731 |
| 72 | 0.013 | 0.048 | 0.112 | >15 |
| 73 | 0.045 to 0.084 | 0.075 to 0.259 | 0.139 to 0.783 | >15 |
| 74 | 0.067 | 0.151 | 0.257 | >15 |
| 75 | 0.047 | 0.081 | 0.525 | >15 |
| 76 | 0.021 | 0.16 | 0.216 | >15 |
| 77 | 0.027 | 0.172 | 0.225 | >15 |
| 78 | 0.076 | 0.059 | ND | >15 |
| 79 | 0.042 | 0.030 | 0.117 | >15 |
| 80 | 0.012 to 0.014 | 0.051 to 0.32 | 0.074 to 0.474 | 14.016 |
| 81 | <0.005 | 0.003 | 0.004 | 3.812 |
| 82 | 0.004 | 0.005 | 0.009 | 2.659 |
| 83 | 0.003 | 0.005 | 0.009 | 5.316 |
| 84 | <0.005 | 0.007 to 0.017 | 0.01 to 0.028 | 18.028 |
| 85 | <0.005 to 0.007 | 0.005 to 0.017 | 0.009 to 0.021 | 8.977 to 11.168 |
| 86 | <0.005 to 0.006 | 0.008 to 0.017 | 0.013 to 0.014 | 20.621 |
| 87 | <0.005 | 0.005 to 0.008 | 0.006 to 0.015 | 4.14 |
| 88 | <0.005 to 0.005 | 0.007 | 0.011 | 2.511 |
| 89 | 0.003 | <0.005 to 0.007 | 0.004 to 0.015 | 6.483 |
| 90 | 0.005 | 0.009 to 0.034 | 0.014 to 0.056 | >15 |

TABLE 1-continued

| Example | Biochemical CDK4 enzyme IC50/uM | Cellular ppRb inhibition IC50/uM | Normalized cellular ppRb inhibition IC50/uM | Biochemical CDK1 enzyme IC50/uM |
|---|---|---|---|---|
| 91 | <0.005 to 0.007 | 0.01 to 0.027 | 0.022 to 0.074 | 13.307 to 14.904 |
| 92 | <0.005 to 0.007 | 0.005 to 0.02 | 0.019 to 0.038 | 25.059 |
| 93 | <0.005 | 0.008 | 0.02 | >15 |
| 94 | 0.041 to 0.044 | 0.025 to 0.154 | 0.034 to 0.206 | >15 |
| 95 | 0.007 | 0.004 to 0.02 | 0.021 to 0.065 | 13.974 to 14.344 |
| 96 | 0.015 to 0.028 | 0.031 to 0.039 | 0.073 to 0.107 | 10.777 |
| 97 | 0.051 | 0.066 | 0.145 | >15 |
| 98 | 0.016 to 0.098 | 0.136 to 0.266 | 0.291 to 0.887 | >15 |
| 99 | 0.071 | 0.463 | 0.618 | >15 |
| 100 | 0.035 | 0.188 | 0.218 | >15 |
| 101 | 0.02 | 0.058 | 0.11 | >15 |
| 102 | 0.018 | 0.039 | 0.071 | >15 |
| 103 | 0.017 | 0.024 to 0.072 | 0.064 to 0.169 | >15 |
| 104 | 0.02 | 0.029 | 0.064 | >15 |
| 105 | 0.012 | 0.061 | 0.1 | >15 |
| 106 | 0.015 | 0.07 | 0.114 | >15 |
| 107 | 0.009 | 0.013 to 0.049 | 0.037 to 0.114 | >15 |
| 108 | 0.013 | 0.061 | 0.069 | >15 |
| 109 | 0.012 | 0.048 | 0.075 | >15 |
| 110 | 0.008 | 0.041 | 0.062 | >15 |
| 111 | 0.041 | 0.371 | 0.452 | 9.17 |
| 112 | 0.011 to 0.034 | 0.092 | 0.231 | >15 |
| 113 | 0.017 to 0.021 | 0.177 to 0.205 | 0.204 to 0.245 | 11.561 to >15 |
| 114 | 0.19 | 1.35 | 7.1 | >15 |
| 115 | 0.02 to 0.051 | 0.135 to 0.306 | 0.369 to 0.407 | >15 |
| 116 | 0.11 | 0.604 | 0.605 | >15 |
| 117 | 0.007 to 0.009 | 0.04 to 0.067 | 0.051 to 0.082 | >15 |
| 118 | <0.005 to 0.014 | 0.034 to 0.147 | 0.047 to 0.153 | >15 |
| 119 | 0.012 | 0.026 to 0.047 | 0.072 to 0.083 | >15 |
| 120 | 0.066 | 0.677 | 1.03 | >15 |
| 121 | 0.079 to 0.107 | 0.184 to 0.489 | 0.199 to 0.791 | >15 |
| 122 | <0.005 to 0.01 | 0.009 | 0.014 | >15 |
| 123 | 0.003 | 0.005 to 0.016 | 0.008 to 0.099 | 29.281 |
| 124 | 0.023 | 0.158 | 0.261 | >15 |
| 125 | 0.015 | 0.083 | 0.161 | >15 |
| 126 | 0.01 to 0.031 | 0.023 to 0.032 | 0.045 to 0.049 | >15 |
| 127 | 0.005 | 0.119 to 0.917 | 0.247 to 1.52 | >15 |
| 128 | 0.009 | 0.081 | 0.14 | >15 |
| 129 | 0.048 | 0.194 | 0.221 | >15 |
| 130 | 0.009 | 0.019 to 0.026 | 0.022 to 0.045 | >15 |
| 131 | 0.004 | 0.014 | 0.024 | >15 |
| 132 | 0.019 | 0.021 to 0.05 | 0.028 to 0.047 | >15 |
| 133 | <0.005 | 0.005 | 0.007 | 13.338 |
| 134 | 0.008 | 0.066 | 0.123 | >15 |
| 135 | 0.007 | 0.019 | 0.038 | >15 |
| 136 | 0.054 | 0.077 | 0.218 | >15 |
| 137 | 0.062 | 0.155 | 0.15 | >15 |
| 138 | 0.106 | 1.6 | ND | >15 |
| 139 | 0.114 | 0.605 | 0.638 | >15 |
| 140 | <0.005 to 0.006 | 0.005 to 0.009 | 0.011 to 0.018 | >15 |
| 141 | 0.045 | 0.024 | 0.034 | >15 |
| 142 | 0.034 | 0.006 | 0.013 | >15 |
| 143 | 0.044 | 0.119 | 0.251 | >15 |
| 144 | 0.019 | 0.031 | 0.049 | >15 |
| 145 | 0.032 | 0.045 | 0.162 | >15 |
| 146 | 0.619 | 2.7 | 2.9 | >15 |
| 147 | 0.027 | 0.257 | 0.31 | >15 |

What is claimed is:

1. A compound according to formula (I)

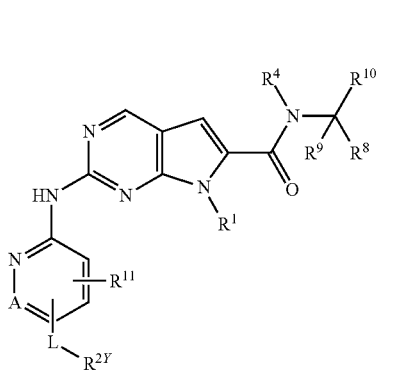

wherein:

$R^1$ is $C_{3-7}$ alkyl; $C_{4-7}$ cycloalkyl optionally substituted with one substituent selected from the group consisting of $C_{1-6}$ alkyl and OH; phenyl optionally substituted with one substitutent selected from the group consisting of $C_{1-6}$ alkyl, $C(CH_3)_2CN$, and OH; piperidinyl optionally substituted with one cyclopropyl or $C_{1-6}$ alkyl; tetrahydropyranyl optionally substituted with one cyclopropyl or $C_{1-6}$ alkyl; or bicyclo[2.2.1]heptanyl;

A is CH or N;

$R^{11}$ is hydrogen or $C_{1-4}$ alkyl;

L is a bond, C(O), or $S(O)_2$;

$R^{2Y}$ is

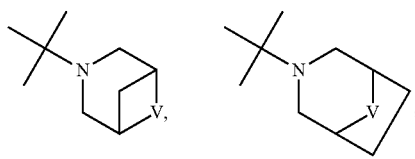

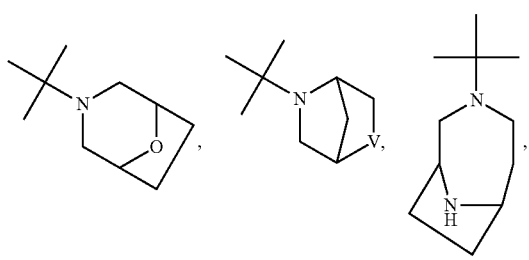

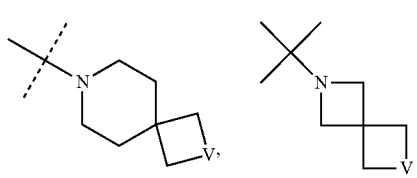

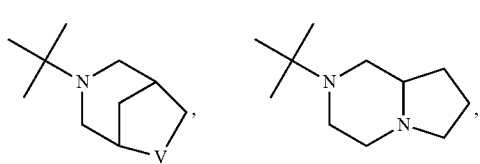

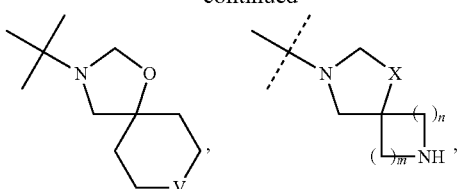

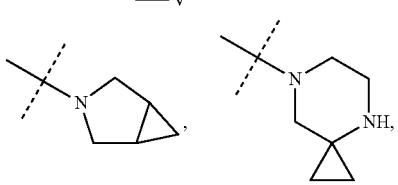

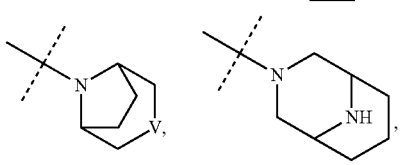

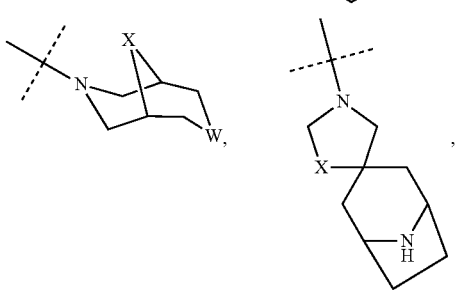

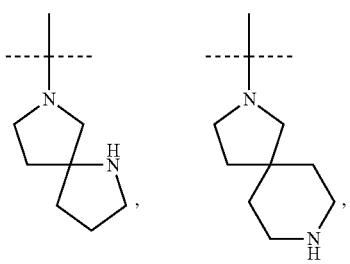

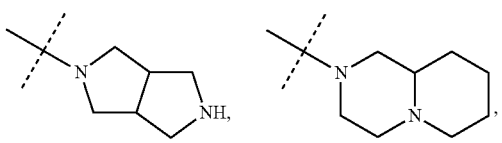

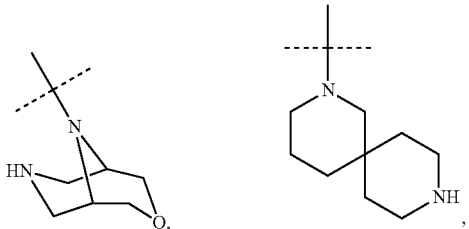

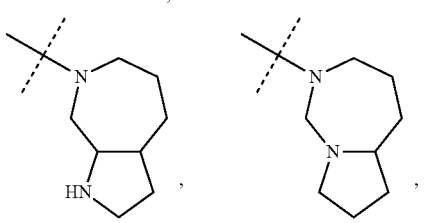

-continued

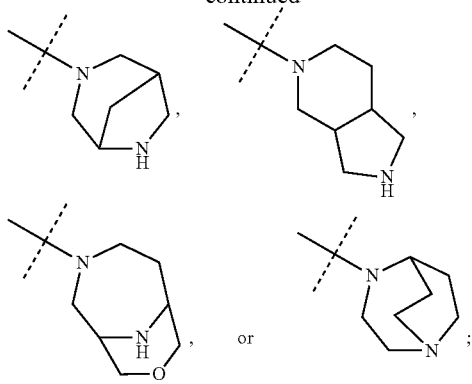

V is NH or CH$_2$;
X is O or CH$_2$;
W is O or NH;
m and n are each independently 1, 2, or 3 provided that m and n are not both 3;
each R$^{2Y}$ is optionally substituted with one to four substituents each independently selected from the group consisting of: C$_{1-3}$ alkyl optionally substituted with one or two substituents each independently selected from the group consisting of hydroxy, NH$_2$, and —S—C$_{1-3}$ alkyl; CD$_3$; halo; oxo; C$_{1-3}$ haloalkyl; hydroxy; NH$_2$; dimethylamino; benzyl; —C(O)—C$_{1-3}$alkyl optionally substituted with one or two substituents each independently selected from the group consisting of NH$_2$,—SCH$_3$ and NHC(O)CH$_3$; —S(O)$_2$—C$_{1-4}$-alkyl; and pyrrolidinyl-C(O)—;
R$^4$ is hydrogen, deuterium, or C(R$^5$)(R$^6$)(R$^7$); and
R$^5$, R$^6$, R$^7$, R$^8$, R$^9$ and R$^{10}$ are each independently H or deuterium; or a pharmaceutically acceptable salt thereof.

2. The compound according claim 1 of formula (I-B)

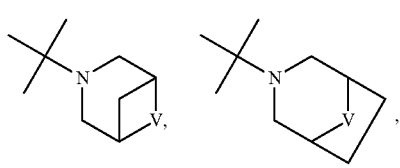

(I-B)

wherein
L is a bond or C(O);
R$^{2Y}$ is

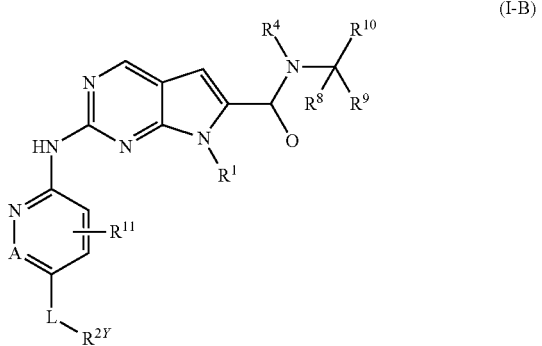

-continued

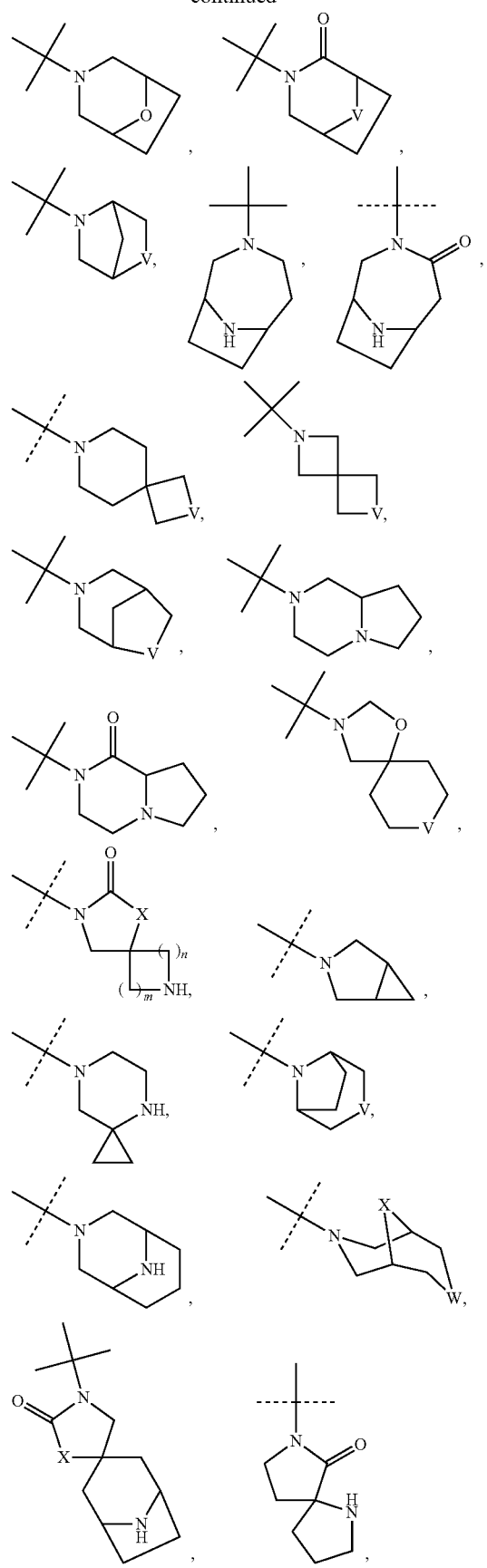

341

-continued

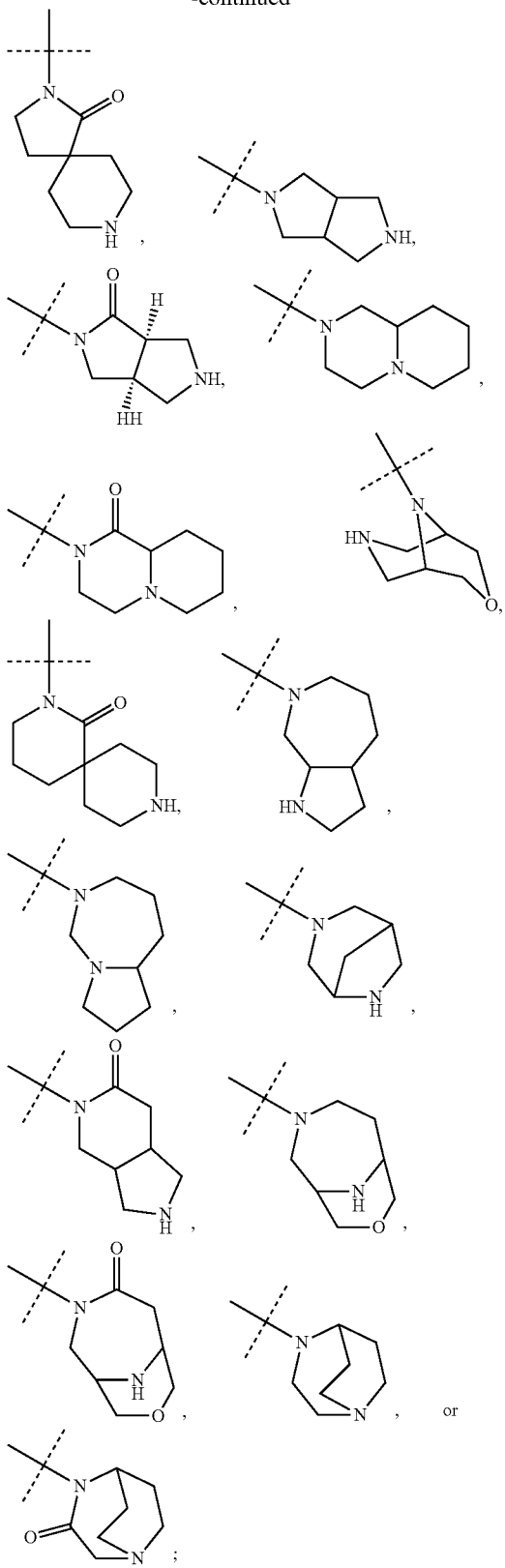

V is NH or CH$_2$;
X is O or CH$_2$;
W is O or NH;

342 m and n are each independently 1, 2, or 3 provided that m and n are not both 3; and each R$^{2Y}$ is optionally substituted with one to four substituents each independently selected from the group consisting of: C$_{1-3}$ alkyl optionally substituted with one or two substituents each independently selected from the group consisting of hydroxy, NH$_2$, and —S—C$_{1-3}$ alkyl; CD$_3$; C$_{1-3}$ haloalkyl; hydroxy; NH$_2$; dimethylamino; benzyl; —C(O)—C$_{1-3}$alkyl optionally substituted with one or two substituents each independently selected from the group consisting of NH$_2$, —SCH$_3$ and NHC(O)CH$_3$; —S(O)$_2$—C$_{1-4}$alkyl; and pyrrolidinyl-C(O)—; or a pharmaceutically acceptable salt thereof.

3. The compound according to claim 1 wherein L is C(O), or a pharmaceutically acceptable salt thereof.

4. The compound according to claim 1 wherein L is a bond, or a pharmaceutically acceptable salt thereof.

5. The compound according to claim 1 wherein A is CH and R$^{11}$ is hydrogen; or a pharmaceutically acceptable salt thereof.

6. The compound according to claim 1 wherein R$^4$ is C(R$^5$)(R$^6$)(R$^7$) and R$^5$, R$^6$, R$^7$, R$^8$, R$^9$ and R$^{10}$ are hydrogen, or a pharmaceutically acceptable salt thereof.

7. The compound according to claim 1 wherein R$^1$ is C$_{4-7}$ cycloalkyl optionally substituted with one C$_{1-6}$ alkyl, or a pharmaceutically acceptable salt thereof.

8. The compound according to claim 1 wherein R$^1$ is cyclobutyl, cyclopentyl, cyclohexyl, or cycloheptyl, or a pharmaceutically acceptable salt thereof.

9. The compound according to claim 1 wherein R$^1$ is unsubstituted cyclopentyl, or a pharmaceutically acceptable salt thereof.

10. The compound according to claim 1 wherein R$^{2Y}$ is unsubstituted, or a pharmaceutically acceptable salt thereof.

11. The compound according to claim 1 wherein R$^{2Y}$ is

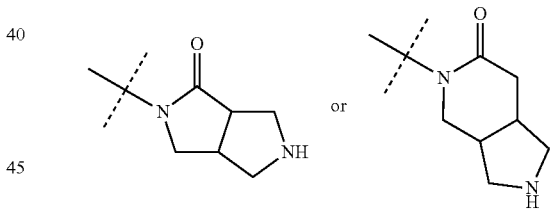

either of which is optionally substituted with one C$_{1-3}$ alkyl, or a pharmaceutically acceptable salt thereof.

12. The compound according to claim 1 wherein R$^{2Y}$ is

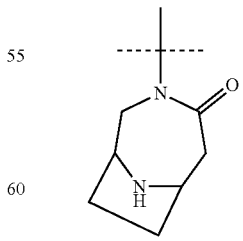

optionally substituted with one C$_{1-3}$ alkyl, or a pharmaceutically acceptable salt thereof.

13. The compound according to claim 1 selected from the group consisting of:

2-(5-(2,6-Diazaspiro[3.3]heptane-2-carbonyl)pyridin-2-ylamino)-7-cyclopentyl-N,N-dimethyl-7H-pyrrolo[2,3-d]pyrimidine-6-carboxamide;

7-(4-tert-Butyl-phenyl)-2-[5-(3,8-diaza-bicyclo[3.2.1]octane-3-carbonyl)-pyridin-2-ylamino]-7H-pyrrolo[2,3-d]pyrimidine-6-carboxylic acid dimethylamide;

7-Cyclopentyl-2-[5-(4-oxo-3,9-diaza-bicyclo[4.2.1]non-3-yl)-pyridin-2-ylamino]-7H-pyrrolo[2,3-d]pyrimidine-6-carboxylic acid dimethylamide;

7-Cyclopentyl-2-[5-((1R,6S)-4-oxo-3,9-diaza-bicyclo[4.2.1]non-3-yl)-pyridin-2-ylamino]-7H-pyrrolo[2,3-d]pyrimidine-6-carboxylic acid dimethylamide;

7-Cyclopentyl-2-[5-(3,8-diaza-bicyclo[3.2.1]octane-3-carbonyl)-pyridin-2-ylamino]-7H-pyrrolo[2,3-d]pyrimidine-6-carboxylic acid dimethylamide;

7-Cycloheptyl-2-[5-(2,5-diaza-bicyclo[2.2.1]heptane-2-carbonyl)-pyridin-2-ylamino]-7H-pyrrolo[2,3-d]pyrimidine-6-carboxylic acid dimethylamide;

7-Cyclopentyl-2-[5-(3,8-diaza-bicyclo[3.2.1]octane-8-carbonyl)-pyridin-2-ylamino]-7H-pyrrolo[2,3-d]pyrimidine-6-carboxylic acid dimethylamide;

2-(5-(2,7-diazaspiro[3.5]nonane-7-carbonyl)pyridin-2-ylamino)-7-cycloheptyl-N,N-dimethyl-7H-pyrrolo[2,3-d]pyrimidine-6-carboxamide;

7-cyclopentyl-2-[5-(8-methyl-3,8-diaza-bicyclo[3.2.1]octane-3-carbonyl)-pyridin-2-ylamino]-7H-pyrrolo[2,3-d]pyrimidine-6-carboxylic acid dimethylamide;

7-Cyclopentyl-2-[5-((S,S)-2,5-diaza-bicyclo[2.2.1]heptane-2-carbonyl)-pyridin-2-ylamino]-7H-pyrrolo[2,3-d]pyrimidine-6-carboxylic acid methylamide;

7-(3-tert-Butyl-phenyl)-2-[5-(3,8-diaza-bicyclo[3.2.1]octane-3-carbonyl)-pyridin-2-ylamino]-7H-pyrrolo[2,3-d]pyrimidine-6-carboxylic acid dimethylamide;

2-(5-((1R,5S)-3-oxa-7,9-diazabicyclo[3.3.1]nonane-9-carbonyl)pyridin-2-ylamino)-7-cyclopentyl-N,N-dimethyl-7H-pyrrolo[2,3-d]pyrimidine-6-carboxamide;

7-[4-(Cyano-dimethyl-methyl)-phenyl]-2-[5-(3,8-diaza-bicyclo[3.2.1]octane-8-carbonyl)-pyridin-2-ylamino]-7H-pyrrolo[2,3-d]pyrimidine-6-carboxylic acid dimethylamide;

7-Cyclopentyl-2-[5-((1S,6R)-3,9-diaza-bicyclo[4.2.1]nonane-3-carbonyl)-pyridin-2-ylamino]-7H-pyrrolo[2,3-d]pyrimidine-6-carboxylic acid dimethylamide;

7-Cyclopentyl-2-[5-((1R,6S)-3,9-diaza-bicyclo[4.2.1]nonane-3-carbonyl)-pyridin-2-ylamino]-7H-pyrrolo[2,3-d]pyrimidine-6-carboxylic acid dimethylamide;

7-Cyclopentyl-2-[5-(3,6-diaza-bicyclo[3.2.1]octane-3-carbonyl)-pyridin-2-ylamino]-7H-pyrrolo[2,3-d]pyrimidine-6-carboxylic acid dimethylamide;

7-cyclopentyl-N,N-dimethyl-2-(5-(5'-oxo-8-azaspiro[bicyclo[3.2.1]octane-3,3'-pyrrolidine]-1'-yl)pyridin-2-ylamino)-7H-pyrrolo[2,3-d]pyrimidine-6-carboxamide;

7-Cyclopentyl-2-[5-(1-oxo-hexahydro-pyrrolo[1,2-a]pyrazin-2-yl)-pyridin-2-ylamino]-7H-pyrrolo[2,3-d]pyrimidine-6-carboxylic acid dimethylamide;

7-cyclopentyl-N,N-dimethyl-2-(5-(2-oxo-1-oxa-3,8-diazaspiro[4.5]decan-3-yl)pyridin-2-ylamino)-7H-pyrrolo[2,3-d]pyrimidine-6-carboxamide;

7-Cyclopentyl-2-[5-((1S,6R)-4-oxo-3,9-diaza-bicyclo[4.2.1]non-3-yl)-pyridin-2-ylamino]-7H-pyrrolo[2,3-d]pyrimidine-6-carboxylic acid dimethylamide;

2-[5-(4-oxo-3,9-diaza-bicyclo[4.2.1]non-3-yl)-pyridin-2-ylamino]-7-phenyl-7H-pyrrolo[2,3-d]pyrimidine-6-carboxylic acid dimethylamide; and 7-cyclohexyl-N,N-dimethyl-2-(5-(4-oxo-3,9-diazabicyclo[4.2.1]nonan-3-yl)pyridin-2-ylamino)-7H-pyrrolo[2,3-d]pyrimidine-6-carboxamide; or a pharmaceutically acceptable salt thereof.

14. The compound according to claim 1 selected from the group consisting of:
7-Cyclopentyl-2-[5-(3,8-diaza-bicyclo[3.2.1]octane-3-carbonyl)-pyridin-2-ylamino]-7H-pyrrolo[2,3-d]pyrimidine-6-carboxylic acid dimethylamide;

7-Cyclopentyl-2-[5-((S,S)-2,5-diaza-bicyclo[2.2.1]heptane-2-carbonyl)-pyridin-2-ylamino]-7H-pyrrolo[2,3-d]pyrimidine-6-carboxylic acid dimethylamide;

7-Cyclopentyl-2-[5-((1R,6S)-4-oxo-3,9-diaza-bicyclo[4.2.1]non-3-yl)-pyridin-2-ylamino]-7H-pyrrolo[2,3-d]pyrimidine-6-carboxylic acid dimethylamide;

7-Cyclopentyl-2-[5-((1S,5S)-3,6-diaza-bicyclo[3.2.1]octane-3-carbonyl)-pyridin-2-ylamino]-7H-pyrrolo[2,3-d]pyrimidine-6-carboxylic acid dimethylamide;

7-Cyclobutyl-2-[5-((1S,6R)-4-oxo-3,9-diaza-bicyclo[4.2.1]non-3-yl)-pyridin-2-ylamino]-7H-pyrrolo[2,3-d]pyrimidine-6-carboxylic acid dimethylamide;

7-Cyclohexyl-2-[5-((1R,6S)-4-oxo-3,9-diaza-bicyclo[4.2.1]non-3-yl)-pyridin-2-ylamino]-7H-pyrrolo[2,3-d]pyrimidine-6-carboxylic acid dimethylamide;

7-Cyclopentyl-2-[5-(3,8-diaza-bicyclo[3.2.1]octane-3-carbonyl)-6-methyl-pyridin-2-ylamino]-7H-pyrrolo[2,3-d]pyrimidine-6-carboxylic acid dimethylamide;

7-Cyclopentyl-2-[5-(3,8-diaza-bicyclo[3.2.1]octane-3-carbonyl)-4-methyl-pyridin-2-ylamino]-7H-pyrrolo[2,3-d]pyrimidine-6-carboxylic acid dimethylamide;

7-Cyclopentyl-2-[5-(3,9-diaza-bicyclo[3.3.1]nonane-3-carbonyl)-pyridin-2-ylamino]-7H-pyrrolo[2,3-d]pyrimidine-6-carboxylic acid dimethylamide;

7-cyclopentyl-N,N-dimethyl-2-(5-(3-oxo-1,4-diazabicyclo[3.2.2]nonan-4-yl)pyridin-2-ylamino)-7H-pyrrolo[2,3-d]pyrimidine-6-carboxamide; and 7-cyclopentyl-N,N-dimethyl-2-(5-((1R,6S)-9-methyl-4-oxo-3,9-diazabicyclo[4.2.1]nonan-3-yl)pyridin-2-ylamino)-7H-pyrrolo[2,3-d]pyrimidine-6-carboxamide; or a pharmaceutically acceptable salt thereof.

15. The compound according to claim 1 selected from the group consisting of:
7-cyclopentyl-N,N-dimethyl-2-(5-((3aS,6aR)-1-oxohexahydropyrrolo[3,4-c]pyrrol-2(1H)-yl)pyridin-2-ylamino)-7H-pyrrolo[2,3-d]pyrimidine-6-carboxamide;

7-cyclopentyl-N,N-dimethyl-2-(5-((3aR,6aS)-1-oxohexahydropyrrolo[3,4-c]pyrrol-2(1H)-yl)pyridin-2-ylamino)-7H-pyrrolo[2,3-d]pyrimidine-6-carboxamide; and 7-cyclopentyl-N,N-dimethyl-2-(5-((3aS,6aS)-5-methyl-1-oxohexahydropyrrolo[3,4-c]pyrrol-2(1H)-yl)pyridin-2-ylamino)-7H-pyrrolo[2,3-d]pyrimidine-6-carboxamide; or a pharmaceutically acceptable salt thereof.

16. The compound according to claim 1 selected from the group consisting of:
7-cyclopentyl-N,N-dimethyl-2-(5-((1R,3r,5S)-2'-oxo-8-azaspiro[bicyclo[3.2.1]octane-3,5'-oxazolidine]-3'-yl)pyridin-2-ylamino)-7H-pyrrolo[2,3-d]pyrimidine-6-carboxamide;

7-cyclopentyl-N,N-dimethyl-2-(5-(2-oxo-1-oxa-3,8-diazaspiro[4.6]undecan-3-yl)pyridin-2-ylamino)-7H-pyrrolo[2,3-d]pyrimidine-6-carboxamide;

7-cyclopentyl-N,N-dimethyl-2-(5-(2-oxo-1-oxa-3,7-diazaspiro[4.5]decan-3-yl)pyridin-2-ylamino)-7H-pyrrolo[2,3-d]pyrimidine-6-carboxamide;

7-Cyclopentyl-2-[5-((S)-2-oxo-1-oxa-3,7-diaza-spiro[4.5]dec-3-yl)-pyridin-2-ylamino]-7H-pyrrolo[2,3-d]pyrimidine-6-carboxylic acid dimethylamide; and 7-Cyclopentyl-2-[5-((R)-2-oxo-1-oxa-3,7-diaza-spiro [4.5]dec-3-yl)-pyridin-2-ylamino]-7H-pyrrolo[2,3-d] pyrimidine-6-carboxylic acid dimethylamide; or a pharmaceutically acceptable salt thereof.

17. A compound 7 cyclopentyl-N,N-dimethyl-2-(5-((1R, 6S)-9-methyl-4-oxo-3,9-diazabicyclo[4.2.1]nonan-3-yl)pyridin-2-ylamino)-7H-pyrrolo[2,3-d]pyrimidine-6-carboxamide having the following formula:

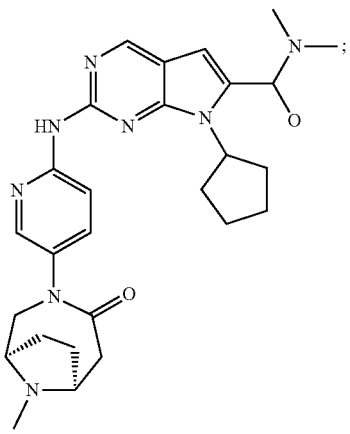 [SMILES: CN(C)C(O)c1cc2cnc(Nc3ccc(N4C[C@H]5CC[C@@H](CC4=O)N5C)cn3)nc2n1C1CCCC1]

or a pharmaceutically acceptable salt thereof.

18. A compound 7 Cyclopentyl-2-[5-(3,8-diaza-bicyclo [3.2.1]octane-3-carbonyl)-pyridin-2-ylamino]-7H-pyrrolo [2,3-d]pyrimidine-6-carboxylic acid dimethylamide having the following formula:

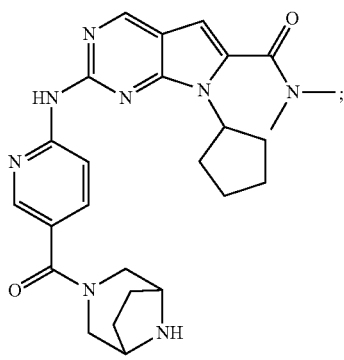 [SMILES: CN(C)C(=O)c1cc2cnc(Nc3ccc(C(=O)N4CC5CCC(C4)N5)cn3)nc2n1C1CCCC1]

or a pharmaceutically acceptable salt thereof.

19. The compound according to claim 1 wherein A is CH; $R^{11}$ is hydrogen; L is a bond and $R^{2Y}$ is

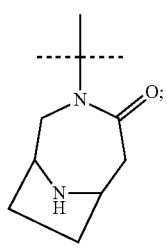

or a pharmaceutically acceptable salt thereof.

20. A compound 7-Cyclopentyl-2-[5-((1R,6S)-4-oxo-3,9-diaza-bicyclo[4.2.1]non-3-yl)-pyridin-2-ylamino]-7H-pyrrolo[2,3-d]pyrimidine-6-carboxylic acid dimethylamide having the following formula:

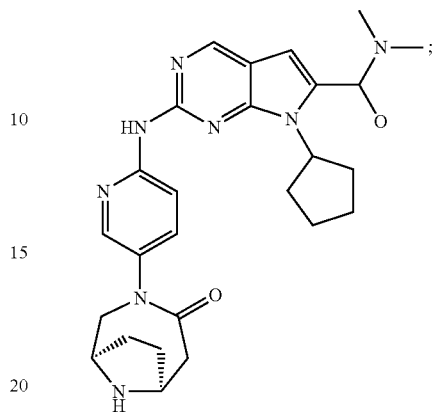

or a pharmaceutically acceptable salt thereof.

21. A compound 7-Cyclopentyl-2-[5-((1R,6S)-4-oxo-3,9-diaza-bicyclo[4.2.1]non-3-yl)-pyridin-2-ylamino]-7H-pyrrolo[2,3-d]pyrimidine-6-carboxylic acid methylamide having the following formula:

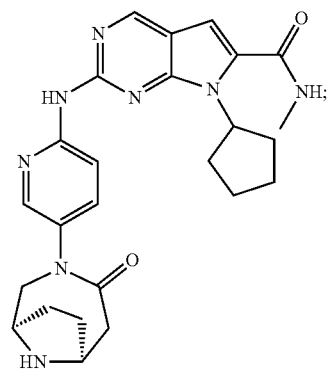 [SMILES: CNC(=O)c1cc2cnc(Nc3ccc(N4C[C@H]5CC[C@@H](CC4=O)N5)cn3)nc2n1C1CCCC1]

or a pharmaceutically acceptable salt thereof.

22. A compound 7-cyclopentyl-2-[5-((1R,6S)-9-methyl-4-oxo-3,9-diaza-bicyclo[4.2.1]non-3-yl)-pyridin-2-ylamino]-7H-pyrrolo[2,3-d]pyrimidine-6-carboxylic acid methylamide having the following formula:

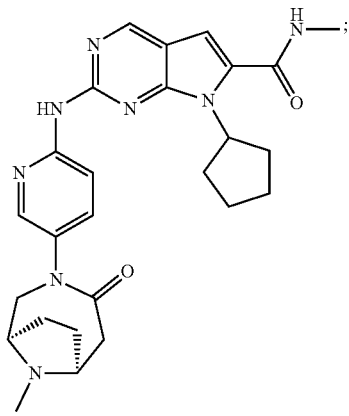 [SMILES: CNC(=O)c1cc2cnc(Nc3ccc(N4C[C@H]5CC[C@@H](CC4=O)N5C)cn3)nc2n1C1CCCC1]

or a pharmaceutically acceptable salt thereof.

23. A pharmaceutical composition comprising a compound according to claim 1, or a pharmaceutically acceptable salt thereof, and a pharmaceutically acceptable carrier or excipient.

24. A pharmaceutical composition comprising a compound according to claim 17, or a pharmaceutically acceptable salt thereof, and a pharmaceutically acceptable carrier or excipient.

25. A pharmaceutical composition comprising a compound according to claim 18, or a pharmaceutically acceptable salt thereof and a pharmaceutically acceptable carrier or excipient.

26. A method for the treatment of breast cancer in a patient in need of treatment thereof comprising administering to the patient an effective amount of a compound according to claim 1, or a pharmaceutically acceptable salt thereof.

27. A method for the treatment of melanoma in a patient in need of treatment thereof comprising administering to the patient an effective amount of a compound according to claim 1, or a pharmaceutically acceptable salt thereof.

28. A method for the treatment of liposarcoma in a patient in need of treatment thereof comprising administering to the patient an effective amount of a compound according to claim 1, or a pharmaceutically acceptable salt thereof.

29. A method for the treatment of mantle cell lymphoma in a patient in need of treatment thereof comprising administering to the patient an effective amount of a compound according to claim 1, or a pharmaceutically acceptable salt thereof.

30. A method for the treatment of head and neck cancer in a patient in need of treatment thereof comprising administering to the patient an effective amount of a compound according to claim 1, or a pharmaceutically acceptable salt thereof.

31. A method for the treatment of breast cancer in a patient in need of treatment thereof comprising administering to the patient an effective amount of a compound according to claim 17, or a pharmaceutically acceptable salt thereof.

32. A method for the treatment of melanoma in a patient in need of treatment thereof comprising administering to the patient an effective amount of a compound according to claim 17, or a pharmaceutically acceptable salt thereof.

33. A method for the treatment of liposarcoma in a patient in need of treatment thereof comprising administering to the patient an effective amount of a compound according to claim 17, or a pharmaceutically acceptable salt thereof.

34. A method for the treatment of mantle cell lymphoma in a patient in need of treatment thereof comprising administering to the patient an effective amount of a compound according to claim 17, or a pharmaceutically acceptable salt thereof.

35. A method for the treatment of head and neck cancer in a patient in need of treatment thereof comprising administering to the patient an effective amount of a compound according to claim 18, or a pharmaceutically acceptable salt thereof.

36. A method for the treatment of breast cancer in a patient in need of treatment thereof comprising administering to the patient an effective amount of a compound according to claim 18, or a pharmaceutically acceptable salt thereof.

37. A method for the treatment of melanoma in a patient in need of treatment thereof comprising administering to the patient an effective amount of a compound according to claim 18, or a pharmaceutically acceptable salt thereof.

38. A method for the treatment of liposarcoma in a patient in need of treatment thereof comprising administering to the patient an effective amount of a compound according to claim 18, or a pharmaceutically acceptable salt thereof.

39. A method for the treatment of mantle cell lymphoma in a patient in need of treatment thereof comprising administering to the patient an effective amount of a compound according to claim 18, or a pharmaceutically acceptable salt thereof.

40. A method for the treatment of head and neck cancer in a patient in need of treatment thereof comprising administering to the patient an effective amount of a compound according to claim 18, or a pharmaceutically acceptable salt thereof.

* * * * *